United States Patent
Wortmann et al.

(10) Patent No.: US 10,772,893 B2
(45) Date of Patent: *Sep. 15, 2020

(54) 2-(MORPHOLIN-4-YL)-1,7-NAPHTHYRIDINES

(71) Applicant: BAYER PHARMA AKTIENGESELLSCHAFT, Berlin (DE)

(72) Inventors: Lars Wortmann, Berlin (DE); Ulrich Lücking, Berlin (DE); Julien Lefranc, Berlin (DE); Hans Briem, Berlin (DE); Marcus Koppitz, Berlin (DE); Knut Eis, Berlin (DE); Franz Von Nussbaum, Lyons (FR); Benjamin Bader, Berlin (DE); Antje Margret Wengner, Berlin (DE); Gerhard Siemeister, Berlin (DE); Wilhelm Bone, Berlin (DE); Philip Lienau, Berlin (DE); Joanna Grudzinska-Goebel, Berlin (DE); Dieter Moosmayer, Berlin (DE); Uwe Eberspächer, Berlin (DE); Hans Schick, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,536

(22) Filed: May 8, 2018

(65) Prior Publication Data

US 2018/0256591 A1    Sep. 13, 2018

Related U.S. Application Data

(63) Continuation of application No. 15/501,079, filed as application No. PCT/EP2015/067804 on Aug. 3, 2015, now Pat. No. 9,993,484.

(30) Foreign Application Priority Data

Aug. 4, 2014 (EP) .................................. 14179692
Mar. 17, 2015 (EP) .................................. 15159342

(51) Int. Cl.
C07D 471/04 (2006.01)
C07D 413/14 (2006.01)
(Continued)

(52) U.S. Cl.
CPC ........ *A61K 31/541* (2013.01); *A61K 31/5377* (2013.01); *A61K 31/5386* (2013.01);
(Continued)

(58) Field of Classification Search
CPC ............................. C07D 471/04; C07D 413/14
(Continued)

(56) References Cited

U.S. PATENT DOCUMENTS 4,008,068 A    2/1977  Krenzer
9,549,932 B2*  1/2017  Wortmann ........... C07D 471/04
(Continued)

FOREIGN PATENT DOCUMENTS

WO    2000/58307    10/2000
WO    2006/039718    4/2006
(Continued)

OTHER PUBLICATIONS

Brown & Baltimore "ATR disruption leads to chromosomal fragmentation and early embryonic lethality" Genes Dev. 14:397-402 (2000).
(Continued)

*Primary Examiner* — Matthew P Coughlin
*Assistant Examiner* — Sagar Patel
(74) *Attorney, Agent, or Firm* — Morrison & Foerster LLP

(57) ABSTRACT

The present invention relates to substituted 2-(morpholin-4-yl)-1,7-naphthyridine compounds of general formula (I) or (Ib),

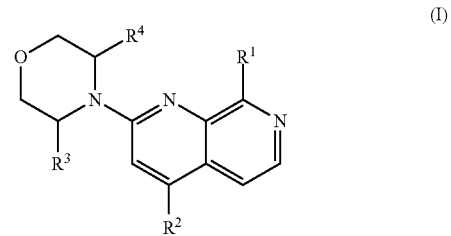

(I)

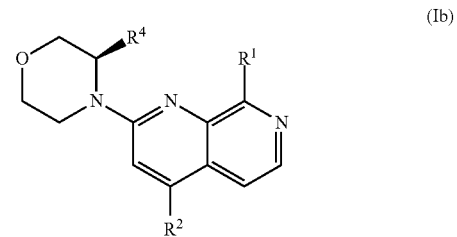

(Ib)

to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative disease as a sole agent or in combination with other active ingredients.

12 Claims, No Drawings

Specification includes a Sequence Listing.

(51) Int. Cl.

| | |
|---|---|
| *A61K 31/541* | (2006.01) |
| *A61K 31/5377* | (2006.01) |
| *A61K 31/5386* | (2006.01) |
| *A61K 31/55* | (2006.01) |
| *A61K 31/675* | (2006.01) |
| *A61K 45/06* | (2006.01) |
| *C07D 491/22* | (2006.01) |
| *C07D 519/00* | (2006.01) |
| *C07F 9/6561* | (2006.01) |

(52) U.S. Cl.
CPC ............ *A61K 31/55* (2013.01); *A61K 31/675* (2013.01); *A61K 45/06* (2013.01); *C07D 471/04* (2013.01); *C07D 491/22* (2013.01); *C07D 519/00* (2013.01); *C07F 9/6561* (2013.01)

(58) Field of Classification Search
USPC .............. 544/127, 140; 546/122; 548/364.7, 548/364.1
See application file for complete search history.

(56) References Cited

U.S. PATENT DOCUMENTS

| | | | |
|---|---|---|---|
| 9,783,536 B2 | 10/2017 | Furuyama | |
| 2019/0142812 A1* | 5/2019 | Lucking | A61K 31/4375 514/231.5 |
| 2020/0016283 A1 | 1/2020 | Cuthbertson | |
| 2020/0063212 A1 | 2/2020 | Wengner | |

FOREIGN PATENT DOCUMENTS

| | | | |
|---|---|---|---|
| WO | WO2007060404 A1 | 5/2007 | |
| WO | 2008/017461 | 2/2008 | |
| WO | WO2008023161 A1 | 2/2008 | |
| WO | WO-2010026121 A1 * | 3/2010 | ........... C07D 401/14 |
| WO | WO2010037765 A2 | 4/2010 | |
| WO | 2010/054398 | 5/2010 | |
| WO | 2010/071837 | 6/2010 | |
| WO | 2010/073034 | 7/2010 | |
| WO | WO 2010/073034 | 7/2010 | |
| WO | WO2010037765 A3 | 7/2010 | |
| WO | 2011/143399 | 11/2011 | |
| WO | 2011/143419 | 11/2011 | |
| WO | 2011/143422 | 11/2011 | |
| WO | 2011/143423 | 11/2011 | |
| WO | 2011/143425 | 11/2011 | |
| WO | 2011/143426 | 11/2011 | |
| WO | 2011/154737 | 12/2011 | |
| WO | 2011/163527 | 12/2011 | |
| WO | WO 2011/163527 | 12/2011 | |
| WO | WO2012003283 A1 | 1/2012 | |
| WO | 2012/138938 | 10/2012 | |
| WO | 2012/178123 | 12/2012 | |
| WO | 2012/178124 | 12/2012 | |
| WO | 2012/178125 | 12/2012 | |
| WO | WO2013016197 A1 | 1/2013 | |
| WO | 2013/049719 | 4/2013 | |
| WO | 2013/049720 | 4/2013 | |
| WO | 2013/049722 | 4/2013 | |
| WO | 2013/049859 | 4/2013 | |
| WO | 2013/071085 | 5/2013 | |
| WO | 2013/071088 | 5/2013 | |
| WO | 2013/071090 | 5/2013 | |
| WO | 2013/071093 | 5/2013 | |
| WO | 2013/071094 | 5/2013 | |
| WO | 2013/152298 | 10/2013 | |
| WO | 2014/062604 | 4/2014 | |
| WO | 2014/089379 | 6/2014 | |
| WO | WO2014109414 A1 | 7/2014 | |
| WO | 2014/143240 | 9/2014 | |
| WO | WO2018153968 A1 | 8/2018 | |
| WO | WO2018153969 A1 | 8/2018 | |
| WO | WO2018153970 A1 | 8/2018 | |
| WO | WO2018153971 A1 | 8/2018 | |
| WO | WO2018153972 A1 | 8/2018 | |
| WO | WO2018153973 A1 | 8/2018 | |
| WO | WO2018153975 A1 | 8/2018 | |
| WO | WO2018206547 A1 | 11/2018 | |
| WO | WO2019005782 A1 | 1/2019 | |
| WO | WO2019025440 A1 | 2/2019 | |
| WO | WO2020039025 A1 | 2/2020 | |

OTHER PUBLICATIONS

Fokas et al. "Targeting ATR in DNA damage response and cancer therapeutics" Cancer Treatment Rev. 40:109-117 (2014).
Foote et al. "Discovery of 4-{4-[(3R)-3-methylmorpholin-4-yl]-6-[1-(methylsulfonyl) cyclopropyl]pyrimidin-2-yl}-1H-indole (AZ20): A potent and selective inhibitor of ATR protein kinase with monotherapy in vivo antitumor activity" J. Med. Chem. 56:2125-2138 (2013).
Gilad et al. "Combining ATR suppression with oncogenic Ras synergistically increases genomic instability, causing synthetic lethality or tumorigenesis in a dosage-dependent manner" Cancer Res. 70:9693-9702 (2010).
López-Lago et al. "Genomic deregulation during metastasis of renal cell carcinoma implements a myofibroblast-like program of gene expression" Cancer Res. 70:9682-9692 (2010).
Llona-Minguez et al. "Chemical strategies for development of ATR inhibitors" Exp. Rev. Mol. Med. 16:e10, 17 pages (2014).
Maréchal & Zou "DNA damage sensing by the ATM and ATR kinases" Cold Spring Harb. Perspect Biol. 5:a012716, 17 pages (2013).
Wagner & Kaufmann "Prospects for the use of ATR inhibitors to treat cancer" Pharmaceut. 3:1311-1334 (2010).
Woods & Turchi "Chemotherapy induced DNA damage response" Cancer Biol. Therap. 14:379-389 (2013).
Zeman & Cimprich "Causes and consequences of replication stress" Nat. Cell Biol. 16:2-9 (2014).
International Search Report for PCT/EP2015/067804, two pages, dated Oct. 22, 2015.
Written Opinion of the ISA for PCT/EP2015/067804, five pages, dated Oct. 22, 2015.
Int'l Preliminary Report on Patentability for PCT/EP2015/067804, six pages, dated Feb. 7, 2017.
Beccalli, et al., J. Chem. Soc., Perkin Trans. 1, 12, 1359-1364 (1996).
Brown et al., Genes & Development 14, 397-402 (2000).
Fokas et al., Cancer Treatment Reviews 40, 109-117 (2014).
Foote et al., J. Med. Chem. 56, 2125-2138 (2013).
Llona-Minguez et al., Exp. Rev. Mol. Med. 16, e10 (2014).
Lopez-Lago, et al., Cancer Res. 70:23, 9682-9692 (2010).
Marechal, et al., Cold Spring Harb Perspect Biol 5a:012716 (2013).
Wagner et al., Pharmaceuticals 3:1311-1334 (2010).
Woods et al., Cancer Bio & Therap. 14:5, 379-389 (2013).
Zeman et al., Nat. Cell Biol., 16:(1), 2-9 (2014).
U.S. Appl. No. 16/488,525, filed Aug. 23, 2019, for Wengner et al. (A copy of U.S. Patent Application is not submitted herewith pursuant to the waiver of 37 C.F.R. § 1.98(a)(2)(iii) issued by the Office on Sep. 21, 2004.).
U.S. Appl. No. 16/635,812, filed internationally on Jul. 31, 2018, for Wengner et al. (A copy of U.S. Patent Application is not submitted herewith pursuant to the waiver of 37 C.F.R. § 1.98(a)(2)(iii) issued by the Office on Sep. 21, 2004.).

* cited by examiner

SEQUENCE LISTING

<160> NUMBER OF SEQ ID NOS: 4

<210> SEQ ID NO 1
<211> LENGTH: 8697
<212> TYPE: DNA
<213> ORGANISM: Artificial Sequence
<220> FEATURE:
<223> OTHER INFORMATION: Synthetic codon-optimized human ATR including GST tag

<400> SEQUENCE: 1

```
atggcctccc ctatactagg ttattggaaa attaagggcc ttgtgcaacc cactcgactt     60
cttttggaat atcttgaaga aaaatatgaa gagcatttgt atgagcgcga tgaaggtgat    120
aaatggcgaa acaaaaagtt tgaattgggt ttggagtttc ccaatcttcc ttattatatt    180
gatggtgatg ttaaattaac acagtctatg ccatcatac gttatatagc tgacaagcac     240
aacatgttgg gtggttgtcc aaaagagcgt gcagagattt caatgcttga aggagcggtt    300
ttggatatta gatacggtgt ttcgagaatt gcatatagta aagactttga aactctcaaa    360
gttgattttc ttagcaagct acctgaaatg ctgaaaatgt tcgaagatcg tttatgtcat    420
aaaacatatt taaatggtga tcatgtaacc catcctgact tcatgttgta tgacgctctt    480
gatgttgttt tatacatgga cccaatgtgc ctggatgcgc tcccaaaatt agtttgtttt    540
aaaaaacgta ttgaagctat cccacaaatt gataagtact gaaatccag caagtatata    600
gcatggcctt tgcagggctg gcaagccacg tttggtggtg cgaccatcc tccaaaatcg    660
gatcagatca aagtttgta caaaaaagca ggctccgact atgacattcc aactacggag    720
aatttgtact ccaaggcga ctacaaggac gacgatgata gatgggtga acatggtttg    780
gagctcgcat ccatgattcc agccctgcgt gaactgggct ccgcaactcc agaggagtac    840
aacacggtgg tgcaaaaacc gcgtcagata ctgtgccagt tcatcgacag aatcctgacg    900
gatgtgaacg tggtggctgt cgagctcgtc aaaaagaccg attctcaacc aacgtccgtc    960
atgctgttgg actttatcca acacatcatg aaatcctccc cgctgatgtt cgttaacgtt   1020
tctggatccc acgaggctaa aggctcctgc atcgagttct caaactggat tatcaccaga   1080
ctgttgcgta ttgctgccac gcctagctgt cacttgctcc acaagaagat ctgcgaagta   1140
atatgctccc tgctgttct gttcaagtcc aaatcacccg ctatatttgg agttctgaca   1200
aaggaattgt tgcagctgtt tgaggacctg gtatacttgc ataggcgtaa cgtgatgggt   1260
catgccgtcg agtggcctgt cgtcatgtct cgcttcctgt ctcagctcga cgaacatatg   1320
ggttatctcc agtccgcacc actccagttg atgtccatgc aaaacctgga gttcatagaa   1380
gtgacgttgc tcatggtgct gactagaatc attgctattg tgttcttccg ccgtcaagag   1440
ttgttgttgt ggcaaatcgg ctgcgtgttg ctggagtatg ctccccaaa gattaagagc   1500
ttggctatat cctttctgac agaactgttc cagctcggcg gtctgccggc ccagccggct   1560
tccacattct tctcctcatt cctggaactg ctgaagcacc tcgttgagat ggacacggac   1620
caactcaagc tgtacgaaga gcccttgtcc aaaattgatta agacactgtt cccctttgag   1680
gcagaggcgt acaggaacat cgagcccgta tatctgaaca tgctgctgga agctctgc    1740
gtgatgtttg aagatggagt actgatgcgc tgaagtccg atctgctgaa ggctgctctg   1800
tgtcatctcc tgcaatactt cttgaaattc gttcctgccg gttacgagtc cgcttttgcaa   1860
gtacgcaagg tgtacgtacg taatatctgc aaggctctgc tggacgtgct cggtattgag   1920
gtagacgccg aatatctgtt gggcccattg tacgctgcgc tgaaaatgga gtcaatggaa   1980
```

```
atcattgagg aaatccagtg ccagacccag caagaaaatc tgagctccaa ctccgacgga    2040
atttctccaa agaggcgccg cttgagcagc tccctgaacc cttcaaagcg tgcaccaaag    2100
cagactgagg aaatcaagca cgtggacatg aaccaaaaga gcatactgtg gtccgcattg    2160
aagcagaaag ccgagtcttt gcagatttcc ctcgaatatt ccggcctgaa aaatcccgta    2220
attgaaatgc tcgagggcat cgccgtagtt ttgcaactga ccgctctgtg tactgtgcac    2280
tgctctcatc agaacatgaa ctgcaggaca ttcaaggact gccagcataa gtctaaaaag    2340
aagccctcag tcgtcatcac ttggatgtct ttggatttct ataccaaggt cctgaagtcc    2400
tgtcgtagcc tgctggagtc agtgcaaaag ttggatctgg aagccaccat cgataaagta    2460
gttaagattt acgacgccct catctacatg caagtcaact ccagcttcga ggaccatatc    2520
ctcgaagatc tgtgcggtat gctgagcctc ccttggatct acagccactc cgatgacgga    2580
tgtctgaagc tcaccacttt tgccgcaaat tgttgaccc tgtcttgccg catatccgac    2640
tcatattcac ctcaagccca atcccgttgt gtattcctgc tcaccctgtt cccacgtcgt    2700
atttttctgg aatggagaac cgccgtatac aactgggctc tgcagtcctc ccacgaagtg    2760
ataagagcct catgtgtctc cggcttcttc atcttgctgc agcaacaaaa ctcttgtaat    2820
cgcgtcccga agatcctgat cgataaggtc aaggacgact ccgacattgt gaagaaagaa    2880
tttgccagca tcttgggcca gctggtctgc acactccacg gtatgttcta cctcacttcc    2940
agcttgacag aacccttctc cgagcatgga cacgtcgatc tgttttgtag aatctgaaa    3000 gcaacttcac agcacgaatg ctcctcctcc cagctcaaag cctctgtctg caagccctt    3060 ctgtttctgc tgaaaaagaa aatcccatca ccggttaaac tcgctttcat cgacaatctc    3120
caccacctgt gcaagcatct ggatttcagg gaggatgaga cagatgtgaa ggccgttctg    3180
ggtactctgc tcaacctgat ggaggaccca gacaaggacg tgagagtggc tttctccggt    3240
aacattaagc atatcctgga aagcctcgat agcgaggacg gatttatcaa agaattgttc    3300
gtcctgcgca tgaaggaagc ttacacgcat gcgcagatct ctcgtaataa cgagctgaag    3360
gacaccctga tattgacaac tggtgatatc ggaagagctg ccaagggcga tttggtgccg    3420
ttcgcgctgc tgcatttgct gcactgcctg ctgtctaagt ccgcttctgt ctctggcgct    3480
gcatacaccg aaattagggc gctggtggct gctaagtccg ttaaactcca gtcttcttc    3540 tcccagtaca aaaaacctat ttgccaattc ttggttgagt ccctgcactc ctcccagatg    3600
accgctctgc ccaacacacc ctgtcagaac gcagatgttc gcaaacagga cgttgcccac    3660
cagagggaga tggcactgaa tacactgtcc gagattgcta atgtgttcga ctttcccgat    3720
ctgaacaggt tcctgactcg tactctccag gtactgctgc ctgacctcgc cgctaaagcc    3780
tctccagctg cttcagccct gatccgtacc ctgggtaaac agctgaatgt caataggaga    3840
gaaatattga tcaacaactt caaatacatc ttttcacacc tggtatgctc ctgctctaag    3900
gacgagctgg agcgtgctct gcattatctg aagaacgaaa ccgaaataga actgggttcc    3960
ttgctccgcc aagatttcca aggtctgcat aacgagctgc tgctcaggat cggcgagcat    4020
taccagcaag tgttcaatgg tttgtcaatt ttggcgtcct tcgcctcctc cgacgaccca    4080
tatcagggcc ctagagacat catcagccca gaactgatgg ctgattatct gcaacctaag    4140
ttgctcggaa tcctcgcatt tttcaacatg caactgttgt caagctcagt cggcattgaa    4200
gataaaaaga tggcgctcaa ctcactgatg agcctcatga agctgatggg cccaaagcat    4260
gtctcctccg tgagggttaa gatgatgacc actctgagga ctggcctgag gtttaaggac    4320
gatttccctg aactgtgctg ccgtgcctgg gattgtttcg tccgttgcct cgatcacgcc    4380
```

```
tgtctcggtt ccctgctgtc ccacgtcatc gtggcactct tgccactgat tcacatacag    4440
cccaaggaaa cggccgcgat atttcactac ctcatcatcg aaaaccgtga cgcggtccag    4500
gatttcctgc atgagatcta cttcctgccc gaccacccgg aactgaagaa gatcaaggcc    4560
gttctgcagg aatatcgtaa agaaacctcc gagtccaccg atctgcagac caccctgcag    4620
ttgtcaatga aggcaatcca acatgagaac gtcgacgtca gaatacacgc actgacctct    4680
ctgaaggaaa cactgtacaa gaaccaagag aagttgatca aatacgctac tgactcagag    4740
acagtagaac ccatcatctc acagctcgtg accgttctcc tcaagggttg ccaggacgct    4800
aactctcagg cgagattgct gtgtggcgag tgcctgggag aattgggcgc cattgacccc    4860
ggtcgcctgg acttcagcac aaccgagact caaggtaaag actttacctt cgtgaccgga    4920
gtcgaggatt cctccttcgc ttacggactg ctcatggaac tcactagagc ctacctggcc    4980
tatgctgaca actctcgcgc acaagattca gccgcttacg caatccaaga gctcctgtca    5040
atttacgact gccgtgagat ggaaacgaat ggtcccggtc accagctgtg gcgccgcttt    5100
ccagaacacg ttcgcgaaat cctggaaccc cacttgaaca ccagatacaa atccagccaa    5160
aagtctactg actggtccgg tgtgaagaag cctatttacc tgtccaaact gggcagcaat    5220
ttcgcagagt ggtccgctag ctgggcgggc tacctgatca ctaaagtgcg ccacgatctc    5280
gcaagcaaaa tcttcacttg ctgctccatt atgatgaagc atgacttcaa ggtgacaatt    5340
tatctgctcc cacacatcct ggtatacgtc ctgctgggct gtaaccagga agaccagcag    5400
gaggtatacg ctgagataat ggcagttttg aagcacgacg atcagcacac cattaacaca    5460
caggacattg cgtctgacct gtgtcaactg tccactcaaa ccgttttctc catgttggac    5520
catttgaccc agtgggcaag gcacaagttc aagccctca aagcagagaa atgccctcac    5580
agcaagagca atcgcaacaa ggttgactcc atggtttcta cagttgatta tgaggactat    5640
caatcagtta cacgctttct ggatctgatt ccacaagaca ctctggctgt ggcatctttc    5700
cgctctaagg cttacactag ggccgtgatg cacttcgaat cctttatcac cgagaaaaaa    5760
cagaacatcc aggagcactt gggtttcctc caaaagctgt acgccgccat gcacgagccg    5820
gacggcgtcg cgggtgtttc cgcaattcgc aaagctgagc cctccctgaa ggaacagatt    5880
ctggagcacg agtcactggg tctgctccgc gatgccacgg cgtgttacga tcgcgcgatt    5940
cagttggagc cagaccaaat catccactat catggtgtag taaagtccat gctgggactg    6000
ggtcagctct ctacggttat cactcaggta acggagtgc atgcgaaccg ctccgaatgg    6060
accgatgagc tcaatactta cagggtggag gcagcgtgga agctcagcca gtgggacttg    6120
gtcgaaaatt acctggctgc ggatggcaag tccacaacgt ggtccgtgcg cctcggccag    6180
ctgctgctgt cagctaaaaa gagggatatt acggctttct acgactctct gaaactcgtc    6240
cgcgccgaac aaattgttcc gctgagcgcc gcgtctttcg aacgcggaag ctaccagaga    6300
ggatatgagt acatcgttcg cctgcacatg ttgtgcgagc tggagcactc tatcaaaccc    6360
ttgttccaac actccccggg tgattcatcc caagaggact ctctgaattg ggtcgctcgt    6420
ttggaaatga cccagaactc ctaccgcgcg aaggaaccta ttctggccct caggcgtgct    6480
ctgctgtcac tcaacaaacg cccggactac aatgagatgg tcgagaatg ttggctgcaa    6540 tcagctcgcg tggcgcgtaa agccggtcat catcaaactg cgtacaacgc tctgctgaac    6600
gccggcgaat cacgcttggc agaactctac gtagagcgcg caaaatggct gtggtccaag    6660
ggtgatgtgc accaggcgct catcgtcctg cagaagggag tggagctgtg tttccccgag    6720
```

| | |
|---|---|
| aacgagacac caccggaagg aaagaacatg ctgatacatg gaagggctat gttgctggtg | 6780 |
| ggacgcttca tggaggaaac agcgaacttc gagtccaatg ctataatgaa gaagtacaaa | 6840 |
| gatgttacag cttgtctgcc cgaatgggag gacggtcact tctacttggc gaagtactat | 6900 |
| gataaattga tgcctatggt aaccgacaac aagatggaga agcaaggtga tctgatccgc | 6960 |
| tatatcgtgc tgcatttcgg tcgctcactg caatacggaa accagtttat ctaccaatcc | 7020 |
| atgccacgta tgttgaccct gtggctggat tacggtacca aagcttacga gtgggaaaaa | 7080 |
| gcgggcagga gcgacagagt gcagatgaga aatgacctgg gtaaaatcaa caaagtcata | 7140 |
| actgaacata ccaactacct cgcgccgtat cagtttctga ctgctttcag ccaactcatc | 7200 |
| tcacgcatct gtcacagcca cgacgaggtt ttcgtggtcc tgatggaaat catcgcaaaa | 7260 |
| gtgttcctgg cctatcctca acaggccatg tggatgatga cggctgtgtc caagtcttca | 7320 |
| taccccatgc gcgttaaccg ttgtaaggaa atcctgaaca aggctatcca catgaagaaa | 7380 |
| agcctggaga gtttgtcgg tgacgctacg agactgaccg acaagttgct ggaattgtgc | 7440 |
| aacaagcctg tggatggaag ctccagcact ctgtctatga gcacgcactt caagatgctg | 7500 |
| aagaagctgg tagaagaggc cacgttttcc gaaatcctga taccctgca gtccgtgatg | 7560 |
| atccctacct tgccttccat cctgggaacc cacgctaacc acgcctctca tgaaccctc | 7620 |
| cccggacact gggcctatat cgctggattt gacgatatgg tcgaaattct ggcatccctg | 7680 |
| cagaagccca aaaagatctc actgaagggt tccgacggta agttctacat aatgatgtgc | 7740 |
| aagcctaagg atgacctcag aaaggactgc cgtctgatgg agttcaactc cctgattaac | 7800 |
| aaatgtctca gaaaggacgc tgagagccgt cgcaggagc tgcacattcg tacatacgca | 7860 |
| gtgatccctc tgaacgatga gtgtggcatc atagagtggg tcaataacac tgcgggactc | 7920 |
| cgcccgattc tgcacaaaact ctacaaagag aagggtgtct atatgacagg taaagagttg | 7980 |
| cgccaatgta tgctccctaa atccgctgcc ctctccgaga agttgaaggt tttcagagaa | 8040 |
| ttcctcctgc caaggcaccc accaatttc cacgaatggt ttctgcgcac attccccgac | 8100 |
| cctacgtcct ggtattcttc ccgctccgcc tactgtcgtt caactgcagt aatgagcatg | 8160 |
| gttggttaca tcctcggtct gggcgaccgc acggagaga acatcctgtt cgactccctg | 8220 |
| accggcgagt gcgtgcacgt ggatttcaat tgcttgttca ataagggtga aacttcgaa | 8280 |
| gtacctgaaa tagtgccttt ccgcctgaca cataacatgg tcaatggcat gggaccaatg | 8340 |
| ggcacggaag gactgttcag aagagcctgc gaggtcacca tgcgcctgat gcgcgatcag | 8400 |
| cgcgagccgc tgatgtcagt actcaagacg tttctgcatg accctctcgt ggagtggtcc | 8460 |
| aagcccgtca aaggccatag caaagcgcct ctgaacgaga ctggagaggt agtgaacgag | 8520 |
| aaggctaaaa cgcacgtcct cgatatagaa cagaggctgc aagtgtgat caagacaaga | 8580 |
| aatcgtgtca cgggtctgcc tctgtccatt gaaggccacg tccactacct gatccaggag | 8640 |
| gccacagacg aaaatctgct ctgccaaatg tacctgggat ggacaccata catgtaa | 8697 |

<210> SEQ ID NO 2
<211> LENGTH: 2493
<212> TYPE: DNA
<213> ORGANISM: Artificial Sequence
<220> FEATURE:
<223> OTHER INFORMATION: Synthetic codon-optimized human ATRIP including
      STREP tag

<400> SEQUENCE: 2

| | |
|---|---|
| atggccagct ggagccaccc tcagttcgaa aagagcgcgg gcctcgagac aagtttgtac | 60 |

```
aaaaaagcag gctccgatta tgacattcca acgaccgaaa atctgtactt tcagggcatg      120
gctggtacct ctgccccagg tagcaagagg agatcagaac ctcctgcacc aaggcccggt      180
ccacctcccg gtactggaca tccaccctct aagcgcgcca gaggctttag cgctgccgcg      240
gcacctgatc ctgatgaccc ttttggtgct cacggtgact ttacagcaga cgatctggag      300
gagctcgaca ctttggcgtc ccaggcactg tcacaatgcc ccgcagccgc tcgcgacgtt      360
tcatccgacc acaaagtgca ccgtttgctc gacggaatgt ctaagaaccc ctccggaaaa      420
aacagggaaa ccgtccctat caaagacaac ttcgagctgg aggtgttgca agcccagtac      480
aaagagctga aggagaagat gaaggtgatg gaggaagagg tcctgatcaa gaacggcgag      540
atcaagattc tgcgcgattc cctgcaccag acggaaagcg tcctggaaga gcagaggcgt      600
tcccactttc tgctggagca ggaaaaaacg caggctctgt ccgacaagga gaaggagttc      660
agcaagaagc tgcaaagctt gcaaagcgaa ctccagttca aagatgctga aatgaatgaa      720
ctccgtacaa agctgcagac cagcgagaga gctaataagc tcgctgcacc gagtgtgtca      780
cacgtatccc cgcgcaagaa tccgagtgta gttatcaagc ctgaagcctg ttctccacaa      840
ttcggcaaaa catccttccc gacaaaggag tccttctccg ccaacatgtc tctgcctcac      900
ccttgtcaga ccgagtcagg ctacaaaccg ctggtcggta gagaggatag taagcccac       960 tctctgcgcg gagattccat aaagcaggag gaagcccaga gtccttcgt cgattcttgg      1020 cgtcaaagga gcaataccca gggttctatc ctcattaact tgctcctgaa gcaacctttg     1080
atccccggct cttccctctc cctgtgtcat ctgctgtcca gctcttccga gtccccagct     1140
ggcacaccgc tgcaacctcc cggcttcggc tccactctcg cgggcatgtc aggactgagg     1200
acgaccggca gctatgacgg ttccttctct ctctccgcct gcgcgaagc gcagaacttg      1260 gcattcacgg gattgaacct ggttgctagg aacgagtgct cacgtgacgg agatccagcc     1320
gaaggtggac gcagagcctt tcctttgtgc caactgcccg gtgctgttca cttcttgcca     1380
ctggtgcagt tcttcatcgg tttgcactgt caagctctgc aggatctggc ggccgctaaa     1440
agatccggtg ctccgggtga ctcacccact catagctcat gcgtctcttc cggtgtggaa     1500
acgaatccgg aggatagtgt atgcattctg gagggttctct cagttaccgc gctctccatt     1560
ctgcagcacc tggtgtgcca ttcaggcgcc gttgtcagtc tcctgctgtc tggagtcgga     1620
gcggactcag ccgcgggtga gggtaaccgc tccctcgtcc atcgcctgtc tgacggcgac     1680
atgaccagcg ctttgcgtgg agtcgcagat gaccaaggtc agcatcccct cttgaagatg     1740
ctgctgcatc tgttggcatt ttcctccgca gctactggtc acctccaagc cagcgtgttg     1800
acccagtgtc tcaaagtgct ggtcaaactg gcggagaaca caagttgcga cttcttgcct     1860
cgcttccaat gcgtgttcca agtactccct aagtgcttgt caccagaaac accgctgcca     1920
agtgtgctcc tggccgttga actgctgagt ctgctggctg accacgacca actggctccc     1980
cagctgtgca gtcacagtga aggttgtctg ctgctcctgc tctacatgta catcacgtca     2040
cgtcccgacc gtgtggcctt ggagactcaa tggttgcagc tggaacagga ggtcgtgtgg     2100
ctcctggcga aactgggagt gcagagtcca ctgccaccag ttacaggaag caactgtcag     2160
tgcaacgtag aggtggtgag agctctgaca gtcatgttgc atcgccaatg gctcactgta     2220
cgcagggcag gcggtccacc ccgtaccgat caacagcgcc gcaccgtaag atgtctgcgc     2280
gacactgttc tgctgctgca tggactgagc caaaaggaca aactgttcat gatgcactgc     2340
gtggaagtgc tgcaccagtt cgaccaagtc atgcccggcg tatccatgct catacgtgga     2400
ctgcccgatg taactgactg cgaggaagct gccctggacg atctgtgtgc tgcggaaact     2460
```
gacgtcgaag atcctgaggt tgaatgcggc taa 2493

<210> SEQ ID NO 3
<211> LENGTH: 2898
<212> TYPE: PRT
<213> ORGANISM: Artificial Sequence
<220> FEATURE:
<223> OTHER INFORMATION: Synthetic human ATR including GST tag corresponding to SEQ ID NO: 1

<400> SEQUENCE: 3

```
Met Ala Ser Pro Ile Leu Gly Tyr Trp Lys Ile Lys Gly Leu Val Gln
1               5                   10                  15

Pro Thr Arg Leu Leu Leu Glu Tyr Leu Glu Glu Lys Tyr Glu Glu His
            20                  25                  30

Leu Tyr Glu Arg Asp Glu Gly Asp Lys Trp Arg Asn Lys Lys Phe Glu
        35                  40                  45

Leu Gly Leu Glu Phe Pro Asn Leu Pro Tyr Tyr Ile Asp Gly Asp Val
    50                  55                  60

Lys Leu Thr Gln Ser Met Ala Ile Ile Arg Tyr Ile Ala Asp Lys His
65                  70                  75                  80

Asn Met Leu Gly Gly Cys Pro Lys Glu Arg Ala Glu Ile Ser Met Leu
                85                  90                  95

Glu Gly Ala Val Leu Asp Ile Arg Tyr Gly Val Ser Arg Ile Ala Tyr
            100                 105                 110

Ser Lys Asp Phe Glu Thr Leu Lys Val Asp Phe Leu Ser Lys Leu Pro
        115                 120                 125

Glu Met Leu Lys Met Phe Glu Asp Arg Leu Cys His Lys Thr Tyr Leu
    130                 135                 140

Asn Gly Asp His Val Thr His Pro Asp Phe Met Leu Tyr Asp Ala Leu
145                 150                 155                 160

Asp Val Val Leu Tyr Met Asp Pro Met Cys Leu Asp Ala Phe Pro Lys
                165                 170                 175

Leu Val Cys Phe Lys Lys Arg Ile Glu Ala Ile Pro Gln Ile Asp Lys
            180                 185                 190

Tyr Leu Lys Ser Ser Lys Tyr Ile Ala Trp Pro Leu Gln Gly Trp Gln
        195                 200                 205

Ala Thr Phe Gly Gly Gly Asp His Pro Pro Lys Ser Asp Gln Ile Thr
    210                 215                 220

Ser Leu Tyr Lys Lys Ala Gly Ser Asp Tyr Asp Ile Pro Thr Thr Glu
225                 230                 235                 240

Asn Leu Tyr Phe Gln Gly Asp Tyr Lys Asp Asp Asp Lys Met Gly
                245                 250                 255

Glu His Gly Leu Glu Leu Ala Ser Met Ile Pro Ala Leu Arg Glu Leu
            260                 265                 270

Gly Ser Ala Thr Pro Glu Glu Tyr Asn Thr Val Val Gln Lys Pro Arg
        275                 280                 285

Gln Ile Leu Cys Gln Phe Ile Asp Arg Ile Leu Thr Asp Val Asn Val
    290                 295                 300

Val Ala Val Glu Leu Val Lys Lys Thr Asp Ser Gln Pro Thr Ser Val
305                 310                 315                 320

Met Leu Leu Asp Phe Ile Gln His Ile Met Lys Ser Ser Pro Leu Met
                325                 330                 335

Phe Val Asn Val Ser Gly Ser His Glu Ala Lys Gly Ser Cys Ile Glu
            340                 345                 350
```

```
Phe Ser Asn Trp Ile Ile Thr Arg Leu Leu Arg Ile Ala Ala Thr Pro
        355                 360                 365

Ser Cys His Leu Leu His Lys Lys Ile Cys Glu Val Ile Cys Ser Leu
    370                 375                 380

Leu Phe Leu Phe Lys Ser Lys Ser Pro Ala Ile Phe Gly Val Leu Thr
385                 390                 395                 400

Lys Glu Leu Leu Gln Leu Phe Glu Asp Leu Val Tyr Leu His Arg Arg
                405                 410                 415

Asn Val Met Gly His Ala Val Glu Trp Pro Val Val Met Ser Arg Phe
            420                 425                 430

Leu Ser Gln Leu Asp Glu His Met Gly Tyr Leu Gln Ser Ala Pro Leu
        435                 440                 445

Gln Leu Met Ser Met Gln Asn Leu Glu Phe Ile Glu Val Thr Leu Leu
    450                 455                 460

Met Val Leu Thr Arg Ile Ile Ala Ile Val Phe Phe Arg Arg Gln Glu
465                 470                 475                 480

Leu Leu Leu Trp Gln Ile Gly Cys Val Leu Leu Glu Tyr Gly Ser Pro
                485                 490                 495

Lys Ile Lys Ser Leu Ala Ile Ser Phe Leu Thr Glu Leu Phe Gln Leu
                500                 505                 510

Gly Gly Leu Pro Ala Gln Pro Ala Ser Thr Phe Phe Ser Ser Phe Leu
            515                 520                 525

Glu Leu Leu Lys His Leu Val Glu Met Asp Thr Asp Gln Leu Lys Leu
        530                 535                 540

Tyr Glu Glu Pro Leu Ser Lys Leu Ile Lys Thr Leu Phe Pro Phe Glu
545                 550                 555                 560

Ala Glu Ala Tyr Arg Asn Ile Glu Pro Val Tyr Leu Asn Met Leu Leu
                565                 570                 575

Glu Lys Leu Cys Val Met Phe Glu Asp Gly Val Leu Met Arg Leu Lys
            580                 585                 590

Ser Asp Leu Leu Lys Ala Ala Leu Cys His Leu Leu Gln Tyr Phe Leu
        595                 600                 605

Lys Phe Val Pro Ala Gly Tyr Glu Ser Ala Leu Gln Val Arg Lys Val
    610                 615                 620

Tyr Val Arg Asn Ile Cys Lys Ala Leu Leu Asp Val Leu Gly Ile Glu
625                 630                 635                 640

Val Asp Ala Glu Tyr Leu Leu Gly Pro Leu Tyr Ala Ala Leu Lys Met
                645                 650                 655

Glu Ser Met Glu Ile Ile Glu Glu Ile Gln Cys Gln Thr Gln Gln Glu
            660                 665                 670

Asn Leu Ser Ser Asn Ser Asp Gly Ile Ser Pro Lys Arg Arg Arg Leu
        675                 680                 685

Ser Ser Ser Leu Asn Pro Ser Lys Arg Ala Pro Lys Gln Thr Glu Glu
    690                 695                 700

Ile Lys His Val Asp Met Asn Gln Lys Ser Ile Leu Trp Ser Ala Leu
705                 710                 715                 720

Lys Gln Lys Ala Glu Ser Leu Gln Ile Ser Leu Glu Tyr Ser Gly Leu
                725                 730                 735

Lys Asn Pro Val Ile Glu Met Leu Glu Gly Ile Ala Val Val Leu Gln
            740                 745                 750

Leu Thr Ala Leu Cys Thr Val His Cys Ser His Gln Asn Met Asn Cys
        755                 760                 765
```

-continued

```
Arg Thr Phe Lys Asp Cys Gln His Lys Ser Lys Lys Lys Pro Ser Val
770                 775                 780
Val Ile Thr Trp Met Ser Leu Asp Phe Tyr Thr Lys Val Leu Lys Ser
785                 790                 795                 800
Cys Arg Ser Leu Leu Glu Ser Val Gln Lys Leu Asp Leu Glu Ala Thr
                805                 810                 815
Ile Asp Lys Val Val Lys Ile Tyr Asp Ala Leu Ile Tyr Met Gln Val
                820                 825                 830
Asn Ser Ser Phe Glu Asp His Ile Leu Glu Asp Leu Cys Gly Met Leu
                835                 840                 845
Ser Leu Pro Trp Ile Tyr Ser His Ser Asp Asp Gly Cys Leu Lys Leu
850                 855                 860
Thr Thr Phe Ala Ala Asn Leu Leu Thr Leu Ser Cys Arg Ile Ser Asp
865                 870                 875                 880
Ser Tyr Ser Pro Gln Ala Gln Ser Arg Cys Val Phe Leu Leu Thr Leu
                885                 890                 895
Phe Pro Arg Arg Ile Phe Leu Glu Trp Arg Thr Ala Val Tyr Asn Trp
                900                 905                 910
Ala Leu Gln Ser Ser His Glu Val Ile Arg Ala Ser Cys Val Ser Gly
                915                 920                 925
Phe Phe Ile Leu Leu Gln Gln Gln Asn Ser Cys Asn Arg Val Pro Lys
930                 935                 940
Ile Leu Ile Asp Lys Val Lys Asp Asp Ser Asp Ile Val Lys Lys Glu
945                 950                 955                 960
Phe Ala Ser Ile Leu Gly Gln Leu Val Cys Thr Leu His Gly Met Phe
                965                 970                 975
Tyr Leu Thr Ser Ser Leu Thr Glu Pro Phe Ser Glu His Gly His Val
                980                 985                 990
Asp Leu Phe Cys Arg Asn Leu Lys Ala Thr Ser Gln His Glu Cys Ser
                995                 1000                1005
Ser Ser Gln Leu Lys Ala Ser Val Cys Lys Pro Phe Leu Phe Leu Leu
    1010                1015                1020
Lys Lys Lys Ile Pro Ser Pro Val Lys Leu Ala Phe Ile Asp Asn Leu
1025                1030                1035                1040
His His Leu Cys Lys His Leu Asp Phe Arg Glu Asp Glu Thr Asp Val
                1045                1050                1055
Lys Ala Val Leu Gly Thr Leu Leu Asn Leu Met Glu Asp Pro Asp Lys
                1060                1065                1070
Asp Val Arg Val Ala Phe Ser Gly Asn Ile Lys His Ile Leu Glu Ser
                1075                1080                1085
Leu Asp Ser Glu Asp Gly Phe Ile Lys Glu Leu Phe Val Leu Arg Met
    1090                1095                1100
Lys Glu Ala Tyr Thr His Ala Gln Ile Ser Arg Asn Asn Glu Leu Lys
1105                1110                1115                1120
Asp Thr Leu Ile Leu Thr Thr Gly Asp Ile Gly Arg Ala Ala Lys Gly
                1125                1130                1135
Asp Leu Val Pro Phe Ala Leu Leu His Leu His Cys Leu Leu Ser
                1140                1145                1150
Lys Ser Ala Ser Val Ser Gly Ala Ala Tyr Thr Glu Ile Arg Ala Leu
                1155                1160                1165
Val Ala Ala Lys Ser Val Lys Leu Gln Ser Phe Phe Ser Gln Tyr Lys
1170                1175                1180
Lys Pro Ile Cys Gln Phe Leu Val Glu Ser Leu His Ser Ser Gln Met
```

```
                1185                1190                1195                1200
        Thr Ala Leu Pro Asn Thr Pro Cys Gln Asn Ala Asp Val Arg Lys Gln
                    1205                1210                1215

Asp Val Ala His Gln Arg Glu Met Ala Leu Asn Thr Leu Ser Glu Ile
            1220                1225                1230

Ala Asn Val Phe Asp Phe Pro Asp Leu Asn Arg Phe Leu Thr Arg Thr
        1235                1240                1245

Leu Gln Val Leu Leu Pro Asp Leu Ala Ala Lys Ala Ser Pro Ala Ala
            1250                1255                1260

Ser Ala Leu Ile Arg Thr Leu Gly Lys Gln Leu Asn Val Asn Arg Arg
        1265                1270                1275                1280

Glu Ile Leu Ile Asn Asn Phe Lys Tyr Ile Phe Ser His Leu Val Cys
                    1285                1290                1295

Ser Cys Ser Lys Asp Glu Leu Glu Arg Ala Leu His Tyr Leu Lys Asn
                1300                1305                1310

Glu Thr Glu Ile Glu Leu Gly Ser Leu Leu Arg Gln Asp Phe Gln Gly
                    1315                1320                1325

Leu His Asn Glu Leu Leu Leu Arg Ile Gly Glu His Tyr Gln Gln Val
                1330                1335                1340

Phe Asn Gly Leu Ser Ile Leu Ala Ser Phe Ala Ser Ser Asp Asp Pro
        1345                1350                1355                1360

Tyr Gln Gly Pro Arg Asp Ile Ile Ser Pro Glu Leu Met Ala Asp Tyr
                    1365                1370                1375

Leu Gln Pro Lys Leu Leu Gly Ile Leu Ala Phe Phe Asn Met Gln Leu
                1380                1385                1390

Leu Ser Ser Ser Val Gly Ile Glu Asp Lys Lys Met Ala Leu Asn Ser
                1395                1400                1405

Leu Met Ser Leu Met Lys Leu Met Gly Pro Lys His Val Ser Ser Val
            1410                1415                1420

Arg Val Lys Met Met Thr Thr Leu Arg Thr Gly Leu Arg Phe Lys Asp
        1425                1430                1435                1440

Asp Phe Pro Glu Leu Cys Cys Arg Ala Trp Asp Cys Phe Val Arg Cys
                    1445                1450                1455

Leu Asp His Ala Cys Leu Gly Ser Leu Leu Ser His Val Ile Val Ala
                1460                1465                1470

Leu Leu Pro Leu Ile His Ile Gln Pro Lys Glu Thr Ala Ala Ile Phe
                1475                1480                1485

His Tyr Leu Ile Ile Glu Asn Arg Asp Ala Val Gln Asp Phe Leu His
                1490                1495                1500

Glu Ile Tyr Phe Leu Pro Asp His Pro Glu Leu Lys Lys Ile Lys Ala
        1505                1510                1515                1520

Val Leu Gln Glu Tyr Arg Lys Glu Thr Ser Glu Ser Thr Asp Leu Gln
                    1525                1530                1535

Thr Thr Leu Gln Leu Ser Met Lys Ala Ile Gln His Glu Asn Val Asp
                1540                1545                1550

Val Arg Ile His Ala Leu Thr Ser Leu Lys Glu Thr Leu Tyr Lys Asn
            1555                1560                1565

Gln Glu Lys Leu Ile Lys Tyr Ala Thr Asp Ser Glu Thr Val Glu Pro
            1570                1575                1580

Ile Ile Ser Gln Leu Val Thr Val Leu Leu Lys Gly Cys Gln Asp Ala
        1585                1590                1595                1600

Asn Ser Gln Ala Arg Leu Leu Cys Gly Glu Cys Leu Gly Glu Leu Gly
                    1605                1610                1615
```

-continued

Ala Ile Asp Pro Gly Arg Leu Asp Phe Ser Thr Thr Glu Thr Gln Gly
            1620                1625                1630

Lys Asp Phe Thr Phe Val Thr Gly Val Glu Asp Ser Ser Phe Ala Tyr
        1635                1640                1645

Gly Leu Leu Met Glu Leu Thr Arg Ala Tyr Leu Ala Tyr Ala Asp Asn
    1650                1655                1660

Ser Arg Ala Gln Asp Ser Ala Ala Tyr Ala Ile Gln Glu Leu Leu Ser
1665                1670                1675                1680

Ile Tyr Asp Cys Arg Glu Met Glu Thr Asn Gly Pro Gly His Gln Leu
            1685                1690                1695

Trp Arg Arg Phe Pro Glu His Val Arg Glu Ile Leu Glu Pro His Leu
        1700                1705                1710

Asn Thr Arg Tyr Lys Ser Ser Gln Lys Ser Thr Asp Trp Ser Gly Val
    1715                1720                1725

Lys Lys Pro Ile Tyr Leu Ser Lys Leu Gly Ser Asn Phe Ala Glu Trp
1730                1735                1740

Ser Ala Ser Trp Ala Gly Tyr Leu Ile Thr Lys Val Arg His Asp Leu
1745                1750                1755                1760

Ala Ser Lys Ile Phe Thr Cys Cys Ser Ile Met Met Lys His Asp Phe
            1765                1770                1775

Lys Val Thr Ile Tyr Leu Leu Pro His Ile Leu Val Tyr Val Leu Leu
        1780                1785                1790

Gly Cys Asn Gln Glu Asp Gln Gln Glu Val Tyr Ala Glu Ile Met Ala
    1795                1800                1805

Val Leu Lys His Asp Asp Gln His Thr Ile Asn Thr Gln Asp Ile Ala
    1810                1815                1820

Ser Asp Leu Cys Gln Leu Ser Thr Gln Thr Val Phe Ser Met Leu Asp
1825                1830                1835                1840

His Leu Thr Gln Trp Ala Arg His Lys Phe Gln Ala Leu Lys Ala Glu
            1845                1850                1855

Lys Cys Pro His Ser Lys Ser Asn Arg Asn Lys Val Asp Ser Met Val
        1860                1865                1870

Ser Thr Val Asp Tyr Glu Asp Tyr Gln Ser Val Thr Arg Phe Leu Asp
    1875                1880                1885

Leu Ile Pro Gln Asp Thr Leu Ala Val Ala Ser Phe Arg Ser Lys Ala
    1890                1895                1900

Tyr Thr Arg Ala Val Met His Phe Glu Ser Phe Ile Thr Glu Lys Lys
1905                1910                1915                1920

Gln Asn Ile Gln Glu His Leu Gly Phe Leu Gln Lys Leu Tyr Ala Ala
            1925                1930                1935

Met His Glu Pro Asp Gly Val Ala Gly Val Ser Ala Ile Arg Lys Ala
        1940                1945                1950

Glu Pro Ser Leu Lys Glu Gln Ile Leu Glu His Glu Ser Leu Gly Leu
    1955                1960                1965

Leu Arg Asp Ala Thr Ala Cys Tyr Asp Arg Ala Ile Gln Leu Glu Pro
    1970                1975                1980

Asp Gln Ile Ile His Tyr His Gly Val Val Lys Ser Met Leu Gly Leu
1985                1990                1995                2000

Gly Gln Leu Ser Thr Val Ile Thr Gln Val Asn Gly Val His Ala Asn
            2005                2010                2015

Arg Ser Glu Trp Thr Asp Glu Leu Asn Thr Tyr Arg Val Glu Ala Ala
        2020                2025                2030

```
Trp Lys Leu Ser Gln Trp Asp Leu Val Glu Asn Tyr Leu Ala Ala Asp
        2035                2040                2045

Gly Lys Ser Thr Thr Trp Ser Val Arg Leu Gly Gln Leu Leu Leu Ser
        2050                2055                2060

Ala Lys Lys Arg Asp Ile Thr Ala Phe Tyr Asp Ser Leu Lys Leu Val
2065                2070                2075                2080

Arg Ala Glu Gln Ile Val Pro Leu Ser Ala Ala Ser Phe Glu Arg Gly
                2085                2090                2095

Ser Tyr Gln Arg Gly Tyr Glu Tyr Ile Val Arg Leu His Met Leu Cys
        2100                2105                2110

Glu Leu Glu His Ser Ile Lys Pro Leu Phe Gln His Ser Pro Gly Asp
        2115                2120                2125

Ser Ser Gln Glu Asp Ser Leu Asn Trp Val Ala Arg Leu Glu Met Thr
        2130                2135                2140

Gln Asn Ser Tyr Arg Ala Lys Glu Pro Ile Leu Ala Leu Arg Arg Ala
2145                2150                2155                2160

Leu Leu Ser Leu Asn Lys Arg Pro Asp Tyr Asn Glu Met Val Gly Glu
                2165                2170                2175

Cys Trp Leu Gln Ser Ala Arg Val Ala Arg Lys Ala Gly His His Gln
        2180                2185                2190

Thr Ala Tyr Asn Ala Leu Leu Asn Ala Gly Glu Ser Arg Leu Ala Glu
        2195                2200                2205

Leu Tyr Val Glu Arg Ala Lys Trp Leu Trp Ser Lys Gly Asp Val His
        2210                2215                2220

Gln Ala Leu Ile Val Leu Gln Lys Gly Val Glu Leu Cys Phe Pro Glu
2225                2230                2235                2240

Asn Glu Thr Pro Pro Glu Gly Lys Asn Met Leu Ile His Gly Arg Ala
                2245                2250                2255

Met Leu Leu Val Gly Arg Phe Met Glu Glu Thr Ala Asn Phe Glu Ser
        2260                2265                2270

Asn Ala Ile Met Lys Lys Tyr Lys Asp Val Thr Ala Cys Leu Pro Glu
        2275                2280                2285

Trp Glu Asp Gly His Phe Tyr Leu Ala Lys Tyr Tyr Asp Lys Leu Met
        2290                2295                2300

Pro Met Val Thr Asp Asn Lys Met Glu Lys Gln Gly Asp Leu Ile Arg
2305                2310                2315                2320

Tyr Ile Val Leu His Phe Gly Arg Ser Leu Gln Tyr Gly Asn Gln Phe
                2325                2330                2335

Ile Tyr Gln Ser Met Pro Arg Met Leu Thr Leu Trp Leu Asp Tyr Gly
        2340                2345                2350

Thr Lys Ala Tyr Glu Trp Glu Lys Ala Gly Arg Ser Asp Arg Val Gln
        2355                2360                2365

Met Arg Asn Asp Leu Gly Lys Ile Asn Lys Val Ile Thr Glu His Thr
        2370                2375                2380

Asn Tyr Leu Ala Pro Tyr Gln Phe Leu Thr Ala Phe Ser Gln Leu Ile
2385                2390                2395                2400

Ser Arg Ile Cys His Ser His Asp Glu Val Phe Val Val Leu Met Glu
                2405                2410                2415

Ile Ile Ala Lys Val Phe Leu Ala Tyr Pro Gln Gln Ala Met Trp Met
        2420                2425                2430

Met Thr Ala Val Ser Lys Ser Ser Tyr Pro Met Arg Val Asn Arg Cys
        2435                2440                2445

Lys Glu Ile Leu Asn Lys Ala Ile His Met Lys Lys Ser Leu Glu Lys
```

-continued

```
            2450                2455                2460

Phe Val Gly Asp Ala Thr Arg Leu Thr Asp Lys Leu Leu Glu Leu Cys
2465                2470                2475                2480

Asn Lys Pro Val Asp Gly Ser Ser Thr Leu Ser Met Ser Thr His
                2485                2490                2495

Phe Lys Met Leu Lys Lys Leu Val Glu Ala Thr Phe Ser Glu Ile
            2500                2505                2510

Leu Ile Pro Leu Gln Ser Val Met Ile Pro Thr Leu Pro Ser Ile Leu
            2515                2520                2525

Gly Thr His Ala Asn His Ala Ser His Glu Pro Phe Pro Gly His Trp
            2530                2535                2540

Ala Tyr Ile Ala Gly Phe Asp Asp Met Val Glu Ile Leu Ala Ser Leu
2545                2550                2555                2560

Gln Lys Pro Lys Lys Ile Ser Leu Lys Gly Ser Asp Gly Lys Phe Tyr
                2565                2570                2575

Ile Met Met Cys Lys Pro Lys Asp Asp Leu Arg Lys Asp Cys Arg Leu
            2580                2585                2590

Met Glu Phe Asn Ser Leu Ile Asn Lys Cys Leu Arg Lys Asp Ala Glu
            2595                2600                2605

Ser Arg Arg Arg Glu Leu His Ile Arg Thr Tyr Ala Val Ile Pro Leu
2610                2615                2620

Asn Asp Glu Cys Gly Ile Ile Glu Trp Val Asn Asn Thr Ala Gly Leu
2625                2630                2635                2640

Arg Pro Ile Leu Thr Lys Leu Tyr Lys Glu Lys Gly Val Tyr Met Thr
                2645                2650                2655

Gly Lys Glu Leu Arg Gln Cys Met Leu Pro Lys Ser Ala Ala Leu Ser
            2660                2665                2670

Glu Lys Leu Lys Val Phe Arg Glu Phe Leu Leu Pro Arg His Pro Pro
            2675                2680                2685

Ile Phe His Glu Trp Phe Leu Arg Thr Phe Pro Asp Pro Thr Ser Trp
            2690                2695                2700

Tyr Ser Ser Arg Ser Ala Tyr Cys Arg Ser Thr Ala Val Met Ser Met
2705                2710                2715                2720

Val Gly Tyr Ile Leu Gly Leu Gly Asp Arg His Gly Glu Asn Ile Leu
                2725                2730                2735

Phe Asp Ser Leu Thr Gly Glu Cys Val His Val Asp Phe Asn Cys Leu
            2740                2745                2750

Phe Asn Lys Gly Glu Thr Phe Glu Val Pro Glu Ile Val Pro Phe Arg
            2755                2760                2765

Leu Thr His Asn Met Val Asn Gly Met Gly Pro Met Gly Thr Glu Gly
            2770                2775                2780

Leu Phe Arg Arg Ala Cys Glu Val Thr Met Arg Leu Met Arg Asp Gln
2785                2790                2795                2800

Arg Glu Pro Leu Met Ser Val Leu Lys Thr Phe Leu His Asp Pro Leu
                2805                2810                2815

Val Glu Trp Ser Lys Pro Val Lys Gly His Ser Lys Ala Pro Leu Asn
            2820                2825                2830

Glu Thr Gly Glu Val Val Asn Glu Lys Ala Lys Thr His Val Leu Asp
            2835                2840                2845

Ile Glu Gln Arg Leu Gln Gly Val Ile Lys Thr Arg Asn Arg Val Thr
            2850                2855                2860

Gly Leu Pro Leu Ser Ile Glu Gly His Val His Tyr Leu Ile Gln Glu
2865                2870                2875                2880
```

```
Ala Thr Asp Glu Asn Leu Leu Cys Gln Met Tyr Leu Gly Trp Thr Pro
                2885                2890                2895

Tyr Met

<210> SEQ ID NO 4
<211> LENGTH: 830
<212> TYPE: PRT
<213> ORGANISM: Artificial Sequence
<220> FEATURE:
<223> OTHER INFORMATION: Synthetic human ATRIP including STREP tag
      corresponding to SEQ ID NO: 2

<400> SEQUENCE: 4

Met Ala Ser Trp Ser His Pro Gln Phe Glu Lys Ser Ala Gly Leu Glu
1               5                   10                  15

Thr Ser Leu Tyr Lys Lys Ala Gly Ser Asp Tyr Asp Ile Pro Thr Thr
            20                  25                  30

Glu Asn Leu Tyr Phe Gln Gly Met Ala Gly Thr Ser Ala Pro Gly Ser
        35                  40                  45

Lys Arg Arg Ser Glu Pro Pro Ala Pro Arg Pro Gly Pro Pro Pro Gly
50                  55                  60

Thr Gly His Pro Pro Ser Lys Arg Ala Arg Gly Phe Ser Ala Ala Ala
65                  70                  75                  80

Ala Pro Asp Pro Asp Asp Pro Phe Gly Ala His Gly Asp Phe Thr Ala
                85                  90                  95

Asp Asp Leu Glu Glu Leu Asp Thr Leu Ala Ser Gln Ala Leu Ser Gln
            100                 105                 110

Cys Pro Ala Ala Ala Arg Asp Val Ser Ser Asp His Lys Val His Arg
        115                 120                 125

Leu Leu Asp Gly Met Ser Lys Asn Pro Ser Gly Lys Asn Arg Glu Thr
130                 135                 140

Val Pro Ile Lys Asp Asn Phe Glu Leu Glu Val Leu Gln Ala Gln Tyr
145                 150                 155                 160

Lys Glu Leu Lys Glu Lys Met Lys Val Met Glu Glu Val Leu Ile
                165                 170                 175

Lys Asn Gly Glu Ile Lys Ile Leu Arg Asp Ser Leu His Gln Thr Glu
            180                 185                 190

Ser Val Leu Glu Glu Gln Arg Arg Ser His Phe Leu Leu Glu Gln Glu
        195                 200                 205

Lys Thr Gln Ala Leu Ser Asp Lys Glu Lys Glu Phe Ser Lys Lys Leu
210                 215                 220

Gln Ser Leu Gln Ser Glu Leu Gln Phe Lys Asp Ala Glu Met Asn Glu
225                 230                 235                 240

Leu Arg Thr Lys Leu Gln Thr Ser Glu Arg Ala Asn Lys Leu Ala Ala
                245                 250                 255

Pro Ser Val Ser His Val Ser Pro Arg Lys Asn Pro Ser Val Val Ile
            260                 265                 270

Lys Pro Glu Ala Cys Ser Pro Gln Phe Gly Lys Thr Ser Phe Pro Thr
        275                 280                 285

Lys Glu Ser Phe Ser Ala Asn Met Ser Leu Pro His Pro Cys Gln Thr
290                 295                 300

Glu Ser Gly Tyr Lys Pro Leu Val Gly Arg Glu Asp Ser Lys Pro His
305                 310                 315                 320

Ser Leu Arg Gly Asp Ser Ile Lys Gln Glu Glu Ala Gln Lys Ser Phe
                325                 330                 335
```

```
Val Asp Ser Trp Arg Gln Arg Ser Asn Thr Gln Gly Ser Ile Leu Ile
            340                 345                 350

Asn Leu Leu Lys Gln Pro Leu Ile Pro Gly Ser Ser Leu Ser Leu
        355                 360                 365

Cys His Leu Leu Ser Ser Ser Glu Ser Pro Ala Gly Thr Pro Leu
    370                 375                 380

Gln Pro Pro Gly Phe Gly Ser Thr Leu Ala Gly Met Ser Gly Leu Arg
385                 390                 395                 400

Thr Thr Gly Ser Tyr Asp Gly Ser Phe Ser Leu Ser Ala Leu Arg Glu
                405                 410                 415

Ala Gln Asn Leu Ala Phe Thr Gly Leu Asn Leu Val Ala Arg Asn Glu
            420                 425                 430

Cys Ser Arg Asp Gly Asp Pro Ala Glu Gly Arg Arg Ala Phe Pro
    435                 440                 445

Leu Cys Gln Leu Pro Gly Ala Val His Phe Leu Pro Leu Val Gln Phe
450                 455                 460

Phe Ile Gly Leu His Cys Gln Ala Leu Gln Asp Leu Ala Ala Ala Lys
465                 470                 475                 480

Arg Ser Gly Ala Pro Gly Asp Ser Pro Thr His Ser Ser Cys Val Ser
                485                 490                 495

Ser Gly Val Glu Thr Asn Pro Glu Asp Ser Val Cys Ile Leu Glu Gly
            500                 505                 510

Phe Ser Val Thr Ala Leu Ser Ile Leu Gln His Leu Val Cys His Ser
        515                 520                 525

Gly Ala Val Val Ser Leu Leu Leu Ser Gly Val Gly Ala Asp Ser Ala
    530                 535                 540

Ala Gly Glu Gly Asn Arg Ser Leu Val His Arg Leu Ser Asp Gly Asp
545                 550                 555                 560

Met Thr Ser Ala Leu Arg Gly Val Ala Asp Asp Gln Gly Gln His Pro
                565                 570                 575

Leu Leu Lys Met Leu Leu His Leu Leu Ala Phe Ser Ser Ala Ala Thr
            580                 585                 590

Gly His Leu Gln Ala Ser Val Leu Thr Gln Cys Leu Lys Val Leu Val
        595                 600                 605

Lys Leu Ala Glu Asn Thr Ser Cys Asp Phe Leu Pro Arg Phe Gln Cys
    610                 615                 620

Val Phe Gln Val Leu Pro Lys Cys Leu Ser Pro Glu Thr Pro Leu Pro
625                 630                 635                 640

Ser Val Leu Leu Ala Val Glu Leu Leu Ser Leu Leu Ala Asp His Asp
                645                 650                 655

Gln Leu Ala Pro Gln Leu Cys Ser His Ser Glu Gly Cys Leu Leu Leu
            660                 665                 670

Leu Leu Tyr Met Tyr Ile Thr Ser Arg Pro Asp Arg Val Ala Leu Glu
        675                 680                 685

Thr Gln Trp Leu Gln Leu Glu Gln Glu Val Val Trp Leu Leu Ala Lys
    690                 695                 700

Leu Gly Val Gln Ser Pro Leu Pro Val Thr Gly Ser Asn Cys Gln
705                 710                 715                 720

Cys Asn Val Glu Val Val Arg Ala Leu Thr Val Met Leu His Arg Gln
                725                 730                 735

Trp Leu Thr Val Arg Arg Ala Gly Gly Pro Pro Arg Thr Asp Gln Gln
            740                 745                 750
```

```
Arg Arg Thr Val Arg Cys Leu Arg Asp Thr Val Leu Leu Leu His Gly
    755             760             765

Leu Ser Gln Lys Asp Lys Leu Phe Met Met His Cys Val Glu Val Leu
    770             775             780

His Gln Phe Asp Gln Val Met Pro Gly Val Ser Met Leu Ile Arg Gly
785             790             795             800

Leu Pro Asp Val Thr Asp Cys Glu Glu Ala Ala Leu Asp Asp Leu Cys
                805             810             815

Ala Ala Glu Thr Asp Val Glu Asp Pro Glu Val Glu Cys Gly
            820             825             830
```

2-(MORPHOLIN-4-YL)-1,7-NAPHTHYRIDINES

CROSS-REFERENCE TO RELATED APPLICATIONS

This application is a continuation of application Ser. No. 15/501,079, filed Feb. 1, 2017, now allowed; which is the U.S. national stage of Int'l Application No. PCT/EP2015/067804, filed Aug. 3, 2015; which claims priority benefit of Application Nos. EP 14179692.0, filed Aug. 4, 2014, and EP 15159342.3, filed Mar. 17, 2015; the entire contents of which are hereby incorporated by reference.

Concurrently with this specification, an ASCII file is being submitted electronically via EFS-Web and forms part of the official record. See Legal Framework for Electronic Filing System—Web (EFS-Web), 74 FR 55200, 55202 (Oct. 27, 2009). The entire content of the ASCII text file entitled "Sequence_Listing.txt" (created on May 8, 2018 and having a size of 45.1 kb) is incorporated herein by reference.

FIELD OF THE INVENTION

The invention relates to substituted 2-(morpholin-4-yl)-1,7-naphthyridine compounds, a process for their production and the use thereof.

BACKGROUND OF THE INVENTION

The integrity of the genome of eukaryotic cells is secured by complex signaling pathways, referred to as the DNA damage response (DDR), and multiple DNA repair mechanisms. Upon recognizing DNA damage activation of the DDR pathways results in cell cycle arrest, suppression of general translation, induction of DNA repair, and, finally, in cell survival or cell death. Proteins that directly recognize aberrant DNA structures, such as the MRE11-Rad50-Nbs1 complex recognizing DNA double strand breaks by binding to double-stranded DNA ends, or RPA (replication protein A) binding to single stranded DNA, recruit and activate the most upstream kinases of the DDR pathway, ATM (ataxia-telangiectasia mutated), ATR (ATM- and Rad3-related, UniProtKB/Swiss-Prot Q13535), and DNA-PKcs (DNA-dependent protein kinase). Whereas ATM is primarily activated by DNA double strand breaks, and DNA-PKcs is mainly involved in non-homologous end joining process of DNA repair, ATR responds to a broad spectrum of DNA damage, including double-strand breaks and lesions derived from interference with DNA replication. Major components of downstream signaling of ATM include Chk2 and p53, whereas ATR signaling involves Chk1 and cdc25. Knockout of the ATR gene in mice is embryonically lethal and ATR knockout cells develop chromosome breaks and undergo apoptosis [E. J. Brown, D. Baltimore: ATR disruption leads to chromosomal fragmentation and early embryonic lethality. Genes Dev. 14, 397-402, 2000]. In contrast, ATM is not essential for cell survival although ATM knockout cells are hypersensitive to ionizing radiation and agents which cause DNA double-strand breaks.

ATR, which forms a complex with ATRIP (ATR-interacting protein, UniProtKB/Swiss-Prot Q8WXE1) is mainly activated by long stretches of single-stranded DNA which are generated by the continuing DNA unwinding activity of helicases upon stalled replication. This replication stress with stalled replication forks may be induced by ultraviolet light, certain chemotherapeutic drugs, hydroxyurea, or aberrant oncogenic signaling resulting in increased replication initiation or origin firing. Activation of ATR results in inhibition of the cell cycle in S or G2 phase via the Chk1-cdc25 pathway and in suppression of late origin firing. The cell gains time to resolve the replication stress and, eventually, to restart replication after the source of stress has been removed. As the ATR pathway ensures cell survival after replication stress it potentially contributes to resistance to chemotherapy. Thus inhibition of ATR kinase activity could be useful for cancer treatment.

In oncogene-driven tumor cells (e.g. Ras mutation/up-regulation, Myc upregulation, CyclinE overexpression) increased replication stress has been observed as compared to healthy normal cells. ATR suppression in Ras oncogene driven cells was reported to result in substantial tumor cell killing [O. Gilad, B Y Nabet, et al.: Combining ATR suppression with oncogenic Ras synergistically increases genomic instability, causing synthetic lethality or tumorigenesis in a dosage-dependent manner. Cancer Res. 70, 9693-9702, 2010].

Although ATM and ATR are principally activated by different types of DNA damage their signaling includes some cross-talk thus that they can, at least partially, substitute for each others function. This finding suggests some tumor-cell selectivity of pharmaceutical inhibition of ATR. A healthy normal cell, which has ATM and ATR pathways in parallel, arrests in G1 phase of the cell cycle upon induced DNA damage even in presence of an ATR inhibitor. In contrast, a tumor cell which most often deficient in ATM and/or p53 signaling relies on the ATR pathway and undergoes cell death in presence of an ATR inhibitor. This suggests that ATR inhibitors may be used for the treatment of tumors with deficient ATM signaling and/or p53 function.

Details of DDR signaling and the functional role of ATM and ATR were recently reviewed in: E. Fokas, R. Prevo et al.: Targeting ATR in DNA damage response and cancer therapeutics. Cancer Treatment Rev 40, 109-117, 2014. J. M. Wagner & S. H. Kaufmann: Prospects for the use of ATR inhibitors to treat cancer. Pharmaceuticals 3, 1311-1334, 2010. D. Woods & J. J. Tuchi: Chemotherapy induced DNA damage response. Cancer Biol. Thera. 14, 379-389, 2013. A. Marechal & L. Zou: DNA damage sensing by the ATM and ATR kinases. Cold Spring Harb. Perspect. Biol. 5, a012716, 2013. M. K. Zeman & K. A. Cimprich: Causes and consequences of replication stress. Nat. Cell Biol. 16, 2-9, 2014. S. Llona-Minguez, A. Haglund et al.: Chemical strategies for development of ATR inhibitors. Exp. Rev. Mol. Med. 16, e10, 2014.

Some inhibitors of ATR kinase are known (J. Med. Chem. 2013, 56, 2125-2138; Exp. Rev. Mol. Med. 16, e10, 2014; WO2010054398A1; WO2010071837A1; WO2010073034A1; WO2011143399A1; WO2011143419A1; WO2011143422A1; WO2011143423A2; WO2011143425A2; WO2011143426A1; WO2011154737A1; WO2011163527A1; WO2012138938A1; WO2012178123A1; WO2012178124A1; WO2012178125A1; WO2013049719A1; WO2013049720A1; WO2013049722A1; WO2013049859A1; WO2013071085A1; WO2013071088A1; WO2013071090A1; WO2013071093A1; WO2013071094A1; WO2013152298A1; WO2014062604A1; WO2014089379A1; WO2014143240).

WO 0058307 describe aryl fused 2,4-disubstituted pyridines as NK3 receptor ligands. However, no 1,7-naphthyridine compounds are exemplified.

WO 2006039718 describe aryl nitrogen-containing bicyclic compounds for the prophylaxis and treatment of protein kinase mediated diseases. However, no 1,7-naphthyridine compounds are exemplified.

WO 2008017461 and the Journal of Medicinal Chemistry 2011, 54(22), 7899-7910 describe 1,7-naphthyridine derivatives as p38 MAP kinase inhibitors. The 8-position of the 1,7-naphthyridine derivatives is substituted with a phenyl ring. No 1,7-naphthyridine compounds are exemplified, which are substituted with a heteroaryl group in the 8-position of the 1,7-naphthyridine.

There is a need for the development of ATR inhibitors for treating diseases, in particular hyperproliferative diseases. The problem to be solved by the present invention is to provide further compounds which inhibit ATR. It was found, surprisingly, that 2-(Morpholin-4-yl)-1,7-naphthyridines of general formula (I) or (Ib) inhibit ATR.

In accordance with a first aspect, the present invention covers compounds of general formula (I)

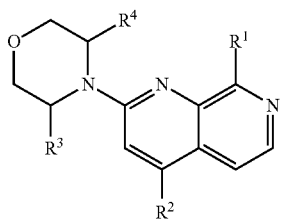

(I)

in which:
$R^1$ represents a group selected from:

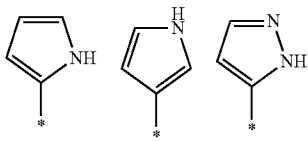

wherein * indicates the point of attachment of said group with the rest of the molecule;
$R^2$ represents hydrogen, halogen, —$NR^7R^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, 4- to 10-membered heterocycloalkenyl, phenyl, heteroaryl, —(CO)$OR^7$, —(CO)$NR^7R^8$, —($SO_2$)$R^9$, —(SO)$R^9$, —$SR^9$, —($SO_2$)$NR^7R^8$, —$NR^7$($SO_2$)$R^9$, —((SO)=$NR^{11}$)$R^{10}$, —N=(SO)$R^9R^{10}$, —$SiR^{10}R^{11}R^{12}$, —(PO)(O$R^7$)$_2$, —(PO)(O$R^7$)$R^{10}$ or —(PO)($R^{10}$)$_2$,
  wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, —$NR^7R^8$, $C_1$-$C_6$-alkyl optionally substituted one or more times with hydroxyl or phenyl, $C_1$-$C_6$-haloalkyl, $C_1$-$C_6$-alkoxy, $C_3$-$C_6$-cycloalkyl, 3- to 6-membered heterocycloalkyl, phenyl, —(CO)$OR^7$, —(CO)$NR^7R^8$, —$NR^7$(CO)$R^{10}$, —$NR^8$(CO)$OR^7$, —NR(CO)$NR^7R^8$, —($SO_2$)$R^9$, —(SO)$R^9$, —$SR^9$, —($SO_2$)$NR^7R^8$, —$NR^7$($SO_2$)$R^9$, —((SO)=$NR^{11}$)$R^{10}$, —N=(SO)$R^9R^{10}$, —(PO)(O$R^7$)$_2$, —(PO)(O$R^7$)$R^{10}$, —(PO)($R^{10}$)$_2$ or with a heteroaryl group which is optionally substituted, one or more times, with $C_1$-$C_4$-alkyl;
  wherein each 4- to 10-membered heterocycloalkenyl is optionally substituted, one or more times, independently from each other, with $C_1$-$C_4$-alkyl;
$R^3$, $R^4$ represent, independently from each other, hydrogen or methyl;
$R^7$, $R^8$ represent, independently from each other, hydrogen, $C_1$-$C_6$-alkyl, $C_3$-$C_6$-cycloalkyl or phenyl, which phenyl is optionally substituted, one or more times, with halogen; or
$R^7$ and $R^8$ together represent a 4-, 5-, 6- or 7-membered cyclic amine group, which is optionally substituted, one or more times, independently from each other, with a substituent selected from $C_1$-$C_6$-alkyl, $C_1$-$C_6$-haloalkyl, said 4-, 5-, 6- or 7-membered cyclic amine group optionally containing one further heteroatom selected from the group consisting of O, N and S;
$R^9$ represents $C_1$-$C_4$-alkyl or phenyl, wherein each $C_1$-$C_4$-alkyl or phenyl is optionally substituted, one or more times, independently from each other, with $R^3$;
$R^{10}$ represents $C_1$-$C_4$-alkyl; or
$R^9$ and $R^{10}$ together, in case of —N=(SO)$R^9R^{10}$ group, represent a 5- to 8-membered heterocycloalkyl group;
$R^{11}$ represents hydrogen, $C_1$-$C_4$-alkyl, —(CO)$OR^7$, —(CO)$NR^7R^8$ or CN;
$R^{12}$ represents hydrogen or $C_1$-$C_4$-alkyl;
$R^1$ represents halogen, OH, —$NR^7R^8$, CN, $NO_2$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_6$-cycloalkyl, —(CO)$OR^7$ or —(CO)$NR^7R^8$;

or a stereoisomer, a tautomer, an N-oxide, a hydrate, a solvate, or a salt thereof, or a mixture of same.

The terms as mentioned in the present text have the following meanings: The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_6$-haloalkyl" is to be understood as meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$ or —$CH_2CF_3$.

The term "$C_1$-$C_4$-hydroxyalkyl" is to be understood as meaning a linear or branched, saturated, monovalent hydrocarbon group in which the term "$C_1$-$C_4$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methylpropyl, 1-hydroxy-2-methyl-propyl group.

The term "$C_1$-$C_6$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof. Particularly, said "$C_1$-$C_6$-alkoxy" can contain 1, 2, 3, 4 or 5 carbon atoms, (a "$C_1$-$C_5$-alkoxy"), preferably 1, 2, 3 or 4 carbon atoms ("$C_1$-$C_4$-alkoxy").

The term "$C_1$-$C_6$-haloalkoxy" is to be understood as meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_2$-$C_6$-alkenyl" is to be understood as meaning a linear or branched, monovalent hydrocarbon group, which contains one or more double bonds, and which has 2, 3, 4, 5 or 6 carbon atoms or 2, 3 or 4 carbon atoms ("$C_2$-$C_4$-alkenyl"), particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methyihexadienyl group. Particularly, said group is vinyl or allyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl"), preferably cyclopropyl.

The term "3- to 10-membered heterocycloalkyl" is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl or $C_1$-$C_6$-haloalkyl group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused. Preferably, the 3- to 6-membered heterocycloalkyl is a tetrahydrofuranyl, tetrahydropyranyl or piperazinyl.

Said heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "3- to 10-membered heterocycloalkoxy" of formula —O-heterocycloalkyl, in which the term "heterocycloalkyl" is defined supra, is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, a $C_1$-$C_6$-alkyl or $C_1$-$C_6$-haloalkyl group and which is connected to the rest of the molecule via an oxygen atom, e.g. a pyrrolidineoxy, tetrahydrofuraneoxy or tetrahydropyranoxy.

The term "4- to 10-membered heterocycloalkenyl" is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a C$_1$-C$_6$-alkyl or C$_1$-C$_6$-haloalkyl group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3,6-dihydro-2H-pyran-4-yl, 3,6-dihydro-2H-thiopyran-4-yl, 1,2,3,6-tetrahydropyridin-4-yl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, 4H-[1,4]thiazinyl or 5,6-dihydroimidazo[1,2-a]pyrazin-7(8H)-yl group or it may be benzo fused.

The term "heteroaryl" is understood as meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), 5 or 6 or 9 or 10 ring atoms (a "5- to 10-membered heteroaryl" group) or particularly 5 or 6 ring atoms ("5- to 6-membered heteroaryl" group), and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, oxepinyl or 1H-pyrrolo[2,3-b]pyridin-4-yl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "C$_1$-C$_6$", as used throughout this text, e.g. in the context of the definition of "C$_1$-C$_6$-alkyl", "C$_1$-C$_6$-haloalkyl", "C$_1$-C$_6$-alkoxy", or "C$_1$-C$_6$-haloalkoxy" is to be understood as meaning an alkyl group having a finite number of carbon atoms of 1 to 6, i.e. 1, 2, 3, 4, 5, or 6 carbon atoms. It is to be understood further that said term "C$_1$-C$_6$" is to be interpreted as any sub-range comprised therein, e.g. C$_1$-C$_6$, C$_2$-C$_5$, C$_3$-C$_4$, C$_1$-C$_2$, C$_1$-C$_3$, C$_1$-C$_4$, C$_1$-C$_5$; particularly C$_1$-C$_2$, C$_1$-C$_3$, C$_1$-C$_4$, C$_1$-C$_5$, C$_1$-C$_6$; more particularly C$_1$-C$_4$; in the case of "C$_1$-C$_6$-haloalkyl" or "C$_1$-C$_6$-haloalkoxy" even more particularly C$_1$-C$_2$.

Similarly, as used herein, the term "C$_2$-C$_6$", as used throughout this text, e.g. in the context of the definitions of "C$_2$-C$_6$-alkenyl" and "C$_2$-C$_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "C$_2$-C$_6$" is to be interpreted as any sub-range comprised therein, e.g. C$_1$-C$_6$, C$_3$-C$_5$, C$_3$-C$_4$, C$_2$-C$_3$, C$_2$-C$_4$. C$_2$-C$_5$; particularly C$_2$-C$_3$.

Further, as used herein, the term "C$_3$-C$_6$", as used throughout this text, e.g. in the context of the definition of "C$_3$-C$_6$-cycloalkyl", is to be understood as meaning a cycloalkyl group having a finite number of carbon atoms of 3 to 6, i.e. 3, 4, 5 or 6 carbon atoms. It is to be understood further that said term "C$_3$-C$_6$" is to be interpreted as any sub-range comprised therein, e.g. C$_3$-C$_6$, C$_4$-C$_5$, C$_3$-C$_5$, C$_3$-C$_4$, C$_4$-C$_6$, C$_5$-C$_6$; particularly C$_3$-C$_6$.

Further, as used herein, the term "C$_2$-C$_4$", as used throughout this text, e.g. in the context of "C$_2$-C$_4$-alkenyl" is to be understood as meaning a alkenyl group having a finite number of carbon atoms of 2 to 4, i.e. 2, 3 or 4 carbon atoms. It is to be understood further that said term "C$_2$-C$_4$" is to be interpreted as any sub-range comprised therein, e.g. C$_2$-C$_4$, C$_2$-C$_3$, C$_3$-C$_4$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

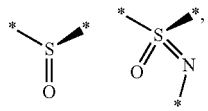

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

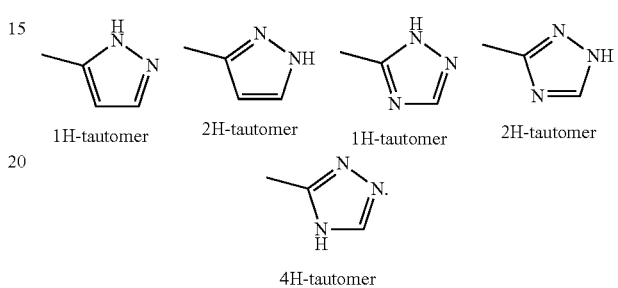

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

When radicals in the compounds of the present invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease (the term "disease" includes but is not limited a condition, a disorder, an injury or a health problem), or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease or a development or advancement of such states and/or the symptoms of such states.

The treatment or prevention of a disease may be partial or complete.

In another embodiment, the present invention covers compounds of general formula (I)

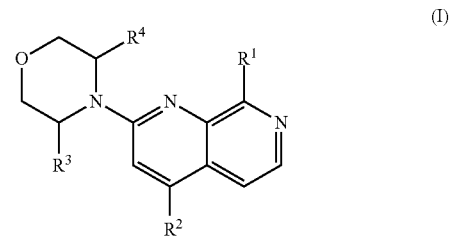

(I)

in which:
$R^1$ represents a group selected from:

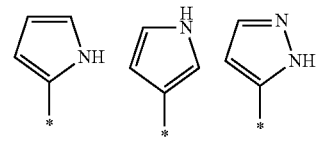

wherein * indicates the point of attachment of said group with the rest of the molecule;

$R^2$ represents hydrogen, halogen, —$NR^7R^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, 4- to 10-membered heterocycloalkenyl, phenyl, heteroaryl, —(CO)$OR^7$, —(CO)$NR^7R^8$, —(SO$_2$)$R^9$, —(SO)$R^9$, —$SR^9$, —(SO$_2$)$NR^7R^8$, —$NR^7$(SO$_2$)$R^9$, —((SO)=$NR^{11}$)$R^{10}$, —N=(SO)$R^9R^{10}$, —$SiR^{10}R^{11}R^{12}$, —(PO)($OR^7$)$_2$, —(PO)($OR^7$)$R^{10}$ or —(PO)($R^{10}$)$_2$, wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, —$NR^7R^8$, $C_1$-$C_6$-alkyl, 3- to 6-membered heterocycloalkyl, 4- to 6-membered heterocycloalkenyl, phenyl, —(CO)$OR^7$, —(CO)$NR^7R^8$, —$NR^7$(CO)$R^{10}$, —$NR^8$(CO)$OR^7$, —$NR^8$(CO)$NR^7R^8$, —(SO$_2$)$R^9$, —(SO)$R^9$, —$SR^9$, —(SO$_2$)$NR^7R^8$, —$NR^7$(SO$_2$)$R^9$, —((SO)=$NR^{11}$)$R^{10}$, —N=(SO)$R^9R^{10}$, —(PO)($OR^7$)$_2$, —(PO)($OR^7$)$R^{10}$, —(PO)($R^{10}$)$_2$ or with a heteroaryl group which is optionally substituted, one or more times, with $C_1$-$C_4$-alkyl;

wherein each 4- to 10-membered heterocycloalkenyl is optionally substituted, one or more times, independently from each other, with $C_1$-$C_4$-alkyl;

$R^3$, $R^4$ represent, independently from each other, hydrogen or methyl;

$R^7$, $R^8$ represent, independently from each other, hydrogen or $C_1$-$C_6$-alkyl; or $R^7$ and $R^8$ together represent a 4-, 5-, 6- or 7-membered cyclic amine group, which is optionally substituted, one or more times, independently from each other, with a substituent selected from $C_1$-$C_6$-alkyl, $C_1$-$C_6$-haloalkyl, said 4-, 5-, 6- or 7-membered cyclic amine group optionally containing one further heteroatom selected from the group consisting of O, N and S;

$R^9$ represents $C_1$-$C_4$-alkyl or phenyl, wherein each $C_1$-$C_4$-alkyl or phenyl is optionally substituted, one or more times, independently from each other, with $R^3$;

$R^{10}$ represents $C_1$-$C_4$-alkyl; or $R^9$ and $R^{10}$ together, in case of —N═(SO)$R^9R^{10}$ group, represent a 5- to 8-membered heterocycloalkyl group;

$R^{11}$ represents hydrogen, $C_1$-$C_4$-alkyl, —(CO)O$R^7$, —(CO)N$R^7R^8$ or CN;

$R^{12}$ represents hydrogen or $C_1$-$C_4$-alkyl;

$R^1$ represents halogen, OH, —N$R^7R^8$, CN, NO$_2$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_6$-cycloalkyl, —(CO)O$R^7$ or —(CO)N$R^7R^8$;

or a stereoisomer, a tautomer, an N-oxide, a hydrate, a solvate, or a salt thereof, or a mixture of same.

In accordance with another embodiment the present invention covers compounds of general formula (I), supra, in which:

$R^1$ represents a group selected from:

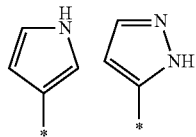

wherein * indicates the point of attachment of said group with the rest of the molecule;

$R^2$ represents hydrogen, fluoro, chloro, CN, $C_1$-$C_4$-alkyl, $C_1$-$C_4$-alkoxy, 3- to 6-membered heterocycloalkoxy, $C_2$-$C_4$-alkenyl, $C_3$-$C_6$-cycloalkyl, 3- to 6-membered heterocycloalkyl, 4- to 6-membered heterocycloalkenyl, phenyl, 5- to 6-membered heteroaryl, —(CO)N$R^7R^8$, —(SO$_2$)$R^9$, —S$R^9$, —((SO)═N$R^{11}$)$R^{10}$, —N═(SO)$R^9R^{10}$, wherein each $C_1$-$C_4$-alkyl, $C_1$-$C_4$-alkoxy, 3- to 6-membered heterocycloalkoxy, $C_2$-$C_4$-alkenyl, $C_3$-$C_6$-cycloalkyl, 3- to 6-membered heterocycloalkyl, phenyl, 5- to 6-membered heteroaryl, is optionally substituted, one or more times, independently from each other, with fluoro, chloro, OH, —N$R^7R^8$, $C_1$-$C_4$-alkyl, 5-membered heterocycloalkyl, phenyl, —N$R^8$(CO)O$R^7$, —(SO$_2$)$R^9$, —((SO)═N$R^{11}$)$R^{10}$, —(PO)(O$R^7$)$_2$ or with a 5- to 6-membered heteroaryl group which is optionally substituted, one or more times, with $C_1$-$C_4$-alkyl;

wherein each 4- to 6-membered heterocycloalkenyl is optionally substituted, one or more times, independently from each other, with $C_1$-$C_4$-alkyl;

$R^3$, $R^4$ represent, independently from each other, hydrogen or methyl;

$R^7$, $R^8$ represent, independently from each other, hydrogen or $C_1$-$C_4$-alkyl;

$R^9$ represents $C_1$-$C_4$-alkyl;

$R^{10}$ represents $C_1$-$C_4$-alkyl; or $R^9$ and $R^{10}$ together, in case of —N═(SO)$R^9R^{10}$ group, represent a 6-membered heterocycloalkyl group;

$R^{11}$ represents hydrogen, $C_1$-$C_4$-alkyl, —(CO)O$R^7$;

or a stereoisomer, a tautomer, an N-oxide, a hydrate, a solvate, or a salt thereof, or a mixture of same.

In accordance with another embodiment the present invention covers compounds of general formula (Ib)

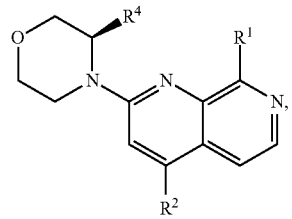

(Ib)

in which $R^1$, $R^2$, $R^4$, $R^7$, $R^8$, $R^9$, $R^{10}$, $R^{11}$, $R^{12}$ and $R^{13}$ are as defined for the compound of general formula (I) supra or infra.

In accordance with another embodiment the present invention covers compounds of general formula (Ib), in which $R^1$ represents:

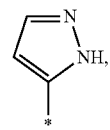

wherein * indicates the point of attachment of said group with the rest of the molecule;

$R^2$ represents hydrogen, fluoro, chloro, CN, methyl, $C_1$-$C_4$-alkoxy, $C_2$-$C_3$-alkenyl, cyclopropyl, 3- to 6-membered heterocycloalkyl, 4- to 6-membered heterocycloalkenyl, phenyl, pyridinyl, thiazolyl, —(SO$_2$)$R^9$, —S$R^9$, —((SO)═N$R^{11}$)$R^{10}$, —N═(SO)$R^9R^{10}$, wherein each methyl, $C_1$-$C_4$-alkoxy, $C_2$-$C_3$-alkenyl, cyclopropyl, 3- to 6-membered heterocycloalkyl, phenyl, pyridinyl or thiazolyl is optionally substituted, one or more times, independently from each other, with fluoro, chloro, OH, —N$R^7R^8$, methyl, 5-membered heterocycloalkyl, —N$R^8$(CO)O$R^7$, —(SO$_2$)$R^9$, —((SO)═N$R^{11}$)$R^{10}$, —(PO)(O$R^7$)$_2$, or with a group selected from:

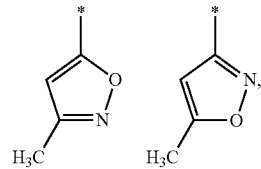

wherein * indicates the point of attachment of said group with the rest of the molecule;

wherein each 4- to 6-membered heterocycloalkenyl is optionally substituted, one or more times, with methyl;

$R^4$ represents hydrogen or methyl;

$R^7$, $R^8$ represent, independently from each other, hydrogen or $C_1$-$C_4$-alkyl;

$R^9$ represents $C_1$-$C_4$-alkyl;

$R^{10}$ represents $C_1$-$C_4$-alkyl; or $R^9$ and $R^{10}$ together, in case of —N═(SO)$R^9R^{10}$ group, represent a 6-membered heterocycloalkyl group;

$R^{11}$ represents hydrogen, methyl, —(CO)O$R^7$;

or a stereoisomer, a tautomer, an N-oxide, a hydrate, a solvate, or a salt thereof, or a mixture of same.

In accordance with another embodiment the present invention covers compounds of general formula (Ib), in which
R$^1$ represents:

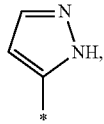

wherein * indicates the point of attachment of said group with the rest of the molecule;
R$^2$ represents hydrogen, fluoro, chloro, CN, methyl, cyclopropyl, C$_2$-C$_3$-alkenyl, C$_1$-C$_4$-alkoxy, 3- to 10-membered heterocycloalkyl, 4- to 10-membered heterocycloalkenyl, 5- to 10-membered heteroaryl, phenyl, —NR$^7$R$^8$, —N=(SO)R$^9$R$^{10}$, —((SO)=NR$^{11}$)R$^{10}$, —(SO$_2$)R$^9$, —SR$^9$,
wherein each methyl, C$_2$-C$_3$-alkenyl, C$_1$-C$_4$-alkoxy, 3- to 10-membered heterocycloalkyl, 5- to 10-membered heteroaryl, phenyl is optionally substituted, one or more times, independently from each other, with fluoro, chloro, OH, —NR$^7$R$^8$, C$_1$-C$_4$-alkyl, cyclopropyl, C$_1$-C$_6$-haloalkyl, C$_1$-C$_4$-alkoxy, C$_1$-C$_4$-hydroxyalkyl, benzyl, 5- to 6-membered heterocycloalkyl, —NR$^8$(CO)OR$^7$, —(SO$_2$)R$^9$, —((SO)=NR$^{11}$)R$^{10}$, —(PO)(OR$^7$)$_2$ or with a group selected from:

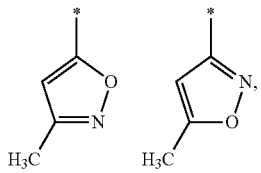

wherein * indicates the point of attachment of said group with the rest of the molecule;
wherein each 4- to 10-membered heterocycloalkenyl is optionally substituted, one or more times, with methyl;
R$^7$, R$^8$ represent, independently from each other, hydrogen, C$_1$-C$_6$-alkyl, cyclopropyl or optionally halogenated phenyl;
R$^9$ represents C$_1$-C$_4$-alkyl;
R$^{10}$ represents C$_1$-C$_4$-alkyl; or
R$^9$ and R$^{10}$ together, in case of —N=(SO)R$^9$R$^{10}$ group, represent a 6-membered heterocycloalkyl group;
R$^{11}$ represents hydrogen, methyl, —(CO)OR$^7$;
or a stereoisomer, a tautomer, an N-oxide, a hydrate, a solvate, or a salt thereof, or a mixture of same.

In accordance with another embodiment the present invention covers compounds of general formula (Ib), in which
R$^1$ represents:

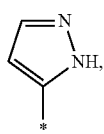 [SMILES: *c1ccn[nH]1]

wherein * indicates the point of attachment of said group with the rest of the molecule;
R$^2$ represents CN, C$_1$-C$_4$-alkoxy, —(SO$_2$)R$^9$, —SR$^9$, cyclopropyl, —NR$^7$R$^8$, —N=(SO)R$^9$R$^{10}$, phenyl, 5- to 10-membered heteroaryl, 3- to 10-membered heterocycloalkyl, 4- to 10-membered heterocycloalkenyl,
wherein each C$_1$-C$_4$-alkoxy, phenyl, 5- to 10-membered heteroaryl, 3- to 10-membered heterocycloalkyl is optionally substituted, one or more times, independently from each other, with fluoro, chloro, —NR$^7$R$^8$, C$_1$-C$_4$-alkyl, cyclopropyl, C$_1$-C$_6$-haloalkyl, C$_1$-C$_4$-alkoxy, C$_1$-C$_4$-hydroxyalkyl, benzyl, 5- to 6-membered heterocycloalkyl, —NR$^8$(CO)OR$^7$, —(SO$_2$)R$^9$, —((SO)=NR$^{11}$)R$^{10}$;
R$^7$, R$^8$ represent, independently from each other, hydrogen, C$_1$-C$_6$-alkyl, cyclopropyl or optionally halogenated phenyl;
R$^9$ represents C$_1$-C$_4$-alkyl;
R$^{10}$ represents C$_1$-C$_4$-alkyl; or
R$^9$ and R$^{10}$ together, in case of —N=(SO)R$^9$R$^{10}$ group, represent a 6-membered heterocycloalkyl group;
R$^{11}$ represents hydrogen;
or a stereoisomer, a tautomer, an N-oxide, a hydrate, a solvate, or a salt thereof, or a mixture of same.

In accordance with another embodiment the present invention covers compounds of general formula (Ib), in which
R$^1$ represents:

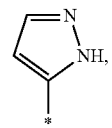

wherein * indicates the point of attachment of said group with the rest of the molecule;
R$^2$ represents CN, methoxy, ethoxy, propoxy, butyloxy, isopropoxy, methylsulfanyl, cyclopropyl, —NR$^7$R$^8$, (4-oxido-1,4λ$^4$-oxathian-4-ylidene)amino, phenyl, pyridinyl, thiazolyl, 1H-pyrrolo[2,3-b]pyridinyl, pyrrolyl, thienyl, pyrazolyl, 1,2-oxazolyl, imidazolyl, tetrahydro-2H-pyranyl, 3,6-dihydro-2H-thiopyranyl, piperidinyl, piperazinyl, 5,6-dihydroimidazo[1,2-a]pyrazin-7(8H)-yl, methanesulphonyl,
wherein each ethoxy, propoxy, butyloxy, phenyl, pyridinyl, thiazolyl, pyrroly, thienyl, pyrazolyl, 1,2-oxazolyl, imidazolyl, piperidinyl or piperazinyl is optionally substituted, one or more times, independently from each other, with fluoro, chloro, —NR$^7$R$^8$, methyl, ethyl, 2,2-dimethylethyl, cyclopropyl, trifluoromethyl, methoxy, hydroxymethyl, benzyl, piperazinyl, —NR$^8$(CO)OR$^7$, methanesulphonyl, —((SO)=NR$^{11}$)R$^{10}$;
R$^7$, R$^8$ represent, independently from each other, hydrogen, methyl, 2,2-dimethylethyl, 2,2-dimethylpropyl, cyclopropyl or fluorophenyl;
R$^{10}$ represents methyl;
R$^{11}$ represents hydrogen;
or a stereoisomer, a tautomer, an N-oxide, a hydrate, a solvate, or a salt thereof, or a mixture of same.

In accordance with another embodiment the present invention covers compounds of general formula (Ib), in which R¹ represents:

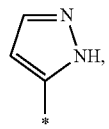

wherein * indicates the point of attachment of said group with the rest of the molecule;

R² represents hydrogen, halogen, —NR⁷R⁸, CN, C₁-C₆-alkyl, C₁-C₆-alkoxy, 3- to 10-membered heterocycloalkoxy, C₂-C₆-alkenyl, C₃-C₆-cycloalkyl, 3- to 10-membered heterocycloalkyl, 4- to 10-membered heterocycloalkenyl, phenyl, heteroaryl, —(CO)OR⁷, —(CO)NR⁷R⁸, —(SO₂)R⁹, —(SO)R⁹, —SR⁹, —(SO₂)NR⁷R⁸, —NR⁷(SO₂)R⁹, —((SO)=NR¹¹)R¹⁰, —N=(SO)R⁹R¹⁰, —SiR¹⁰R¹¹R¹², —(PO)(OR⁷)₂, —(PO)(OR⁷)R¹⁰ or —(PO)(R¹⁰)₂, wherein each C₁-C₆-alkyl, C₁-C₆-alkoxy, 3- to 10-membered heterocycloalkoxy, C₂-C₆-alkenyl, C₃-C₆-cycloalkyl, 3- to 10-membered heterocycloalkyl, phenyl or heteroaryl is optionally substituted, one or more times, independently from each other, with halogen, OH, —NR⁷R⁸, C₁-C₆-alkyl optionally substituted with hydroxyl or phenyl, C₁-C₆-haloalkyl, C₁-C₆-alkoxy, C₃-C₆-cycloalkyl, 3- to 6-membered heterocycloalkyl, phenyl, —(CO)OR⁷, —(CO)NR⁷R⁸, —NR⁷(CO)R¹⁰, NR⁸(CO)OR⁷, —NR⁸(CO) NR⁷R⁸, —(SO₂)R⁹, —(SO)R⁹, —SR⁹, —(SO₂)NR⁷R⁸, —NR⁷(SO₂)R⁹, —((SO)=NR¹¹)R¹⁰, —N=(SO)R⁹R¹⁰, —(PO)(OR⁷)₂, —(PO)(OR⁷)R¹⁰, —(PO)(R¹⁰)₂ or with a heteroaryl group which is optionally substituted, one or more times, with C₁-C₄-alkyl;

wherein each 4- to 10-membered heterocycloalkenyl is optionally substituted, one or more times, independently from each other, with C₁-C₄-alkyl;

R³, R⁴ represent, independently from each other, hydrogen or methyl;

R⁷, R⁸ represent, independently from each other, hydrogen, C₁-C₆-alkyl, C₃-C₆-cycloalkyl or phenyl, which phenyl is optionally substituted, one or more times, with halogen; or R⁷ and R⁸ together represent a 4-, 5-, 6- or 7-membered cyclic amine group, which is optionally substituted, one or more times, independently from each other, with a substituent selected from C₁-C₆-alkyl, C₁-C₆-haloalkyl, said 4-, 5-, 6- or 7-membered cyclic amine group optionally containing one further heteroatom selected from the group consisting of O, N and S;

R⁹ represents C₁-C₄-alkyl or phenyl, wherein each C₁-C₄-alkyl or phenyl is optionally substituted, one or more times, independently from each other, with R³;

R¹⁰ represents C₁-C₄-alkyl; or R⁹ and R¹ together, in case of —N=(SO)R⁹R¹⁰ group, represent a 5- to 8-membered heterocycloalkyl group;

R¹¹ represents hydrogen, C₁-C₄-alkyl, —(CO)OR⁷, —(CO)NR⁷R⁸ or CN;

R¹² represents hydrogen or C₁-C₄-alkyl;

R¹³ represents halogen, OH, —NR⁷R⁸, CN, NO₂, C₁-C₆-alkyl, C₁-C₆-haloalkyl, C₁-C₆-alkoxy, C₁-C₆-haloalkoxy, C₂-C₆-alkenyl, C₃-C₆-cycloalkyl, —(CO)OR⁷ or —(CO)NR⁷R⁸.

In accordance with another embodiment the present invention covers compounds of general formula (Ib), in which R¹ represents:

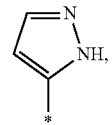

wherein * indicates the point of attachment of said group with the rest of the molecule;

R² represents hydrogen, halogen, —NR⁷R⁸, CN, C₁-C₆-alkyl, C₁-C₄-alkoxy, 3- to 10-membered heterocycloalkoxy, C₂-C₄-alkenyl, C₃-C₆-cycloalkyl, 3- to 10-membered heterocycloalkyl, 4- to 10-membered heterocycloalkenyl, phenyl, heteroaryl, —(CO)NR⁷R⁸, —(SO₂)R⁹, —(SO)R⁹, —SR⁹, —N=(SO)R⁹R¹⁰, —(PO)(OR⁷)₂, —(PO)(OR⁷)R¹⁰, —(PO)(R¹⁰)₂, wherein each C₁-C₆-alkyl, C₁-C₄-alkoxy, C₃-C₆-cycloalkyl, 3- to 10-membered heterocycloalkyl, phenyl or heteroaryl is optionally substituted, one or more times, independently from each other, with
halogen, OH, amino, —NR⁷R⁸,
C₁-C₄-alkyl optionally substituted with hydroxyl or phenyl,
C₁-C₂-haloalkyl, C₁-C₃-alkoxy, C₃-C₆-cycloalkyl, 3- to 6-membered heterocycloalkyl, phenyl, —(CO)OR⁷, —(CO)NR⁷R⁸, —NR⁷(CO)R¹⁰, —NR⁸(CO)OR⁷, —(SO₂)R⁹, —SR⁹, —NR⁷(SO₂)R⁹, —((SO)=NR¹¹)R¹⁰, —(PO)(OR⁷)₂, —(PO)(OR⁷)R¹⁰, or with a heteroaryl group;

wherein each 4- to 10-membered heterocycloalkenyl is optionally substituted, one or more times, independently from each other, with methyl;

R⁴ represents hydrogen or methyl;

R⁷, R⁸ represent, independently from each other, hydrogen, C₁-C₆-alkyl, C₃-C₆-cycloalkyl or phenyl, which phenyl is optionally substituted, one or more times, with halogen;

R⁹ represents C₁-C₄-alkyl or phenyl, wherein each C₁-C₄-alkyl or phenyl is optionally substituted, one or more times, independently from each other, with R³;

R¹⁰ represents C₁-C₄-alkyl; or

R⁹ and R¹ together, in case of —N=(SO)R⁹R¹⁰ group, represent a 5- to 8-membered heterocycloalkyl group;

R¹¹ represents hydrogen, C₁-C₄-alkyl, —(CO)OR⁷, —(CO)NR⁷R⁸ or CN;

R¹³ represents halogen, OH or C₁-C₆-alkoxy.

In accordance with another embodiment the present invention covers compounds of general formula (Ib), in which R¹ represents:

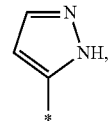

wherein * indicates the point of attachment of said group with the rest of the molecule;

R² represents hydrogen, chloro,-amino, propylamino, dimethylamino, methyl(propyl)amino, methyl(2-methylpropyl)amino, 2,2-dimethylpropyl(methyl)amino, cyclopropyl(methyl)amino, methyl(phenyl)amino, CN, methyl, ethyl, propan-2-yl, 3-methylbutan-2-yl, pentan-3-yl, hexan-2-yl, 3,3-dimethylbutan-2-yl, methoxy, ethoxy, propoxy, butoxy, 2-methyl-propan-1-yloxy, propan-2- yloxy, (2-oxotetrahydrofuran-3-yl)oxy, propenyl, cyclopropyl, cyclohexyl, azetidinyl,-pyrrolidinyl, 2-oxo-1,3-oxazolidin-2-one, tetrahydro-2H-pyranyl, tetrahydro-2H-thiopyran-4-yl, piperidinyl, piperazinyl, morpholinyl, azepanyl, 2-oxo-pyrrolidin-1-yl, 2-oxo-piperidin-1-yl, 3-oxo-piperazin-1-yl, 2-oxo-1,3-oxazinan-3-yl, 1-oxido-tetrahydro-2H-thiopyran-4-yl, 1,1-dioxidotetrahydro-2H-thiopyran-4-yl, 1,1-dioxido-1,2-thiazolidin-2-yl, 5,6-dihydroimidazo[1,2-a]pyrazin-7(8H)-yl, 3-oxa-8-azabicyclo[3.2.1]oct-8-yl, 1,3,3-trimethyl-6-azabicyclo[3.2.1]oct-6-yl, (3aR,6aS)-tetrahydro-1H-furo[3,4-c]pyrrol-5(3H)-yl, (1S,4S)-2-oxa-5-azabicyclo[2.2.1]hept-5-yl, 1,1-dioxido-1-thia-6-azaspiro[3.3]hept-6-yl, 2,5-dihydro-1H-pyrrol-1-yl, 3,6-dihydro-2H-pyran-4-yl, 1,2,5,6-tetrahydropyridin-3-yl, 1,2,3,6-tetrahydropyridin-4-yl, 3,6-dihydro-2H-thiopyran-4-yl, phenyl, 1,3-dihydro-2H-isoindol-2-yl, 3,4-dihydroquinolin-1(2H)-yl, 3,4-dihydroisoquinolin-2(1H)-yl, pyrrolyl, pyrazolyl, thiophenyl, imidazolyl, oxazolyl, thiazolyl, triazolyl, oxadiazolyl, pyridinyl, pyrimidinyl, 2-oxo-1,2-dihydropyridin-4-yl, indolyl, benzothiophenyl, quinolinyl, isoquinolinyl, 1H-pyrrolo[2,3-b]pyridin-4-yl, 6,7-dihydro-5H-pyrrolo[1,2-a]imidazol-3-yl, —(CO)NH$_2$, methylsulfonyl, ethylsulfonyl, propan-2-ylsulfonyl, phenylsulfonyl, methylsulfinyl, ethylsulfinyl, propan-2-ylsulfinyl, phenylsulfinyl, methylsulfanyl, ethylsulfanyl, propan-2-ylsulfanyl, phenylsulfanyl, —N=(SO)dimethyl, —N=(SO)diethyl,

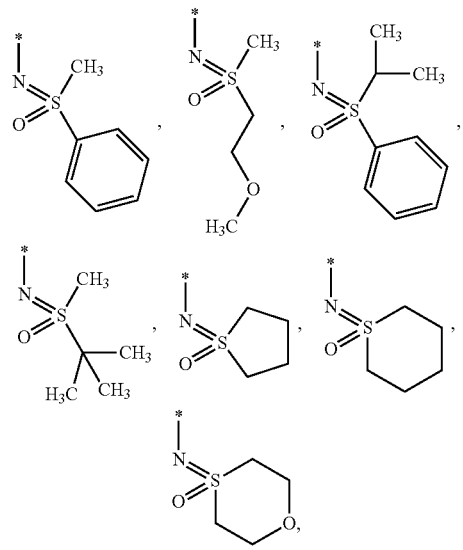

wherein * indicates the point of attachment of said group with the rest of the molecule, —(PO)(O-methyl)$_2$, —(PO)(O-ethyl)methyl, —(PO)(O-2-methylpropyl)methyl, —(PO)(O-ethyl)$_2$-methylpropyl, —(PO)dimethyl, —(PO)diethyl, wherein each methyl, ethyl, propan-2-yl, 3-methylbutan-2-yl, pentan-3-yl, hexan-2-yl, 3,3-dimethylbutan-2-yl, methoxy, ethoxy, propoxy, 2-methyl-propan-1-yloxy, butoxy, cyclopropyl, cyclohexyl, azetidinyl, pyrrolidinyl, piperidinyl, piperazinyl, morpholinyl, 3-oxo-piperazin-1-yl, phenyl, pyrrolyl, pyrazolyl, thiophenyl, imidazolyl, oxazolyl, thiazolyl, triazolyl, oxadiazolyl, pyridinyl, pyrimidinyl, indolyl,

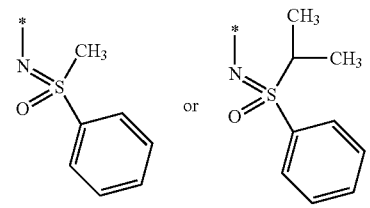

is optionally substituted, one or more times, independently from each other, with fluoro, chloro, bromo, OH, amino, —NH-cyclopropyl, dimethylamino, methyl, ethyl, propan-1-yl, propan-2-yl, 2-methylpropyl, tert-butyl, hydroxymethyl, 2-hydroxyethyl, 2-methyl-2-hydroxypropan-1-yl, 2-hydroxypropan-2-yl, benzyl, fluoroethyl, difluoromethyl, trifluoromethyl, methoxy, ethoxy, isopropoxy, methoxymethyl, cyclopropyl, cyclobutyl, tetrahydrofuranyl, tetrahydropyranyl, phenyl, —(CO)O-methyl, (CO)O-tert-butyl, —(CO)NH$_2$, —(CO)NH-methyl, —(CO)NH-tert-butyl, —(CO)dimethylamino, —(CO)piperidin-1-yl, —(CO)NH-cyclopropyl, —NH(CO)methyl, —NH(CO)O-tert-butyl, methylsulfonyl, ethylsulfonyl, propan-2-ylsulfonyl, phenylsulfonyl, methylsulfanyl, —(SO$_2$)NR$^7$R$^8$, NH(SO$_2$)methyl, —((SO)=NH)methyl, —((SO)=NH)ethyl, —((SO)=NH)propan-2-yl, —((SO)=N-methyl)methyl, —((SO)=N—(CO)O-ethyl)methyl, —((SO)=N—(CN))methyl, —((SO)=N—(CO)NH-ethyl)methyl, —(PO)(O-methyl)$_2$, —(PO)(OH)(O-methyl) or with furanyl or pyrazolyl, wherein each 1,2,5,6-tetrahydropyridin-3-yl, 1,2,3,6-tetrahydropyridin-4-yl is optionally substituted, one or more times, independently from each other, with methyl;

R$_4$ represents hydrogen or methyl.

In accordance with another embodiment the present invention covers compounds of general formula (Ib), in which R$^1$ represents:

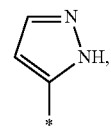

wherein * indicates the point of attachment of said group with the rest of the molecule;

R$^2$ represents 2,2-dimethylpropyl(methyl)amino, cyclopropyl(methyl)amino, methyl(phenyl)amino, 3-methylbutan-2-yl, cyclopropyl, tetrahydro-2H-pyranyl, tetrahydro-2H-thiopyran-4-yl, piperidinyl, piperazinyl, 5,6-dihydroimidazo[1,2-a]pyrazin-7(8H)-yl, 3,6-dihydro-2H-thiopyran-4-yl, phenyl, pyrrolyl, pyrazolyl, thiophenyl, imidazolyl, oxazolyl, thiazolyl, pyridinyl, 1H-pyrrolo[2,3-b]pyridin-4-yl or 6,7-dihydro-5H-pyrrolo[1,2-a]imidazol-3-yl, wherein each 3-methylbutan-2-yl, cyclopropyl, piperidinyl, piperazinyl, phenyl, pyrrolyl, pyrazolyl, thiophenyl, imidazolyl, oxazolyl, thiazolyl or pyridinyl is optionally substituted, one or two or three times, independently from each other, with fluoro, chloro, OH, amino, methyl, ethyl, propan-1-yl, propan-2-yl, tert-butyl, hydroxymethyl, benzyl, fluoroethyl, trifluoromethyl, methoxy, cyclopropyl, —(CO)O-methyl, methylsulfonyl, methylsulfanyl or —((SO)=NH)methyl;

R⁴ represents methyl.

In accordance with another embodiment the present invention covers compounds of general formula (Ib), in which R¹ represents:

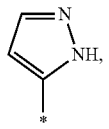

wherein * indicates the point of attachment of said group with the rest of the molecule;

R² represents tetrahydro-2H-thiopyran-4-yl, piperidinyl, 5,6-dihydroimidazo[1,2-a]pyrazin-7(8H)-yl, phenyl, pyrrolyl, pyrazolyl, oxazolyl, pyridinyl or 6,7-dihydro-5H-pyrrolo[1,2-a]imidazol-3-yl,
wherein each piperidinyl, phenyl, pyrrolyl, pyrazolyl, oxazolyl or pyridinyl is optionally substituted, one or two times, independently from each other, with fluoro, amino, methyl, ethyl, propan-2-yl, hydroxymethyl, methoxy, cyclopropyl, methylsulfonyl, methylsulfanyl or —((SO)=NH)methyl;

R⁴ represents methyl.

In another embodiment the present invention relates to compounds of formula (Ib), in which R¹ represents:

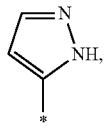

wherein * indicates the point of attachment of said group with the rest of the molecule;

R² represents 2,2-dimethylpropyl(methyl)amino, cyclopropyl(methyl)amino, methyl(phenyl)amino, 3-methylbutan-2-yl, cyclopropyl, tetrahydro-2H-pyranyl, tetrahydro-2H-thiopyran-4-yl, piperidin-4-yl, piperazin-1-yl, 5,6-dihydroimidazo[1,2-a]pyrazin-7(8H)-yl, 3,6-dihydro-2H-thiopyran-4-yl, phenyl, pyrrol-2-yl, 1H-pyrazol-5-yl, 1H-pyrazol-4-yl, thiophen-2-yl, thiophen-3-yl, 1H-imidazol-5-yl, 1,2-oxazol-5-yl, 1,3-thiazol-5-yl, pyridine-3-yl, pyridine-4-yl, 1H-pyrrolo[2,3-b]pyridin-4-yl or 6,7-dihydro-5H-pyrrolo[1,2-a]imidazol-3-yl,
wherein each 3-methylbutan-2-yl, cyclopropyl, piperidin-4-yl, piperazin-1-yl, phenyl, pyrrol-2-yl, 1H-pyrazol-5-yl, 1H-pyrazol-4-yl, thiophen-2-yl, thiophen-3-yl, 1H-imidazol-5-yl, 1,2-oxazol-5-yl, 1,3-thiazol-5-yl, pyridine-3-yl or pyridine-4-yl is optionally substituted, one or two or three times, independently from each other, with fluoro, chloro, OH, amino, methyl, ethyl, propan-1-yl, propan-2-yl, tert-butyl, hydroxymethyl, benzyl, 2-fluoroethyl, trifluoromethyl, methoxy, cyclopropyl, —(CO)O-methyl, methylsulfonyl, methylsulfanyl or —((SO)=NH)methyl;

R⁴ represents methyl.

In another embodiment the present invention relates to compounds of formula (Ib), in which R¹ represents:

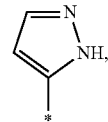

wherein * indicates the point of attachment of said group with the rest of the molecule;

R² represents tetrahydro-2H-thiopyran-4-yl, piperidin-4-yl, 5,6-dihydroimidazo[1,2-a]pyrazin-7(8H)-yl, phenyl, pyrrol-2-yl, 1H-pyrazol-5-yl, 1H-pyrazol-4-yl, 1,2-oxazol-5-yl, 1,3-thiazol-5-yl, pyridine-3-yl, 6,7-dihydro-5H-pyrrolo[1,2-a]imidazol-3-yl,
wherein each piperidin-4-yl, phenyl, pyrrol-2-yl, 1H-pyrazol-5-yl, 1H-pyrazol-4-yl, 1,2-oxazol-5-yl, pyridine-3-yl is optionally substituted, one or two times, independently from each other, with fluoro, OH, amino, methyl, ethyl, propan-2-yl, hydoxymethyl, 2-fluoroethyl, methoxy, cyclopropyl, ethylsulfonyl, methylsulfanyl, —((SO)=NH)methyl, R⁴ represents methyl.

In another embodiment the present invention relates to compounds of formula (Ib), in which R¹ represents:

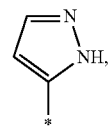

wherein * indicates the point of attachment of said group with the rest of the molecule;

R² represents phenyl, pyrazolyl, thiophenyl or pyridinyl,
wherein each phenyl, pyrazolyl, thiophenyl or pyridinyl is optionally substituted, one or two times, independently from each other, with fluoro, chloro, amino, methyl, ethyl, propan-1-yl, propan-2-yl, tert-butyl, benzyl, fluoroethyl, trifluoromethyl, methoxy, cyclopropyl, methylsulfonyl, methylsulfanyl, —((SO)=NH)methyl, R⁴ represents methyl.

In another embodiment the present invention relates to compounds of formula (Ib), in which R¹ represents:

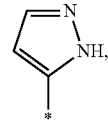

wherein * indicates the point of attachment of said group with the rest of the molecule;

R² represents phenyl, 1H-pyrazol-4-yl, 1H-pyrazol-5-yl, thiophen-2-yl, thiophen-3-yl or pyridine-3-yl, pyridine-4-yl, wherein each phenyl, 1H-pyrazol-4-yl, 1H-pyrazol-5-yl, thiophen-2-yl, thiophen-3-yl, pyridine-3-yl or pyridine-4-yl, is optionally substituted, one or two times, independently from each other, with fluoro, chloro, amino, methyl, ethyl, propan-1-yl, propan-2-yl, tert-butyl, benzyl, fluoroethyl, trifluoromethyl, methoxy, cyclopropyl, methylsulfonyl, methylsulfanyl, —((SO)=NH)methyl, $R^4$ represents methyl.

In another embodiment the present invention relates to compounds of formula (Ib), in which $R^1$ represents:

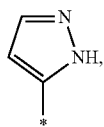 [SMILES: *c1ccn[nH]1]

wherein * indicates the point of attachment of said group with the rest of the molecule;

$R^2$ represents phenyl, 1H-pyrazol-4-yl, 1H-pyrazol-5-yl or pyridine-3-yl, wherein each phenyl, 1H-pyrazol-4-yl, 1H-pyrazol-5-yl or pyridine-3-yl, is optionally substituted, one or two times, independently from each other, with fluoro, amino, methyl, ethyl, propan-1-yl, propan-2-yl, tert-butyl, benzyl, fluoroethyl, trifluoromethyl, methoxy, cyclopropyl, methylsulfonyl, methylsulfanyl, —((SO)=NH)methyl, $R^4$ represents methyl.

In another embodiment the present invention relates to compounds of formula (I) or (Ib), in which $R^1$ represents a group selected from

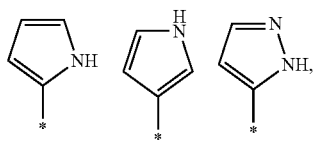

wherein * indicates the point of attachment of said group with the rest of the molecule.

In another embodiment the present invention relates to compounds of formula (I) or (Ib), in which $R^1$ represents a group selected from

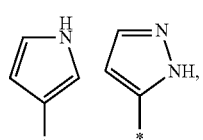

wherein * indicates the point of attachment of said group with the rest of the molecule.

In another embodiment the present invention relates to compounds of formula (I) or (Ib), in which $R^1$ represents

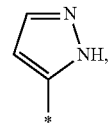

wherein * indicates the point of attachment of said group with the rest of the molecule.

In another embodiment the present invention relates to compounds of formula (I) or (Ib), in which $R^2$ represents hydrogen, fluoro, chloro, CN, $C_1$-$C_4$-alkyl, $C_1$-$C_4$-alkoxy, 3- to 6-membered heterocycloalkoxy, $C_2$-$C_4$-alkenyl, $C_3$-$C_6$-cycloalkyl, 3- to 6-membered heterocycloalkyl, 4- to 6-membered heterocycloalkenyl, phenyl, pyridinyl, thiazolyl, —(CO)NR$^7$R$^8$, —(SO$_2$)R$^9$, —SR$^9$, —((SO)=NR$^{11}$)R$^{10}$, —N=(SO)R$^9$R$^{10}$, wherein each $C_1$-$C_4$-alkyl, $C_1$-$C_4$-alkoxy, 3- to 6-membered heterocycloalkoxy, $C_2$-$C_4$-alkenyl, $C_3$-$C_6$-cycloalkyl, 3- to 6-membered heterocycloalkyl, phenyl, pyridinyl or thiazolyl is optionally substituted, one or more times, independently from each other, with fluoro, chloro, OH, —NR$^7$R$^8$, $C_1$-$C_4$-alkyl, 5-membered heterocycloalkyl, phenyl, —NR$^8$(CO)OR$^7$, —(SO$_2$)R$^9$, —((SO)=NR$^{11}$)R$^{10}$, —(PO)(OR$^7$)$_2$ or a group selected from:

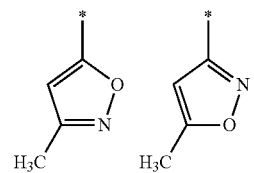

wherein * indicates the point of attachment of said group with the rest of the molecule;

wherein each 4- to 6-membered heterocycloalkenyl is optionally substituted, one or more times, with $C_1$-$C_4$-alkyl.

In another embodiment, the present invention relates to compounds of formula (I) or (Ib), in which $R^2$ represents hydrogen, fluoro, chloro, CN, $C_1$-$C_4$-alkyl, $C_1$-$C_4$-alkoxy, 3- to 6-membered heterocycloalkoxy, $C_2$-$C_3$-alkenyl, $C_3$-$C_6$-cycloalkyl, 3- to 6-membered heterocycloalkyl, 4- to 6-membered heterocycloalkenyl, phenyl, pyridinyl, thiazolyl, —(CO)NR$^7$R$^8$, —(SO$_2$)R$^9$, —SR$^9$, —((SO)=NR$^{11}$)R$^{10}$, —N=(SO)R$^9$R$^{10}$, wherein each $C_1$-$C_4$-alkyl, $C_1$-$C_4$-alkoxy, 3- to 6-membered heterocycloalkoxy, $C_2$-$C_4$-alkenyl, $C_3$-$C_6$-cycloalkyl, 3- to 6-membered heterocycloalkyl, phenyl, pyridinyl or thiazolyl is optionally substituted, one or more times, independently from each other, with fluoro, chloro, OH, —NR$^7$R$^8$, $C_1$-$C_4$-alkyl, 5-membered heterocycloalkyl, phenyl, —NR(CO)OR$^7$, —(SO$_2$)R$^9$, —((SO)=NR$^{11}$)R$^{10}$, —(PO)(OR$^7$)$_2$ or a group selected from:

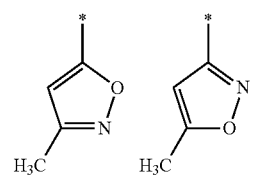

wherein * indicates the point of attachment of said group with the rest of the molecule;
wherein each 4- to 6-membered heterocycloalkenyl is optionally substituted, one or more times, independently from each other, with $C_1$-$C_4$-alkyl.

In another embodiment the present invention relates to compounds of general formula (I) or (Ib), in which $R^2$ represents hydrogen, halogen, —$NR^7R^8$, CN, $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, 4- to 10-membered heterocycloalkenyl, phenyl, heteroaryl, —(CO)$OR^7$, —(CO)$NR^7R^8$, —($SO_2$)$R^9$, —(SO)$R^9$, —$SR^9$, —($SO_2$)$NR^7R^8$, —$NR^7$($SO_2$)$R^9$, —((SO)═$NR^{11}$)$R^{10}$, —N═(SO)$R^9R^{10}$, —$SiR^{10}R^{11}R^{12}$, —(PO)($OR^7$)$_2$, —(PO)($OR^7$)$R^{10}$ or —(PO)($R^{10}$)$_2$,
wherein each $C_1$-$C_6$-alkyl, $C_1$-$C_6$-alkoxy, 3- to 10-membered heterocycloalkoxy, $C_2$-$C_6$-alkenyl, $C_3$-$C_6$-cycloalkyl, 3- to 10-membered heterocycloalkyl, phenyl or heteroaryl is optionally substituted, one or more times, independently from each other, with halogen, OH, —$NR^7R^8$, $C_1$-$C_6$-alkyl optionally substituted with hydroxy or phenyl, $C_1$-$C_6$-haloalkyl, $C_1$-$C_6$-alkoxy, $C_3$-$C_6$-cycloalkyl, 3- to 6-membered heterocycloalkyl, phenyl, —(CO)$OR^7$, —(CO)$NR^7R^8$, —$NR^7$(CO)$R^{10}$, —$NR^8$(CO)$OR^7$, —$NR^8$(CO) $NR^7R^8$, —($SO_2$)$R^9$, —(SO)$R^9$, —$SR^9$, —($SO_2$)$NR^7R^8$, —$NR^7$($SO_2$)$R^9$, —((SO)═$NR^{11}$)$R^{10}$, —N═(SO)$R^9R^{10}$, —(PO) ($OR^7$)$_2$, —(PO)($OR^7$)$R^{10}$, —(PO)($R^{10}$)$_2$ or with a heteroaryl group which is optionally substituted, one or more times, with $C_1$-$C_4$-alkyl;
wherein each 4- to 10-membered heterocycloalkenyl is optionally substituted, one or more times, independently from each other, with $C_1$-$C_4$-alkyl.

In another embodiment the present invention relates to compounds of formula (I) or (Ib), in which $R^2$ represents CN, methoxy, ethoxy, propoxy, butyloxy, isopropoxy, methylsulfanyl, cyclopropyl, —$NR^7R^8$, (4-oxido-1,4λ⁴-oxathian-4-ylidene)amino, phenyl, pyridinyl, thiazolyl, 1H-pyrrolo[2,3-b]pyridin-4-yl, pyrrolyl, thienyl, pyrazolyl, 1,2-oxazolyl, imidazolyl, tetrahydro-2H-pyranyl, 3,6-dihydro-2H-thiopyranyl, piperidinyl, piperazinyl, 5,6-dihydroimidazo[1,2-a]pyrazin-7(8H)-yl, methanesulphonyl, —((SO)═$NR^{11}$)$R^{10}$,
wherein each ethoxy, propoxy, butyloxy, phenyl, pyridinyl, thiazolyl, pyrroly, thienyl, pyrazolyl, 1,2-oxazolyl, imidazolyl, piperidinyl or piperazinyl is optionally substituted, one or more times, independently from each other, with fluoro, chloro, —$NR^7R^8$, methyl, ethyl, 2,2,-dimethylethyl, cyclopropyl, trifluoromethyl, methoxy, hydroxymethyl, benzyl, piperazinyl, —$NR^8$ (CO)$OR^7$, methanesulphonyl, S-methylsulfonimidoyl.

In another embodiment the present invention relates to compounds of formula (I) or (Ib), in which $R^2$ represents hydrogen, chloro,-amino, propylamino, dimethylamino, methyl(propyl)amino, methyl(2-methylpropyl)amino, 2,2-dimethylpropyl(methyl)amino, cyclopropyl(methyl)amino, methyl(phenyl)amino, CN, methyl, ethyl, propan-2-yl, 3-methylbutan-2-yl, pentan-3-yl, hexan-2-yl, 3,3-dimethylbutan-2-yl, methoxy, ethoxy, propoxy, butoxy, 2-methyl-propan-1-yloxy, propan-2-yloxy, (2-oxotetrahydrofuran-3-yl)oxy, propenyl, cyclopropyl, cyclohexyl, azetidinyl,-pyrrolidinyl, 2-oxo-1,3-oxazolidin-2-one, tetrahydro-2H-pyranyl, tetrahydro-2H-thiopyran-4-yl, piperidinyl, piperazinyl, morpholinyl, azepanyl, 2-oxo-pyrrolidin-1-yl, 2-oxo-piperidin-1-yl, 3-oxo-piperazin-1-yl, 2-oxo-1,3-oxazinan-3-yl, 1-oxidotetrahydro-2H-thiopyran-4-yl, 1,1-dioxidotetrahydro-2H-thiopyran-4-yl, 1,1-dioxido-1,2-thiazolidin-2-yl, 5,6-dihydroimidazo[1,2-a]pyrazin-7(8H)-yl, 3-oxa-8-azabicyclo[3.2.1]oct-8-yl, 1,3,3-trimethyl-6-azabicyclo[3.2.1]oct-6-yl, (3aR,6aS)-tetrahydro-1H-furo[3,4-c]pyrrol-5(3H)-yl, (1S,4S)-2-oxa-5-azabicyclo[2.2.1]hept-5-yl, 1,1-dioxido-1-thia-6-azaspiro[3.3]hept-6-yl 2,5-dihydro-1H-pyrrol-1-yl, 3,6-dihydro-2H-pyran-4-yl, 1,2,5,6-tetrahydropyridin-3-yl, 1,2,3,6-tetrahydropyridin-4-yl, 3,6-dihydro-2H-thiopyran-4-yl, phenyl, 1,3-dihydro-2H-isoindol-2-yl, 3,4-dihydroquinolin-1(2H)-yl, 3,4-dihydroisoquinolin-2(1H)-yl, pyrrolyl, pyrazolyl, thiophenyl, imidazolyl, oxazolyl, thiazolyl, triazolyl, oxadiazolyl, pyridinyl, pyrimidinyl, 2-oxo-1,2-dihydropyridin-4-yl, indolyl, benzothiophenyl, quinolinyl, isoquinolinyl, 1H-pyrrolo[2,3-b]pyridin-4-yl, 6,7-dihydro-5H-pyrrolo[1,2-a]imidazol-3-yl, —(CO)$NH_2$, methylsulfonyl, ethylsulfonyl, propan-2-ylsulfonyl, phenylsulfonyl, methylsulfinyl, ethylsulfinyl, propan-2-ylsulfinyl, phenylsulfinyl, methylsulfanyl, ethylsulfanyl, propan-2-ylsulfanyl, phenylsulfanyl, —N═(SO)dimethyl, —N═(SO)diethyl,

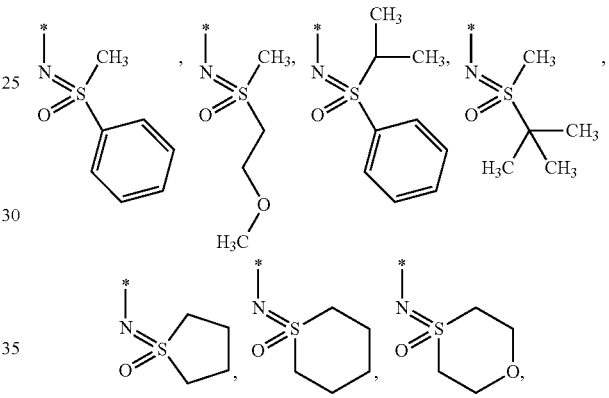

wherein * indicates the point of attachment of said group with the rest of the molecule, —(PO)(O-methyl)$_2$, —(PO)(O-ethyl)methyl, —(PO)(O-2-methylpropyl)methyl, —(PO)(O-ethyl)$_2$-methylpropyl, —(PO)dimethyl, —(PO)diethyl,
wherein each methyl, ethyl, propan-2-yl, 3-methylbutan-2-yl, pentan-3-yl, hexan-2-yl, 3,3-dimethylbutan-2-yl, methoxy, ethoxy, propoxy, 2-methyl-propan-1-yloxy, butoxy, cyclopropyl, cyclohexyl, azetidinyl, pyrrolidinyl, piperidinyl, piperazinyl, morpholinyl, 3-oxo-piperazin-1-yl, phenyl, pyrrolyl, pyrazolyl, thiophenyl, imidazolyl, oxazolyl, thiazolyl, triazolyl, oxadiazolyl, pyridinyl, pyrimidinyl, indolyl,

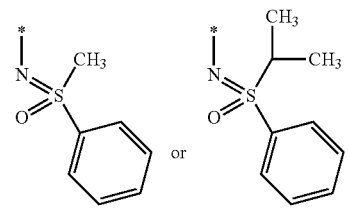 [SMILES: *N=S(C)(=O)c1ccccc1 ; *N=S(=O)(c1ccccc1)C(C)C]

is optionally substituted, one or more times, independently from each other, with fluoro, chloro, bromo, OH, amino, —NH-cyclopropyl, dimethylamino, methyl, ethyl, propan-1-yl, propan-2-yl, 2-methylpropyl, tert-butyl, hydroxymethyl, 2-hydroxyethyl, 2-methyl-2-hydroxypropan-1-yl, 2-hydroxypropan-2-yl, benzyl, fluoroethyl, difluoromethyl, trifluoromethyl, methoxy, ethoxy, isopropoxy, methoxymethyl, cyclopropyl, cyclobutyl, tetrahydrofuranyl, tetrahydropyranyl, phenyl, —(CO)O-methyl, (CO)O-tert-butyl, —(CO)NH$_2$, —(CO)NH-methyl, —(CO)NH-tert-butyl, —(CO)dimethylamino, —(CO)piperidin-1-yl, —(CO)NH-cyclopropyl, —NH(CO)methyl, —NH(CO)O-tert-butyl, methylsulfonyl, ethylsulfonyl, propan-2-ylsulfonyl, phenylsulfonyl, methylsulfanyl, —(SO$_2$)NR$^7$R$^8$, NH(SO$_2$)methyl, —((SO)=NH)methyl, —((SO)=NH)ethyl, —((SO)=NH)propan-2-yl, —((SO)=N-methyl)methyl, —((SO)=N—(CO)O-ethyl)methyl, —((SO)=N—(CN))methyl, —((SO)=N—(CO)NH-ethyl)methyl, —(PO)(O-methyl)$_2$, —(PO)(OH)(O-methyl) or with furanyl, pyrazolyl,
  wherein each 1,2,5,6-tetrahydropyridin-3-yl, 1,2,3,6-tetrahydropyridin-4-yl is optionally substituted, one or more times, independently from each other, with methyl.

In another embodiment the present invention relates to compounds of formula (I) or (Ib), in which
  R$^2$ represents 2,2-dimethylpropyl(methyl)amino, cyclopropyl(methyl)amino, methyl(phenyl)amino, 3-methylbutan-2-yl, cyclopropyl, tetrahydro-2H-pyranyl, tetrahydro-2H-thiopyran-4-yl, piperidinyl, piperazinyl, 5,6-dihydroimidazo[1,2-a]pyrazin-7(8H)-yl, 3,6-dihydro-2H-thiopyran-4-yl, phenyl, pyrrolyl, pyrazolyl, thiophenyl, imidazolyl, oxazolyl, thiazolyl, pyridinyl, 1H-pyrrolo[2,3-b]pyridin-4-yl, 6,7-dihydro-5H-pyrrolo[1,2-a]imidazol-3-yl,
    wherein each 3-methylbutan-2-yl, cyclopropyl, piperidinyl, piperazinyl, phenyl, pyrrolyl, pyrazolyl, thiophenyl, imidazolyl, oxazolyl, thiazolyl, pyridinyl, is optionally substituted, one or two or three times, independently from each other, with
      fluoro, chloro, OH, amino, methyl, ethyl, propan-1-yl, propan-2-yl, tert-butyl, hydroxymethyl, benzyl, fluoroethyl, trifluoromethyl, methoxy, cyclopropyl, —(CO)O-methyl, methylsulfonyl, methylsulfanyl, —((SO)=NH)methyl.

In another embodiment the present invention relates to compounds of formula (I) or (Ib), in which
  R$^2$ represents tetrahydro-2H-thiopyran-4-yl, piperidinyl, 5,6-dihydroimidazo[1,2-a]pyrazin-7(8H)-yl, phenyl, pyrrolyl, pyrazolyl, oxazolyl, pyridinyl, 6,7-dihydro-5H-pyrrolo[1,2-a]imidazol-3-yl,
    wherein each piperidinyl, phenyl, pyrrolyl, pyrazolyl, oxazolyl, pyridinyl, is optionally substituted, one or two times, independently from each other, with
      fluoro, amino, methyl, ethyl, propan-2-yl, hydroxymethyl, methoxy, cyclopropyl, methylsulfonyl, methylsulfanyl, —((SO)=NH)methyl.

In another embodiment the present invention relates to compounds of formula (I) or (Ib), in which
  R$^2$ represents 2,2-dimethylpropyl(methyl)amino, cyclopropyl(methyl)amino, methyl(phenyl)amino, 3-methylbutan-2-yl, cyclopropyl, tetrahydro-2H-pyranyl, tetrahydro-2H-thiopyran-4-yl, piperidin-4-yl, piperazin-1-yl, 5,6-dihydroimidazo[1,2-a]pyrazin-7(8H)-yl, 3,6-dihydro-2H-thiopyran-4-yl, phenyl, pyrrol-2-yl, 1H-pyrazol-5-yl, 1H-pyrazol-4-yl, thiophen-2-yl, thiophen-3-yl, 1H-imidazol-5-yl, 1,2-oxazol-5-yl, 1,3-thiazol-5-yl, pyridine-3-yl, pyridine-4-yl, 1H-pyrrolo[2,3-b]pyridin-4-yl or 6,7-dihydro-5H-pyrrolo[1,2-a]imidazol-3-yl,
    wherein each 3-methylbutan-2-yl, cyclopropyl, piperidin-4-yl, piperazin-1-yl, phenyl, pyrrol-2-yl, 1H-pyrazol-5-yl, 1H-pyrazol-4-yl, thiophen-2-yl, thiophen-3-yl, 1H-imidazol-5-yl, 1,2-oxazol-5-yl, 1,3-thiazol-5-yl, pyridine-3-yl or pyridine-4-yl is optionally substituted, one or two or three times, independently from each other, with
      fluoro, chloro, OH, amino, methyl, ethyl, propan-1-yl, propan-2-yl, tert-butyl, hydoxymethyl, benzyl, 2-fluoroethyl, trifluoromethyl, methoxy, cyclopropyl, —(CO)O-methyl, methylsulfonyl, methylsulfanyl or —((SO)=NH)methyl.

In another embodiment the present invention relates to compounds of formula (I) or (Ib), in which
  R$^2$ represents tetrahydro-2H-thiopyran-4-yl, piperidin-4-yl, 5,6-dihydroimidazo[1,2-a]pyrazin-7(8H)-yl, phenyl, pyrrol-2-yl, 1H-pyrazol-5-yl, 1H-pyrazol-4-yl, 1,2-oxazol-5-yl, 1,3-thiazol-5-yl, pyridine-3-yl or 6,7-dihydro-5H-pyrrolo[1,2-a]imidazol-3-yl,
    wherein each piperidin-4-yl, phenyl, pyrrol-2-yl, 1H-pyrazol-5-yl, 1H-pyrazol-4-yl, 1,2-oxazol-5-yl or pyridine-3-yl is optionally substituted, one or two times, independently from each other, with
      fluoro, OH, amino, methyl, ethyl, propan-2-yl, hydoxymethyl, 2-fluoroethyl, methoxy, cyclopropyl, ethylsulfonyl, methylsulfanyl or —((SO)=NH)methyl.

In another embodiment the present invention relates to compounds of general formula (I) or (Ib), in which R$^2$ represents 5- to 6-membered heteroaryl, which is optionally substituted, one or two times, independently from each other, with fluoro, chloro, methyl, ethyl, 2,2,-dimethylethyl, cyclopropyl, trifluoromethyl, methoxy, benzyl or methanesulphonyl.

In another embodiment the present invention relates to compounds of formula (I) or (Ib), in which
  R$^2$ represents phenyl, pyrazolyl, thiophenyl or pyridinyl,
    wherein each phenyl, pyrazolyl, thiophenyl or pyridinyl is optionally substituted, one or two times, independently from each other, with
      fluoro, chloro, amino, methyl, ethyl, propan-1-yl, propan-2-yl, tert-butyl, benzyl, fluoroethyl, trifluoromethyl, methoxy, cyclopropyl, methylsulfonyl, methylsulfanyl or —((SO)=NH)methyl.

In another embodiment the present invention relates to compounds of formula (I) or (Ib), in which
  R$^2$ represents phenyl, 1H-pyrazol-4-yl, 1H-pyrazol-5-yl, thiophen-2-yl, thiophen-3-yl, pyridine-3-yl or pyridine-4-yl,
    wherein each phenyl, 1H-pyrazol-4-yl, 1H-pyrazol-5-yl, thiophen-2-yl, thiophen-3-yl, pyridine-3-yl or pyridine-4-yl is optionally substituted, one or two times, independently from each other, with
      fluoro, chloro, amino, methyl, ethyl, propan-1-yl, propan-2-yl, tert-butyl, benzyl, fluoroethyl, trifluoromethyl, methoxy, cyclopropyl, methylsulfonyl, methylsulfanyl or —((SO)=NH)methyl.

In another embodiment the present invention relates to compounds of formula (I) or (Ib), in which
  R$^2$ represents phenyl, 1H-pyrazol-4-yl, 1H-pyrazol-5-yl or pyridine-3-yl,
    wherein each phenyl, 1H-pyrazol-4-yl, 1H-pyrazol-5-yl or pyridine-3-yl is optionally substituted, one or two times, independently from each other, with
      fluoro, amino, methyl, ethyl, propan-1-yl, propan-2-yl, tert-butyl, benzyl, fluoroethyl, trifluoromethyl, methoxy, cyclopropyl, methylsulfonyl, methylsulfanyl or —((SO)=NH)methyl.

In another embodiment the present invention relates to compounds of general formula (I) or (Ib), in which $R^2$ represents 5-membered heteroaryl, which is optionally substituted, one or two times, independently from each other, with chloro, methyl, ethyl, 2,2,-dimethylethyl, cyclopropyl, trifluoromethyl, benzyl, methanesulphonyl.

In another embodiment the present invention relates to compounds of general formula (I) or (Ib), in which $R^2$ represents pyridinyl, thiazolyl, pyrrolyl, thienyl, imidazolyl, pyrazolyl, wherein each pyridinyl, thiazolyl, pyrrolyl, thienyl, imidazolyl, pyrazolyl is optionally substituted, one or two times, independently from each other, with fluoro, chloro, methyl, ethyl, 2,2,-dimethylethyl, cyclopropyl, trifluoromethyl, methoxy, benzyl, methanesulphonyl.

In another embodiment the present invention relates to compounds of formula (I) or (Ib), in which $R^2$ represents a group

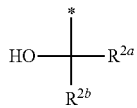

wherein * indicates the point of attachment of said group with the rest of the molecule;
wherein $R^{2a}$ represents $C_1$-$C_4$-alkyl and $R^{2b}$ represents $C_1$-$C_4$-alkyl, $C_3$-$C_6$-cycloalkyl or a 5- to 6-membered heterocycloalkyl group, wherein each $C_1$-$C_4$-alkyl is optionally substituted, independently from each other, one or more times, with fluoro, or
$R^{2a}$ and $R^{2b}$ represent together a $C_3$-$C_6$-cycloalkyl group or a 5- to 6-membered heterocycloalkyl group.

In another embodiment the present invention relates to compounds of formula (I) or (Ib), in which $R^2$ represents a group

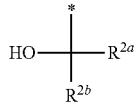

wherein * indicates the point of attachment of said group with the rest of the molecule;
wherein $R^{2a}$ represents methyl and $R^{2b}$ represents $C_1$-$C_4$-alkyl, $C_3$-$C_6$-cycloalkyl or a 5- to 6-membered heterocycloalkyl group or
$R^{2a}$ and $R^{2b}$ represent together a $C_3$-$C_6$-cycloalkyl group or a 5- to 6-membered heterocycloalkyl group.

In another embodiment the present invention relates to compounds of formula (I), in which $R^3$ represents methyl and $R^4$ represents H.

In another embodiment the present invention relates to compounds of formula (I), in which $R^3$ represents H and $R^4$ represents methyl.

In another embodiment the present invention relates to compounds of formula (I), in which $R^3$ represents H and $R^4$ represents H.

In another embodiment the present invention relates to compounds of formula (I), in which $R^3$ represents methyl and $R^4$ represents methyl.

In another embodiment the present invention relates to compounds of formula (I) or (Ib), in which $R^4$ represents H or methyl.

In another embodiment the present invention relates to compounds of formula (I) or (Ib), in which $R^4$ represents H.

In a preferred embodiment the present invention relates to compounds of formula (I) or (Ib), in which $R^4$ represents methyl.

In another preferred embodiment the present invention relates to compounds of formula (I) or (Ib), in which $R^4$ represents methyl in the absolute configuration R.

In another embodiment the present invention relates to compounds of formula (I) or (Ib), in which $R^7$ represents hydrogen and $R^8$ represents hydrogen.

In another embodiment the present invention relates to compounds of formula (I) or (Ib), in which $R^7$ represents hydrogen and $R^8$ represents $C_1$-$C_4$-alkyl.

In another embodiment the present invention relates to compounds of formula (I) or (Ib), in which $R^7$ represents $C_1$-$C_4$-alkyl and $R^8$ represents $C_1$-$C_4$-alkyl.

In another embodiment the present invention relates to compounds of formula (I) or (Ib), in which $R^9$ represents methyl, ethyl, propyl or phenyl optionally substituted with $R^{13}$.

In another embodiment the present invention relates to compounds of formula (I) or (Ib), in which $R^{10}$ represents methyl, ethyl or propyl.

In another embodiment the present invention relates to compounds of formula (I) or (Ib), in which $R^{11}$ represents hydrogen, methyl, ethyl or —(CO)OR$^7$.

In another embodiment the present invention relates to compounds of formula (I) or (Ib), in which $R^{12}$ represents hydrogen, methyl, ethyl or propyl.

In a further embodiment the invention relates to compounds of formula (I) or (Ib), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I) or (Ib), supra.

More particularly still, the present invention covers the title compounds of general formula (I) or (Ib), which are disclosed in the Example section of this text, infra.

In accordance with another aspect, the present invention covers methods of preparing compounds of the present invention, said methods comprising the steps as described below in the schemes 1 to 6 and/or the Experimental Section.

In particular, the present invention covers a method to prepare compounds of general formula 5,

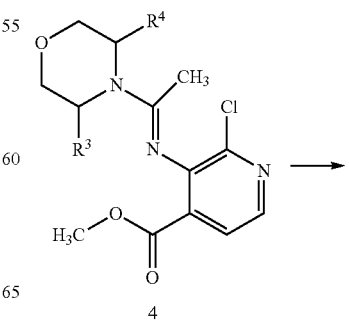

4

-continued

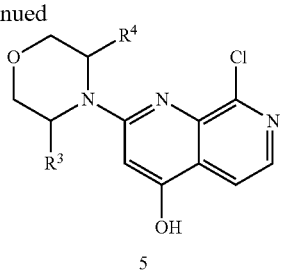

characterized in that compounds of general formula 4, in which $R^3$ and $R^4$ have the same meaning as defined for the compounds of general formula (I) or (Ib) are reacted in an organic solvent at a temperature between −20° C. and the boiling point of the solvent, preferably between −5° C. and 30° C., using a strong base to obtain compounds of general formula (5).

The preparation of compounds of general formula 5 can be performed in an aprotic organic solvent, preferably in tetrahydrofuran or N,N-dimethylformamide.

Preferred strong bases which can be used for the preparation of compounds of general formula 5 are UHMDS, KHMDS, NaHMDS or LDA.

In particular, the present invention covers a method to prepare compounds of general formula 8,

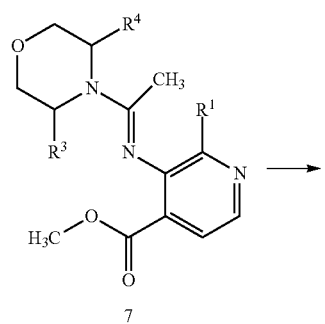

characterized in that compounds of general formula 7, in which $R^1$, $R^3$ and $R^4$ have the same meaning as defined for the compounds of general formula (I) or (Ib) are reacted in an organic solvent at a temperature between −20° C. and the boiling point of the solvent, preferably between −5° C. and 30° C., using a strong base to obtain compounds of general formula (8).

The preparation of compounds of general formula 8 can be performed in an aprotic organic solvent, preferably in tetrahydrofuran or N,N-dimethylformamide.

Preferred strong bases which can be used for the preparation of compounds of general formula 8 are UHMDS, KHMDS, NaHMDS or LDA.

In accordance with a further aspect, the present invention covers intermediate compounds which are useful in the preparation of compounds of the present invention of general formula (I) or (Ib), particularly in the methods described herein. In particular, the present invention covers compounds of general formula 5,

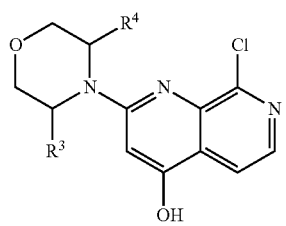

in which $R^3$ and $R^4$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 8,

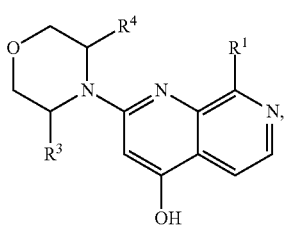

in which $R^1$, $R^3$ and $R^4$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 9,

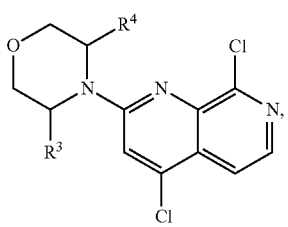

in which $R^3$ and $R^4$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 11,

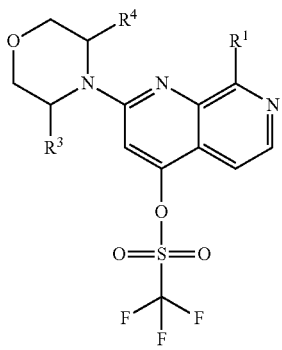

11 in which $R^1$, $R^3$ and $R^4$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 12,

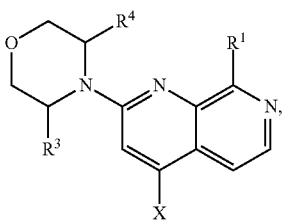

12 in which $R^1$, $R^3$ and $R^4$ are as defined for the compound of general formula (I) or (Ib), supra, and X is chloro, bromo or iodo.

In accordance with a further aspect, the present invention covers intermediate compounds which are useful in the preparation of compounds of the present invention of general formula (I) or (Ib), particularly in the methods described herein. In particular, the present invention covers compounds of general formula 15,

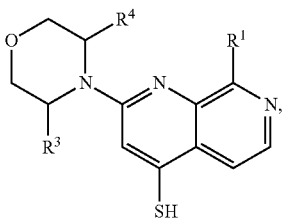

15 in which $R^1$, $R^3$ and $R^4$ are as defined for the compound of general formula (I) or (Ib) supra.

In accordance with a further aspect, the present invention covers intermediate compounds which are useful in the preparation of compounds of the present invention of general formula (I) or (Ib), particularly in the methods described herein. In particular, the present invention covers compounds of general formula 16,

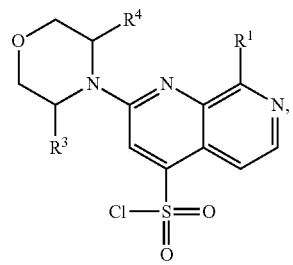

16 in which $R^1$, $R^3$ and $R^4$ are as defined for the compound of general formula (I) or (Ib) supra.

In accordance with a further aspect, the present invention covers intermediate compounds which are useful in the preparation of compounds of the present invention of general formula (Ib), particularly in the methods described herein. In particular, the present invention covers compounds of general formula 39,

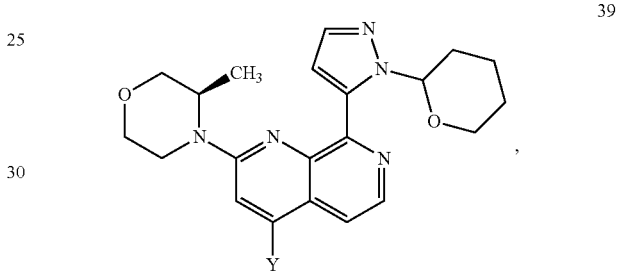

39 in which Y represents OH, $-O-SO_2-CF_3$, Cl, Br, I, SH or $-SO_2Cl$, preferably OH, $-O-SO_2-CF_3$ or Cl.

In accordance with a further aspect, the present invention covers intermediate compounds which are useful in the preparation of compounds of the present invention of general formula (I) or (Ib), particularly in the methods described herein. In particular, the present invention covers compounds of formula

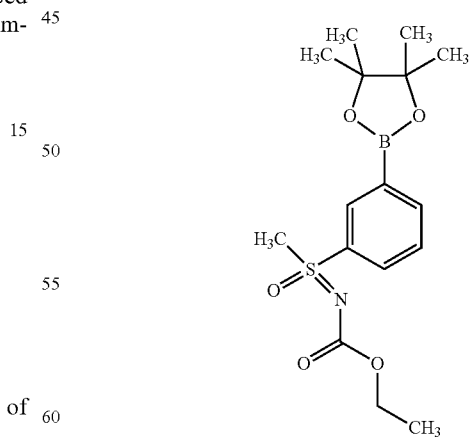

(also referred to as 4,4,5,5-tetramethyl-(3-(N-(ethoxycarbonyl)-S-methylsulfonimidoyl)phenyl)-1,3,2-dioxaborolan).

In accordance with a further aspect, the present invention covers intermediate compounds which are useful in the preparation of compounds of the present invention of general formula (I) or (Ib), particularly in the methods described herein. In particular, the present invention covers compounds of formula

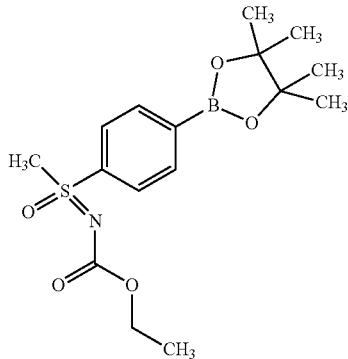

(also referred to as 4,4,5,5-tetramethyl-(4-(N-(ethoxycarbonyl)-S-methylsulfonimidoyl)phenyl)-1,3,2-dioxaborolane).

In accordance with yet another aspect, the present invention covers the use of the intermediate compounds of general formula 5,

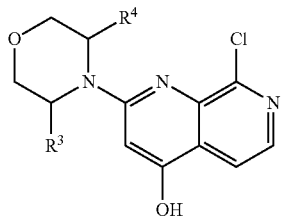

in which $R^3$ and $R^4$ are as defined for the compound of general formula (I) or (Ib) supra, for the preparation of a compound of general formula (I) or (Ib) as defined supra.

In accordance with yet another aspect, the present invention covers the use of the intermediate compounds of general formula 8,

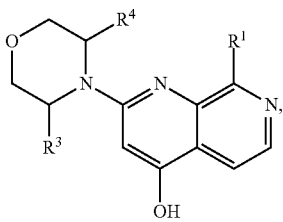

in which $R^1$, $R^3$ and $R^4$ are as defined for the compound of general formula (I) or (Ib) supra, for the preparation of a compound of general formula (I) or (Ib) as defined supra.

In accordance with yet another aspect, the present invention covers the use of the intermediate compounds of general formula 9,

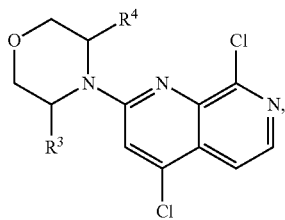

in which $R^3$ and $R^4$ are as defined for the compound of general formula (I) or (Ib) supra, for the preparation of a compound of general formula (I) or (Ib) as defined supra.

In accordance with yet another aspect, the present invention covers the use of the intermediate compounds of general formula 11,

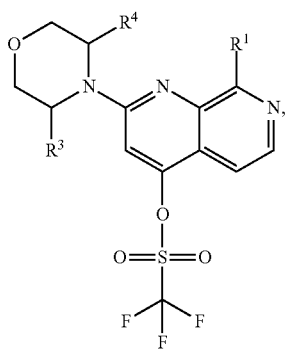

in which $R^1$, $R^3$ and $R^4$ are as defined for the compound of general formula (I) or (Ib) supra, for the preparation of a compound of general formula (I) or (Ib) as defined supra.

In accordance with yet another aspect, the present invention covers the use of the intermediate compounds of general formula 12,

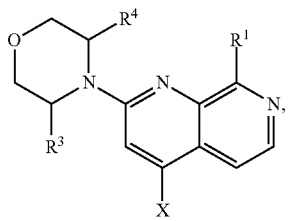

in which $R^1$, $R^3$ and $R^4$ are as defined for the compound of general formula (I) or (Ib), supra, and X is chloro, bromo or iodo, for the preparation of a compound of general formula (I) or (Ib) as defined supra.

In accordance with yet another aspect, the present invention covers the use of the intermediate compounds of general formula 15,

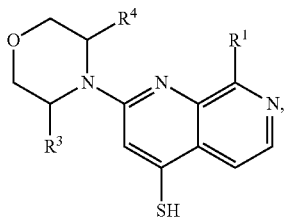

15 in which R¹, R³ and R⁴ are as defined for the compound of general formula (I) or (Ib) supra, for the preparation of a compound of general formula (I) or (Ib) as defined supra.

In accordance with yet another aspect, the present invention covers the use of the intermediate compounds of general formula 16,

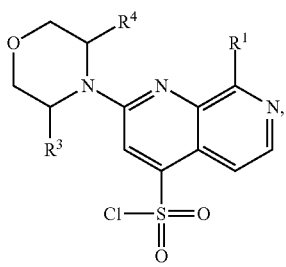

16 in which R¹, R³ and R⁴ are as defined for the compound of general formula (I) or (Ib) supra, for the preparation of a compound of general formula (I) or (Ib) as defined supra.

In accordance with yet another aspect, the present invention covers the use of the intermediate compounds of general formula 39,

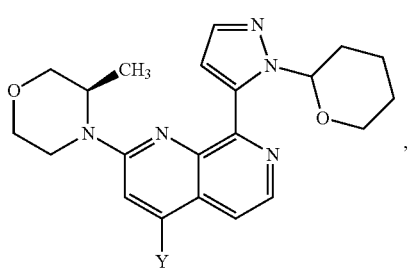

39 in which Y represents OH, —O—SO₂—CF₃, Cl, Br, I, SH or —SO₂Cl, preferably OH, —O—SO₂—CF₃ or Cl for the preparation of a compound of general formula (I) or (Ib) as defined supra.

The compounds of general formula (I) or (Ib) according to the invention show a valuable spectrum of action which could not have been predicted. They are therefore suitable for use as medicaments for the treatment and/or prophylaxis of diseases in humans and animals.

In particular, said compounds of the present invention have surprisingly been found to effectively inhibit ATR kinase and may therefore be used for the treatment or prophylaxis of diseases mediated by ATR kinase, in particular hyperproliferative diseases.

The present invention relates to a method for using the compounds and/or pharmaceutical compositions of the present invention, to treat diseases, in particular hyperproliferative diseases. Compounds can be utilized to inhibit, block, reduce, decrease, etc., cell proliferation and/or cell division, and/or produce apoptosis. This method comprises administering to a mammal in need thereof, in particular a human, an amount of a compound of this invention which is effective to treat the disease. Hyperproliferative diseases include but are not limited to, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those diseases also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These diseases have been well characterized in humans, but also exist with a similar etiology in other mammals, and can be treated by administering compounds or pharmaceutical compositions of the present invention.

The present invention relates to the treatment of hyperproliferative diseases with deficient ATM signaling and/or p53 function, in particular of lung carcinoma, in particular small-cell lung cancer, colorectal cancer, bladder cancer, lymphomas, gliomas, and ovarian cancer.

In particular, the present invention relates to the treatment of lung carcinoma, in particular small-cell lung cancer, colorectal cancer, bladder cancer, lymphomas, in particular diffuse large B-cell lymphoma (DLBC) and mantle cell lymphoma (MCL), prostate cancer, in particular castration-resistant prostate cancer, gliomas, and ovarian cancer The present invention further provides for the use of the compounds of general formula (I) or (Ib) and/or of the pharmaceutical compositions of the present invention for the production of a medicament for the treatment and/or prophylaxis of diseases, especially of the aforementioned diseases, in particular of a hyperproliferative disease.

A further subject matter of the present invention is the use of the compounds of general formula (I) or (Ib) and/or of the pharmaceutical compositions of the present invention in the manufacture of a medicament for the treatment and/or prophylaxis of disorders, in particular the disorders mentioned above.

The present invention furthermore relates to the compounds of general formula (I) or (Ib) for use in a method for the treatment and/or prophylaxis of a disease, in particular of a hyper-proliferative disease.

The present invention further provides a method for treatment and/or prophylaxis of diseases, especially the aforementioned diseases, in particular of a hyperproliferative disease, using an effective amount of the compounds of general formula (I) or (Ib) and/or of the pharmaceutical compositions of the present invention.

The present invention further provides the compounds of general formula (I) or (Ib) and/or of the pharmaceutical compositions of the present invention for use in the treatment and/or prophylaxis of diseases, especially of the aforementioned diseases, in particular of a hyperproliferative disease. The present invention further provides the compounds of general formula (I) or (Ib) and/or of the pharmaceutical compositions of the present invention for use in a method for treatment and/or prophylaxis of the aforementioned diseases, in particular of a hyperproliferative disease.

The present invention further provides a pharmaceutical composition comprising the compound of general formula (I) or (Ib), or a stereoisomer, a tautomer, an N-oxide, a hydrate, a solvate, or a salt thereof, particularly a pharmaceutically acceptable salt thereof, or a mixture of same, with one or more excipient(s), in particular pharmaceutically suitable excipients, which are inert and nontoxic. Conventional procedures for preparing such pharmaceutical compositions in appropriate dosage forms can be utilized.

The present invention furthermore relates to pharmaceutical compositions, in particular medicaments, which comprise at least one compound according to the invention, conventionally together with one or more pharmaceutically suitable excipient, and to their use for the above mentioned purposes.

Pharmaceutically acceptable excipients are non-toxic, preferably they are non-toxic and inert. Pharmaceutically acceptable excipients include, inter alia,
- fillers and excipients (for example cellulose, microcrystalline cellulose, such as, for example, Avicel®, lactose, mannitol, starch, calcium phosphate such as, for example, Di-Cafos®),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat)
- solvents (for example water, ethanol, Isopropanol, glycerol, propylene glycol, medium chain-length triglycerides fatty oils, liquid polyethylene glycols, paraffins),
- surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxethylene fatty acid esters, polyoxyethylene fatty alcohol ethers, glycerol fatty acid esters, poloxamers such as, for example, Pluronic®),
- buffers and also acids and bases (for example phosphates, carbonates, citric acid, acetic acid, hydrochloric acid, sodium hydroxide solution, ammonium carbonate, trometamol, triethanolamine)
- isotonicity agents (for example glucose, sodium chloride),
- adsorbents (for example highly-disperse silicas)
- viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine),
- disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®),
- flow regulators, lubricants, glidant and mould release agents (for example magnesium stearate, stearic acid, talc, highly-disperse silicas such as, for example, Aerosil®),
- coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®),
- capsule materials (for example gelatine, hydroxypropylmethylcellulose),
- synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and blockcopolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide), flavourings, sweeteners, flavour- and/or odour-masking agents.

Further excipients and procedures are described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

The present invention furthermore relates to a pharmaceutical combination, in particular a medicament, comprising at least one compound according to the invention and at least one or more further active ingredients, in particular for the treatment and/or prophylaxis of the above mentioned diseases.

The present invention further provides a pharmaceutical combination comprising:
one or more active ingredients selected from a compound of general formula (I) or (Ib), and
one or more active ingredients selected from antihyperproliferative, cytostatic or cytotoxic substances for treatment of cancers.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein, for example, a first active ingredient and a second active ingredient are present together in one unit dosage or in a single entity. One example of a "fixed combination" is a pharmaceutical composition wherein a first active ingredient and a second active ingredient are present in admixture for simultaneous administration, such as in a formulation. Another example of a "fixed combination" is a pharmaceutical combination wherein a first active ingredient and a second active ingredient are present in one unit without being in admixture.

A non-fixed combination or "kit-of-parts" in the present invention is used as known to persons skilled in the art and is defined as a combination wherein a first active ingredient and a second active ingredient are present in more than one unit. One example of a non-fixed combination or kit-of-parts is a combination wherein the first active ingredient and the second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutically active ingredients where the combination causes no unacceptable adverse effects. The present invention relates also to such pharmaceutical combinations. For example, the compounds of this invention can be combined with known chemotherapeutic agents and/or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

For example, the compounds of the present invention can be combined with known antihyperproliferative, cytostatic or cytotoxic substances for treatment of cancers.

Examples of suitable antihyperproliferative, cytostatic or cytotoxic combination active ingredients include:
131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta(methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

In a preferred embodiment the pharmaceutical combination of the present invention comprises
a compound of general formula (I) or (Ib), and
one or more active ingredients selected from carboplatin and cisplatin.

Generally, the use of antihyperproliferative, cytostatic or cytotoxic combination active ingredients in combination with a compound or pharmaceutical composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

In addition, the compounds of general formula (I) can also be used in combination with radiotherapy and/or surgical intervention.

In a further embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In another embodiment of the present invention, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

The compounds of general formula (I) or (Ib) can act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds of general formula (I) or (Ib) can be administered in administration forms suitable for these administration routes.

Suitable administration forms for oral administration are those which release the compounds of general formula (I) or (Ib) in a rapid and/or modified manner, work according to the prior art and contain the compounds of general formula (I) or (Ib) in crystalline and/or amorphous and/or dissolved form, for example tablets (uncoated or coated tablets, for example with enteric or retarded-dissolution or insoluble coatings which control the release of the compound of general formula (I) or (Ib)), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbal route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are pharmaceutical forms for inhalation or inhalation medicaments (including powder inhalers, nebulizers), nasal drops, solutions or sprays; tablets, films/wafers or capsules for lingual, sublingual or buccal administration, films/wafers or capsules, suppositories, ear or eye preparations (for example eye baths, ocular insert, ear drops, ear powders, ear-rinses, ear tampons), vaginal capsules, aqueous suspensions (lotions, shaking mixtures), lipophilic suspensions, ointments, creams, transdermal therapeutic systems (for example patches), milk, pastes, foams, dusting powders, implants, intrauterine coils, vaginal rings or stents.

The compounds of general formula (I) or (Ib) can be converted to the administration forms mentioned. This can be done in a manner known per se, by mixing with pharmaceutically suitable excipients.

These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

Pharmaceutically acceptable excipients are non-toxic, preferably they are non-toxic and inert. Pharmaceutically acceptable excipients include, inter alia: fillers and excipients (for example cellulose, microcrystalline cellulose, such as, for example, Avicel®, lactose, mannitol, starch, calcium phosphate such as, for example, Di-Cafos®), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat)

solvents (for example water, ethanol, Isopropanol, glycerol, propylene glycol, medium chain-length triglycerides fatty oils, liquid polyethylene glycols, paraffins), surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxethylene fatty acid esters, polyoxyethylene fatty alcohol ethers, glycerol fatty acid esters, poloxamers such as, for example, Pluronic®), buffers and also acids and bases (for example phosphates, carbonates, citric acid, acetic acid, hydrochloric acid, sodium hydroxide solution, ammonium carbonate, trometamol, triethanolamine)

isotonicity agents (for example glucose, sodium chloride), adsorbents (for example highly-disperse silicas)

viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine), disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®), flow regulators, lubricants, glidant and mould release agents (for example magnesium stearate, stearic acid, talc, highly-disperse silicas such as, for example, Aerosil®), coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®), capsule materials (for example gelatine, hydroxypropylmethylcellulose), synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention further provides medicaments which comprise at least one compound of general formula (I) or (Ib), typically together with one or more inert, non-toxic, pharmaceutically suitable excipients, and the use thereof for the aforementioned purposes.

Based upon standard laboratory techniques known to evaluate compounds useful for the treatment of hyperproliferative diseases by standard toxicity tests and by standard pharmacological assays for the determination of treatment of the conditions identified above in mammals, and by comparison of these results with the results of known active ingredients or medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are, unless indicated otherwise, percentages by weight; parts are parts by weight. Solvent ratios, dilution ratios and concentration data for liquid/liquid solutions are based in each case on volume.

Syntheses of Compounds (Overview):

The compounds of the present invention can be prepared as described in the following section. The schemes and the procedures described below illustrate general synthetic routes to the compounds of general formula (I) of the invention and are not intended to be limiting. It is clear to the person skilled in the art that the order of transformations as exemplified in the schemes can be modified in various ways. The order of transformations exemplified in the schemes is therefore not intended to be limiting. In addition, interconversion of any of the substituents can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example P. G. M. Wuts and T. W. Greene in "Protective Groups in Organic Synthesis", 4$^{th}$ edition, Wiley 2006). Specific examples are described in the subsequent paragraphs. Further, it is possible that two or more successive steps may be performed without work-up being performed between said steps, e.g. a "one-pot" reaction, as is well-known to the person skilled in the art.

The syntheses of the 2-(morpholin-4-yl)-1,7-naphthyridine derivatives according to the present invention are preferably carried out according to the general synthetic sequence, shown in schemes 1-6.

Scheme 1

Route for the preparation of compounds of general formula 8, wherein R$^1$, R$^3$ and R$^4$ have the meaning as given for general formula (I), supra and R has the meaning as alkyl. In addition, the substituents R$^1$ can bear a protecting group and the interconversion of any of the substituents R$^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

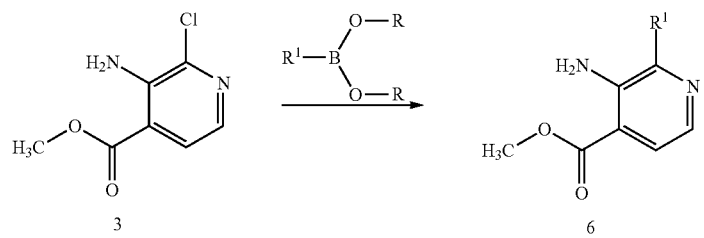

3            6

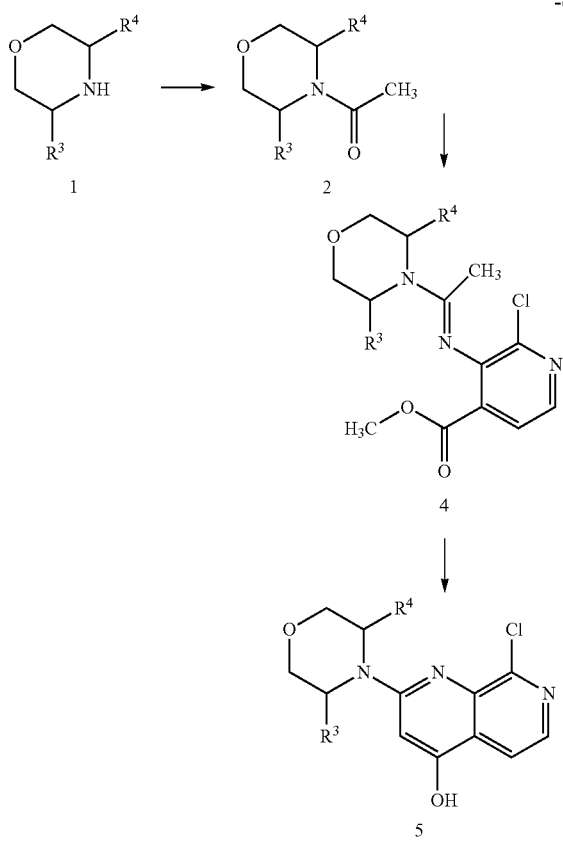
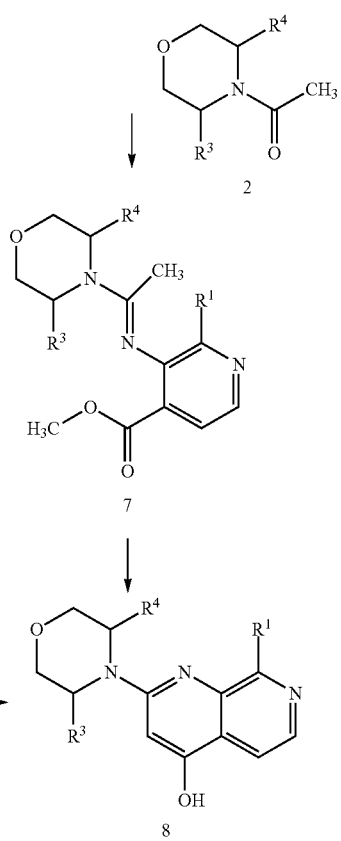

The starting material methyl 3-amino-2-chloropyridine-4-carboxylate 3 (CAS No: 173435-41-1) is commercially available or can be prepared according to a literature procedure (see *Journal of Heterocyclic Chemistry*, 38(1), 99-104; 2001).

Step 1→2 (Scheme 1)
Amide Formation

In the first step (scheme 1), morpholine derivative 1 (which is commercially available or described in the literature) can be converted to the corresponding acetamide 2 using an acetylating agent. The starting morpholine could either be used as a salt (e.g. HCl salt) or as the free amine.

For example the morpholine 1 can be acetylated using acetyl chloride in an organic solvent such as dichloromethane in the presence of a base such as $K_2CO_3$. The acetylation can also be performed using acetic anhydride in pyridine. Alternatively, acetic acid, a base and an activating reagent generating an active ester in situ in an organic solvent can be used for the transformation. For a review see: C. A. G. N. Montalbetti and V. Falque *Tetrahedron* 2005, 61, 10827-10852 and references therein).

Step 3→4 (Scheme 1)
Amidine Formation

Methyl 3-amino-2-chloropyridine-4-carboxylate 3 is reacted with morpholine amide of formula 2 in an amidine forming reaction to give compounds of the general formula 4. Typically the reaction is performed with $POCl_3$ neat or in an organic solvent at a temperature range between 0° C. and the boiling point of the selected solvent. Preferably a halogenated solvent such as chloroform, DCE or DCM is used for the reaction.

Step 4→5 (Scheme 1)
Naphthyridine Formation

The amidines of formula 4 can be converted to the corresponding 2-(morpholin-4-yl)-1,7-naphthyridines of formula 5. Typically the reaction is performed in an organic solvent at a temperature between −20° C. and the boiling point of the selected solvent using a strong base. Preferably LiHMDS, KHMDS, NaHMDS or LDA are used as base.

Step 5→8 (Scheme 1)
Palladium Catalyzed Reaction with Boronic Acids

The chloronaphthyridines of formula 5 can be reacted with a boronic acid derivative $R^1$—$B(OR)_2$ to give a compound of formula 8. The boronic acid derivative may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—). The NH groups of the heterocycle $R^1$ of the boronic acid derivatives may be masked by any suitable protecting group (see Green, Wuts, "*Protective groups in organic synthesis*" 1999, John Wiley & Sons and references cited therein). The corresponding protective group may be removed at any suitable step of the synthesis. Preferably THP (tetrahydropyranyl), BOC (tert-Butoxycarbonyl) or PMB (para-Methoxybenzyl) are used as protective groups during the synthesis.

The coupling reaction is catalyzed by palladium catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis (triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

The steps for the synthesis sequence giving rise to naphthyridines of formula 8 may be also interchanged using similar reaction conditions for each step as described above. For example:
3→6→7→8

Step 8→10 (Scheme 2)
Transformation of Hydroxy to Chloro Substituent

In the next step, the hydroxy-naphthyridine of formula 8 is converted to the corresponding chloro-naphthyridine 10. This reaction is typically performed using $POCl_3$ without any additional solvent. The reaction is typically carried out at elevated temperatures.

The steps for the synthesis sequence giving rise to naphthyridines of formula 10 may also be interchanged using similar reaction conditions for each step as described above. For example:
5→9→10

Step 8→11 (Scheme 2)
Triflate Formation

The hydroxy-naphthyridine of the general formula 8 can be converted to the corresponding triflate of formula 11. Typically the hydroxy-naphthyridine 8 is reacted with a triflating reagent such as for example N-Phenylbis(trifluoromethanesulfonimide) with or without a base in an organic solvent such as for example dichloromethane.

Scheme 2

Route for the preparation of compounds of general formula 10 and 11, wherein $R^1$, $R^3$ and $R^4$ have the meaning as given for general formula (I), supra and R has the meaning as alkyl. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

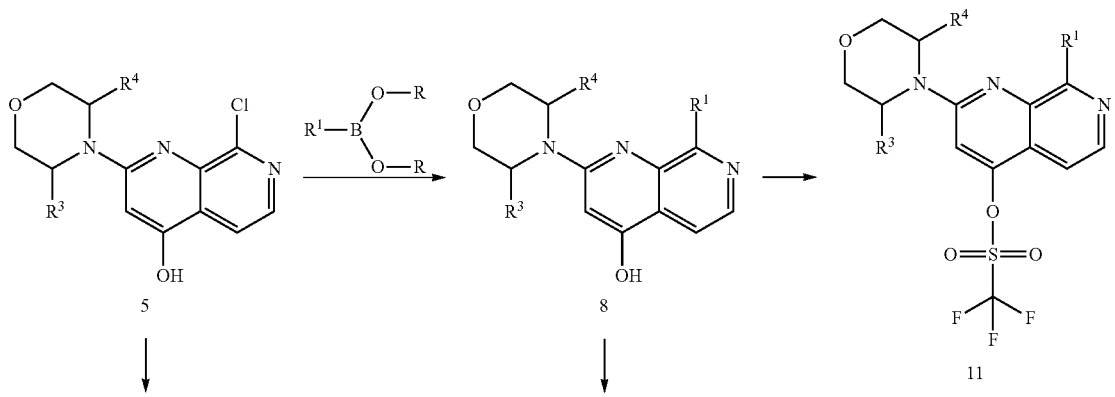

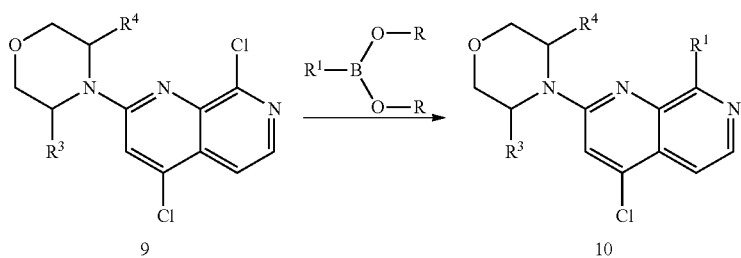

Scheme 3

Route for the preparation of compounds of general formula 12, 13, 18, 19 and 20, wherein $R^1$, $R^3$, $R^4$, $R^7$, $R^8$ and $R^9$ have the meaning as given for general formula (I), supra and R″ has meaning as $C_1$—$C_6$-alkyl or 3- to 10-membered heterocycloalkyl. In addition, the substituents $R^1$ can bear a protecting group and the interconversion of any of the substituents $R^1$ can be achieved before and/or after the exemplified transformations.
These modifications can besuch as the introduction of protecting groups or cleavage of protecting groups.
Appropriate protecting groups and their introduction and cleavage are well-known to the person skilled in the art
(see for example T.W. Greene and P.G.M. Wuts in Protective Groups in Organic Synthesis, 3rd edition, Wiley 1999).
Specific examples are described in the subsequent paragraphs.

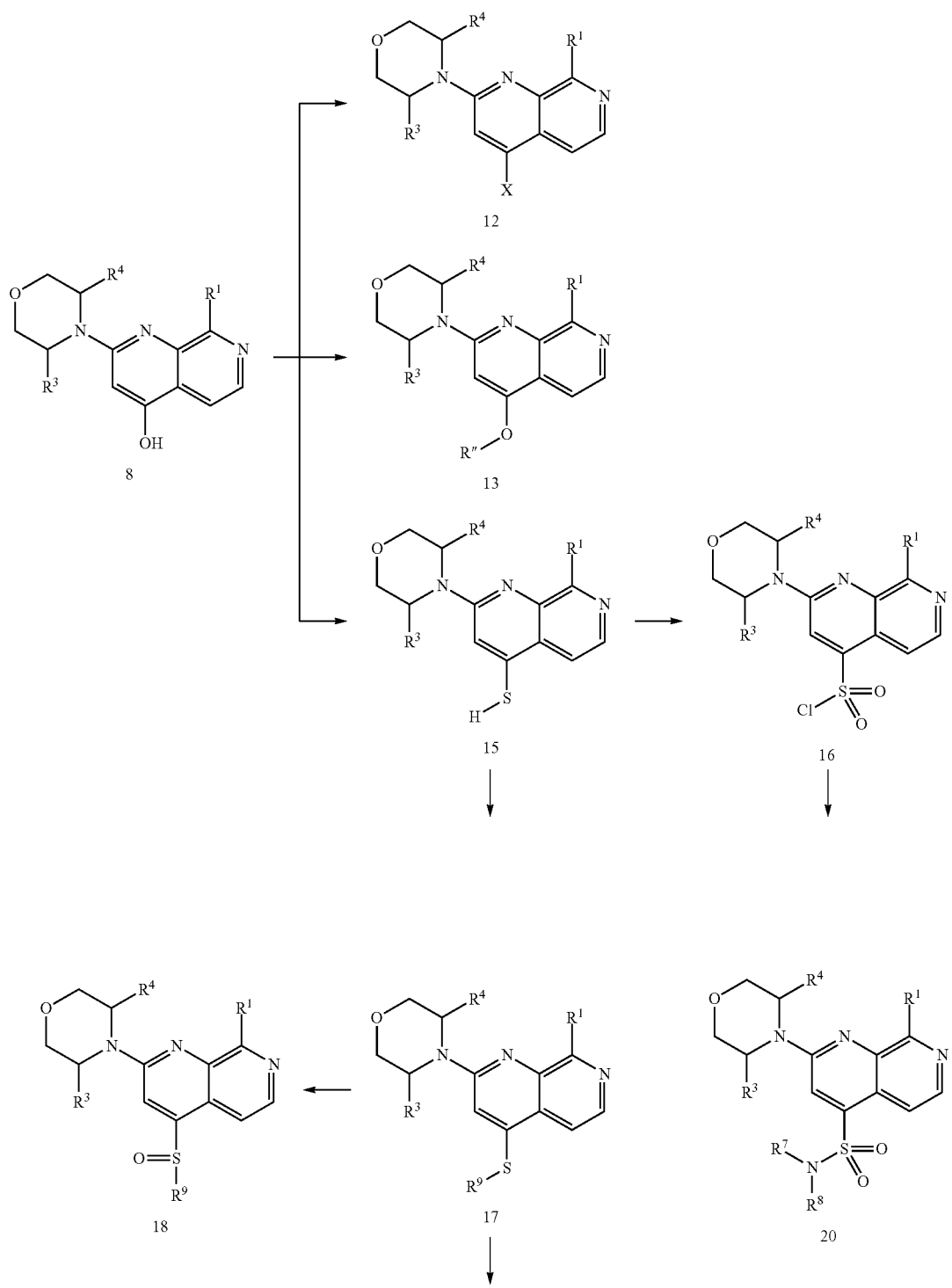

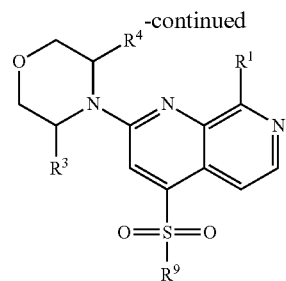

19

X = Cl, Br, I

Step 8→12 (Scheme 3)
Conversion of Hydroxy to Halogen (F, Br, Cl, I)

The transformation of hydroxy-naphthyridine 8 to a halogen compound of formula 12 can be performed (for halogen=Cl) for example using chlorinating reagents such as trichlorophosphate with or without an organic solvent. Typically the reactions are performed at elevated temperatures. For halogen=Br reagents such as phosphorus tribromide or phosphorus oxytribromide can be used. For halogen=F see for example *J. of Org. Chem.,* 2013, 78, 4184-4189. For halogen=I see for example *Journal of Organic Chemistry,* 2009, 74, 5111-5114 and references therein.

Step 8→13 (Scheme 3)
Conversion of Hydroxy to Ethers

Hydroxy-naphthyridines of formula 8 can be converted to the corresponding ether of general formula 13, in which R" is $C_1$-$C_6$-alkyl or 3- to 10-membered heterocycloalkyl. The reaction is performed using halides (preferably Cl, Br or I), tosylates, mesylates or triflates. This reaction is performed in a solvent such as for example acetonitrile, DMF or a 1:1 mixture of methanol and water. The reaction is performed in the presence of a base such as for example $CsCO_3$ or $K_2CO_3$. The reaction is performed at temperatures ranging from room temperature to the boiling point of the respective solvent. Furthermore, the reaction can be performed at temperatures above the boiling point under pressure. The reaction is preferably completed after 1 to 16 hours.

Alternatively, the ether of general formula 13 can be synthesized via a Mitsunobu reaction from an alcohol in the presence of a phosphine (such as for example triphenylphoshine) and an azodicarboxylate (e.g. diisopropyl azodicarboxylate) in a solvent such as for example THF.

Step 8→15 (Scheme 3)
Conversion of Hydroxy to Thiol

For the conversion of hydroxy-naphthyridines of formula 8 to thiols of formula 15 for example Lawesson's reagent or diphosphorus pentasulfide in an organic solvent can be used. Typically these reactions are run at elevated temperatures.

Step 15→20 (Scheme 3)
Conversion of Thiol to Sulfonamide

Thiols of general formula 15 can be converted to the corresponding sulfonamides 20 via the intermediate sulfonylchlorides of formula 16 in analogy to literature procedures. For example see European J. of Medicinal Chemistry 2013, 60, 42-50 and references therein.

Step 15→17 (Scheme 3)
Conversion of Thiol to Thioether

Thiols of formula 15 can be alkylated to the corresponding thioethers 17. The reaction is performed using alkyl halides (preferably Cl, Br or I), tosylates, mesylates, or triflates. This reaction is performed in a solvent such as for example acetonitrile, DMF or a 1:1 mixture of methanol and water. The reaction is performed in the presence of a base such as for example $CsCO_3$ or $K_2CO_3$. The reaction is performed at temperatures ranging from room temperature to the boiling point of the respective solvent. Furthermore, the reaction can be performed at temperatures above the boiling point under pressure. The reaction is preferably completed after 1 to 16 hours.

Step 17→18 (Scheme 3)
Conversion of Thioether to Sulfoxide

Thioethers of formula 17 can be oxidized to the corresponding sulfoxides 18. Typically an oxidizing reagent in an organic solvent is used (for example 3-chloro-benzenecarboperoxoic acid in dichloromethane).

Step 17→19 (Scheme 3)
Conversion of Thioether to Sulfone

Thioethers of general formula 17 can be oxidized to the corresponding sulfoxides 19. Typically an oxidizing reagent in an organic solvent is used (for example 3-chloro-benzenecarboperoxoic acid in dichloromethane).

Scheme 4

Route for the preparation of compounds of general formula 17, 19, 21, 23, 24, 26 and 27, wherein $R^1$, $R^3$, $R^4$, $R^7$, $R^8$ and $R^9$ have the meaning as given for general formula (I), supra. The group A represents $C_2$—$C_6$-alkenyl, $C_5$—$C_6$-cycloalkenyl or 4- to 10-membered heterocycloalkenyl and the group D represents $C_2$—$C_6$-alkyl, $C_5$—$C_6$-cycloalkyl or 4- to 10-membered heterocycloalkyl. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

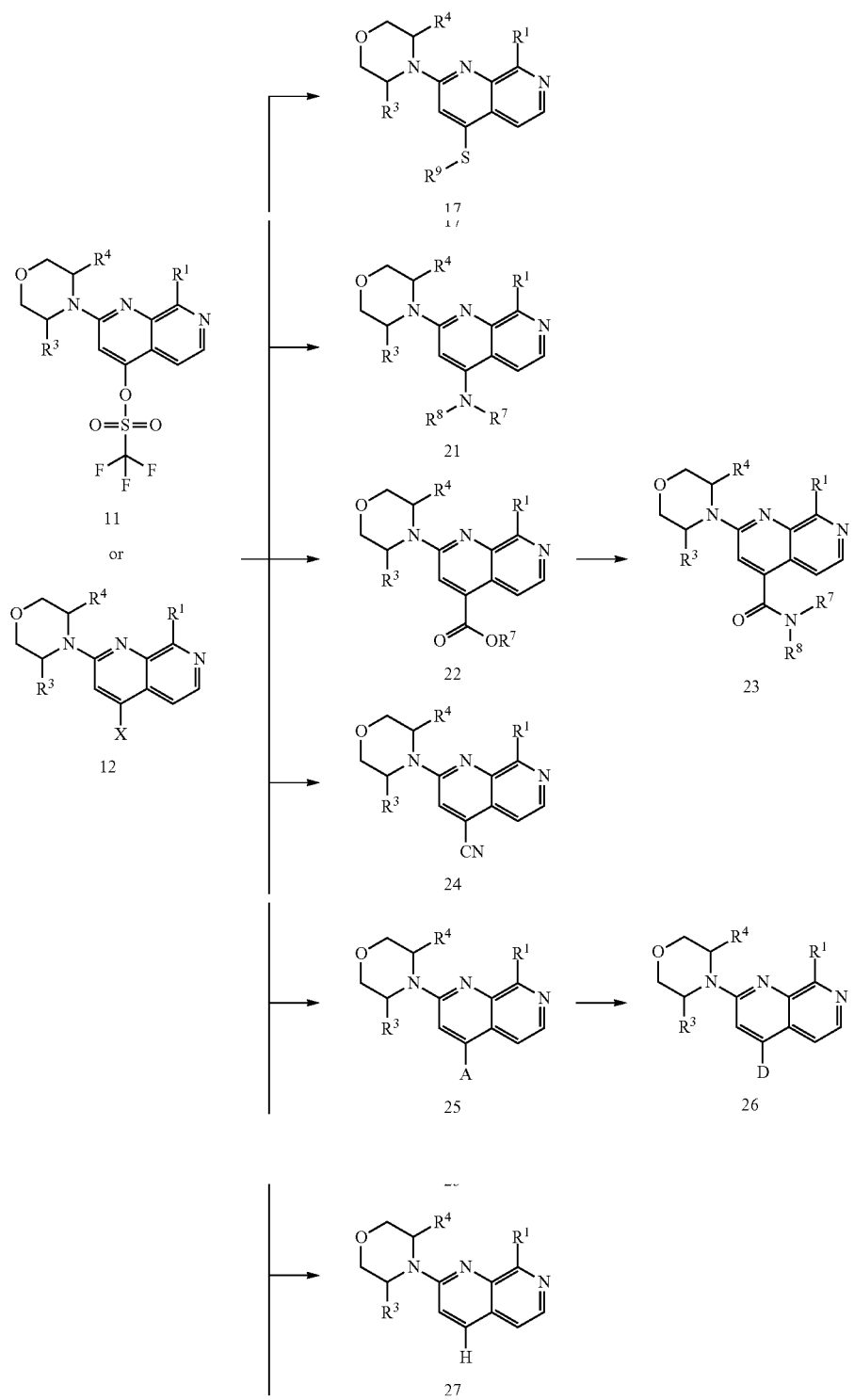

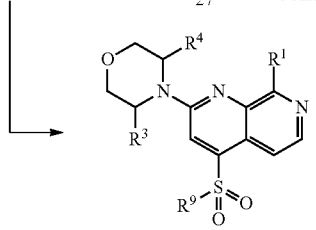

19

X = Cl, Br, I

Step 12→17 (Scheme 4)
Conversion to Thioether

Halogen compounds of the general formula 12 can be converted to the corresponding thioethers of general formula 17 by nucleophilic substitution with thiols. Typically a base such as for example KOtBu, NaH, caesium carbonate, potassium carbonate in an organic solvent such as for example tert-butanol, DMSO or DMF are used. Typically the reaction is performed at elevated temperature. See for example: *Journal of Medicinal Chemistry,* 2008, 51, 3466-3479 and references therein.

Step 11 or 12→21 (Scheme 4)
C—N Cross Coupling Reaction or Nudeophilic Substitution Halogen compounds of general formula 12 or triflates of general formula 11 can be converted to the corresponding amines 21 by a C—N cross coupling reaction. Typically a metal catalyst, a ligand and a base in an organic solvent is used. For a recent review see for example: Chem. Soc. Rev., 2013, 42, 9283 or *"Metal-Catalyzed Cross-Coupling Reactions* (2 Volume Set)", 2004 by Armin de Meijere (Editor), Franyois Diederich (Editor) and literature references therein.

Alternatively halogen compound of general formula 12 can be converted to the corresponding amines 21 via a nucleophilic substitution reaction. Typically nucleophilic amines in combination with a base (for example triethylamine, Hünig's base, potassium carbonate) in an organic solvent (for example iPrOH, DCM, DMSO, DMF) are used. See for example: *Bioorganic and Medicinal Chemistry Letters,* 2011, 21, 5502-5505 and references therein.

Step 11 or 12→22 (Scheme 4)
Hydrocarbonylation

Halogen compounds of general formula 12 or triflates of general formula 11 can be converted to the corresponding esters 22 by a metal catalyzed carbonylation reaction. Typically carbonmonoxide and a palladium catalyst with or without a ligand (for example: palladium acetate/1,3-bis-(diphenylphosphino)propane; bis-triphenylphosphine-palladium(II) chloride/-triphenyiphosphine), an alcohol as nucleophile (for example: methanol, ethanol) in an organic solvent (for example: DMF, methanol, ethanol) is used. See for example: *Journal of Medicinal Chemistry,* 2008, 51, 1649-1667 or *Synthesis,* 2001, 7, 1098-1109 and references therein.

Step 22-23 (Scheme 4)
Amide Formation

Esters of general formula 22 can be converted to the corresponding amides of general formula 23. Typically an amine is reacted in combination with a base (as for example sodium hydroxide or magnesium methanolate) in a solvent (as for example methanol, isopropanol, water). Alternatively the ester 22 can be reacted with an amine and n-butyllithium or trimethylaluminum in an organic solvent (such as for example THF, toluene) to form amides of formula 23. See for example *Chem. Commun.,* 2008, 1100-1102 and references therein.

Alternatively the ester of general formula 22 can be hydrolyzed to the corresponding carboxylic acid (using for example KOH, water, methanol as ester hydrolysis conditions) and reacted further to the corresponding amides 23 under classical amide coupling conditions. For a review for amide coupling conditions using the free carboxylic acid and an amine in combination with an activating agent see for example *Chem. Soc. Rev.,* 2009, 38, 606-631 and references therein.

Step 11 or 12→24 (Scheme 4)
Nitrile Formation

Halogen compounds of general formula 12 or triflates of general formula 11 can be converted to the corresponding nitriles 24. Typically a palladium catalyst and a ligand (such as for example 1,1'-bis-(diphenylphosphino)ferrocene/tris-(dibenzylideneacetone)dipalladium(0)), zinc (II) cyanide in solvent (such as for example N,N-dimethyl acetamide/water) is used. See for example *Tetrahedron Letters,* 2006, 47, 3303-3305 and references therein.

Step 11 or 12→25 (Scheme 4)
C—C Cross Coupling Reaction

Halogen compounds of general formula 12 or triflates of general formula 11 can be reacted with a boronic acid derivative A-B(OR)$_2$ to give a compound of formula 25. The group A represents $C_1$-$C_6$-alkyl, $C_2$-$C_6$-alkenyl, $C_3$-$C_6$-cycloalkyl, 3- to 10-membered heterocycloalkyl, 4- to 10-membered heterocycloalkenyl, phenyl, heteroaryl. The boronic acid derivative may be a boronic acid (R═—H) or an ester of the boronic acid, e.g. its isopropyl ester (R═—CH(CH$_3$)$_2$), preferably an ester derived from pinacol in which the boronic acid intermediate forms a 2-aryl-4,4,5,5-tetramethyl-1,3,2-dioxaborolane (R—R═—C(CH$_3$)$_2$—C(CH$_3$)$_2$—). The group A of the boronic acid derivatives may be masked by any suitable protecting group (see Green, Wuts, *"Protective groups in organic synthesis"* 1999, John Wiley & Sons). The corresponding protective group may be removed at any suitable step of the synthesis.

The coupling reaction is catalyzed by palladium catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature to the boiling point of the solvent. Further on, the reaction can be performed at temperatures above the boiling point under pressure. The reaction is preferably completed after 1 to 36 hours.

Step 25→26 (Scheme 4)

Hydrogenation of Double Bond

Unsaturated derivatives of formula 25 (wherein the group A represents C$_2$-C$_6$-alkenyl, C$_5$-C$_6$-cycloalkenyl, 4- to 10-membered heterocycloalkenyl). can be hydrogenated to the corresponding saturated derivatives of general formula 26 (wherein the group D represents C$_2$-C$_6$-alkyl, C$_5$-C$_6$-cycloalkyl, 4- to 10-membered heterocycloalkyl). Typically hydrogen (at atmospheric or elevated pressure) is used in combination with a heterogeneous or homogeneous catalyst such as for example palladium on charcoal in an organic solvent such as ethyl acetate, methanol or acetic acid.

Step 12→27 (Scheme 4)

Dehalogenation Reaction

Halides of general formula 12 can be dehalogenated for example by a hydrogenation reaction to obtain naphthyridines of general formula 27. Typically hydrogen (at atmospheric or elevated pressure), a base as for example triethylamine and a heterogeneous metal catalyst such as for example palladium on activated carbon in an organic solvent such as for example ethanol, ethyl acetate, acetic acid is used.

Step 11 or 12→19 (Scheme 4)

Sulfonylation Reaction

A halide of general formula 12 or a triflate of general formula 11 can be converted to the corresponding sulfone of general formula 19 by reaction with an alkyl sulfinic acid sodium salt or aryl sulfinic acid sodium salt with a base such as for example 4-(N,N-dimethlyamino)pyridine or pyridine in an organic solvent as for example N,N-dimethyl-formamide. Typically the reaction is performed at elevated temperature. The reaction can also be mediated by copper (see for example *European Journal of Medicinal Chemistry*, 2004, vol. 39, 735-744).

Scheme 5

Route for the preparation of compounds of general formula 38, wherein R$^1$, R$^3$, R$^4$, R$^9$ and R$^{11}$ have the meaning as given for general formula (I), supra. In addition, the substituents R$^1$ can bear a protecting group and the interconversion of any of the substituents R$^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

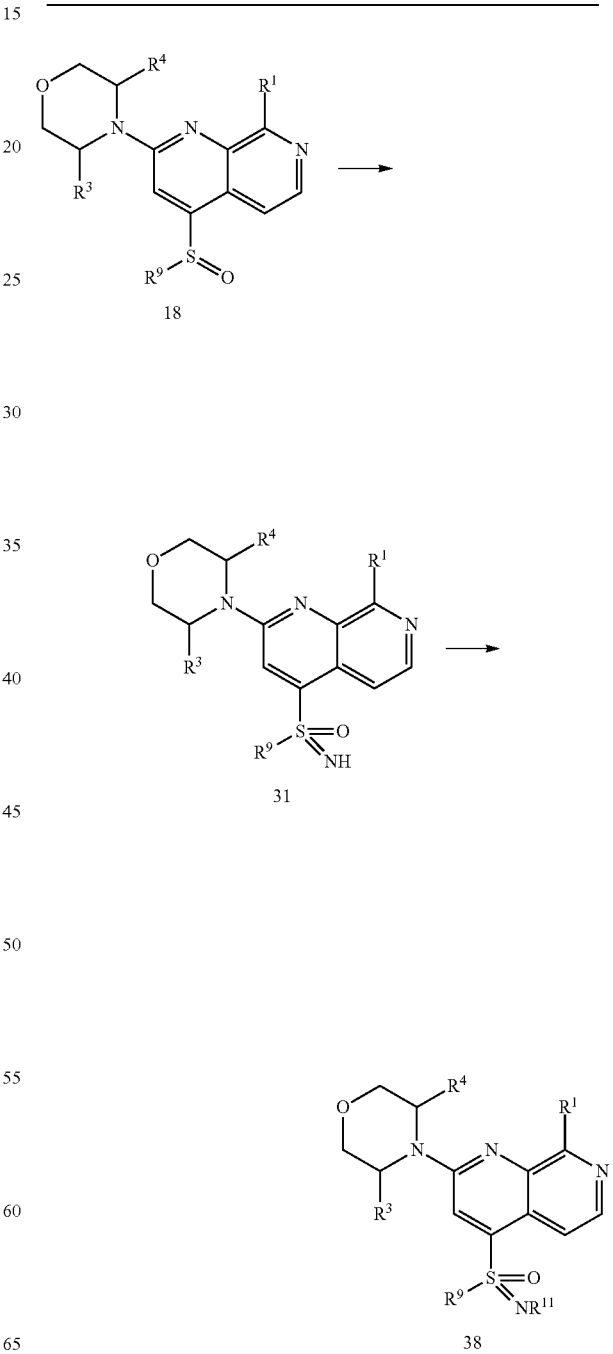

Step 18→31 (Scheme 5)
Sulfoximine Formation

Sulfoxide 18 is converted to the corresponding sulfoximine 31 in a two step procedure. Typically, the sulfoxide 18 is converted to a protected sulfoximine intermediate using a described procedure (*Org. Lett.*, 2004, 6, 1305-1307 and references therein). Deprotection to the sulfoximine to 31 is performed using a base such as for example $K_2CO_3$ in methanol. Additional options to convert the sulfoxide 18 to an unprotected sulfoximine 31 are the use of hydrazoic acid prepared in situ (e.g. *J. Chem Med Chem*, 2013, 8, 1021) or the use of O-(mesitylenesulfonyl)hydroxylamine (MSH) (e.g. *J. Org. Chem.*, 1973, 38, 1239).

Step 31→38 (Scheme 5)
Functionalization of the Sulfoximine Nitrogen

Functionalization of the nitrogen of sulfoximines of general formula 31 can be performed using previously described methods: N-unprotected sulfoximines of formula 31 may be reacted to give N-functionalized derivatives of formula 38. There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Reaction with isocyanates: see for example: a) V J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lacking et al, US2007/0191393.

Reaction with chloroformiates: see for example: a) P. B. Kirby et al, DE2129678; b) DJ. Cram et al, J. Am. Chem. Soc. 1974, 96, 2183; c) P. Stoss et al, Chem. Ber. 1978, 111, 1453; d) U. Lacking et al, WO2005/37800.

Reaction with bromocyane: see for example: a) D. T. Sauer et al, Inorganic Chemistry 1972, 11, 238; b) C. Bolm et al, Org. Lett. 2007, 9, 2951; c) U. Lacking et al, WO 2011/29537.

Scheme 6

Route for the preparation of compounds of general formula 32, 33, 34, 35, 36 and 37, wherein $R^1$, $R^3$, $R^4$, $R^7$, $R^8$, $R^9$, $R^{10}$, $R^{11}$ and $R^{12}$ have the meaning as given for general formula (I), supra. In addition, the substituents $R^1$ can bear a protecting group and the interconversion of any of the substituents $R^1$ can be achieved before and/or after the exemplified transformations. These modifications can be such as the introduction of protecting groups or cleavage of protecting groups. Appropriate protecting groups and their introduction and cleavage are well-known to the person skilled in the art (see for example T.W. Greene and P.G.M. Wuts in Protective Groups in Organic Synthesis, 3rd edition, Wiley 1999). Specific examples are described in the subsequent paragraphs.

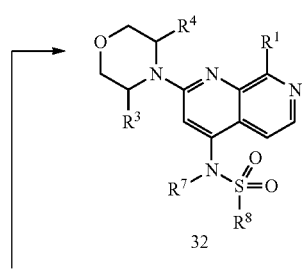

Step 11→32 (Scheme 6)

A triflate of general formula 11 can be converted to the corresponding sulfonamide 32 under palladium catalysis in analogy to literature procedures. For example see *J. Am. Chem. Soc.*, 2009, 131, 16720-16734 and references therein.

Step 11→33 (Scheme 6)

A triflate of general formula 11 can be converted to the corresponding sulfoximines 33 under palladium catalysis in analogy to literature procedures. For example see US2001/144345.

Step 11→34 (Scheme 6)

A triflate of general formula 11 can be converted to the corresponding sililated compound 34 under palladium catalysis in analogy to literature procedures. For example see *Org. Lett.* 2007, 9, 3785-3788 and references therein.

Step 11→35 (Scheme 6)
A triflate of general formula 11 can be converted to the phosphonate 35 under palladium catalysis in analogy to literature procedures. For example see US2008/9465
Step 11→36 (Scheme 6)
A triflate of general formula 11 can be converted to the phosphinate 36 under palladium catalysis in analogy to literature procedures. For example see *Adv. Synth. Cat.,* 2013, 355, 1361-1373 and references therein.
Step 11→37 (Scheme 6)
A triflate of general formula 11 can be converted to the phosphine oxide 37 under palladium catalysis in analogy to literature procedures. For example see US2007/4648

EXPERIMENTAL SECTION

The following table lists the abbreviations used in this paragraph, and in the examples section.

| | |
|---|---|
| Boc | tert-butyloxycarbonyl |
| BuLi | Butyllithium |
| conc. | concentrated |
| DCE | Dichloroethane |
| DCM | Dichloromethane |
| DMAP | N,N-Dimethylaminopyridine |
| DME | Dimethoxyethane |
| DMF | Dimethylformamide |
| DMSO | Dimethyl sulfoxide |
| EA | Ethyl acetate |
| EtOAc | Ethyl acetate |
| EtOH | Ethanol |
| HPLC, LC | high performance liquid chromatography |
| h | hour |
| LiHMDS | Lithium bis(trimethylsilyl)amide |
| KHMDS | Potassium bis(trimethylsilyl)amide |
| KOtBU | Potassium tert-butoxide |
| min | minute |
| LCMS, LC-MS, LC/MS | Liquid chromatography-mass spectrometry |
| LDA | Lithium diisopropylamide |
| MS | mass spectroscopy |
| NMR | nuclear magnetic resonance |
| NMO | N-metylmorpholine-N-oxide |
| NaHMDS | Sodium bis(trimethylsilyl)amide |
| PE | Petrol ether |
| Pd(dppf)Cl$_2$ | [1,1'-Bis-diphenylphosphino-ferrocene]palladium(II) dichloride |
| Rac | Racemate |
| R$_f$ | Retardation factor |
| R$_t$ | Retention time |
| sat. | saturated |
| rt, RT | Room temperature |
| TFA | Trifluoroacetic acid |
| THF | Tetrahydrofuran |
| TLC | thin-layer chromatography |

Chemical names were generated using ACD/Name Batch Version 12.01 or Autonom 2000.

All reagents, for which the synthesis is not described in the experimental part, are either commercially available or synthesized as described in literature references.
Analytical Methods
LC-MS Method 1:
column: Ascentis Express C18, 2.7 μm, 3 cm×2.1 mm
column temp.: 30° C.
injection volume: 1 μl
detection: MM-ES+APCI+DAD (254 nm)
fragment.potential: 50 V
mass range: 80-800 m/z
mobile phase A: water/0.1% formic acid
mobile phase B: methanol/0.1% formic acid
system time delay: 0.2 min
gradient:

| time in min | % A | % B | flow rate in ml/min |
|---|---|---|---|
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

LC-MS Method 2:
MS instrument type: Micromass Quatro Micro; HPLC instrument type: Agilent 1100 Series; UV DAD; column: Chromolith Flash RP-18E 25-2 mm; mobile phase A: 0.0375% TFA in water, mobile phase B: 0.01875% TFA in acetonitrile; gradient: 0.0 min 100% A→1.0 min 95% A→3.0 min 95% A→3.5 min 5% A→3.51 min 5% A→4.0 min 95% A; flow rate: 0.8 ml/min; column temp: 50° C.; UV detection: 220 nm & 254 nm.
LC-MS Method 3:
System: MS (LBA639)
  Binary Solvent Manager
  Sample Manager
  Organizer
  Column Manger
  PDA
  ELSD
Injection volume: 1 μl
Column: Acquity UPLC BEH C18 1.7 50×2.1 mm
Eluent A1: H2O+0.1% Vol. HCOOH (99%)
  A2: H2O+0.2% Vol. NH3 (32%)
  B1: Acetonitril
Flow rate: 0.8 ml/min
Temperature: 60° C.
Eluent Gradient A1+B1: 0-1.6 min 1-99% B1; 1.6-2.0 min 99% B1
LC-MS Method 4:
Instrument MS: Waters ZQ; Instrument HPLC: Waters UPLC Acquity; Column: Acquity BEH C18 (Waters), 50 mm×2.1 mm, 1.7 μm; eluent A: water+0.1 vol % formic acid, eluent B: acetonitrile (Lichrosolv Merck); gradient: 0.0 min 99% A-1.6 min 1% A-1.8 min 1% A—1.81 min 99% A—2.0 min 99% A; temperature: 60° C.; flow: 0.8 mL/min; UV-Detection PDA 210-400 nmnm—plus fixed wavelength 254 nm; MS ESI (+), Scan region 170-800 m/z
Preparative HPLC
Autopurifler: Acidic Conditions

| | |
|---|---|
| System: | Waters Autopurificationsystem: Pump 2545, Sample Manager 2767, CFO, DAD 2996, ELSD 2424, SQD |
| Column: | XBrigde C18 5 μm 100 × 30 mm |
| Solvent: | A = H$_2$O + 0.1% Vol. HCOOH (99%) |
| | B = MeCN |
| Gradient: | 0.00-0.50 min 5% B, 25 ml/min |
| | 0.51-5.50 min 10-100% B, 70 ml/min |
| | 5.51-6.50 min 100% B, 70 mL/min |
| Temperature: | RT |
| Solution: | max. 250 mg/max. 2.5 mL DMSO or DMF |
| Injection: | 1 × 2.5 ml |
| Detection: | DAD scan range 210-400 nm |
| | MS ESI+, ESI-, scan range 160-1000 m/z |

Autopurifler: Basic Conditions

| | |
|---|---|
| System: | Waters Autopurificationsystem: Pump 2545, Sample Manager 2767, CFO, DAD 2996, ELSD 2424, SQD |
| Column: | XBrigde C18 5 μm 100 × 30 mm |
| Solvent: | A = H$_2$O + 0.2% Vol. NH$_3$ (32%) |
| | B = MeCN |

-continued

| Gradient: | 0.00-0.50 min 5% B, 25 ml/min |
| --- | --- |
| | 0.51-5.50 min 10-100% B, 70 ml/min |
| | 5.51-6.50 min 100% B, 70 ml/min |
| Temperature: | RT |
| Solution: | max. 250 mg/max. 2.5 mL DMSO or DMF |
| Injection: | 1 × 2.5 ml |
| Detection: | DAD scan range 210-400 nm |
| | MS ESI+, ESI−, scan range 160-1000 m/z |

Preparation of Intermediates

Intermediate-1

Step a methyl-2-chloro-3-[1-morpholin-4-yleth-(E)-ylideneamino]isonicotinate

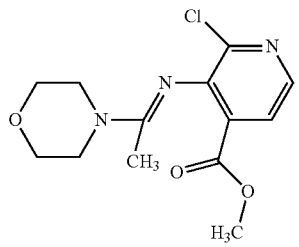 [SMILES: COC(=O)c1ccnc(Cl)c1/N=C(\C)N1CCOCC1]

Under argon and at a temperature of 0° C., 2.44 ml (25.40 mmol) of phosphorus oxychloride were added to a solution of 2.17 ml (18.8 mmol) of N-acetylmorpholine in 12 ml of absolute dichloroethane. The yellow solution was stirred at room temperature for 30 min. 1.75 g (9.39 mmol) of methyl 3-amino-2-chloroisonicotinate were then added. The mixture was stirred at 80° C. for 3 h. Dichloroethane was distilled off. Without work-up, the residue was purified by column chromatography [Puriflash silica gel 60 (80 g 30 μm); ethyl acetate/methanol 1:1, (300 ml)]. In this manner, methyl 2-chloro-3-[1-morpholin-4-yleth-(E)-ylideneamino] isonicotinate was obtained in a yield of 2.5 g (89% of theory) as a yellow oil. $^1$H NMR (400 MHz, CDCl$_3$): δ [ppm]=1.79-1.84 (2H), 2.14 (3H), 3.66-67 (4H), 3.88-3.91 (4H), 3.93 (3H), 7.77 (1H), 8.56 (2H).

Step b 8-chloro-2-(morpholin-4-yl)-[1,7]naphthyridin-4-ol

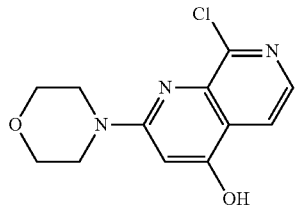 [SMILES: Oc1cc(N2CCOCC2)nc2c(Cl)nccc12]

Under argon and at 0° C., 20.1 ml (20.1 mmol) of lithium bis(trimethylsilyl)amide were added dropwise to a solution of 2.0 g (6.7 mmol) of methyl 2-chloro-3-[1-morpholin-4-yleth-(E)-ylideneamino]isonicotinate in 20 ml of dry N,N-dimethytformamide. The mixture was then stirred at room temperature for 3 h. For work-up, 2 ml of water were added and the mixture was concentrated. The residue was chromatographed [Puriflash silica gel 60 (80 g, 30 μm), ethyl acetate/methanol 1:1 (500 ml)]. 1.16 g (65% of theory) of 8-chloro-2-morpholin-4-yl-[1,7]naphthyridin-4-ol were isolated as a light-yellow solid. $^1$H NMR (400 MHz, DMSO): δ [ppm]=3.63-3.65 (4H), 3.72-3.74 (4H), 6.62 (1H), 7.73 (1H), 7.98 (1H), 11.62 (1H).

Intermediate-2

2-(morpholin-4-yl)-8-[2-(tetrahydropyran-2-yl)-2H-pyrazol-3-yl]-[1,7]naphthyridin-4-ol

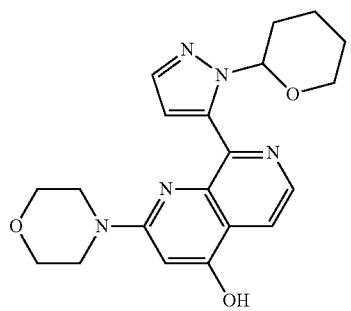

Under argon, 244 mg (0.30 mmol) of [1,1′-bis(diphenylphosphino)ferrocene]dichloropalladium(II) complex with dichloromethane (1:1) and 650 mg (2.00 mmol) of caesium carbonate were added to a suspension of 556 mg (2.00 mmol) of 1-(tetrahydropyran-2-yl)-5-(4,4,5,5-tetramethyl-[1,3,2]dioxaborolane-2-yl)-1H-pyrazole and 266 mg (1.00 mmol) of 8-chloro-2-morpholin-4-yl-[1,7]naphthyridin-4-ol in 4.0 ml of absolute 1,4-dioxane. The reaction mixture was stirred at 80° C. for 16 h. The brown reaction solution was purified via column chromatography [silica gel 60 (30 g); ethyl acetate (200 ml)]. In this manner, 206 mg (54% of theory) of 2-morpholin-4-yl-8-[2-(tetrahydropyran-2-yl)-2H-pyrazol-3-yl]-[1,7]naphthyridin-4-ol were isolated as a yellow oil. LCMS (method 1): m/z: [M+H]$^+$=382.3, R$_L$=3.0 min.

Intermediate-3

2-(morpholin-4-yl)-8-[2-(tetrahydropyran-2-yl)-2H-pyrazol-3-yl]-[1,7]naphthyridin-4-yl-trifluoromethanesulphonate

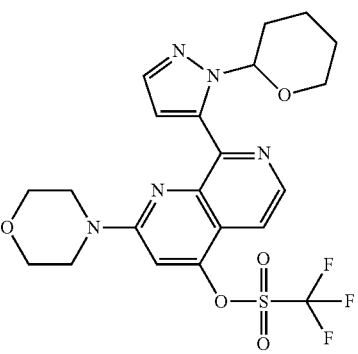 [SMILES: O=S(=O)(Oc1cc(N2CCOCC2)nc2c(-c3ccnn3C3CCCCO3)nccc12)C(F)(F)F]

Under argon, 25 μl (0.15 mmol) of diisopropylethylamine were added to a solution of 28 mg (0.07 mmol) of 2-morpholin-4-yl-8-[2-(tetrahydropyran-2-yl)-2H-pyrazol-3-yl]-[1,7]naphthyridin-4-ol and 39 mg (0.11 mmol) of N-phenylbis(trifluoromethanesulphonimide) in 3.0 ml of absolute dichloromethane. The reaction mixture was stirred at room temperature for 16 h. The brown reaction solution was purified via column chromatography [silica gel 60 (12 g, 30 μm); ethyl acetate (100 ml)]. 34 mg (88% of theory) of 2-morpholin-4-yl-8-[2-(tetrahydropyran-2-yl)-2H-pyrazol-3-yl]-[1,7]naphthyridin-4-yl trifluoromethanesulphonate were isolated as a yellow oil. $^1$H NMR (400 MHz, CDCl$_3$): δ [ppm]=1.48-1.52 (1H), 1.63-1.71 (2H), 2.04-2.10 (2H), 2.48-2.54 (1H), 3.62-3.75 (4H), 3.80-3.83 (4H), 3.92 (1H), 6.04-6.06 (1H), 6.96 (1H), 7.10 (1H), 7.26 (1H), 7.61 (1H), 7.69 (1H), 8.53 (1H).

Intermediate-4

4,8-dichloro-2-(morpholin-4-yl)-[1,7]naphthyridine

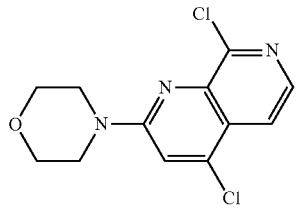 [SMILES: Clc1cc(N2CCOCC2)nc2c(Cl)nccc12]

3 g (11.3 mmol) of 8-chloro-2-(morpholin-4-yl)-[1,7]naphthyridin-4-ol were suspended in 10 ml (107 mmol) of phosphorus oxychloride, and the mixture was stirred at 95° C. for 3 h. A clear brown solution was formed. For work-up, the mixture was, with ice-cooling, carefully adjusted to pH 8 using 5N sodium hydroxide solution. This aqueous phase was extracted three times with in each case 50 ml of dichloromethane. The combined organic phases were dried over sodium sulphate and then concentrated to dryness. The resulting brown solid was triturated with 10 ml of methanol, filtered off and then dried. This gave 2.48 g (77% of theory) of 4,8-dichlori-2-(morpholin-4-yl)-[1,7]naphthyridine as a light-brown solid. LC-MS (method 1): m/z: [M+H]$^+$=284.2, R$_t$=3.53 min.

Intermediate-5

4-chloro-2-(morpholin-4-yl)-8-[2-(tetrahydropyran-2-yl)-2H-pyrazol-3-yl]-[1,7]naphthyridine

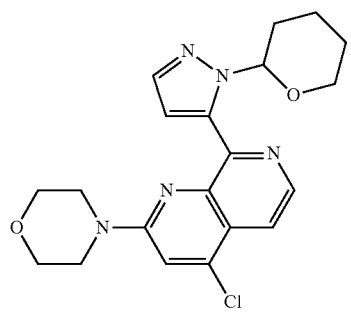 [SMILES: Clc1cc(N2CCOCC2)nc2c(-c3ccnn3C3CCCCO3)nccc12]

Under argon, 813 mg (0.7 mmol) of tetrakis(triphenylphosphine)palladium(0) and 2.92 g (21.1 mmol) of potassium carbonate were added to a suspension of 2 g (7.04 mmol) of 4,8-dichloro-2-(morpholin-4-yl)-[1,7]naphthyridine and 2.94 g (10.56 mmol) of 1-(tetrahydro-2H-pyran-2-yl)-3-(4,4,5,5-tetramethyl-1,3,2-dioxaborolan-2-yl)-1H-pyrazole in 30 ml of dimethoxyethane and 3 ml of water. The reaction mixture was stirred at 100° C. for 2 h. For work-up, 20 ml of sodium bicarbonate solution were added to the mixture. The precipitated solid was filtered off and washed with 5 ml of water. This gave 2 g (71% of theory) of 4-chloro-2-(morpholin-4-yl)-8-[2-(tetrahydropyran-2-yl)-2H-pyrazol-3-yl]-[1,7]naphthyridine as a yellow solid. LC-MS (method 1): m/z: [M+H]$^+$=400.3, R$_t$=3.62 min.

Intermediate-6

8-chloro-4-isopropoxy-2-(morpholin-4-yl)-1,7-naphthyridine

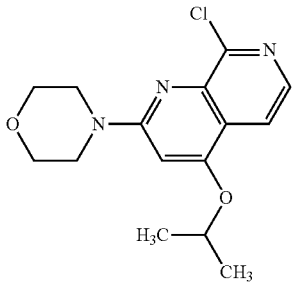 [SMILES: CC(C)Oc1cc(N2CCOCC2)nc2c(Cl)nccc12]

A suspension of 8-Chloro-2-(morpholin-4-yl)-[1,7]naphthyridin-4-ol (2.66 g, 10 mmol), 2-iodopropane (2 ml, 20 mmol) and potassium carbonate (1.66 g, 12 mmol) in acetonitrile (100 ml) were stirred for 8 hours at 85° C. The reaction mixture was allowed to cool to ambient temperature, the solvent was distilled off under reduced pressure and the residue was dissolved in water (30 ml) and dichloromethane (50 ml). The layers were separated and the aqueous phase was extracted with dichloromethane (3×30 ml). The combined organic phases were dried over sodium sulphate and the solvent distilled off under reduced pressure.

The residue was crystallized from methanol (10 ml) and dried. The title compound was obtained in 2 g as white solid. $^1$H-NMR (400 MHz, DMSO-d6): δ [ppm]=1.38 (6H), 3.67-3.82 (8H), 4.99-5.12 (1H), 6.83 (1H), 7.68 (1H), 7.99 (1H).

Intermediate-7

Step a 1-((R)-3-methylmorpholin-4-yl)ethanone

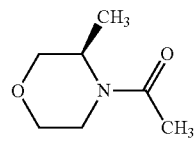

12.8 g (127 mmol) of (R)-3-methylmorpholine and 52.7 g (381 mmol) of potassium carbonate were suspended in 300 ml of dichloromethane, the mixture was stirred at room temperature for 30 min, 19.9 g (254 mmol) of acetyl chloride were added and the mixture was stirred at room temperature for 18 h. The conversion was monitored by NMR. For work-up, the precipitated solid was filtered off with suction and washed with 200 ml of dichloromethane. The mother liquor was concentrated to dryness. 17.19 g (95% of theory) of 1-[(R)-3-methylmorpholin-4-yl]ethanone were isolated as a yellow oil. $^1$H NMR (400 MHz, CDCl$_3$): δ [ppm]=1.23-1.35 (3H), 2.04-2.08 (3H), 2.98 (1/2H), 3.40-3.49 (2H), 3.53-3.60 (1H), 3.66-3.69 (1H), 3.79 (1/2H), 3.87 (1H), 4.24 (1/2H), 4.56 (1/2H).

Step b methyl 2-chloro-3-[1-((R)-3-methylmorpholin-4-yl)eth-(E)-ylideneamino]isonicotinate

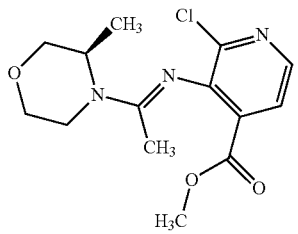 [SMILES: COC(=O)c1ccnc(Cl)c1/N=C(\C)N1CCOC[C@H]1C]

Under argon and at a temperature of 0° C., 17.1 ml (188 mmol) of phosphorus oxychloride were added to a solution of 9.00 g (62.8 mmol) of 1-[(R)-3-methylmorpholin-4-yl]ethanone in 78 ml of absolute 1,2-dichloroethane. The yellow solution was stirred at room temperature for 30 min. 11.7 g (62.8 mmol) of methyl 3-amino-2-chloroisonicotinate were then added. The mixture was stirred at 80° C. for 1 h, at room temperature overnight and on the next day at 80° C. for another 5 h. The 1,2-dichloroethane was distilled off. For work-up, the mixture was taken up in 200 ml of dichloromethane and 100 ml of water, sodium carbonate was added slowly and a little at a time with vigorous stirring (pH=9) and the mixture was extracted three times with in each case 250 ml of dichloromethane. The combined organic phases were dried over sodium sulphate and then concentrated to dryness under reduced pressure. In this manner, methyl 2-chloro-3-[1-((R)-3-methylmorpholin-4-yl)eth-(E)-ylideneamino]isonicotinate was obtained in a yield of 19.5 g (100% of theory) as a brown oil which was used without further purification in the next step. $^1$H NMR (400 MHz, CDCl$_3$): δ [ppm]=1.37 (3H), 1.78 (3H), 3.35 (1H); 3.58 (1H), 3.72-3.75 (3H), 3.83 (3H), 3.95 (1H), 4.28 (1H), 7.52 (1H), 8.01 (1H). LC-MS (method 1): Rt=0.23 min; MS (ESI/APCIpos) m/z=312.2 [M+H]+.

Step c 8-chloro-2-((R)-3-methylmorpholin-4-yl)-[1,7]naphthyridin-4-ol

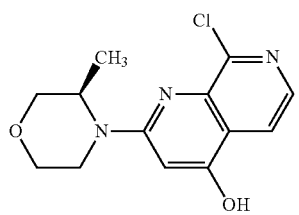 [SMILES: C[C@@H]1COCCN1c1cc(O)c2ccnc(Cl)c2n1]

Under argon and at 0° C., a solution of 31.4 g (187 mmol) of lithium bis(trimethylsilyl)amide dissolved in 250 ml of dry tetrahydrofuran was added dropwise over a period of 15 min to a solution of 19.5 g (62.8 mmol) of methyl 2-chloro-3-[1-((R)-3-methylmorpholin-4-yl)eth-(E)-ylideneamino]isonicotinate in 600 ml of dry tetrahydrofuran. The mixture was then stirred at room temperature for 3 h. For work-up, 50 ml of water were carefully added and the mixture was concentrated to dryness under reduced pressure. The residue was taken up in 600 ml of saturated ammonium chloride solution and extracted four times with in each case 200 ml of dichloromethane/isopropanol (4:1). The combined organic phases were dried over sodium sulphate, filtered and, under reduced pressure, concentrated to dryness. The residue was recrystallized from 250 ml of acetonitrile (7.56 g). The mother liquor was concentrated and the residue was recrystallized again from 125 ml of acetonitrile (3.65 g). 11.2 g (64% of theory, 1st fraction, clean) and 2.63 g (14% of theory, 2nd fraction, about 90% pure, concentrated mother liquor) of 8-chloro-2-((R)-3-methylmorpholin-4-yl)-[1,7]naphthyridin-4-ol were isolated as a yellow-orange solid. $^1$H NMR (400 MHz, DMSO-d$_6$): δ [ppm]=1.21 (3H), 3.18 (1H), 3.49 (1H), 3.65 (1H), 3.77 (1H), 3.98 (1H), 4.15 (1H), 4.41 (1H), 6.59 (1H), 7.72 (1H), 7.97 (1H), 11.59 (1H). LC-MS (method 1): R$_t$=3.05 min; MS (ESI/APCIpos) m/z=280.2 [M+H]$^+$.

Intermediate-8

4,8-dichloro-2-[(3R)-3-methylmorpholin-4-yl]-1,7-naphthyridine

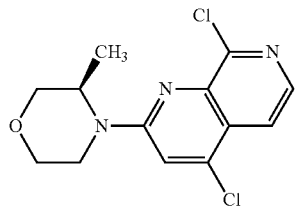

0.50 g (1.8 mmol) of 8-chloro-2-[(3R)-3-methylmorpholin-4-yl]-1,7-naphthyridin-4-ol were suspended in 1.6 ml (17 mmol) of phosphorus oxychloride, and the mixture was stirred at 95° C. for 3 h. The reaction was cooled to room temperature and then placed in an ice bath. The reaction was carefully quenched by dropwise addition of NaOH (3N) until pH 9. The aqueous phase was extracted 3 times with CH$_2$Cl$_2$. The organic layer was dried (silicon filter) and concentrated under reduced pressure. The crude mixture was then stirred with MeOH and filter. The solid was dried under reduced pressure at 40° C. The desired compound was obtained without further purification. $^1$H-NMR (300 MHz, DMSO-d$_6$): δ [ppm]=1.25 (3H), 3.19-3.31 (1H), 3.50 (1H), 3.61-3.69 (1H), 3.74-3.81 (1H), 3.99 (1H), 4.29 (1H), 4.57-4.67 (1H), 7.77-7.81 (2H), 8.14 (1H). LC-MS (Method 3): m/z: [M+H]$^+$=299, R$_t$=1.24 min.

Intermediate-9

2-(((R)-3-methylmorpholin-4-yl)-8-([2-(tetrahydro-pyran-2-yl)-2H-pyrazol-3-yl]-[1,7]naphthyridin-4-ol

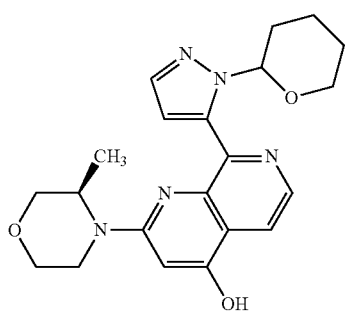 [SMILES: C[C@@H]1COCCN1c1cc(O)c2ccnc(-c3ccnn3C3CCCCO3)c2n1]

Under argon, 146 mg (0.18 mmol) of [1,1'-bis(diphenylphosphino)ferrocene]dichloropalladium(II) complex with dichloromethane (1:1) and 2.33 g (7.15 mmol) of caesium carbonate were added to a suspension of 500 mg (1.79 mmol) of 8-chloro-2-((R)-3-methylmorpholin-4-yl)-[1,7]naphthyridin-4-ol and 746 mg (2.68 mmol) of 1-(tetrahydropyran-2-yl)-5-(4,4,5,5-tetramethyl-[1,3,2]dioxaborolane-2-yl)-1H-pyrazole in 7.5 ml of absolute 1,4-dioxane. The reaction mixture was stirred at 90° C. for 16 h. The brown reaction solution was purified via column chromatography [silica gel 60 (30 g); ethyl acetate (200 ml)]. In this manner, 506 mg (72% of theory) of 2-[(R)-3-methylmorpholin-4-yl)-8-[2-(tetrahydropyran-2-yl)-2H-pyrazol-3-yl]-[1,7]naphthyridin-4-ol were isolated as a yellow oil. LCMS (method 1): m/z: [M+H]$^+$=396.3, R$_t$=3.11 min.

Intermediate-10

2-[(3R)-3-methylmorpholin-4-yl]-8-[1-(tetrahydro-2H-pyran-2-yl)-1H-pyrazol-5-yl]-1,7-naphthyridin-4-yl trifluoromehanesulfonate

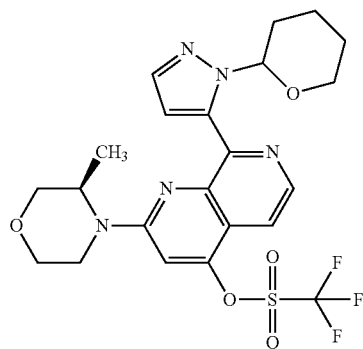 [SMILES: C[C@@H]1COCCN1c1cc(OS(=O)(=O)C(F)(F)F)c2ccnc(-c3ccnn3C3CCCCO3)c2n1]

Under argon a solution of 4.81 g (11.74 mmol) of 2-[(3R)-3-methylmorpholin-4-yl]-8-[1-(tetrahydro-2H-pyran-2-yl)-1H-pyrazol-5-yl]-1,7-naphthyridin-4-ol, 6.43 g (18 mmol) N-Phenylbis(trifluoromethanesulfonimide) and 4.18 ml (24 mmol) N,N-Diisopropylethylamin in 100 ml absolute dichloromethane was stirred for 3 days at room temperature. The solvent was distilled off under reduced pressure and the residue was chromatographed twice [silica gel 60 (400 g); dichlormethane/methanol, 98:2/ethyl acetate]. The title compound was obtained in 2.6 g (42% of theory) as yellow solid. LC-MS (method 1): m/z: [M+H]+=528.2, Rt=4.00 min.

Intermediate-11

Step a 1-((S)-3-methylmorpholin-4-yl)ethanone

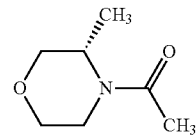

12.8 g (127 mmol) of (S)-3-methylmorpholine and 52.7 g (381 mmol) of potassium carbonate were suspended in 300 ml dichloromethane, the mixture was stirred at room temperature for 30 min, 19.9 g (254 mmol) of acetyl chloride were added with ice bath cooling and the mixture was stirred at room temperature for 7 d. The potassium carbonate was filtered off with suction and washed. With ice bath cooling, 43 ml (248 mmol) of N,N-diisopropylethylamine were added to the mother liquor, and the mixture was stirred at room temperature for 1 h. The solution was washed three times with in each case 200 ml of water, dried over sodium sulphate, filtered and concentrated to dryness under reduced pressure. 9.39 g (69% of theory) of 1-((S)-3-methylmorpholin-4-yl)ethanone were isolated as a brown oil. $^1$H NMR (400 MHz, CDCl$_3$): δ [ppm]=1.23-1.35 (3H), 2.04-2.08 (3H), 2.98 (1/2H), 3.40-3.49 (2H), 3.53-3.60 (1H), 3.66-3.69 (1H), 3.79 (1/2H), 3.87 (1H), 4.24 (1/2H), 4.56 (1/2H).

Step b methyl 2-chloro-3-[1-((S)-3-methylmorpholin-4-yl)eth-(E)-ylideneamino]isonicotinate

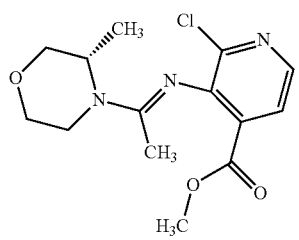 [SMILES: COC(=O)c1ccnc(Cl)c1/N=C(\C)N1CCOC[C@@H]1C]

Under argon and at a temperature of 0° C., 18.3 ml of (197 mmol) of phosphorus oxychloride were added to a solution of 9.39 g (65.6 mmol) of 1-((S)-3-methylmorpholin-4-yl)ethanone in 83 ml of absolute 1,2-dichloroethane. The yellow solution was stirred at room temperature for 30 min. 12.37 g (65.6 mmol) of methyl 3-amino-2-chloroisonicotinate were then added. The mixture was stirred at 80° C. for 5 h. The 1,2-dichloroethane was distilled off. For work-up, the mixture was taken up in 200 ml of dichloromethane and 100 ml of water, with vigorous stirring, by slowly adding, a little at a time, solid sodium carbonate, the pH was adjusted to pH=9 and the mixture was then extracted three times with in each case 250 ml of dichloromethane. The combined organic phases were dried over sodium sulphate and then concentrated under reduced pressure. In this manner, methyl 2-chloro-3-[1-((S)-3-methylmorpholin-4-yl)eth-(E)-ylideneamino]isonicotinate was obtained in a yield of 19.2 g (94% of theory) as a brown oil which was reacted further without further purification. $^1$H NMR (400 MHz, CDCl$_3$): δ [ppm]=1.37 (3H), 1.78 (3H), 3.35 (1H); 3.58 (1H), 3.72-3.75 (3H), 3.83 (3H), 3.95 (1H), 4.28 (1H), 7.52 (1H), 8.01 (1H). LC-MS (method 1): R$_t$=0.23 min; MS (ESI/APCIpos) m/z=312.2 [M+H]$^+$.

Step c 8-chloro-2-((S)-3-methylmorpholin-4-yl)-[1,7]naphthyridin-4-ol

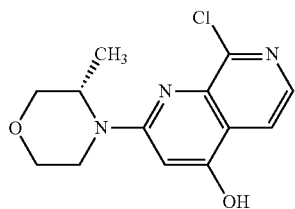 [SMILES: C[C@H]1COCCN1c1cc(O)c2ccnc(Cl)c2n1]

Under argon at 0° C., a solution of 30.8 g (184 mmol) of lithium bis(trimethylsilyl)amide, dissolved in 250 ml of dry tetrahydrofuran, was added dropwise over a period of 15 min to a solution of 19.2 g (61.5 mmol) of methyl 2-chloro-3-[1-(S)-3-methylmorpholin-4-yl)eth-(E)-ylideneamino]isonicotinate in 600 ml of dry tetrahydrofuran. The mixture was then stirred at room temperature for 3 h. For work-up, 50 ml of water were carefully added and the mixture was concentrated under reduced pressure. The residue was taken up in 600 ml of saturated ammonium chloride solution and extracted four times with in each case 200 ml of dichloromethane/isopropanol (4:1). The combined organic phases were dried over sodium sulphate, filtered and, under reduced pressure, concentrated to dryness. The residue was recrystallized from 250 ml of acetonitrile (5.7 g). The mother liquor was concentrated and the residue was recrystallized again from 125 ml of acetonitrile (5.0 g). 10.7 g (62% of theory, 1st fraction, clean) and 4.53 g (24% of theory, 2nd fraction, about 90% pure, concentrated mother liquor) of 8-chloro-2-((S)-3-methylmorpholin-4-yl)-[1,7]naphthyridin-4-ol were isolated as a brown solid. $^1$H NMR (400 MHz, DMSO-d$_6$): δ [ppm]=1.21 (3H), 3.18 (1H), 3.49 (1H), 3.65 (1H), 3.76 (1H), 3.98 (1H), 4.15 (1H), 4.40 (1H), 6.60 (1H), 7.72 (1H), 7.97 (1H), 11.6 (1H). LC-MS (method 1): R$_t$=3.05 min; MS (ESI/APCIpos) m/z=280.2 [M+H]$^+$.

Step d 2-((S)-3-methylmorpholin-4-yl)-8-[(2-(tetrahydropyran-2-yl)-2H-pyrazol-3-yl]-[1,7]naphthyridin-4-ol

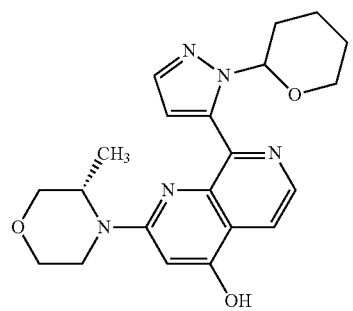 [SMILES: C[C@H]1COCCN1c1cc(O)c2ccnc(-c3ccnn3C3CCCCO3)c2n1]

Under argon, 583 mg (0.75 mmol) of [1,1'-bis(diphenylphosphino)ferrocene]dichloropalladium(II) complex with dichloromethane (1:1) and 9.31 g (28.6 mmol) of caesium carbonate were added to a suspension of 2.00 g (7.15 mmol) of 8-chloro-2-((S)-3-methyl-morpholin-4-yl)-[1,7]naphthyridin-4-ol and 2.98 g (10.7 mmol) of 1-(tetrahydropyran-2H-pyran-2-yl)-1H-pyrazol-5-boronic acid pinacol ester in 80 ml of absolute 1,4-dioxane. The reaction mixture was degassed three times and stirred at 85° C. for 3 h. Since, according to LC/MS, conversion was incomplete and there was no further conversion (starting material:product about 40:60), another 2 g of 1-(tetrahydropyran-2H-pyran-2-yl)-1H-pyrazole-5-boronic acid pinacol ester, 200 mg of [1,1'-bis(diphenylphosphino)ferrocene]dichloropalladium(II) complex with dichloromethane (1:1) and 3 g of caesium carbonate were added to the reaction solution and the mixture was stirred at 85° C. for 1 h. The solvent was distilled off and 100 ml of saturated ammonium chloride solution were added to the residue. The aqueous phase was extracted four times with in each case 100 ml of dichloromethane/isopropanol 4:1. The combined organic phases were dried over sodium sulphate and then concentrated to dryness under reduced pressure. The residue was chromatographed [silica gel 60 (2×80 g, 50 μm); dichloromethane/methanol 96:4 to 90:10]. This gave 402 mg (13% of theory) of 2-((S)-3-methylmorpholin-4-yl)-8-[2-(tetrahydropyran-2-yl)-2H-pyrazol-3-yl]-[1,7]naphthyridin-4-ol as a brown solid. $^1$H NMR (400 MHz, DMSO-d$_6$): δ [ppm]=1.18 (3H), 1.44-1.61 (3H), 1.91-2.00 (2H), 2.32-2.40 (1H), 3.09-3.18 (1H), 3.21-3.28 (1H), 3.45 (1H), 3.60-3.76 (3H), 3.91-4.02 (2H), 4.30 (1H), 6.09 (1H), 6.59 (1H), 6.91 (1H), 7.59 (1H), 7.77 (1H), 8.33 (1H), 11.46 (1H). LC-MS (method 1): R$_t$=3.08 min; MS (ESI/APCIpos) m/z=396.2 [M+H]$^+$.

Intermediate-12

8-chloro-2-[(3R)-3-methylmorpholin-4-yl]-4-(propan-2-yloxy)-1,7-naphthyridine

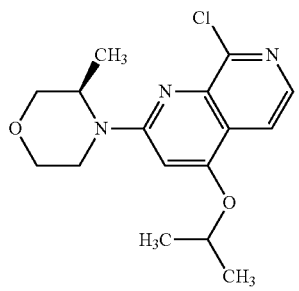 [SMILES: CC(C)Oc1cc(N2CCOC[C@H]2C)nc2c(Cl)nccc12]

2.96 g (21.5 mmol) of potassium carbonate were added to a solution of 5 g (18 mmol) of 8-chloro-2-(morpholin-4-yl)-[1,7]naphthyridin-4-ol and 3.57 ml (36 mmol) of 2-iodopropane in 50 ml of dry acetonitrile. The suspension was stirred at 85° C. for 2 h. The course of the reaction was monitored by LCMS. 100 ml of water were added to the mixture. The aqueous phase was extracted three times with in each case 50 ml ethyl acetate. The combined organic phases were dried over sodium sulphate and then concentrated to dryness. The residue was chromatographed [silica gel 60 (80 g, 30 μm); ethyl acetate (500 ml)]. 4 g (70% of theory) of 8-chloro-2-[(3R)-3-methylmorpholin-4-yl]-4-(propan-2-yloxy)-1,7-naphthyridine were obtained as a beige solid. LC-MS (method 1): m/z: [M+H]$^+$=322.2, R$_t$=3.79 min.

Intermediate-13

Step a 4,8-dichloro-2-(morpholin-4-yl)-[1,7]naphthyridine

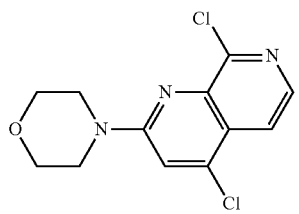

3 g (11.3 mmol) of 8-chloro-2-(morpholin-4-yl)-[1,7]naphthyridin-4-ol were suspended in 10 ml (107 mmol) of phosphorus oxychloride, and the mixture was stirred at 95° C. for 3 h. A clear brown solution was formed. For work-up, the mixture was, with ice-cooling, carefully adjusted to pH 8 using 5N sodium hydroxide solution. This aqueous phase was extracted three times with in each case 50 ml of dichloromethane. The combined organic phases were dried over sodium sulphate and then concentrated to dryness. The resulting brown solid was triturated with 10 ml of methanol, filtered off and then dried. This gave 2.48 g (77% of theory) of 4,8-dichlori-2-(morpholin-4-yl)-[1,7]naphthyridine as a light-brown solid. LC-MS (method 1): m/z: [M+H]$^+$=284.2, R$_t$=3.53 min.

Step b 4-chloro-2-(morpholin-4-yl)-8-[2-(tetrahydropyran-2-yl)-2H-pyrazol-3-yl]-[1,7]naphthyridine

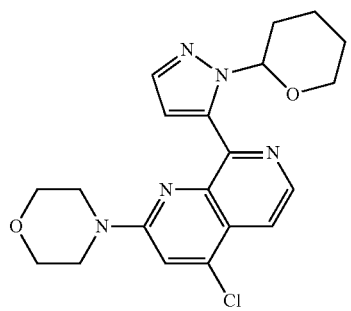 [SMILES: Clc1cc(N2CCOCC2)nc2c(-c3ccnn3C3CCCCO3)nccc12]

Under argon, 813 mg (0.7 mmol) of tetrakis(triphenylphosphine)palladium(0) and 2.92 g (21.1 mmol) of potassium carbonate were added to a suspension of 2 g (7.04 mmol) of 4,8-dichloro-2-(morpholin-4-yl)-[1,7]naphthyridine and 2.94 g (10.56 mmol) of 1-(tetrahydro-2H-pyran-2-yl)-3-(4,4,5,5-tetramethyl-1,3,2-dioxaborolan-2-yl)-1H-pyrazole in 30 ml of dimethoxyethane and 3 ml of water. The reaction mixture was stirred at 100° C. for 2 h. For work-up, 20 ml of sodium bicarbonate solution were added to the mixture. The precipitated solid was filtered off and washed with 5 ml of water. This gave 2 g (71% of theory) of 4-chloro-2-(morpholin-4-yl)-8-[2-(tetrahydropyran-2-yl)-2H-pyrazol-3-yl]-[1,7]naphthyridine as a yellow solid. LC-MS (method 1): m/z: [M+H]$^+$=400.3, R$_t$=3.62 min.

Intermediate-14

Step a

1-[(3R,5S)-3,5-dimethylmorpholin-4-yl]ethanone

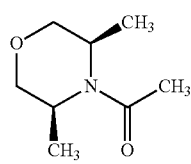

(3R,5S)-3,5-Dimethylmorpholine (0.50 g, 4.3 mmol, 1 eq.) was solubilized in pyridine (8.6 mL, 0.11 mol, 25 eq.) and acetic anhydride (4.0 mL, 42 mmol, 10 eq.) was added. The reaction was stirred for 16 hours at room temperature. The reaction mixture was then concentrated under reduced pressure and the desired product was obtained in 95% yield (0.64 g). $^1$H NMR (400 MHz, DMSO-d$_6$) δ ppm: 1.22 (6H), 2.00 (3H), 3.44 (2H), 3.65 (2H), 4.00 (2H). LC-MS (Method 3): m/z: [M+H]$^+$=158, R$_t$=0.57 min.

Step b methyl 2-chloro-3-[(E)-{1-[(3R,5S)-3,5-dimethyl-morpholin-4-yl]ethylidene}amino]isonicotinate

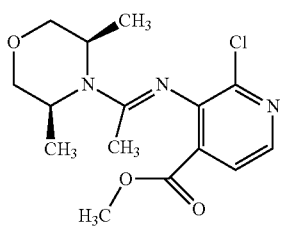 [SMILES: COC(=O)c1ccnc(Cl)c1/N=C(\C)N1[C@H](C)COC[C@@H]1C]

1-[(3R,5S)-3,5-Dimethylmorpholin-4-yl]ethanone (0.54 g, 3.4 mmol, 2.3 eq.) was solubilized in DCE (2.7 mL) and the reaction mixture was cooled to 0° C. POCl$_3$ (0.46 mL, 4.3 mmol, 3.3 eq.) was added slowly and the reaction was warmed up to rt. After 30 minutes, methyl 3-amino-2-chloroisonicotinate (0.28, 1.5 mmol, 1 eq.) was added in one portion and the mixture was stirred at 80° C. After 6 hours, the reaction was cooled to room temperature and the solvent was removed under reduced pressure. The crude mixture was diluted with CH$_2$Cl$_2$ and washed three times with sat. NaHCO$_3$. The organic phase was dried (MgSO$_4$) and concentrated under reduced pressure. The crude mixture was purified by flash chromatography (gradient: 100% hexane to 100% EtOAc). The desired product was obtained in 58% yield (0.28 g). $^1$H NMR (400 MHz, DMSO-d$_6$) δ ppm: 1.29 (3H), 1.33 (3H), 1.77 (3H), 3.56 (2H), 3.72 (2H), 3.77 (3H), 4.06-4.24 (2H), 7.56 (1H), 8.01 (1H). LC-MS (Method 3): m/z: [M+H]$^+$=326, R$_t$=0.85 min.

Step c 8-chloro-2-[(3R,5S)-3,5-dimethylmorpholin-4-yl]-4-isopropoxy-1,7-naphthyridine

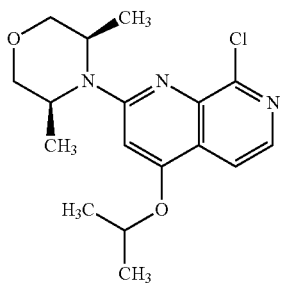 [SMILES: CC(C)Oc1cc(N2[C@H](C)COC[C@@H]2C)nc2c(Cl)nccc12]

Methyl 2-chloro-3-[(E)-{1-[(3R,5S)-3,5-dimethylmorpholin-4-yl]ethylidene}amino]isonicotinate (0.28 g, 0.86 mmol, 1 eq.) was solubilised in dry THF (6 mL) under inert atmosphere (Argon). The reaction mixture was cooled to 0° C. and a solution of LiHMDS (1.0 M in THF, 2.5 mL, 2.6 mmol, 3 eq.) was added slowly. The reaction mixture was stirred for 16 h at room temperature. The reaction was quenched with H$_2$O and concentrated under reduced pressure. The crude 8-chloro-2-[(3R,5S)-3,5-dimethylmorpholin-4-yl]-1,7-naphthyridin-4-ol (0.36 g) was used in the next step without further purification. CH$_3$CN (10 mL) was added to 8-chloro-2-[(3R,5S)-3,5-dimethylmorpholin-4-yl]-1,7-naphthyridin-4-ol (0.20 g, 0.68 mmol, 1 eq.). 2-Iodopropane (0.13 mL, 1.4 mmol, 2 eq.) and K$_2$CO$_3$ (0.14 g, 0.81 mmol, 1.2 eq.) were sequentially added to the suspension. The reaction mixture was stirred at 85° C. for 16 h. The reaction was cooled to room temperature and diluted with EtOAc and washed three times with H$_2$O. The organic phase was dried (MgSO$_4$) and concentrated under reduced pressure. The desired product was obtained without further purification in 60% yield over two steps. $^1$H-NMR (400 MHz, DMSO-d$_6$): δ [ppm]: 1.31 (6H), 1.39 (6H), 3.64 (2H), 3.83 (2H), 4.54 (2H), 5.04 (1H), 6.66 (1H), 7.68 (1H), 7.97 (1H). LC-MS (Method 3): m/z: [M+H]$^+$=336, R$_t$=1.39 min.

Intermediate-15

Step a

1-[(3R,5R)-3,5-dimethylmorpholin-4-yl]ethanone

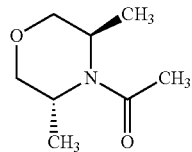

(3R,5R)-3,5-Dimethylmorpholine (0.50 g, 4.3 mmol, 1 eq.) was solubilized in pyridine (8.6 mL, 0.11 mmol, 25 eq.) and acetic anhydride (4.0 mL, 0.42 mmol, 10 eq.) was added. The reaction was stirred for 16 hours at room temperature. The reaction mixture was then concentrated under reduced pressure and the desired product was obtained in quantitative yield. $^1$H NMR (400 MHz, DMSO-d$_6$) δ ppm: 1.26 (6H), 2.00 (3H), 3.43-3.59 (2H), 3.83-3.97 (4H). LC-MS (Method 3): m/z: [M+H]$^+$=158, R$_t$=0.56 min.

Step b methyl 2-chloro-3-[(E)-{1-[(3R,5R)-3,5-dimethyl-morpholin-4-yl]ethylidene}amino]isonicotinate

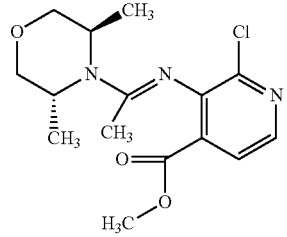

1-[(3R,5R)-3,5-Dimethylmorpholin-4-yl]ethanone (0.70 g, 4.4 mmol, 2.3 eq.) was solubilized in DCE (10 mL) and the reaction mixture was cooled to 0° C. POCl$_3$ (0.59 mL, 6.4 mmol, 3.3 eq.) was added slowly and the reaction was warmed up to rt. After 30 minutes, methyl 3-amino-2-chloroisonicotinate (0.36 g, 1.9 mmol, 1 eq.) was added in one portion and the mixture was stirred at rt. After 48 hours, the reaction was quenched with sat. NaHCO$_3$ and extracted three times with CH$_2$Cl$_2$. The organic phase was dried (MgSO$_4$) and concentrated under reduced pressure. The crude mixture was purified by flash chromatography (gradient: 100% hexane to 100% EtOAc). The desired product was obtained in 18% yield (0.12 g). $^1$H NMR (400 MHz, DMSO-$d_6$) δ ppm: 1.26 (3H), 1.33 (3H), 1.79 (3H), 3.55 (2H), 3.77 (3H), 3.89-4.00 (4H), 7.54-7.58 (1H), 8.02-8.06 (1H).

Step c 8-chloro-2-[(3R,5R)-3,5-dimethylmorpholin-4-yl]-4-isopropoxy-1,7-naphthyridine

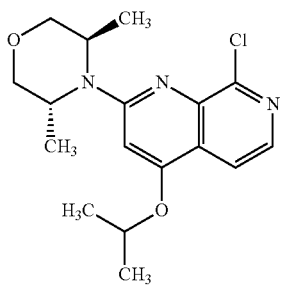 [SMILES: CC(C)Oc1cc(N2[C@H](C)COC[C@H]2C)nc2c(Cl)nccc12]

Methyl 2-chloro-3-[(E)-{1-[(3R,5R)-3,5-dimethylmorpholin-4-yl]ethylidene}amino]isonicotinate (0.12 g, 0.36 mmol, 1 eq.) was solubilised in dry THF (2.5 mL) under inert atmosphere (Argon). The reaction mixture was cooled to 0° C. and a solution of LiHMDS (1.0 M in THF, 1.1 mL, 1.1 mmol, 3 eq.) was added slowly. The reaction mixture was stirred for 16 h at room temperature. The reaction was quenched with H$_2$O and concentrated under reduced pressure The crude 8-chloro-2-[(3R,5R)-3,5-dimethylmorpholin-4-yl]-1,7-naphthyridin-4-ol (0.36 g) was used in the next step without further purification. CH$_3$CN (6.8 mL) was added to 8-chloro-2-[(3R,5R)-3,5-dimethylmorpholin-4-yl]-1,7-naphthyridin-4-ol (0.14 g, 0.46 mmol, 1 eq.). 2-Iodopropane (0.10 mL, 0.90 mmol, 2 eq.) and K$_2$CO$_3$ (74 mg, 0.55 mmol, 1.2 eq.) were sequentially added to the suspension. The reaction mixture was stirred at 85° C. for 48 h. The reaction was cooled to room temperature and diluted with H$_2$O, extracted three times with CH$_2$Cl$_2$ and washed with sat. NaCl. The organic phase was dried (silicon filter) and concentrated under reduced pressure. The desired product was obtained without further purification in 52% yield over two steps (81 mg). $^1$H-NMR (400 MHz, DMSO-$d_6$): δ [ppm]: 1.26 (6H), 1.39 (6H), 3.58-3.64 (2H), 3.99-4.04 (2H), 4.17-4.25 (2H), 4.97-5.07 (1H), 6.85 (1H), 7.73 (1H), 8.06 (1H). LC-MS (Method 3): m/z: [M+H]$^+$=336, R$_t$=1.38 min.

Intermediate-16

Step a 1-bromo-3-(methylsulfinyl)benzene

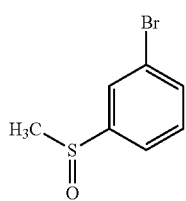

To a solution of (3-bromophenyl)(methyl)sulfane (50.0 g, 0.246 mol) in CH$_3$CN (500 mL) was added FeCl$_3$ (1.2 g, 7.4 mmol) with stirring. After the addition, the mixture was stirred at room temperature for 10 min and then cooled to 0° C. H$_5$IO$_6$ (62.0 g, 0.272 mol) was added in portions and then the mixture was stirred at 0° C. for 1 h. TLC (PE:EA=3:1, R$_f$=0.4) showed the most of starting material was consumed. The reaction mixture was quenched by the addition of saturated aqueous NH$_4$Cl (1.0 L) and extracted with EA (300 mL×3). The combined organic layers were washed with brine, dried over Na$_2$SO$_4$, filtered and concentrated under reduced pressure to give 1-bromo-3-(methylsulfinyl)benzene (55.0 g) as yellow oil, which was used directly in the next step without further purification.

Step b 1-bromo-3-(N-(ethoxycarbonyl)-S-methylsulfonimidoyl)

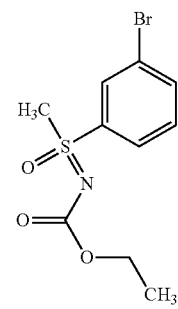 [SMILES: CCOC(=O)N=S(C)(=O)c1cccc(Br)c1]

To a suspension of 1-bromo-3-(methylsulfinyl)benzene (55.0 g, 0.251 mol), ethyl carbamate (45.0 g, 0.505 mol), MgO (40.3 g, 1.0 mol) and Rh$_2$(OAc)$_4$ (2.6 g, 7.6 mmol) in DCM (600 mL) was added PhI(OAc)$_2$ (122.0 g 0.378 mol) carefully under N$_2$. The mixture was stirred at room temperature for 5 days. TLC (PE:EA=1:1, R$_f$=0.8) showed the most of starting material was consumed. The mixture was filtered and the filtrate was concentrated under reduced pressure to give the crude compound, which was chromatographed on silica gel (PE:EA=20:1-5:1) to give 1-bromo-3-(N-(ethoxycarbonyl)-S-methylsulfonimidoyl)benzene (55.0 g, 81.4% of theory) as white solid. $^1$H NMR (400 MHz, CDCl$_3$): δ=8.15-8.14 (1H), 7.94-7.92 (1H), 7.81-7.80 (1H), 7.51-7.47 (1H), 4.13-4.08 (2H), 3.32 (3H), 1.25 (3H).

Step c 4,4,5,5-tetra methyl-(3-(N-(ethoxycarbonyl)-S-methylsulfonimidoyl)phenyl)-1,3,2-dioxa borolane

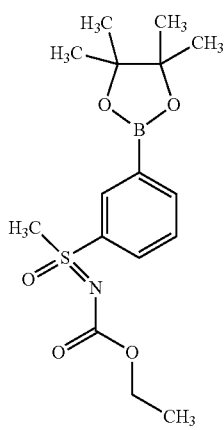 [SMILES: CCOC(=O)N=S(C)(=O)c1cccc(B2OC(C)(C)C(C)(C)O2)c1]

To a solution of 1-bromo-4-(N-(ethoxycarbonyl)-S-methylsulfonimidoyl)benzene (55.0 g, 0.18 mol) in anhydrous dioxane (600 mL) was added 4,4,4',4',5,5,5',5'-octamethyl-2,2'-bi(1,3,2-dioxaborolane) (53.0 g, 0.209 mol), KOAc (35.3 g, 0.34 mol) and Pd(dppf)Cl$_2$ (4.0 g, 5.47 mmol) under N$_2$. After the addition, the mixture was stirred at 80° C. for 4 h. TLC (PE:EA=1:1, R$_f$=0.6) showed the most of starting material was consumed. The mixture was filtered and to the filtrate was added CH$_3$COOH (20.0 g, 0.33 mol) and Pinacol (30.0 g, 0.253 mol). The resulting mixture was stirred at room temperature for 18 h. The mixture was concentrated and chromatographed on silica gel (PE:EA=0:1~5:1) to give the crude, which was washed by PE/EA (100 mL×2, PE:EA=1:10) to give 4,4,5,5-tetramethyl-(3-(N-(ethoxycarbonyl)-S-methylsulfonimidoyl)phenyl)-1,3,2-dioxaborolane (35.0 g, 55.2% of theory) as white solid. $^1$H NMR (400 MHz, MeOD-d$_4$): δ=8.40 (1H), 8.09-8.07 (1H), 7.61-7.58 (1H), 4.13-4.07 (2H), 3.32 (3H), 1.35 (12H), 1.25-1.22 (3H). LC-MS method 2: (ES-API) m/z=272.0 (M+H−82)$^+$.

Intermediate-17

Step a 1-bromo-4-(methylsulfinyl)benzene

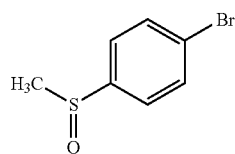

To a solution of (3-bromophenyl)(methyl)sulfane (100.0 g 0.492 mol) in CH$_3$CN (500 mL) was added FeCl$_3$ (2.4 g, 14.8 mmol) with stirring. After the addition, the mixture was stirred at room temperature for 10 min and then cooled to 0° C. H$_5$IO$_6$ (124.2 g, 0.545 mol) was added in portions and the mixture was stirred at 0° C. for 1 h. TLC (PE:EA=5:1, R$_f$=0.2) showed the most of starting material was consumed. The reaction mixture was quenched by the addition of saturated aqueous NH$_4$Cl (1.0 L) and extracted with EA (300 mL×4). The organic layers were washed with brine (300 mL), dried over Na$_2$SO$_4$ and concentrated. The residue was purified by chromatography on silica gel (PE/EA=20:1~5:1) to give 1-bromo-4-(methylsulfinyl)benzene (103.0 g, 95.5% of theory) as a white solid.

Step b 1-bromo-4-(N-(ethoxycarbonyl)-S-methylsulfonimidoyl)benzene

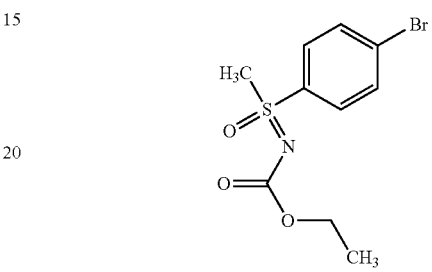

To a suspension of 1-bromo-4-(methylsulfinyl)benzene (100.0 g, 0.456 mol), ethyl carbamate (77.0 g, 0.864 mol), MgO (73.4 g 1.821 mol) and Rh$_2$(OAc)$_4$ (4.7 g 10.63 mmol) in DCM (1.5 L) was added PhI(OAc)$_2$ (221.5 g, 0.688 mol) carefully under N$_2$. The mixture was stirred at room temperature for 7 days. TLC (PE:EA=1:1, R$_f$=0.7) showed the most of starting material was consumed. The mixture was filtered and the filtrate was concentrated under reduced pressure. The residue was purified by chromatography on silica gel (PE/EA=20:1~5:1) to give 1-bromo-4-(N-(ethoxycarbonyl)-S-methylsulfonimidoyl)benzene (95.0 g, 68.0% of theory) as a white solid. $^1$H NMR (400 MHz, CDCl$_3$): δ=7.87-7.85 (2H), 7.76-7.74 (2H), 4.13-4.08 (2H), 3.30 (3H), 1.28-1.22 (3H).

Step c 4,4,5,5-tetramethyl-(4-(N-(ethoxycarbonyl)-S-methylsulfonimidoyl)phenyl)-1,3,2-dioxaborolane

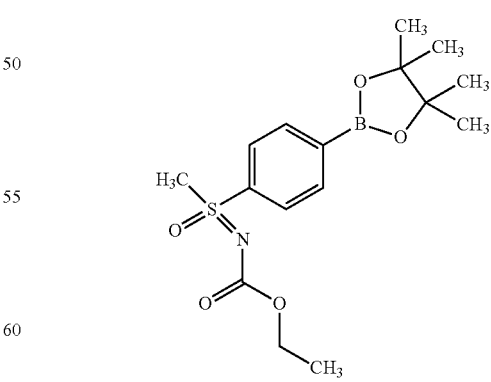

To a solution of 1-bromo-4-(N-(ethoxycarbonyl)-S-methylsulfonimidoyl)benzene (95.0 g 0.310 mol) in anhydrous dioxane (1.5 L) was added 4,4,4',4',5,5,5',5'-octamethyl-2,2'-bi(1,3,2-dioxaborolane) (95.0 g, 0.374 mol), KOAc (61.0 g 0.622 mol) and Pd(dppf)Cl$_2$(7.0 g, 9.57 mmol) under N$_2$. After the addition, the mixture was stirred at 80° C. for 18 h. The mixture was filtered and to the filtrate was added CH$_3$COOH (18.0 g, 0.30 mol) and pinacol (18.0 g, 0.152 mol). The mixture was stirred at room temperature for 18 h. The mixture was concentrated and the residue was first purified by chromatography on silica gel (PE/EA=20:1~5:1) and then washed by EA/PE (100 mL×2, EA/PE=1:10) to give the title compound (87.0 g, 79.5% of theory) as a white solid. $^1$H NMR (400 MHz, MeOD-d4): δ=8.04-7.97 (4H), 4.13-4.06 (2H), 3.30 (3H), 1.36 (12H), 1.25-1.21 (3H). LC-MS method 2: (ES-API) m/z=272.1 (M+H−82)$^+$.

Intermediate-18

4-chloro-2-[(3R)-3-methylmorpholin-4-yl-8-(1-(tetrahydro-2H-pyran-2-yl)-1H-pyrazol-5-yl]-1,7-naphthyridine

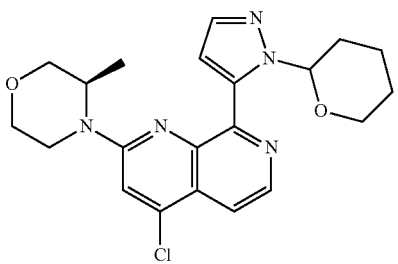 [SMILES: C[C@@H]1COCCN1c1cc(Cl)c2ccnc(-c3ccnn3C3CCCCO3)c2n1]

Intermediate-8 (0.5 g, 1.7 mmol), 1-(tetrahydro-2H-pyran-2-yl)-5-(4,4,5,5-tetramethyl-1,3,2-dioxaborolan-2-yl)-1H-pyrazole (0.47 g, 1.7 mmol) and PdCl$_2$(PPh$_3$)$_2$(0.12 g, 0.17 mmol) were solubilisend in DME (15 mL). Potassium carbonate (2.5 mL, 5.0 mmol, 2M aq. Solution) was added and the reaction was heated for 10 minutes under microwave irradiation at 130° C. The reaction mixture was dried by filtration through a silicon filter and concentrated under reduced pressure. The crude material was purified by Flash column chromatography (Hexane\ethyl acetate). The title compound was obtained in 45% yield (0.5 g).

$^1$H-NMR (400 MHz, DMSO-d$_6$): δ [ppm]=1.21 (dd, 3H), 1.40-1.64 (m, 3H), 1.90-2.03 (m, 2H), 2.30-2.39 (m, 1H), 3.15-3.28 (m, 2H), 3.41-3.52 (m, 1H), 3.57-3.78 (m, 3H), 3.92-3.99 (m, 1H), 4.12 (t, 1H), 4.44-4.54 (m, 1H), 5.99-6.09 (m, 1H), 6.92 (dd, 1H), 7.62 (s, 1H), 7.76 (d, 1H), 7.83 (d, 1H), 8.49 (d, 1H).

Preparation of the Compounds of the Present Invention

Example 1

4-[(2-(morpholin-4-yl)-8-[2H-pyrazol-3-yl]-[1,7]naphthyridine-4-yl]phenyl-N-ethoxycarbonyl-S-methylsulphoximide Step a 4-[(2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide

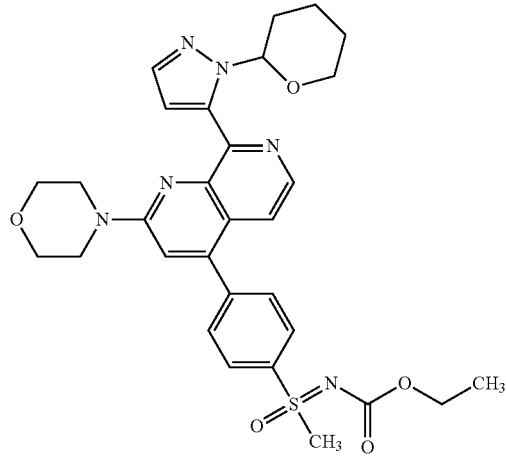 [SMILES: CCOC(=O)N=S(C)(=O)c1ccc(-c2cc(N3CCOCC3)nc3c(-c4ccnn4C4CCCCO4)nccc23)cc1]

Under argon, 48 mg (0.06 mmol) of [1,1'-bis(diphenylphosphino)ferrocene]dichloropalladium(II) complex with dichloromethane (1:1, Pd(dppf)Cl$_2$) and 761 mg (2.34 mmol) of caesium carbonate were added to a suspension of 300 mg (0.58 mmol) of 2-(morpholin-4-yl)-8-[2-(tetrahydropyran-2-yl)-2H-pyrazol-3-yl]-[1,7]naphthyridin-4-yl trifluoromethanesulphonate and 413 mg (1.17 mmol) of pinacol ester in 7.5 ml of absolute dioxane. The reaction mixture was stirred at 100° C. for 3 h. The mixture was chromatographed directly without work-up [silica gel 60 (25 g, 30 μm); ethyl acetate (100 ml)]. This gave 280 mg (81% of theory) of 4-[(2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide as a yellow oil. LC-MS (method 1): m/z: [M+H]$^+$=591.3, R$_t$=3.43 min.

Step b

4-[(2-(morpholin-4-yl)-8-[2H-pyrazol-3-yl]-[1,7]naphthyridine-4-yl]phenyl-N-ethoxycarbonyl-S-methylsulphoximide

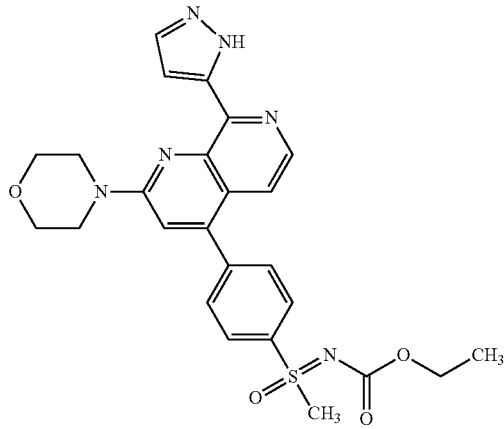 [SMILES: CCOC(=O)N=S(C)(=O)c1ccc(-c2cc(N3CCOCC3)nc3c(-c4ccn[nH]4)nccc23)cc1]

185 mg (0.31 mmol) of 4-[(2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were dissolved in 20 ml of ethanol, and 4 ml of (8 mmol) of 2N hydrochloric acid were added. After 1 h, LCMS showed complete removal of the protective group. Ethanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. This gave 158 mg (99% of theory) of 4-[(2-(Morpholin-4-yl)-8-[2H-pyrazol-3-yl]-[1,7]-naphthyridine-4-yl]phenyl-N-ethoxycarbonyl-S-methylsulphoximide as a colourless solid. m.p. 230-232° C. $^1$H NMR (400 MHz, DMSO-d$_6$): δ [ppm]=1.12-1.15 (3H), 3.56 (3H), 3.80 (8H), 3.91-4.00 (2H), 7.33-7.35 (1H), 7.42 (1H), 7.57 (1H), 7.65 (1H), 7.88-7.90 (2H), 8.15-8.17 (2H), 8.35-8.36 (1H), 13.40 (1H). LC-MS (method 1): m/z: [M+H]$^+$=507.3, R$_t$=2.93 min.

Example 2

4-[(2-(Morpholin-4-yl)-8-(2H-pyrazol-3-yl)-[1,7]naphthyridine-4-yl]phenyl-S-methylsulphoximide

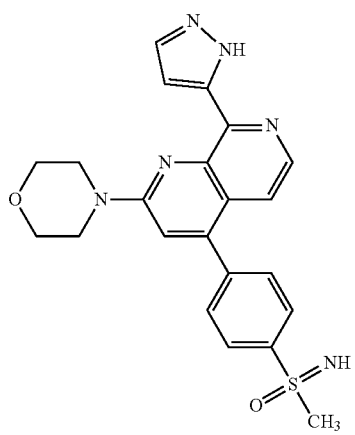 [SMILES: CS(=N)(=O)c1ccc(-c2cc(N3CCOCC3)nc3c(-c4ccn[nH]4)nccc23)cc1]

158 mg (0.312 mmol) of 4-[(2-(morpholin-4-yl)-8-[-2H-pyrazol-3-yl]-[1,7]naphthyridine-4-yl]phenyl-N-ethoxycarbonyl-S-methylsulphoximide were suspended in 10 ml of sodium methoxide (33%), and the mixture was stirred at 60° C. for 30 min. For work-up, 20 ml of water were added and the mixture was then extracted three times with in each case 20 ml of dichloromethane. The combined organic phases were dried over sodium sulphate and concentrated. The solid formed was triturated with 5 ml of methanol, filtered off and dried. This gave 88 mg (65% of theory) of 4-[(2-(morpholin-4-yl)-8-(2H-pyrazol-3-yl)-[1,7]naphthyridine-4-yl]phenyl-S-methylsulphoximide as a yellow solid. m.p. 271-273° C. $^1$H NMR (400 MHz, DMSO-d$_6$): δ [ppm]=3.17 (3H), 3.80 (8H), 4.35 (1H), 7.35-7.37 (1H), 7.42 (1H), 7.54 (1H), 7.65 (1H), 7.79-7.82 (2H), 8.12-8.14 (2H), 8.34-8.35 (1H), 13.40 (1H). LC-MS (method 1): m/z: [M+H]$^+$=435.3, R$_t$=2.62 min.

Example 3

4-[6-(methylsulfonyl)pyridin-3-yl]-2-(morpholin-4-yl)-8-(1H-pyrazol-5-yl)-1,7-naphthyridine Step a 4-[6-(methylsulfonyl)pyridin-3-yl]-2-(morpholin-4-yl)-8-[1-(tetrahydro-2H-pyran-2-yl)-1H-pyrazol-5-yl]-1,7-naphthyridine

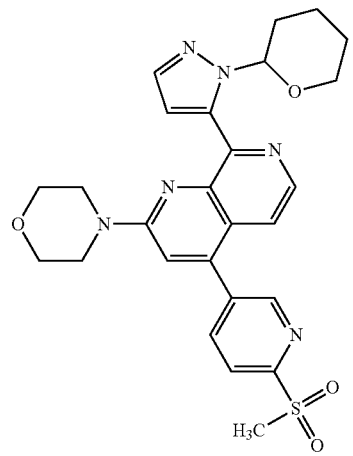 [SMILES: CS(=O)(=O)c1ccc(-c2cc(N3CCOCC3)nc3c(-c4ccnn4C4CCCCO4)nccc23)cn1]

Under argon, 16 mg (0.019 mmol) [1,1'-bis(diphenylphosphino)ferrocene]dichloropalladium(II) were added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 78 mg (0.39 mmol) [6-(methylsulfonyl)pyridin-3-yl]boronic acid in 1.4 ml dioxane and 254 mg (0.78 mmol) caesium carbonate. The mixture was stirred at 110° C. for 4 hours. After cooling, the reaction mixture was diluted with ethyl acetate and an aqueous solution of sodium chloride. The mixture was extracted with ethyl acetate (2x) and the combined organic phases were filtered using a Whatman filter. The organic phase was concentrated and the crude product (168 mg) was used without further purification.

Step b

4-[6-(methylsulfonyl)pyridin-3-yl]-2-(morpholin-4-yl)-8-(1H-pyrazol-5-yl)-1,7-naphthyridine

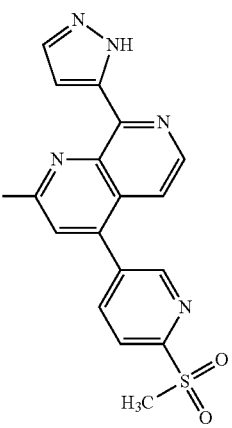

0.37 ml (0.73 mmol) 2N aqueous solution of hydrogen chloride was added to a solution of 165 mg crude 4-[6-(methylsulfonyl)pyridin-3-yl]-2-(morpholin-4-yl)-8-[1-(tetrahydro-2H-pyran-2-yl)-1H-pyrazol-5-yl]-1,7-naphthyridine in 1.5 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: acidic conditions) to give 9 mg (0.02 mmol) of the desired product. $^1$H-NMR (400 MHz, DMSO-d6): δ [ppm]= 3.40 (3H), 3.82 (8H), 7.38 (1H), 7.43 (1H), 7.66 (1H), 7.70 (1H), 8.26 (1H), 8.36 (1H), 8.40 (1H), 9.01 (1H), 13.42 (1H).

Example 4

4-(3,6-dihydro-2H-pyran-4-yl)-2-(morpholin-4-yl)-8-(1H-pyrazol-3-yl)-([1,7]naphthyridine

Step a 4-(3,6-dihydro-2H-pyran-4-yl)-2-(morpholin-4-yl)-8-[2-(tetrahydropyran-2-yl)-2H-pyrazol-3-yl]-[1,7]naphthyridine

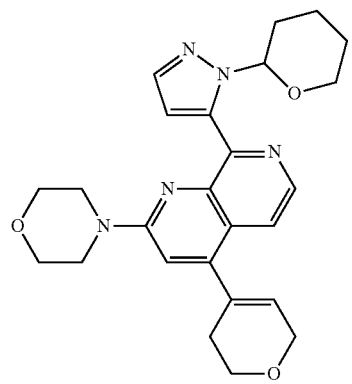 [SMILES: C1=C(c2cc(N3CCOCC3)nc3c(-c4ccnn4C4CCCCO4)nccc23)CCOC1]

Under argon, 40 mg (0.05 mmol) of [1,1′-bis(diphenylphosphino)ferrocene]dichloropalladium(II) complex with dichloromethane (1:1, Pd(dppf)Cl$_2$) and 635 mg (1.95 mmol) of caesium carbonate were added to a suspension of 250 mg (0.49 mmol) of 2-(morpholin-4-yl)-8-[2-(tetrahydropyran-2-yl)-2H-pyrazol-3-yl]-[1,7]naphthyridin-4-yl trifluoromethanesulphonate and 205 mg (0.97 mmol) of 3,6-dihydro-2H-pyran-4-boronic acid and pinacol ester in 5.0 ml of absolute dioxane. The reaction mixture was stirred at 110° C. for 4 h. The mixture was chromatographed directly without work-up [silica gel 60 (25 g, 30 μm); ethyl acetate (100 ml)]. This gave 55 mg (25% of theory) of 4-(3,6-dihydro-2H-pyran-4-yl)-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=448.4, R$_t$=3.43 min.

Step b 4-(3,6-dihydro-2H-pyran-4-yl)-2-(morpholin-4-yl)-8-(1H-pyrazol-3-yl)-[1,7]naphthyridine

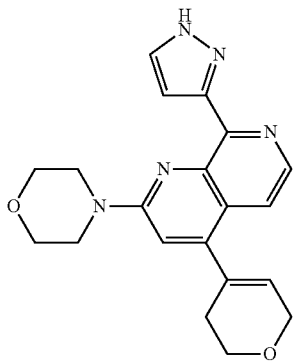 [SMILES: C1=C(c2cc(N3CCOCC3)nc3c(-c4cc[nH]n4)nccc23)CCOC1]

A drop of water and 1 ml (13 mmol) of trifluoroacetic acid were added to 50 mg (0.11 mmol) of 4-(3,6-dihydro-2H-pyran-4-yl)-2-(morpholin-4-yl)-8-[2-(tetrahydropyran-2-yl)-2H-pyrazol-3-yl]-[1,7]naphthyridine. After one hour of stirring at room temperature, the trifluoroacetic acid was distilled off and the residue was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (25 g, 30 μm); ethyl acetate (100 ml)]. This gave 15 mg (37% of theory) of 4-(3,6-dihydro-2H-pyran-4-yl)-2-(morpholin-4-yl)-8-(1H-pyrazol-3-yl)-[1,7]naphthyridine as a yellow solid. m.p. 233-235° C. $^1$H NMR (400 MHz, DMSO): δ [ppm]=3.76-3.78 (10H), 3.90-3.92 (2H), 4.29-4.31 (2H), 5.99 (1H), 7.38 (2H), 7.61 (1H), 7.66-7.67 (1H), 8.35-8.36 (1H), 13.35 (1H). LC-MS (method 1): m/z: [M+H]$^+$=364.3, R$_t$=2.71 min.

Example 5

4-(4-(N,S-dimethylsulfonimidoyl)phenyl)-2-[morpholin-4-yl]-8-(1H-pyrazol-5-yl)-1,7-naphthyridine

Step a

4-[4-(N,S-dimethylsulfonimidoyl)phenyl]-2-(morpholin-4-yl)-8-[1-(tetrahydro-2H-pyran-2-yl)-1H-pyrazol-5-yl]-1,7-naphthyridine

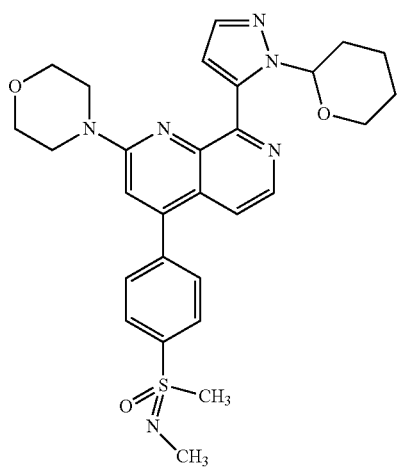 [SMILES: CN=S(C)(=O)c1ccc(-c2cc(N3CCOCC3)nc3c(-c4ccnn4C4CCCCO4)nccc23)cc1]

2-[Morpholin-4-yl]-4-[4-(S-methylsulfonimidoyl)phenyl]-8-[1-(tetrahydro-2H-pyran-2-yl)-1H-pyrazol-5-yl]-1,7-naphthyridine (83 mg, 0.16 mmol, 1 eq.) was solubilized in THF (3 mL) and NaH (60% in mineral oil, 15 mg, 0.38 mmol, 2.4 eq). The reaction mixture was stirred for 30 minutes at rt and iodomethane (35 µL, 0.56 mmol, 3.5 eq.) was added. The reaction was stirred for 16 hours at rt and then quenched by addition of H$_2$O. The aqueous phase was extracted 3 times with CH$_2$Cl$_2$ and the organic phase was dried (MgSO$_4$), filtered and concentrated under reduced pressure. The crude material was purified by preparative HPLC (basic) and the desired compound was obtained in 63% yield (57 mg). $^1$H-NMR (400 MHz, DMSO-d$_6$): δ [ppm]: 1.40-1.66 (3H), 1.92-2.05 (2H), 2.34-2.45 (1H), 2.55 (3H), 3.22 (3H), 3.24-3.30 (1H), 3.72 (9H), 6.06-6.12 (1H), 6.94 (1H), 7.43 (1H), 7.52 (1H), 7.64 (1H), 7.85 (2H), 8.03 (2H), 8.39 (1H). LC-MS (Method 3): m/z: [M+H]$^+$=533, R$_t$=0.94 min.

Step b 4-(4-(N,S-dimethylsulfonimidoyl)phenyl)-2-[morpholin-4-yl]-8-(1H-pyrazol-5-yl)-1,7-naphthyridine

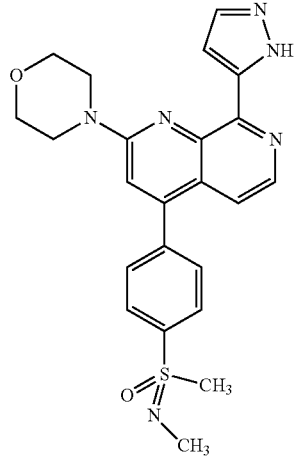 [SMILES: CN=S(C)(=O)c1ccc(-c2cc(N3CCOCC3)nc3c(-c4ccn[nH]4)nccc23)cc1]

4-[4-(N,S-Dimethylsulfonimidoyl)phenyl]-2-[morpholin-4-yl]-8-[1-(tetrahydro-2H-pyran-2-yl)-1H-pyrazol-5-yl]-1,7-naphthyridine (57 mg, 0.11 mmol, 1 eq.) was solubilised in CH$_2$Cl$_2$ (1.5 mL) and H$_2$O (1.5 mL). Formic acid (1 mL) was added and the reaction mixture was stirred for 1 h at rt. The mixture was neutralised with sat. NaHCO$_3$ and the aqueous phase was extracted 3 times with CH$_2$Cl$_2$. The organic phase was dried (silicon filter) and concentrated under reduced pressure. The crude material was purified by flash column chromatography (gradient from 100% Hex to 100% EtOAc). The title compound was obtained in 70% yield (46 mg). $^1$H-NMR (400 MHz, DMSO-d$_6$): δ[ppm]: 2.55 (3H), 3.22 (3H), 3.80 (8H), 7.38 (1H), 7.43 (1H), 7.57 (1H), 7.64 (1H), 7.84 (2H), 8.03 (2H), 8.35 (1H), 13.42 (1H). LC-MS (Method 3): m/z: [M+H]$^+$=449, R$_t$=0.91 min.

Example 6

4-[4-methyl-6-(methylsulfonyl)pyridin-3-yl]-2-(morpholin-4-yl)-8-(1H-pyrazol-5-yl)-1,7-naphthyridine

Step a

4-[4-methyl-6-(methylsulfonyl)pyrdin-3-yl]-2-(morpholin-4-yl)-8-[1-(tetrahydro-2H-pyran-2-yl)-1H-pyrazol-5-yl]-1,7-naphthyridine

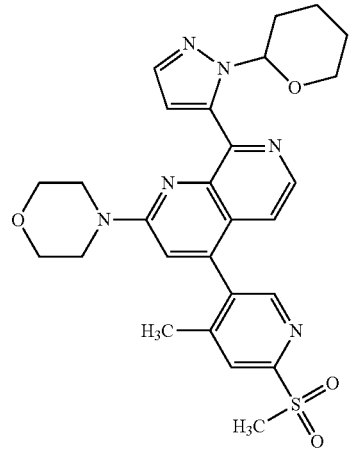 [SMILES: Cc1cc(S(C)(=O)=O)ncc1-c1cc(N2CCOCC2)nc2c(-c3ccnn3C3CCCCO3)nccc12]

Under argon, 16 mg (0.019 mmol) [1,1'-bis(diphenylphosphino)ferrocene]dichloropalladium(II) were added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 116 mg (0.39 mmol) 4-methyl-2-(methylsulfonyl)-5-(4,4,5,5-tetramethyl-1,3,2-dioxaborolan-2-yl)pyridine in 1.4 ml dioxane and 254 mg (0.78 mmol) caesium carbonate. The mixture was stirred at 130° C. for 10 minutes in a microwave oven. After cooling, the reaction mixture was diluted with DCM and filtered using a Whatman filter. The organic phase was concentrated and the crude product (164 mg) was used without further purification.

Step b

4-[4-methyl-6-(methylsulfonyl)pyridin-3-yl]-2-(morpholin-4-yl)-8-(1H-pyrazol-5-yl)-1,7-naphthyridine

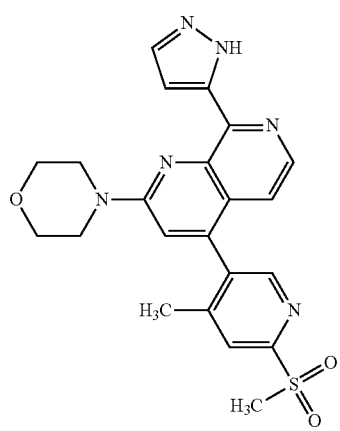 [SMILES: Cc1cc(S(C)(=O)=O)ncc1-c1cc(N2CCOCC2)nc2c(-c3ccn[nH]3)nccc12]

0.31 ml (0.61 mmol) 2N aqueous solution of hydrogen chloride was added to a solution of 164 mg crude 4-[4-methyl-6-(methylsulfonyl)pyridin-3-yl]-2-(morpholin-4-yl)-8-[1-(tetrahydro-2H-pyran-2-yl)-1H-pyrazol-5-yl]-1,7-naphthyridine in 1.0 ml methanol and the reaction mixture was stirred at room temperature for 1 hour. The mixture was basified by addition of an aqueous sodium bicarbonate solution and extracted with ethyl acetate (2×). The combined organic phases were dried (Na$_2$SO$_4$), filtered and concentrated. The residue was purified by preperative HPLC (Autopurifier: basic conditions) to give 31 mg (0.07 mmol) of the desired product. $^1$H-NMR (400 MHz, DMSO-d6): δ[ppm]=2.24 (3H), 3.37 (3H), 3.80 (8H), 7.00 (1H), 7.45 (1H), 7.65 (2H), 8.19 (1H), 8.30 (1H), 8.69 (1H), 13.44 (1H).

Example 7

4-(4-methanesulphonylphenyl)-2-(morpholin-4-yl)-8-(1H-pyrazol-3-yl)-[1,7]naphthyridine Step a 4-(4-methanesulphonylphenyl)-2-(morpholin-4-yl)-8-[2-(tetrahydropyran-2-yl)-2H-pyrazol-3-yl]-[1,7]naphthyridine

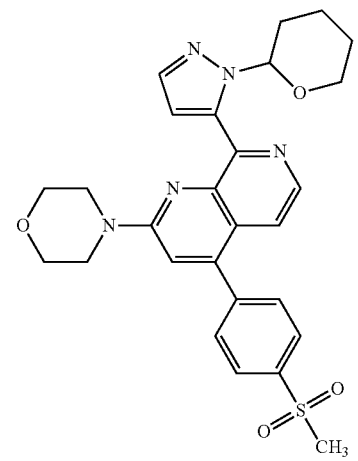 [SMILES: CS(=O)(=O)c1ccc(-c2cc(N3CCOCC3)nc3c(-c4ccnn4C4CCCCO4)nccc23)cc1]

Under argon, 25 mg (0.03 mmol) of [1,1'-bis(diphenylphosphino)ferrocene]dichloropalladium(II) complex with dichloromethane (1:1, Pd(dppf)Cl$_2$) and 391 mg (1.2 mmol) of caesium carbonate were added to a suspension of 154 mg (0.3 mmol) of 2-(morpholin-4-yl)-8-[2-(tetrahydropyran-2-yl)-2H-pyrazol-3-yl]-[1,7]naphthyridin-4-yltrifluoromethanesulphonate and 169 mg (0.6 mmol) of 4-methylsulphonylphenylboronic acid pinacol ester in 3.0 ml of absolute dioxane. The reaction mixture was stirred at 90° C. for 2 h. The mixture was chromatographed directly without work-up [silica gel 60 (12 g, 30 µm); ethyl acetate (100 ml)]. This gave 110 mg (71% of theory) of 4-(4-methanesulphonylphenyl)-2-(morpholin-4-yl)-8-[2-(tetrahydropyran-2-yl)-2H-pyrazol-3-yl]-[1,7]naphthyridine as a yellow foam. LC-MS (method 1): m/z: [M+H]$^+$=520.3, R$_t$=3.38 min.

Step b 4-(4-methanesulphonylphenyl)-2-(morpholin-4-yl)-
8-(1H-pyrazol-3-yl)-[1,7]naphthyridine

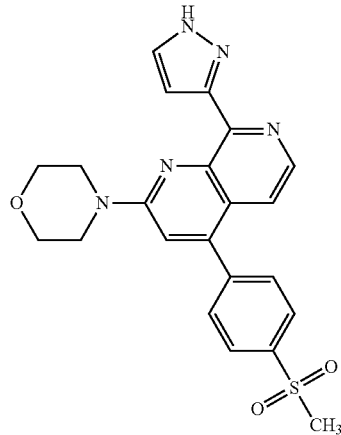 [SMILES: CS(=O)(=O)c1ccc(-c2cc(N3CCOCC3)nc3c(-c4cc[nH]n4)nccc23)cc1]

A drop of water and 2 ml of (26 mmol) of trifluoroacetic acid were added to 110 mg (0.21 mmol) of 4-(4-methanesulphonylphenyl)-2-(morpholin-4-yl)-8-[2-(tetrahydropyran-2-yl)-2H-pyrazol-3-yl]-[1,7]naphthyridine. After 3 h, LCMS showed complete removal of the protective group. The trifluoroacetic acid was removed using a rotary evaporator and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of methanol were added to the residue. The resulting precipitated solid was filtered off using a frit and then dried. This gave 75 mg (81% of theory) of 4-(4-methanesulphonylphenyl)-2-(morpholin-4-yl)-8-(1H-pyrazol-3-yl)-[1,7]naphthyridine as a yellow solid. m.p. 260-262° C. $^1$H NMR (400 MHz, DMSO, δ ppm): 3.33 (3H), 3.80 (8H), 7.36 (1H), 7.40 (1H), 7.56 (1H), 7.67 (1H), 7.86 (2H), 8.14 (2H), 8.33 (1H), 13.40 (1H).

Example 8

4-(2-methanesulphonylphenyl)-2-(morpholin-4-yl)-
8-(1H-pyrazol-3-yl)-[1,7]naphthyridine Hydrochloride Step a 4-(2-methanesulphonylphenyl)-2-(morpholin-4-yl)-
8-[2-(tetrahydropyran-2-yl)-2H-pyrazol-3-yl]-[1,7]
naphthyridine

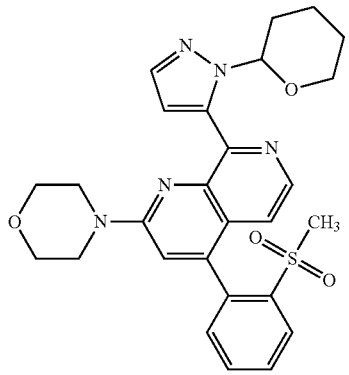 [SMILES: CS(=O)(=O)c1ccccc1-c1cc(N2CCOCC2)nc2c(-c3ccnn3C3CCCCO3)nccc12]

Under argon, 30 mg (0.04 mmol) of [1,1'-bis(diphenylphosphino)ferrocene]dichloropalladium(II) complex with dichloromethane (1:1, Pd(dppf)Cl$_2$) and 482 mg (1.48 mmol) of caesium carbonate were added to a suspension of 190 mg (0.37 mmol) of 2-(morpholin-4-yl)-8-[2-(tetrahydropyran-2-yl)-2H-pyrazol-3-yl]-[1,7]naphthyridin-4-yl trifluoromethanesulphonate and 148 mg (0.74 mmol) of 2-methanesulphonylphenylboronic acid in 2.0 ml of absolute dimethylformamide. The reaction mixture was stirred at 90° C. for 2 h. The mixture was chromatographed directly without work-up [silica gel 60 (25 g, 30 µm); chloroform/methanol 95:5 (100 ml)]. This gave 60 mg (31% of theory) of 4-(2-methanesulphonylphenyl)-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=520.3, R$_f$=2.92 min.

Step b 4-(2-methanesulphonylpheyl)-2-(morpholin-4-yl)-8-
(1H-pyrazol-3-yl)-[1,7]naphthyridine

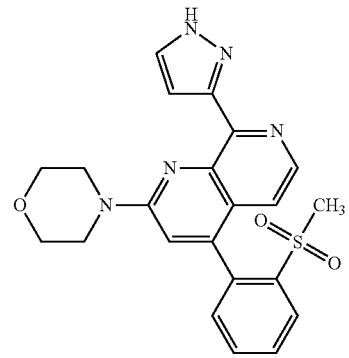 [SMILES: CS(=O)(=O)c1ccccc1-c1cc(N2CCOCC2)nc2c(-c3cc[nH]n3)nccc12]

A drop of water and 1 ml (13 mmol) of trifluoroacetic acid were added to 60 mg (0.12 mmol) of 4-(2-methanesulphonylphenyl)-2-(morpholin-4-yl)-8-[2-(tetrahydropyran-2-yl)-2H-pyrazol-3-yl]-[1,7]naphthyridine. After 10 min, the trifluoroacetic acid was distilled off and the residue was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, m); chloroform/methanol 95:5 (100 ml)]. This gave 20 mg (40% of theory) of 4-(2-methanesulphonylphenyl)-2-(morpholin-4-yl)-8-[2-(tetrahydropyran-2-yl)-1H-pyrazol-3-yl]-[1,7]naphthyridine as a yellow solid. LC-MS (method 1): m/z: [M+H]$^+$=436.2, R$_f$=2.72 min.

Step c

4-(2-methanesulphonylphenyl)-2-(morpholin-4-yl)-8-(1H-pyrazol-3-yl)-[1,7]naphthyridine Hydrochloride

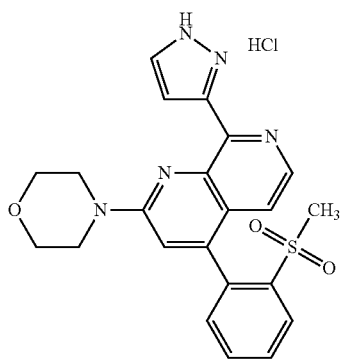 [SMILES: CS(=O)(=O)c1ccccc1-c1cc(N2CCOCC2)nc2c(-c3cc[nH]n3)nccc12 ; Cl]

20 mg (0.046 mmol) of 4-(2-methanesulphonylphenyl)-2-(morpholin-4-yl)-8-(1H-pyrazol-3-yl)-[1,7]naphthyridine were dissolved in 3 ml of 2-butanol, and 18 μl of trimethylchlorosilane were added. The mixture was stirred in the open vessel at room temperature for 1 h. The solid formed was filtered off with suction and dried. This gave 15 mg (69% of theory) of 4-(2-methanesulphonylphenyl)-2-(morpholin-4-yl)-8-(1H-pyrazol-3-yl)-[1,7]naphthyridine hydrochloride as a yellow solid. m.p. 173-175° C. $^1$H NMR (400 MHz, CD$_3$OD, δ ppm): 3.05 (3H), 3.87-3.97 (8H), 7.36 (1H), 7.56-7.58 (1H), 7.72 (1H), 7.87 (1H), 7.89-7.95 (2H), 7.99 (1H), 8.19 (1H), 8.29 (1H), 8.29-8.31 (1H). LC-MS (method 1): m/z: [M+H]$^+$=436.2, R$_t$=2.72 min.

Example 9 dimethyl {4-[2-(morpholin-4-yl)-8-(1H-pyrazol-5-yl)-1,7-naphthyridin-4-yl]phenyl}phosphonate

Step a dimethyl (4-{2-(morpholin-4-yl)-8-[1-(tetrahydro-2H-pyran-2-yl)-1H-pyrazol-5-yl]-1,7-naphthyridin-4-yl}phenyl)phosphonate

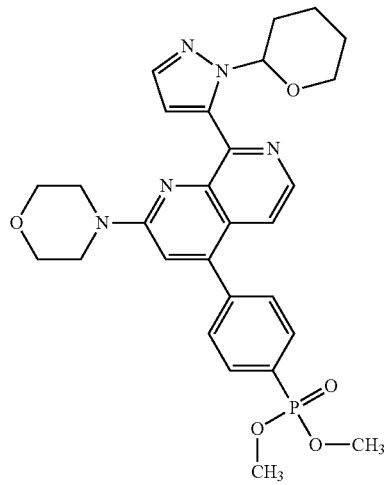 [SMILES: COP(=O)(OC)c1ccc(-c2cc(N3CCOCC3)nc3c(-c4ccnn4C4CCCCO4)nccc23)cc1]

Under argon, 12 mg (0.015 mmol) [1,1'-bis(diphenylphosphino)ferrocene]dichloropalladium(II) were added to a mixture of 75 mg (0.15 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 91 mg (0.29 mmo) dimethyl [4-(4,4,5,5-tetramethyl-1,3,2-dioxaborolan-2-yl)phenyl]phosphonate in 1.1 ml dioxane and 190 mg (0.58 mmol) caesium carbonate. The mixture was stirred at 110° C. for 150 minutes. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and the residue was purified by column chromatography (ethyl acetate) to give 53 mg (0.10 mmol) of the desired product.

Step b dimethyl {4-[2-(morpholin-4-yl)-8-(1H-pyrazol-5-yl)-1,7-naphthyridin-4-yl]phenyl}phosphonate

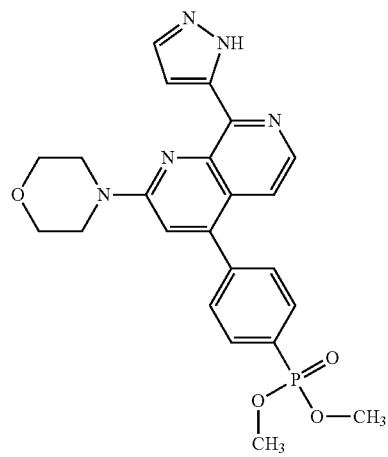 [SMILES: COP(=O)(OC)c1ccc(-c2cc(N3CCOCC3)nc3c(-c4ccn[nH]4)nccc23)cc1]

0.11 ml (0.22 mmol) 2N aqueous solution of hydrogen chloride was added to a solution of 53 mg dimethyl (4-{2-(morpholin-4-yl)-8-[1-(tetrahydro-2H-pyran-2-yl)-1H-pyrazol-5-yl]-1,7-naphthyridin-4-yl}phenyl)phosphonate in 0.4 ml methanol and the reaction mixture was stirred at room temperature for 1 hour. Aqueous sodium bicarbonate solution was added and the mixture was extracted with ethyl acetate (2×). The combined organic phases were filtered using a Whatman filter and concentrated to give 38 mg (0.08 mmol) of the desired product. $^1$H-NMR (400 MHz, CDCl$_3$): δ[ppm]=3.83 (4H), 3.87 (3H), 3.89 (3H), 3.98 (4H), 7.20 (1H), 7.39 (2H), 7.62 (2H), 7.78 (1H), 8.00 (1H), 8.04 (1H), 8.44 (1H).

Example 10

4-Isopropenyl-2-(morpholin-4-yl)-8-(1H-pyrazol-3-yl)-[1,7]naphthyridine

Step a 4-isopropenyl-2-(morpholin-4-yl)-8-[2-(tetrahydropyran-2-yl)-2H-pyrazol-3-yl]-[1,7]naphthyridine

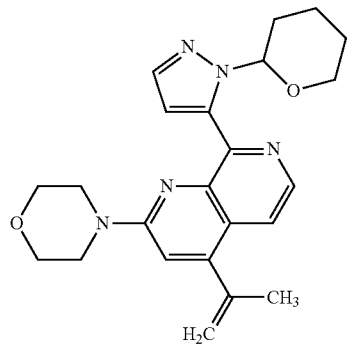 [SMILES: C=C(C)c1cc(N2CCOCC2)nc2c(-c3ccnn3C3CCCCO3)nccc12]

Under argon, 24 mg (29 μmol) of [1,1'-bis(diphenylphosphino)ferrocene]dichloropalladium(II) complex with dichloromethane (1:1, Pd(dppf)Cl$_2$) and 286 mg (0.88 mmol) of caesium carbonate were added to a suspension of 150 mg (0.29 mmol) of 2-(morpholin-4-yl)-8-[2-(tetrahydropyran-2-yl)-2H-pyrazol-3-yl]-[1,7]naphthyridin-4-yl trifluoromethanesulphonate and 483 mg (1.46 mmol) of tributylisopropenylstannane in 2.0 ml of absolute dioxane. The reaction mixture was stirred at 110° C. for 16 h. 20 ml of water were added to the mixture. The aqueous phase was extracted three times with in each case 20 ml of dichloromethane. The combined organic phases were dried over sodium sulphate and then concentrated to dryness. The residue was chromatographed [silica gel 60 (12 g, 30 μm); chloroform (100 ml)]. This gave 50 mg (42% of theory) of 4-isopropenyl-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=406.4, R$_t$=3.58 min.

Step b

4-Isopropenyl-2-(morpholin-4-yl)-8-(1H-pyrazol-3-yl)-[1,7]naphthyridine

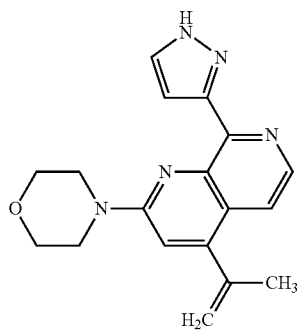 [SMILES: C=C(C)c1cc(N2CCOCC2)nc2c(-c3cc[nH]n3)nccc12]

A drop of water and 1 ml (13 mmol) of trifluoroacetic acid were added to 50 mg (0.12 mmol) of 4-isopropenyl-2-(morpholin-4-yl)-8-[2-(tetrahydropyran-2-yl)-2H-pyrazol-3-yl]-[1,7]naphthyridine. The mixture was allowed to stand at room temperature for one hour, the trifluoroacetic acid was then distilled off and the residue was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, 30 μm); chloroform/methanol 95:5 (100 ml)]. This gave 30 mg (76% of theory) of 4-isopropenyl-2-(morpholin-4-yl)-8-(1H-pyrazol-3-yl)-[1,7]naphthyridine as a yellow solid. m.p. 53-55° C. $^1$H NMR (400 MHz, CDCl$_3$, δ ppm): 2.17 (3H), 3.70-3.73 (4H), 3.89-3.92 (4H), 5.12 (1H), 5.46 (1H), 7.02 (1H), 7.28 (1H), 7.53 (1H), 7.68 (1H), 8.39 (1H). LC-MS (method 1): m/z: [M+H]$^+$=322.3, R$_t$=2.85 min.

Example 11

2-(morpholin-4-yl)-4-phenyl-8-(1H-pyrazol-3-yl)-[1,7]naphthyridine

Step a 2-(morpholin-4-yl)-4-phenyl-8-[2-(tetrahydropyran-2-yl)-2H-pyrazol-3-yl]-[1,7]naphthyridine

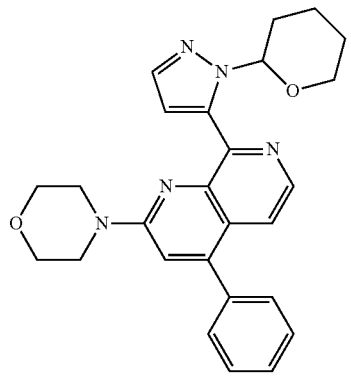 [SMILES: c1ccc(-c2cc(N3CCOCC3)nc3c(-c4ccnn4C4CCCCO4)nccc23)cc1]

Under argon, 74 mg (0.09 mmol) of [1,1'-bis(diphenylphosphino)ferrocene]dichloropalladium(II) complex with dichloromethane (1:1, Pd(dppf)Cl$_2$) and 391 mg (1.2 mmol) of caesium carbonate were added to a suspension of 154 mg (0.3 mmol) of 2-(morpholin-4-yl)-8-[2-(tetrahydropyran-2-yl)-2H-pyrazol-3-yl]-[1,7]naphthyridin-4-yl trifluoromethanesulphonate and 245 mg (1.2 mmol) of phenylboronic acid pinacol ester in 6.0 ml of absolute dioxane. The reaction mixture was stirred at 90° C. for 2 h. The mixture was chromatographed directly without work-up [silica gel 60 (12 g, 30 μm); ethyl acetate (100 ml)]. This gave 47 mg (36% of theory) of 2-(morpholin-4-yl)-4-phenyl-8-[2-(tetrahydropyran-2-yl)-2H-pyrazol-3-yl]-[1,7]naphthyridine as a yellow oil. LC-MS (method 1): m/z: [M+H]$^+$=442.3, R$_t$=3.81 min.

Step b 2-(morpholin-4-yl)-4-phenyl-8-(1H-pyrazol-3-yl)-[1,7]naphthyridine

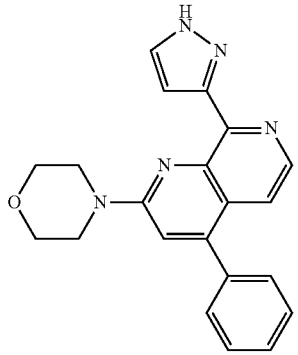 [SMILES: c1ccc(-c2cc(N3CCOCC3)nc3c(-c4cc[nH]n4)nccc23)cc1]

A drop of water and 1 ml (13 mmol) of trifluoroacetic acid were added to 47 mg (0.11 mmol) of 2-(morpholin-4-yl)-4-phenyl-8-[2-(tetrahydropyran-2-yl)-2H-pyrazol-3-yl]-[1,7]naphthyridine. After 10 min, LCMS showed complete removal of the protective group. The trifluoroacetic acid was removed on a rotary evaporator and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of methanol were added to the residue. The resulting precipitated solid was filtered off using a frit and then dried. This gave 30 mg (75% of theory) of 2-(morpholin-4-yl)-4-phenyl-8-(1H-pyrazol-3-yl)-[1,7]naphthyridine as a yellow solid. m.p. 89-91° C. $^1$H NMR (400 MHz, CDCl$_3$, δ ppm): 3.74-3.76 (4H), 3.91-3.93 (4H), 7.14 (1H), 7.31 (1H), 7.41 (1H), 7.45-7.47 (2H), 7.50-7.55 (3H), 7.70 (1H), 8.35 (1H). LC-MS (method 1): m/z: [M+H]$^+$=358.3, R$_t$=3.16 min.

Example 12

4-[4-(S-ethylsulfonimidoyl)phenyl]-2-(morpholin-4-yl)-8-(1H-pyrazol-5-yl)-1,7-naphthyridine Step a 4-[4-(ethylsulfanyl)phenyl]-2-(morpholin-4-yl)-8-[1-(tetrahydro-2H-pyran-2-yl)-1H-pyrazol-5-yl]-1,7-naphthyridine

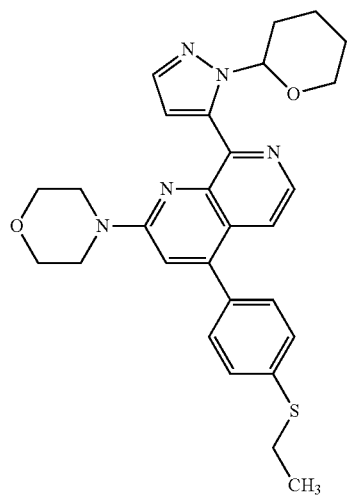 [SMILES: CCSc1ccc(-c2cc(N3CCOCC3)nc3c(-c4ccnn4C4CCCCO4)nccc23)cc1]

Under argon, 24 mg (0.029 mmol) [1,1'-bis(diphenylphosphino)ferrocene]dichloropalladium(I) was added to a mixture of 150 mg (0.29 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 106 mg (0.58 mmol) [4-(ethylsulfanyl)phenyl]boronic acid in 2.1 ml dioxane and 381 mg (1.17 mmol) caesium carbonate. The mixture was stirred at 110° C. for 10 minutes. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and residue was purified by column chromatography (DCM/ethanol 0%-30%) to give 150 mg (0.03 mmol) of the desired product, containing slight impurities, that was used without further purifications.

Step b

N-[ethyl(4-{2-(morpholin-4-yl)-8-[1-(tetrahydro-2H-pyran-2-yl)-1H-pyrazol-5-yl]-1,7-naphthyridin-4-yl}phenyl)-λ$^4$-sulfanylidene]-2,2,2-trifluoroacetamide

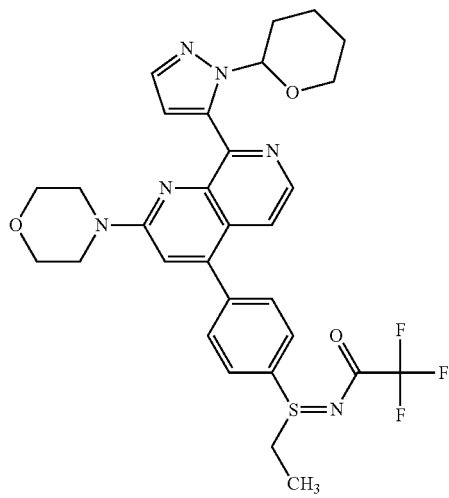 [SMILES: CC/S(=N/C(=O)C(F)(F)F)c1ccc(-c2cc(N3CCOCC3)nc3c(-c4ccnn4C4CCCCO4)nccc23)cc1]

Under an atmosphere of argon, a solution of 49 mg (0.43 mmol) 2,2,2-trifluoroacetamide in 0.16 ml THF was added dropwise to a solution of 27 mg (0.29 mmol) sodium tert.-butoxide in 0.23 ml THF, so that the temperature of the mixture remained below 10° C. Subsequently, a freshly prepared solution of 53 mg (0.19 mmol) 1,3-dibromo-5,5-dimethylhydantoin in 0.23 mL THF was added dropwise to the stirred mixture, so that the temperature of the mixture remained below 10° C. Then the mixture was stirred for 10 minutes at 10° C. Finally, a solution of 145 mg (0.29 mmol) 4-[4-(ethylsulfanyl)phenyl]-2-(morpholin-4-yl)-8-[1-(tetrahydro-2H-pyran-2-yl)-1H-pyrazol-5-yl]-1,7-naphthyridine in 0.23 ml THF was added dropwise to the stirred mixture, so that the temperature of the mixture remained below 10° C. The mixture was stirred for 90 minutes at 10° C. and then at room temperature overnight. The batch was diluted with 0.6 ml of toluene under cooling and an aqueous solution of 36 mg (0.29 mmol) sodium sulfite in 1.1 mL water was added so that the temperature of the mixture remained below 15° C. The batch was extracted three times with ethyl acetate. The combined organic phases were washed with an aqueous solution of sodium chloride, filtered using a Whatman filter and concentrated. The residue was purified by column chromatography on silica gel (ethyl acetate) to give 33 mg of the desired product. $^1$H-NMR (400 MHz, CDCl$_3$): δ[ppm]=1.42 (3H), 1.61 (5H), 2.12 (2H), 2.59 (1H), 3.39 (2H), 3.48 (1H), 3.79 (6H), 3.98 (1H), 6.10 (1H), 7.00 (1H), 7.08 (1H), 7.37 (1H), 7.75 (3H), 7.97 (2H), 8.43 (1H).

Step c

4-[4-(S-ethylsulfonimidoyl)phenyl]-2-(morpholin-4-yl)-8-[1-(tetrahydro-2H-pyran-2-yl)-1H-pyrazol-5-yl]-1,7-naphthyridine

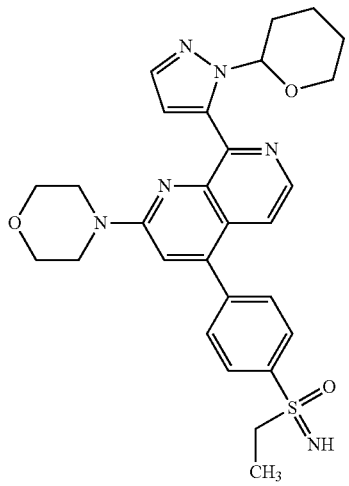 [SMILES: CCS(=N)(=O)c1ccc(-c2cc(N3CCOCC3)nc3c(-c4ccnn4C4CCCCO4)nccc23)cc1]

33 mg (0.054 mmol)N-[ethyl(4-{2-(morpholin-4-yl)-8-[1-(tetrahydro-2H-pyran-2-yl)-1H-pyrazol-5-yl]-1,7-naphthyridin-4-yl}phenyl)-λ$^4$-sulfanylidene]-2,2,2-trifluoroacetamide was dissolved in 1.05 ml methanol. To this solution 0.37 ml water was added. The pH was adjusted to 10.5 by addition of an aqueous solution of potassium hydroxide (25%). 28 mg (0.046 mmol) Oxone® was added and the mixture was stirred at room temperature for 4 hours. Additional 28 mg (0.046 mmol) Oxone® was added. The pH was adjusted to 10.5 by addition of an aqueous solution of potassium hydroxide (25%). The batch was stirred at room temperature for 90 minutes. The pH was adjusted to 10.5 by addition of an aqueous solution of potassium hydroxide (25%) and the batch was stirred at room temperature for 4 days. The batch was filtered and the filtrate was adjusted to pH 6-7 by the addition of 1N aqueous hydrogen chloride solution. The mixture was diluted with aqueous sodium chloride solution and extracted with DCM (2×). The combined organic phases were washed with an aqueous solution of sodium sulfite (10%), filtered using a Whatman filter, and concentrated to give 25 mg crude product that was used without further purification.

Step d

4-[4-(S-ethylsulfonimidoyl)phenyl]-2-(morpholin-4-yl)-8-(1H-pyrazol-5-yl)-1,7-naphthyridine

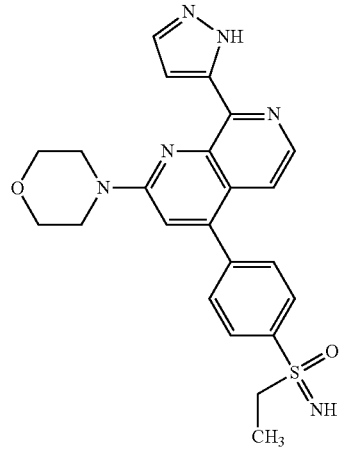 [SMILES: CCS(=N)(=O)c1ccc(-c2cc(N3CCOCC3)nc3c(-c4ccn[nH]4)nccc23)cc1]

0.05 ml (0.11 mmol) 2N aqueous solution of hydrogen chloride was added to a solution of 25 mg crude 4-[4-(S-ethylsulfonimidoyl)phenyl]-2-(morpholin-4-yl)-8-[1-(tetrahydro-2H-pyran-2-yl)-1H-pyrazol-5-yl]-1,7-naphthyridine in 0.22 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: basic conditions) to give 5 mg (0.01 mmol) of the desired product. $^1$H-NMR (400 MHz, DMSO-d6): δ[ppm]= 1.15 (3H), 3.22 (2H), 3.81 (8H), 4.34 (1H), 7.36 (1H), 7.44 (1H), 7.56 (1H), 7.65 (1H), 7.81 (2H), 8.08 (2H), 8.35 (1H), 13.43 (1H).

Example 13

3-[(2-(morpholin-4-yl)-8-[2H-pyrazol-3-yl]-[1,7] naphthyridine-4-yl]phenyl-N-ethoxycarbonyl-S-methylsulphoximide Step a 3-[(-2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide

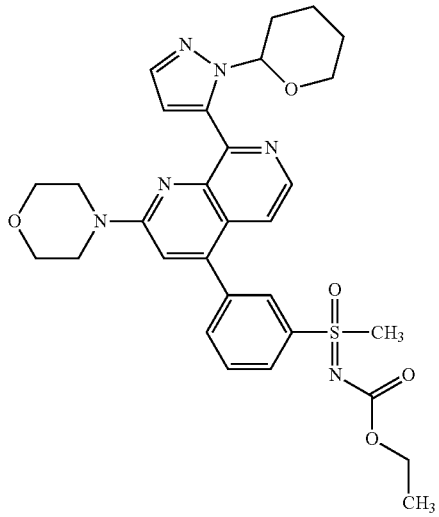 [SMILES: CCOC(=O)N=S(C)(=O)c1cccc(-c2cc(N3CCOCC3)nc3c(-c4ccnn4C4CCCCO4)nccc23)c1]

Under argon, 48 mg (0.06 mmol) of [1,1′-bis(diphenylphosphino)ferrocene]dichloropalladium(II) complex with dichloromethane (1:1, Pd(dppf)Cl$_2$) and 761 mg (2.34 mmol) of caesium carbonate were added to a suspension of 300 mg (0.58 mmol) of 2-(morpholin-4-yl)-8-[2-(tetrahydropyran-2-yl)-2H-pyrazol-3-yl]-[1,7]naphthyridin-4-yl trifluoromethanesulphonate and 413 mg (1.17 mmol) of pinacol ester in 7.5 ml of absolute dioxane. The reaction mixture was stirred at 100° C. for 3 h. The mixture was chromatographed directly without work-up [silica gel 60 (25 g, 30 μm); ethyl acetate (100 ml)]. This gave 270 mg (78% of theory) of 3-[(-2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide as a yellow oil. LC-MS (method 1): m/z: [M+H]$^+$=591.3, R$_t$=3.42 min.

Step b

3-[(2-(morpholin-4-yl)-8-[2H-pyrazol-3-yl]-[1,7]naphthyridine-4-yl]phenyl-N-ethoxycarbonyl-S-methylsulphoximide

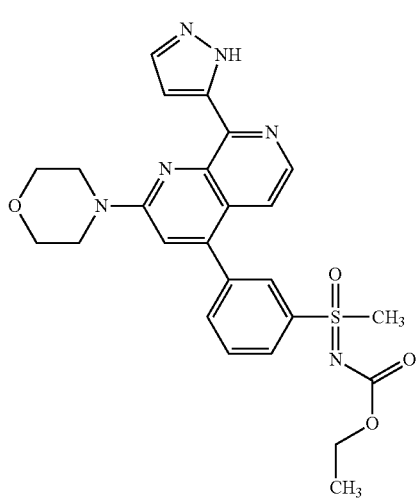 [SMILES: CCOC(=O)N=S(C)(=O)c1cccc(-c2cc(N3CCOCC3)nc3c(-c4ccn[nH]4)nccc23)c1]

260 mg (0.44 mmol) of 3-[(-2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were dissolved in 10 ml of ethanol, and 5 ml of (10 mmol) of 2N hydrochloric acid were added. After 1 h, LCMS showed complete removal of the protective group. Ethanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (25 g, 30 μm); ethyl acetate (100 ml)]. This gave 160 mg (72% of theory) of 3-[(2-(morpholin-4-yl)-8-[2H-pyrazol-3-yl]-[1,7]naphthyridine-4-yl]phenyl-N-ethoxycarbonyl-S-methylsulphoximide as a yellow solid. m.p. 115-117° C. $^1$H NMR (400 MHz, DMSO-d$_6$): δ[ppm]= 1.09-1.13 (3H), 3.57 (3H), 3.81 (8H), 3.98-4.00 (2H), 7.34-7.35 (1H), 7.42 (1H), 7.56 (1H), 7.65 (1H), 7.91-7.96 (1H), 7.98-7.99 (1H), 8.10-8.33 (2H), 8.33-8.34 (1H), 13.40 (1H). LC-MS (method 1): m/z: [M+H]$^+$=507.3, R$_t$=2.93 min.

Example 14

4-(1-methyl-1,2,3,6-tetrahydropyridin-4-yl)-2-(morpholin-4-yl)-8-(1H-pyrazol-5-yl)-1,7-naphthyridine Step a 4-(1-methyl-1,2,3,6-tetrahydropyridin-4-yl)-2-(morpholin-4-yl)-8-[1-(tetrahydro-2H-pyran-2-yl)-1H-pyrazol-5-yl]-1,7-naphthyridine

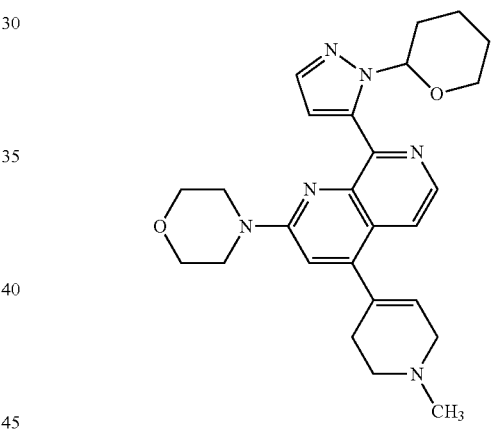

Under argon, 12 mg (0.015 mmol) [1,1′-bis(diphenylphosphino)ferrocene]dichloropalladium(II) was added to a mixture of 75 mg (0.15 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 65 mg (0.29 mmol) 1-methyl-4-(4,4,5,5-tetramethyl-1,3,2-dioxaborolan-2-yl)-1,2,3,6-tetrahydropyridine in 1.1 ml dioxane and 190 mg (0.58 mmol) caesium carbonate. The mixture was stirred at 110° C. for 150 minutes. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and the crude product (142 mg) was used without further purification.

Step b 4-(1-methyl-1,2,3,6-tetrahydropyridin-4-yl)-2-(morpholin-4-yl)-8-(1H-pyrazol-5-yl)-1,7-naphthyridine

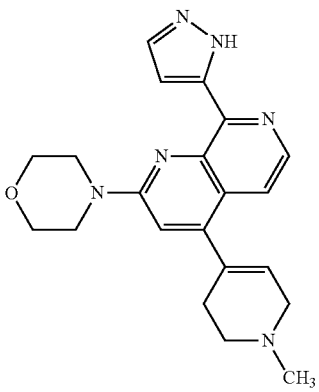 [SMILES: CN1CC=C(c2cc(N3CCOCC3)nc3c(-c4ccn[nH]4)nccc23)CC1]

0.36 ml (0.71 mmol) 2N aqueous solution of hydrogen chloride was added to a solution of 142 mg crude 4-(1-methyl-1,2,3,6-tetrahydropyridin-4-yl)-2-(morpholin-4-yl)-8-[1-(tetrahydro-2H-pyran-2-yl)-1H-pyrazol-5-yl]-1,7-naphthyridine in 1.4 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: basic conditions) to give 22 mg (0.06 mmol) of the desired product. $^1$H-NMR (400 MHz, CDCl$_3$): δ[ppm] =2.51 (3H), 2.59 (2H), 2.78 (2H), 3.23 (2H), 3.76 (4H), 3.96 (4H), 5.89 (1H), 7.07 (1H), 7.31 (1H), 7.57 (1H), 7.73 (1H), 8.43 (1H), 12.99 (1H).

Example 15

4-(3-methanesulphonylphenyl)-2-(morpholin-4-yl)-8-(1H-pyrazol-3-yl)-[1,7]naphthyridine Step a 4-(3-methanesulphonylphenyl)-2-(morpholin-4-yl)-8-[2-(tetrahydropyran-2-yl)-2H-pyrazol-3-yl]-[1,7]naphthyridine

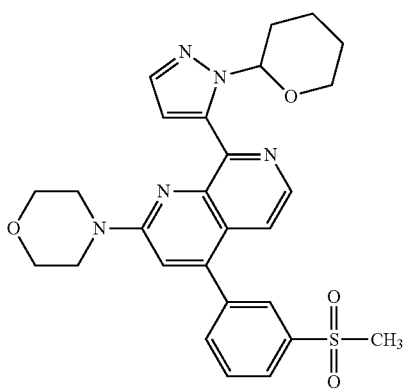 [SMILES: CS(=O)(=O)c1cccc(-c2cc(N3CCOCC3)nc3c(-c4ccnn4C4CCCCO4)nccc23)c1]

Under argon, 24 mg (0.03 mmol) of [1,1'-bis(diphenylphosphino)ferrocene]dichloropalladium(II) complex with dichloromethane (1:1, Pd(dppf)Cl$_2$) and 381 mg (1.17 mmol) of caesium carbonate were added to a suspension of 150 mg (0.29 mmol) of 2-(morpholin-4-yl)-8-[2-(tetrahydropyran-2-yl)-2H-pyrazol-3-yl]-[1,7]naphthyridin-4-yl trifluoromethanesulphonate and 165 mg (0.58 mmol) of 2-(3-methanesulphonylphenyl)-4,4,5,5-tetramethyl-[1,3,2] dioxaborolane in 5.0 ml of absolute dioxane. The reaction mixture was stirred at 90° C. for 16 h. The mixture was chromatographed directly without work-up [silica gel 60 (25 g 30 μm); chloroform/methanol 95:5 (100 ml)]. This gave 80 mg (53% of theory) of 4-(3-methanesulphonylphenyl)-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=520.3, R$_t$=3.33 min.

Step b 4-(3-methanesulphonylphenyl)-2-(morpholin-4-yl)-8-(1H-pyrazol-3-yl)-[1,7]naphthyridine

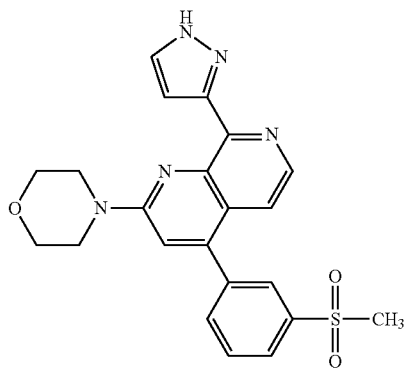 [SMILES: CS(=O)(=O)c1cccc(-c2cc(N3CCOCC3)nc3c(-c4cc[nH]n4)nccc23)c1]

A drop of water and 1 ml (13 mmol) of trifluoroacetic acid were added to 80 mg (0.15 mmol) of 4-(3-methanesulphonylphenyl)-2-(morpholin-4-yl)-8-[2-(tetrahydropyran-2-yl)-2H-pyrazol-3-yl]-[1,7]naphthyridine. After one hour of stirring at room temperature, the trifluoroacetic acid was distilled off and the residue was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, 30 μm); chloroform/methanol 90:10 (100 ml)]. This gave 30 mg (45% of theory) of 4-(3-methanesulphonylphenyl)-2-(morpholin-4-yl)-8-(2H-pyrazol-3-yl)-[1,7]naphthyridine as a yellow solid. m.p. 255-257° C. $^1$H NMR (400 MHz, DMSO, δ ppm): 3.30 (3H), 3.81 (8H), 7.36 (1H), 7.43 (1H), 7.56 (1H), 7.64 (1H), 7.86-7.95 (2H), 8.10-8.13 (2H), 8.35 (1H), 13.41 (1H). LC-MS (method 1): m/z: [M+H]$^+$=436.2, R$_t$=2.80 min.

Example 16

4-[5-methyl-6-(methylsulfonyl)pyrdin-3-yl]-2-(morpholin-4-yl)-8-(1H-pyrazol-5-yl)-1,7-naphthyridine

Step a

4-[5-methyl-6-(methylsulfonyl)pyrdin-3-yl]-2-(morpholin-4-yl)-8-[1-(tetrahydro-2H-pyran-2-yl)-1H-pyrazol-5-yl]-1,7-naphthyridine

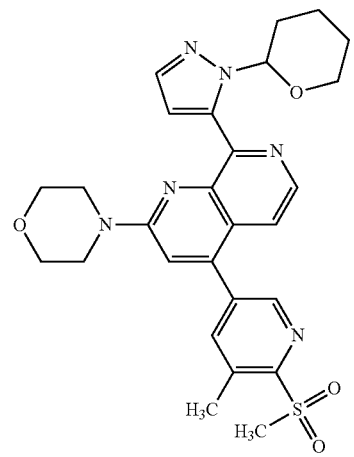 [SMILES: Cc1cc(-c2cc(N3CCOCC3)nc3c(-c4ccnn4C4CCCCO4)nccc23)cnc1S(C)(=O)=O]

Under argon, 16 mg (0.019 mmol) [1,1'-bis(diphenylphosphino)ferrocene]dichloropalladium(II) were added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 116 mg (0.39 mmol) 3-methyl-2-(methylsulfonyl)-5-(4,4,5,5-tetramethyl-1,3,2-dioxaborolan-2-yl)pyridine in 1.4 ml dioxane and 254 mg (0.78 mmol) caesium carbonate. The mixture was stirred at 130° C. for 10 minutes in a microwave oven. After cooling, the reaction mixture was diluted with DCM and filtered using a Whatman filter. The organic phase was concentrated and the crude product (119 mg) was used without further purification.

Step b

4-[5-methyl-6-(methylsulfonyl)pyrdin-3-yl]-2-(morpholin-4-yl)-8-(1H-pyrazol-5-yl)-1,7-naphthyridine

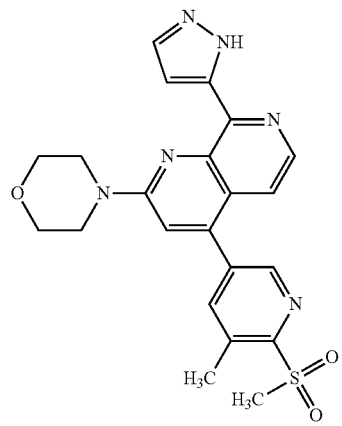 [SMILES: Cc1cc(-c2cc(N3CCOCC3)nc3c(-c4ccn[nH]4)nccc23)cnc1S(C)(=O)=O]

0.22 ml (0.45 mmol) 2N aqueous solution of hydrogen chloride was added to a solution of 119 mg crude 4-[5-methyl-6-(methylsulfonyl)pyridin-3-yl]-2-(morpholin-4-yl)-8-[1-(tetrahydro-2H-pyran-2-yl)-1H-pyrazol-5-yl]-1,7-naphthyridine in 1.0 ml methanol and the reaction mixture was stirred at room temperature for 1 hour. The mixture was basified by addition of an aqueous sodium bicarbonate solution and extracted with ethyl acetate (2×). The combined organic phases were dried ($Na_2SO_4$), filtered and concentrated. The residue was purified by preparative HPLC (Autopurifier: basic conditions) to give 7 mg (0.016 mmol) of the desired product. $^1$H-NMR (400 MHz, DMSO-d6): δ[ppm]=2.73 (3H), 3.48 (3H), 3.81 (8H), 7.41 (2H), 7.66 (2H), 8.22 (1H), 8.35 (1H), 8.73 (1H), 13.44 (1H).

Example 17

2-(morpholin-4-yl)-8-(1H-pyrazol-5-yl)-4-(1,2,3,6-tetrahydropyridin-4-yl)-1,7-naphthyridine

Step a 2-(morpholin-4-yl)-8-[1-(tetrahydro-2H-pyran-2-yl)-1H-pyrazol-5-yl]-4-(1,2,3,6-tetrahydropyridin-4-yl)-1,7-naphthyridine

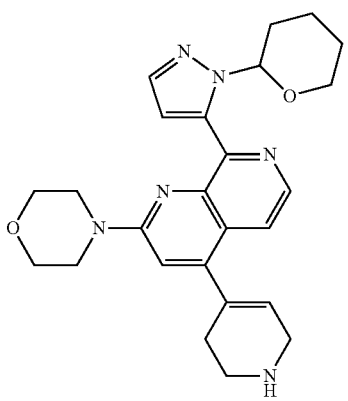 [SMILES: C1=C(c2cc(N3CCOCC3)nc3c(-c4ccnn4C4CCCCO4)nccc23)CCNC1]

Under argon, 12 mg (0.015 mmol) [1,1'-bis(diphenylphosphino)ferrocene]dichloropalladium(I) was added to a mixture of 75 mg (0.15 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 71 mg (0.29 mmol) 4-(4,4,5,5-tetramethyl-1,3,2-dioxaborolan-2-yl)-1,2,3,6-tetrahydropyridine hydrochloride (1:1) in 1.1 ml dioxane and 285 mg (0.88 mmol) caesium carbonate. The mixture was stirred at 110° C. for 4 hours. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and residue was purified by preparative HPLC (Autopurifier: basic conditions) to give 16 mg (0.04 mmol) of the desired product. $^1$H-NMR (400 MHz, CDCl$_3$): δ[ppm] =1.76 (5H), 2.09 (2H), 2.52 (3H), 3.23 (2H), 3.47 (1H), 3.69 (5H), 3.83 (4H), 3.98 (1H), 5.93 (1H), 6.03 (1H), 6.95 (1H), 6.97 (1H), 7.64 (1H), 7.72 (1H), 8.43 (1H).

Step b 2-(morpholin-4-yl)-8-(1H-pyrazol-5-yl)-4-(1,2,3,6-tetrahydropyridin-4-yl)-1,7-naphthyridine

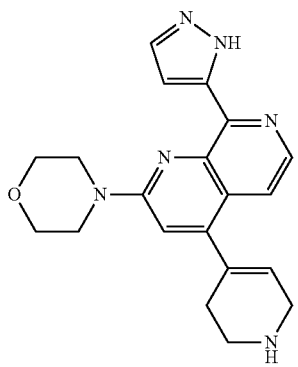 [SMILES: C1=C(c2cc(N3CCOCC3)nc3c(-c4ccn[nH]4)nccc23)CCNC1]

0.04 ml (0.08 mmol) 2N aqueous solution of hydrogen chloride was added to a solution of 16 mg (0.036 mmol) 2-(morpholin-4-yl)-8-[1-(tetrahydro-2H-pyran-2-yl)-1H-pyrazol-5-yl]-4-(1,2,3,6-tetrahydropyridin-4-yl)-1,7-naphthyridine in 0.17 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated to give 11 mg (0.030 mmol) of the desired product. $^1$H-NMR (400 MHz, DMSO-d6): δ[ppm]=2.32 (2H), 2.98 (2H), 3.42 (2H), 3.67 (1H), 3.76 (8H), 5.90 (1H), 7.29 (1H), 7.36 (1H), 7.63 (1H), 7.67 (1H), 8.35 (1H), 13.30 (1H).

Example 18

4-cyclopropyl-2-(morpholin-4-yl)-8-(1H-pyrazol-3-yl)-[1,7]naphthyridine

Step a 4-cyclopropyl-2-(morpholin-4-yl)-8-[2-(tetrahydropyran-2-yl)-2H-pyrazol-3-yl]-[1,7]naphthyridine

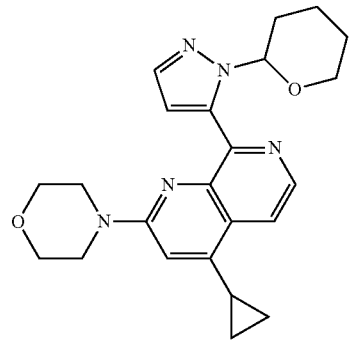 [SMILES: c1cc2c(C3CC3)cc(N3CCOCC3)nc2c(-c2ccnn2C2CCCCO2)n1]

Under argon, 80 mg (0.1 mmol) of [1,1'-bis(diphenylphosphino)ferrocene]dichloropalladium(II) complex with dichloromethane (1:1, Pd(dppf)Cl$_2$) and 635 mg (2.0 mmol) of caesium carbonate were added to a suspension of 250 mg (0.49 mmol) of 2-(morpholin-4-yl)-8-[2-(tetrahydropyran-2-yl)-2H-pyrazol-3-yl]-[1,7]naphthyridin-4-yl trifluoromethanesulphonate and 84 mg (0.97 mmol) of 2-cyclopropyl-4,4,5,5-tetramethyl-[1,3,2]dioxaborolane in 5 ml of absolute dioxane. The reaction mixture was stirred at 110° C. for 4 h. The mixture was chromatographed directly without work-up [silica gel 60 (40 g, 30 μm); chloroform/methanol (1:1, 100 ml)]. This gave 150 mg (76% of theory) of 4-cyclopropyl-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=406.3, R$_t$=3.53 min.

Step b 4-cyclopropyl-2-(morpholin-4-yl)-8-(1H-pyrazol-3-yl)-[1,7]naphthyridine

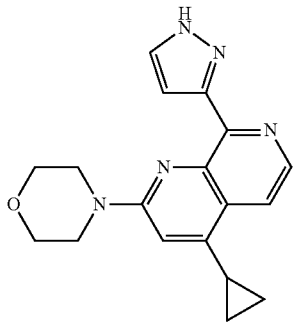 [SMILES: c1cc2c(C3CC3)cc(N3CCOCC3)nc2c(-c2cc[nH]n2)n1]

A drop of water and 1 ml (13 mmol) of trifluoroacetic acid were added to 150 mg (0.37 mmol) of 4-cyclopropyl-2-(morpholin-4-yl)-8-[2-(tetrahydropyran-2-yl)-2H-pyrazol-3-yl]-[1,7]naphthyridine. After 1 h, LCMS showed complete removal of the protective group. The trifluoroacetic acid was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of methanol were added to the residue, resulting in the precipitation of a solid. The latter was filtered off and dried. This gave 30 mg (25% of theory) of 4-cyclopropyl-2-(morpholin-4-yl)-8-(1H-pyrazol-3-yl)-[1,7]naphthyridine as a yellow solid. m.p. 211-214° C. $^1$H NMR (400 MHz, DMSO): δ[ppm]=0.92-0.96 (2H), 1.10-1.14 (2H), 2.42-2.44 (1H), 3.72-3.73 (4H), 3.77-3.78 (4H), 7.08 (1H), 7.36 (1H), 7.61 (1H), 7.99-8.00 (1H), 8.40-8.42 (1H), 13.34 (1H). LC-MS (method 1): m/z: [M+H]$^+$=322.3, R$_t$=2.68 min.

Example 19

3-[(2-(morpholin-4-yl)-8-(2H-pyrazol-3-yl)-[1,7]naphthyridine-4-yl]phenyl-S-methylsulphoximide

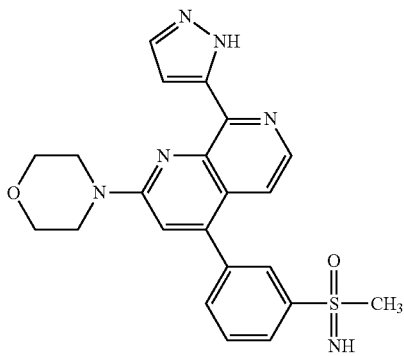 [SMILES: CS(=N)(=O)c1cccc(-c2cc(N3CCOCC3)nc3c(-c4ccn[nH]4)nccc23)c1]

120 mg (0.24 mmol) of 3-[(2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were suspended in 8 ml of sodium methoxide (33%), and the mixture was stirred at 60° C. for 30 min. For work-up, 20 ml of water were added and the mixture was then extracted three times with in each case 20 ml of dichloromethane. The combined organic phases were dried over sodium sulphate and concentrated. This gave 100 mg (97% of theory) 3-[(2-(morpholin-4-yl)-8-(2H-pyrazol-3-yl)-[1,7]naphthyridine-4-yl]phenyl-S-methylsulphoximide as a yellow solid. m.p. 227-229° C. $^1$H NMR (400 MHz, CDCl$_3$-d$_6$): δ[ppm]=3.22 (3H), 3.79-3.81 (4H), 3.94-3.96 (4H), 7.20 (1H), 7.30-7.32 (1H), 7.35-7.36 (1H), 7.73-7.76 (3H), 8.18-8.20 (2H), 8.40-8.41 (1H). LC-MS (method 1): m/z: [M+H]$^+$=435.3, R$_t$=2.63 min.

Example 20

4-methyl-2-(morpholin-4-yl)-8-(1H-pyrazol-3-yl)-[1,7]naphthyridine Hydrochloride Step a 4-methyl-2-(morpholin-4-yl)-8-[2-(tetrahydropyran-2-yl)-2H-pyrazol-3-yl]-[1,7]naphthyridine

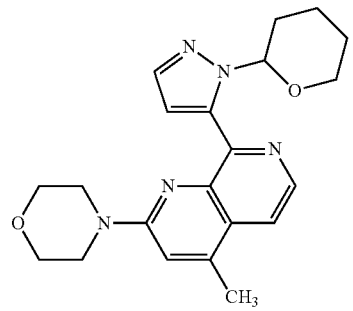 [SMILES: Cc1cc(N2CCOCC2)nc2c(-c3ccnn3C3CCCCO3)nccc12]

Under argon, 91 mg (0.11 mmol) of [1,1'-bis(diphenylphosphino)ferrocene]dichloropalladium(II) complex with dichloromethane (1:1, Pd(dppf)Cl$_2$) and 241 mg (0.74 mmol) of caesium carbonate were added to a suspension of 190 mg (0.37 mmol) of 2-(morpholin-4-yl)-8-[2-(tetrahydropyran-2-yl)-2H-pyrazol-3-yl]-[1,7]naphthyridin-4-yl trifluoromethanesulphonate and 44 mg (0.74 mmol) of methylboronic acid in 2.5 ml of absolute dioxane. The reaction mixture was stirred at 90° C. for 2 h. The mixture was chromatographed directly without work-up [silica gel 60 (40 g, 30 μm); chloroform/methanol (95:5, 100 ml)]. This gave 120 mg (86% of theory) of 4-methyl-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$= 380.3, R$_t$=3.23 min.

Step b 4-methyl-2-(morpholin-4-yl)-8-(1H-pyrazol-3-yl)-[1,7]naphthyridine

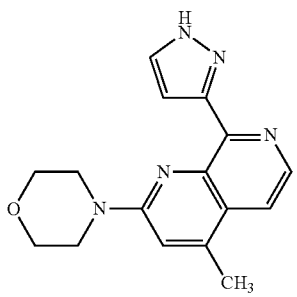 [SMILES: Cc1cc(N2CCOCC2)nc2c(-c3cc[nH]n3)nccc12]

A drop of water and 2 ml of (26 mmol) of trifluoroacetic acid were added to 120 mg (0.32 mmol) of 4-methyl-2-(morpholin-4-yl)-8-[2-(tetrahydropyran-2-yl)-2H-pyrazol-3-yl]-[1,7]naphthyridine. After 1 h, LCMS showed complete removal of the protective group. The trifluoroacetic acid was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, 30 μm); chloroform (100 ml)]. This gave 45 mg (48% of theory) of 4-methyl-2-(morpholin-4-yl)-8-(1H-pyrazol-3-yl)-[1,7]naphthyridine as a yellow solid. After brief exposure to air, this solid became discoloured. For this reason, the compound was converted into the corresponding hydrochloride. LC-MS (method 1): m/z: [M+H]$^+$=296.3, R$_t$=2.53 min.

Step c 4-methyl-2-(morpholin-4-yl)-8-(1H-pyrazol-3-yl)-[1,7]naphthyridine Hydrochloride

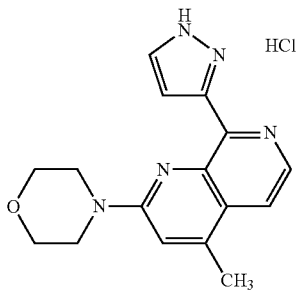 [SMILES: Cc1cc(N2CCOCC2)nc2c(-c3cc[nH]n3)nccc12 ; Cl]

45 mg (0.15 mmol) of 4-methyl-2-(morpholin-4-yl)-8-(1H-pyrazol-3-yl)-[1,7]naphthyridine were dissolved in 4.0 ml of 2-butanol, and 58 μl (0.46 mmol) of trimethylchlorosilane were added. The reaction solution was stirred at room temperature for 1 h. The precipitated solid was filtered off and then dried. This gave 45 mg (89% of theory) of 4-methyl-2-(morpholin-4-yl)-8-(1H-pyrazol-3-yl)-[1,7]naphthyridine hydrochloride as a yellow solid. m.p. 164-166° C. $^1$H NMR (400 MHz, DMSO, δ ppm): 2.69 (3H), 3.81-3.86 (8H), 7.55 (1H), 7.82 (1H), 8.11-8.14 (2H), 8.38 (1H). LC-MS (method 1): m/z: [M+H]$^+$=296.3, R$_t$=2.51 min.

Example 21

4-[2-(methylsulfonyl)-1,3-thiazol-4-yl]-2-(morpholin-4-yl)-8-(1H-pyrazol-5-yl)-1,7-naphthyridine Step a 4-[2-(methylsulfonyl)-1,3-triazol-4-yl]-2-(morpholin-4-yl)-8-[1-(tetrahydro-2H-pyran-2-yl)-1H-pyrazol-5-yl]-1,7-naphthyridine

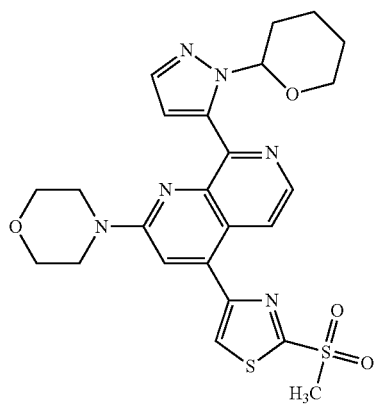 [SMILES: CS(=O)(=O)c1nc(-c2cc(N3CCOCC3)nc3c(-c4ccnn4C4CCCCO4)nccc23)cs1]

Under argon, 16 mg (0.019 mmol) [1,1'-bis(diphenylphosphino)ferrocene]dichloropalladium(II) were added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 113 mg (0.39 mmol) 2-(methylsulfonyl)-4-(4,4,5,5-tetramethyl-1,3,2-dioxaborolan-2-yl)-1,3-thiazole in 1.4 ml dioxane and 254 mg (0.78 mmol) caesium carbonate. The mixture was stirred at 110° C. for 2 hours. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and the crude product (263 mg) was used without further purification.

Step b 4-([2-(methylsulfonyl)-1,3-thiazol-4-yl]-2-(morpholin-4-yl)-8-(1H-pyrazol-5-yl)-1,7-naphthyridine

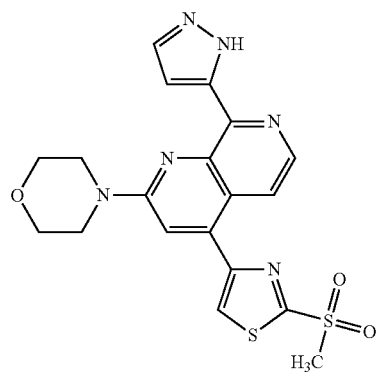 [SMILES: CS(=O)(=O)c1nc(-c2cc(N3CCOCC3)nc3c(-c4ccn[nH]4)nccc23)cs1]

0.58 ml (1.15 mmol) 2N aqueous solution of hydrogen chloride was added to a solution of 263 mg crude 4-[2-(methylsulfonyl)-1,3-thiazol-4-yl]-2-(morpholin-4-yl)-8-[1-(tetrahydro-2H-pyran-2-yl)-1H-pyrazol-5-yl]-1,7-naphthyridine in 2.3 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: acidic conditions) to give 3 mg (0.007 mmol) of the desired product. $^1$H-NMR (400 MHz, DMSO-d6): δ[ppm]=3.61 (3H), 3.82 (8H), 7.41 (1H), 7.66 (1H), 7.82 (1H), 7.95 (1H), 8.41 (1H), 8.82 (1H), 13.42 (1H).

Example 22

4-[2-(morpholin-4-yl)-8-(1H-pyrazol-5-yl)-1,7-naphthyridin-4-yl]pyridin-2(1H)-one

Step a

4-(2-methoxypyridin-4-yl)-2-(morpholin-4-yl)-8-(1H-pyrazol-5-yl)-1,7-naphthyridine

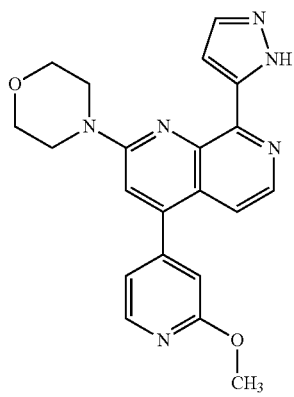 [SMILES: COc1cc(-c2cc(N3CCOCC3)nc3c(-c4ccn[nH]4)nccc23)ccn1]

A mixture of 2-(morpholin-4-yl)-8-[1-(tetrahydro-2H-pyran-2-yl)-1H-pyrazol-5-yl]-1,7-naphthyridin-4-yl trifluoromethanesulfonate (320 mg, 0.21 mmol), (2-methoxypyridin-4-yl)boronic acid (94 mg, 0.62 mmol), Bis(triphenylphosphin)palladium(II)chlorid (14 mg, 0,021 mmol), Caesiumcarbonate (235 mg, 0.72 mmol) in Dioxane (4 ml) were heated in a sealed tube in the Microwave at 100. C for 30 minutes. A solution of conc. HCl (10 ml) was added and the reaction was stirred at ambient temperature for 16 hours and at 50° C. for another 2 hours. The reaction mixture was filtered through a plug of Celite (1 cm). The Celite was washed with ethyl acetate (50 ml) and methanol (20 ml). The filtrate was dried over Na$_2$SO$_4$, the solvent was removed under reduced pressure. The title compound was obtained as crude product and used without further purification in the next step.

Step b

4-([2-(morpholin-4-yl)-8-(1H-pyrazol-5-yl)-1,7-naphthyridin-4-yl]pyridin-2(1H)-one

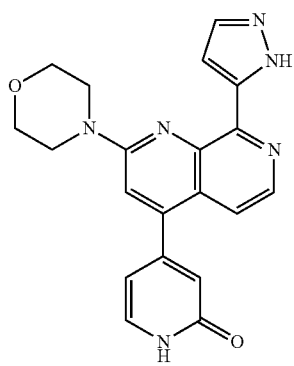 [SMILES: O=c1cc(-c2cc(N3CCOCC3)nc3c(-c4ccn[nH]4)nccc23)cc[nH]1]

Crude 4-(2-methoxypyridin-4-yl)-2-(morpholin-4-yl)-8-(1H-pyrazol-5-yl)-1,7-naphthyridine (1.882 g, purity ca. 10%) was added to a solution of concentrated HBr in acetic acid (2 ml) and acetic acid (15 ml) and stirred at 100° C. for 2 hours. The reaction was cooled to ambient temperature, dichloromethane (30 ml) and a saturated aqueous solution of NaHCO$_3$ (50 ml) was added. The layers were separated and the aqueous phase was extracted with dichloromethane (2×10 ml). The combined organic layers were dried over Na$_2$SO$_4$. The solvent was removed under reduced pressure and the crude product (188 mg) was purified by HPLC chromatography (acidic conditions). The title compound was obtained in 1% yield (1.6 mg). $^1$H-NMR (400 MHz, DMSO): δ[ppm]=3.80 (8H), 6.33 (1H), 6.50 (1H), 7.41-7.66 (5H), 8.36 (1H), 11.89 (1H), 13.44 (1H).

Example 23

5-[2-(morpholin-4-yl)-8-(1H-pyrazol-5-yl)-1,7-naphthyridin-4-yl]pyridin-2(1H)-one

Step a

4-(6-methoxypyridin-3-yl)-2-(morpholin-4-yl)-8-(1H-pyrazol-5-yl)-1,7-naphthyridine

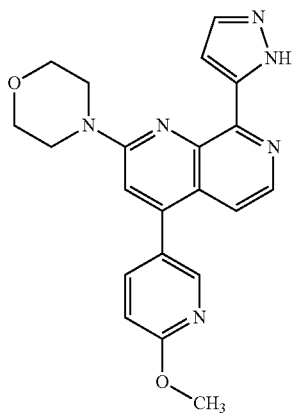 [SMILES: COc1ccc(-c2cc(N3CCOCC3)nc3c(-c4ccn[nH]4)nccc23)cn1]

A mixture of 2-(morpholin-4-yl)-8-[1-(tetrahydro-2H-pyran-2-yl)-1H-pyrazol-5-yl]-1,7-naphthyridin-4-yl trifluoromethanesulfonate (605 mg, 0.39 mmol), (6-methoxypyridin-3-yl)boronic acid (178 mg, 1.17 mmol), Bis(triphenylphosphin)palladium(II)chlorid (27 mg, 0,039 mmol), Caesiumcarbonate (443 mg, 1.36 mmol) in Dioxane (4 ml) were heated in a sealed tube in the Microwave at 100° C. for 30 minutes. A solution of conc. HCl (10 ml) was added and the reaction was stirred at ambient temperature for 16 hours and at 50° C. for another 2 hours. The reaction mixture was filtered through a plug of Celite (1 cm). The Celite was washed with ethyl acetate (50 ml) and methanol (20 ml). The filtrate was dried over Na$_2$SO$_4$, the solvent was removed under reduced pressure. The title compound was obtained as crude product and used without further purification in the next step.

Step b

5-[2-(morpholin-4-yl)-8-(1H-pyrazol-5-yl)-1,7-naphthyridin-4-yl]pyridin-2(1H)-one

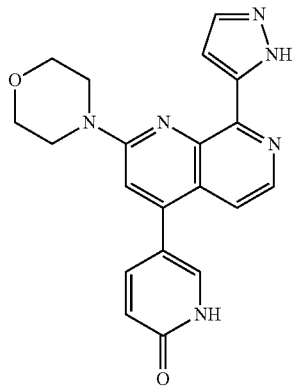 [SMILES: O=c1ccc(-c2cc(N3CCOCC3)nc3c(-c4ccn[nH]4)nccc23)c[nH]1]

Crude 4-(6-methoxypyridin-3-yl)-2-(morpholin-4-yl)-8-(1H-pyrazol-5-yl)-1,7-naphthyridine (1.344 g, purity ca. 10%) was added to a solution of concentrated HBr in acetic acid (2 ml) and acetic acid (15 ml) and stirred at 100° C. for 2 hours. The reaction was cooled to ambient temperature, dichloromethane (30 ml) and a saturated aqueous solution of NaHCO₃ (50 ml) was added. The layers were separated and the aqueous phase was extracted with dichloromethane (2×10 ml). The combined organic layers were dried over Na₂SO₄. The solvent was removed under reduced pressure and the crude product (188 mg) was purified by HPLC chromatography (acidic conditions). The title compound was obtained in 2% yield (2.3 mg). H-NMR (400 MHz, DMSO): δ[ppm]=3.79 (8H), 6.51 (1H), 7.40 (1H), 7.48 (1H), 7.51 (1H), 7.64-7.70 (3H), 8.36 (1H), 12.10 (1H), 13.40 (1H).

Example 24

4-([2-fluoro-4-(methylsulfonyl)phenyl)-2-(morpholin-4-yl)-8-(1H-pyrazol-5-yl)-1,7-naphthyridine Step a 4-[2-fluoro-4-(methylsulfanyl)phenyl]-2-(morpholin-4-yl)-8-[1-(tetrahydro-2H-pyran-2-yl)-1H-pyrazol-5-yl]-1,7-naphthyridine

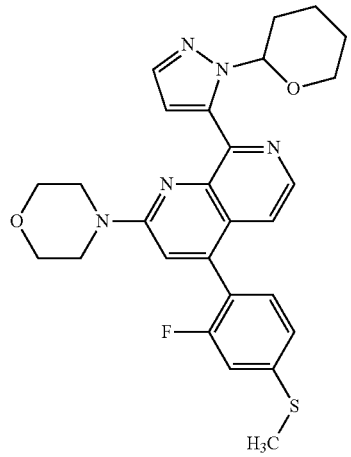 [SMILES: CSc1ccc(-c2cc(N3CCOCC3)nc3c(-c4ccnn4C4CCCCO4)nccc23)c(F)c1]

Under argon, 24 mg (0.029 mmol) [1,1'-bis(diphenylphosphino)ferrocene]dichloropalladium(II) were added to a mixture of 150 mg (0.29 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 108 mg (0.58 mmol) [2-fluoro-4-(methylsulfanyl)phenyl]boronic acid in 2.1 ml dioxane and 381 mg (1.17 mmol) caesium carbonate. The mixture was stirred at 110° C. for 2 hours. After cooling, the reaction mixture was diluted with ethyl acetate and washed with aqueous sodium chloride solution. The organic phase was filtered using a Whatman filter and concentrated. The residue was purified by column chromatography (hexane/ethyl acetate 20%-70%) to give 126 mg (0.25 mmol) of the desired product.

Step b 4-([2-fluoro-4-(methylsulfonyl)phenyl)-2-(morpholin-4-yl)-8-(1-(tetrahydro-2H-pyran-2-yl)-1H-pyrazol-5-yl]-1,7-naphthyridine

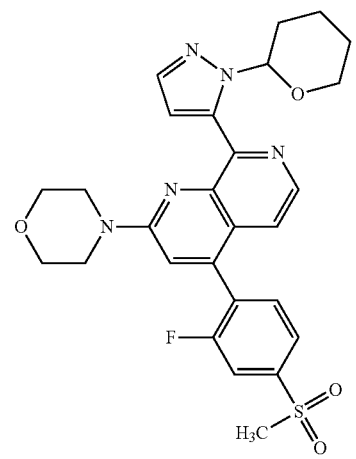 [SMILES: CS(=O)(=O)c1ccc(-c2cc(N3CCOCC3)nc3c(-c4ccnn4C4CCCCO4)nccc23)c(F)c1]

Under argon, 2 mg (0.006 mmol) tetrapropylammonium perruthenate (TPAP) and 14 mg (0.127 mmol) N-methylmorpholine-N-oxide (NMO) were added to a solution of 64 mg (0.127 mmol) 4-[2-fluoro-4-(methylsulfanyl)phenyl]-2-(morpholin-4-yl)-8-[1-(tetrahydro-2H-pyran-2-yl)-1H-pyrazol-5-yl]-1,7-naphthyridine in 1.4 mL DCM and 1.4 mL acetonitrile at 0° C. The mixture was stirred for 4 hours at 0° C. Additional 14 mg (0.127 mmol) N-methylmorpholine-N-oxide (NMO) was added and the mixture was stirred at 0° C. for 7 hours and then for 40 minutes at 10° C. Finally, the batch was concentrated to give 81 mg crude product that was used without further purification.

Step c

4-[2-fluoro-4-(methylsulfonyl)phenyl]-2-(morpholin-4-yl)-8-(1H-pyrazol-5-yl)-1,7-naphthyridine

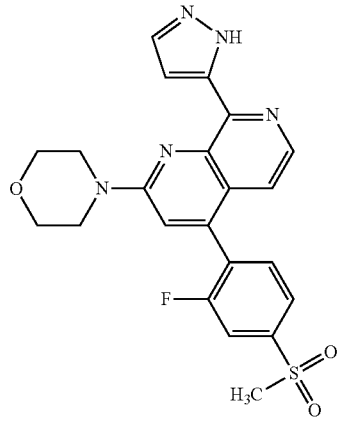 [SMILES: CS(=O)(=O)c1ccc(-c2cc(N3CCOCC3)nc3c(-c4ccn[nH]4)nccc23)c(F)c1]

0.17 ml (0.35 mmol) 2N aqueous solution of hydrogen chloride was added to a solution of 81 mg crude 4-[2-fluoro-4-(methylsulfonyl)phenyl]-2-(morpholin-4-yl)-8-[1-(tetrahydro-2H-pyran-2-yl)-1H-pyrazol-5-yl]-1,7-naphthyridine in 0.7 ml methanol and the reaction mixture was stirred at room temperature for 1 hour. The mixture was basified by addition of an aqueous sodium bicarbonate solution and extracted with ethyl acetate (2×). The combined organic phases were dried ($Na_2SO_4$), filtered and concentrated. The residue was purified by preperative HPLC (Autopurifier: acidic conditions) to give 18 mg (0.04 mmol) of the desired product. $^1$H-NMR (400 MHz, DMSO): δ[ppm]=3.40 (3H), 3.80 (8H), 7.20 (1H), 7.44 (1H), 7.70 (2H), 7.88 (1H), 8.00 (1H), 8.06 (1H), 8.33 (1H), 13.55 (1H).

Example 25

2-(morpholin-4-yl)-4-(4-[S-(propan-2-yl)sulfonimidoyl]phenyl)-8-(1H-pyrazol-5-yl)-1,7-naphthyridine Step a 2-(morpholin-4-yl)-4-[4-(propan-2-ylsulfanyl)phenyl]-8-[1-(tetrahydro-2H-pyran-2-yl)-1H-pyrazol-5-yl]-1,7-naphthyridine

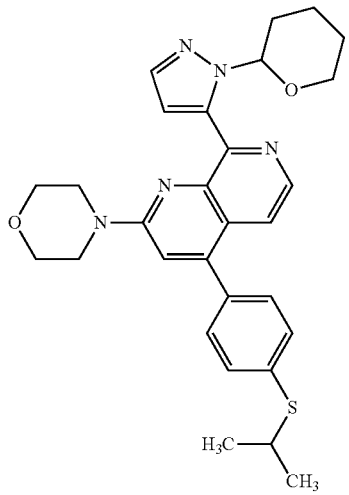 [SMILES: CC(C)Sc1ccc(-c2cc(N3CCOCC3)nc3c(-c4ccnn4C4CCCCO4)nccc23)cc1]

Under argon, 16 mg (0.019 mmol) [1,1'-bis(diphenylphosphino)ferrocene]dichloropalladium(II) was added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate and 76 mg (0.39 mmol) [4-(propan-2-ylsulfanyl)phenyl]boronic acid in 1.4 ml dioxane and 253 mg (0.78 mmol) caesium carbonate. The mixture was stirred at 110° C. for 2 hours. After cooling, the reaction mixture was diluted with ethyl acetate and an aqueous solution of sodium chloride. The mixture was extracted with ethyl acetate (2×) and the combined organic phases were filtered using a Whatman filter. The organic phase was concentrated and residue was purified by column chromatography (hexane/ethyl acetate 20%-80%) to give 74 mg (0.14 mmol) of the desired product, containing slight impurities, that was used without further purifications.

Step b 2,2,2-trifluoro-N-[(4-{2-(morpholin-4-yl)-8-[1-(tetrahydro-2H-pyran-2-yl)-1H-pyrazol-5-yl]-1,7-naphthyridin-4-yl}phenyl)(propan-2-yl)-λ$^4$-sulfanylidene]acetamide

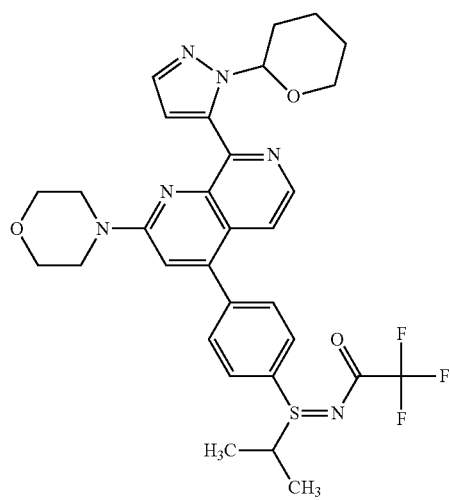 [SMILES: CC(C)/S(=N/C(=O)C(F)(F)F)c1ccc(-c2cc(N3CCOCC3)nc3c(-c4ccnn4C4CCCCO4)nccc23)cc1]

Under an atmosphere of argon, a solution of 39 mg (0.35 mmol) 2,2,2-trifluoroacetamide in 0.13 ml THF was added dropwise to a solution of 22 mg (0.23 mmol) sodium tert.-butoxide in 0.19 ml THF, so that the temperature of the mixture remained below 10° C. Subsequently, a freshly prepared solution of 43 mg (0.15 mmol) 1,3-dibromo-5,5-dimethylhydantoin in 0.19 ml THF was added dropwise to the stirred mixture, so that the temperature of the mixture remained below 10° C. Then the mixture was stirred for 10 minutes at 10° C. Finally, a solution of 120 mg (0.23 mmol) 2-(morpholin-4-yl)-4-[4-(propan-2-ylsulfanyl)phenyl]-8-[1-(tetrahydro-2H-pyran-2-yl)-1H-pyrazol-5-yl]-1,7-naphthyridine in 0.23 ml THF was added dropwise to the stirred mixture, so that the temperature of the mixture remained below 10° C. The mixture was stirred for 80 minutes at 10°

C. and then at room temperature overnight. The batch was diluted with 0.5 ml toluene under cooling and an aqueous solution of 29 mg (0.23 mmol) sodium sulfite in 0.9 ml water was added so that the temperature of the mixture remained below 10° C. The batch was extracted three times with ethyl acetate. The combined organic phases were washed with an aqueous solution of sodium chloride, filtered using a Whatman filter and concentrated. The residue was purified by column chromatography on silica gel (ethyl acetate) to give 28 mg of the desired product containing slight impurities.

Step c

4-[4-(S-isopropylsulfonimidoyl)phenyl]-2-(morpholin-4-yl)-8-[1-(tetrahydro-2H-pyran-2-yl)-1H-pyrazol-5-yl]-1,7-naphthyridine

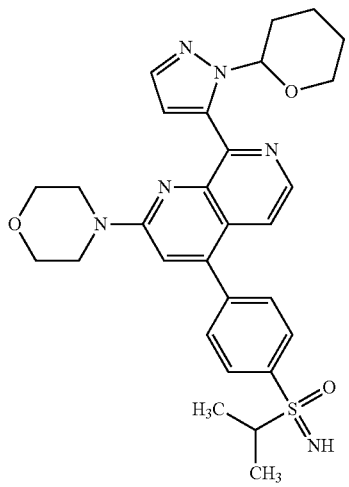 [SMILES: CC(C)S(=N)(=O)c1ccc(-c2cc(N3CCOCC3)nc3c(-c4ccnn4C4CCCCO4)nccc23)cc1]

28 mg (0.035 mmol) 2,2,2-trifluoro-N-[(4-{2-(morpholin-4-yl)-8-[1-(tetrahydro-2H-pyran-2-yl)-1H-pyrazol-5-yl]-1,7-naphthyridin-4-yl}phenyl)(propan-2-yl)-λ⁴-sulfanylidene]acetamide was dissolved in 0.87 ml methanol. To this solution 0.31 ml water was added. The pH was adjusted to 10.5 by addition of an aqueous solution of potassium hydroxide (25%). 23 mg (0.038 mmol) Oxone® was added and the mixture was stirred at room temperature for 4 hours. Additional amount 23 mg (0.038 mmol) Oxone® was added. The pH was adjusted to 10.5 by addition of an aqueous solution of potassium hydroxide (25%). The batch was stirred at room temperature for 90 minutes. The pH was adjusted to 10.5 by addition of an aqueous solution of potassium hydroxide (25%) and the batch was stirred at room temperature for 4 days. The batch was filtered and the filtrate was adjusted to pH 6-7 by the addition of 1N aqueous hydrogen chloride solution. The mixture was diluted with aqueous sodium chloride solution and extracted with DCM (2×). The combined organic phases were washed with an aqueous solution of sodium sulfite (10%), filtered using a Whatman filter, and concentrated to give 21 mg crude product that was used without further purification.

Step d 2-(morpholin-4-yl)-4-(4-[S-(propan-2-yl)sulfonimidoyl]phenyl)-8-(1H-pyrazol-5-yl)-1,7-naphthyridine

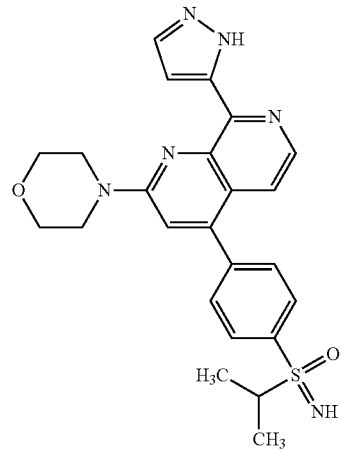 [SMILES: CC(C)S(=N)(=O)c1ccc(-c2cc(N3CCOCC3)nc3c(-c4ccn[nH]4)nccc23)cc1]

0.04 ml (0.11 mmol) 2N aqueous solution of hydrogen chloride was added to a solution of 21 mg crude 2-(morpholin-4-yl)-4-{4-[S-(propan-2-yl)sulfonimidoyl]phenyl}-8-[1-(tetrahydro-2H-pyran-2-yl)-1H-pyrazol-5-yl]-1,7-naphthyridine in 0.18 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: basic conditions) to give 4 mg (0.01 mmol) of the desired product. ¹H-NMR (400 MHz, DMSO-d6): δ[ppm]=1.22 (6H), 3.35 (1H), 3.81 (8H), 4.30 (1H), 7.36 (1H), 7.44 (1H), 7.57 (1H), 7.65 (1H), 7.82 (2H), 8.05 (2H), 8.35 (1H), 13.43 (1H).

Example 26

4-(4-methanesulphonylphenyl)-2-((R)-3-methylmorpholin-4-yl)-8-(2H-pyrazol-3-yl)-[1,7]naphthyridine Step a 4-(4-methanesulphonylphenyl)-2-((R)-3-methylmorpholin-4-yl)-8-[2-(tetrahydropyran-2-yl)-2H-pyrazol-3-yl]-[1,7]naphthyridine

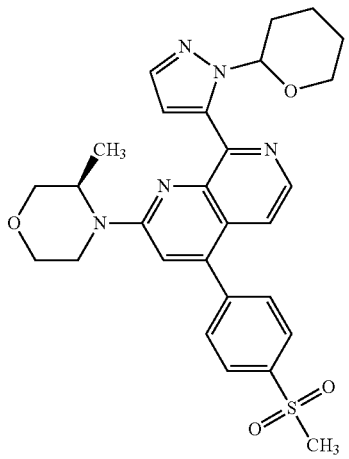 [SMILES: C[C@@H]1COCCN1c1cc(-c2ccc(S(C)(=O)=O)cc2)c2ccnc(-c3ccnn3C3CCCCO3)c2n1]

Under argon, 120 mg (227 µmol) of 2-((R)-3-methylmorpholin-4-yl)-8-[2-(tetrahydropyran-2-yl)-2H-pyrazol-3-yl]-[1,7]naphthyridin-4-yl trifluoromethanesulphonate, 76 mg (0.38 mmol) of 4-(methanesulphonyl)phenylboronic acid, 18 mg (22.7 µmol) of [1,1'-bis(diphenylphosphino)-ferrocene]dichloropalladium(II)×dichloromethane and 296 mg (0.91 mmol) of caesium carbonate were weighed out and dissolved in 1.5 ml of absolute 1,4-dioxane. The mixture was degassed three times and stirred at 90° C. for 2 h. The course of the reaction was monitored by LC/MS. Since conversion was incomplete, another 52 mg of 4-(methanesulphonyl)phenylboronic acid, 18 mg of [1,1'-bis(diphenylphosphino)ferrocene]dichloropalladium(II)×dichloromethane and 296 mg of caesium carbonate were added to the reaction solution and the mixture was stirred at 90° C. for 20 h. Under reduced pressure, the mixture was concentrated to dryness. The residue was chromatographed [silica gel 60 (40 g, 50 µm); dichloromethane/methanol 98:2 to 95:5]. 79 mg (65% of theory) of 4-(4-methanesulphonylphenyl)-2-((R)-3-methylmorpholin-4-yl)-8-[2-(tetrahydropyran-2-yl)-2H-pyrazol-3-yl]-[1,7]naphthyridine were obtained as a yellow solid.

$^1$H NMR (400 MHz, CDCl$_3$): δ[ppm]=1.34 (3H), 1.48-1.74 (3H), 2.08-2.11 (2H), 2.56 (1H), 3.19 (3H), 3.34 (1H), 3.46 (1H), 3.59 (1H), 3.71-3.84 (3H), 3.94 (1H), 4.02-4.24 (2H), 4.44 (1H), 6.08 (1H), 6.98 (1H), 7.01 (1H), 7.69-7.72 (3H), 8.14 (2H), 8.40 (1H). LC-MS (method 1): R$_t$=3.46 min; MS (ESI/APCIpos) m/z=534.3 [M+H]$^+$.

Step b 4-(4-methanesulphonylphenyl)-2-((R)-3-methylmorpholin-4-yl)-8-(2H-pyrazol-3-yl)-[1,7]naphthyridine

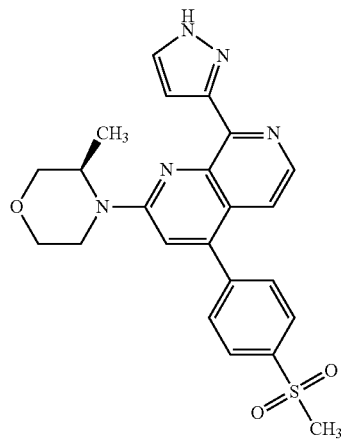 [SMILES: C[C@@H]1COCCN1c1cc(-c2ccc(S(C)(=O)=O)cc2)c2ccnc(-c3cc[nH]n3)c2n1]

79 mg (0.15 mmol) of 4-(4-methanesulphonylphenyl)-2-((R)-3-methylmorpholin-4-yl)-8-[2-(tetrahydropyran-2-yl)-2H-pyrazol-3-yl]-[1,7]naphthyridine were dissolved in 5 ml of methanol, 1 ml of 2N hydrochloric acid (2 mmol) was added and the mixture was stirred at room temperature for 1 h. After 1 h, LC/MS showed complete removal of the protective group. The methanol was removed under reduced pressure and the residue was adjusted to pH=7 using saturated sodium bicarbonate solution. The aqueous phase was extracted five times with in each case 10 ml of dichloromethane. The combined organic phases were dried over sodium sulphate and concentrated to dryness under reduced pressure. The residue was washed twice with in each case 4 ml of methanol, filtered off and dried. This gave 44 mg (66% of theory) of 4-(4-methanesulphonylphenyl)-2-((R)-3-methylmorpholin-4-yl)-8-(2H-pyrazol-3-yl)-[1,7]naphthyridine as a yellow solid. $^1$H NMR (400 MHz, DMSO-d$_6$): δ[ppm] =1.31 (3H), 3.33 (3H), 3.32-3.40 (1H), 3.57 (1H), 3.72 (1H), 3.83 (1H), 4.05 (1H), 4.24 (1H), 4.66 (1H), 7.35 (1H), 7.43 (1H), 7.50 (1H), 7.61 (1H), 7.87 (2H), 8.13 (2H), 8.33 (1H), 13.4 (1H). LC-MS (method 1): R$_t$=2.88 min; MS (ESI/APCIpos) m/z=450.2 [M+H]$^+$.

Example 27

2-((R)-3-methylmorpholin-4-yl)-4-phenyl-8-(2H-pyrazol-3-yl)-[1,7]naphthyridine

Step a 2-((R)-3-methylmorpholin-4-yl)-4-phenyl-8-[2-(tetrahydropyran-2-yl)-2H-pyrazol-3-yl]-[1,7]naphthyridine

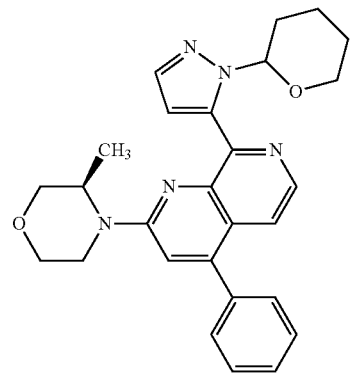 [SMILES: C[C@@H]1COCCN1c1cc(-c2ccccc2)c2ccnc(-c3ccnn3C3CCCCO3)c2n1]

Under argon, 120 mg (227 µmol) of 2-((R)-3-methylmorpholin-4-yl)-8-[2-(tetrahydropyran-2-yl)-2H-pyrazol-3-yl]-[1,7]naphthyridin-4-yl trifluoromethanesulphonate, 46 mg (0.38 mmol) of benzeneboronic acid, 18 mg (0.0227 mmol) of [1,1'-bis(diphenylphosphino)ferrocene]-dichloropalladium(II)×dichloromethane and 296 mg (0.91 mmol) of caesium carbonate were weighed out and dissolved in 1.5 ml of absolute 1,4-dioxane. The mixture was degassed three times and stirred at 90° C. for 1 h. The course of the reaction was monitored by LC/MS. The mixture was concentrated to dryness under reduced pressure. The residue was chromatographed [silica gel 60 (40 & 50 µm); dichloromethane/methanol 98:2 to 95:5]. This gave 90 mg (87% of theory) of 2-((R)-3-methylmorpholin-4-yl)-4-phenyl-8-[2-(tetrahydropyran-2-yl)-2H-pyrazol-3-yl]-[1,7]naphthyridine as a yellow solid. $^1$H NMR (400 MHz, CDCl$_3$): δ[ppm]=1.33 (3H), 1.48-1.51 (1H), 1.62-1.77 (2H), 2.07-2.10 (2H), 2.56 (1H), 3.32 (1H), 3.46 (1H), 3.58 (1H), 3.69-3.83 (2H), 3.94-3.98 (1H), 4.03-4.52 (3H), 6.05 (1H), 6.97 (1H), 7.02 (1H), 7.47-7.56 (6H), 7.71 (1H), 8.38 (1H). LC-MS (method 1): R$_t$=3.89 min; MS (ESI/APCIpos) m/z=456.3 [M+H]$^+$.

Step b 2-((R)-3-methylmorpholin-4-yl)-4-phenyl-8-(2H-pyrazol-3-yl)-[1,7]naphthyridine Example 28

4-(3-methanesulphonylphenyl)-2-((R)-3-methylmorpholin-4-yl)-8-(2H-pyrazol-3-yl)-[1,7]naphthyridine Step a 4-(3-methanesulphonylphenyl)-2-((R)-3-methylmorpholin-4-yl)-8-[2-(tetrahydropyran-2-yl)-2H-pyrazol-3-yl]-[1,7]naphthyridine

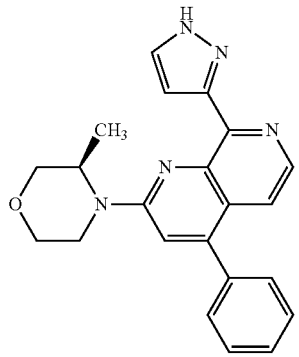 [SMILES: C[C@@H]1COCCN1c1cc(-c2ccccc2)c2ccnc(-c3cc[nH]n3)c2n1]

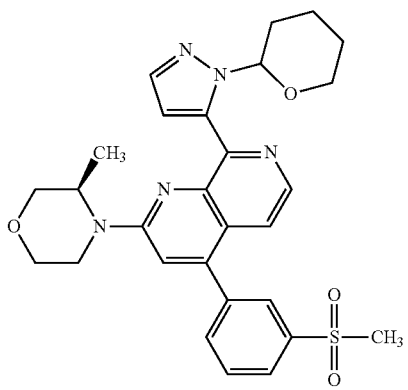 [SMILES: C[C@@H]1COCCN1c1cc(-c2cccc(S(C)(=O)=O)c2)c2ccnc(-c3ccnn3C3CCCCO3)c2n1]

90 mg (0.20 m mol) of 2-((R)-3-methylmorpholin-4-yl)-4-phenyl-8-[2-(tetrahydropyran-2-yl)-2H-pyrazol-3-yl]-[1,7]naphthyridine were dissolved in 5 ml of methanol, 1 ml of 2N hydrochloric acid (2 mmol) was added and the mixture was stirred at room temperature for 1 h. After 1 h, LC/MS showed complete removal of the protective group. The methanol was removed under reduced pressure and the residue was adjusted to pH=7 using saturated sodium bicarbonate solution. The aqueous phase was extracted five times with in each case 10 ml of dichloromethane. The combined organic phases were dried over sodium sulphate and then, under reduced pressure, concentrated to dryness. The residue was chromatographed twice [silica gel 60 (25 g, 30 μm); dichloromethane/methanol 96:4]. This gave 52 mg (71% of theory) of 2-((R)-3-methylmorpholin-4-yl)-4-phenyl-8-(2H-pyrazol-3-yl)-[1,7]naphthyridine as an orange solid. $^1$H NMR (400 MHz, CDCl$_3$): δ[ppm]=1.46 (3H), 3.57 (1H), 3.72 (1H), 3.84-3.94 (2H), 4.04 (1H), 4.17 (1H), 4.46 (1H), 7.14 (1H), 7.32 (1H), 7.43 (1H), 7.47-7.58 (5H), 7.72 (1H), 8.38 (1H). $^{13}$C NMR (101 MHz, CDCl$_3$): δ[ppm]=13.6, 40.6, 48.6, 66.7, 71.1, 106.3, 113.5, 117.8, 126.9, 120.8, 129.0, 129.2, 137.2, 140.1, 140.4, 140.5, 143.0 144.7, 149.9, 156.8. LC-MS (method 1): R$_t$=3.32 min; MS (ESI/APCIpos) m/z=372.2 [M+H]$^+$.

Under argon, 120 mg (227 μmol) of 2-((R)-3-methylmorpholin-4-yl)-8-[2-(tetrahydropyran-2-yl)-2H-pyrazol-3-yl]-[1,7]naphthyridine-4-yl trifluoromethanesulphonate, 76 mg (0.38 mmol) of 3-(methanesulphonyl)phenylboronic acid, 18 mg (22.7 μmol) of [1,1'-bis(diphenylphosphino)-ferrocene]dichloropalladium(II)×dichloromethane and 296 mg (0.91 mmol) of caesium carbonate were weighed out and dissolved in 1.5 ml of absolute 1,4-dioxane. The mixture was degassed three times and stirred at 90° C. for 90 min. The course of the reaction was monitored by LC/MS. Under reduced pressure, the mixture was concentrated to dryness. The residue was chromatographed [silica gel 60 (25 g 30 μm); dichloromethane/methanol 98:2]. This gave 72 mg (60% of theory) of 4-(3-methanesulphonylphenyl)-2-((R)-3-methylmorpholin-4-yl)-8-[2-(tetrahydropyran-2-yl)-2H-pyrazol-3-yl]-[1,7]naphthyridine as a yellow solid. $^1$H NMR (400 MHz, CDCl$_3$): δ[ppm]=1.32-1.37 (3H), 1.49-1.69 (1H), 1.69 (2H), 2.09 (2H), 2.55 (1H), 2.68 (3H), 3.27-3.39 (1H), 3.47 (1H), 3.59 (1H); 3.77 (2H), 3.94-4.48 (4H), 6.10 (1H), 6.93-6.95 (1H), 7.02-7.08 (1H), 7.20-7.25 (1H), 7.42 (1H), 7.71-7.79 (3H), 8.32-8.35 (2H). LC-MS (method 1): R$_t$=3.43 min; MS (ESI/APCIpos) m/z=534.3 [M+H]$^+$.

Step b 4-(3-methanesulphonylphenyl)-2-((R)-3-methylmorpholin-4-yl)-8-(2H-pyrazol-3-yl)-[1,7]naphthyridine

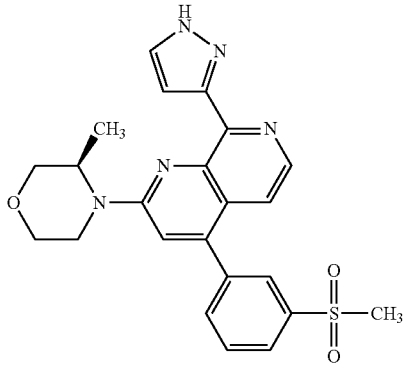 [SMILES: C[C@@H]1COCCN1c1cc(-c2cccc(S(C)(=O)=O)c2)c2ccnc(-c3cc[nH]n3)c2n1]

72 mg (0.13 mmol) of 4-(3-methanesulphonylphenyl)-2-((R)-3-methylmorpholin-4-yl)-8-[2-(tetrahydropyran-2-yl)-2H-pyrazol-3-yl]-[1,7]naphthyridine were dissolved in 5 ml of methanol, 1 ml of 2N hydrochloric acid (2 mmol) was added and the mixture was stirred at room temperature for 1 h. After 1 h, LC/MS showed complete removal of the protective group. The methanol was removed under reduced pressure and the residue was adjusted to pH=7 using saturated sodium bicarbonate solution. The aqueous phase was extracted five times with in each case 10 ml of dichloromethane. The combined organic phases were dried over sodium sulphate and then, under reduced pressure, concentrated to dryness. The residue was chromatographed twice [silica gel 60 (25 g, 30 μm); dichloromethane/methanol 96:4]. This gave 37 mg (61% of theory) of 4-(3-methanesulphonylphenyl)-2-((R)-3-methylmorpholin-4-yl)-8-(2H-pyrazol-3-yl)-[1,7]naphthyridine as an orange solid. $^1$H NMR (400 MHz, CDCl$_3$): δ[ppm]=1.46 (3H), 2.66 (3H), 3.58 (1H), 3.72 (1H), 3.83-3.92 (2H), 4.04-4.20 (2H), 4.39 (1H), 6.91 (1H), 7.33-7.37 (2H), 7.42 (1H), 7.73-7.80 (3H), 8.33 (2H). LC-MS (method 1): R$_t$=2.80 min; MS (ESI/APCIpos) m/z=450.2 [M+H]$^+$.

Example 29

4-cyclopropyl-2-((R)-3-methylmorpholin-4-yl)-8-(1H-pyrazol-3-yl)-([1,7-naphthyridine

Step a 4-cyclopropyl-2-((R)-3-methylmorpholin-4-yl)-8-(2-(tetrahydropyran-2-yl)-2H-pyrazol-3-yl]-[1,7]naphthyridin

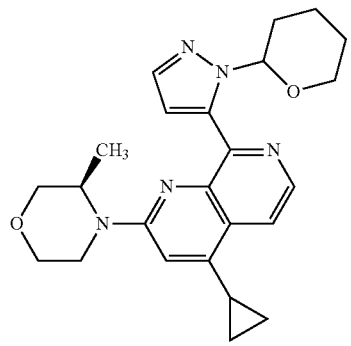 [SMILES: C[C@@H]1COCCN1c1cc(C2CC2)c2ccnc(-c3ccnn3C3CCCCO3)c2n1]

Under argon, 82 mg (0.1 mmol) of [1,1'-bis(diphenylphosphino)ferrocene]dichloropalladium(II) complex with dichloromethane (1:1, Pd(dppf)Cl$_2$) and 652 mg (2.0 mmol) of caesium carbonate were added to a suspension of 264 mg (0.5 mmol) of 2-[(3R)-3-methylmorpholin-4-yl]-8-[1-(tetrahydro-2H-pyran-2-yl)-1H-pyrazol-5-yl]-[1,7]naphthyridin-4-yl trifluoromethanesulphonate and 86 mg (1 mmol) of 2-cyclopropyl-4,4,5,5-tetramethyl-[1,3,2]dioxaborolane in 5 ml of absolute dioxane. The reaction mixture was stirred at 110° C. for 4 h. Without work-up, the mixture was chromatographed directly [Puri-Flash, silica gel 60 (25 g, 30 μm); ethyl acetate (100 ml)]. This gave 100 mg (48% of theory) of 4-cyclopropyl-2-((R)-3-methylmorpholin-4-yl)-8-[2-(tetrahydropyran-2-yl)-2H-pyrazol-3-yl]-[1,7]naphthyridine as a yellow solid. $^{13}$C NMR (101 MHz, CDCl$_3$-d$_6$): δ[ppm]=6.9, 7.0, 12.5, 13.5, 22.8, 25.0, 30.0, 39.4, 39.7, 47.1, 47.7, 66.9, 67.0, 67.6, 71.1, 84.8, 108.8, 110.2, 116.6, 128.0, 128.1, 138.5, 138.6, 139.0, 139.1, 140.3, 141.7, 148.2, 149.6, 156.6, 156.7.

Step b 4-cyclopropyl-2-((R)-3-methylmorpholin-4-yl)-8-(1H-pyrazol-3-yl)-[1,7]-naphthyridine

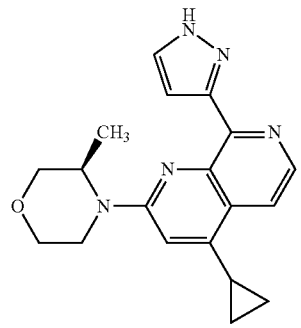 [SMILES: C[C@@H]1COCCN1c1cc(C2CC2)c2ccnc(-c3cc[nH]n3)c2n1]

100 mg (0.24 mmol) of 4-cyclopropyl-2-((R)-3-methylmorpholin-4-yl)-8-[2-(tetrahydropyran-2-yl)-2H-pyrazol-3-yl]-[1,7]naphthyridine were dissolved in 5 ml of methanol, and 1 ml (2 mmol) of 2N hydrochloric acid was added. After 1 h, LCMS showed complete removal of the protective group. The methanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [Puri-Flash, silica gel 60 (12 g, 30 μm); ethyl acetate (100 ml)]. This gave 70 mg (88% of theory) of 4-cyclopropyl-2-((R)-3-methylmorpholin-4-yl)-8-(1H-pyrazol-3-yl)-[1,7]naphthyridine as a yellow solid. m.p. 74-76° C. $^1$H NMR (400 MHz, CDCl$_3$): δ[ppm]=0.78-0.82 (2H), 1.14-1.17 (2H), 1.38-1.40 (3H), 2.24-2.28 (1H), 3.46-3.52 (1H), 3.64-3.71 (1H), 3.80-3.96 (3H), 4.11-4.15 (1H), 4.37-4.39 (1H), 6.86 (1H), 7.26-7.26 (1H), 7.68-7.69 (1H), 7.81-7.83 (1H), 8.44-8.45 (1H).

Example 30

Step a

4-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide

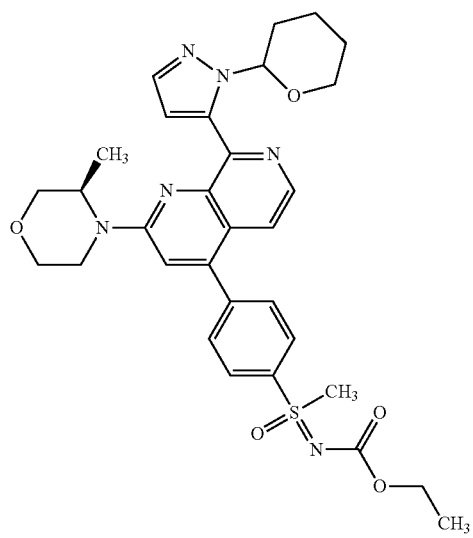 [SMILES: CCOC(=O)N=S(C)(=O)c1ccc(-c2cc(N3CCOC[C@H]3C)nc3c(-c4ccnn4C4CCCCO4)nccc23)cc1]

Under argon, 48 mg (0.06 mmol) of [1,1'-bis(diphenylphosphino)ferrocene]dichloropalladium(II) complex with dichloromethane (1:1, Pd(dppf)Cl$_2$) and 761 mg (2.34 mmol) of caesium carbonate were added to a suspension of 308 mg (0.58 mmol) of 2-((R)-3-methylmorpholin-4-yl)-8-[2-(tetrahydropyran-2-yl)-2H-pyrazol-3-yl]-[1,7]naphthyridin-4-yl trifluoromethanesulphonate and 413 mg (1.17 mmol) of pinacol ester in 7.5 ml of absolute dioxane. The reaction mixture was stirred at 90° C. for 2 h. The mixture was chromatographed directly without work-up [silica gel 60 (25 g, 30 μm); ethyl acetate (100 ml)]. This gave 245 mg (69% of theory) of 4-[(2-(morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide as a yellow foam. LC-MS (method 1): m/z: [M+H]$^+$=605.3, R$_t$=3.52 min.

Step b

4-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-(S)-methylsulphoximide

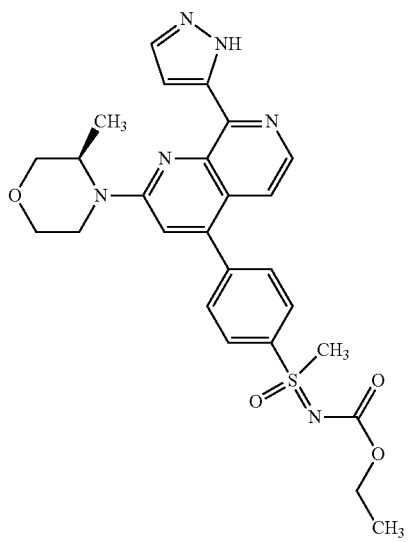 [SMILES: CCOC(=O)N=S(C)(=O)c1ccc(-c2cc(N3CCOC[C@H]3C)nc3c(-c4ccn[nH]4)nccc23)cc1]

240 mg (0.40 mmol) of 4-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were dissolved in 10 ml of ethanol, and 4 ml of (8 mmol) of 2N hydrochloric acid were added. After 1 h, LCMS showed complete removal of the protective group. Ethanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. This gave 200 mg (97% of theory) of 2-((R)-3-methylmorpholin-4-yl)-8-(1H-pyrazol-3-yl)-[1,7]naphthyridine-4-carbonitrile as a yellow solid. LC-MS (method 1): m/z: [M+H]$^+$=521.3, R$_t$=3.00 min.

133

Step c

4-[2-((R)-3-methylmorpholin-4-yl)-8-(2H-pyrazol-3-yl)-[1,7]naphthyridine-4-yl]phenyl-S-methylsulphoximide

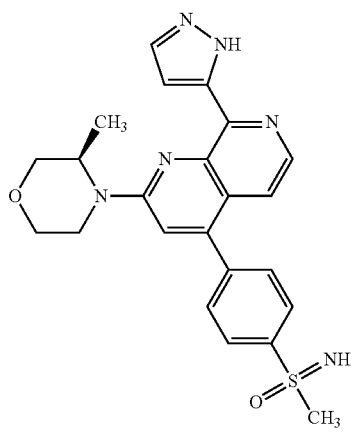 [SMILES: C[C@@H]1COCCN1c1cc(-c2ccc(S(C)(=N)=O)cc2)c2ccnc(-c3ccn[nH]3)c2n1]

170 mg (0.33 mmol) of 4-[2-((R)-3-methylmorpholin-4-yl)-8-(2H-pyrazol-3-yl)-[1,7]naphthyridine-4-yl]phenyl-S-methylsulphoximide were suspended in 5 ml of sodium methoxide (33%), and the mixture was stirred at 60° C. for 30 min. For work-up, 20 ml of water were added and the mixture was then extracted three times with in each case 20 ml of dichloromethane. The combined organic phases were dried over sodium sulphate and concentrated. The solid formed was triturated with 5 ml of methanol, filtered off and dried. This gave 88 mg (57% of theory) of 4-[2-((R)-3-methylmorpholin-4-yl)-8-(2H-pyrazol-3-yl)-[1,7]naphthyridine-4-yl]phenyl-S-methylsulphoximide as a yellow solid. m.p. 233-236° C. $^1$H NMR (400 MHz, DMSO-d$_6$): δ[ppm]= 1.30-1.32 (3H), 3.17 (3H), 3.54 (1H), 3.55-3.57 (1H), 3.70-3.73 (1H), 3.81-3.84 (1H), 4.22-4.25 (1H), 4.35 (1H), 7.35-7.36 (1H), 7.42 (1H), 7.48 (1H), 7.65 (1H), 7.80-7.82 (2H), 8.12-8.14 (2H), 8.33-8.34 (1H), 13.40 (1H). LC-MS (method 1): m/z: [M+H]$^+$=449.3, R$_t$=2.69 min.

134

Example 31

3-[2-((R)-3-methylmorpholin-4-yl)-8-(2H-pyrazol-3-yl)-[1,7]naphthyridine-4-yl]phenyl-S-methylsulphoximide

Step a

3-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide

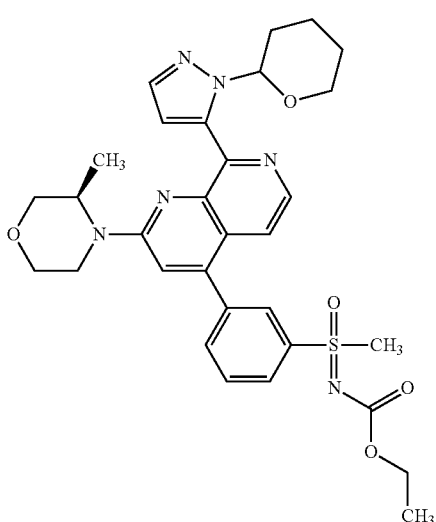

Under argon, 48 mg (0.06 mmol) of [1,1'-bis(diphenylphosphino)ferrocene]dichloropalladium(II) complex with dichloromethane (1:1, Pd(dppf)Cl$_2$) and 761 mg (2.34 mmol) of caesium carbonate were added to a suspension of 308 mg (0.58 mmol) of 2-((R)-3-methylmorpholin-4-yl)-8-[2-(tetrahydropyran-2-yl)-2H-pyrazol-3-yl]-[1,7]naphthyridin-4-yl trifluoromethanesulphonate and 413 mg (1.17 mmol) of pinacol ester in 7.5 ml of absolute dioxane. The reaction mixture was stirred at 90° C. for 2 h. The mixture was chromatographed directly without work-up [silica gel 60 (25 g, 30 μm); ethyl acetate (100 ml)]. This gave 289 mg (82% of theory) of 3-[2-((R)-3-methylmorpholin-4-yl)-8-[2-(tetrahydropyran-2-yl)-2H-pyrazol-3-yl]-[1,7]naphthyridine-4-yl]phenyl-N-ethoxy-carbonyl-S-methylsulphoximide as a yellow oil. LC-MS (method 1): m/z: [M+H]$^+$=605.3, R$_t$=3.56 min.

Step b

4-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide

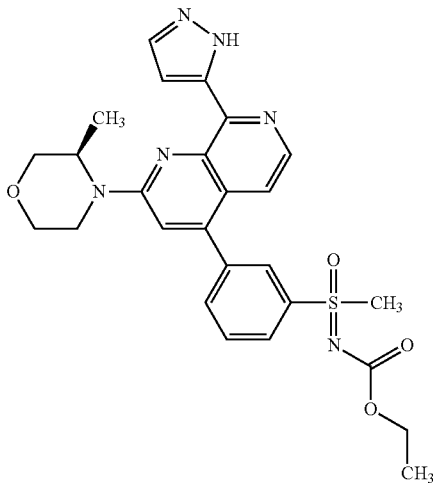 [SMILES: CCOC(=O)N=S(C)(=O)c1cccc(-c2cc(N3CCOC[C@H]3C)nc3c(-c4ccn[nH]4)nccc23)c1]

280 mg (0.46 mmol) of 3-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were dissolved in 10 ml of ethanol, and 4 ml of (10 mmol) of 2N hydrochloric acid were added. After 1 h, LCMS showed complete removal of the protective group. Ethanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (25 g, 30 μm); ethyl acetate (100 ml)]. This gave 220 mg (91% of theory) of 2-((R)-3-methylmorpholin-4-yl)-8-(1H-pyrazol-3-yl)-[1,7]naphthyridine-4-carbonitrile as a yellow solid. LC-MS (method 1): m/z: [M+H]$^+$=521.3, R$_t$=3.04 min.

Step c

3-[2-((R)-3-methylmorpholin-4-yl)-8-(2H-pyrazol-3-yl)-[1,7]naphthyridine-4-yl]phenyl-S-methylsulphoximide

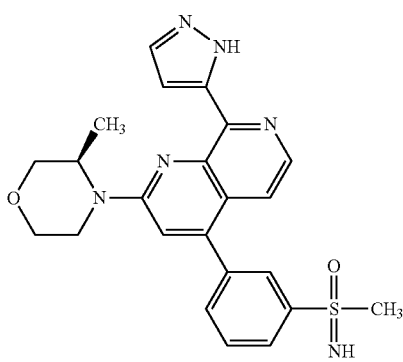 [SMILES: C[C@@H]1COCCN1c1cc(-c2cccc(S(C)(=N)=O)c2)c2ccnc(-c3ccn[nH]3)c2n1]

210 mg (0.40 mmol) of 4-[2-((R)-3-methylmorpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide were suspended in 5 ml of sodium methoxide (33%), and the mixture was stirred at 60° C. for 30 min. For work-up, 20 ml of water were added and the mixture was then extracted three times with in each case 20 ml of dichloromethane. The combined organic phases were dried over sodium sulphate and concentrated. This gave 165 mg (91% of theory) of 3-[2-((R)-3-methylmorpholin-4-yl)-8-(2H-pyrazol-3-yl)-[1,7]naphthyridine-4-yl]phenyl-S-methylsulphoximide as a yellow solid. m.p. 79-81° C. $^1$H NMR (400 MHz, DMSO-d$_6$): δ[ppm]=1.30-1.32 (3H), 3.18 (3H), 3.57-3.58 (1H), 3.71-3.75 (1H), 3.82-3.85 (1H), 4.03-4.06 (1H), 4.21-4.24 (1H), 4.34 (1H), 4.67-4.68 (1H), 7.35-7.36 (1H), 7.42 (1H), 7.48 (1H), 7.65 (1H), 7.80-7.82 (2H), 8.12-8.14 (2H), 8.33-8.34 (1H), 13.40 (1H). LC-MS (method 1): m/z: [M+H]$^+$=449.3, R$_t$=2.69 min.

Example 32

4-methanesulphonyl-2-(morpholin-4-yl)-8-[2-(tetrahydropyran-2-yl)-2H-pyrazol-3-yl]-[1,7]naphthyridine Step a 4-methanesulphonyl-2-(morpholin-4-yl)-8-[2-(tetrahydropyran-2-yl)-2H-pyrazol-3-yl]-[1,7]naphthyridine

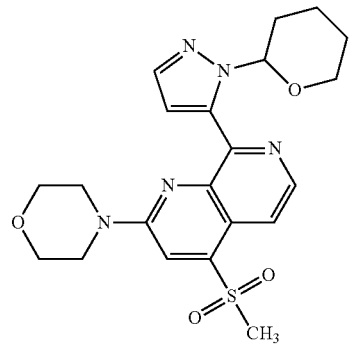 [SMILES: CS(=O)(=O)c1cc(N2CCOCC2)nc2c(-c3ccnn3C3CCCCO3)nccc12]

A solution of 500 mg (1.25 mmol) of 4-chloro-2-(morpholin-4-yl)-8-[2-(tetrahydropyran-2-yl)-2H-pyrazol-3-yl]-[1,7]naphthyridine, 140 mg (1.38 mmol) of sodium methanesulphinate, 45 mg (0.13 mmol) of copper(II) trifluoromethanesulphonate and 29 mg (0.25 mmol) of (±)-trans-1,2-diaminocyclohexane in 5 ml of dimethyl sulphoxide was stirred at 100° C. for 16 h. 20 ml of water were added to the reaction mixture. The resulting precipitated solid was filtered off. The solid was purified by column chromatography [Puri-Flash, silica gel 60 (40 g 30 μm), dichloromethane/methanol 1:1 (300 ml)]. In this manner, 4-methanesulphonyl-2-(morpholin-4-yl)-8-[2-(tetrahydropyran-2-yl)-2H-pyrazol-3-yl]-[1,7]naphthyridine was obtained as a yellow solid in a yield of 300 mg (54% of theory). LC-MS (method 1): m/z: [M+H]$^+$=444.3, R$_t$=3.24 min.

Step b 4-methanesulphonyl-2-(morpholin-4-yl)-8-[2-(tetrahydropyran-2-yl)-2H-pyrazol-3-yl]-[1,7]naphthyridine

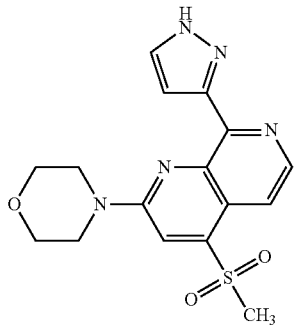 [SMILES: CS(=O)(=O)c1cc(N2CCOCC2)nc2c(-c3cc[nH]n3)nccc12]

300 mg (0.67 mmol) of 4-methanesulphonyl-2-(morpholin-4-yl)-8-[2-(tetrahydropyran-2-yl)-2H-pyrazol-3-yl]-[1,7]naphthyridine were dissolved in 5 ml of methanol, and 1 ml (4 mmol) of 2N hydrochloric acid was added. After 1 h, LCMS showed complete removal of the protective group. Methanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The solid residue was triturated with 5 ml of methanol, filtered off and dried. This gave 146 mg (60% of theory) of 4-methanesulphonyl-2-(morpholin-4-yl)-8-[2-(tetrahydropyran-2-yl)-2H-pyrazol-3-yl]-[1,7]naphthyridine as a yellow solid. m.p. 271-273° C. $^1$H NMR (400 MHz, DMSO, δ ppm): 3.48 (3H), 3.80 (8H), 7.35 (1H), 7.65 (1H), 7.93 (1H), 8.14-8.16 (1H), 8.49-8.50 (1H), 13.43 (1H). LC-MS (method 1): m/z: [M+H]$^+$=360.2, R$_t$=2.78 min.

Example 33

2-[(3R)-3-methylmorpholin-4-yl]-4-(methylsulfonyl)-8-(1H-pyrazol-5-yl)-1,7-naphthyridine Step a 2-[(3R)-3-methylmorpholin-4-yl]-4-(methylsulfonyl)-8-[1-(tetrahydro-2H-pyran-2-yl)-1H-pyrazol-5-yl]-1,7-naphthyridine

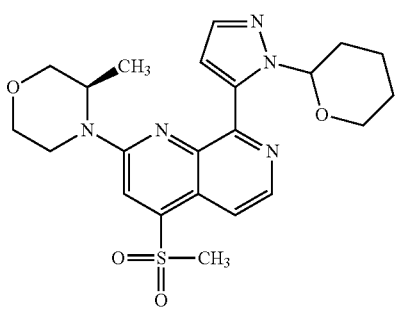 [SMILES: C[C@@H]1COCCN1c1cc(S(C)(=O)=O)c2ccnc(-c3ccnn3C3CCCCO3)c2n1]

4-Chloro-2-[(3R)-3-methylmorpholin-4-yl]-8-[1-(tetrahydro-2H-pyran-2-yl)-1H-pyrazol-5-yl]-1,7-naphthyridine (50 mg, 0.12 mmol, 1 eq.) was solubilised in DMF (4 mL). Methanesulfinic acid sodium salt (25 mg, 0.24 mmol, 2 eq.) and DMAP (1.5 mg, 0.012 mmol, 0.1 eq.) were added. The reaction was stirred for 16 h at 120° C. After cooling to rt, the reaction mixture was concentrated under reduced pressure and the crude was purified by flash column chromatography (gradient 100% hexane to 100% EtOAc). The desired product was obtained in 74% yield (46 mg). $^1$H-NMR (400 MHz, DMSO-d$_6$): δ[ppm]: 1.24 (3H), 1.39-1.65 (3H), 1.89-2.03 (2H), 2.34-2.43 (1H), 3.20-3.29 (1H), 3.41-3.54 (5H), 3.58-3.73 (2H), 3.77 (1H), 3.94-4.01 (1H), 4.12 (1H), 4.45-4.56 (1H), 5.97-6.08 (1H), 6.89 (1H), 7.64 (1H), 7.84 (1H), 8.19 (1H), 8.54 (1H). LC-MS (Method 3): m/z: [M+H]$^+$=458, R$_t$=1.01 min.

Step b

2-[(3R)-3-methylmorpholin-4-yl]-4-(methylsulfonyl)-8-(1H-pyrazol-5-yl)-1,7-naphthyridine

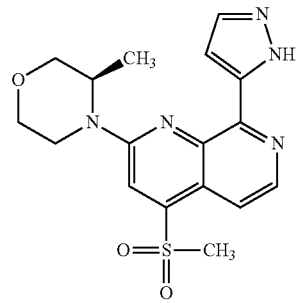 [SMILES: C[C@@H]1COCCN1c1cc(S(C)(=O)=O)c2ccnc(-c3ccn[nH]3)c2n1]

2-[(3R)-3-Methylmorpholin-4-yl]-4-(methylsulfonyl)-8-[1-(tetrahydro-2H-pyran-2-yl)-1H-pyrazol-5-yl]-1,7-naphthyridine (38 mg, 0.084 mmol, 1 eq.) was solubilised in CH$_2$Cl$_2$ (1.5 mL) and H$_2$O (1 mL). Formic acid was added (1 mL) and the reaction was stirred for 2 h at rt. The mixture was then quenched with sat. NaHCO$_3$ and the aqueous phase was extracted three times with CH$_2$Cl$_2$. The organic phase was dried (silicon filter) and concentrated under reduced pressure. The crude mixture was purified by flash column chromatography (gradient from 100% hex to 100% EtOAc to EtOAc/EtOH: 8/2). The desired compound was obtained in 85% yield. $^1$H-NMR (400 MHz, DMSO-d$_6$): δ[ppm]: 1.32 (3H), 3.36-3.46 (1H), 3.49 (3H), 3.57 (1H), 3.71 (1H), 3.84 (1H), 4.06 (1H), 4.17 (1H), 4.57-4.66 (1H), 7.37 (1H), 7.63-7.66 (1H), 7.88 (1H), 8.14 (1H), 8.49 (1H), 13.46 (1H). LC-MS (Method 3): m/z: [M+H]$^+$=374, R$_t$=0.81 min.

Example 34

2-(morpholin-4-yl)-8-(1H-pyrazol-3-yl)-[1,7]naphthyridine-4-carbonitrile

Step a 2-(morpholin-4-yl)-8-[2-(tetrahydropyran-2-yl)-2H-pyrazol-3-yl]-[1,7]naphthyridine-4-carbonitrile

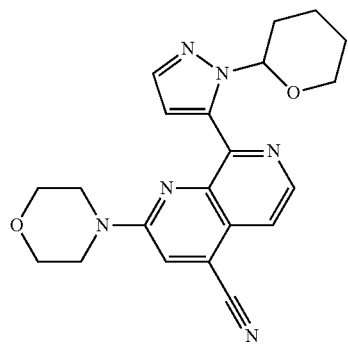 [SMILES: N#Cc1cc(N2CCOCC2)nc2c(-c3ccnn3C3CCCCO3)nccc12]

Under argon, 34 mg (0.029 mmol) of tetrakis(triphenylphosphine)palladium(0) were added to a suspension of 500 mg (0.97 mmol) of 2-(morpholin-4-yl)-8-[2-(tetrahydropyran-2-yl)-2H-pyrazol-3-yl]-[1,7]naphthyridin-4-yl trifluoromethanesulphonate and 43 mg (0.37 mmol) of zinc cyanide in 5 ml of absolute dimethylformamide. The reaction mixture was stirred at 130° C. for 1 h. 30 ml of sodium bicarbonate solution were added to the mixture. The aqueous phase was extracted three times with in each case 40 ml of dichloromethane. The combined organic phases were dried over sodium sulphate and then concentrated to dryness. The residue was triturated with 10 ml of ethyl acetate, filtered off and then dried. This gave 260 mg (68% of theory) of 2-(morpholin-4-yl)-8-[2-(tetrahydropyran-2-yl)-2H-pyrazol-3-yl]-[1,7]naphthyridine-4-carbonitrile as a colourless solid. LC-MS (method 1): m/z: $[M+H]^+=391.3$, $R_t=3.44$ min.

Step b 2-(morpholin-4-yl)-8-(1H-pyrazol-3-yl)-[1,7]naphthyridine-4-carbonitrile

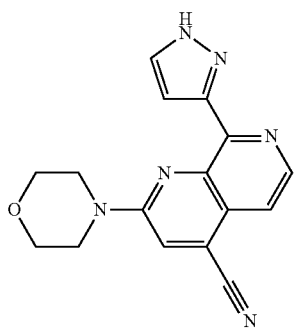 [SMILES: N#Cc1cc(N2CCOCC2)nc2c(-c3cc[nH]n3)nccc12]

A drop of water and 2 ml (26 mmol) of trifluoroacetic acid were added to 100 mg (0.26 mmol) of 2-(morpholin-4-yl)-8-[2-(tetrahydropyran-2-yl)-2H-pyrazol-3-yl]-[1,7]naphthyridine-4-carbonitrile. After 16 h, LCMS showed complete removal of the protective group. The trifluoroacetic acid was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was triturated with 5 ml of chloroform, filtered off and then dried. This gave 30 mg (38% of theory) of 2-morpholin-4-yl-8-(1H-pyrazol-3-yl)-[1,7]naphthyridine-4-carbonitrile as a yellow solid. m.p. 256-258° C. $^1$H NMR (400 MHz, DMSO): δ[ppm]=3.79 (8H), 7.36 (1H), 7.65-7.66 (1H), 7.68-7.69 (1H), 8.28 (1H), 8.49-8.51 (1H), 13.42 (1H). LC-MS (method 1): m/z: $[M+H]^+=306.1$, $R_t=2.93$ min.

Example 35

2-((R)-3-methylmorpholin-4-yl)-8-(-2H-pyrazol-3-yl]-[1,7]naphthyridine-4-carbonitrile

Step a 2-((R)-3-methylmorpholin-4-yl)-8-[2-(tetrahydropyran-2-yl)-2H-pyrazol-3-yl]-[1,7]naphthyridine-4-carbonitrile

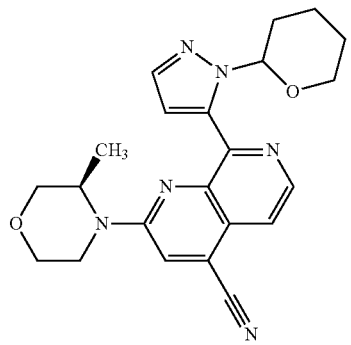 [SMILES: C[C@@H]1COCCN1c1cc(C#N)c2ccnc(-c3ccnn3C3CCCCO3)c2n1]

Under argon, 4 mg (0.004 mmol) of tetrakis(triphenylphosphine)palladium(0) were added to a suspension of 60 mg (0.114 mmol) of 2-((R)-3-methylmorpholin-4-yl)-8-[2-(tetrahydropyran-2-yl)-2H-pyrazol-3-yl]-[1,7]naphthyridin-4-yl trifluoromethanesulphonate and 14 mg (0.114 mmol) of zinc cyanide in 2 ml of absolute dimethylformamide. The reaction mixture was stirred at 100° C. for 15 min. For work-up, a mixture of 25 ml of water and 25 ml of 50 percent strength ammonia solution was added to the mixture. The precipitated solid was filtered off with suction and washed with 10 ml of water. The solid was then dried under reduced pressure. 35 mg (76% of theory) of 2-((R)-3-methylmorpholin-4-yl)-8-[2-(tetrahydropyran-2-yl)-2H-pyrazol-3-yl]-[1,7]naphthyridine-4-carbonitrile were obtained as a yellow solid. LC-MS (method 1): m/z: $[M+H]^+=405.3$, $R_t=3.53$ min.

Step b 2-((R)-3-methylmorpholin-4-yl)-8-(-2H-pyrazol-3-yl]-[1,7]naphthyridine-4-carbonitrile

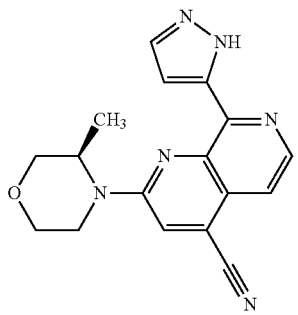 [SMILES: C[C@@H]1COCCN1c1cc(C#N)c2ccnc(-c3ccn[nH]3)c2n1]

1 ml (2 mmol) of 2N hydrochloric acid was added to a solution of 35 mg (0.087 mmol) of 2-((R)-3-methylmorpholin-4-yl)-8-[2-(tetrahydropyran-2-yl)-2H-pyrazol-3-yl]-[1,7]naphthyridine-4-carbonitrile in 2 ml of methanol. The solution was stirred at 50° C. for 18 h. After 18 h, LCMS showed complete removal of the protective group. Methanol was distilled off under reduced pressure and the residue that remained was adjusted to pH 7 using sodium bicarbonate solution. A solid precipitated out; this was separated off and washed with 10 ml of water. The solid was then dried under reduced pressure. This gave 18 mg (58% of theory) of 2-((R)-3-methylmorpholin-4-yl)-8-(-2H-pyrazol-3-yl]-[1,7]naphthyridine-4-carbonitrile as a yellow solid. LC-MS (method 1): m/z: [M+H]+=321.2, Rt=3.08 min.

Example 36

2-morpholin-4-yl-8-(1H-pyrazol-3-yl)-[1,7]naphthyridine-4-carboxamide

Step a 2-morpholin-4-yl-8-[2-(tetrahydropyran-2-yl)-2H-pyrazol-3-yl]-[1,7]naphthyridine-4-carboxamide

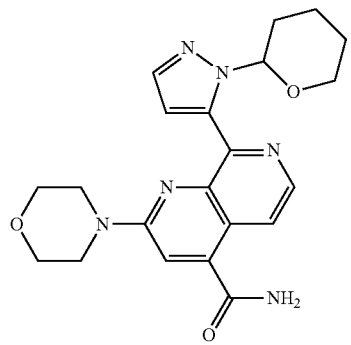 [SMILES: NC(=O)c1cc(N2CCOCC2)nc2c(-c3ccnn3C3CCCCO3)nccc12]

47 mg (0.85 mmol) of potassium hydroxide in a drop of water were added to a suspension of 300 mg (0.77 mmol) of 2-(morpholin-4-yl)-8-[2-(tetrahydropyran-2-yl)-2H-pyrazol-3-yl]-[1,7]naphthyridine-4-carbonitrile in 15 ml of isopropanol, and the mixture was stirred at 70° C. for 6 h. The solvent was distilled off and the residue was used without further purification for protective group removal. This gave 2-morpholin-4-yl-8-[2-(tetrahydropyran-2-yl)-2H-pyrazol-3-yl]-[1,7]naphthyridine-4-carboxamide as a yellow solid in a yield of 314 mg (100% of theory). LC-MS (method 1): m/z: [M+H]+=409.3, $R_t$=2.62 min.

Step b 2-morpholin-4-yl-8-(1H-pyrazol-3-yl)-[1,7]naphthyridine-4-carboxamide

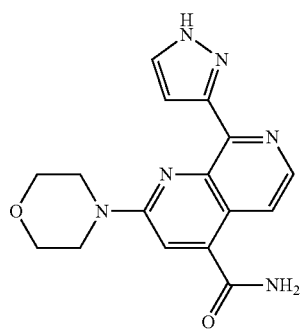 [SMILES: NC(=O)c1cc(N2CCOCC2)nc2c(-c3cc[nH]n3)nccc12]

A drop of water and 1 ml (13 mmol) of trifluoroacetic acid were added to 95 mg (0.23 mmol) of 2-(morpholin-4-yl)-8-[2-(tetrahydropyran-2-yl)-2H-pyrazol-3-yl]-[1,7]naphthyridine-4-carboxamide. After 2 h, LCMS showed complete removal of the protective group. The trifluoroacetic acid was distilled off under reduced pressure and the residue that remained was adjusted to pH 7 using sodium bicarbonate solution. The precipitated solid was filtered off with suction and dried. The product was chromatographed [silica gel 60 (12 g, 30 μm); chloroform/methanol (1:1, 300 ml)]. This gave 20 mg (25% of theory) of 2-(morpholin-4-yl)-8-(1H-pyrazol-3-yl)-[1,7]naphthyridine-4-carboxamide as a yellow solid. m.p. 282-285° C. $^1$H NMR (400 MHz, DMSO, δ ppm): 3.79 (8H), 7.36 (1H), 7.61 (2H), 7.83-7.84 (1H), 7.89 (1H), 8.23 (1H), 8.37-8.39 (1H), 13.36 (1H).

Example 37

4-methanesulphonylmethyl-2-morpholin-4-yl-8-(2H-pyrazol-3-yl)-[1,7]naphthyridine

Step a potassium 2-(morpholin-4-yl)-8-[1-(tetrahydro-2H-pyran-2-yl)-1H-pyrazol-5-yl]-1,7-naphthyridine-4-carboxylate

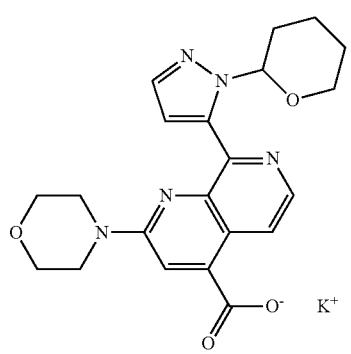 [SMILES: O=C([O-])c1cc(N2CCOCC2)nc2c(-c3ccnn3C3CCCCO3)nccc12 ; [K+]]

3.3 g (8.45 mmol) of 2-(morpholin-4-yl)-8-[2-(tetrahydropyran-2-yl)-2H-pyrazol-3-yl]-[1,7]-naphthyridine-4-carbonitrile were suspended in 33 ml of 2-methoxyethanol, 1.4 g (25.4 mmol) of potassium hydroxide in 772 μl of water were added and the mixture was stirred at 150° C. for 7 h. Since conversion was still incomplete, the mixture was stirred at 130° C. for a further 14 h. For work-up, most of the solvent was removed. The residue was triturated with 10 ml of isopropanol and 50 ml of diethyl ether. The resulting precipitated yellow solid was filtered off and dried under reduced pressure. This gave 2.74 g (72% of theory) of potassium 2-(morpholin-4-yl)-8-[1-(tetrahydro-2H-pyran-2-yl)-1H-pyrazol-5-yl]-1,7-naphthyridine-4-carboxylate as a yellow solid. LC-MS (method 1): m/z: $[M+H]^+$=410.3, $R_t$=3.03 min.

Step b methyl 2-(morpholin-4-yl)-8-[2-(tetrahydropyran-2-yl)-2H-pyrazol-3-yl]-[1,7]naphthyridine-4-carboxylate

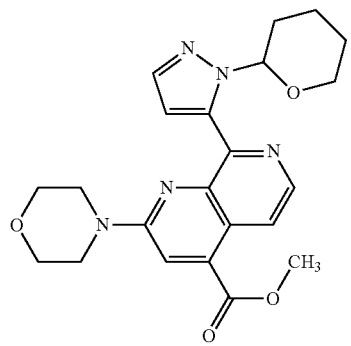 [SMILES: COC(=O)c1cc(N2CCOCC2)nc2c(-c3ccnn3C3CCCCO3)nccc12]

630 mg (1.41 mmol) of potassium 2-(morpholin-4-yl)-8-[1-(tetrahydro-2H-pyran-2-yl)-1H-pyrazol-5-yl]-[1,7]naphthyridine-4-carboxylate were suspended in 10 ml of tetrahydrofuran, 459 mg (1.41 mmol) of caesium carbonate and 102 μl (1.69 mmol) of methyl iodide were added and the mixture was stirred at 80° C. for 32 h. For work-up, most of the solvent was removed. 20 ml of water were added to the residue, and the mixture was extracted three times with in each case 30 ml of chloroform. The combined organic phases were dried over sodium sulphate and then concentrated to dryness. This gave 405 mg (68% of theory) of methyl 2-(morpholin-4-yl)-8-[2-(tetrahydropyran-2-yl)-2H-pyrazol-3-yl]-[1,7]naphthyridine-4-carboxylate as a yellow solid. LC-MS (method 1): m/z: $[M+H]^+$=424.4, $R_t$=3.50 min.

Step c

{2-(morpholin-4-yl)-8-[1-(tetrahydro-2H-pyran-2-yl)-1H-pyrazol-5-yl]-1,7-naphthyridine-4-yl}methanol

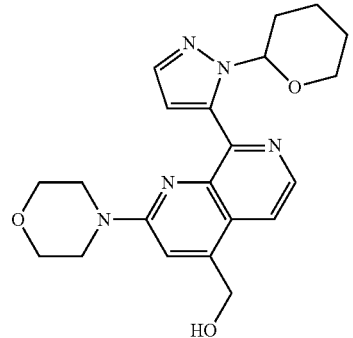 [SMILES: OCc1cc(N2CCOCC2)nc2c(-c3ccnn3C3CCCCO3)nccc12]

At 0° C. and under an atmosphere of argon, 178 mg (4.68 mmol) of lithium aluminium hydride were added to a solution of 660 mg (1.56 mmol) of methyl 2-(morpholin-4-yl)-8-[2-(tetrahydropyran-2-yl)-2H-pyrazol-3-yl]-[1,7] naphthyridine-4-carboxylate in 16 ml of absolute tetrahydrofuran, and the mixture was stirred at 0° C. for 30 min. With ice-cooling, 20 ml of saturated ammonium chloride solution were added to the reaction mixture, and the mixture was then extracted three times with in each case 30 ml of chloroform. The combined organic phases were dried over sodium sulphate and concentrated under reduced pressure. This gave 570 mg (93% of theory) of {2-(morpholin-4-yl)-8-[1-(tetrahydro-2H-pyran-2-yl)-1H-pyrazol-5-yl]-1,7-naphthyridine-4-yl}methanol as a crude product. The latter consisted of two compounds. According to $^1$H NMR spectrum, this crude product contained 30% of {2-(morpholin-4-yl)-8-[1-(tetrahydro-2H-pyran-2-yl)-1H-pyrazol-5-yl]-1,7-naphthyridine-4-yl}methanol and 70% of a compound having 2 extra mass units. It was not possible to separate the two products by chromatography, and therefore they were used as crude product in the next step. LC-MS (method 1): m/z: $[M+H]^+$=396.3, $R_t$=2.95 min.

Step d 2-(morpholin-4-yl)-8-[2-(tetrahydropyran-2-yl)-2H-pyrazol-3-yl]-[1,7]naphthyridine-4-ylmethyl methanesulphonate

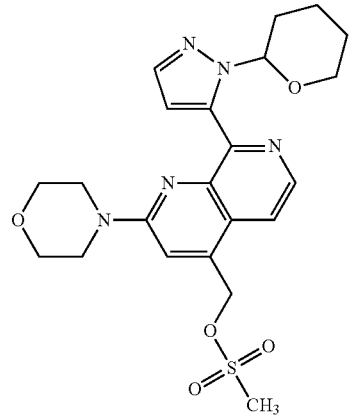 [SMILES: CS(=O)(=O)OCc1cc(N2CCOCC2)nc2c(-c3ccnn3C3CCCCO3)nccc12]

Under argon and at 10° C., 56 µl (0.72 mmol) of methanesulphonyl chloride were added dropwise to a solution of 260 mg (0.66 mmol) of {2-(morpholin-4-yl)-8-[1-(tetrahydro-2H-pyran-2-yl)-1H-pyrazol-5-yl]-1,7-naphthyridine-4-yl}methanol and 119 µl (0.86 mmol) of triethylamine in 10 ml of absolute tetrahydrofuran, and the mixture was stirred at 10° C. for 1 h. The precipitated solid was filtered off and the filtrate was concentrated under reduced pressure. This gave 311 mg (100% of theory) of 2-(morpholin-4-yl)-8-[2-(tetrahydropyran-2-yl)-2H-pyrazol-3-yl]-[1,7]naphthyridine-4-ylmethyl methanesulphonate as a brown solid. This crude product was used without further purification for the next synthesis. LC-MS (method 1): m/z: [M+H]$^+$=474.3, $R_t$=3.24 min.

Step e 4-methanesulphonylmethyl-2-(morpholin-4-yl-)8-[2-(tetrahydropyran-2-yl)-2H-pyrazol-3-yl]-[1,7]naphthyridine

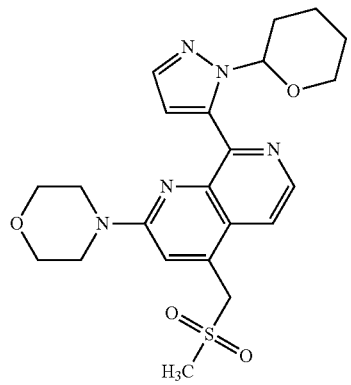 [SMILES: CS(=O)(=O)Cc1cc(N2CCOCC2)nc2c(-c3ccnn3C3CCCCO3)nccc12]

Sodium methylsulphinate was added a little at a time to a solution of 311 mg (0.66 mmol) of 2-(morpholin-4-yl)-8-[2-(tetrahydropyran-2-yl)-2H-pyrazol-3-yl]-[1,7]naphthyridine-4-ylmethyl methanesulphonate in 10 ml of absolute dimethyl sulphoxide, and the mixture was then stirred at 120° C. for 20 min. The mixture was diluted with 10 ml of water and then extracted three times with in each case 10 ml of dichloromethane. The combined organic solutions were dried over sodium sulphate and then concentrated under reduced pressure. The residue was chromatographed [PuriFlash, silica gel 60 (25 g, 30 µm); dichloromethane/methanol 95:5]. This gave 80 mg (27% of theory) of 4-methanesulphonylmethyl-2-(morpholin-4-yl-)8-[2-(tetrahydropyran-2-yl)-2H-pyrazol-3-yl]-[1,7]naphthyridine as a yellow solid. LC-MS (method 1): m/z: [M+H]$^+$=458.3, $R_t$=2.89 min.

Step f 4-methanesulphonylmethyl-2-morpholin-4-yl-8-(2H-pyrazol-3-yl)-[1,7]naphthyridine

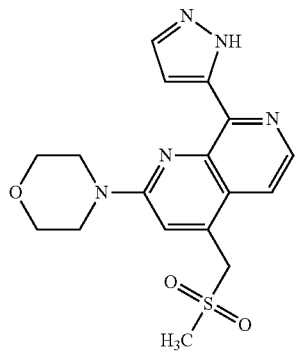 [SMILES: CS(=O)(=O)Cc1cc(N2CCOCC2)nc2c(-c3ccn[nH]3)nccc12]

30 mg (0.07 mmol) of 4-methanesulphonylmethyl-2-(morpholin-4-yl-)8-[2-(tetrahydropyran-2-yl)-2H-pyrazol-3-yl]-[1,7]naphthyridine were dissolved in 1 ml of methanol, and 0.5 ml (1 mmol) of 2N hydrochloric acid was added. After 1 h, LCMS showed complete removal of the protective group. Methanol was distilled off under reduced pressure and the residue that remained was adjusted to pH 7 using sodium bicarbonate solution. The resulting precipitated solid was filtered off and dried under reduced pressure. This gave 24 mg (98% of theory) of 4-methanesulphonylmethyl-2-morpholin-4-yl-8-(2H-pyrazol-3-yl)-[1,7]naphthyridine as a yellow solid. m.p. 272-274° C. $^1$H NMR (400 MHz, DMSO): δ[ppm]=3.10 (3H), 3.74-3.81 (8H), 5.00 (2H), 7.36 (1H), 7.64 (2H), 7.94 (1H), 8.40 (3H), 13.31 (1H).

Example 38

[2-(morpholin-4-yl)-8-(2H-pyrazol-3-yl)-[1,7]naphthyridine-4-yl]methanol

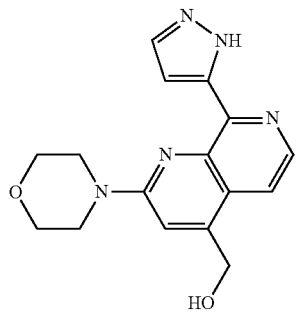 [SMILES: OCc1cc(N2CCOCC2)nc2c(-c3ccn[nH]3)nccc12]

50 mg (0.126 mmol) of [2-(morpholin-4-yl)-8-[1-(tetrahydro-2H-pyran-2-yl)-1H-pyrazol-5-yl]-1,7-naphthyridine-4-yl}methanol were dissolved in 1 ml of methanol, and 0.5 ml (1 mmol) of 2N hydrochloric acid was added. After 1 h, LCMS showed complete removal of the protective group. Methanol was distilled off under reduced pressure and the residue that remained was adjusted to pH 7 using sodium bicarbonate solution. The aqueous phase was extracted three times with in each case 10 ml of dichloromethane. The combined organic phases were dried over sodium sulphate and concentrated under reduced pressure. The residue was purified using a Flashmaster chromatography [silica gel 60 (25 g, 30 µm); dichloromethane/methanol 95:5]. This gave 20 mg (51% of theory) of [2-(morpholin-4-yl)-8-(2H-pyrazol-3-yl)-[1,7]-naphthyridine-4-yl]methanol as a yellow solid. $^1$H NMR (400 MHz, DMSO): δ[ppm]=3.81 (8H), 4.95 (2H), 7.47-7.48 (1H), 7.68 (1H), 7.89-7.92 (2H), 8.35-8.36 (1H), 13.31 (1H). LC-MS (method 1): m/z: [M+H]$^+$=312.2, R$_t$=2.31 min.

Example 39

4-(1-methanesulphonycyclopropyl)-2-(morpholin-4-yl)-8-(2H-pyrazol-3-yl)-[1,7]naphthyridine Step a 4-(1-methanesulphonylcyclopropyl)-2-(morpholin-4-yl)-8-(2-(tetrahydropyran-2-yl)-2H-pyrazol-3-yl)-[1,7]naphthyridine

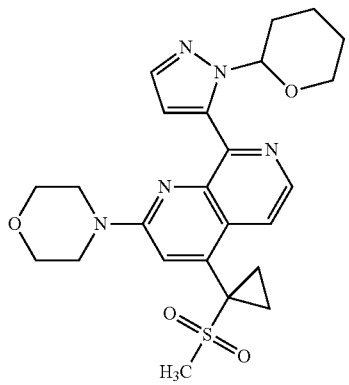 [SMILES: CS(=O)(=O)C1(c2cc(N3CCOCC3)nc3c(-c4ccnn4C4CCCCO4)nccc23)CC1]

330 µl of 50 percent strength sodium hydroxide solution were added to a solution of 150 mg (0.328 mmol) of 4-methanesulphonylmethyl-2-(morpholin-4-yl)-8-[2-(tetrahydropyran-2-yl)-2H-pyrazol-3-yl]-[1,7]naphthyridine, 28 µl (0.319 mmol) of 1,2-dibromoethane and 10 mg (0.032 mmol) of tetrabutylammonium bromide in 960 µl of absolute tetrahydrofuran, and the mixture was then stirred at room temperature for 1 h. The colour of the suspension changed from dark-green to dark-brown. Another 28 µl (0.319 mmol) of 1,2-dibromoethane, 10 mg (0.032 mmol) of tetrabutylammonium bromide and 330 µl of 50 percent strength sodium hydroxide solution were added, and the mixture was stirred at 60° C. for 3 h. The mixture was diluted with 10 ml of water and then extracted three times with in each case 10 ml of dichloromethane. The combined organic phases were dried over sodium sulphate and concentrated under reduced pressure. The residue was purified twice by column chromatography on a Flashmaster [silica gel 60 (2×25 g, 30 µm), dichloromethane/methanol 95:5]. This gave 23 mg (15% of theory) of 4-(1-methanesulphonylcyclopropyl)-2-(morpholin-4-yl)-8-[2-(tetrahydropyran-2-yl)-2H-pyrazol-3-yl]-[1,7]naphthyridine as a yellow solid. The solid, which was impure, was used without further purification for the next step. LC-MS (method 1): m/z: [M+H]$^+$=484.2, R$_t$=2.75 min.

Step b 4-(1-methanesulphonylcyclopropyl)-2-(morpholin-4-yl)-8-(2H-pyrazol-3-yl)-[1,7]naphthyridine

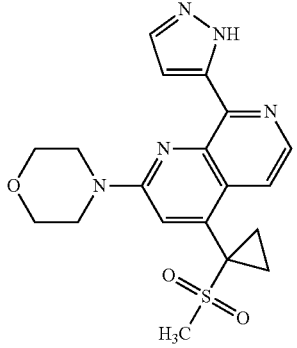 [SMILES: CS(=O)(=O)C1(c2cc(N3CCOCC3)nc3c(-c4ccn[nH]4)nccc23)CC1]

0.5 ml of (1 mmol) of 2N hydrochloric acid was added to a solution of 23 mg (0.048 mmol) of 4-(1-methanesulphonylcyclopropyl)-2-(morpholin-4-yl)-8-[2-(tetrahydropyran-2-yl)-2H-pyrazol-3-yl]-[1,7]naphthyridine in 1 ml of methanol. The solution was stirred at 50° C. for 18 h. After 18 h, LCMS showed complete removal of the protective group. Methanol was distilled off under reduced pressure and the residue that remained was adjusted to pH 7 using sodium bicarbonate solution. The aqueous phase was extracted three times with in each case 10 ml of dichloromethane. The combined organic phases were dried over sodium sulphate and concentrated under reduced pressure. This gave 18 mg (85% of theory) of 4-(1-methanesulphonylcyclopropyl)-2-(morpholin-4-yl)-8-(2H-pyrazol-3-yl)-[1,7]-naphthyridine as a yellow solid. m.p. 220-234° C. $^1$H NMR (400 MHz, DMSO): δ[ppm]=1.39-2.09 (4H), 3.06 (3H), 3.79-3.80 (8H), 7.36 (1H), 7.61 (1H), 7.82-7.88 (2H), 8.39-8.41 (1H), 13.36 (1H). LC-MS (method 1): m/z: [M+H]$^+$=400.30, R$_t$=2.21 min.

Example 40

4-Isopropoxy-2-(morpholin-4-yl)-8-(1H-pyrazol-3-yl)-[1,7]naphthyridine

Step a 4-isopropoxy-2-(morpholin-4-yl)-8-[2-(tetrahydropyran-2-yl)-2H-pyrazol-3-yl]-[1,7]naphthyridin

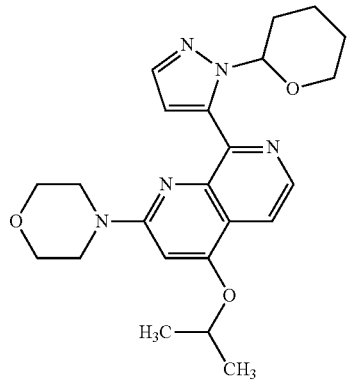 [SMILES: CC(C)Oc1cc(N2CCOCC2)nc2c(-c3ccnn3C3CCCCO3)nccc12]

44 mg (0.31 mmol) of potassium carbonate were added to a solution of 100 mg (0.26 mmol) of 2-(morpholin-4-yl)-8-[2-(tetrahydropyran-2-yl)-2H-pyrazol-3-yl]-[1,7]naphthyridin-4-ol and 45 mg (0.26 mmol) of iodopropane in 6 ml of dry acetonitrile (MeCN). The suspension was stirred at 85° C. for 7 h. The course of the reaction was monitored by LCMS. The solvent was removed and the residue that remained was chromatographed [silica gel 60 (12 g, 30 μm); ethyl acetate (100 ml)]. This gave 90 mg (81% of theory) of 4-isopropoxy-2-(morpholin-4-yl)-8-(1H-pyrazol-3-yl)-[1,7]naphthyridine as a yellow oil. LC-MS (method 1): m/z: [M+H]$^+$=424.3, $R_f$=3.66 min.

Step b

4-Isopropoxy-2-(morpholin-4-yl)-8-(1H-pyrazol-3-yl)-[1,7]naphthyridine

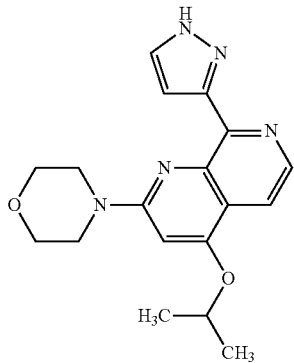

A drop of water and 1 ml (13 mmol) of trifluoroacetic acid were added to 80 mg (0.19 mmol) of 4-isopropoxy-2-(morpholin-4-yl)-8-(1H-pyrazol-3-yl)-[1,7]naphthyridine. After 10 min, LCMS showed complete removal of the protective group. The trifluoroacetic acid was removed under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, 30 μm); ethyl acetate (100 ml)]. This gave 40 mg (59% of theory) of 4-isopropoxy-2-(morpholin-4-yl)-8-(1H-pyrazol-3-yl)-[1,7]naphthyridine as a yellow foam. m.p. 73-74° C. $^1$H NMR (400 MHz, CDCl$_3$, δ ppm): 1.48 (6H), 3.64-3.67 (4H), 3.89-3.92 (4H), 4.75-4.78 (1H), 6.37 (1H), 7.23 (1H), 7.67 (1H), 7.71 (1H), 8.38 (1H). LC-MS (method 1): m/z: [M+H]$^+$=340.3, $R_f$=2.95 min.

Example 41

2-(morpholin-4-yl)-4-(propan-2-yloxy)-8-(1H-pyrrol-2-yl)-1,7-naphthyridine

Step a tert-butyl 2-[2-(morpholin-4-yl)-4-(propan-2-yloxy)-1,7-naphthyridin-8-yl]-1H-pyrrole-1-carboxylate

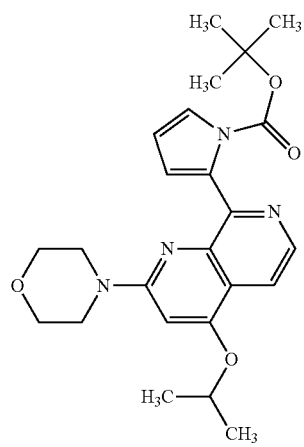 [SMILES: CC(C)Oc1cc(N2CCOCC2)nc2c(-c3cccn3C(=O)OC(C)(C)C)nccc12]

Under argon, 20 mg (0.024 mmol) [1,1'-bis(diphenylphosphino)ferrocene]dichloropalladium(II) were added to a mixture of 75 mg (0.24 mmol) 8-chloro-2-(morpholin-4-yl)-4-(propan-2-yloxy)-1,7-naphthyridine and 57 mg (0.27 mmol) [1-(tert-butoxycarbonyl)-1H-pyrrol-2-yl]boronic acid in 2 ml acetonitrile and 2 ml 2M aqueous solution of potassium carbonate. The mixture was stirred in a microwave oven at 130° C. for 10 minutes. After cooling, DCM was added and the mixture was filtered using a Whatman filter. The organic phase was concentrated and the residue was purified by HPLC separation (Autopurifier: basic conditions) to give 35 mg (0.08 mmol) of the desired product. $^1$H-NMR (400 MHz, DMSO-d6): δ[ppm]=0.92 (9H), 1.37 (6H), 3.52 (4H), 3.63 (4H), 5.05 (1H), 6.29 (1H), 6.39 (1H), 6.76 (1H), 7.37 (1H), 7.63 (1H), 8.20 (1H).

Step b 2-(morpholin-4-yl)-4-(propan-2-yloxy)-8-(1H-pyrrol-2-yl)-1,7-naphthyridine

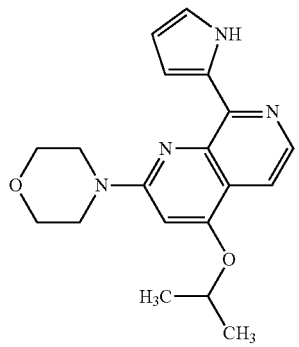 [SMILES: CC(C)Oc1cc(N2CCOCC2)nc2c(-c3ccc[nH]3)nccc12]

7 µl (0.096 mmol) TFA were added to a solution of 9 mg (0.020 mmol) tert-butyl 2-[2-(morpholin-4-yl)-4-(propan-2-yloxy)-1,7-naphthyridin-8-yl]-1H-pyrrole-1-carboxylate in 2 ml DCM and the reaction mixture was stirred at room temperature for 150 minutes. Additional 7 µl (0.096 mmol) TFA was added and the reaction mixture was stirred overnight. Additional 23 µl (0.32 mmol) TFA was added and the reaction mixture was stirred for 8 hours. The mixture was basified by addition of aqueous sodium bicarbonate solution and extracted with DCM (2×). The combined organic phases were filtered using a Whatman filter and concentrated to give 9 mg (0.027 mmol) of the desired product. $^1$H-NMR (400 MHz, CDCl$_3$): δ[ppm]=1.50 (6H), 3.70 (4H), 3.96 (4H), 4.80 (1H), 6.41 (2H), 7.03 (1H), 7.48 (1H), 7.61 (1H), 8.31 (1H), 11.53 (1H).

Example 42

4-(3-(S-methylsulfonimidoyl)propoxy)-2-(morpholin-4-yl)-8-(1H-pyrazol-5-yl)-1,7-naphthyridine Step a 2,2,2-trifluoro-N-[(3-hydroxypropyl)(methyl)oxido-λ$^6$-sulfanylidene]acetamide

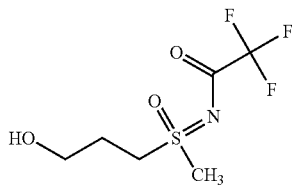

A mixture of 1.00 g (2.83 mmol)N-[{3-[(benzyloxy)methoxy]propyl}(methyl)oxido-λ$^6$-sulfanylidene]-2,2,2-trifluoroacetamide and 0.75 g palladium on charcoal (10%) in 100 ml ethanol was stirred under a hydrogen atmosphere for 90 minutes at 80° C. 0.50 g palladium on charcoal (10%) are added and the mixture is stirred for additional 3 hours under a hydrogen atmosphere at 80° C. After cooling, the reaction mixture was filtered and the filtrate was concentrated to give 0.61 g of the desired product that was used without further purification. $^1$H-NMR (400 MHz, CDCl$_3$): δ [ppm]=2.18 (2H), 3.41 (3H), 3.61 (1H), 3.72 (1H), 3.86 (2H).

Step b 2,2,2-trifluoro-N-{methyl[3-({2-(morpholin-4-yl)-8-[1-(tetrahydro-2H-pyran-2-yl)-1H-pyrazol-5-yl]-1,7-naphthyridin-4-yl}oxy)propyl]oxido-λ$^6$-sulfanylidene}acetamide

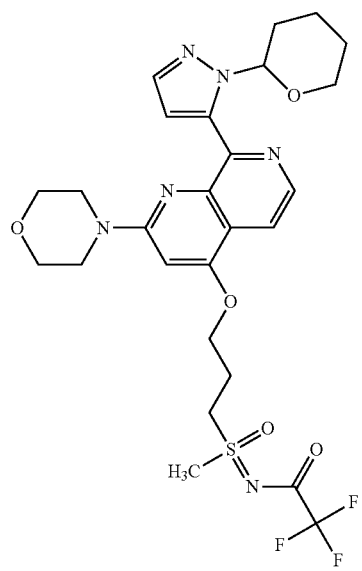 [SMILES: CS(=O)(CCCOc1cc(N2CCOCC2)nc2c(-c3ccnn3C3CCCCO3)nccc12)=NC(=O)C(F)(F)F]

A solution of 26 µl (0.13 mmol) diisopropyl azodicarboxylate in 0.1 ml THF was added dropwise to a mixture of 50 mg (0.13 mmol) 2-(morpholin-4-yl)-8-[1-(tetrahydro-2H-pyran-2-yl)-1H-pyrazol-5-yl]-1,7-naphthyridin-4-ol, 28 mg crude 2,2,2-trifluoro-N-[(3-hydroxypropyl)(methyl)oxido-λ$^6$-sulfanylidene]acetamide and 34 mg (0.13 mmol) triphenylphosphine in 0.5 ml THF and the batch was stirred at room temperature for 6 hours. 94 mg (0.36 mmol) triphenylphosphine and 71 µl (0.36 mmol) diisopropyl azodicarboxylate were added and the mixture was stirred at room temperature overnight. Finally, 34 mg (0.13 mmol) triphenylphosphine and 26 µl (0.13 mmol) diisopropyl azodicarboxylate were added and the mixture was stirred for 6 hours before it was concentrated. The residue was purified by column chromatography on silica gel (DCM to DCM/ethanol 15%) to give 34 mg of the product with approximately 70% purity.

Step c

4-[3-(S-methylsulfonimidoyl)propoxy]-2-(morpholin-4-yl)-8-[1-(tetrahydro-2H-pyran-2-yl)-1H-pyrazol-5-yl]-1,7-naphthyridine

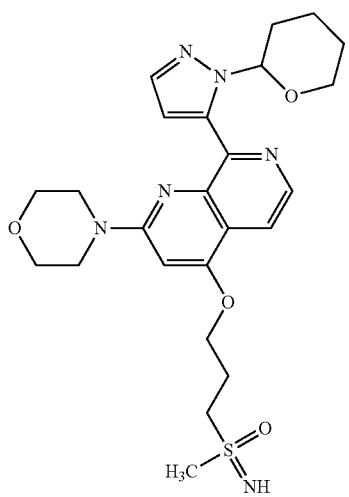 [SMILES: CS(=N)(=O)CCCOc1cc(N2CCOCC2)nc2c(-c3ccnn3C3CCCCO3)nccc12]

39 mg (0.29 mmol) potassium carbonate was added to a solution of 34 mg 2,2,2-trifluoro-N-{methyl [3-({2-(morpholin-4-yl)-8-[1-(tetrahydro-2H-pyran-2-yl)-1H-pyrazol-5-yl]-1,7-naphthyridin-4-yl}oxy)propyl]oxido-$\lambda^6$-sulfanylidene}acetamide (purity approximately 70%) in 1.2 ml methanol and the reaction mixture was stirred at room temperature for 90 minutes. Aqueous sodium chloride solution was added and the mixture was extracted with ethyl acetate (2×). The combined organic phases were filtered using a Whatman filter and concentrated to give 27 mg of the desired product with a purity of approximately 66%.

Step d 4-(3-(S-methylsulfonimidoyl)propoxy)-2-(morpholin-4-yl)-8-(1H-pyrazol-5-yl)-1,7-naphthyridine

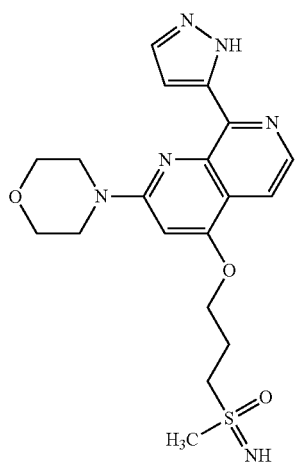 [SMILES: CS(=N)(=O)CCCOc1cc(N2CCOCC2)nc2c(-c3ccn[nH]3)nccc12]

0.06 ml (0.12 mmol) 2N aqueous solution of hydrogen chloride was added to a solution of 27 mg 4-[3-(S-methylsulfonimidoyl)propoxy]-2-(morpholin-4-yl)-8-[1-(tetrahydro-2H-pyran-2-yl)-1H-pyrazol-5-yl]-1,7-naphthyridine (purity approximately 66%) in 0.25 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: acidic conditions) to give 3 mg (0.007 mmol) of the desired product. $^1$H-NMR (400 MHz, DMSO-d6): δ[ppm]=2.32 (2H), 2.99 (3H), 3.31 (2H), 3.75 (4H), 3.80 (4H), 4.41 (2H), 6.90 (1H), 7.38 (1H), 7.62 (1H), 7.81 (1H), 8.35 (1H), 13.37 (1H).

Example 43

4-ethoxy-2-(morpholin-4-yl)-8-(1H-pyrazol-3-yl)-[1,7]naphthyridine

Step a 4-ethoxy-2-(morpholin-4-yl)-8-[2-(tetrahydropyran-2-yl)-2H-pyrazol-3-yl]-[1,7]naphthyridine

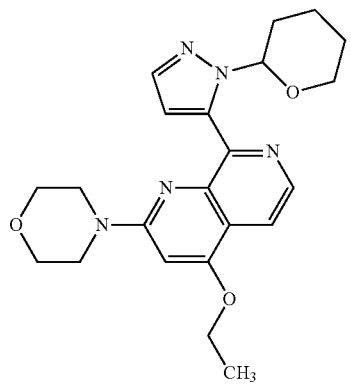 [SMILES: CCOc1cc(N2CCOCC2)nc2c(-c3ccnn3C3CCCCO3)nccc12]

44 mg (0.31 mmol) of potassium carbonate were added to a solution of 100 mg (0.26 mmol) of 2-(morpholin-4-yl)-8-[2-(tetrahydropyran-2-yl)-2H-pyrazol-3-yl]-[1,7]naphthyridin-4-ol and 21 µl (0.26 mmol) of iodoethane in 6 ml of dry acetonitrile (MeCN). The suspension was stirred at 85° C. for 2 h. The course of the reaction was monitored by LCMS. The solvent was removed and the residue that remained was reacted further without purification. LC-MS (method 1): m/z: [M+H]$^+$=410.3, R$_t$=3.53 min.

Step b

4-ethoxy-2-(morpholin-4-yl)-8-(1H-pyrazol-3-yl)-[1,7]naphthyridine

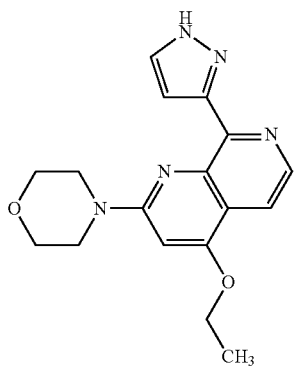 [SMILES: CCOc1cc(N2CCOCC2)nc2c(-c3cc[nH]n3)nccc12]

One drop of water and 1 ml (13 mmol) of trifluoroacetic acid were added to 107 mg (0.26 mmol) of 4-ethoxy-2-(morpholin-4-yl)-8-[2-(tetrahydropyran-2-yl)-2H-pyrazol-3-yl]-[1,7]naphthyridine. After 1 h, LCMS showed complete removal of the protective group. The trifluoroacetic acid was removed under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of methanol were added to the residue. The resulting precipitated solid was filtered off and then dried. This gave 25 mg (29% of theory) of 4-ethoxy-2-(morpholin-4-yl)-8-(1H-pyrazol-3-yl)-[1,7]naphthyridine as a yellow solid. m.p. 173-175° C. $^1$H NMR (400 MHz, CDCl$_3$, δ ppm): 1.57-1.61 (3H), 3.70-3.72 (4H), 3.92-3.95 (4H), 4.22-4.27 (2H), 6.41 (1H), 7.25 (2H), 7.70 (1H), 7.75 (1H), 8.42 (1H). LC-MS (method 1): m/z: [M+H]$^+$=326.3, R$_t$=2.81 min.

Example 44

4-methoxy-2-(morpholin-4-yl)-8-(1H-pyrazol-3-yl)-[1,7]naphthyridine

Step a

4-methoxy-2-(morpholin-4-yl)-8-[2-(tetrahydropyran-2-yl)-2H-pyrazol-3-yl]-[1,7]naphthyridine

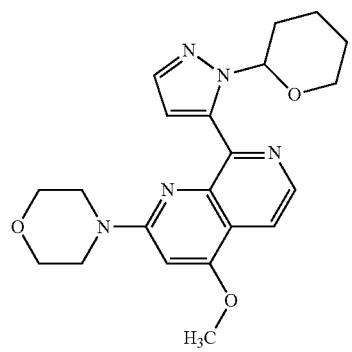 [SMILES: COc1cc(N2CCOCC2)nc2c(-c3ccnn3C3CCCCO3)nccc12]

44 mg (0.31 mmol) of potassium carbonate were added to a solution of 100 mg (0.26 mmol) of 2-(morpholin-4-yl)-8-[2-(tetrahydropyran-2-yl)-2H-pyrazol-3-yl]-[1,7]naphthyridin-4-ol and 32 μl (0.26 mmol) of methyl iodide in 6 ml of dry acetonitrile. The suspension was stirred at 85° C. for 2 h. The course of the reaction was monitored by LCMS. The solvent was removed and the residue that remained was reacted further without purification. LC-MS (method 1): m/z: [M+H]*=396.3, R$_t$=3.33 min.

Step b

4-methoxy-2-(morpholin-4-yl)-8-(1H-pyrazol-3-yl)-[1,7]naphthyridine

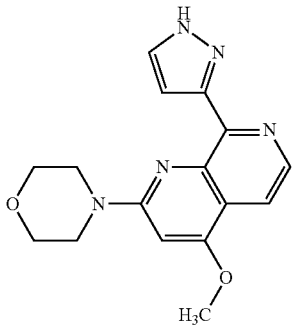 [SMILES: COc1cc(N2CCOCC2)nc2c(-c3cc[nH]n3)nccc12]

A drop of water and 1 ml (13 mmol) of trifluoroacetic acid were added to 103 mg (0.26 mmol) of 4-methoxy-2-(morpholin-4-yl)-8-[2-(tetrahydropyran-2-yl)-2H-pyrazol-3-yl]-[1,7]naphthyridine. After 10 min, LCMS showed complete removal of the protective group. The trifluoroacetic acid was removed under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was triturated with 5 ml of methanol. The resulting precipitated solid was filtered off and then dried. This gave 30 mg (35% of theory) of 4-methoxy-2-(morpholin-4-yl)-8-(1H-pyrazol-3-yl)-[1,7]naphthyridine as a yellow solid. m.p. 234-235° C. $^1$H NMR (400 MHz, CDCl$_3$, δ ppm): 3.67-3.69 (4H), 3.91-3.93 (4H), 4.01 (3H), 6.36 (1H), 7.25 (1H), 7.68 (2H), 8.40 (1H). LC-MS (method 1): m/z: [M+H]$^+$=312.3, R$_t$=2.60 min.

Example 45

2-methyl-1-([2-(morpholin-4-yl)-8-(1H-pyrazol-5-yl)-1,7-naphthyridin-4-yl]oxy)propan-2-ol Step a 2-methyl-1-({2-(morpholin-4-yl)-8-[1-(tetrahydro-2H-pyran-2-yl)-1H-pyrazol-5-yl]-1,7-naphthyridin-4-yl}oxy)propan-2-ol

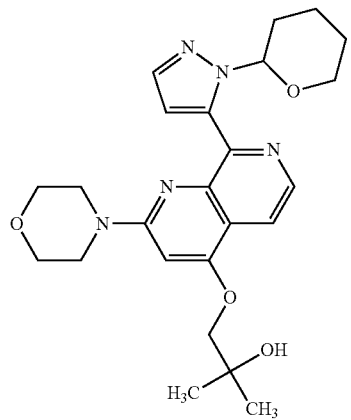 [SMILES: CC(C)(O)COc1cc(N2CCOCC2)nc2c(-c3ccnn3C3CCCCO3)nccc12]

87 mg (0.63 mmol) potassium carbonate was added to a mixture of 60 mg (0.16 mmol) 2-(morpholin-4-yl)-8-[1-(tetrahydro-2H-pyran-2-yl)-1H-pyrazol-5-yl]-1,7-naphthyridin-4-ol and 102 mg (0.94 mmol) 1-chloro-2-methylpropan-2-ol in 5.0 ml ethanol and 0.5 ml water and the mixture was stirred at 70° C. for 20 hours. 51 mg (0.47 mmol) 1-chloro-2-methylpropan-2-ol and 44 mg (0.32 mmol) potassium carbonate were added and the mixture was stirred for additional 24 hours at 70° C. After cooling, the reaction mixture was diluted with water and extracted with DCM (2×). The combined organic phases were dried (MgSO$_4$), filtered and concentrated. The residue was purified by preparative HPLC (Autopurifier: basic conditions) to give 17 mg (0.04 mmol) of the desired product.

Step b 2-methyl-1-([2-(morpholin-4-yl)-8-(1H-pyrazol-5-yl)-1,7-naphthyridin-4-yl]oxy)propan-2-ol

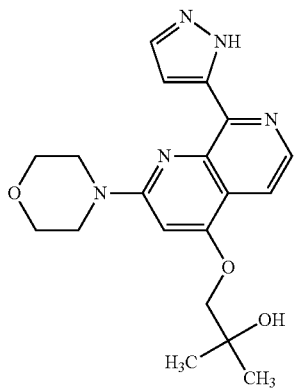 [SMILES: CC(C)(O)COc1cc(N2CCOCC2)nc2c(-c3ccn[nH]3)nccc12]

0.04 ml (0.08 mmol) 2N aqueous solution of hydrogen chloride was added to a solution of 16 mg 2-methyl-1-({2-(morpholin-4-yl)-8-[1-(tetrahydro-2H-pyran-2-yl)-1H-pyrazol-5-yl]-1,7-naphthyridin-4-yl}oxy)propan-2-ol in 0.2 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated to give 5 mg (0.01 mmol) of the desired product. $^1$H-NMR (400 MHz, CDCl$_3$): δ[ppm]=1.50 (6H), 3.72 (4H), 3.95 (4H), 4.02 (2H), 6.45 (1H), 7.28 (1H), 7.72 (1H), 7.73 (1H), 8.44 (1H),

Example 46

2-(morpholin-4-yl)-8-(1H-pyrazol-5-yl)-4-(tetrahydrofuran-2-ylmethoxy)-1,7-naphthyridine

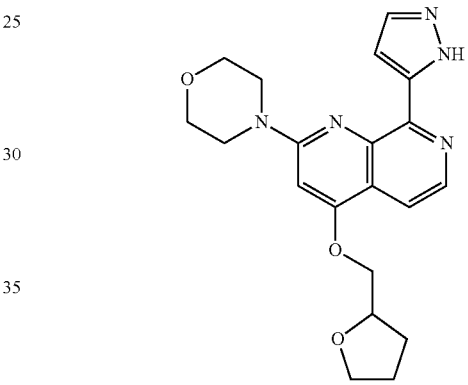

A mixture of 2-(morpholin-4-yl)-8-[1-(tetrahydro-2H-pyran-2-yl)-1H-pyrazol-5-yl]-1,7-naphthyridin-4-ol (259 mg, 0.43 mmol), 2-(bromomethyl)tetrahydrofuran (126 mg, 0.68 mmol) and Caesiumcarbonate (181 mg, 0.56 mmol) in DMF (1.63 ml) was heated in a sealed tube in the microwave at 100° C. for one hour. The reaction mixture was allowed to cool to ambient temperature, a solution of concentrated aqueous HCl (0.49 ml) was added and the reaction was stirred at this temperature for two hours. The solvent was evaporated under reduced pressure, the residue was taken up in dichloromethane (10 ml) and water (10 ml). The layers were separated and the aqueous layer was extracted with dichloromethane (2×10 ml). The combined organic layers were dried over Na$_2$SO$_4$ and the solvent was removed under reduced pressure. The crude product was purified by HPLC chromatography (acidic conditions). The title compound was obtained in 4% yield (7 mg). $^1$H-NMR (400 MHz, DMSO): δ[ppm]=1.75-2.15 (4H), 3.73-3.88 (10H), 4.25-4.36 (3H), 6.94 (1H), 7.39 (1H), 7.70 (1H), 7.75 (1H), 8.36 (1H), 13.52 (1H).

Example 47

3-([2-(morpholin-4-yl)-8-(1H-pyrazol-5-yl)-1,7-naphthyridin-4-yl]oxy)dihydrofuran-2(3H)-one

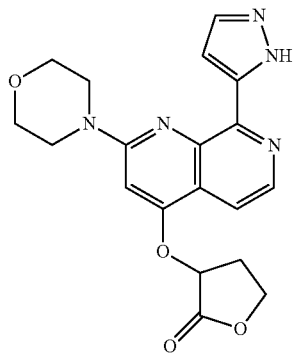 [SMILES: O=C1OCCC1Oc1cc(N2CCOCC2)nc2c(-c3ccn[nH]3)nccc12]

A mixture of 2-(morpholin-4-yl)-8-[1-(tetrahydro-2H-pyran-2-yl)-1H-pyrazol-5-yl]-1,7-naphthyridin-4-ol (242 mg, 0.40 mmol), 3-bromodihydrofuran-2(3H)-one (99 mg, 0.60 mmol) and Caesiumcarbonate (169 mg, 0.52 mmol) in DMF (2 ml) was heated in a sealed tube in the microwave at 100° C. for one hour. The reaction mixture was allowed to cool to ambient temperature, a solution of concentrated aqueous HCl (0.49 ml) was added and the reaction was stirred at this temperature for two hours. The solvent was evaporated under reduced pressure, the residue was taken up in dichloromethane (10 ml) and water (10 ml). The layers were separated and the aqueous layer was extracted with dichloromethane (2×10 ml). The combined organic layers were dried over $Na_2SO_4$ and the solvent was removed under reduced pressure. The crude product was purified by HPLC chromatography (acidic conditions). The title compound was obtained in 4% yield (7 mg). $^1$H-NMR (400 MHz, DMSO): δ[ppm]=2.91-2.95 (1H), 3.67-3.80 (9H), 4.36 (1H), 4.55 (1H), 5.80 (1H), 7.08 (1H), 7.36 (1H), 7.61 (1H), 7.70 (1H), 8.34 (1H), 13.33 (1H).

Example 48

4-[(3-methyl-1,2-oxazol-5-yl)methoxy]-2-(morpholin-4-yl)-8-(1H-pyrazol-5-yl)-1,7-naphthyridine

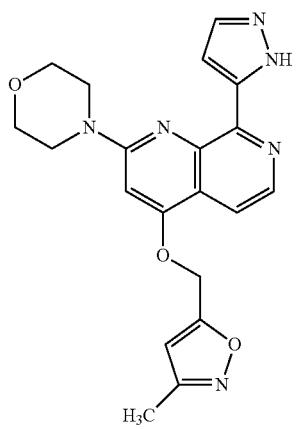 [SMILES: Cc1cc(COc2cc(N3CCOCC3)nc3c(-c4ccn[nH]4)nccc23)on1]

A mixture of 2-(morpholin-4-yl)-8-[1-(tetrahydro-2H-pyran-2-yl)-1H-pyrazol-5-yl]-1,7-naphthyridin-4-ol (283 mg, 0.47 mmol), 5-(bromomethyl)-3-methyl-1,2-oxazole (123 mg, 0.70 mmol) and Caesiumcarbonate (197 mg, 0.61 mmol) in DMF (1.78 ml) was heated in a sealed tube in the microwave at 100° C. for one hour. The reaction mixture was allowed to cool to ambient temperature, a solution of concentrated aqueous HCl (0.7 ml) was added and the reaction was stirred at this temperature for two hours. The solvent was evaporated under reduced pressure, the residue was taken up in dichloromethane (10 ml) and water (10 ml). The layers were separated and the aqueous layer was extracted with dichloromethane (2×10 ml). The combined organic layers were dried over $Na_2SO_4$ and the solvent was removed under reduced pressure. The crude product was purified by HPLC chromatography (acidic conditions). The title compound was obtained in 3% yield (6 mg). $^1$H-NMR (400 MHz, DMSO): δ[ppm]=2.27 (3H), 3.76 (8H), 5.57 (2H), 6.65 (1H), 7.06 (1H), 7.36 (1H), 7.61 (1H), 7.69 (1H), 8.32 (1H), 13.35 (1H).

Example 49

4-[(5-methyl-1,2-oxazol-3-yl)methoxy]-2-(morpholin-4-yl)-8-(1H-pyrazol-5-yl)-1,7-naphthyridine

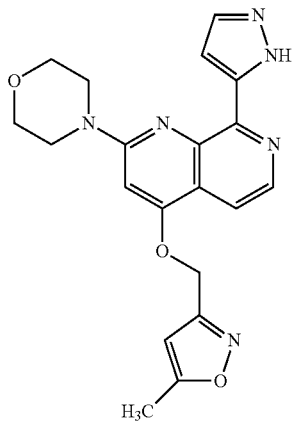 [SMILES: Cc1cc(COc2cc(N3CCOCC3)nc3c(-c4ccn[nH]4)nccc23)no1]

A mixture of 2-(morpholin-4-yl)-8-[1-(tetrahydro-2H-pyran-2-yl)-1H-pyrazol-5-yl]-1,7-naphthyridin-4-ol (264 mg, 0.35 mmol), 3-(bromomethyl)-5-methyl-1,2-oxazole (91 mg, 0.51 mmol) and Caesiumcarbonate (147 mg, 0.45 mmol) in DMF (1.32 ml) was heated in a sealed tube in the microwave at 100° C. for one hour. The reaction mixture was allowed to cool to ambient temperature, a solution of concentrated aqueous HCl (0.51 ml) was added and the reaction was stirred at this temperature for two hours. The solvent was evaporated under reduced pressure, the residue was taken up in dichloromethane (10 ml) and water (10 ml). The layers were separated and the aqueous layer was extracted with dichloromethane (2×10 ml). The combined organic layers were dried over $Na_2SO_4$ and the solvent was removed under reduced pressure. The crude product was purified by HPLC chromatography (acidic conditions). The title compound was obtained in 10 mg yield. $^1$H-NMR (400 MHz, DMSO): δ[ppm]=2.46 (3H), 3.77 (8H), 5.49 (2H), 6.52 (1H), 7.09 (1H), 7.39 (1H), 7.62 (1H), 7.72 (1H), 8.34 (1H), 13.38 (1H).

Example 50

4-benzyloxy-2-(morpholin-4-yl)-8-(1H-pyrazol-3-yl)-[1,7]naphthyridine

Step a 4-benzyloxy-2-(morpholin-4-yl)-8-[2-(tetrahydropyran-2-yl)-2H-pyrazol-3-yl]-[1,7]naphthyridine

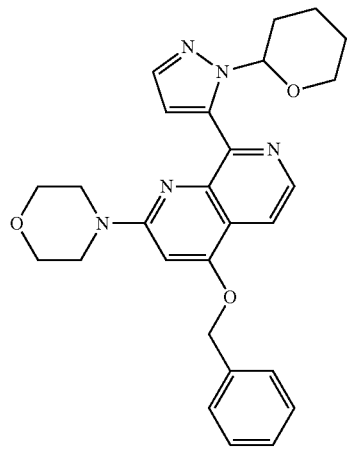 [SMILES: c1ccc(COc2cc(N3CCOCC3)nc3c(-c4ccnn4C4CCCCO4)nccc23)cc1]

44 mg (0.31 mmol) of potassium carbonate were added to a solution of 100 mg (0.26 mmol) of 2-(morpholin-4-yl)-8-[2-(tetrahydropyran-2-yl)-2H-pyrazol-3-yl]-[1,7]naphthyridin-4-ol, 31 µl (0.26 mmol) of benzyl bromide and 4 mg (0.024 mmol) of potassium iodide in 6 ml of dry acetonitrile (MeCN). The suspension was stirred at 85° C. for 2 h. The course of the reaction was monitored by LCMS. The solvent was removed and the residue that remained was chromatographed [silica gel 60 (12 g, 30 µm); ethyl acetate (100 ml)]. This gave 90 mg (73% of theory) of 4-benzyloxy-2-(morpholin-4-yl)-8-[2-(tetrahydropyran-2-yl)-2H-pyrazol-3-yl]-[1,7]naphthyridine as a yellow oil. LC-MS (method 1): m/z: [M+H]$^+$=472.3, R$_t$=3.86 min.

Step b 4-benzyloxy-2-(morpholin-4-yl)-8-(1H-pyrazol-3-yl)-[1,7]naphthyridine

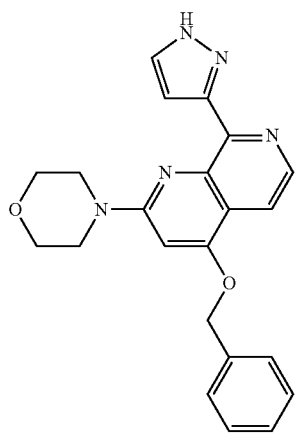 [SMILES: c1ccc(COc2cc(N3CCOCC3)nc3c(-c4cc[nH]n4)nccc23)cc1]

A drop of water and 1 ml (13 mmol) of trifluoroacetic acid were added to 90 mg (0.19 mmol) of 4-benzyloxy-2-(morpholin-4-yl)-8-[2-(tetrahydropyran-2-yl)-2H-pyrazol-3-yl]-[1,7]naphthyridine. After 10 min, LCMS showed complete removal of the protective group. The trifluoroacetic acid was removed under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of methanol were added to the residue. The resulting precipitated solid was filtered off and then dried. This gave 40 mg (54% of theory) of 4-benzyloxy-2-(morpholin-4-yl)-8-(1H-pyrazol-3-yl)-[1,7]naphthyridine as a yellow solid. m.p. 217-219° C. $^1$H NMR (400 MHz, CDCl$_3$, δ ppm): 3.69-3.71 (t, 4H), 3.92-3.94 (t, 4H), 5.29 (s, 2H), 6.52 (s, 1H), 7.41-7.51 (m, 6H), 7.70 (d, 1H), 7.79 (d, 1H), 8.42 (d, 1H). LC-MS (method 1): m/z: [M+H]$^+$=388.3, R$_t$=3.23 min.

Example 51

4-Isopropoxy-2-((R)-3-methylmorpholin-4-yl)-8-(1H-pyrazol-3-yl)-[1,7]naphthyridine

Step a

4-Isopropoxy-2-((R)-3-methylmorpholin-4-yl)-8-[2-(tetrahydropyran-2-yl)-2H-pyrazol-3-yl]-[1,7]naphthyridine

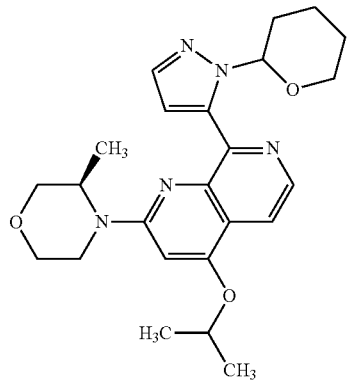 [SMILES: CC(C)Oc1cc(N2CCOC[C@H]2C)nc2c(-c3ccnn3C3CCCCO3)nccc12]

84 mg (0.61 mmol) of potassium carbonate were added to a solution of 200 mg (0.51 mmol) of 2-[(R)-3-methylmorpholin-4-yl]-8-[2-(tetrahydropyran-2-yl)-2H-pyrazol-3-yl]-[1,7]naphthyridin-4-ol and 101 µl (1.01 mmol) of iodopropane in 4 ml of dry acetonitrile. The suspension was stirred at 85° C. for 3 h. The course of the reaction was monitored by LCMS. The solvent was removed and the residue that remained was chromatographed [silica gel 60 (25 g 30 µm); ethyl acetate (100 ml)]. This gave 60 mg (27% of theory) of 4-isopropoxy-2-((R)-3-methylmorpholin-4-yl)-8-[2-(tetrahydropyran-2-yl)-2H-pyrazol-3-yl]-[1,7]naphthyridine as a yellow oil. LCMS (method 1): m/z: [M+H]$^+$=438.4, R$_t$=3.73 min.

Step b

4-Isopropoxy-2-((R)-3-methylmorpholin-4-yl)-8-(1H-pyrazol-3-yl)-[1,7]naphthyridine

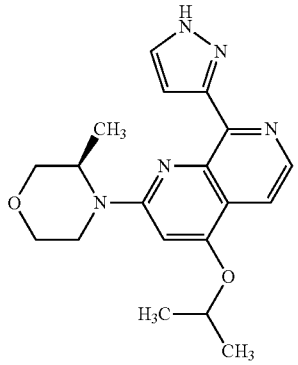 [SMILES: CC(C)Oc1cc(N2CCOC[C@H]2C)nc2c(-c3cc[nH]n3)nccc12]

80 mg (0.18 mmol) of 4-isopropoxy-2-((R)-3-methylmorpholin-4-yl)-8-[2-(tetrahydropyran-2-yl)-2H-pyrazol-3-yl]-[1,7]naphthyridine were dissolved in 2 ml of methanol, and 2 ml (4 mmol) of 2N hydrochloric acid were added. After 1 h, LCMS showed complete removal of the protective group. Ethanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (25 g, 30 μm); ethyl acetate (100 ml)]. This gave 45 mg (70% of theory) of 4-isopropoxy-2-((R)-3-methylmorpholin-4-yl)-8-(1H-pyrazol-3-yl)-[1,7]naphthyridine as a yellow solid. m.p. 75-77° C. $^1$H NMR (400 MHz, CDCl$_3$): δ[ppm]=1.38-1.41 (3H), 1.47-1.49 (6H), 3.44-3.51 (1H), 3.65-3.72 (1H), 3.81-3.91 (3H), 4.01-4.15 (1H), 4.30-4.33 (1H), 4.74-4.79 (1H), 6.37 (1H), 7.22 (1H), 7.67-7.68 (1H), 7.70-7.72 (1H), 8.36-8.37 (1H). LC-MS (method 1): m/z: [M+H]$^+$=354.4, R$_t$=2.92 min.

Example 52 tert-butyl [4-({2-[(3R)-3-methylmorpholin-4-yl]-8-(1H-pyrazol-5-yl)-1,7-naphthyridin-4-yl}oxy)butyl]carbamate

Step a tert-butyl [4-({2-[(3R)-3-methylmorpholin-4-yl]-8-[(1-(tetrahydro-2H-pyran-2-yl)-1H-pyrazol-5-yl]-1,7-naphthyridin-4-yl}oxy)butyl]carbamate

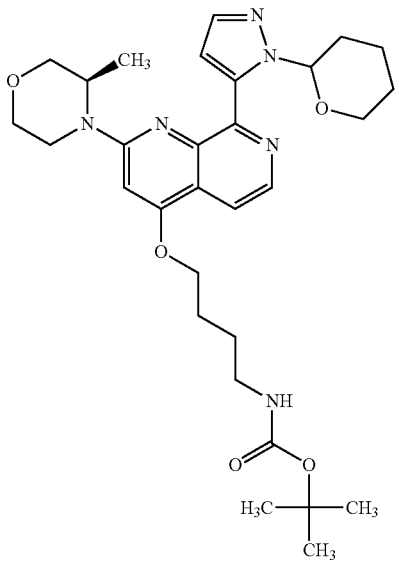 [SMILES: C[C@@H]1COCCN1c1cc(OCCCCNC(=O)OC(C)(C)C)c2ccnc(-c3ccnn3C3CCCCO3)c2n1]

2-[(3R)-3-methylmorpholin-4-yl]-8-[1-(tetra hydro-2H-pyran-2-yl)-1H-pyrazol-5-yl]-1,7-naphthyridin-4-ol (0.41, 1.0 mmol, 1 eq.) was solubilized in DMF (12 mL). 4-(Boc-amino)butyl bromide (0.53 g, 2.1 mmol, 2 eq.) and K$_2$CO$_3$ (0.72 g 5.2 mmol, 5 eq.) were added to the mixture. The reaction was stirred at rt for 16 hours. The suspension was diluted with EtOAc and filtered. The organic phase was concentrated under reduced pressure and the crude material purified by flash chromatography (gradient Hex/EtOAc 9/1 to 100% EtOAc). The desired product was obtained in 87% yield (0.52 g). $^1$H-NMR (400 MHz, DMSO-d$_6$): δ[ppm]: 1.14-1.24 (3H), 1.38 (9H), 1.41-1.69 (5H), 1.80-1.90 (2H), 1.99 (2H), 2.30-2.42 (1H), 3.03 (2H), 3.10-3.29 (2H), 3.40-3.52 (1H), 3.73 (3H), 3.91-3.99 (1H), 4.12 (1H), 4.27 (2H), 4.45-4.58 (1H), 6.01-6.13 (1H), 6.75 (1H), 6.84-6.95 (2H), 7.60 (1H), 7.75 (1H), 8.35 (1H). LC-MS (Method 3): m/z: [M+H]$^+$=567, R$_t$=1.31 min.

Step b tert-butyl [4-({2-[(3R)-3-methylmorpholin-4-yl]-8-(1H-pyrazol-5-yl)-1,7-naphthyridin-4-yl}oxy)butyl] carbamate

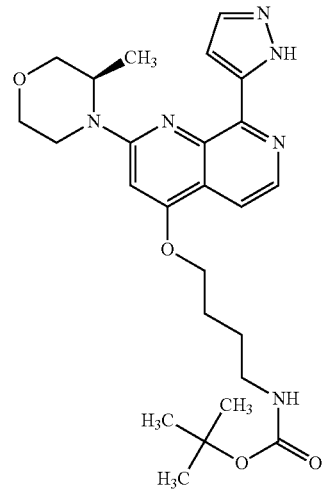 [SMILES: C[C@@H]1COCCN1c1cc(OCCCCNC(=O)OC(C)(C)C)c2ccnc(-c3ccn[nH]3)c2n1]

Tert-butyl [4-({2-[(3R)-3-methylmorpholin-4-yl]-8-[1-(tetrahydro-2H-pyran-2-yl)-1H-pyrazol-5-yl]-1,7-naphthyridin-4-yl}oxy)butyl]carbamate (20 mg, 0.035 mmol, 1 eq.) was solubilized in CH$_2$Cl$_2$ (0.5 mL) and water (0.5 mL). Acetic acid (0.12 mL, 1.8 mmol, 50 eq.) was added. After 2 hours, formic acid (0.10 mL, 2.6 mmol, 75 eq.) was added and the reaction was stirred at rt for 1 hour. The reaction mixture was neutralised by addition of sat. NaHCO$_3$ and the aqueous phase was extracted 3 times with CH$_2$Cl$_2$. The organic phase was dried (silicon filter) and concentrated under reduced pressure. The crude mixture was purified by flash column chromatography (gradient 1/1Hex/EtOAc to 100% EtOAc to 9/1 EtOAc/MeOH). The desired product was obtained in 68% yield (12 mg). $^1$H-NMR (400 MHz, DMSO-d$_6$): δ[ppm]: 1.20-1.30 (4H), 1.37 (9H), 1.57-1.67 (2H), 1.80-1.89 (2H), 3.03 (2H), 3.56 (1H), 3.71 (1H), 3.83 (1H), 4.05 (1H), 4.15 (1H), 4.27 (2H), 4.56-4.65 (1H), 6.81 (1H), 6.89 (1H), 7.37 (1H), 7.60 (1H), 7.71 (1H), 8.32 (1H), 13.37 (1H). LC-MS (Method 3): m/z: [M+H]$^+$=483, R$_t$=0.98 min.

Example 53

4-methoxy-2-((R)-3-methylmorpholin-4-yl)-8-(1H-pyrazol-3-yl)-[1,7]naphthyridine Step a 8-chloro-4-methoxy-2-((R)-3-methylmorpholin-4-yl)-[1,7]naphthyridine

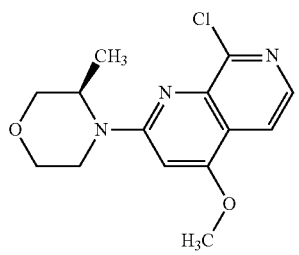 [SMILES: COc1cc(N2CCOC[C@H]2C)nc2c(Cl)nccc12]

320 mg (2.32 mmol) of potassium carbonate were added to a solution of 540 mg (1.93 mmol) of 8-chloro-2-((R)-3-methylmorpholin-4-yl)-[1,7]naphthyridin-4-ol and 144 µl (2.32 mmol) of iodomethane in 10 ml of acetonitrile. The suspension was stirred at 80° C. for 5 h. For work-up, 20 ml of water were added to the mixture. The aqueous phase was extracted three times with in each case 30 ml of dichloromethane. The combined organic phases were dried over sodium sulphate and then concentrated to dryness. The crude product was separated by column chromatography [PuriFlash, silica gel 60 (25 g, 30 µm); ethyl acetate (200 ml)]. This gave 270 mg (48%) of 8-chloro-4-methoxy-2-((R)-3-methylmorpholin-4-yl)-[1,7]naphthyridine as a yellow oil. LCMS (method 1): m/z: [M+H]$^+$=294.3, R$_t$=3.43 min.

Step b 4-methoxy-2-((R)-3-methylmorpholin-4-yl)-8-[2-(tetrahydropyran-2-yl)-2H-pyrazol-3-yl]-[1,7]naphthyridine

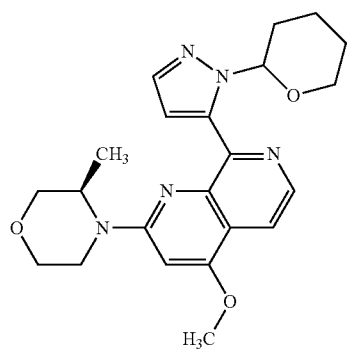 [SMILES: COc1cc(N2CCOC[C@H]2C)nc2c(-c3ccnn3C3CCCCO3)nccc12]

Under argon, 145 mg (0.18 mmol) of [1,1'-bis(diphenylphosphino)ferrocene]dichloropalladium(II) complex with dichloromethane (1:1) and 1.15 g (3.54 mmol) of caesium carbonate were added to a suspension of 260 mg (0.89 mmol) of 8-chloro-4-methoxy-2-((R)-3-methylmorpholin-4-yl)-[1,7]naphthyridine and 369 mg (1.33 mmol) of 1-(tetrahydropyran-2-yl)-5-(4,4,5,5-tetramethyl-[1,3,2]dioxaborolane-2-yl)-1H-pyrazole in 12 ml of absolute 1,4-dioxane. The reaction mixture was stirred at 95° C. for 6 h. The brown reaction solution was purified via column chromatography [silica gel 60 (30 g); ethyl acetate (200 ml)]. In this manner, 360 mg (99% of theory) of 4-methoxy-2-((R)-3-methylmorpholin-4-yl)-8-[2-(tetrahydropyran-2-yl)-2H-pyrazol-3-yl]-[1,7]naphthyridine were isolated as a yellow solid. LCMS (method 1): m/z: [M+H]$^+$=410.3, R$_t$=3.46 min.

Step c 4-methoxy-2-((R)-3-methylmorpholin-4-yl)-8-(1H-pyrazol-3-yl)-[1,7]naphthyridine

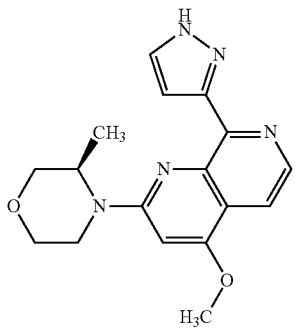 [SMILES: COc1cc(N2CCOC[C@H]2C)nc2c(-c3cc[nH]n3)nccc12]

360 mg (0.88 mmol) of 4-isopropoxy-2-((R)-3-methylmorpholin-4-yl)-8-[2-(tetrahydropyran-2-yl)-2H-pyrazol-3-yl]-[1,7]naphthyridine were dissolved in 10 ml of methanol, and 2 ml (4 mmol) of 2N hydrochloric acid were added. After 1 h, LCMS showed complete removal of the protective group. The methanol was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. 5 ml of ethyl acetate were added to the residue. The resulting precipitated solid was filtered off and dried. This gave 120 mg (42% of theory) of 4-methoxy-2-((R)-3-methylmorpholin-4-yl)-8-(1H-pyrazol-3-yl)-[1,7]naphthyridine and 100 mg (35% of theory) of slightly contaminated product as a beige solid. m.p. 193-195° C. $^1$H NMR (400 MHz, DMSO): δ[ppm]=1.27-1.29 (3H), 3.31-3.32 (1H), 3.56-3.57 (1H), 3.70-3.73 (1H), 3.82-3.85 (1H), 3.85-4.06 (1H), 4.04 (3H), 4.15-4.17 (1H), 4.61-4.63 (1H), 6.82 (1H), 7.37 (1H), 7.61 (1H), 7.70-7.71 (1H), 8.32-8.33 (1H), 13.36 (1H).

Example 54 tert-butyl [3-({2-[(3R)-3-methylmorpholin-4-yl]-8-(1H-pyrazol-5-yl)-1,7-naphthyridin-4-yl}oxy)propyl]carbamate

Step a tert-butyl [3-({2-[(3R)-3-methylmorpholin-4-yl]-8-[1-(tetrahydro-2H-pyran-2-yl)-1H-pyrazol-5-yl]-1,7-naphthyridin-4-yl}oxy)propyl]carbamate

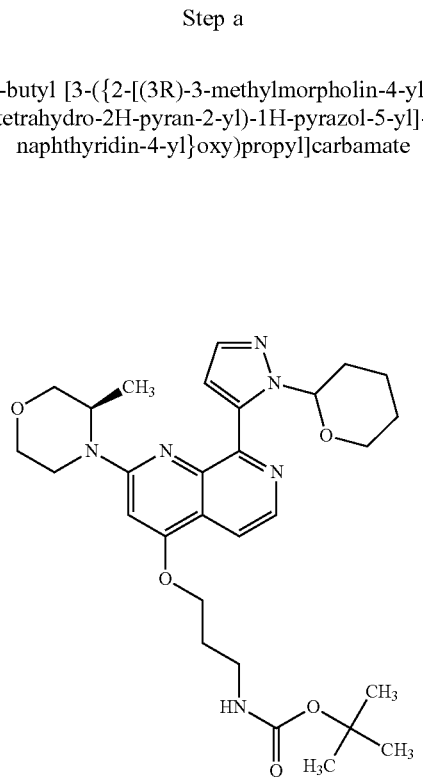

2-[(3R)-3-Methylmorpholin-4-yl]-8-[1-(tetrahydro-2H-pyran-2-yl)-1H-pyrazol-5-yl]-1,7-naphthyridin-4-ol (0.37 g, 0.93 mmol, 1 eq.) was solubilized in DMF (6 mL). N-Boc-3-chloropropylamine (0.36 g,& 1.9 mmol, 2 eq.) and $K_2CO_3$ (0.64 g 4.7 mmol, 5 eq.) were added to the mixture. The reaction was stirred at 120° C. for 16 hours. After cooling to rt, the mixture was filtered, the solid was washed with $CH_2Cl_2$ and the filtrate was concentrated under reduced pressure. The crude material was purified by flash chromatography (gradient 100% Hexane to 100% EtOAc). The desired product was obtained in 70% yield (0.36 g). $^1$H-NMR (400 MHz, DMSO-$d_6$): δ[ppm]: 1.13-1.23 (3H), 1.36 (9H), 1.40-1.64 (3H), 1.89-2.04 (4H), 2.30-2.41 (1H), 3.10-3.29 (4H), 3.40-3.51 (1H), 3.57-3.79 (3H), 3.92-3.99 (1H), 4.07-4.17 (1H), 4.27 (2H), 4.45-4.58 (1H), 6.01-6.13 (1H), 6.71-6.77 (1H), 6.88-6.98 (2H), 7.60 (1H), 7.77 (1H), 8.36 (1H). LC-MS (Method 3): m/z: [M+H]$^+$=553 R$_t$=1.23 min.

Step b tert-butyl [3-({2-[(3R)-3-methylmorpholin-4-yl]-8-(1H-pyrazol-5-yl)-1,7-naphthyridin-4-yl}oxy)propyl]carbamate

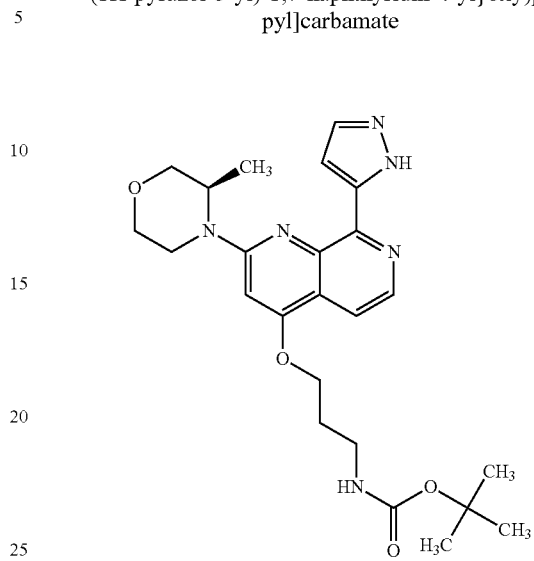

Tert-butyl [3-({2-[(3R)-3-methylmorpholin-4-yl]-8-[1-(tetrahydro-2H-pyran-2-yl)-1H-pyrazol-5-yl]-1,7-naphthyridin-4-yl}oxy)propyl]carbamate (20 mg, 0.036 mmol, 1 eq.) was solubilized in $CH_2Cl_2$ (0.5 mL) and water (0.5 mL). Formic acid (0.10 mL, 2.7 mmol, 75 eq.) was added and the reaction was stirred at rt for 1 hour. The reaction mixture was neutralised by addition of sat. $NaHCO_3$ and the aqueous phase was extracted 3 times with $CH_2Cl_2$. The organic phase was dried (silicon filter) and concentrated under reduced pressure. The desired product was obtained without further purification in 86% yield (15 mg). $^1$H-NMR (400 MHz, DMSO-$d_6$): δ[ppm]: 1.26 (3H), 1.36 (9H), 1.93-2.02 (2H), 3.18 (2H), 3.25-3.30 (1H), 3.55 (1H), 3.70 (1H), 3.82 (1H), 4.05 (1H), 4.15 (1H), 4.27 (2H), 4.55-4.63 (1H), 6.80 (1H), 6.95 (1H), 7.37 (1H), 7.61 (1H), 7.73 (1H), 8.33 (1H), 13.37 (1H). LC-MS (Method 3): m/z: [M+H]$^+$=469, R$_t$=0.96 min.

Example 55

2-({2-[(3R)-3-methylmorpholin-4-yl]-8-(1H-pyrazol-5-yl)-1,7-naphthyridin-4-yl}oxy)ethanamine

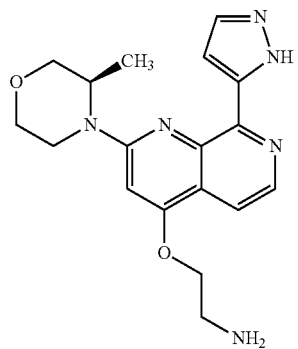 [SMILES: C[C@@H]1COCCN1c1cc(OCCN)c2ccnc(-c3ccn[nH]3)c2n1]

Tert-butyl [2-({2-[(3R)-3-methylmorpholin-4-yl]-8-[1-(tetrahydro-2H-pyran-2-yl)-1H-pyrazol-5-yl]-1,7-naphthyridin-4-yl}oxy)ethyl]carbamate (0.36 g, 0.67 mmol, 1 eq.) was solubilised in CH$_2$Cl$_2$ (4.3 mL) and trifluoroacetic acid (2.6 mL, 33 mmol, 50 eq.) was added. The reaction was stirred for 16 h at rt and quenched with sat NaHCO$_3$. The aqueous phase was extracted 3 times with EtOAc and the organic phase was washed with H$_2$O and sat. NaCl. The organic phase was dried (silicon filter) and concentrated under reduced pressure. The crude material was purified by flash column chromatography (gradient hex/EtOAc:7/3 to 100% EtOAc to EtOAc/EtOH:9/1). The combined fractions were concentrated and EtOH was added. The suspension was filtered and the solid was dried under reduced pressure. The desired product was obtained in 11% yield (26 mg). $^1$H-NMR (400 MHz, DMSO-d$_6$): δ[ppm]: 1.26 (3H), 3.24-3.31 (1H), 3.55 (1H), 3.67-3.78 (3H), 3.83 (1H), 4.05 (1H), 4.17 (1H), 4.32-4.41 (3H), 4.57-4.67 (1H), 6.85 (1H), 7.37 (1H), 7.60 (1H), 7.75 (1H), 8.33 (1H), 9.77 (1H), 13.37 (1H).

Example 56 tert-butyl [2-({2-[(3R)-3-methylmorpholin-4-yl]-8-(1H-pyrazol-5-yl)-1,7-naphthyridin-4-yl}oxy)ethyl]carbamate Step a tert-butyl [2-({2-[(3R)-3-methylmorpholin-4-yl]-8-[1-(tetrahydro-2H-pyran-2-yl)-1H-pyrazol-5-yl]-1,7-naphthyridin-4-yl}oxy)ethyl]carbamate

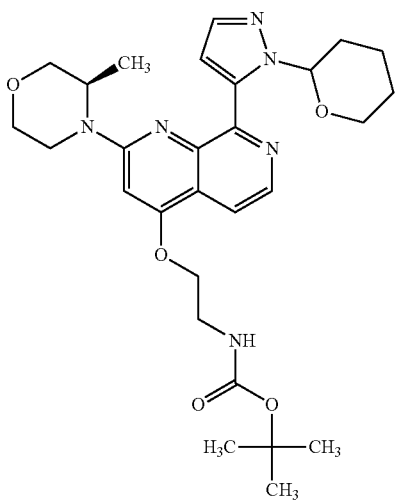 [SMILES: C[C@@H]1COCCN1c1cc(OCCNC(=O)OC(C)(C)C)c2ccnc(-c3ccnn3C3CCCCO3)c2n1]

2-[(3R)-3-Methylmorpholin-4-yl]-8-[1-(tetrahydro-2H-pyran-2-yl)-1H-pyrazol-5-yl]-1,7-naphthyridin-4-ol (0.40 g, 1.0 mmol, 1 eq.) was solubilised in DMF (10 mL). K$_2$CO$_3$ (0.70 g, 5.0 mmol, 2 eq.) and tert-butyl (2-bromoethyl)carbamate (0.45 g, 2.0 mmol, 2 eq.) were sequentially added. The reaction was stirred for 16 hours at rt. The reaction was then diluted with EtOAc and the suspension was filtered. The filtrate was concentrated under reduced pressure and purified ny flash column chromatography (gradient Hex/EtOAc: 8/2 to hex/EtOAc 1/9). The desired product was obtained in 84% yield (0.46 g). $^1$H-NMR (400 MHz, DMSO-d$_6$): δ[ppm]: 1.19 (3H), 1.32-1.49 (11H), 1.49-1.64 (1H), 1.89-2.04 (2H), 2.30-2.40 (1H), 3.10-3.30 (2H), 3.40-3.51 (3H), 3.73 (3H), 3.90-3.99 (1H), 4.09-4.18 (1H), 4.19-4.23 (2H), 4.47-4.59 (1H), 6.01-6.13 (1H), 6.78 (1H), 6.92 (1H), 7.21 (1H), 7.60 (1H), 7.88 (1H), 8.34 (1H). LC-MS (Method 3): m/z: [M+H]$^+$=539, R$_t$=1.23 min.

Step b tert-butyl [2-({2-[(3R)-3-methylmorpholin-4-yl]-8-(1H-pyrazol-5-yl)-1,7-naphthyridin-4-yl}oxy)ethyl]carbamate

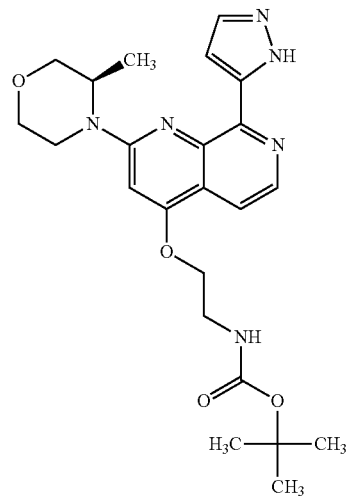 [SMILES: C[C@@H]1COCCN1c1cc(OCCNC(=O)OC(C)(C)C)c2ccnc(-c3ccn[nH]3)c2n1]

Tert-butyl [2-({2-[(3R)-3-methylmorpholin-4-yl]-8-[1-(tetrahydro-2H-pyran-2-yl)-1H-pyrazol-5-yl]-1,7-naphthyridin-4-yl}oxy)ethyl]carbamate (0.10 g, 0.19 mmol, 1 eq.) was solubilised in CH$_2$Cl$_2$ (1.2 mL) and trifluoroacetic acid (0.29 mL, 3.7 mmol, 20 eq.) was added. The reaction was stirred for 1 h at rt and quenched with sat NaHCO$_3$. The suspension was filtered and the solid was purified by flash column chromatography (gradient from hex/EtOAc: 1/1 to 100% EtOAc to 100% EtOH). The desired product was obtained in 28% yield (24 mg). $^1$H-NMR (400 MHz, DMSO-d$_6$): δ[ppm]: 1.26 (3H), 1.39 (9H), 3.24-3.30 (1H), 3.46 (2H), 3.52-3.62 (1H), 3.70 (1H), 3.82 (1H), 3.99-4.09 (1H), 4.17 (1H), 4.22 (2H), 4.61 (1H), 6.84 (1H), 7.21 (1H), 7.37 (1H), 7.60 (1H), 7.83 (1H), 8.31 (1H), 13.36 (1H).

Example 57

4-({2-[(3R)-3-methylmorpholin-4-yl]-8-(1H-pyrazol-5-yl)-1,7-naphthyridin-4-yl}oxy)butan-1-amine

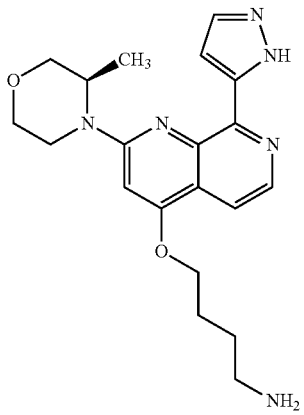 [SMILES: C[C@@H]1COCCN1c1cc(OCCCCN)c2ccnc(-c3ccn[nH]3)c2n1]

Tert-butyl [4-({2-[(3R)-3-methylmorpholin-4-yl]-8-[1-(tetrahydro-2H-pyran-2-yl)-1H-pyrazol-5-yl]-1,7-naphthyridin-4-yl}oxy)butyl]carbamate (0.10 g, 0.18 mmol, 1 eq.) was solubilised in CH$_2$Cl$_2$ (1.1 mL) and TFA (0.27 mL, 3.5 mmol, 20 eq.) was added. The reaction was stirred at rt for 30 min and quenched with sat. NaHCO$_3$. The suspension was filtered and the solid was dried under reduced pressure. The desired product was obtained without further purification in quantitative yield. $^1$H-NMR (400 MHz, DMSO-d$_6$): δ[ppm]: $^1$H-NMR (400 MHz, DMSO-d$_6$): δ[ppm]: 1.27 (3H), 1.73-1.84 (2H), 1.88-1.98 (2H), 2.86-2.95 (2H), 3.56 (1H), 3.71 (1H), 3.84 (1H), 4.02-4.10 (1H), 4.15 (1H), 4.30 (2H), 4.61 (1H), 6.82 (1H), 7.37 (1H), 7.57 (1H), 7.61 (2H), 7.71 (1H), 8.33 (1H), 13.36 (1H).

Example 58

2-[(3R,5S)-3,5-dimethylmorpholin-4-yl]-4-Isopropoxy-8-(1H-pyrazol-5-yl)-1,7-naphthyridine

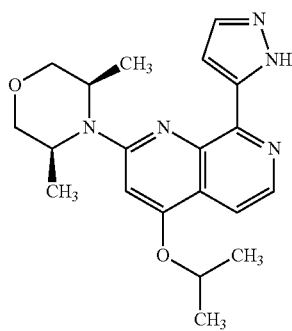 [SMILES: CC(C)Oc1cc(N2[C@H](C)COC[C@@H]2C)nc2c(-c3ccn[nH]3)nccc12]

8-Chloro-2-[(3R,5S)-3,5-dimethylmorpholin-4-yl]-4-isopropoxy-1,7-naphthyridine (0.10 g, 0.28 mmol, 1 eq.) was solubilised in DME (3 mL). 1-(2-Tetrahydropyranyl)-1H-pyrazole-5-boronic acid pinacol ester (0.24 g, 0.84 mmol, 3 eq.), K$_2$CO$_3$ (0.11 & 0.84 mmol, 3 eq.), bis(triphenylphosphin)palladium(II)chloride (20 mg, 0.030 mmol, 0.1 eq.) and H$_2$O (1.5 mL) were added sequentially. The reaction was heated under microwave irradiation at 130° C. for 10 min. The crude reaction mixture was filtered through a silicon filter and concentrated under reduced pressure. The crude mixture was purified by preparative HPLC (H$_2$O (HCOOH)/CH$_3$CN: 50:50 to 30:70). The purified product was concentrated under reduced pressure, solubilised in CH$_2$Cl$_2$ and washed two times with sat. NaHCO$_3$. The organic phase was dried (MgSO$_4$) and concentrated under reduced pressure. The desired product was obtained as a solid in 54% yield (56 mg). $^1$H-NMR (400 MHz, DMSO-d$_6$): δ[ppm]: 1.37 (6H), 1.41 (6H), 3.69 (2H), 3.88 (2H), 4.50 (2H), 5.07 (1H), 6.70 (1H), 7.36 (1H), 7.60 (1H), 7.69 (1H), 8.29 (1H), 13.38 (1H).

Example 59

2-[(3R,5R)-3,5-dimethylmorpholin-4-yl]-4-Isopropoxy-8-(1H-pyrazol-5-yl)-1,7-naphthyridine

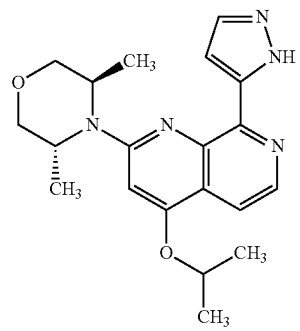 [SMILES: CC(C)Oc1cc(N2[C@H](C)COC[C@H]2C)nc2c(-c3ccn[nH]3)nccc12]

8-Chloro-2-[(3R,5R)-3,5-dimethylmorpholin-4-yl]-4-isopropoxy-1,7-naphthyridine (40 mg, 0.12 mmol, 1 eq.), 1-(2-tetrahydropyranyl)-1H-pyrazole-5-boronic acid pinacol ester (50 mg, 0.18 mmol, 1.5 eq.), K$_2$CO$_3$ (2 M in H$_2$O, 0.18 mL, 0.36 mmol, 3 eq.) and bis(triphenylphosphin)palladium (II)chloride (8.5 mg, 0.011 mmol, 0.1 eq.) were added sequentially to DME (1.1 mL). The reaction was heated under microwave irradiation at 130° C. for 10 min. The reaction mixture was filtered through a silicon filter and concentrated under reduced pressure. The crude mixture was purified by preparative HPLC (H$_2$O(HCOOH)/CH$_3$CN: 48:52 to 68:32). The desired product was obtained in 20% yield (9.8 mg). $^1$H-NMR (400 MHz, DMSO-d$_6$): δ[ppm]: 1.26 (6H), 1.41 (6H), 3.67 (2H), 4.11 (2H), 4.22-4.31 (2H), 4.99-5.09 (1H), 6.83 (1H), 7.44 (1H), 7.61 (1H), 7.73 (1H), 8.36 (1H), 13.28-13.56 (1H).

Example 60

2-(morpholin-4-yl)-8-(1H-pyrazol-5-yl)-4-(tetrahydro-2H-pyran-4-yl)-1,7-naphthyridine

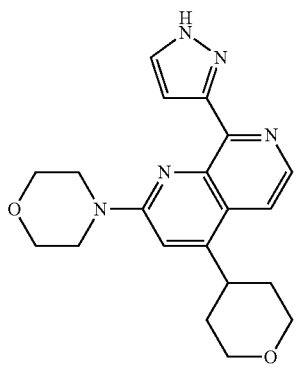 [SMILES: c1cc2c(C3CCOCC3)cc(N3CCOCC3)nc2c(-c2cc[nH]n2)n1]

75 mg (0.20 mmol) of 4-(3,6-dihydro-2H-pyran-4-yl)-2-(morpholin-4-yl)-8-(1H-pyrazol-5-yl)-1,7-naphthyridine were dissolved in 50 ml of methanol, 50 mg of palladium/carbon (10 percent) were added and the mixture was hydrogenated at 2 bar at room temperature for 3 h. The reaction solution was then filtered through celite and concentrated under reduced pressure. The residue was triturated with methanol, the solid was filtered off and dried under reduced pressure. This gave 2-(morpholin-4H-pyrazo-4-)-8-(1H-pyrazol-5-yl)-4-(tetrahydro-2H-pyran-4-yl)-1,7-naphthyridine in a yield of 30 mg (40% of theory). m.p. 303-304° C. $^1$H NMR (400 MHz, DMSO-d$_6$): δ[ppm]=1.76 (2H), 1.89 (2H), 3.53 (1H), 3.63 (2H), 3.77 (8H), 4.01 (2H), 7.36 (2H), 7.61 (1H), 7.88 (1H), 8.38 (1H), 13.33 (1H).

Example 61

2-(morpholin-4-yl)-8-(1H-pyrazol-3-yl)-[1,7]naphthyridine Hydrochloride

Step a 2-(morpholin-4-yl)-8-[2-(tetrahydropyran-2-yl)-2H-pyrazol-3-yl]-[1,7]naphthyridine

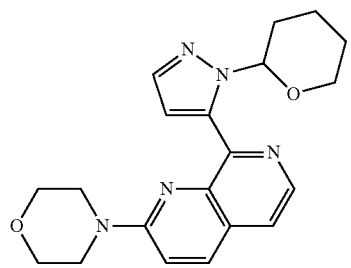 [SMILES: c1cc2ccc(N3CCOCC3)nc2c(-c2ccnn2C2CCCCO2)n1]

Under argon, 40 mg (0.05 mmol) of [1,1'-bis(diphenylphosphino)ferrocene]dichloropalladium(II) complex with dichloromethane (1:1, Pd(dppf)Cl$_2$) and 635 mg (1.95 mmol) of caesium carbonate were added to a suspension of 250 mg (0.49 mmol) of 2-(morpholin-4-yl)-8-[2-(tetrahydropyran-2-yl)-2H-pyrazol-3-yl]-[1,7]naphthyridin-4-yl trifluoromethanesulphonate and 205 mg (0.97 mmol) 3,6-dihydro-2H-pyran-4-boronic acid pinacol ester in 5.0 ml of absolute dioxane. The reaction mixture was stirred at 110° C. for 4 h. The mixture was chromatographed directly without work-up [silica gel 60 (25 g, 30 μm); ethyl acetate (100 ml)]. This gave 30 mg (17% of theory) of 2-(morpholin-4-yl)-8-[2-(tetrahydropyran-2-yl)-2H-pyrazol-3-yl]-[1,7]naphthyridine as a colourless oil. LC-MS (method 1): m/z: [M+H]$^+$=366.3, R$_t$=3.09 min.

Step b 2-(morpholin-4-yl)-8-(1H-pyrazol-3-yl)-[1,7]naphthyridine

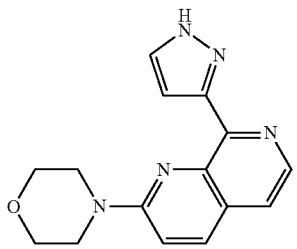 [SMILES: c1cc2ccc(N3CCOCC3)nc2c(-c2cc[nH]n2)n1]

A drop of water and 0.5 ml (6.5 mmol) of trifluoroacetic acid were added to 30 mg (0.08 mmol) of 2-(morpholin-4-yl)-8-[2-(tetrahydropyran-2-yl)-2H-pyrazol-3-yl]-[1,7]naphthyridine. After 1 h, LCMS showed complete removal of the protective group. The trifluoroacetic acid was distilled off under reduced pressure and the residue that remained was adjusted to pH 7 using sodium bicarbonate solution. The aqueous phase was extracted three times with in each case 20 ml of dichloromethane. The combined organic phases were dried over sodium sulphate and then concentrated to dryness. The residue was chromatographed [silica gel 60 (12 g, 30 μm); chloroform (100 ml)]. This gave 20 mg (87% of theory) of 2-(morpholin-4-yl)-8-(1H-pyrazol-3-yl)-[1,7]naphthyridine as a yellow solid. Since the latter was still impure, the corresponding hydrochloride was prepared. LC-MS (method 1): m/z: [M+H]$^+$=282.3, R$_t$=2.42 min.

Step c 2-(morpholin-4-yl)-8-(1H-pyrazol-3-yl)-[1,7]naphthyridine Hydrochloride

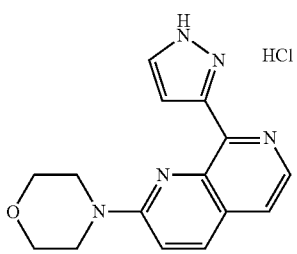 [SMILES: c1cc2ccc(N3CCOCC3)nc2c(-c2cc[nH]n2)n1 ; Cl]

20 mg (0.07 mmol) of 2-(morpholin-4-yl)-8-(1H-pyrazol-3-yl)-[1,7]naphthyridine were dissolved in 3.0 ml of 2-butanol and 28 μl (0.21 mmol) of trimethylchlorosilane were added. The reaction solution was stirred at room temperature for 1 h. The precipitated solid was filtered off and then dried. This gave 17 mg (75% of theory) of 2-(morpholin-4-yl)-8-

(1H-pyrazol-3-yl)-[1,7]naphthyridine hydrochloride as a yellow solid. m.p. 151-153° C. $^1$H NMR (400 MHz, DMSO): δ[ppm]=3.80-3.85 (8H), 7.61-7.62 (1H), 7.89-7.91 (1H), 8.11-8.13 (2H), 8.33-8.34 (1H), 8.41-8.43 (1H).

Example 62

4-chloro-2-morpholin-4-yl-8-(1H-pyrazol-3-yl)-[1,7] naphthyridine

Step a methyl 3-tert-butoxycarbonylamino-2-chloroisonicotinate

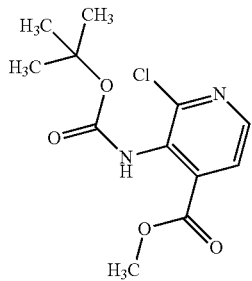 [SMILES: COC(=O)c1ccnc(Cl)c1NC(=O)OC(C)(C)C]

Under argon and at room temperature, 1.92 g (8.7 mmol) of di-tert-butyl dicarbonate and 244 mg (2 mmol) of 4-dimethylaminopyridine were added to a solution of 1.49 g (8 mmol) of methyl 3-amino-2-chloroisonicotinate in 20 ml of dry tetrahydrofuran. The mixture was stirred at room temperature for 16 h. For work-up, the reaction mixture was adjusted to pH 7 using 2N hydrochloric acid. The resulting precipitated solid was filtered off with suction and washed with 10 ml of water. In this manner, methyl 3-tert-butoxycarbonylamino-2-chloroisonicotinate was obtained in a yield of 1.2 g (52% of theory) as a colourless solid. This solid was a mixture of the product and the double Boc protected compound. The mixture was used for the next step without further purification.

Step b 1-(3-amino-2-chloropyridin-4-yl)-3-morpholin-4-yl-propane-1,3-dione

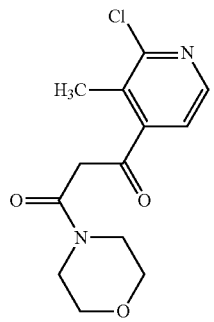 [SMILES: Cc1c(C(=O)CC(=O)N2CCOCC2)ccnc1Cl]

Under argon and at room temperature, 6.76 ml (6.76 mmol) of lithium bis(trimethylsilyl)amide were added dropwise to a solution of 484 μl (4.19 mmol) of N-acetylmorpholine and 1.2 g (4.2 mmol) of methyl 3-tert-butoxycarbonylamino-2-chloroisonicotinate in 10 ml of dry tetrahydrofuran. The mixture was stirred at room temperature for 6 h. For work-up, the reaction mixture was adjusted to pH=1 using 2N hydrochloric acid and stirred at room temperature for 16 h. LC-MS showed complete removal of the protective group. The mixture was extracted three times with in each case 50 ml of dichloromethane. The combined organic phases were dried with sodium sulphate and then concentrated to dryness. In this manner, 1-(3-amino-2-chloropyridin-4-yl)-3-morpholin-4-yl-propane-1,3-dione was obtained in a yield of 680 mg (57% of theory) as a yellow solid. $^1$H NMR (400 MHz, CDCl$_3$): δ[ppm]=3.49-3.52 (2H), 3.64-3.74 (6H), 4.08 (s, 2H), 6.73 (s, 2H), 7.57 (d, 1H), 7.75 (d, 1H).

Step c

1-{3-amino-2-[2-(4-methoxybenzyl)-2H-pyrazol-3-yl]pyridin-4-yl}-3-(morpholin-4-yl)propane-1,3-dione

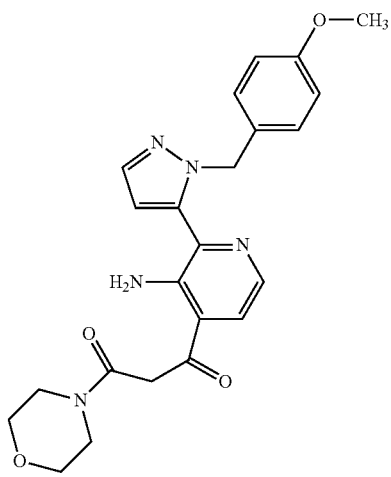 [SMILES: COc1ccc(Cn2nccc2-c2nccc(C(=O)CC(=O)N3CCOCC3)c2N)cc1]

Under argon, 207 mg (0.66 mmol) of 1-(4-methoxybenzyl)-5-(4,4,5,5-tetramethyl-[1,3,2]dioxaborolane-2-yl)-1H-pyrazole, 195 mg (0.6 mmol) of caesium carbonate, 95 mg (0.33 mmol) of 1-(3-amino-2-chloropyridin-4-yl)-3-morpholin-4-ylpropane-1,3-dione and 20 mg (0.02 mmol) of [1,1'-bis(diphenylphosphino)ferrocene]dichloropalladium (II) complex with dichloromethane (1:1) in 2.5 ml of dioxane were stirred in a microwave vessel at 100° C. for 2 h. Without work-up, the residue was purified by column chromatography [Puriflash silica gel 60 (25 g, 30 μm); ethyl acetate/methanol 1:1, (200 ml)]. In this manner, 1-{3-amino-2-[2-(4-methoxybenzyl)-2H-pyrazol-3-yl]pyridin-4-yl}-3-(morpholin-4-yl)propane-1,3-dione was obtained in a yield of 38 mg (26% of theory) as a light-yellow oil. $^1$H NMR (400 MHz, CDCl$_3$): δ[ppm]=3.48-3.51 (2H), 3.64-3.68 (6H), 4.09 (2H), 5.37 (2H), 6.43 (2H), 6.55 (1H), 6.69-6.73 (2H), 6.95-6.97 (2H), 7.58-7.62 (2H), 8.09 (1H).

Step d

4-chloro-2-morpholin-4-yl-8-(1H-pyrazol-3-yl)-[1,7]naphthyridine

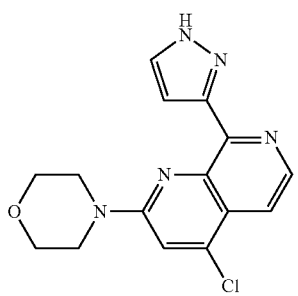 [SMILES: Clc1cc(N2CCOCC2)nc2c(-c3cc[nH]n3)nccc12]

Under argon, 45 mg (0.1 mmol) of 1-{3-amino-2-[2-(4-methoxybenzyl)-2H-pyrazol-3-yl]pyridin-4-yl}-3-(morpholin-4-yl)propane-1,3-dione and 500 µl (5.36 mmol) of phosphorus oxychloride were stirred at 120° C. for 3 h. Without work-up, the residue was purified by column chromatography [Puriflash silica gel 60 (12 g, 30 µm); ethyl acetate/methanol 1:1, (100 ml)]. In this manner, 4-chloro-2-morpholin-4-yl-8-(1H-pyrazol-3-yl)-[1,7]naphthyridine was obtained in a yield of 25 mg (79% of theory) as a yellow solid. $^1$H NMR (400 MHz, DMSO): δ [ppm]=3.69-3.79 (8H), 7.36 (1H), 7.64 (1H), 7.78 (1H), 7.85 (1H), 8.45 (1H). LCMS (method 1): m/z: [M+H]$^+$=316.3, R$_t$=3.0 min.

Example 63

2-[(3R)-3-methylmorpholin-4-yl]-4-(methylsulfanyl)-8-(1H-pyrazol-5-yl)-1,7-naphthyridine

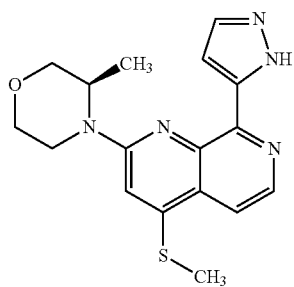 [SMILES: CSc1cc(N2CCOC[C@H]2C)nc2c(-c3ccn[nH]3)nccc12]

4-Chloro-2-[(3R)-3-methylmorpholin-4-yl]-8-[1-(tetrahydro-2H-pyran-2-yl)-1H-pyrazol-5-yl]-1,7-naphthyridine (50 mg, 0.12 mmol, 1 eq.) was solubilised in DMF (3 mL). Sodium methanethiolate (8.5 mg, 0.12 mmol, 1 eq.) was added and the reaction was stirred at 50° C. for 2 h. Sat. NH$_4$Cl was added to the mixture and the aqueous phase was extracted 3 times with CH$_2$Cl$_2$. The organic phase was dried (silicon filter) and concentrated under reduced pressure. The crude mixture was purified by preparative HPLC (H$_2$O (HCOOH)/CH$_3$CN: 56:44 to 36:64). The desired product was obtained in 75% yield. $^1$H-NMR (400 MHz, DMSO-d$_6$): δ [ppm]: 1.28 (3H), 2.69 (3H), 3.34 (1H), 3.56 (1H), 3.71 (1H), 3.83 (1H), 4.05 (1H), 4.17 (1H), 4.61-4.68 (1H), 7.08 (1H), 7.37 (1H), 7.61 (1H), 7.66 (1H), 8.36 (1H), 13.36 (br. s, 1H).

Example 64

N-{2-[(3R)-3-methylmorpholin-4-yl]-8-(1H-pyrazol-5-yl)-1,7-naphthyridin-4-yl}-1,4λ$^4$-oxathian-4-imine 4-oxide

Step a

N-(2-[(3R)-3-methylmorpholin-4-yl]-8-{1-[(2R)-tetrahydro-2H-pyran-2-yl]-1H-pyrazol-5-yl}-1,7-naphthyridin-4-yl)-1,4λ$^4$-oxathian-4-imine 4-oxide

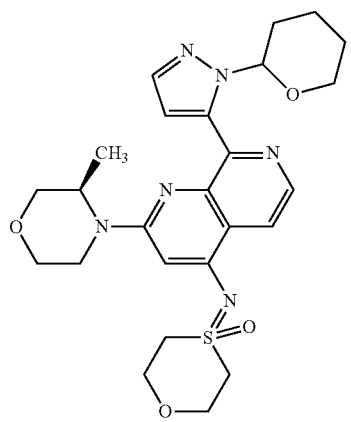 [SMILES: C[C@@H]1COCCN1c1cc(N=S2(=O)CCOCC2)c2ccnc(-c3ccnn3C3CCCCO3)c2n1]

Under argon, 8 mg (0.014 mmol) 4,5-bis(diphenylphosphino)-9,9-dimethylxanthene and 7 mg (0.007 mmol) tris(dibenzylideneacetone)dipalladium(0) were added to a mixture of 75 mg (0.142 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 25 mg (0.19 mmol) 1,4λ$^4$-oxathian-4-imine 4-oxide and 69 mg (0.21 mmol) caesium carbonate in 0.67 ml toluene. The mixture was stirred at 110° C. for 3 hours. After cooling, the reaction mixture was diluted with ethyl acetate/THF and washed with an aqueous solution of sodium chloride. The organic phase was filtered using a Whatman filter and concentrated to give 113 mg crude product that was used without further purification.

Step b

N-{2-[(3R)-3-methylmorpholin-4-yl]-8-(1H-pyrazol-5-yl)-1,7-naphthyridin-4-yl}-1,4λ$^4$-oxathian-4-imine 4-oxide

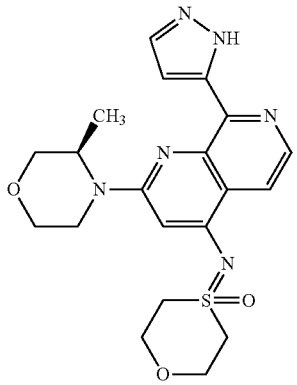 [SMILES: C[C@@H]1COCCN1c1cc(N=S2(=O)CCOCC2)c2ccnc(-c3ccn[nH]3)c2n1]

0.25 ml (0.51 mmol) 2N aqueous solution of hydrogen chloride was added to a solution of 113 mg crude N-(2-[(3R)-3-methylmorpholin-4-yl]-8-{1-[(2R)-tetrahydro-2H-pyran-2-yl]-1H-pyrazol-5-yl}-1,7-naphthyridin-4-yl)-1,4λ$^4$-oxathian-4-imine 4-oxide in 1.0 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 23 mg (0.05 mmol) of the desired product. $^1$H-NMR (400 MHz, CDCl$_3$): δ [ppm]=1.43 (3H), 3.43 (2H), 3.51 (1H), 3.61 (2H), 3.70 (1H), 3.85 (1H), 3.92 (2H), 4.14 (3H), 4.30 (2H), 4.38 (1H), 6.97 (1H), 7.26 (1H), 7.72 (1H), 7.89 (1H), 8.43 (1H).

Example 65

4-{[dimethyl(oxido)-λ$^6$-sulfanylidene]amino}-2-(morpholin-4-yl)-8-(1H-pyrazol-5-yl)-1,7-naphthyridine Step a 4-{[dimethyl(oxido)-λ$^6$-sulfanylidene]amino}-2-(morpholin-4-yl)-8-[1-(tetrahydro-2H-pyran-2-yl)-1H-pyrazol-5-yl]-1,7-naphthyridine

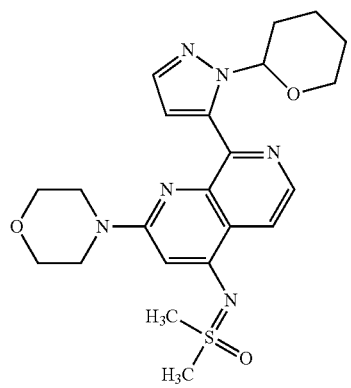 [SMILES: CS(C)(=O)=Nc1cc(N2CCOCC2)nc2c(-c3ccnn3C3CCCCO3)nccc12]

Under argon, 11 mg (0.019 mmol) 4,5-bis(diphenylphosphino)-9,9-dimethylxanthene and 9 mg (0.010 mmol) tris(dibenzylideneacetone)dipalladium(0) were added to a mixture of 100 mg (0.20 mmol) 2-(morpholin-4-yl)-8-[1-(tetrahydro-2H-pyran-2-yl)-1H-pyrazol-5-yl]-1,7-naphthyridin-4-yl trifluoromethanesulfonate, 24 mg (0.26 mmol) S,S-dimethylsulfoximin and 95 mg (0.29 mmol) caesium carbonate in 0.92 ml toluene. The mixture was stirred at 110° C. for 3 hours. After cooling, the reaction mixture was diluted with ethyl acetate/THF and washed with an aqueous solution of sodium chloride. The organic phase was filtered using a Whatman filter and concentrated to give 136 mg crude product that was used without further purification.

Step b

4-{[dimethyl(oxido)-λ$^6$-sulfanylidene]amino}-2-(morpholin-4-yl)-8-(1H-pyrazol-5-yl)-1,7-naphthyridine

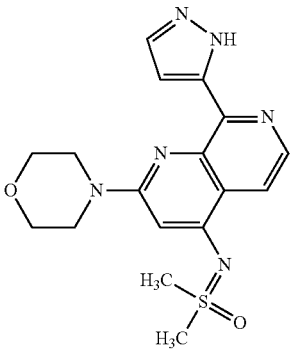 [SMILES: CS(C)(=O)=Nc1cc(N2CCOCC2)nc2c(-c3ccn[nH]3)nccc12]

0.34 ml (0.68 mmol) 2N aqueous solution of hydrogen chloride was added to a solution of 135 mg crude 4-{[dimethyl(oxido)-λ$^6$-sulfanylidene]amino}-2-(morpholin-4-yl)-8-[1-(tetrahydro-2H-pyran-2-yl)-1H-pyrazol-5-yl]-1,7-naphthyridine in 1.4 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preperative HPLC (Autopurifier: acidic conditions) to give 23 mg (0.06 mmol) of the desired product. $^1$H-NMR (400 MHz, CDCl$_3$): δ [ppm]=3.39 (6H), 3.70 (4H), 3.94 (4H), 6.93 (1H), 7.25 (1H), 7.72 (1H), 7.82 (1H), 8.43 (1H).

Example 66

2-[(3R)-3-methylmorpholin-4-yl]-4-(piperazin-1-yl)-8-(1H-pyrazol-5-yl)-1,7-naphthyridine Step a 2-[(3R)-3-methylmorpholin-4-yl]-4-(piperazin-1-yl)-8-[1-(tetrahydro-2H-pyran-2-yl)-1H-pyrazol-5-yl]-1,7-naphthyridine

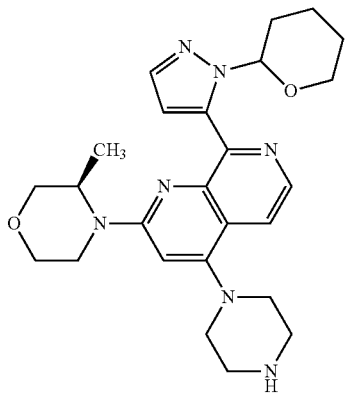 [SMILES: C[C@@H]1COCCN1c1cc(N2CCNCC2)c2ccnc(-c3ccnn3C3CCCCO3)c2n1]

Under argon, a mixture of 75 mg (0.14 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, and 42 mg (0.48 mmol) piperazine in 0.21 ml acetonitrile was stirred at 70° C. for 90 minutes. After cooling, the reaction mixture was diluted with ethyl acetate and washed with an aqueous solution of sodium chloride. The organic phase was filtered using a Whatman filter and concentrated to give 91 mg crude product that was used without further purification.

Step b

2-[(3R)-3-methylmorpholin-4-yl]-4-(piperazin-1-yl)-8-(1H-pyrazol-5-yl)-1,7-naphthyridine

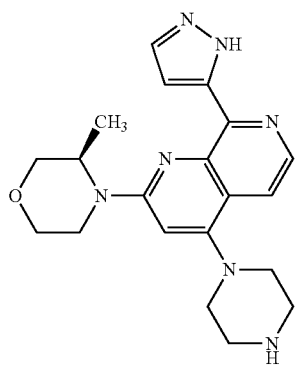 [SMILES: C[C@@H]1COCCN1c1cc(N2CCNCC2)c2ccnc(-c3ccn[nH]3)c2n1]

0.30 ml (0.60 mmol) 2N aqueous solution of hydrogen chloride was added to a solution of 120 mg crude 2-[(3R)-3-methylmorpholin-4-yl]-4-(piperazin-1-yl)-8-[1-(tetrahydro-2H-pyran-2-yl)-1H-pyrazol-5-yl]-1,7-naphthyridine in 1.2 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 27 mg (0.07 mmol) of the desired product. $^1$H-NMR (400 MHz, CDCl$_3$): δ [ppm]= 1.44 (3H), 3.21 (8H), 3.54 (1H), 3.73 (1H), 3.87 (1H), 3.95 (2H), 4.18 (1H), 4.40 (1H), 6.56 (1H), 7.27 (1H), 7.57 (1H), 7.71 (1H), 8.40 (1H).

Example 67

4-isopropoxy-2-((S)-3-methylmorpholin-4-yl)-8-(1H-pyrazol-3-yl)-[1,7]naphthyridine Step a 4-isopropoxy-2-((S)-3-methylmorpholin-4-yl)-8-[2-(tetrahydropyran-2-yl)-2H-pyrazol-3-yl]-[1,7]naphthyridine

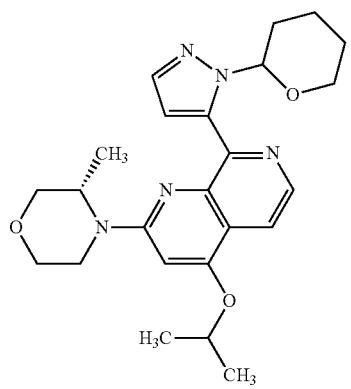 [SMILES: CC(C)Oc1cc(N2CCOC[C@@H]2C)nc2c(-c3ccnn3C3CCCCO3)nccc12]

96 mg (0.69 mmol) of potassium carbonate were added to a solution of 380 mg (0.58 mmol) of 2-[(3S)-3-methylmorpholin-4-yl]-8-(2-tetra hydropyran-2-ylpyrazol-3-yl)-1,7-naphthyridin-4-ol and 0.12 ml (1.15 mmol) of 2-iodopropane in 20 ml of acetonitrile. The suspension was stirred in a microwave vessel at 70° C. for 16 h. Under reduced pressure, the mixture was concentrated to dryness. The residue was taken up in 50 ml of water and extracted four times with in each case 50 ml of dichloromethane. The combined organic phases were dried over sodium sulphate and then, under reduced pressure, concentrated to dryness. The residue was chromatographed [silica gel 60 (40 g, 50 μm); ethyl acetate 100%]. 139 mg (55% of theory) of 4-isopropoxy-2-((S)-3-methylmorpholin-4-yl)-8-[2-(tetrahydropyran-2-yl)-2H-pyrazol-3-yl]-[1,7]naphthyridine were obtained as a beige solid. $^1$H NMR (400 MHz, CDCl$_3$): δ [ppm]=1.30 (3H), 1.48 (m, 1H), 1.49 (6H), 1.56-1.77 (2H), 2.02-2.10 (2H), 2.52 (1H), 3.27 (1H), 3.44 (1H), 3.57 (1H); 3.70-3.82 (2H), 3.93-4.16 (3H), 4.35 (1H), 4.78 (1H), 6.02 (1H), 6.32 (1H); 6.94 (1H), 7.67 (1H), 7.78 (1H), 6.39 (1H). LC-MS (method 1): R$_t$=3.75 min; MS (ESI/APCIpos) m/z=438.3 [M+H]$^+$.

183

Step b 4-isopropoxy-2-((S)-3-methylmorpholin-4-yl)-8-(1H-pyrazol-3-yl)-[1,7]naphthyridine

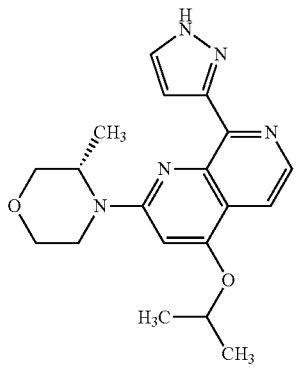 [SMILES: CC(C)Oc1cc(N2CCOC[C@@H]2C)nc2c(-c3cc[nH]n3)nccc12]

127 mg (0.29 mmol) of (3S)-4-[4-isopropoxy-8-(2-tetra hydropyran-2-ylpyrazol-3-yl)-1,7-naphthyridin-2-yl]-3-methylmorpholine were dissolved in 10 ml of methanol, 1.5 ml of 2N hydrochloric acid (3 mmol) were added and the mixture was stirred at room temperature for 1 h. After 1 h, the LC/MS showed complete removal of the protective group. The methanol was removed under reduced pressure. Saturated sodium bicarbonate solution (pH=7) was added to the residue. The aqueous phase was extracted five times with in each case 10 ml of dichloromethane. The combined organic phases were dried over sodium sulphate and then, under reduced pressure, concentrated to dryness. This gave 89 mg (87% of theory) of 4-isopropoxy-2-((S)-3-methylmorpholin-4-yl)-8-(1H-pyrazol-3-yl)-[1,7]naphthyridine as a yellow solid. $^1$H NMR (400 MHz, CDCl$_3$): δ [ppm]=1.41 (3H), 1.50 (6H), 3.50 (1H), 3.70 (1H), 3.85 (1H), 3.90 (1H), 3.92 (1H), 4.15 (1H), 4.34 (1H), 4.80 (1H), 6.39 (1H), 7.24 (1H), 7.69 (1H), 7.73 (1H), 8.39 (1H), 13.18 (1H). $^{13}$C NMR (101 MHz, CDCl$_3$): δ [ppm]=13.4, 21.6, 21.7, 40.8, 48.9, 66.8, 71.0, 71.7, 91.9, 105.7, 114.3, 123.4, 139.9, 140.0, 140.8, 143.2, 143.9, 158.9, 161.0. LC-MS (method 1): R$_t$=2.90 min; MS (ESI/APCIpos) m/z=354.3 [M+H]$^+$.

Example 68

2-(morpholin-4-yl)-4-(propan-2-yloxy)-8-(1H-pyrrol-3-yl)-1,7-naphthyridine

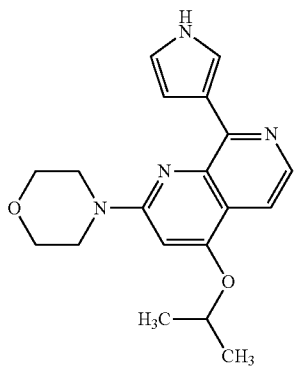 [SMILES: CC(C)Oc1cc(N2CCOCC2)nc2c(-c3cc[nH]c3)nccc12]

184

Under argon, 13 mg (0.016 mmol) [1,1'-bis(diphenylphosphino)ferrocene]dichloropalladium(II) were added to a mixture of 50 mg (0.16 mmol) 8-chloro-2-(morpholin-4-yl)-4-(propan-2-yloxy)-1,7-naphthyridine and 34 mg (0.18 mmol) 3-(4,4,5,5-tetramethyl-1,3,2-dioxaborolan-2-yl)-1H-pyrrole in 1.5 ml acetonitrile and 1.5 ml 2M aqueous solution of potassium carbonate. The mixture was stirred in a at 130° C. in a microwave oven for 10 minutes. After cooling, DCM was added and the mixture was filtered using a Whatman filter. The organic phase was concentrated and the residue was purified by preparative HPLC separation (Autopurifier: acidic conditions) to give 5 mg (0.01 mmol) of the desired product. $^1$H-NMR (400 MHz, DMSO-d6): δ [ppm]=1.38 (6H), 3.67 (4H), 3.78 (4H), 5.02 (1H), 6.78 (2H), 6.98 (1H), 7.44 (1H), 8.07 (1H), 8.17 (1H), 10.94 (1H).

Example 69

4-(1-ethyl-1H-pyrazol-5-yl)-2-[(3R)-3-methylmorpholin-4-yl]-8-(1H-pyrazol-5-yl)-1,7-naphthyridine

Step a 4-(1-ethyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

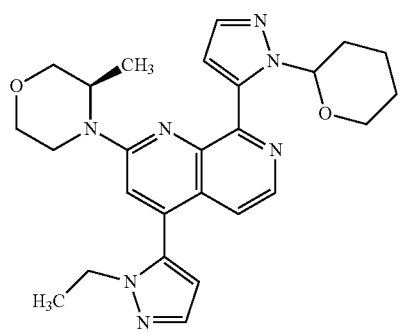

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) (1-ethyl-1H-pyrazol-5-yl) boronic acid, 15 mg (0.02 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2 ml MeCN and 1 ml water was degased with argon. Under argon, the reaction mixture was stirred at 130° C. for 10 min in a microwave reactor. After cooling the reaction mixture was diluted with saturated aqueous sodium chloride solution and extracted with ethyl acetate (2×). The combined organic phases were filtered using a Whatman filter and concentrated to give the crude product that was used without further purification in the next step.

Step b 4-(1-ethyl-1H-pyrazol-5-yl)-2-[(3R)-3-methylmorpholin-4-yl]-8-(1H-pyrazol-5-yl)-1,7-naphthyridine

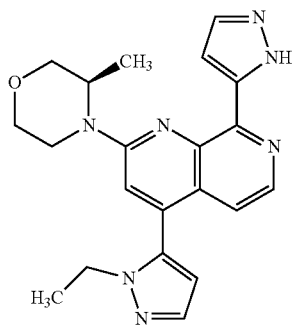

A solution of 104 mg of crude 4-(1-ethyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine from step a in 2 ml of methanol and 0.2 ml of 2N hydrochloric acid was stirred for 1 h at room temperature. The reaction mixture was diluted with saturated aqueous sodium chloride solution and extracted with ethyl acetate (2×). The combined organic phases were dried over magnesium sulphate and then concentrated to dryness. The residue was purified by preparative HPLC (Autopurifier: basic conditions) to give 11 mg (0.03 mmol) of the desired product.

$^1$H-NMR (400 MHz, DMSO-d6): δ [ppm]=1.22 (3H), 1.30 (3H), 3.35-3.40 (1H), 3.58 (1H), 3.72 (1H), 3.82 (1H), 3.99 (2H), 4.03-4.09 (1H), 4.23 (1H), 4.64 (1H), 6.55 (1H), 7.19 (1H), 7.44 (1H), 7.58 (1H), 7.65 (1H), 7.70 (1H), 8.35 (1H), 13.45 (1H).

Example 70

4-(1-methyl-1H-imidazol-5-yl)-2-[(3R)-3-methylmorpholin-4-yl]-8-(1H-pyrazol-5-yl)-1,7-naphthyridine Step a 4-(1-methyl-1H-imidazol-5-yl)-2-[(3R)-3-methylmorpholin-4-yl]-8-[1-(tetrahydro-2H-pyran-2-yl)-1H-pyrazol-5-yl]-1,7-naphthyridine

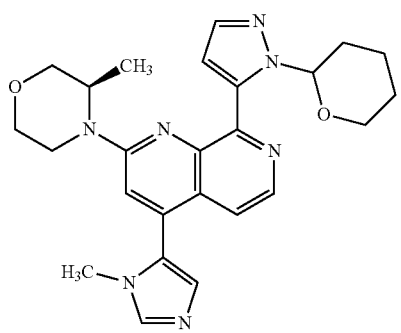 [SMILES: C[C@@H]1COCCN1c1cc(-c2cncn2C)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 79 mg (0.38 mmol) 1-methyl-5-(4,4,5,5-tetramethyl-1,3,2-dioxaborolan-2-yl)-1H-imidazole, 15 mg (0.02 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2 ml MeCN and 1 ml water was degased with argon. Under argon, the reaction mixture was stirred at 130° C. for 10 min in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(1-methyl-1H-imidazol-5-yl)-2-[(3R)-3-methylmorpholin-4-yl]-8-(1H-pyrazol-5-yl)-1,7-naphthyridine

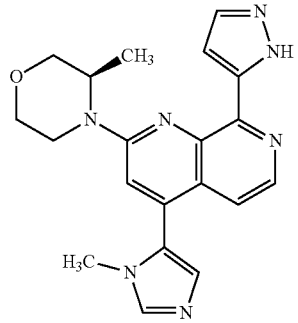 [SMILES: C[C@@H]1COCCN1c1cc(-c2cncn2C)c2ccnc(-c3ccn[nH]3)c2n1]

A solution of 99 mg of crude 4-(1-methyl-1H-imidazol-5-yl)-2-[(3R)-3-methylmorpholin-4-yl]-8-[1-(tetrahydro-2H-pyran-2-yl)-1H-pyrazol-5-yl]-1,7-naphthyridine from step a in 2 ml of methanol and 0.2 ml of 2N hydrochloric acid was stirred for 1 h at room temperature. The reaction mixture was diluted with saturated aqueous sodium chloride solution and extracted with ethyl acetate (2×). The combined organic phases were dried over magnesium sulphate and then concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=1.30 (3H), 3.50-3.65 (4H), 3.72 (1H), 3.83 (1H), 4.06 (1H), 4.23 (1H), 4.54-4.71 (1H), 7.24 (1H), 7.43 (2H), 7.51 (1H), 7.65 (1H), 7.93 (1H), 8.36 (1H), 13.43 (1H).

Example 71

2-{2-[(3R)-3-methylmorpholin-4-yl]-8-(1H-pyrazol-5-yl)-1,7-naphthyridin-4-yl}aniline

Step a

2-{2-[(3R)-3-methylmorpholin-4-yl]-8-[1-(tetrahydro-2H-pyran-2-yl)-1H-pyrazol-5-yl]-1,7-naphthyridin-4-yl}aniline

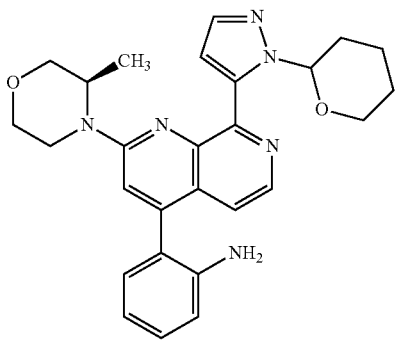

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 52 mg (0.38 mmol) (2-aminophenyl)boronic acid, 15 mg (0.02 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-{2-[(3R)-3-methylmorpholin-4-yl]-8-(1H-pyrazol-5-yl)-1,7-naphthyridin-4-yl]aniline

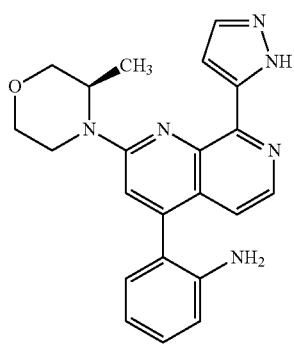 [SMILES: C[C@@H]1COCCN1c1cc(-c2ccccc2N)c2ccnc(-c3ccn[nH]3)c2n1]

A solution of 163 mg of crude 2-{2-[(3R)-3-methylmorpholin-4-yl]-8-[1-(tetrahydro-2H-pyran-2-yl)-1H-pyrazol-5-yl]-1,7-naphthyridin-4-yl}aniline from step a in 7.8 ml of methanol and 0.35 ml of 2N hydrochloric acid was stirred for 90 min at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 17 mg (0.04 mmol) of the desired product.

$^1$H-NMR (400 MHz, DMSO-d6): δ [ppm]=1.31 (3H), 3.45-3.64 (1H), 3.71 (1H), 3.82 (1H), 3.91-4.12 (1H), 4.21 (1H), 4.61 (1H), 4.84 (2H), 6.70 (1H), 6.82 (1H), 7.02 (1H), 7.08-7.27 (2H), 7.35 (1H), 7.44 (1H), 7.64 (1H), 8.28 (1H), 13.28 (1H).

Example 72

4-(2,3-difluorophenyl)-2-[(3R)-3-methylmorpholin-4-yl]-8-(1H-pyrazol-5-yl)-1,7-naphthyridine

Step a 4-(2,3-difluorophenyl)-2-[(3R)-3-methylmorpholin-4-yl]-8-[1-(tetrahydro-2H-pyran-2-yl)-1H-pyrazol-5-yl]-1,7-naphthyridine

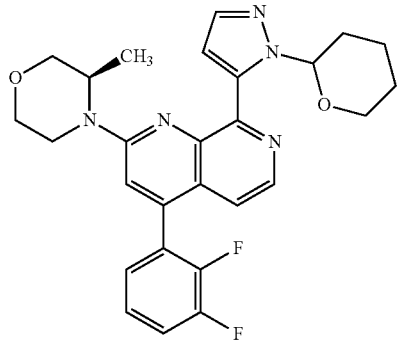 [SMILES: C[C@@H]1COCCN1c1cc(-c2cccc(F)c2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 60 mg (0.38 mmol) (2,3-difluorophenyl)boronic acid, 15 mg (0.02 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(2,3-difluorophenyl)-2-[(3R)-3-methylmorpholin-4-yl]-8-(1H-pyrazol-5-yl)-1,7-naphthyridine

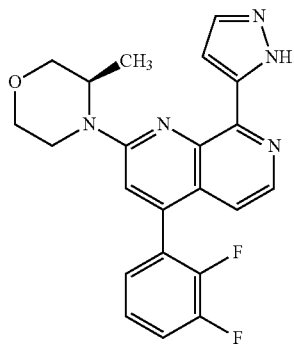 [SMILES: C[C@@H]1COCCN1c1cc(-c2cccc(F)c2F)c2ccnc(-c3ccn[nH]3)c2n1]

A solution of 133 mg of crude 4-(2,3-difluorophenyl)-2-[(3R)-3-methylmorpholin-4-yl]-8-[1-(tetrahydro-2H-pyran-2-yl)-1H-pyrazol-5-yl]-1,7-naphthyridine from step a in 6.1 ml of methanol and 0.27 ml of 2N hydrochloric acid was stirred for 90 min at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 20 mg (0.05 mmol) of the desired product.
$^1$H-NMR (400 MHz, DMSO-d6): δ [ppm]=1.31 (3H), 3.39 (1H), 3.58 (1H), 3.72 (1H), 3.83 (1H), 4.05 (1H), 4.23 (1H), 4.64 (1H), 7.22 (1H), 7.35-7.52 (3H), 7.52-7.75 (4H), 8.33 (1H), 13.09 (1H).

Example 73

4-[2-methyl-6-(methylsulfonyl)pyridin-3-yl]-2-[(3R)-3-methylmorpholin-4-yl]-8-(1H-pyrazol-5-yl)-1,7-naphthyridine

Step a

4-[2-methyl-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

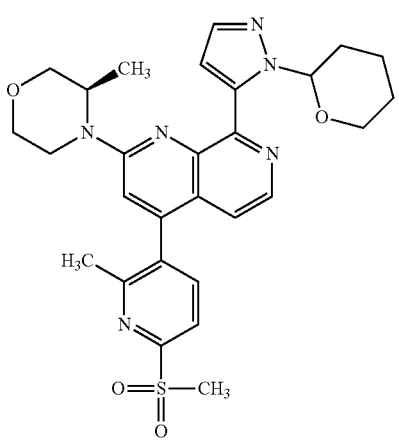 [SMILES: Cc1nc(S(C)(=O)=O)ccc1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 84 mg (0.28 mmol) 2-methyl-6-(methylsulfonyl)-3-(4,4,5,5-tetramethyl-1,3,2-dioxaborolan-2-yl)pyridine, 12 mg (0.014 mmol) of [1,1'-bis(diphenylphosphino)ferrocene]dichloropalladium(II) complex with dichloromethane (1:1, Pd(dppf)Cl$_2$) and 185 mg (0.57 mmol) of caesium carbonate in 1.0 ml of dioxane was degased with argon. Under argon, the reaction mixture was stirred at 110° C. for 2 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-methyl-6-(methylsulfonyl)pyridin-3-yl]-2-[(3R)-3-methylmorpholin-4-yl]-8-(1H-pyrazol-5-yl)-1,7-naphthyridine

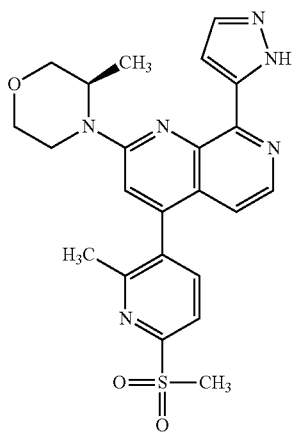 [SMILES: Cc1nc(S(C)(=O)=O)ccc1-c1cc(N2CCOC[C@H]2C)nc2c(-c3ccn[nH]3)nccc12]

A solution of 152 mg of crude 4-[2-methyl-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine from step a in 1.3 ml of methanol and 0.3 ml of 2N hydrochloric acid was stirred for 1 h at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 36 mg (0.08 mmol) of the desired product. $^1$H-NMR (400 MHz, DMSO-d6): δ [ppm]=1.29 (3H), 2.36 (3H), 3.33-3.44 (4H), 3.46-3.63 (1H), 3.66-3.76 (1H), 3.76-3.88 (1H), 4.04 (1H), 4.21 (1H), 4.55-4.64 (1H), 6.99 (1H), 7.43 (1H), 7.51-7.61 (1H), 7.64 (1H), 7.97-8.15 (2H), 8.29 (1H), 13.41 (1H).

Example 74

4-[2-fluoro-4-(methylsulfonyl)phenyl]-2-[(3R)-3-methylmorpholin-4-yl]-8-(1H-pyrazol-5-yl)-1,7-naphthyridine

Step a

4-[2-fluoro-4-(methylsulfanyl)phenyl]-2-[(3R)-3-methylmorpholin-4-yl]-8-[1-(tetrahydro-2H-pyran-2-yl)-1H-pyrazol-5-yl]-1,7-naphthyridine

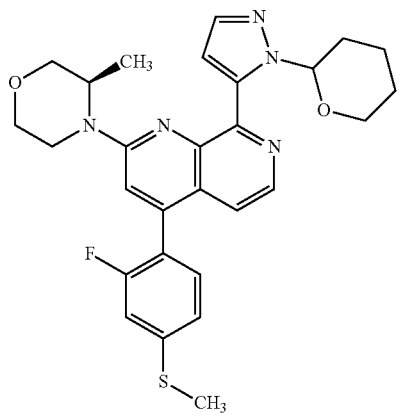 [SMILES: CSc1ccc(-c2cc(N3CCOC[C@H]3C)nc3c(-c4ccnn4C4CCCCO4)nccc23)c(F)c1]

A suspension of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 106 mg (0.57 mmol) [2-fluoro-4-(methylsulfanyl)phenyl]boronic acid, 23 mg (0.028 mmol) of [1,1'-bis(diphenylphosphino)ferrocene]dichloropalladium(II) complex with dichloromethane (1:1, Pd(dppf)Cl$_2$) and 371 mg (1.14 mmol) of caesium carbonate in 2.0 ml of dioxane was degased with argon. Under argon, the reaction mixture was stirred at 110° C. for 150 min. After cooling the reaction mixture was diluted with saturated aqueous sodium chloride solution and extracted with ethyl acetate (2×). The combined organic phases were filtered using a Whatman filter and then concentrated. The residue was purified by flash chromatography (gradient Hex/EtOAc 9/1 to 100% EtOAc) to give 96 mg (0.18 mmol) of the desired product.

$^1$H-NMR (400 MHz, DMSO-d6): δ [ppm]=1.21 (3H), 1.35-1.56 (3H), 1.87-2.08 (2H), 2.29-2.43 (1H), 2.58 (3H), 3.08-3.26 (2H), 3.39-3.58 (1H), 3.58-3.66 (1H), 3.66-3.79 (2H), 3.95 (1H), 4.16 (1H), 4.47-4.58 (1H), 6.10 (1H), 6.94 (1H), 7.23 (1H), 7.26-7.32 (1H), 7.35 (1H), 7.43 (1H), 7.48 (1H), 7.62 (1H), 8.34 (1H).

Step b

4-[2-fluoro-4-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine

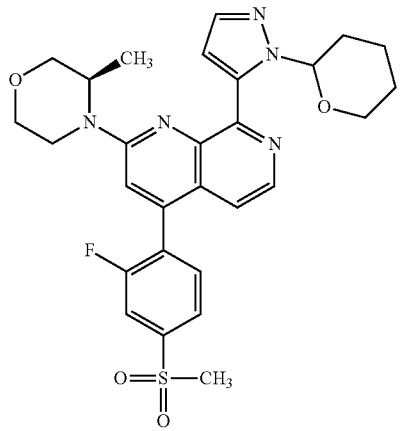 [SMILES: C[C@@H]1COCCN1c1cc(-c2ccc(S(C)(=O)=O)cc2F)c2ccnc(-c3ccnn3C3CCCCO3)c2n1]

2.7 mg (0.009 mmol) TPAP and 20.7 mg (0.18 mmol) 4-methylmorpholine N-oxide were added to a stirred solution of 92 mg (0.18 mmol) of 4-[2-fluoro-4-(methylsulfanyl)phenyl]-2-[(3R)-3-methylmorpholin-4-yl]-8-[1-(tetrahydro-2H-pyran-2-yl)-1H-pyrazol-5-yl]-1,7-naphthyridine in 2 ml DCM and 2 ml MeCN at 0°. After 4 h, additional 2.7 mg (0.009 mmol) TPAP was added and the ice bath removed. After 14 h at Rt, additional 2.7 mg (0.009 mmol) TPAP and 20.7 mg (0.18 mmol) 4-methylmorpholine N-oxide were added and the mixture was stirred at room temperature. After 18 h at Rt, additional 2.7 mg (0.009 mmol) TPAP and 20.7 mg (0.18 mmol) 4-methylmorpholine N-oxide were added and the mixture was stirred at room temperature. After 16 h at Rt, additional 2.7 mg (0.009 mmol) TPAP and 20.7 mg (0.18 mmol) 4-methylmorpholine N-oxide were added and the mixture was stirred at room temperature. The reaction was filtered using a Whatman filter and concentrated to give the crude product that was used without further purification in the next step.

Step c

4-[2-fluoro-4-(methylsulfonyl)phenyl]-2-[(3R)-3-methylmorpholin-4-yl]-8-(1H-pyrazol-5-yl)-1,7-naphthyridine

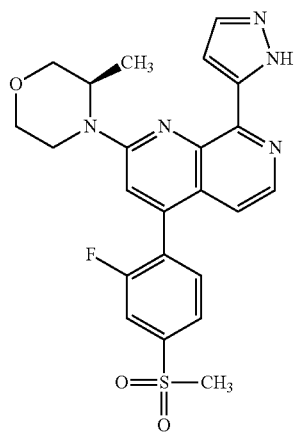 [SMILES: C[C@@H]1COCCN1c1cc(-c2ccc(S(C)(=O)=O)cc2F)c2ccnc(-c3ccn[nH]3)c2n1]

A solution of 134 mg of crude 4-[2-fluoro-4-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine from step b in 5.4 ml of methanol and 0.25 ml of 2N hydrochloric acid was stirred for 90 min at room temperature. The reaction mixture was treated with 10 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 23 mg (0.05 mmol) of the desired product.

$^1$H-NMR (400 MHz, DMSO-d6): δ [ppm]=1.30 (3H), 3.33-3.42 (4H), 3.50-3.61 (1H), 3.66-3.76 (1H), 3.81 (1H), 3.95-4.09 (1H), 4.21 (1H), 4.54-4.71 (1H), 7.15 (1H), 7.42 (1H), 7.56-7.70 (2H), 7.87 (1H), 7.98 (1H), 8.03 (1H), 8.31 (1H), 13.40 (1H).

Example 75

4-fluoro-2-[2-[(3R)-3-methylmorpholin-4-yl]-8-(1H-pyrazol-5-yl)-1,7-naphthyridin-4-yl]aniline Step a 4-fluoro-2-{2-[(3R)-3-methylmorpholin-4-yl]-8-[1-(tetrahydro-2H-pyran-2-yl)-1H-pyrazol-5-yl]-1,7-naphthyridin-4-yl}aniline

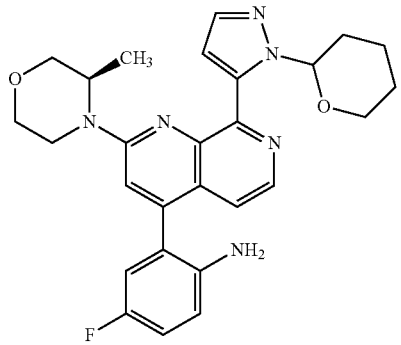 [SMILES: C[C@@H]1COCCN1c1cc(-c2cc(F)ccc2N)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 58 mg (0.38 mmol) (2-amino-5-fluorophenyl)boronic acid, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-fluoro-2-[2-[(3R)-3-methylmorpholin-4-yl]-8-(1H-pyrazol-5-yl)-1,7-naphthyridin-4-yl]aniline

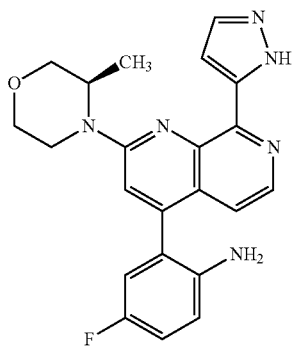 [SMILES: C[C@@H]1COCCN1c1cc(-c2cc(F)ccc2N)c2ccnc(-c3ccn[nH]3)c2n1]

A solution of 59 mg of crude 4-fluoro-2-{2-[(3R)-3-methylmorpholin-4-yl]-8-[1-(tetrahydro-2H-pyran-2-yl)-1H-pyrazol-5-yl]-1,7-naphthyridin-4-yl}aniline from step a in 3.0 ml of methanol and 0.12 ml of 2N hydrochloric acid was stirred for 3 h at room temperature. The reaction mixture was diluted with saturated aqueous sodium chloride solution and extracted with ethyl acetate (2×). The combined organic phases were filtered using a Whatman filter and then concentrated to dryness. The residue was purified by preparative HPLC (Autopurifier: basic conditions) to give 22 mg (0.05 mmol) of the desired product.

$^1$H-NMR (400 MHz, DMSO-d6): δ [ppm]=1.31 (3H), 3.57 (1H), 3.65-3.76 (1H), 3.76-3.88 (1H), 4.05 (1H), 4.22 (1H), 4.62 (1H), 4.74 (2H), 6.81 (1H), 6.94 (1H), 7.07 (1H), 7.14 (1H), 7.39 (1H), 7.44 (1H), 7.59-7.73 (m, 1H), 8.29 (1H), 13.42 (1H).

Example 76

4-(1-benzyl-1H-imidazol-5-yl)-2-[(3R)-3-methyl-morpholin-4-yl]-8-(1H-pyrazol-5-yl)-1,7-naphthyridine

Step a 4-(1-benzyl-1H-imidazol-5-yl)-2-[(3R)-3-methyl-morpholin-4-yl]-8-[1-(tetrahydro-2H-pyran-2-yl)-1H-pyrazol-5-yl]-1,7-naphthyridine

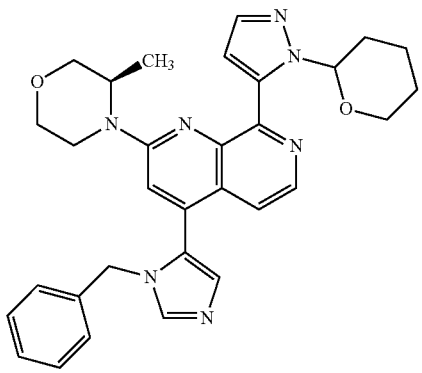 [SMILES: C[C@@H]1COCCN1c1cc(-c2cncn2Cc2ccccc2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethane-sulfonate, 53 mg (0.19 mmol) 1-benzyl-5-(4,4,5,5-tetramethyl-1,3,2-dioxaborolan-2-yl)-1H-imidazole, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of cesium carbonate was degased with argon. Under argon, the reaction mixture was stirred at 110° C. for 90 minutes. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(1-benzyl-1H-imidazol-5-yl)-2-[(3R)-3-methyl-morpholin-4-yl]-8-(1H-pyrazol-5-yl)-1,7-naphthyridine

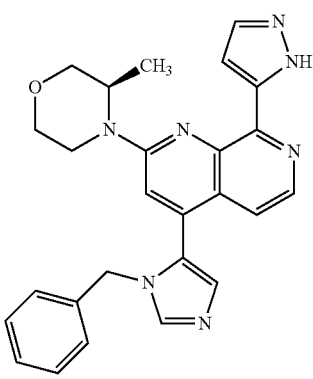 [SMILES: C[C@@H]1COCCN1c1cc(-c2cncn2Cc2ccccc2)c2ccnc(-c3ccn[nH]3)c2n1]

A solution of 170 mg of crude 4-(1-benzyl-1H-imidazol-5-yl)-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.32 ml of 2N hydrochloric acid was stirred for 3 h at room temperature. The reaction mixture was diluted with saturated aqueous sodium chloride solution and extracted with ethyl acetate (2×). The combined organic phases were filtered using a Whatman filter and then concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=1.17 (3H), 3.22 (1H), 3.51 (1H), 3.65 (1H), 3.76 (1H), 3.90-4.07 (2H), 4.32 (1H), 5.24 (2H), 6.86 (2H), 7.11-7.24 (4H), 7.26 (1H), 7.34 (1H), 7.38 (1H), 7.63 (1H), 8.13 (1H), 8.29 (1H), 13.40 (1H).

Example 77

4-(2-fluorophenyl)-2-[(3R)-3-methylmorpholin-4-yl]-8-(1H-pyrazol-5-yl)-1,7-naphthyridine

Step a 4-(2-fluorophenyl)-2-[(3R)-3-methylmorpholin-4-yl]-8-[1-(tetrahydro-2H-pyran-2-yl)-1H-pyrazol-5-yl]-1,7-naphthyridine

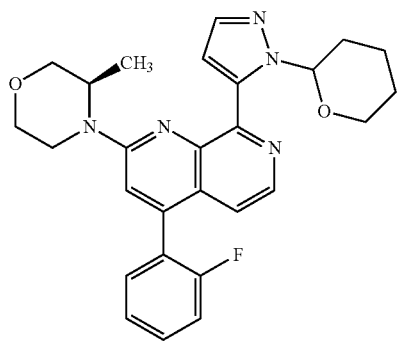 [SMILES: C[C@@H]1COCCN1c1cc(-c2ccccc2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethane-sulfonate, 53 mg (0.38 mmol) (2-fluorophenyl)boronic acid, 15 mg (0.02 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(2-fluorophenyl)-2-[(3R)-3-methylmorpholin-4-yl]-8-(1H-pyrazol-5-yl)-1,7-naphthyridine

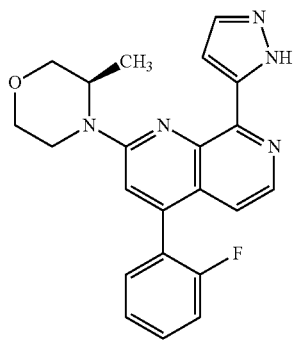 [SMILES: C[C@@H]1COCCN1c1cc(-c2ccccc2F)c2ccnc(-c3ccn[nH]3)c2n1]

A solution of 126 mg of 4-(2-fluorophenyl)-2-[(3R)-3-methylmorpholin-4-yl]-8-[1-(tetrahydro-2H-pyran-2-yl)-1H-pyrazol-5-yl]-1,7-naphthyridine from step a in 6 ml of methanol and 0.27 ml of 2N hydrochloric acid was stirred for 90 min at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 16 mg (0.04 mmol) of the desired product.

$^1$H-NMR (400 MHz, DMSO-d6): δ [ppm]=1.31 (3H), 3.39 (1H), 3.58 (1H), 3.64-3.77 (1H), 3.82 (1H), 4.05 (1H), 4.23 (1H), 4.65 (1H), 7.15 (1H), 7.39-7.69 (7H), 8.32 (1H), 13.33 (1H).

Example 78

2-[(3R)-3-methylmorpholin-4-yl]-4-(2-methyl-1,3-thiazol-5-yl)-8-(1H-pyrazol-5-yl)-1,7-naphthyridine

Step a

2-[(3R)-3-methylmorpholin-4-yl]-4-(2-methyl-1,3-thiazol-5-yl)-8-[1-(tetrahydro-2H-pyran-2-yl)-1H-pyrazol-5-yl]-1,7-naphthyridine

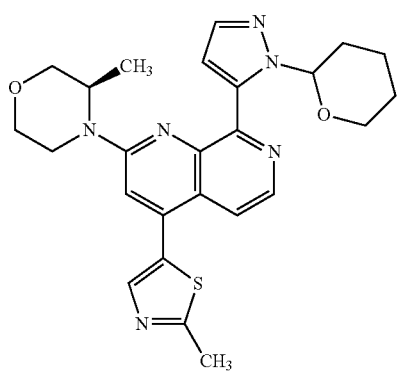 [SMILES: Cc1ncc(-c2cc(N3CCOC[C@H]3C)nc3c(-c4ccnn4C4CCCCO4)nccc23)s1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 85 mg (0.38 mmol) 2-methyl-5-(4,4,5,5-tetramethyl-1,3,2-dioxaborolan-2-yl)-1,3-thiazole, 15 mg (0.019 mmol) of [1,1'-bis(diphenylphosphino)ferrocene]dichloropalladium(II) complex with dichloromethane (1:1, Pd(dppf)Cl$_2$) and 105 mg (0.76 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(2-methyl-1,3-thiazol-5-yl)-8-(1H-pyrazol-5-yl)-1,7-naphthyridine

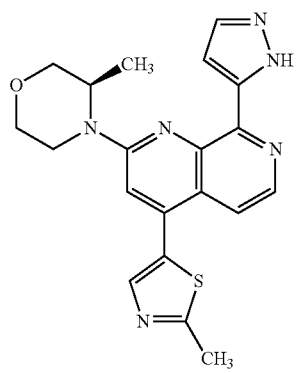 [SMILES: Cc1ncc(-c2cc(N3CCOC[C@H]3C)nc3c(-c4ccn[nH]4)nccc23)s1]

A solution of 183 mg of crude 2-[(3R)-3-methylmorpholin-4-yl]-4-(2-methyl-1,3-thiazol-5-yl)-8-[1-(tetrahydro-2H-pyran-2-yl)-1H-pyrazol-5-yl]-1,7-naphthyridine from step a in 1.8 ml of methanol and 0.44 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 14 mg (0.04 mmol) of the desired product.

$^1$H-NMR (400 MHz, DMSO-d6): δ [ppm]=1.30 (3H), 2.79 (3H), 3.57 (1H), 3.71 (1H), 3.83 (1H), 4.05 (1H), 4.21 (1H), 4.56-4.71 (1H), 7.40 (1H), 7.55 (1H), 7.65 (1H), 7.73 (1H), 8.07 (1H), 8.39 (1H), 13.41 (1H).

Example 79

4-[4-methyl-6-(methylsulfonyl)pyridin-3-yl]-2-[(3R)-3-methylmorpholin-4-yl]-8-(1H-pyrazol-5-yl)-1,7-naphthyridine

Step a

4-[4-methyl-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

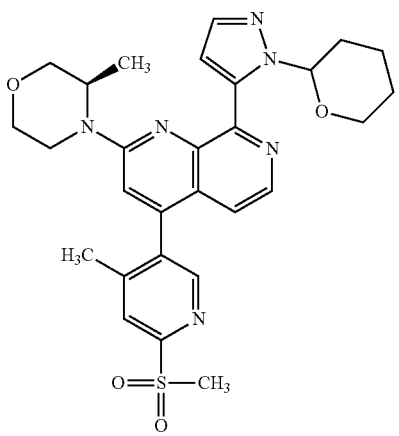 [SMILES: Cc1cc(S(C)(=O)=O)ncc1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 84 mg (0.28 mmol) 4-methyl-2-(methylsulfonyl)-5-(4,4,5,5-tetramethyl-1,3,2-dioxaborolan-2-yl)pyridine, 11 mg (0.014 mmol) of [1,1'-bis(diphenylphosphino)ferrocene]dichloropalladium(II) complex with dichloromethane (1:1, Pd(dppf)Cl$_2$) and 185 mg (0.56 mmol) of caesium carbonate in 1.0 ml of dioxane was degased with argon. Under argon, the reaction mixture was stirred at 110° C. for 2 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[4-methyl-6-(methylsulfonyl)pyridin-3-yl]-2-[(3R)-3-methylmorpholin-4-yl]-8-(1H-pyrazol-5-yl)-1,7-naphthyridine

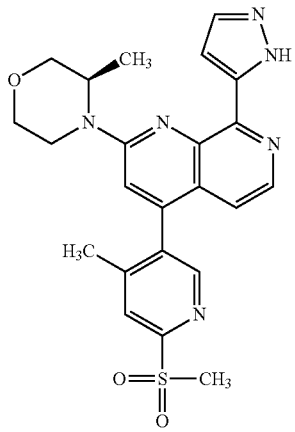 [SMILES: Cc1cc(S(C)(=O)=O)ncc1-c1cc(N2CCOC[C@H]2C)nc2c(-c3ccn[nH]3)nccc12]

A solution of 152 mg of 4-[4-methyl-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine from step a in 1.3 ml of methanol and 0.32 ml of 2N hydrochloric acid was stirred for 60 min at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 33 mg (0.07 mmol) of the desired product.

$^1$H-NMR (400 MHz, DMSO-d6): δ [ppm]=1.30 (3H), 2.23 (3H), 3.35 (4H), 3.57 (1H), 3.65-3.76 (1H), 3.76-3.89 (1H), 4.04 (1H), 4.14-4.32 (1H), 4.60 (1H), 6.98 (1H), 7.43 (1H), 7.57 (1H), 7.64 (1H), 8.17 (1H), 8.28 (1H), 8.68 (1H), 13.41 (1H).

Example 80

4-(1-cyclopropyl-1H-pyrazol-5-yl)-2-[(3R)-3-methylmorpholin-4-yl]-8-(1H-pyrazol-5-yl)-1,7-naphthyridine

Step a 4-(1-cyclopropyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

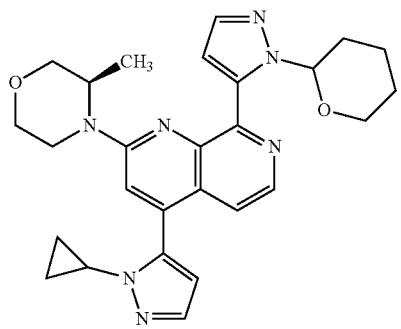 [SMILES: C[C@@H]1COCCN1c1cc(-c2ccnn2C2CC2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 57 mg (0.38 mmol) (1-cyclopropyl-1H-pyrazol-5-yl)boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 1 h. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(1-cyclopropyl-1H-pyrazol-5-yl)-2-[(3R)-3-methylmorpholin-4-yl]-8-(1H-pyrazol-5-yl)-1,7-naphthyridine

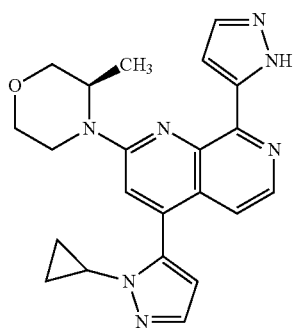 [SMILES: C[C@@H]1COCCN1c1cc(-c2ccnn2C2CC2)c2ccnc(-c3ccn[nH]3)c2n1]

A solution of 96 mg of crude 4-(1-cyclopropyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine from step a in 5.0 ml of methanol and 0.20 ml of 2N hydrochloric acid was stirred for 3 h at room temperature. The reaction mixture was treated with 2 ml of a saturated aqueous sodium bicarboante solution and extracted with ethyl acetate (2×). The combined organic phases were filtered using a Whatman filter and then concentrated to dryness. The residue was purified by preparative HPLC (Autopurifier: basic conditions) to give 6 mg (0.02 mmol) of the desired product.

$^1$H-NMR (400 MHz, DMSO-d6): δ [ppm]=0.74-0.83 (2H), 0.91-1.02 (2H), 1.30 (3H), 3.39 (1H), 3.52-3.64 (2H), 3.73 (1H), 3.83 (1H), 4.06 (1H), 4.23 (1H), 4.60-4.71 (1H), 6.59 (1H), 7.28 (1H), 7.43 (1H), 7.53-7.79 (3H), 8.36 (1H), 13.01 (1H).

Example 81

4-[2-fluoro-4-(piperazin-1-yl)phenyl]-2-[(3R)-3-methylmorpholin-4-yl]-8-(1H-pyrazol-5-yl)-1,7-naphthyridine Step a 4-[2-fluoro-4-(piperazin-1-yl)phenyl]-2-[(3R)-3-methylmorpholin-4-yl]-8-[1-(tetrahydro-2H-pyran-2-yl)-1H-pyrazol-5-yl]-1,7-naphthyridine

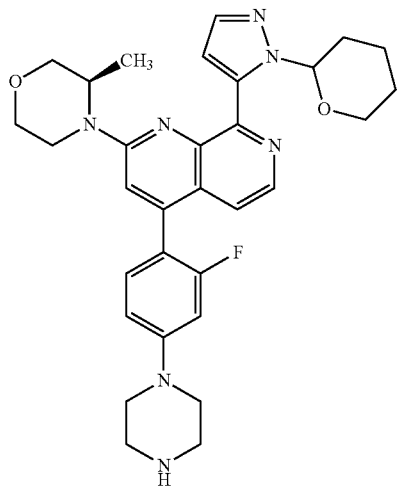 [SMILES: C[C@@H]1COCCN1c1cc(-c2ccc(N3CCNCC3)cc2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 85 mg (0.38 mmol) [2-fluoro-4-(piperazin-1-yl)phenyl]boronic acid, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-fluoro-4-(piperazin-1-yl)phenyl]-2-[(3R)-3-methylmorpholin-4-yl]-8-(1H-pyrazol-5-yl)-1,7-naphthyridine

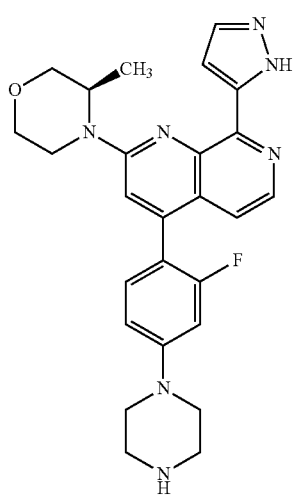 [SMILES: C[C@@H]1COCCN1c1cc(-c2ccc(N3CCNCC3)cc2F)c2ccnc(-c3ccn[nH]3)c2n1]

A solution of 106 mg of crude 4-[2-fluoro-4-(piperazin-1-yl)phenyl]-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.38 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: acidic conditions) to give 20 mg (0.04 mmol) of the desired product.

$^1$H-NMR (400 MHz, DMSO-d6): δ [ppm]=1.29 (3H), 2.78-3.01 (m, 4H), 3.20-3.43 (m, 5H), 3.57 (1H), 3.72 (1H), 3.82 (1H), 4.04 (1H), 4.20 (1H), 4.62 (1H), 6.81-7.03 (2H), 7.25 (1H), 7.30-7.49 (3H), 7.65 (1H), 8.25 (1H), 8.32 (1H).

Example 82

2-[(3R)-3-methylmorpholin-4-yl]-4-[4-(methylsulfonyl)piperazin-1-yl]-8-(1H-pyrazol-5-yl)-1,7-naphthyridine

Step a

2-[(3R)-3-methylmorpholin-4-yl]-4-[4-(methylsulfonyl)piperazin-1-yl]-8-[1-(tetrahydro-2H-pyran-2-yl)-1H-pyrazol-5-yl]-1,7-naphthyridine

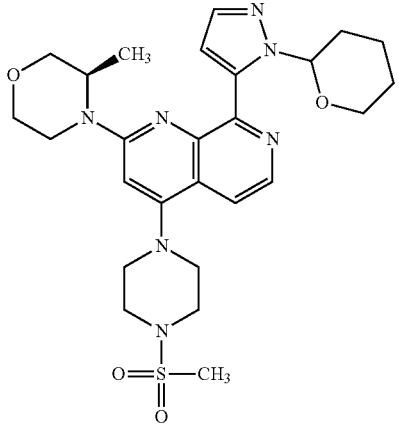 [SMILES: C[C@@H]1COCCN1c1cc(N2CCN(S(C)(=O)=O)CC2)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 159 mg (0.97 mmol) 1-(methylsulfonyl)piperazine in 0.42 ml of MeCN was stirred at 70° C. for 8 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

2-[(3R)-3-methylmorpholin-4-yl]-4-[4-(methylsulfonyl)piperazin-1-yl]-8-(1H-pyrazol-5-yl)-1,7-naphthyridine

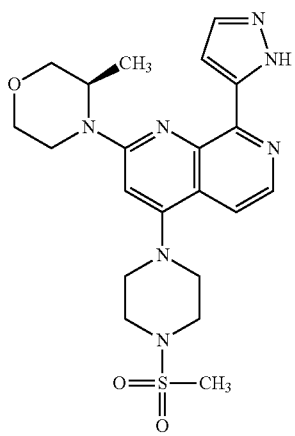 [SMILES: C[C@@H]1COCCN1c1cc(N2CCN(S(C)(=O)=O)CC2)c2ccnc(-c3ccn[nH]3)c2n1]

A solution of 267 mg of crude 2-[(3R)-3-methylmorpholin-4-yl]-4-[4-(methylsulfonyl)piperazin-1-yl]-8-[1-(tetrahydro-2H-pyran-2-yl)-1H-pyrazol-5-yl]-1,7-naphthyridine from step a in 2.3 ml of methanol and 0.57 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 55 mg (0.12 mmol) of the desired product.

$^1$H-NMR (400 MHz, DMSO-d6): δ [ppm]=1.27 (3H), 3.00 (3H), 3.18-3.31 (5H), 3.38-3.49 (4H), 3.55 (1H), 3.70 (1H), 3.83 (1H), 4.05 (1H), 4.13 (1H), 4.53-4.64 (1H), 6.84 (1H), 7.35 (1H), 7.53-7.71 (2H), 8.33 (1H), 13.21 (1H).

Example 83

N-(2,2-dimethylpropyl)-N-methyl-2-[(3R)-3-methylmorpholin-4-yl]-8-(1H-pyrazol-5-yl)-1,7-naphthyridin-4-amine Step a N-(2,2-dimethylpropyl)-N-methyl-2-[(3R)-3-methylmorpholin-4-yl]-8-[1-(tetrahydro-2H-pyran-2-yl)-1H-pyrazol-5-yl]-1,7-naphthyridin-4-amine

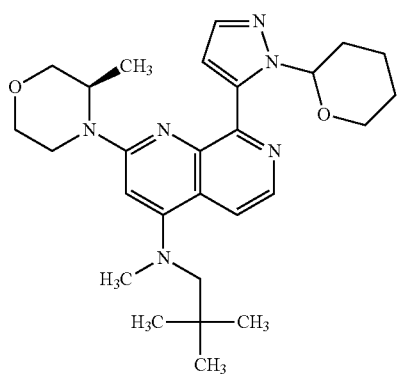 [SMILES: C[C@@H]1COCCN1c1cc(N(C)CC(C)(C)C)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 98 mg (0.97 mmol) N,2,2-trimethylpropan-1-amine in 0.42 ml of MeCN was stirred at 70° C. for 7 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

N-(2,2-dimethylpropyl)-N-methyl-2-[(3R)-3-methylmorpholin-4-yl]-8-(1H-pyrazol-5-yl)-1,7-naphthyridin-4-amine

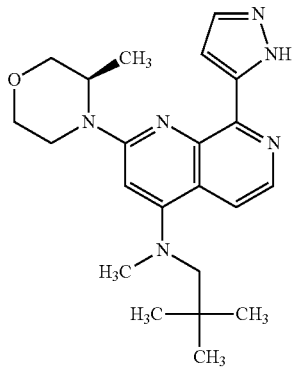 [SMILES: C[C@@H]1COCCN1c1cc(N(C)CC(C)(C)C)c2ccnc(-c3ccn[nH]3)c2n1]

A solution of 205 mg of crude N-(2,2-dimethylpropyl)-N-methyl-2-[(3R)-3-methylmorpholin-4-yl]-8-[1-(tetrahydro-2H-pyran-2-yl)-1H-pyrazol-5-yl]-1,7-naphthyridin-4-amine from step a in 2.0 ml of methanol and 0.50 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 47 mg (0.12 mmol) of the desired product.

$^1$H-NMR (400 MHz, DMSO-d6): δ [ppm]=0.90 (9H), 1.23 (3H), 3.09 (3H), 3.16-3.31 (2H), 3.36-3.42 (1H), 3.56 (1H), 3.63-3.78 (1H), 3.82 (1H), 3.92-4.18 (2H), 4.49-4.61 (1H), 6.99 (1H), 7.34 (1H), 7.60 (1H), 7.73 (1H), 8.30 (1H), 13.36 (1H).

Example 84

(1-{2-[(3R)-3-methylmorpholin-4-yl]-8-(1H-pyrazol-5-yl)-1,7-naphthyridin-4-yl}piperidin-4-yl)methanol Step a (1-{2-[(3R)-3-methylmorpholin-4-yl]-8-[1-(tetrahydro-2H-pyran-2-yl)-1H-pyrazol-5-yl]-1,7-naphthyridin-4-yl}piperidin-4-yl)methanol

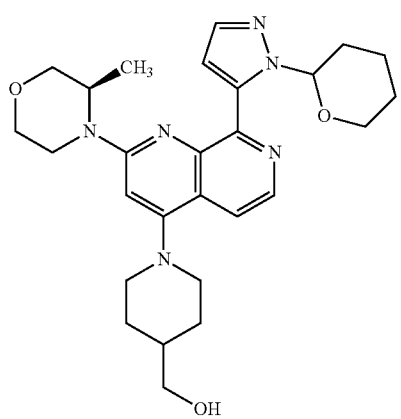 [SMILES: C[C@@H]1COCCN1c1cc(N2CCC(CO)CC2)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 111 mg (0.97 mmol) piperidin-4-ylmethanol in 0.42 ml of MeCN was stirred at 70° C. for 3 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b (1-{2-[(3R)-3-methylmorpholin-4-yl]-8-(1H-pyrazol-5-yl)-1,7-naphthyridin-4-yl}piperidin-4-yl)methanol

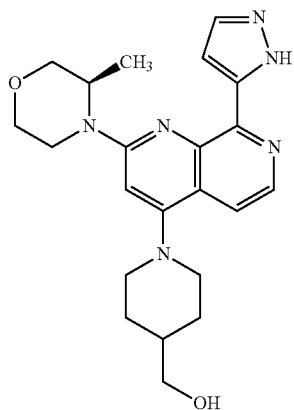 [SMILES: C[C@@H]1COCCN1c1cc(N2CCC(CO)CC2)c2ccnc(-c3ccn[nH]3)c2n1]

A solution of 345 mg of crude (1-{2-[(3R)-3-methylmorpholin-4-yl]-8-[1-(tetrahydro-2H-pyran-2-yl)-1H-pyrazol-5-yl]-1,7-naphthyridin-4-yl}piperidin-4-yl)methanol from step a in 3.2 ml of methanol and 0.81 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 37 mg (0.09 mmol) of the desired product.

$^1$H-NMR (400 MHz, DMSO-d6): δ [ppm]=1.26 (3H), 1.38-1.55 (2H), 1.55-1.71 (1H), 1.76-1.96 (2H), 2.71-2.93 (2H), 3.22-3.31 (1H), 3.36-3.43 (2H), 3.43-3.61 (3H), 3.70 (1H), 3.82 (1H), 4.03 (1H), 4.11 (1H), 4.51-4.62 (2H), 6.74 (1H), 7.34 (1H), 7.56 (1H), 7.61 (1H), 8.31 (1H), 13.33 (1H).

Example 85

N-cyclopropyl-N-methyl-2-[(3R)-3-methylmorpholin-4-yl]-8-(1H-pyrazol-5-yl)-1,7-naphthyridin-4-amine Step a N-cyclopropyl-N-methyl-2-[(3R)-3-methylmorpholin-4-yl]-8-[1-(tetrahydro-2H-pyran-2-yl)-1H-pyrazol-5-yl]-1,7-naphthyridin-4-amine

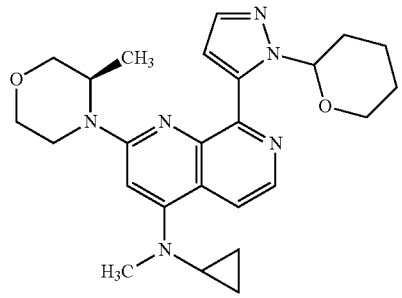 [SMILES: C[C@@H]1COCCN1c1cc(N(C)C2CC2)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 69 mg (0.97 mmol)N-methylcyclopropanamine in 0.42 ml of MeCN was stirred at 70° C. for 7 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

N-cyclopropyl-N-methyl-2-[(3R)-3-methylmorpholin-4-yl]-8-(1H-pyrazol-5-yl)-1,7-naphthyridin-4-amine

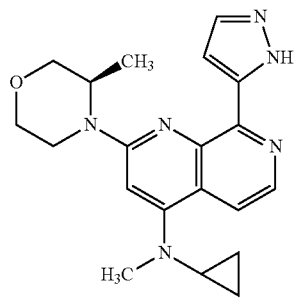 [SMILES: C[C@@H]1COCCN1c1cc(N(C)C2CC2)c2ccnc(-c3ccn[nH]3)c2n1]

A solution of 188 mg of crude N-cyclopropyl-N-methyl-2-[(3R)-3-methylmorpholin-4-yl]-8-[1-(tetrahydro-2H-pyran-2-yl)-1H-pyrazol-5-yl]-1,7-naphthyridin-4-amine from step a in 1.9 ml of methanol and 0.48 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 45 mg (0.12 mmol) of the desired product.

$^1$H-NMR (400 MHz, DMSO-d6): δ [ppm]=0.34-0.56 (2H), 0.75-0.89 (2H), 1.27 (3H), 2.78-2.89 (1H), 3.08 (3H), 3.23-3.32 (1H), 3.56 (1H), 3.66-3.76 (1H), 3.83 (1H), 3.99-4.14 (2H), 4.46-4.58 (1H), 6.86 (1H), 7.33 (1H), 7.60 (1H), 7.65 (1H), 8.25 (1H), 13.36 (1H).

Example 86

4-(5,6-dihydroimidazo[1,2-a]pyrazin-7(8H)-yl)-2-[(3R)-3-methylmorpholin-4-yl]-8-(1H-pyrazol-5-yl)-1,7-naphthyridine

Step a

4-(5,6-dihydroimidazo[1,2-a]pyrazin-7(8H)-yl)-2-[(3R)-3-methylmorpholin-4-yl]-8-[1-(tetrahydro-2H-pyran-2-yl)-1H-pyrazol-5-yl]-1,7-naphthyridine

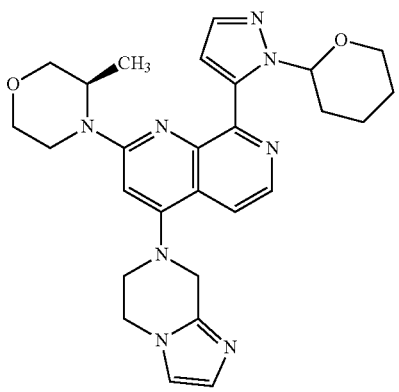 [SMILES: C[C@@H]1COCCN1c1cc(N2CCn3ccnc3C2)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 119 mg (0.97 mmol) 5,6,7,8-tetrahydroimidazo[1,2-a]pyrazine in 0.42 ml of MeCN was stirred at 70° C. for 48 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

4-(5,6-dihydroimidazo[1,2-a]pyrazin-7(8H)-yl)-2-[(3R)-3-methylmorpholin-4-yl]-8-(1H-pyrazol-5-yl)-1,7-naphthyridine

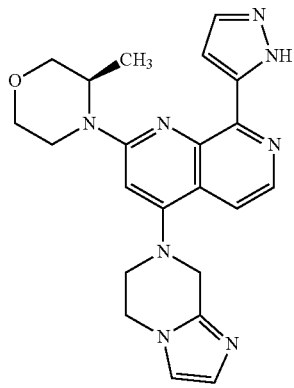 [SMILES: C[C@@H]1COCCN1c1cc(N2CCn3ccnc3C2)c2ccnc(-c3ccn[nH]3)c2n1]

A solution of 106 mg of crude 4-(5,6-dihydroimidazo[1,2-a]pyrazin-7(8H)-yl)-2-[(3R)-3-methylmorpholin-4-yl]-8-[1-(tetrahydro-2H-pyran-2-yl)-1H-pyrazol-5-yl]-1,7-naphthyridine from step a in 5.0 ml of methanol and 0.21 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 6 mg (0.01 mmol) of the desired product.

$^1$H-NMR (400 MHz, DMSO-d6): δ [ppm]=1.28 (3H), 3.55 (1H), 3.61-3.75 (3H), 3.83 (1H), 4.05 (1H), 4.19 (1H), 4.25-4.36 (2H), 4.41-4.52 (2H), 4.62 (1H), 6.91 (1H), 6.96 (1H), 7.22 (1H), 7.36 (1H), 7.62 (1H), 7.68 (1H), 8.33 (1H), 13.38 (1H).

Example 87

N-(4-fluorophenyl)-N-methyl-2-[(3R)-3-methylmorpholin-4-yl]-8-(1H-pyrazol-5-yl)-1,7-naphthyridin-4-amine

Step a

N-(4-fluorophenyl)-N-methyl-2-[(3R)-3-methylmorpholin-4-yl]-8-[1-(tetrahydro-2H-pyran-2-yl)-1H-pyrazol-5-yl]-1,7-naphthyridin-4-amine

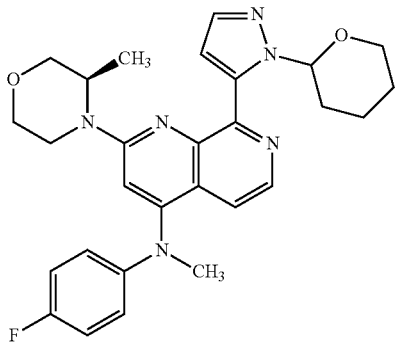 [SMILES: C[C@@H]1COCCN1c1cc(N(C)c2ccc(F)cc2)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 121 mg (0.97 mmol) 4-fluoro-N-methylaniline in 0.42 ml of MeCN was stirred at 70° C. for 3 h under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

N-(4-fluorophenyl)-N-methyl-2-[(3R)-3-methylmorpholin-4-yl]-8-(1H-pyrazol-5-yl)-1,7-naphthyridin-4-amine

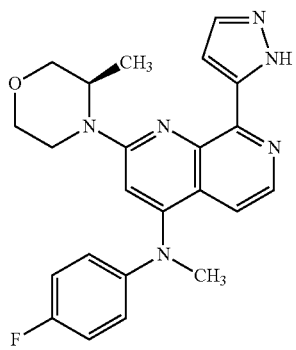 [SMILES: C[C@@H]1COCCN1c1cc(N(C)c2ccc(F)cc2)c2ccnc(-c3ccn[nH]3)c2n1]

A solution of 273 mg of crude N-(4-fluorophenyl)-N-methyl-2-[(3R)-3-methylmorpholin-4-yl]-8-[1-(tetrahydro-2H-pyran-2-yl)-1H-pyrazol-5-yl]-1,7-naphthyridin-4-amine from step a in 2.5 ml of methanol and 0.63 ml of 2N hydrochloric acid was stirred for 1 h at room temperature. The reaction mixture was diluted with saturated aqueous sodium bicarbonate solution and extracted with ethyl acetate/THF (1:1) (2×). The combined organic phases were filtered using a Whatman filter and then concentrated to dryness. The residue was purified by preparative HPLC (Autopurifier: basic conditions) to give 54 mg (0.13 mmol) of the desired product.

$^1$H-NMR (400 MHz, DMSO-d6): δ [ppm]=1.30 (3H), 3.45 (3H), 3.58 (1H), 3.73 (1H), 3.84 (1H), 4.06 (1H), 4.16 (1H), 4.54-4.66 (1H), 6.95-7.02 (2H), 7.03-7.15 (4H), 7.36 (1H), 7.62 (1H), 8.08 (1H), 13.26 (1H).

Example 88

2-[(3R)-3-methylmorpholin-4-yl]-4-(6-methylpyridin-3-yl)-8-(1H-pyrazol-5-yl)-1,7-naphthyridine

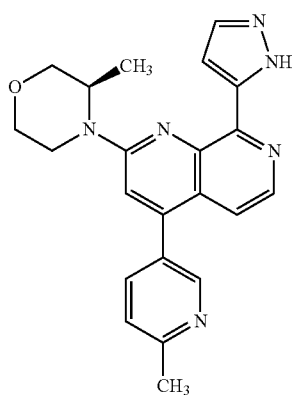 [SMILES: Cc1ccc(-c2cc(N3CCOC[C@H]3C)nc3c(-c4ccn[nH]4)nccc23)cn1]

Intermediate-10 (0.10 g, 0.19 mmol) was solubilised in dioxane (1 ml). 2-Methyl-5-pyridinylboronic acid (52 mg, 0.38 mmol) was added in one portion followed by addition of caesium carbonate (0.25 g, 0.76 mmol) and PdCl$_2$(dppf) in complex with dichloromethane (31 mg, 0.038 mmol). The reaction was heated for 4 hours in a sealed tube at 110° C. The reaction was then cooled to rt and filtered. The solid was washed with ethyl acetate and the filtrate was concentrated under reduced pressure. The crude material was purified by preparative HPLC (acetonitrile/water/formic acid mixture). The combined fractions were concentrated under reduced pressure, solubilised in dichloromethane and 3N hydrochloric acid was added. The mixture was stirred overnight at rt and then quenched with a saturated aqueous solution of sodium hydrogen carbonate. The aqueous phase was extracted three times with dichloromethane. The organic phase was dried, filtered and concentrated under reduced pressure. The title compound was obtained in 53% yield (39 mg).

$^1$H-NMR (400 MHz, DMSO-d$_6$): δ [ppm]=1.29 (d, 3H), 2.59 (s, 3H), 3.35-3.42 (m, 1H), 3.56 (t, 1H), 3.71 (d, 1H), 3.82 (d, 1H), 4.05 (d, 1H), 4.23 (d, 1H), 4.61-4.71 (m, 1H), 7.38 (d, 1H), 7.43 (s, 1H), 7.47 (d, 2H), 7.63 (s, 1H), 7.92 (dd, 1H), 8.32 (d, 1H), 8.64 (d, 1H), 13.43 (s, 1H).

Example 89

4-(2-fluoropyridin-3-yl)-2-[(3R)-3-methylmorpholin-4-yl]-8-(1H-pyrazol-5-yl)-1,7-naphthyridine

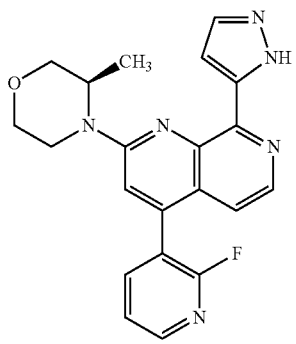 [SMILES: C[C@@H]1COCCN1c1cc(-c2cccnc2F)c2ccnc(-c3ccn[nH]3)c2n1]

Intermediate-10 (0.25 g, 0.47 mmol) was solubilised in dioxane (2.5 ml). (2-Fluoropyridin-3-yl)boronic acid (0.20 g, 1.4 mmol) was added in one portion followed by addition of caesium carbonate (0.62 g, 1.90 mmol) and PdCl$_2$(dppf) in complex with dichloromethane (77 mg, 0.094 mmol). The reaction was heated for 4 hours in a sealed tube at 110° C. The reaction was then cooled to rt and filtered. The solid was washed with dichloromethane and the filtrate was concentrated under reduced pressure. The crude material was purified by flash column chromatography (hexane/ethyl acetate/ethanol mixture). The combined fractions were concentrated under reduced pressure, solubilised in methanol (3 ml) and 3N hydrochloric acid (10 ml) was added. The mixture was stirred for 2 hours rt and then basified with a 3M sodium hydroxide solution. The suspension was filtered and washed with water. The solid was dried under reduced pressure at 60° C. The title compound was obtained in 90% yield (109 mg).

$^1$H-NMR (400 MHz, DMSO-d$_6$): δ [ppm]=1.30 (d, 3H), 3.29-3.41 (m, 1H), 3.51-3.61 (m, 1H), 3.67-3.75 (m, 1H), 3.78-3.86 (m, 1H), 4.00-4.09 (m, 1H), 4.17-4.26 (m, 1H), 4.59-4.68 (m, 1H), 7.17 (dd, 1H), 7.43 (s, 1H), 7.58-7.68 (m, 3H), 8.14-8.22 (m, 1H), 8.32 (d, 1H), 8.44-8.48 (m, 1H), 13.43 (br. s, 1H).

Example 90

4-(2-fluoro-4-methylpyridin-3-yl)-2-[(3R)-3-methyl-morpholin-4-yl]-8-(1H-pyrazol-5-yl)-1,7-naphthyridine

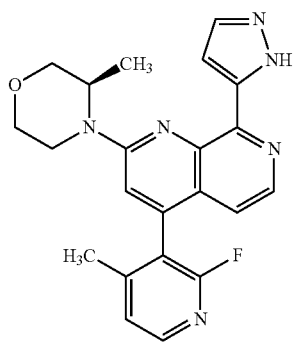 [SMILES: Cc1ccnc(F)c1-c1cc(N2CCOC[C@H]2C)nc2c(-c3ccn[nH]3)nccc12]

Intermediate-10 (0.10 g, 0.19 mmol) was solubilised in dioxane (1 ml). (2-Fluoro-4-methylpyridin-3-yl)boronic acid (61 mg, 0.38 mmol) was added in one portion followed by addition of caesium carbonate (0.25 g, 0.76 mmol) and PdCl$_2$(dppf) in complex with dichloromethane (31 mg, 0.038 mmol). The reaction was heated for 4 hours in a sealed tube at 110° C. The reaction was then cooled to rt and filtered. The filtrate was concentrated under reduced pressure. The crude material was purified by preparative HPLC (acetonitrile/water/formic acid mixture). The combined fractions were concentrated under reduced pressure, solubilised in dichloromethane and washed with a saturated solution of sodium hydrogen carbonate. The organic phase was dried (silicon filter) and concentrated under reduced pressure. The title compound was obtained in 47% yield (36 mg).

$^1$H-NMR (400 MHz, CHLOROFORM-d): δ [ppm]=1.47 (dd, 3H), 2.16 (d, 3H), 3.58 (td, 1H), 3.70-3.78 (m, 1H), 3.90-3.95 (m, 2H), 4.01-4.09 (m, 1H), 4.19 (dd, 1H), 4.37-4.46 (m, 1H), 6.94 (d, 1H), 7.13 (d, 1H), 7.26 (d, 1H), 7.32-7.35 (m, 1H), 7.74 (d, 1H), 8.27 (d, 1H), 8.37 (d, 1H).

Example 91

2-[(3R)-3-methylmorpholin-4-yl]-4-(1-methyl-1H-pyrrol-2-yl)-8-(1H-pyrazol-5-yl)-1,7-naphthyridine

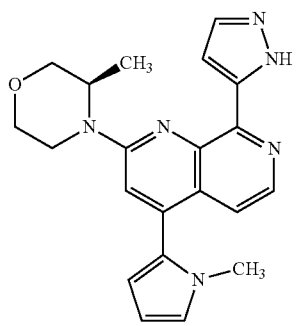 [SMILES: C[C@@H]1COCCN1c1cc(-c2cccn2C)c2ccnc(-c3ccn[nH]3)c2n1]

Intermediate-10 (0.10 g, 0.19 mmol 1-methyl-2-(4,4,5,5-tetramethyl-1,3,2-dioxaborolan-2-yl)-1H-pyrrole (79 mg, 0.38 mmol), aq. potassium carbonate (0.29 ml, 2 M) and PdCl$_2$(PPh$_3$)$_2$ (13 mg, 0.019 mmol) were solubilised in dimethoxyethane (5 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in dichloromethane and washed with a saturated solution of sodium hydrogen carbonate. The organic phase was dried (silicon filter) and concentrated under reduced pressure. The title compound was obtained in 53% yield (39 mg).

$^1$H-NMR (400 MHz, DMSO-d$_6$): δ [ppm]=1.29 (d, 3H), 3.28-3.39 (m, 1H), 3.52-3.62 (m, 4H), 3.68-3.76 (m, 1H), 3.78-3.86 (m, 1H), 4.00-4.09 (m, 1H), 4.18-4.26 (m, 1H), 4.59-4.68 (m, 1H), 6.22-6.28 (m, 1H), 6.35 (dd, 1H), 7.07 (dd, 1H), 7.41 (s, 2H), 7.48 (d, 1H), 7.64 (br. s, 1H), 8.34 (d, 1H), 13.41 (br. s, 1H).

Example 92

4-(6-fluoro-5-methylpyridin-3-yl)-2-[(3R)-3-methyl-morpholin-4-yl]-8-(1H-pyrazol-5-yl)-1,7-naphthyridine

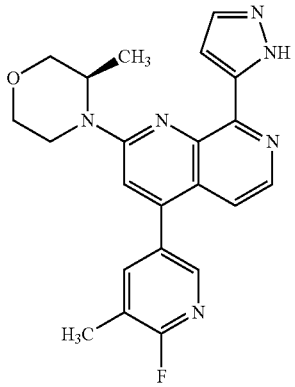 [SMILES: Cc1cc(-c2cc(N3CCOC[C@H]3C)nc3c(-c4ccn[nH]4)nccc23)cnc1F]

Intermediate-10 (0.075 g, 0.14 mmol) was solubilised in dioxane (3.2 ml). (6-Fluoro-5-methylpyridin-3-yl)boronic acid (44 mg, 0.28 mmol) was added in one portion followed by addition of caesium carbonate (0.19 g, 0.59 mmol) and PdCl$_2$(dppf) in complex with dichloromethane (11 mg, 0.014 mmol). The reaction was heated for 4 hours in a sealed tube at 110° C. The reaction was then cooled to rt and filtered. The filtrate was concentrated under reduced pressure. The crude material was purified by flash column chromatography (hexane/ethyl acetate mixture). The combined fractions were concentrated under reduced pressure, solubilised in methanol (1.5 ml) and 3N hydrochloric acid (1.6 ml) was added. The mixture was stirred overnight at rt and then basified with a 3M sodium hydroxide solution. The suspension was filtered and washed with water. The solid was purified by preparative HPLC (acetonitrile/water/formic acid mixture). The title compound was obtained in 20% yield (11 mg).

$^1$H-NMR (400 MHz, DMSO-d$_6$): δ [ppm]=1.30 (dd, 3H), 2.12 (s, 3H), 3.36-3.39 (m, 1H), 3.52-3.63 (m, 1H), 3.68-3.76 (m, 1H), 3.78-3.85 (m, 1H), 4.01-4.09 (m, 1H), 4.18-4.27 (m, 1H), 4.57-4.66 (m, 1H), 7.00 (dd, 1H), 7.33 (s, 1H), 7.40-7.45 (m, 1H), 7.51 (d, 1H), 7.65 (d, 1H), 8.17 (d, 1H), 8.29 (d, 1H), 13.42 (br. s, 1H).

Example 93

4-(2-fluoro-6-methylpyridin-3-yl)-2-[(3R)-3-methyl-morpholin-4-yl]-8-(1H-pyrazol-5-yl)-1,7-naphthyridine

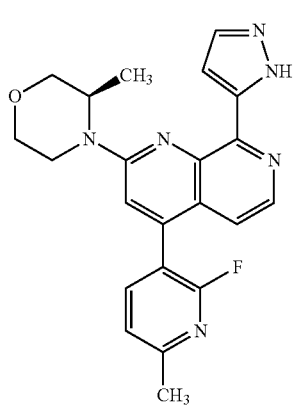 [SMILES: Cc1ccc(-c2cc(N3CCOC[C@H]3C)nc3c(-c4ccn[nH]4)nccc23)c(F)n1]

Intermediate-10 (0.075 g, 0.14 mmol) was solubilised in dioxane (3.2 ml) under argon. (2-Fluoro-6-methylpyridin-3-yl)boronic acid (44 mg, 0.28 mmol) was added in one portion followed by addition of caesium carbonate (0.19 g, 0.59 mmol) and PdCl$_2$(dppf) in complex with dichloromethane (11 mg, 0.014 mmol). The reaction was heated for 4 hours in a sealed tube at 110° C. The reaction was then cooled to rt and filtered. The filtrate was concentrated under reduced pressure. The crude material was purified by flash column chromatography (hexane/ethyl acetate mixture). The combined fractions were concentrated under reduced pressure, solubilised in methanol (1 ml) and 3N hydrochloric acid (1 ml) was added. The mixture was stirred overnight at rt and then basified with a 3M sodium hydroxide solution. The suspension was filtered and washed with water. The solid was purified by preparative HPLC (acetonitrile/water/formic acid mixture). The title compound was obtained in 54% yield (19 mg).

$^1$H-NMR (400 MHz, DMSO-d$_6$): δ [ppm]=1.30 (d, 3H), 2.56 (s, 3H), 3.36-3.40 (m, 1H), 3.52-3.61 (m, 1H), 3.67-3.75 (m, 1H), 3.79-3.86 (m, 1H), 4.00-4.07 (m, 1H), 4.17-4.24 (m, 1H), 4.58-4.66 (m, 1H), 7.18 (dd, 1H), 7.41 (d, 1H), 7.46 (dd, 1H), 7.58 (s, 1H), 7.65 (d, 1H), 8.04 (dd, 1H), 8.32 (d, 1H), 13.41 (br. s, 1H).

Example 94

4-(6-fluoropyridin-3-yl)-2-[(3R)-3-methylmorpholin-4-yl]-8-(1H-pyrazol-5-yl)-1,7-naphthyridine

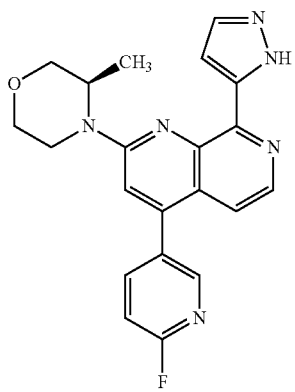 [SMILES: C[C@@H]1COCCN1c1cc(-c2ccc(F)nc2)c2ccnc(-c3ccn[nH]3)c2n1]

Intermediate-10 (0.075 g, 0.14 mmol) was solubilised in dioxane (3.2 ml) under argon. (6-Fluoropyridin-3-yl)boronic acid (40 mg, 0.28 mmol) was added in one portion followed by addition of caesium carbonate (0.19 g, 0.59 mmol) and PdCl$_2$(dppf) in complex with dichloromethane (11 mg, 0.014 mmol). The reaction was heated for 4 hours in a sealed tube at 110° C. The reaction was then cooled to rt and filtered. The filtrate was concentrated under reduced pressure. The crude material was purified by flash column chromatography (hexane/ethyl acetate mixture). The combined fractions were concentrated under reduced pressure, solubilised in methanol (1.4 ml) and 3N hydrochloric acid (1.4 ml) was added. The mixture was stirred overnight at rt and then basified with a 3M sodium hydroxide solution. The suspension was filtered and washed with water. The solid was purified by preparative HPLC (acetonitrile/water/formic acid mixture). The title compound was obtained in 10% yield (5 mg).

$^1$H-NMR (400 MHz, DMSO-d$_6$): δ [ppm]=1.30 (d, 3H), 3.35-3.41 (m, 1H), 3.52-3.61 (m, 1H), 3.67-3.75 (m, 1H), 3.79-3.86 (m, 1H), 4.01-4.09 (m, 1H), 4.19-4.28 (m, 1H), 4.62-4.71 (m, 1H), 7.37 (d, 1H), 7.39-7.46 (m, 2H), 7.55 (s, 1H), 7.62-7.68 (m, 1H), 8.21-8.29 (m, 1H), 8.34 (d, 1H), 8.48 (d, 1H), 13.43 (br. s, 1H).

Example 95

4-(6-methoxypyridin-3-yl)-2-[(3R)-3-methylmorpholin-4-yl]-8-(1H-pyrazol-5-yl)-1,7-naphthyridine

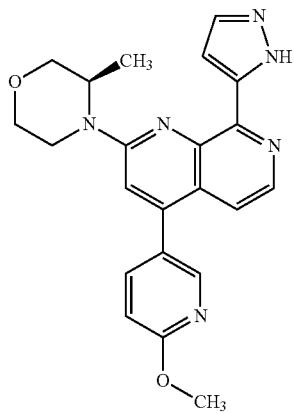 [SMILES: COc1ccc(-c2cc(N3CCOC[C@H]3C)nc3c(-c4ccn[nH]4)nccc23)cn1]

4-(6-Fluoropyridin-3-yl)-2-[(3R)-3-methylmorpholin-4-yl]-8-(1H-pyrazol-5-yl)-1,7-naphthyridine (10 mg, 0.026 mmol) was solubilised in methanol (3 ml) and the mixture was stirred overnight at 50° C. Sodium methoxide was then added to the mixture (7.1 mg, 0.13 mmol) and the reaction was stirred for additional 18 hours at 50° C. The reaction mixture was cooled to rt and concentrated under reduced pressure. The crude material was purified by preparative HPLC (acetonitrile/water/formic acid mixture) and the title compound was obtained in 59% yield (6.3 mg).

$^1$H-NMR (400 MHz, DMSO-$d_6$): δ [ppm]=1.30 (d, 3H), 3.34-3.40 (m, 1H), 3.50-3.62 (m, 1H), 3.68-3.75 (m, 1H), 3.79-3.86 (m, 1H), 3.96 (s, 3H), 4.01-4.09 (m, 1H), 4.19-4.28 (m, 1H), 4.61-4.71 (m, 1H), 7.04 (d, 1H), 7.42 (d, 2H), 7.47 (s, 1H), 7.64 (br. s, 1H), 7.96 (dd, 1H), 8.33 (d, 1H), 8.40 (d, 1H), 13.41 (br. s, 1H).

Example 96

4-(6-methoxy-5-methylpyridin-3-yl)-2-[(3R)-3-methylmorpholin-4-yl]-8-(1H-pyrazol-5-yl)-1,7-naphthyridine

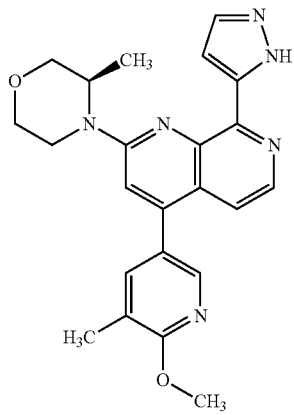 [SMILES: COc1ncc(-c2cc(N3CCOC[C@H]3C)nc3c(-c4ccn[nH]4)nccc23)cc1C]

4-(6-fluoro-5-methylpyridin-3-yl)-2-[(3R)-3-methylmorpholin-4-yl]-8-(1H-pyrazol-5-yl)-1,7-naphthyridine (13 mg, 0.031 mmol) was solubilised in methanol (3 ml) and the mixture was stirred overnight at 50° C. Sodium methoxide was then added to the mixture (8.3 mg, 0.16 mmol) and the reaction was stirred for additional 18 hours at 50° C. Sodium methoxide was again added (8.3 mg, 0.16 mmol) and the reaction was stirred for 24 hours at 50° C. The reaction mixture was cooled to rt and concentrated under reduced pressure. The crude material was purified by preparative HPLC (acetonitrile/water/formic acid mixture) and the title compound was obtained in 93% yield (12 mg).

$^1$H-NMR (400 MHz, DMSO-$d_6$): δ [ppm]=1.30 (dd, 3H), 2.04 (s, 3H), 3.34-3.40 (m, 1H), 3.52-3.63 (m, 1H), 3.68-3.76 (m, 1H), 3.77-3.85 (m, 1H), 3.89-3.96 (m, 3H), 4.00-4.08 (m, 1H), 4.17-4.26 (m, 1H), 4.56-4.67 (m, 1H), 6.91 (s, 1H), 7.00-7.06 (m, 1H), 7.39-7.47 (m, 2H), 7.64 (br. s, 1H), 8.07 (s, 1H), 8.29 (d, 1H), 13.41 (br. s, 1H).

Example 97

4-(6-fluoro-2-methylpyridin-3-yl)-2-[(3R)-3-methylmorpholin-4-yl]-8-(1H-pyrazol-5-yl)-1,7-naphthyridine

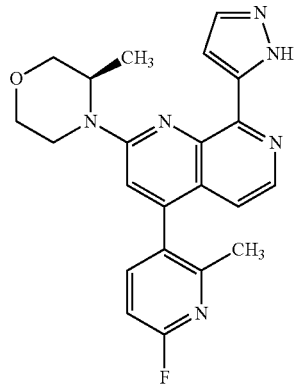 [SMILES: Cc1nc(F)ccc1-c1cc(N2CCOC[C@H]2C)nc2c(-c3ccn[nH]3)nccc12]

Intermediate-10 (0.075 g, 0.14 mmol) was solubilised in dioxane (3.2 ml) under argon. (6-Fluoro-2-methylpyridin-3-yl)boronic acid (44 mg, 0.28 mmol) was added in one portion followed by addition of caesium carbonate (0.19 g, 0.59 mmol) and PdCl$_2$(dppf) in complex with dichloromethane (11 mg, 0.014 mmol). The reaction was heated for 4 hours in a sealed tube at 110° C. The reaction was then cooled to rt and filtered. The filtrate was concentrated under reduced pressure. The crude material was purified by preparative HPLC (acetonitrile/water/formic acid mixture) followed by flash column chromatography (hexane/ethyl acetate mixture). The title compound was obtained in 68% yield (41 mg).

$^1$H-NMR (400 MHz, DMSO-$d_6$): δ [ppm]=1.29 (t, 3H), 2.21 (d, 3H), 3.28-3.39 (m, 1H), 3.52-3.62 (m, 1H), 3.68-3.76 (m, 1H), 3.77-3.85 (m, 1H), 4.00-4.08 (m, 1H), 4.17-4.27 (m, 1H), 4.56-4.66 (m, 1H), 7.02 (dd, 1H), 7.21 (dd, 1H), 7.44 (br. s., 1H), 7.51 (d, 1H), 7.64 (br. s., 1H), 7.94 (t, 1H), 8.29 (d, 1H), 13.43 (br. s, 1H).

Example 98

2-[(3R)-3-methylmorpholin-4-yl]-4-[1-methyl-3-(trifluoromethyl)-1H-pyrazol-5-yl]-8-(1H-pyrazol-5-yl)-1,7-naphthyridine

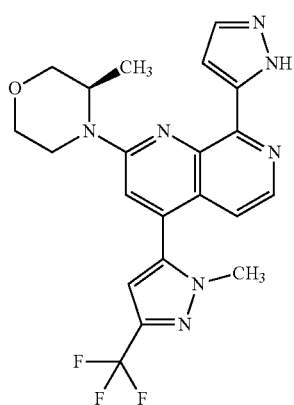 [SMILES: C[C@@H]1COCCN1c1cc(-c2cc(C(F)(F)F)nn2C)c2ccnc(-c3ccn[nH]3)c2n1]

Intermediate-18 (0.060 g, 0.14 mmol) was solubilised in dioxane (3.3 ml) under argon. [1-Methyl-3-(trifluoromethyl)-1H-pyrazol-5-yl]boronic acid (56 mg, 0.28 mmol) was added in one portion followed by addition of caesium carbonate (0.19 g, 0.58 mmol) and PdCl$_2$(dppf) in complex with dichloromethane (11 mg, 0.014 mmol). The reaction was heated for 4 hours in a sealed tube at 110° C. The reaction was then cooled to rt and filtered. The filtrate was concentrated under reduced pressure and purified by flash column chromatography (hexane/ethyl acetate mixture) followed by preparative TLC (hexane/MTBE mixture). The combined fractions were concentrated under reduced pressure, solubilised in methanol (1 ml) and 3N hydrochloric acid (2 ml) was added. The mixture was stirred overnight at rt and then basified with a 3M sodium hydroxide solution. The suspension was filtered and washed with water. The solid was dried under reduced pressure at 60° C. The title compound was obtained in 6% yield (4 mg).

$^1$H-NMR (400 MHz, DMSO-d$_6$): δ [ppm]=1.30 (d, 3H), 3.36-3.42 (m, 1H), 3.52-3.62 (m, 1H), 3.68-3.75 (m, 1H), 3.79-3.87 (m, 4H), 4.01-4.09 (m, 1H), 4.19-4.27 (m, 1H), 4.59-4.68 (m, 1H), 7.13 (s, 1H), 7.25 (d, 1H), 7.43 (br. s, 1H), 7.65 (br. s, 1H), 7.72 (s, 1H), 8.36 (d, 1H), 13.45 (br. s, 1H).

Example 99

2-[(3R)-3-methylmorpholin-4-yl]-4-(3-methyl-2-thienyl)-8-(1H-pyrazol-5-yl)-1,7-naphthyridine

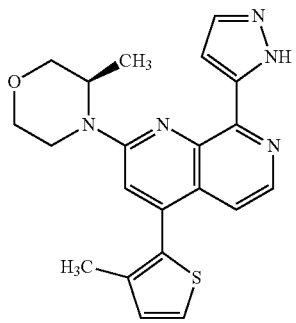 [SMILES: Cc1ccsc1-c1cc(N2CCOC[C@H]2C)nc2c(-c3ccn[nH]3)nccc12]

Intermediate-10 (0.075 g, 0.14 mmol), (3-methylthiophen-2-yl)boronic acid (40 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in methanol (2 ml) and 3M hydrochloric acid (2 ml) was added. The reaction was stirred overnight at rt and then basified with a 3M sodium hydroxide solution. The suspension was filtered and washed with water. The solid was dried under reduced pressure at 60° C. The title compound was obtained in 66% yield (38 mg).

$^1$H-NMR (400 MHz, DMSO-d$_6$): δ [ppm]=1.29 (d, 3H), 2.09 (s, 3H), 3.28-3.39 (m, 1H), 3.51-3.62 (m, 1H), 3.67-3.75 (m, 1H), 3.78-3.85 (m, 1H), 3.99-4.08 (m, 1H), 4.15-4.25 (m, 1H), 4.58-4.67 (m, 1H), 7.16 (d, 1H), 7.32 (d, 1H), 7.41 (d, 1H), 7.46 (s, 1H), 7.64 (d, 1H), 7.73 (d, 1H), 8.34 (d, 1H), 13.35 (br. s, 1H).

Example 100

2-[(3R)-3-methylmorpholin-4-yl]-4-(5-methyl-2-thienyl)-8-(1H-pyrazol-5-yl)-1,7-naphthyridine

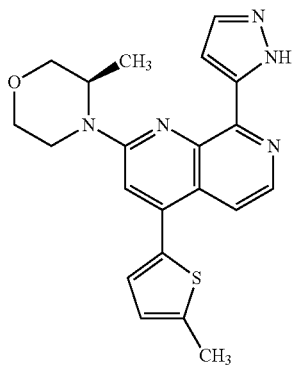

Intermediate-10 (0.075 g, 0.14 mmol), (5-methylthiophen-2-yl)boronic acid (40 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in methanol (2 ml) and 3M hydrochloric acid (2 ml) was added. The reaction was stirred overnight at rt and then basified with a 3M sodium hydroxide solution. The suspension was filtered and washed with water. The solid was dried under reduced pressure at 60° C. The title compound was obtained in 67% yield (39 mg).

$^1$H-NMR (400 MHz, DMSO-d$_6$): δ [ppm]=1.28 (d, 3H), 2.57 (d, 3H), 3.28-3.39 (m, 1H), 3.51-3.61 (m, 1H), 3.67-3.75 (m, 1H), 3.78-3.85 (m, 1H), 4.00-4.08 (m, 1H), 4.15-4.23 (m, 1H), 4.58-4.67 (m, 1H), 7.02 (dd, 1H), 7.34-7.45 (m, 3H), 7.63 (s, 1H), 7.86 (d, 1H), 8.38 (d, 1H), 13.40 (br. s, 1H).

Example 101

2-[(3R)-3-methylmorpholin-4-yl]-4-(4-methyl-3-thienyl)-8-(1H-pyrazol-5-yl)-1,7-naphthyridine

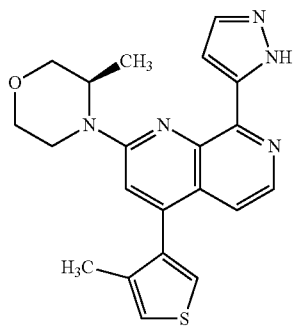 [SMILES: Cc1cscc1-c1cc(N2CCOC[C@H]2C)nc2c(-c3ccn[nH]3)nccc12]

Intermediate-10 (0.075 g, 0.14 mmol), (4-methylthiophen-3-yl)boronic acid (40 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in dichloromethane (2 ml) and 3M hydrochloric acid (2 ml) was added. The reaction was stirred overnight at rt and then basified with a 3M sodium hydroxide solution and extracted three times with dichloromethane. The organic phase was dried (silicon filter) and concentrated under reduced pressure. The title compound was obtained in 76% yield (45 mg).

$^1$H-NMR (400 MHz, DMSO-d$_6$): δ [ppm]=1.29 (d, 3H), 2.03 (d, 3H), 3.33 (s, 3H), 3.51-3.62 (m, 1H), 3.67-3.75 (m, 1H), 3.77-3.84 (m, 1H), 4.00-4.08 (m, 1H), 4.17-4.26 (m, 1H), 4.57-4.67 (m, 1H), 7.17 (d, 1H), 7.37-7.47 (m, 3H), 7.64 (d, 1H), 7.68 (d, 1H), 8.31 (d, 1H), 13.40 (br. s, 1H).

Example 102

4-(3-chloro-2-thienyl)-2-[(3R)-3-methylmorpholin-4-yl]-8-(1H-pyrazol-5-yl)-1,7-naphthyridine

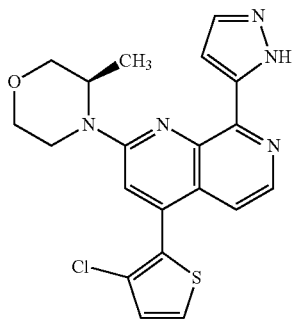 [SMILES: C[C@@H]1COCCN1c1cc(-c2sccc2Cl)c2ccnc(-c3ccn[nH]3)c2n1]

Intermediate-10 (0.075 g, 0.14 mmol), (3-chlorothiophen-2-yl)boronic acid (46 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/ammonium hydroxyde). The combined fractions were concentrated under reduced pressure, solubilised in methanol (2 ml) and 3M hydrochloric acid (2 ml) was added. The reaction was stirred overnight at rt and then basified with a 3M sodium hydroxide solution. The suspension was filtered and washed with water. The solid was dried under reduced pressure at 60° C. The title compound was obtained in 4% yield (2 mg).

$^1$H-NMR (400 MHz, DMSO-d$_6$): δ [ppm]=1.29 (d, 3H), 3.34-3.39 (m, 1H), 3.52-3.62 (m, 1H), 3.68-3.75 (m, 1H), 3.78-3.85 (m, 1H), 3.99-4.08 (m, 1H), 4.16-4.25 (m, 1H), 4.58-4.67 (m, 1H), 7.28 (d, 1H), 7.35 (d, 1H), 7.40 (s, 1H), 7.58 (s, 1H), 7.65 (s, 1H), 7.98 (d, 1H), 8.36 (d, 1H), 13.41 (br. s, 1H).

Example 103

2-[(3R)-3-methylmorpholin-4-yl]-4-(2-methyl-3-thienyl)-8-(1H-pyrazol-5-yl)-1,7-naphthyridine

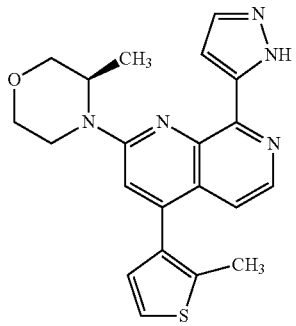 [SMILES: Cc1sccc1-c1cc(N2CCOC[C@H]2C)nc2c(-c3ccn[nH]3)nccc12]

Intermediate-10 (0.10 g, 0.19 mmol), 2-methylthiophene-3-boronic acid pinacol ester (85 mg, 0.38 mmol), aq. potassium carbonate (0.28 ml, 2 M) and PdCl$_2$(PPh$_3$)$_2$ (13 mg, 0.019 mmol) were solubilised in dimethoxyethane (5 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in methanol (2 ml) and concentrated hydrochloric acid (1.5 ml) was added. The reaction was stirred overnight at rt and then basified with a saturated solution of sodium hydrogen carbonate and extracted three times with dichloromethane. The organic phase was dried (silicon filter) and concentrated under reduced pressure. The title compound was obtained in 48% yield (37 mg).

$^1$H-NMR (400 MHz, DMSO-d$_6$): δ [ppm]=1.28 (d, 3H), 2.32 (s, 3H), 3.34-3.38 (m, 1H), 3.51-3.62 (m, 1H), 3.66-3.75 (m, 1H), 3.79 (d, 1H), 4.00-4.08 (m, 1H), 4.16-4.25 (m, 1H), 4.57-4.66 (m, 1H), 7.12 (d, 1H), 7.23 (d, 1H), 7.40 (d, 2H), 7.53 (d, 1H), 7.63 (br. s., 1H), 8.31 (d, 1H), 13.41 (br. s, 1H).

Example 104

2-[(3R)-3-methylmorpholin-4-yl]-8-(1H-pyrazol-5-yl)-4-(1H-pyrrolo[2,3-b]pyridin-4-yl)-1,7-naphthyridine

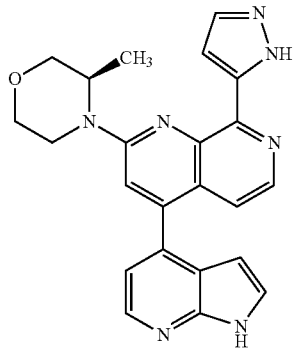 [SMILES: C[C@@H]1COCCN1c1cc(-c2ccnc3[nH]ccc23)c2ccnc(-c3ccn[nH]3)c2n1]

Intermediate-10 (0.075 g, 0.14 mmol), 4-(4,4,5,5-tetramethyl-1,3,2-dioxaborolan-2-yl)-1 h-pyrrolo[2,3-b]pyridine (69 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was diluted with water and extracted with dichloromethane and the ethyl acetate. The combined organic phases were dried (silicon filter) and concentrated under reduced pressure. The crude material was purified by preparative HPLC (acetonitrile/water/formic acid). The combined fractions were concentrated under reduced pressure, solubilised in methanol (2 ml) and concentrated hydrochloric acid (1.5 ml) was added. The reaction was stirred overnight at rt and then basified with a saturated solution of sodium hydrogen carbonate and extracted three times with dichloromethane. The organic phase was dried (silicon filter) and concentrated under reduced pressure. The title compound was obtained in 71% yield (43 mg).

$^1$H-NMR (400 MHz, DMSO-d$_6$): δ [ppm]=1.31 (d, 3H), 3.35-3.42 (m, 1H), 3.57 (t, 1H), 3.72 (d, 1H), 3.81 (d, 1H), 4.05 (d, 1H), 4.22 (d, 1H), 4.58-4.67 (m, 1H), 6.13-6.18 (m, 1H), 7.22 (t, 2H), 7.46 (s, 1H), 7.54 (s, 2H), 7.63-7.67 (m, 1H), 8.26 (d, 1H), 8.40 (d, 1H), 11.96 (br. s, 1H), 13.44 (br. s, 1H).

Example 105

4-(3,5-dimethyl-1,2-oxazol-4-yl)-2-[(3R)-3-methylmorpholin-4-yl]-8-(1H-pyrazol-5-yl)-1,7-naphthyridine

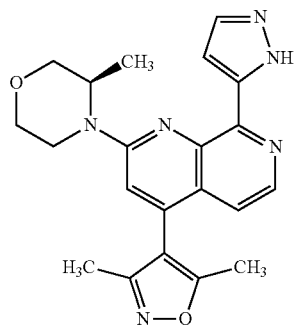 [SMILES: Cc1noc(C)c1-c1cc(N2CCOC[C@H]2C)nc2c(-c3ccn[nH]3)nccc12]

Intermediate-10 (0.075 g, 0.14 mmol), 3,5-dimethylisoxazole-4-boronic acid (40 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was diluted with water and filtered. The solid was purified by preparative HPLC (acetonitrile/water/formic acid). The combined fractions were concentrated under reduced pressure, solubilised in methanol (2 ml) and concentrated hydrochloric acid (1.5 ml) was added. The reaction was stirred overnight at rt and then basified with a saturated solution of sodium hydrogen carbonate and extracted three times with dichloromethane. The organic phase was dried (silicon filter) and concentrated under reduced pressure. The title compound was obtained in 42% yield (24 mg).

$^1$H-NMR (400 MHz, DMSO-d$_6$): δ [ppm]=1.29 (d, 3H), 2.12 (s, 3H), 2.32 (s, 3H), 3.35-3.40 (m, 1H), 3.57 (t, 1H), 3.72 (d, 1H), 3.82 (d, 1H), 4.05 (d, 1H), 4.22 (d, 1H), 4.61 (d, 1H), 7.21-7.28 (m, 1H), 7.42 (s, 1H), 7.52 (s, 1H), 7.62-7.67 (m, 1H), 8.33 (d, 1H), 13.43 (br. s, 1H).

Example 106

4-(3-chloro-2-methoxypyridin-4-yl)-2-[(3R)-3-methylmorpholin-4-yl]-8-(1H-pyrazol-5-yl)-1,7-naphthyridine

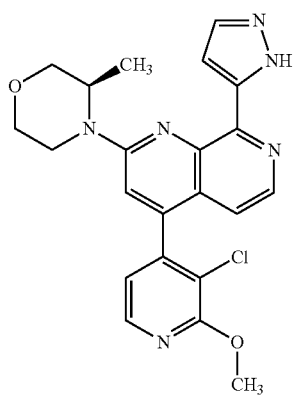 [SMILES: COc1nccc(-c2cc(N3CCOC[C@H]3C)nc3c(-c4ccn[nH]4)nccc23)c1Cl]

Intermediate-10 (0.075 g, 0.14 mmol), 3-chloro-2-methoxypyridine-4-boronic acid (53 mg, 0.28 mmol), aq. potassium carbonate (0.21 ml, 2 M) and PdCl$_2$(PPh$_3$)$_2$ (10 mg, 0.019 mmol) were solubilised in dimethoxyethane (4 ml). The reaction mixture was stirred for 10 minutes at 130° C. under microwave irradiation. After cooling to rt, the reaction mixture was diluted with water and filtered. The solid was purified by preparative HPLC (acetonitrile/water/formic acid). The combined fractions were concentrated under reduced pressure, solubilised in methanol (2 ml) and concentrated hydrochloric acid (1.5 ml) was added. The reaction was stirred 2 hours at rt and then basified with a saturated solution of sodium hydrogen carbonate and extracted three times with dichloromethane. The organic phase was dried (silicon filter) and concentrated under reduced pressure. The title compound was obtained in 22% yield (14 mg).

$^1$H-NMR (400 MHz, DMSO-d$_6$): δ [ppm]=1.25-1.33 (m, 3H), 3.34-3.40 (m, 1H), 3.52-3.61 (m, 1H), 3.67-3.74 (m, 1H), 3.78-3.85 (m, 1H), 4.04 (s, 4H), 4.16-4.24 (m, 1H), 4.55-4.64 (m, 1H), 7.01-7.06 (m, 1H), 7.18 (d, 1H), 7.42 (s, 1H), 7.51-7.55 (m, 1H), 7.61-7.67 (m, 1H), 8.25-8.34 (m, 2H), 13.42 (br. s, 1H).

Example 107

2-[(3R)-3-methylmorpholin-4-yl]-8-(1H-pyrazol-5-yl)-4-(tetrahydro-2H-pyran-4-yl)-1,7-naphthyridine

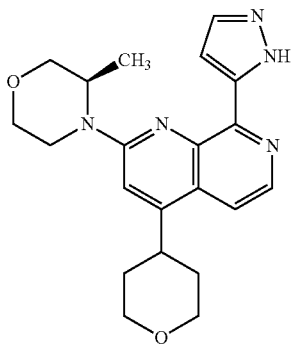 [SMILES: C[C@@H]1COCCN1c1cc(C2CCOCC2)c2ccnc(-c3ccn[nH]3)c2n1]

Intermediate-18 (0.10 g, 0.22 mmol) and 3,6-dihydro-2H-pyran-4-boronic acid pinacolester (95 mg, 0.43 mmol) were solubilised in dioxane (5 ml). Caesium carbonate (0.28 g, 0.87 mmol) and PdCl$_2$(dppf) in complex with dichloromethane (18 mg, 0.021 mmol) were added sequentially. The reaction was heated for 4 hours in a sealed tube at 110° C. 3,6-Dihydro-2H-pyran-4-boronic acid pinacolester (53 mg, 0.22 mmol) was added and the reaction was stirred for 48 hours at 110° C. The reaction was then cooled to rt, diluted with water and extracted with ethyl acetate. The organic phase was dried (MgSO$_4$), filtered and concentrated under reduced pressure. The crude mixture was solubilised in dichloromethane (6 ml) and 1M hydrochloric acid (1.2 ml) was added. The reaction was stirred overnight and basified using a saturated solution of sodium hydrogen carbonate. The reaction mixture was diluted with water and extracted with dichloromethane. The organic phase was washed with brine, dried (MgSO$_4$), filtered and concentrated under reduced pressure. The crude material (42 mg) was solubilised in methanol (2 ml) and was hydrogenated in an autoclave (10.5 bar) at rt for 18 hours using 10% Pd/C (20 mg). The reaction mixture was filtered through Celite® and concentrated under reduced pressure. The crude material was purified by flash chromatography (hexane/ethyl acetate mixture) and the title compound was obtained in 10% yield (11 mg).

$^1$H-NMR (400 MHz, DMSO-d$_6$): d [ppm]=1.26 (d, 3H), 1.73-1.81 (m, 2H), 1.89 (qd, 2H), 3.33-3.35 (m, 1H), 3.50-3.58 (m, 2H), 3.59-3.67 (m, 2H), 3.70-3.75 (m, 1H), 3.79-3.84 (m, 1H), 3.96-4.09 (m, 3H), 4.19 (d, 1H), 4.60-4.70 (m, 1H), 7.31 (s, 1H), 7.37 (s, 1H), 7.60 (s, 1H), 7.89 (d, 1H), 8.37 (d, 1H), 13.36 (br. s., 1H).

Example 108

4-(3,6-dihydro-2H-thiopyran-4-yl)-2-[(3R)-3-methylmorpholin-4-yl]-8-(1H-pyrazol-5-yl)-1,7-naphthyridine

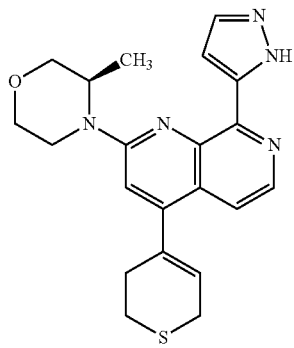 [SMILES: C[C@@H]1COCCN1c1cc(C2=CCSCC2)c2ccnc(-c3ccn[nH]3)c2n1]

Intermediate-10 (0.30 g, 0.53 mmol), 2-(3,6-dihydro-2H-thiopyran-4-yl)-4,4,5,5-tetramethyl-1,3,2-dioxaborolane (0.25 g, 1.1 mmol), aq. potassium carbonate (0.85 ml, 2 M) and $PdCl_2(PPh_3)_2$ (40 mg, 0.056 mmol) were solubilised in dimethoxyethane (12 ml). The reaction mixture was stirred for 10 minutes at 130° C. under microwave irradiation. After cooling to rt, the reaction mixture was dried by filtration and the filtrate was concentrated under reduced pressure. The crude material was purified by preparative HPLC (acetonitrile/water/formic acid mixture). The combined fractions were concentrated under reduced pressure, solubilised in dichloromethane and washed with a saturated solution of sodium hydrogen carbonate. The organic phase was dried (silicon filter) and concentrated under reduced pressure. The title compound was obtained in 45% yield (100 mg).

$^1$H-NMR (400 MHz, DMSO-$d_6$): δ [ppm]=1.27 (d, 3H), 2.56-2.62 (m, 2H), 2.93 (t, 2H), 3.26-3.32 (m, 1H), 3.36-3.40 (m, 2H), 3.55 (td, 1H), 3.70 (dd, 1H), 3.81 (d, 1H), 4.00-4.08 (m, 1H), 4.18 (d, 1H), 4.57-4.64 (m, 1H), 6.00-6.04 (m, 1H), 7.30 (s, 1H), 7.38 (br. s., 1H), 7.58 (d, 1H), 7.62 (br. s., 1H), 8.34 (d, 1H), 13.38 (br. s., 1H).

Example 109

2-[(3R)-3-methylmorpholin-4-yl]-4-(4-methylpiperidin-1-yl)-8-(1H-pyrazol-5-yl)-1,7-naphthyridine

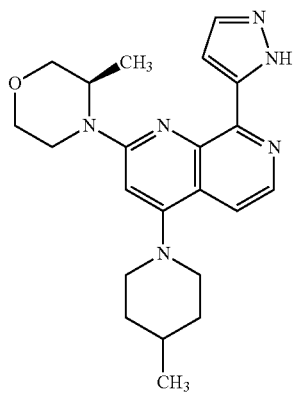 [SMILES: CC1CCN(c2cc(N3CCOC[C@H]3C)nc3c(-c4ccn[nH]4)nccc23)CC1]

Intermediate-10 (0.075 g, 0.14 mmol) was solubilised in N-methyl-2-pyrrolidone (2 ml) and 4-methylpiperidine (0.061, 51 mg, 0.50 mmol) was added. The reaction mixture was stirred at 70° C. overnight. The mixture was cooled to rt, diluted with ethyl acetate and washed with a half saturated solution of sodium chloride. The organic phase was dried (silicon filter) and concentrated under reduced pressure. The crude material was purified by preparative HPLC $^1$H-NMR (400 MHz, DMSO-$d_6$): δ [ppm]=0.98 (d, 3H), 1.21 (d, 4H), 1.35-1.49 (m, 2H), 1.49-1.63 (m, 1H), 1.75 (d, 2H), 2.69-2.82 (m, 2H), 3.19-3.28 (m, 1H), 3.39-3.50 (m, 3H), 3.65 (dd, 1H), 3.77 (d, 1H), 4.03-4.10 (m, 1H), 4.52 (dd, 1H), 6.69 (s, 1H), 7.30 (s, 1H), 7.51 (d, 1H), 7.56 (s, 1H), 8.26 (d, 1H), 13.31 (br. s., 1H).

Example 110

4-(1-tert-butyl-1H-pyrazol-5-yl)-2-[(3R)-3-methylmorpholin-4-yl]-8-(1H-pyrazol-5-yl)-1,7-naphthyridine

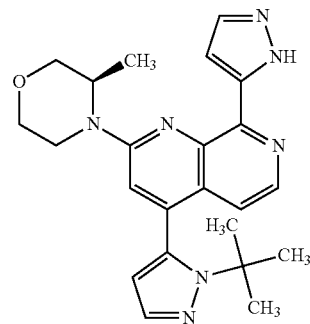 [SMILES: C[C@@H]1COCCN1c1cc(-c2ccnn2C(C)(C)C)c2ccnc(-c3ccn[nH]3)c2n1]

Intermediate-10 (0.1 g, 0.19 mmol), 1-tert-butyl-1H-pyrazole-5-boronic acid pinacol ester (95 mg, 0.0.38 mmol), aq. potassium carbonate (0.81 ml, 2 M) and $PdCl_2(PPh_3)_2$ (13 mg, 0.019 mmol) were solubilised in dimethoxyethane (7 ml). The reaction mixture was stirred for 10 minutes at 130° C. under microwave irradiation. After cooling to rt, the reaction mixture was diluted with dichloromethane and dried by filtration and the filtrate was concentrated under reduced pressure. The crude material was purified by preparative HPLC (acetonitrile/water/formic acid mixture). The combined fractions were concentrated under reduced pressure, solubilised in methanol (2 ml) and concentrated hydrochloric acid (1 ml) was added. The mixture was stirred for 2 hours at rt and then quenched with a saturated aqueous solution of sodium hydrogen carbonate. The aqueous phase was extracted three times with dichloromethane. The organic phase was dried (silicon filter) and concentrated under reduced pressure. The title compound was obtained in 18% yield (15 mg).

$^1$H-NMR (400 MHz, DMSO-$d_6$): δ [ppm]=1.21-1.31 (m, 3H), 1.38 (s, 9H), 3.35-3.41 (m, 1H), 3.52-3.63 (m, 1H), 3.67-3.76 (m, 1H), 3.77-3.85 (m, 1H), 4.00-4.10 (m, 1H), 4.17-4.27 (m, 1H), 4.56-4.65 (m, 1H), 6.34-6.40 (m, 1H), 6.96 (t, 1H), 7.44 (s, 1H), 7.59-7.68 (m, 3H), 8.30-8.35 (m, 1H), 13.44 (br. s, 1H).

Example 111

2-[(3R)-3-methylmorpholin-4-yl]-4-(1-methyl-1H-pyrazol-5-yl)-8-(1H-pyrazol-5-yl)-1,7-naphthyridine

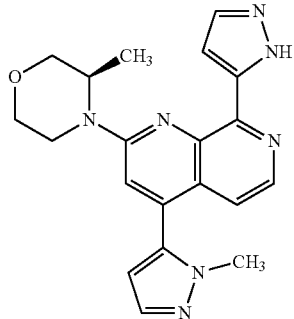 [SMILES: C[C@@H]1COCCN1c1cc(-c2ccnn2C)c2ccnc(-c3ccn[nH]3)c2n1]

Intermediate-10 (0.5 g, 0.95 mmol), 1-methyl-5-(4,4,5,5-tetramethyl-1,3,2-dioxaborolan-2-yl)-1H-pyrazole (415 mg, 1.9 mmol), aq. potassium carbonate (1.4 ml, 2 M) and PdCl$_2$(PPh$_3$)$_2$ (67 mg, 0.094 mmol) were solubilised in dimethoxyethane (60 ml). The reaction mixture was stirred for 20 minutes at 130° C. under microwave irradiation. After cooling to rt, the reaction mixture was filtered through a silicon filter and concentrated under reduced pressure. The crude material was purified by flash column chromatography (hexane/ethyl acetate/ethanol mixture). The desired fractions were concentrated under reduced pressure and solubilised in conc. sulphuric acid (5 ml). The mixture was stirred for 3 h at rt. The mixture was then poured into ice and basified using solid sodium hydrogen carbonate. The suspension was filtered and the solid was stirred with ethanol at 40° C., filtered and dried under reduced pressure. The title compound was obtained in 78% yield (0.28 g).

$^1$H-NMR (400 MHz, DMSO-d$_6$): δ [ppm]=1.30 (d, 3H), 3.30-3.40 (m, 1H), 3.51-3.62 (m, 1H), 3.68-3.77 (m, 4H), 3.79-3.86 (m, 1H), 4.01-4.09 (m, 1H), 4.18-4.28 (m, 1H), 4.60-4.69 (m, 1H), 6.59 (d, 1H), 7.27 (d, 1H), 7.42 (s, 1H), 7.60 (s, 1H), 7.63-7.69 (m, 2H), 8.35 (d, 1H), 13.42 (br. s, 1H).

Example 112

2-[(3R)-3-methylmorpholin-4-yl]-4-(3-methyl-1,2-oxazol-5-yl)-8-(1H-pyrazol-5-yl)-1,7-naphthyridine

Step a

2-[(3R)-3-methylmorpholin-4-yl]-4-(3-methyl-1,2-oxazol-5-yl)-8-[1-(tetrahydro-2H-pyran-2-yl)-w1H-pyrazol-5-yl]-1,7-naphthyridine

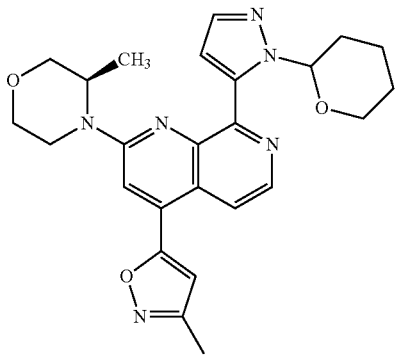 [SMILES: Cc1cc(-c2cc(N3CCOC[C@H]3C)nc3c(-c4ccnn4C4CCCCO4)nccc23)on1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 79 mg (0.38 mmol) 3-methyl-5-(4,4,5,5-tetramethyl-1,3,2-dioxaborolan-2-yl)-1,2-oxazole, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(3-methyl-1,2-oxazol-5-yl)-8-(1H-pyrazol-5-yl)-1,7-naphthyridine

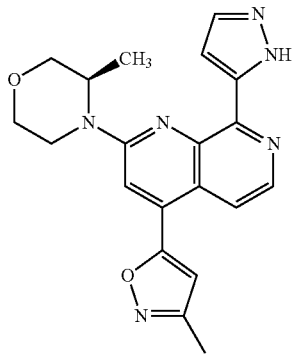 [SMILES: Cc1cc(-c2cc(N3CCOC[C@H]3C)nc3c(-c4ccn[nH]4)nccc23)on1]

A solution of 160 mg of crude 2-[(3R)-3-methylmorpholin-4-yl]-4-(3-methyl-1,2-oxazol-5-yl)-8-[1-(tetrahydro-2H-pyran-2-yl)-1H-pyrazol-5-yl]-1,7-naphthyridine from step a in 6.7 ml of methanol and 0.35 ml of 2N hydrochloric acid was stirred for 1 h at room temperature. The reaction mixture was diluted with a saturated aqueous sodium chloride solution and extracted with ethyl acetate (2×). The combined organic phases were dried (MgSO$_4$), filtered and concentrated to dryness. The residue was purified by preparative HPLC (Autopurifier: basic conditions) to give 4 mg (0.01 mmol) of the desired product.

$^1$H-NMR (400 MHz, DMSO-d6): δ [ppm]=1.30 (3H), 2.40 (3H), 3.37 (1H), 3.51-3.64 (1H), 3.73 (1H), 3.84 (1H), 4.00-4.11 (1H), 4.23 (1H), 4.58-4.72 (1H), 7.22 (1H), 7.36-7.44 (1H), 7.59-7.67 (1H), 7.79 (1H), 7.92 (1H), 8.43 (1H), 13.36-13.48 (1H).

Example 113

4-(1-ethyl-3-methyl-1H-pyrazol-5-yl)-2-[(3R)-3-methylmorpholin-4-yl]-8-(1H-pyrazol-5-yl)-1,7-naphthyridine

Step a

4-(1-ethyl-3-methyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

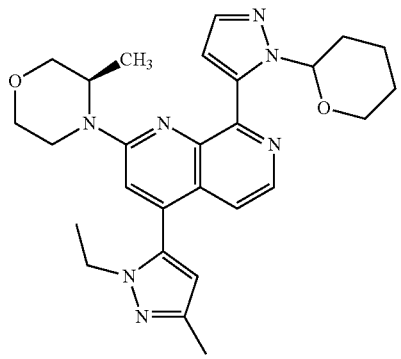 [SMILES: CCn1nc(C)cc1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 90 mg (0.38 mmol) 1-ethyl-3-methyl-5-(4,4,5,5-tetramethyl-1,3,2-dioxaborolan-2-yl)-1H-pyrazole, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-(1-ethyl-3-methyl-1H-pyrazol-5-yl)-2-[(3R)-3-methylmorpholin-4-yl]-8-(1H-pyrazol-5-yl)-1,7-naphthyridine

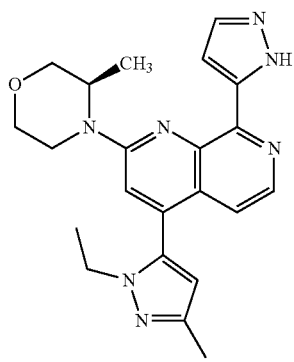 [SMILES: CCn1nc(C)cc1-c1cc(N2CCOC[C@H]2C)nc2c(-c3ccn[nH]3)nccc12]

A solution of 127 mg of crude 4-(1-ethyl-3-methyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine from step a in 2.5 ml of methanol and 0.26 ml of 2N hydrochloric acid was stirred for 90 minutes at room temperature. The reaction mixture was diluted with a saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 18 mg (0.04 mmol) of the desired product.

$^1$H-NMR (400 MHz, DMSO-d6): δ [ppm]=1.20 (3H), 1.29 (3H), 2.28 (3H), 3.51-3.63 (1H), 3.72 (1H), 3.82 (1H), 3.89 (2H), 4.05 (1H), 4.22 (1H), 4.63 (1H), 6.33 (1H), 7.24 (1H), 7.43 (1H), 7.54 (1H), 7.64 (1H), 8.35 (1H), 13.44 (1H).

Example 114

4-(1,4-dimethyl-1H-pyrazol-5-yl)-2-[(3R)-3-methylmorpholin-4-yl]-8-(1H-pyrazol-5-yl)-1,7-naphthyridine

Step a

4-(1,4-dimethyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

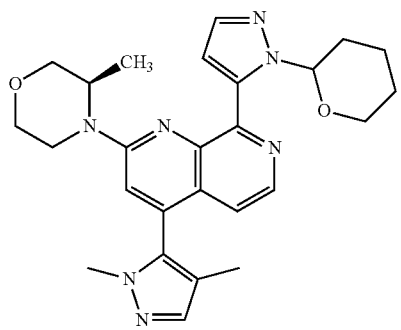 [SMILES: Cc1cnn(C)c1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) 1(1,4-dimethyl-1H-pyrazol-5-yl)boronic acid, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-(1,4-dimethyl-1H-pyrazol-5-yl)-2-[(3R)-3-methyl-morpholin-4-yl]-8-(1H-pyrazol-5-yl)-1,7-naphthyridine

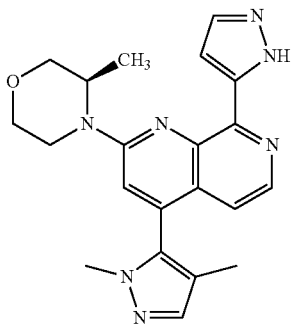 [SMILES: Cc1cnn(C)c1-c1cc(N2CCOC[C@H]2C)nc2c(-c3ccn[nH]3)nccc12]

A solution of 102 mg of crude 4-(1,4-dimethyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine from step a in 4.2 ml of methanol and 0.22 ml of 2N hydrochloric acid was stirred for 1 hour at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 12 mg (0.03 mmol) of the desired product.

$^1$H-NMR (400 MHz, DMSO-d6): δ [ppm]=1.30 (3H), 1.88 (3H), 3.49-3.69 (4H), 3.69-3.76 (1H), 3.82 (1H), 4.06 (1H), 4.25 (1H), 4.64 (1H), 7.05 (1H), 7.44 (1H), 7.50 (1H), 7.58 (1H), 7.65 (1H), 8.35 (1H), 13.44 (1H).

Example 115

4-[2-methyl-6-(methylsulfanyl)pyridin-3-yl]-2-[(3R)-3-methylmorpholin-4-yl]-8-(1H-pyrazol-5-yl)-1,7-naphthyridine

Step a

4-[2-methyl-6-(methylsulfanyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

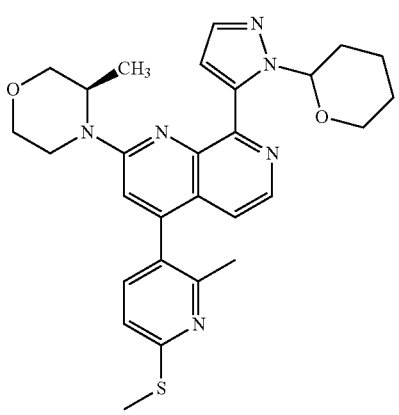 [SMILES: CSc1ccc(-c2cc(N3CCOC[C@H]3C)nc3c(-c4ccnn4C4CCCCO4)nccc23)c(C)n1]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 26 mg (0.14 mmol) [2-methyl-6-(methylsulfanyl)pyridin-3-yl]boronic acid, 11 mg (0.014 mmol) of [1,1'-bis(diphenylphosphino)ferrocene]dichloropalladium(II) complex with dichloromethane (1:1, Pd(dppf)Cl$_2$) and 49 mg (0.36 mmol) of potassium carbonate in 3.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-methyl-6-(methylsulfanyl)pyridin-3-yl]-2-[(3R)-3-methylmorpholin-4-yl]-8-(1H-pyrazol-5-yl)-1,7-naphthyridine

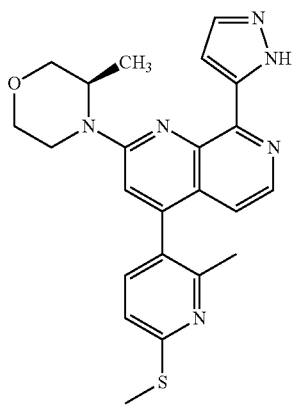 [SMILES: CSc1ccc(-c2cc(N3CCOC[C@H]3C)nc3c(-c4ccn[nH]4)nccc23)c(C)n1]

A solution of 119 mg of crude 4-[2-methyl-6-(methylsulfanyl)pyridin-3-yl]-2-[(3R)-3-methylmorpholin-4-yl]-8-[1-(tetrahydro-2H-pyran-2-yl)-1H-pyrazol-5-yl]-1,7-naphthyridine from step a in 5.5 ml of methanol and 0.23 ml of 2N hydrochloric acid was stirred for 1 hour at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 15 mg (0.04 mmol) of the desired product.

$^1$H-NMR (400 MHz, DMSO-d6): δ [ppm]=1.30 (3H), 2.24 (3H), 2.55-2.63 (3H), 3.49-3.64 (1H), 3.72 (1H), 3.82 (1H), 3.98-4.13 (1H), 4.22 (1H), 4.61 (1H), 7.05 (1H), 7.32 (1H), 7.37-7.53 (2H), 7.53-7.70 (2H), 8.30 (1H), 13.42 (1H).

Example 116

4-[2-methyl-6-(S-methylsulfonimidoyl)pyridin-3-yl]-2-[(3R)-3-methylmorpholin-4-yl]-8-(1H-pyrazol-5-yl)-1,7-naphthyridine

Step a

4-[2-methyl-6-(methylsulfanyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

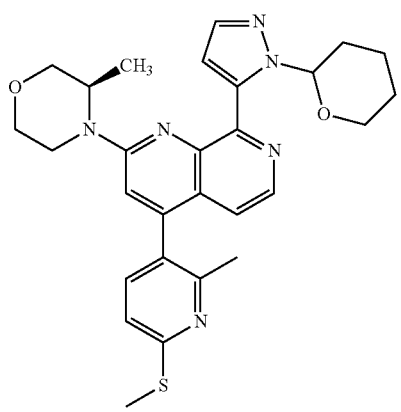 [SMILES: CSc1ccc(-c2cc(N3CCOC[C@H]3C)nc3c(-c4ccnn4C4CCCCO4)nccc23)c(C)n1]

A suspension of 250 mg (0.47 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 87 mg (0.47 mmol) [2-methyl-6-(methylsulfanyl)pyridin-3-yl]boronic acid, 38 mg (0.047 mmol) of [1,1'-bis(diphenylphosphino)ferrocene]dichloropalladium(II) complex with dichloromethane (1:1, Pd(dppf)Cl$_2$) and 164 mg (1.19 mmol) of potassium carbonate in 10.0 ml of MeCN and 3.3 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated. The residue was purified by column chromatography (gradient from 100% Hex to 100% EtOAc) to give 170 mg (0.33 mmol) of the desired product.

$^1$H-NMR (400 MHz, DMSO-d6): δ [ppm]=1.15-1.35 (3H), 1.46 (2H), 1.52-1.69 (1H), 1.88-2.07 (2H), 2.25 (3H), 2.30-2.45 (1H), 2.56-2.64 (3H), 3.14-3.29 (2H), 3.39-3.55 (1H), 3.58-3.68 (1H), 3.68-3.82 (2H), 3.97 (1H), 4.18 (1H), 4.52 (1H), 6.08-6.22 (1H), 6.93-7.06 (1H), 7.10 (1H), 7.32 (1H), 7.37-7.48 (1H), 7.56-7.68 (2H), 8.33 (1H).

Step b 2,2,2-trifluoro-N-[methyl(6-methyl-5-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-yl)-λ$^4$-sulfanylidene]acetamide

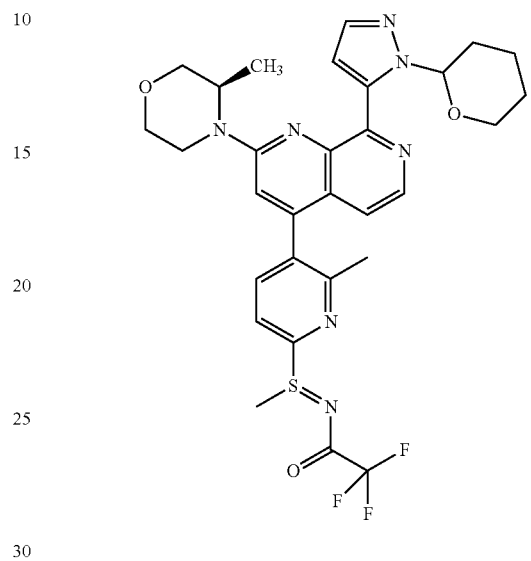

Under an atmosphere of argon, a solution of 43 mg (0.38 mmol) 2,2,2-trifluoroacetamide in 0.20 ml THF was added dropwise to a solution of 24 mg (0.25 mmol) sodium tert.-butoxide in 0.25 ml THF, so that the temperature of the mixture remained below 10° C. Subsequently, a freshly prepared solution of 47 mg (0.16 mmol) 1,3-dibromo-5,5-dimethylhydantoin in 0.25 ml THF was added dropwise to the stirred mixture, so that the temperature of the mixture remained below 10° C. Then the mixture was stirred for 10 minutes at 10° C. Finally, a solution of 130 mg (0.25 mmol) 4-[2-methyl-6-(methylsulfanyl)pyridin-3-yl]-2-[(3R)-3-methylmorpholin-4-yl]-8-[1-(tetrahydro-2H-pyran-2-yl)-1H-pyrazol-5-yl]-1,7-naphthyridine in 0.8 ml THF was added dropwise to the stirred mixture, so that the temperature of the mixture remained below 10° C. The mixture was stirred for 3 hours at 10° C. and then at room temperature overnight. The batch was diluted with 1.0 ml toluene under cooling and an aqueous solution of 32 mg (0.25 mmol) sodium sulfite in 0.9 ml water was added so that the temperature of the mixture remained below 15° C. The batch was extracted three times with ethyl acetate. The combined organic phases were washed with an aqueous solution of sodium chloride, filtered using a Whatman filter and concentrated. The residue was purified by column chromatography on silica gel (ethyl acetate) to give 28 mg of the desired product containing slight impurities.

Step c

4-[2-methyl-6-(S-methylsulfonimidoyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

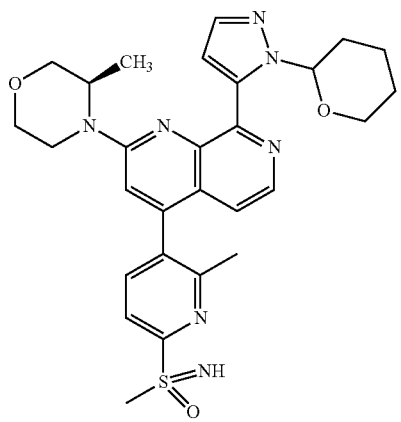 [SMILES: Cc1nc(S(C)(=N)=O)ccc1-c1cc(N2CCOC[C@H]2C)nc2c(-c3ccnn3C3CCCCO3)nccc12]

28 mg (0.045 mmol) 2,2,2-trifluoro-N-[methyl-5-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-yl)-λ4-sulfanylidene]acetamide was dissolved in 0.87 ml methanol. To this solution 0.31 ml water was added. The pH was adjusted to 10.5 by addition of an aqueous solution of potassium hydroxide (25%). 23 mg (0.038 mmol) Oxone® was added and the mixture was stirred at room temperature for 5 hours. Additional amount 23 mg (0.038 mmol) Oxone® was added. The pH was adjusted to 10.5 by addition of an aqueous solution of potassium hydroxide (25%). The batch was stirred at room temperature for 3 hours. The batch was filtered and the filtrate was adjusted to pH 6-7 by the addition of 1N aqueous hydrogen chloride solution. The mixture was diluted with aqueous sodium chloride solution and extracted with DCM (2×). The combined organic phases were washed with an aqueous solution of sodium sulfite (10%), filtered using a Whatman filter, and concentrated to give 10 mg crude product that was used without further purification.

Step d

4-[2-methyl-6-(S-methylsulfonimidoyl)pyridin-3-yl]-2-[(3R)-3-methylmorpholin-4-yl]-8-(1H-pyrazol-5-yl)-1,7-naphthyridine

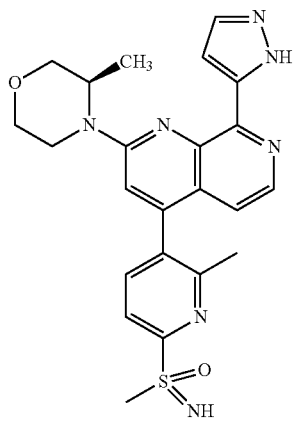 [SMILES: Cc1nc(S(C)(=N)=O)ccc1-c1cc(N2CCOC[C@H]2C)nc2c(-c3ccn[nH]3)nccc12]

A solution of 10 mg of crude 4-[2-methyl-6-(S-methylsulfonimidoyl)pyridin-3-yl]-2-[(3R)-3-methylmorpholin-4-yl]-8-[1-(tetrahydro-2H-pyran-2-yl)-1H-pyrazol-5-yl]-1,7-naphthyridine from step c in 1.0 ml of methanol and 0.02 ml of 2N hydrochloric acid was stirred for 2 hour at room temperature. The reaction mixture was diluted with saturated aqueous sodium bicarbonate solution and extracted with ethyl acetate (2×). The combined organic phases were dried (MgSO₄), filtered and concentrated to dryness. The residue was purified by preparative HPLC (Autopurifier: acidic conditions) to give 2 mg (0.004 mmol) of the desired product.

¹H-NMR (400 MHz, DMSO-d6): δ [ppm]=1.23-1.40 (3H), 2.22-2.41 (3H), 3.25 (3H), 3.38 (1H), 3.46-3.65 (1H), 3.72 (1H), 3.82 (1H), 4.05 (1H), 4.13-4.32 (1H), 4.53 (1H), 4.62 (1H), 6.91-7.11 (1H), 7.46 (1H), 7.58 (1H), 7.66 (1H), 7.99-8.17 (2H), 8.31 (1H).

Example 117

2-[(3R)-3-methylmorpholin-4-yl]-4-(1-propyl-1H-pyrazol-5-yl)-8-(1H-pyrazol-5-yl)-1,7-naphthyridine

Step a

2-[(3R)-3-methylmorpholin-4-yl]-4-(1-propyl-1H-pyrazol-5-yl)-8-[1-(tetrahydro-2H-pyran-2-yl)-1H-pyrazol-5-yl]-1,7-naphthyridine

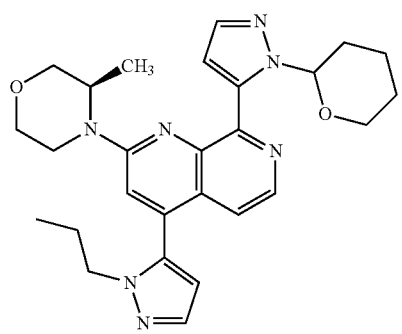 [SMILES: CCCn1nccc1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 34 mg (0.14 mmol) 1-propyl-5-(4,4,5,5-tetramethyl-1,3,2-dioxaborolan-2-yl)-1H-pyrazole, 11 mg (0.014 mmol) of [1,1'-bis(diphenylphosphino)ferrocene]dichloropalladium(II) complex with dichloromethane (1:1, Pd(dppf)Cl₂) and 49 mg (0.36 mmol) of potassium carbonate in 3.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(1-propyl-1H-pyrazol-5-yl)-8-(1H-pyrazol-5-yl)-1,7-naphthyridine

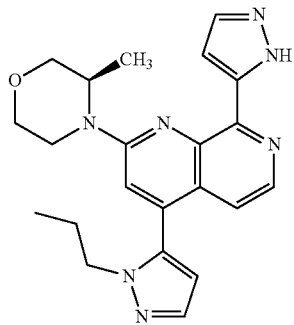 [SMILES: CCCn1nccc1-c1cc(N2CCOC[C@H]2C)nc2c(-c3ccn[nH]3)nccc12]

A solution of 110 mg of crude 2-[(3R)-3-methylmorpholin-4-yl]-4-(1-propyl-1H-pyrazol-5-yl)-8-[1-(tetrahydro-2H-pyran-2-yl)-1H-pyrazol-5-yl]-1,7-naphthyridine from step a in 5.4 ml of methanol and 0.23 ml of 2N hydrochloric acid was stirred for 1 hour at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 11 mg (0.03 mmol) of the desired product.

$^1$H-NMR (400 MHz, DMSO-d6): δ [ppm]=0.64 (3H), 1.29 (3H), 1.63 (2H), 3.34 (1H), 3.59 (1H), 3.73 (1H), 3.82 (1H), 3.89-4.02 (2H), 4.02-4.12 (1H), 4.23 (1H), 4.63 (1H), 6.55 (1H), 7.21 (1H), 7.44 (1H), 7.57 (1H), 7.60-7.74 (2H), 8.35 (1H), 13.43 (1H).

Example 118

4-(6,7-dihydro-5H-pyrrolo[1,2-a]imidazol-3-yl)-2-[(3R)-3-methylmorpholin-4-yl]-8-(1H-pyrazol-5-yl)-1,7-naphthyridine

Step a 4-(6,7-dihydro-5H-pyrrolo[1,2-a]imidazol-3-yl)-2-[(3R)-3-methylmorpholin-4-yl]-8-[1-(tetrahydro-2H-pyran-2-yl)-1H-pyrazol-5-yl]-1,7-naphthyridine

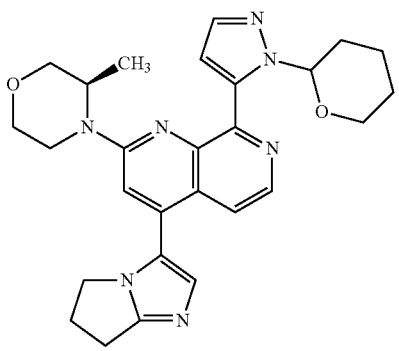 [SMILES: C[C@@H]1COCCN1c1cc(-c2cnc3n2CCC3)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 57 mg (0.38 mmol) 6,7-dihydro-5H-pyrrolo[1,2-a]imidazol-3-ylboronic acid, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(6,7-dihydro-5H-pyrrolo[1,2-a]imidazol-3-yl)-2-[(3R)-3-methylmorpholin-4-yl]-8-(1H-pyrazol-5-yl)-1,7-naphthyridine

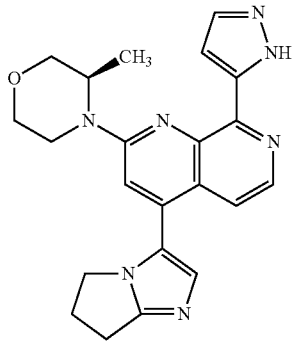 [SMILES: C[C@@H]1COCCN1c1cc(-c2cnc3n2CCC3)c2ccnc(-c3ccn[nH]3)c2n1]

A solution of 166 mg of crude 4-(6,7-dihydro-5H-pyrrolo[1,2-a]imidazol-3-yl)-2-[(3R)-3-methylmorpholin-4-yl]-8-[1-(tetrahydro-2H-pyran-2-yl)-1H-pyrazol-5-yl]-1,7-naphthyridine from step a in 3.2 ml of methanol and 0.34 ml of 2N hydrochloric acid was stirred for 90 minutes at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 1 mg (0.002 mmol) of the desired product.

$^1$H-NMR (400 MHz, DMSO-d6): δ [ppm]=1.19-1.42 (3H), 2.54-2.71 (2H), 2.81-3.00 (2H), 3.58 (1H), 3.73 (1H), 3.84 (1H), 3.97-4.15 (3H), 4.21 (1H), 4.63 (1H), 7.29-7.51 (3H), 7.64 (1H), 7.78 (1H), 8.37 (1H), 13.42 (1H).

Example 119

4-[1-ethyl-3-(trifluoromethyl)-1H-pyrazol-5-yl]-2-[(3R)-3-methylmorpholin-4-yl]-8-(1H-pyrazol-5-yl)-1,7-naphthyridine

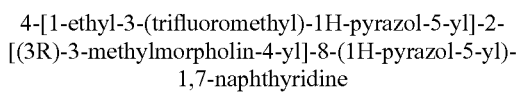

Step a

4-[1-ethyl-3-(trifluoromethyl)-1H-pyrazol-5-yl]-2-[(3R)-3-methylmorpholin-4-yl]-8-[1-(tetrahydro-2H-pyran-2-yl)-1H-pyrazol-5-yl]-1,7-naphthyridine

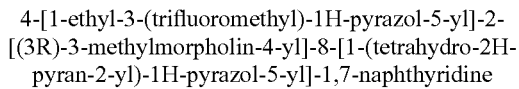

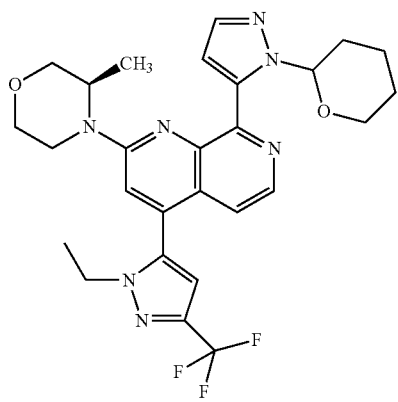 [SMILES: CCn1nc(C(F)(F)F)cc1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 30 mg (0.14 mmol) [1-ethyl-3-(trifluoromethyl)-1H-pyrazol-5-yl]boronic acid, 11 mg (0.014 mmol) of [1,1'-bis(diphenylphosphino)ferrocene]dichloropalladium(II) complex with dichloromethane (1:1, Pd(dppf)Cl$_2$) and 49 mg (0.36 mmol) of potassium carbonate in 3.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[1-ethyl-3-(trifluoromethyl)-1H-pyrazol-5-yl]-2-[(3R)-3-methylmorpholin-4-yl]-8-(1H-pyrazol-5-yl)-1,7-naphthyridine

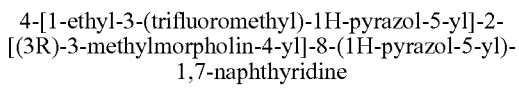

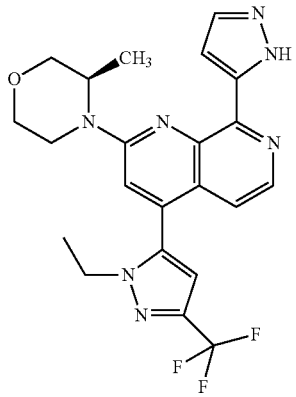 [SMILES: CCn1nc(C(F)(F)F)cc1-c1cc(N2CCOC[C@H]2C)nc2c(-c3ccn[nH]3)nccc12]

A solution of 118 mg of crude 4-[1-ethyl-3-(trifluoromethyl)-1H-pyrazol-5-yl]-2-[(3R)-3-methylmorpholin-4-yl]-8-[1-(tetrahydro-2H-pyran-2-yl)-1H-pyrazol-5-yl]-1,7-naphthyridine from step a in 5.2 ml of methanol and 0.22 ml of 2N hydrochloric acid was stirred for 1 hour at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 1 mg (0.002 mmol) of the desired product.

$^1$H-NMR (400 MHz, DMSO-d6): δ [ppm]=1.11-1.38 (6H), 3.36 (1H), 3.58 (1H), 3.72 (1H), 3.83 (1H), 4.07 (3H), 4.24 (1H), 4.64 (1H), 7.10 (1H), 7.17 (1H), 7.36-7.48 (1H), 7.66 (1H), 7.72 (1H), 8.36 (1H), 13.40 (1H).

Example 120 methyl 5-{2-[(3R)-3-methylmorpholin-4-yl]-8-(1H-pyrazol-5-yl)-1,7-naphthyridin-4-yl}-1H-pyrrole-2-carboxylate

Step a

1-tert-butyl 2-methyl 5-{2-[(3R)-3-methylmorpholin-4-yl]-8-[1-(tetrahydro-2H-pyran-2-yl)-1H-pyrazol-5-yl]-1,7-naphthyridin-4-yl}-1H-pyrrole-1,2-dicarboxylate

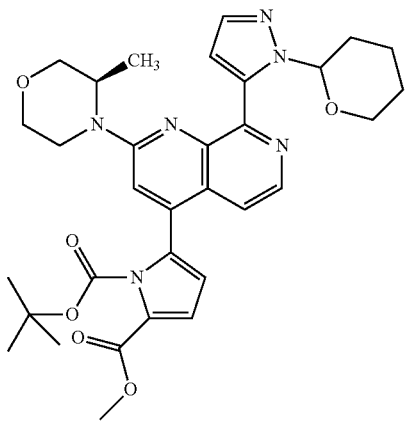 [SMILES: COC(=O)c1ccc(-c2cc(N3CCOC[C@H]3C)nc3c(-c4ccnn4C4CCCCO4)nccc23)n1C(=O)OC(C)(C)C]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 38 mg (0.14 mmol) [1-(tert-butoxycarbonyl)-5-(methoxycarbonyl)-1H-pyrrol-2-yl]boronic acid, 11 mg (0.014 mmol) of [1,1'-bis(diphenylphosphino)ferrocene]dichloropalladium(II) complex with dichloromethane (1:1, Pd(dppf)Cl$_2$) and 49 mg (0.36 mmol) of potassium carbonate in 3.0 ml of MeCN and 1.0 ml water was degased with argon. Under argon, the reaction mixture was stirred at 130° C. for 10 minutes in a microwave reactor. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b methyl 5-{2-[(3R)-3-methylmorpholin-4-yl]-8-(1H-pyrazol-5-yl)-1,7-naphthyridin-4-yl}-1H-pyrrole-2-carboxylate

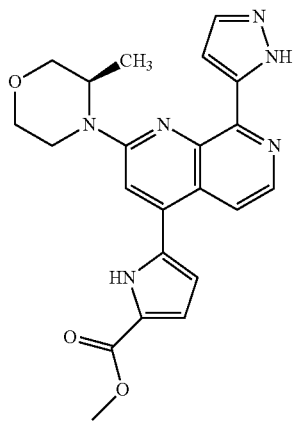 [SMILES: COC(=O)c1ccc(-c2cc(N3CCOC[C@H]3C)nc3c(-c4ccn[nH]4)nccc23)[nH]1]

A solution of 115 mg of crude 1-tert-butyl 2-methyl 5-{2-[(3R)-3-methylmorpholin-4-yl]-8-[1-(tetrahydro-2H-pyran-2-yl)-1H-pyrazol-5-yl]-1,7-naphthyridin-4-yl}-1H-pyrrole-1,2-dicarboxylate from step a in 5.5 ml of methanol and 0.23 ml of 2N hydrochloric acid was stirred for 1 hour at room temperature. The reaction mixture was diluted with saturated aqueous chloride solution and extracted with ethyl acetate (2×). The combined organic phases were dried (MgSO$_4$), filtered and concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=1.32 (3H), 3.36-3.44 (1H), 3.52-3.65 (1H), 3.72 (1H), 3.78-3.93 (4H), 3.99-4.16 (1H), 4.24 (1H), 4.66 (1H), 6.72 (1H), 7.03 (1H), 7.39 (1H), 7.49-7.59 (1H), 7.59-7.70 (1H), 7.84 (1H), 8.38 (1H), 12.60 (1H), 13.40 (1H).

Example 121

2-[(3R)-3-methylmorpholin-4-yl]-8-(1H-pyrazol-5-yl)-4-(1,2-thiazol-5-yl)-1,7-naphthyridine Step a 2-[(3R)-3-methylmorpholin-4-yl]-8-[1-(tetrahydro-2H-pyran-2-yl)-1H-pyrazol-5-yl]-4-(1,2-thiazol-5-yl)-1,7-naphthyridine

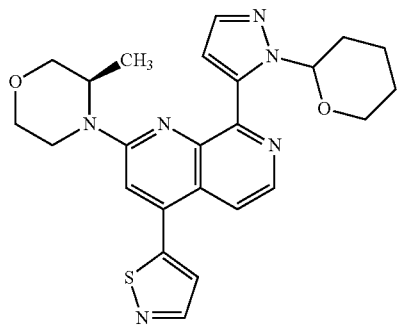 [SMILES: C[C@@H]1COCCN1c1cc(-c2ccns2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 80 mg (0.38 mmol) 5-(4,4,5,5-tetramethyl-1,3,2-dioxaborolan-2-yl)-1,2-thiazole, 15 mg (0.019 mmol) of [1,1'-bis(diphenylphosphino)ferrocene]dichloropalladium (II) complex with dichloromethane (1:1, Pd(dppf)Cl$_2$) and 247 mg (0.76 mmol) of ceasium carbonate in 1.3 ml of dioxane was degased with argon. Under argon, the reaction mixture was stirred at 110° C. for 2 hours. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-8-(1H-pyrazol-5-yl)-4-(1,2-thiazol-5-yl)-1,7-naphthyridine

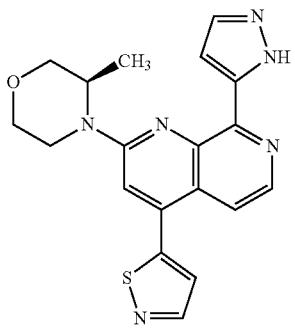 [SMILES: C[C@@H]1COCCN1c1cc(-c2ccns2)c2ccnc(-c3ccn[nH]3)c2n1]

A solution of 155 mg of crude 2-[(3R)-3-methylmorpholin-4-yl]-8-[1-(tetrahydro-2H-pyran-2-yl)-1H-pyrazol-5-yl]-4-(1,2-thiazol-5-yl)-1,7-naphthyridine from step a in 1.5 ml of methanol and 0.39 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=1.31 (3H), 3.40 (1H), 3.57 (1H), 3.72 (1H), 3.83 (1H), 4.05 (1H), 4.17-4.34 (1H), 4.59-4.83 (1H), 7.41 (1H), 7.57-7.75 (3H), 7.89 (1H), 8.40 (1H), 8.80 (1H), 13.39 (1H).

Example 122

N,N-dimethyl-2-{2-[(3R)-3-methylmorpholin-4-yl]-8-(1H-pyrazol-5-yl)-1,7-naphthyridin-4-yl}aniline Step a N,N-dimethyl-2-{2-[(3R)-3-methylmorpholin-4-yl]-8-[1-(tetrahydro-2H-pyran-2-yl)-1H-pyrazol-5-yl]-1,7-naphthyridin-4-yl}aniline

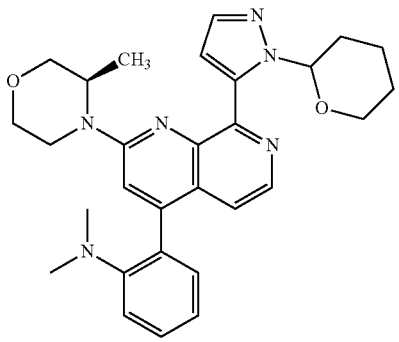 [SMILES: C[C@@H]1COCCN1c1cc(-c2ccccc2N(C)C)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 63 mg (0.38 mmol) [2-(dimethylamino)phenyl]boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of ceasium carbonate in 1.4 ml of dioxane was degased with argon. Under argon, the reaction mixture was stirred at 110° C. for 2 hours. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

N,N-dimethyl-2-{2-[(3R)-3-methylmorpholin-4-yl]-8-(1H-pyrazol-5-yl)-1,7-naphthyridin-4-yl}aniline

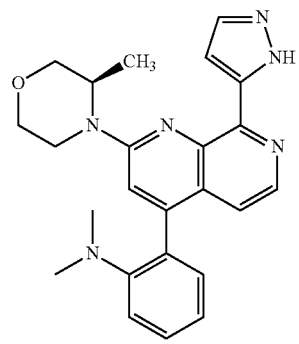 [SMILES: C[C@@H]1COCCN1c1cc(-c2ccccc2N(C)C)c2ccnc(-c3ccn[nH]3)c2n1]

A solution of 180 mg of crude N,N-dimethyl-2-{2-[(3R)-3-methylmorpholin-4-yl]-8-[1-(tetrahydro-2H-pyran-2-yl)-1H-pyrazol-5-yl]-1,7-naphthyridin-4-yl}aniline from step a in 1.7 ml of methanol and 0.42 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 40 mg (0.10 mmol) of the desired product.

$^1$H-NMR (400 MHz, DMSO-d6): δ [ppm]=1.28 (3H), 2.45 (6H), 3.60 (1H), 3.70-3.78 (1H), 3.78-3.86 (1H), 3.97-4.12 (1H), 4.21 (1H), 4.59 (1H), 7.03-7.19 (2H), 7.19-7.29 (2H), 7.36-7.54 (3H), 7.64 (1H), 8.25 (1H), 13.40 (1H).

Example 123

4-(2,4-difluorophenyl)-2-[(3R)-3-methylmorpholin-4-yl]-8-(1H-pyrazol-5-yl)-1,7-naphthyridine Step a 4-(2,4-difluorophenyl)-2-[(3R)-3-methylmorpholin-4-yl]-8-[1-(tetrahydro-2H-pyran-2-yl)-1H-pyrazol-5-yl]-1,7-naphthyridine

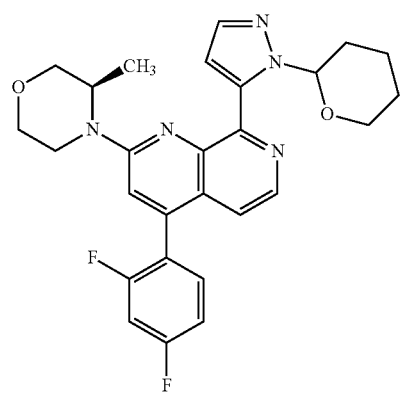 [SMILES: C[C@@H]1COCCN1c1cc(-c2ccc(F)cc2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 60 mg (0.38 mmol) (2,4-difluorophenyl)boronic acid, 15 mg (0.019 mmol) of [1,1'-bis(diphenylphosphino)ferrocene]-dichloropalladium(II) complex with dichloromethane (1:1, Pd(dppf)Cl$_2$) and 247 mg (0.76 mmol) of ceasium carbonate in 1.4 ml of dioxane was degased with argon. Under argon, the reaction mixture was stirred at 110° C. for 90 minutes. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(2,4-difluorophenyl)-2-[(3R)-3-methylmorpholin-4-yl]-8-(1H-pyrazol-5-yl)-1,7-naphthyridine

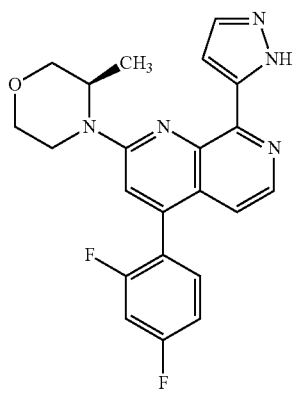 [SMILES: C[C@@H]1COCCN1c1cc(-c2ccc(F)cc2F)c2ccnc(-c3ccn[nH]3)c2n1]

A solution of 126 mg of crude 4-(2,4-difluorophenyl)-2-[(3R)-3-methylmorpholin-4-yl]-8-[1-(tetrahydro-2H-pyran-2-yl)-1H-pyrazol-5-yl]-1,7-naphthyridine from step a in 5.7 ml of methanol and 0.26 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 12 mg (0.03 mmol) of the desired product.

$^1$H-NMR (400 MHz, DMSO-d6): δ [ppm]=1.30 (3H), 3.38 (1H), 3.57 (1H), 3.68-3.75 (1H), 3.82 (1H), 4.05 (1H), 4.22 (1H), 4.64 (1H), 7.17 (1H), 7.31-7.38 (1H), 7.42 (1H), 7.49-7.58 (2H), 7.60-7.70 (2H), 8.32 (1H), 13.18 (1H).

Example 124

4-(1-isopropyl-1H-pyrazol-5-yl)-2-[(3R)-3-methylmorpholin-4-yl]-8-(1H-pyrazol-5-yl)-1,7-naphthyridine Step a 4-(1-isopropyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

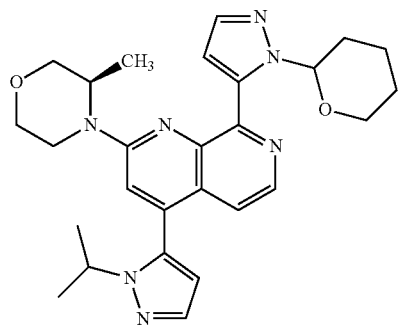 [SMILES: CC(C)n1nccc1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 58 mg (0.38 mmol) (1-isopropyl-1H-pyrazol-5-yl)boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of ceasium carbonate in 2.0 ml of dioxane was degased with argon. Under argon, the reaction mixture was stirred at 110° C. for 60 minutes. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(1-isopropyl-1H-pyrazol-5-yl)-2-[(3R)-3-methylmorpholin-4-yl]-8-(1H-pyrazol-5-yl)-1,7-naphthyridine

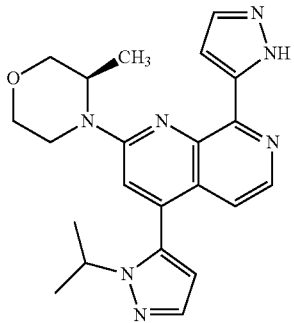 [SMILES: CC(C)n1nccc1-c1cc(N2CCOC[C@H]2C)nc2c(-c3ccn[nH]3)nccc12]

A solution of 126 mg of crude 4-(1-isopropyl-1H-pyrazol-5-yl)-2-[(3R)-3-methylmorpholin-4-yl]-8-[1-(tetrahydro- 2H-pyran-2-yl)-1H-pyrazol-5-yl]-1,7-naphthyridine from step a in 4.0 ml of methanol and 0.20 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 14 mg (0.03 mmol) of the desired product.

$^1$H-NMR (400 MHz, DMSO-d6): δ [ppm]=1.32 (9H), 3.59 (1H), 3.72 (1H), 3.82 (1H), 4.06 (1H), 4.13-4.31 (2H), 4.52-4.74 (1H), 6.51 (1H), 7.14 (1H), 7.43 (1H), 7.54 (1H), 7.66 (1H), 7.71 (1H), 8.35 (1H), 13.43 (1H).

Example 125 ethyl methyl{2-[(3R)-3-methylmorpholin-4-yl]-8-(1H-pyrazol-5-yl)-1,7-naphthyridin-4-yl}phosphinate Step a ethyl methyl{2-[(3R)-3-methylmorpholin-4-yl]-8-[1-(tetrahydro-2H-pyran-2-yl)-1H-pyrazol-5-yl]-1,7-naphthyridin-4-yl}phosphinate

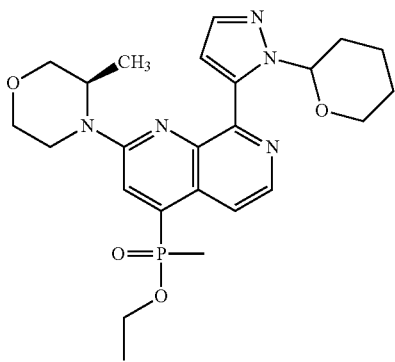 [SMILES: CCOP(C)(=O)c1cc(N2CCOC[C@H]2C)nc2c(-c3ccnn3C3CCCCO3)nccc12]

A mixture of 250 mg (0.47 mmol) of 2-[(3R)-3-methyl-morpholin-4-yl]-8-[1-(tetrahydro-2H-pyran-2-yl)-1H-pyrazol-5-yl]-1,7-naphthyridin-4-yl trifluoromethanesulfonate, 53 mg (0.47 mmol) ethyl methylphosphinate, 2 mg (0.009 mmol) palladium(II) acetate, 6 mg (0.01 mmol) of 1,1'-bis(diphenylphosphino)ferrocene and 0.11 ml (0.62 mmol) of ethyldiisopropylamine in 2.1 ml of DMF and 0.24 ml 1,2-dimethoxyethane was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The aqueous phase was saturated with solid sodium chloride and extracted with a mixture of THF and ethyl acetet (1:1). The combined organic phases were filtered using a Whatman filter and then concentrated to give the crude product that was used without further purification in the next step.

Step b ethyl methyl{2-[(3R)-3-methylmorpholin-4-yl]-8-(1H-pyrazol-5-yl)-1,7-naphthyridin-4-yl}phosphinate

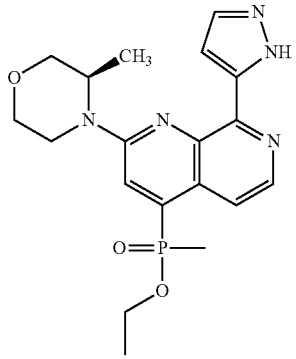 [SMILES: CCOP(C)(=O)c1cc(N2CCOC[C@H]2C)nc2c(-c3ccn[nH]3)nccc12]

A solution of 310 mg of crude ethyl methyl{2-[(3R)-3-methylmorpholin-4-yl]-8-[1-(tetrahydro-2H-pyran-2-yl)-1H-pyrazol-5-yl]-1,7-naphthyridin-4-yl}phosphinate from step a in 2.9 ml of methanol and 0.75 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 15 mg of an apparent salt of the desired product. The material was taken up in 13 ml of ethyl acetate and 2 ml of saturated aqueous sodium chloride solution and the mixture was stirred for 15 minutes. The mixture was filtered using a Whatman filter and concentrated to give 8 mg (0.02 mmol) of the desired product.

$^1$H-NMR (400 MHz, DMSO-d6): δ [ppm]=1.18-1.28 (3H), 1.28-1.37 (3H), 1.81-1.97 (3H), 3.58 (1H), 3.72 (1H), 3.85 (1H), 3.88-3.98 (1H), 4.00-4.12 (2H), 4.12-4.21 (1H), 4.60 (1H), 7.37 (1H), 7.65 (1H), 7.80 (1H), 8.11 (1H), 8.33-8.51 (1H), 13.45 (1H).

Example 126

4-{[diethyl(oxido)-λ$^6$-sulfanylidene]amino}-2-[(3R)-3-methylmorpholin-4-yl]-8-(1H-pyrazol-5-yl)-1,7-naphthyridine Step a 4-{[diethyl(oxido)-λ$^6$-sulfanylidene]amino}-2-[(3R)-3-methylmorpholin-4-yl]-8-[1-(tetrahydro-2H-pyran-2-yl)-1H-pyrazol-5-yl]-1,7-naphthyridine

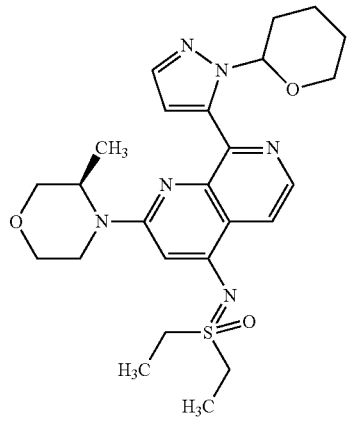 [SMILES: CCS(=O)(CC)=Nc1cc(N2CCOC[C@H]2C)nc2c(-c3ccnn3C3CCCCO3)nccc12]

Under argon, 8 mg (0.014 mmol) 4,5-bis(diphenylphosphino)-9,9-dimethylxanthene and 7 mg (0.007 mmol) tris(dibenzylideneacetone)dipalladium(0) were added to a mixture of 75 mg (0.142 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 22 mg (0.19 mmol) (S-ethylsulfonimidoyl)ethane and 69 mg (0.21 mmol) caesium carbonate in 0.67 ml toluene. The mixture was stirred at 110° C. for 3 hours. After cooling, the reaction mixture was diluted with ethyl acetate and washed with an aqueous solution of sodium chloride. The organic phase was filtered using a Whatman filter and concentrated to give the crude product that was used without further purification.

Step b

4-{[diethyl(oxido)-$\lambda^6$-sulfanylidene]amino}-2-[(3R)-3-methylmorpholin-4-yl]-8-(1H-pyrazol-5-yl)-1,7-naphthyridine

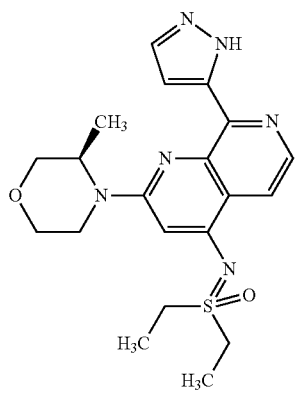 [SMILES: CCS(=O)(CC)=Nc1cc(N2CCOC[C@H]2C)nc2c(-c3ccn[nH]3)nccc12]

0.14 ml (0.29 mmol) 2N aqueous solution of hydrogen chloride was added to a solution of 71 mg crude 4-{[diethyl(oxido)-$\lambda^6$-sulfanylidene]amino}-2-[(3R)-3-methylmorpholin-4-yl]-8-[1-(tetrahydro-2H-pyran-2-yl)-1H-pyrazol-5-yl]-1,7-naphthyridine in 3.2 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 25 mg (0.06 mmol) of the desired product.

$^1$H-NMR (400 MHz, DMSO-d6): δ [ppm]=1.25 (3H), 1.29-1.40 (6H), 3.20-3.31 (1H), 3.48-3.67 (5H), 3.71 (1H), 3.83 (1H), 3.94-4.14 (2H), 4.39 (1H), 6.84 (s, 1H), 7.34 (1H), 7.60 (1H), 7.88 (1H), 8.29 (1H), 13.35 (1H).

Example 127 isobutyl methyl{2-[(3R)-3-methylmorpholin-4-yl]-8-(1H-pyrazol-5-yl)-1,7-naphthyridin-4-yl}phosphinate Step a isobutyl methyl{2-[(3R)-3-methylmorpholin-4-yl]-8-[1-(tetrahydro-2H-pyran-2-yl)-1H-pyrazol-5-yl]-1,7-naphthyridin-4-yl}phosphinate

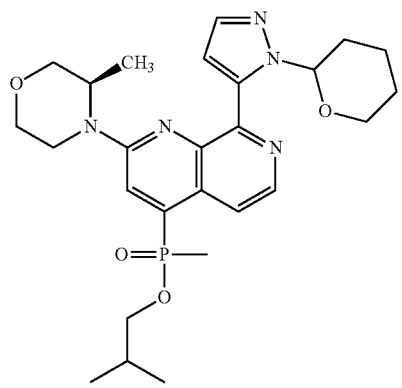 [SMILES: CC(C)COP(C)(=O)c1cc(N2CCOC[C@H]2C)nc2c(-c3ccnn3C3CCCCO3)nccc12]

A mixture of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 26 mg (0.19 mmol) methylphosphonic acid isobutylester, 1 mg (0.004 mmol) palladium(II) acetate, 2 mg (0.004 mmol) of 1,1'-bis(diphenylphosphino)ferrocene and 0.01 ml (0.25 mmol) of ethyldiisopropylamine in 0.9 ml of DMF and 0.1 ml 1,2-dimethoxyethane was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The aqueous phase was saturated with solid sodium chloride and extracted with a mixture of THF and ethyl acetet (1:1). The combined organic phases were filtered using a Whatman filter and then concentrated to give the crude product that was used without further purification in the next step.

Step b isobutyl methyl{2-[(3R)-3-methylmorpholin-4-yl]-8-(1H-pyrazol-5-yl)-1,7-naphthyridin-4-yl}phosphinate

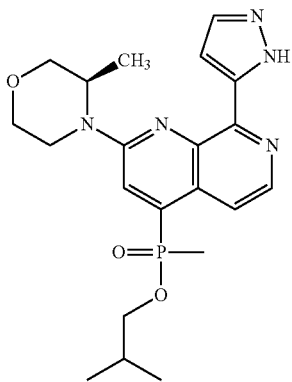 [SMILES: CC(C)COP(C)(=O)c1cc(N2CCOC[C@H]2C)nc2c(-c3ccn[nH]3)nccc12]

A solution of 135 mg of crude isobutyl methyl{2-[(3R)-3-methylmorpholin-4-yl]-8-[1-(tetrahydro-2H-pyran-2-yl)-1H-pyrazol-5-yl]-1,7-naphthyridin-4-yl}phosphinate from step a in 1.2 ml of methanol and 0.3 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 26 mg (0.06 mmol) of the desired product.

$^1$H-NMR (400 MHz, DMSO-d6): δ [ppm]=0.88 (6H), 1.31 (3H), 1.90 (3H), 3.30-3.45 (1H), 3.52-3.64 (2H), 3.72 (1H), 3.76-3.91 (2H), 4.07 (1H), 4.11-4.27 (2H), 4.47-4.71 (1H), 7.37 (1H), 7.64 (1H), 7.79 (1H), 8.10 (1H), 8.44 (1H), 13.41 (1H).

Example 128

2-{2-[(3R)-3-methylmorpholin-4-yl]-8-(1H-pyrazol-5-yl)-1,7-naphthyridin-4-yl}propan-2-ol

Step a methyl 2-[(3R)-3-methylmorpholin-4-yl]-8-[1-(tetrahydro-2H-pyran-2-yl)-1H-pyrazol-5-yl]-1,7-naphthyridine-4-carboxylate

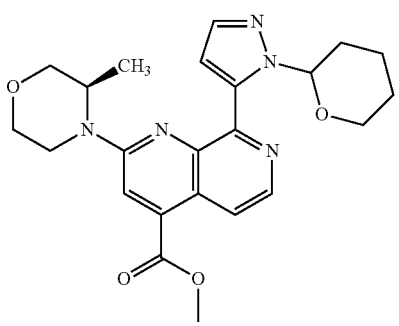 [SMILES: COC(=O)c1cc(N2CCOC[C@H]2C)nc2c(-c3ccnn3C3CCCCO3)nccc12]

In an autoclave, a mixture of 2527 mg (4.79 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 203 mg (0.48 mmol) 1,3-bis(diphenylphosphino)propane, 108 mg (0.48 mmol) palladium(II) acetate and 1.3 ml triethylamine (9.6 mmol) in 34 ml of DMF and 18 ml of methanol was purged with carbon monoxide at room temperature. The autoclave was pressured with carbonmonoxide to 16.5 bar and the mixture was stirred at room temperature for 30 minutes. The autoclave was depressurized and then pressured with carbon monoxide to 20.9 bar. The mixture was stirred at 80° C. for 20 hours. The autoclave was depressurized and after cooling, the mixture was diluted with water and extracted with ethyl acetate (2×). The combined organic phases were dried (Na$_2$SO$_4$), filtered and concentrated. The residue was purified by column chromatography (gradient from 100% Hex to 100% EtOAc) to give 1537 mg (3.51 mmol) of the desired product.

$^1$H-NMR (400 MHz, DMSO-d6): δ [ppm]=1.22 (3H), 1.35-1.52 (2H), 1.52-1.72 (1H), 1.82-2.05 (2H), 2.28-2.45 (1H), 3.14-3.31 (2H), 3.43-3.57 (1H), 3.57-3.85 (3H), 3.91-4.05 (4H), 4.12 (1H), 4.40-4.61 (1H), 5.90-6.18 (1H), 6.89 (1H), 7.59-7.68 (1H), 7.86 (1H), 8.19 (1H), 8.47 (1H).

Step b

2-{2-[(3R)-3-methylmorpholin-4-yl]-8-[1-(tetrahydro-2H-pyran-2-yl)-1H-pyrazol-5-yl]-1,7-naphthyridin-4-yl}propan-2-ol

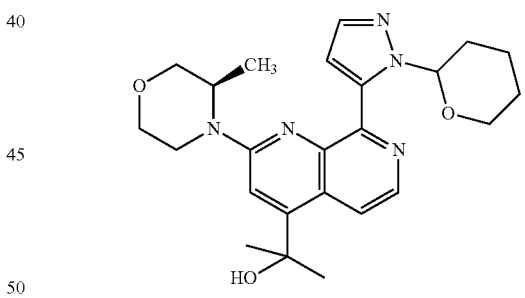

0.23 ml (0.69 mmol) of a 3.0 M solution of methylmagnesium bromide in diethylether was added dropwise to a stirred solution of 100 mg (0.23 mmol) methyl 2-[(3R)-3-methylmorpholin-4-yl]-8-[1-(tetrahydro-2H-pyran-2-yl)-1H-pyrazol-5-yl]-1,7-naphthyridine-4-carboxylate in 3.8 ml of THF at 0° C. The mixture was stirred at 0° C. for 30 minutes and then the icebath was removed and the mixture was stirred at room temperature for 150 minutes. The mixture was diluted with a saturated aqueous solution of ammonium chloride and extracted with ethyl acetate (2×). The combined organic phases were filtered using a Whatman filter and then concentrated to give the crude product that was used without further purification in the next step.

Step c

2-{2-[(3R)-3-methylmorpholin-4-yl]-8-(1H-pyrazol-5-yl)-1,7-naphthyridin-4-yl}propan-2-ol

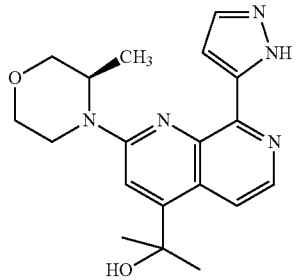 [SMILES: C[C@@H]1COCCN1c1cc(C(C)(C)O)c2ccnc(-c3ccn[nH]3)c2n1]

A solution of 91 mg of crude 2-{2-[(3R)-3-methylmorpholin-4-yl]-8-[1-(tetrahydro-2H-pyran-2-yl)-1H-pyrazol-5-yl]-1,7-naphthyridin-4-yl}propan-2-ol from step b in 1.8 ml of methanol and 0.21 ml of 2N hydrochloric acid was stirred for 3 hours at room temperature. The reaction mixture was diluted with saturated aqueous sodium chloride solution and extracted with ethyl acetate (2×). The combined organic phases were dried (MgSO$_4$), filtered and concentrated to dryness. The residue was purified by preparative HPLC (Autopurifier: basic conditions) to give 14 mg (0.04 mmol) of the desired product.

$^1$H-NMR (400 MHz, DMSO-d6): δ [ppm]=1.28 (3H), 1.69 (6H), 3.57 (1H), 3.72 (1H), 3.84 (1H), 4.06 (1H), 4.09-4.18 (1H), 4.58 (1H), 5.59 (1H), 7.35 (1H), 7.42 (1H), 7.61 (1H), 8.26-8.38 (2H), 13.35 (1H).

Example 129

3-{2-[(3R)-3-methylmorpholin-4-yl]-8-(1H-pyrazol-5-yl)-1,7-naphthyridin-4-yl}pentan-3-ol

Step a

3-{2-[(3R)-3-methylmorpholin-4-yl]-8-[1-(tetrahydro-2H-pyran-2-yl)-1H-pyrazol-5-yl]-1,7-naphthyridin-4-yl}pentan-3-ol

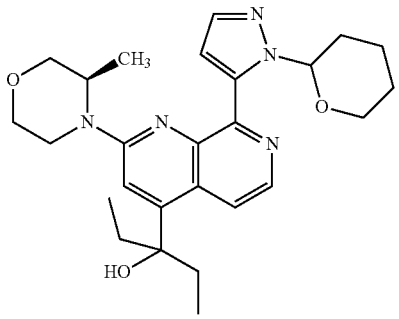 [SMILES: CCC(O)(CC)c1cc(N2CCOC[C@H]2C)nc2c(-c3ccnn3C3CCCCO3)nccc12]

0.46 ml (1.37 mmol) of a 3.0 M solution of ethylmagnesium bromide in diethylether was added dropwise to a stirred solution of 200 mg (0.46 mmol) methyl 2-[(3R)-3-methylmorpholin-4-yl]-8-[1-(tetrahydro-2H-pyran-2-yl)-1H-pyrazol-5-yl]-1,7-naphthyridine-4-carboxylate in 7.7 ml of THF at 0° C. The mixture was stirred at 0° C. for 30 minutes and then the icebath was removed and the mixture was stirred at room temperature for 150 minutes. The mixture was diluted with a saturated aqueous solution of ammonium chloride and extracted with ethyl acetate (2×). The combined organic phases were filtered using a Whatman filter and then concentrated to give the crude product that was used without further purification in the next step.

Step b

3-{2-[(3R)-3-methylmorpholin-4-yl]-8-(1H-pyrazol-5-yl)-1,7-naphthyridin-4-yl}pentan-3-ol

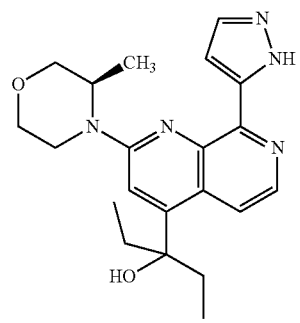 [SMILES: CCC(O)(CC)c1cc(N2CCOC[C@H]2C)nc2c(-c3ccn[nH]3)nccc12]

A solution of 211 mg of crude 3-{2-[(3R)-3-methylmorpholin-4-yl]-8-[1-(tetrahydro-2H-pyran-2-yl)-1H-pyrazol-5-yl]-1,7-naphthyridin-4-yl}pentan-3-ol from step a in 5.0 ml of methanol and 0.45 ml of 2N hydrochloric acid was stirred for 3 hours at room temperature. The reaction mixture was diluted with saturated aqueous sodium chloride solution and extracted with ethyl acetate (2×). The combined organic phases were dried (MgSO$_4$), filtered and concentrated to dryness. The residue was purified by preparative HPLC (Autopurifier: acidic conditions) to give 6 mg (0.02 mmol) of the desired product.

$^1$H-NMR (400 MHz, DMSO-d6): δ [ppm]=0.66 (6H), 1.26 (3H), 1.84-2.07 (2H), 2.17 (2H), 3.59 (1H), 3.75 (1H), 3.84 (1H), 3.99-4.15 (2H), 4.51 (1H), 5.17 (1H), 7.35 (1H), 7.53 (1H), 7.61 (1H), 8.11 (1H), 8.31 (1H), 13.34 (1H).

Example 130

4-(5-chloropyridin-3-yl)-2-[(3R)-3-methylmorpholin-4-yl]-8-(1H-pyrazol-5-yl)-1,7-naphthyridine

Step a 4-(5-chloropyridin-3-yl)-2-[(3R)-3-methylmorpholin-4-yl]-8-[1-(tetrahydro-2H-pyran-2-yl)-1H-pyrazol-5-yl]-1,7-naphthyridine

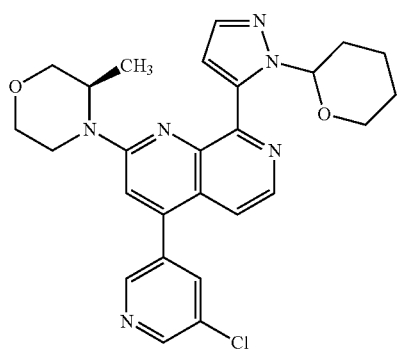 [SMILES: C[C@@H]1COCCN1c1cc(-c2cncc(Cl)c2)c2ccnc(-c3ccnn3C3CCCCO3)c2n1]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 45 mg (0.28 mmol) (5-chloropyridin-3-yl)boronic acid, 11 mg (0.014 mmol) of [1,1'-bis(diphenylphosphino)ferrocene]-dichloropalladium(II) complex with dichloromethane (1:1, Pd(dppf)Cl$_2$) and 185 mg (0.57 mmol) of caesium carbonate in 1.0 ml of dioxane was degased with argon. Under argon, the reaction mixture was stirred at 110° C. for 90 minutes. After cooling the reaction mixture was diluted with saturated aqueous ammonium chloride solution and extracted with ethyl acetate (2×). The combined organic phases were filtered using a Whatman filter and then concentrated to give the crude product that was used without further purification in the next step.

Step b 4-(5-chloropyridin-3-yl)-2-[(3R)-3-methylmorpholin-4-yl]-8-(1H-pyrazol-5-yl)-1,7-naphthyridine

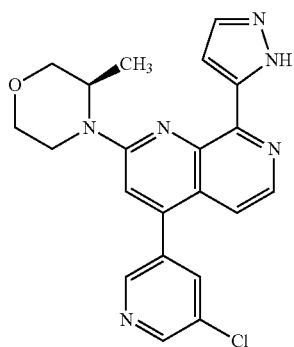 [SMILES: C[C@@H]1COCCN1c1cc(-c2cncc(Cl)c2)c2ccnc(-c3ccn[nH]3)c2n1]

A solution of 120 mg of crude 4-(5-chloropyridin-3-yl)-2-[(3R)-3-methylmorpholin-4-yl]-8-[1-(tetrahydro-2H-pyran-2-yl)-1H-pyrazol-5-yl]-1,7-naphthyridine from step a in 5.0 ml of methanol and 0.24 ml of 2N hydrochloric acid was stirred for 2 hour at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 8 mg (0.02 mmol) of the desired product.

$^1$H-NMR (400 MHz, DMSO-d6): δ [ppm]=1.31 (3H), 3.36-3.41 (1H), 3.57 (1H), 3.72 (1H), 3.84 (1H), 4.06 (1H), 4.25 (1H), 4.55-4.77 (1H), 7.38 (1H), 7.43 (1H), 7.59 (1H), 7.66 (1H), 8.26 (1H), 8.35 (1H), 8.75 (1H), 8.83 (1H), 13.34 (1H).

Example 131

5-fluoro-2-{2-[(3R)-3-methylmorpholin-4-yl]-8-(1H-pyrazol-5-yl)-1,7-naphthyridin-4-yl}aniline Step a 5-fluoro-2-{2-[(3R)-3-methylmorpholin-4-yl]-8-[1-(tetrahydro-2H-pyran-2-yl)-1H-pyrazol-5-yl]-1,7-naphthyridin-4-yl}aniline

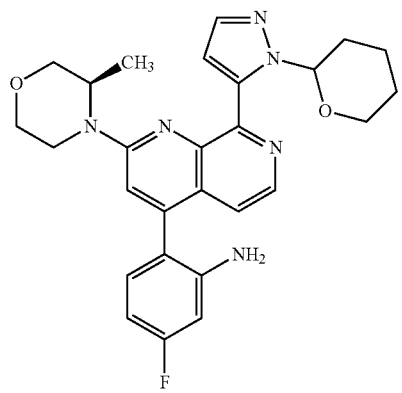 [SMILES: C[C@@H]1COCCN1c1cc(-c2ccc(F)cc2N)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 90 mg (0.38 mmol) 5-fluoro-2-(4,4,5,5-tetramethyl-1,3,2-dioxaborolan-2-yl)aniline, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 5-fluoro-2-{2-[(3R)-3-methylmorpholin-4-yl]-8-(1H-pyrazol-5-yl)-1,7-naphthyridin-4-yl}aniline

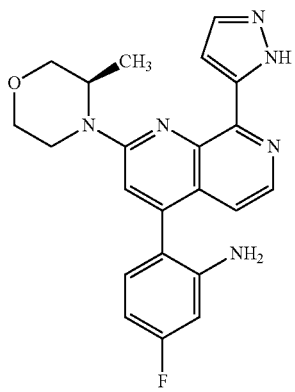 [SMILES: C[C@@H]1COCCN1c1cc(-c2ccc(F)cc2N)c2ccnc(-c3ccn[nH]3)c2n1]

A solution of 147 mg of crude 5-fluoro-2-{2-[(3R)-3-methylmorpholin-4-yl]-8-[1-(tetrahydro-2H-pyran-2-yl)-1H-pyrazol-5-yl]-1,7-naphthyridin-4-yl}aniline from step a in 5.8 ml of methanol and 0.30 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 14 mg (0.03 mmol) of the desired product.

$^1$H-NMR (400 MHz, DMSO-d6): δ [ppm]=1.31 (3H), 3.48-3.65 (1H), 3.66-3.77 (1H), 3.82 (1H), 4.05 (1H), 4.15-4.30 (1H), 4.50-4.73 (1H), 5.20 (2H), 6.37-6.54 (1H), 6.58 (1H), 7.04 (1H), 7.14 (1H), 7.35 (1H), 7.44 (1H), 7.64 (1H), 8.28 (1H), 13.41 (1H).

Example 132

4-[2-fluoro-3-(methylsulfonyl)phenyl]-2-[(3R)-3-methylmorpholin-4-yl]-8-(1H-pyrazol-5-yl)-1,7-naphthyridine Step a 4-[2-fluoro-3-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine

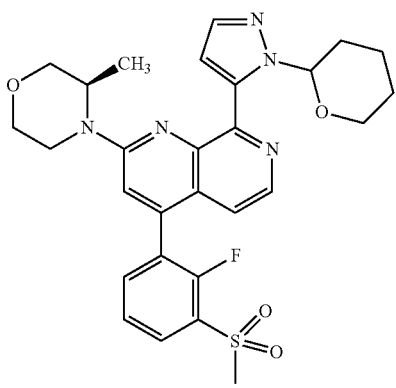 [SMILES: C[C@@H]1COCCN1c1cc(-c2cccc(S(C)(=O)=O)c2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 57 mg (0.19 mmol) 2-[2-fluoro-3-(methylsulfonyl)phenyl]-4,4,5,5-tetramethyl-1,3,2-dioxaborolane, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 2.0 ml of dioxane was degased with argon. Under argon, the reaction mixture was stirred at 110° C. for 90 minutes. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-fluoro-3-(methylsulfonyl)phenyl]-2-[(3R)-3-methylmorpholin-4-yl]-8-(1H-pyrazol-5-yl)-1,7-naphthyridine

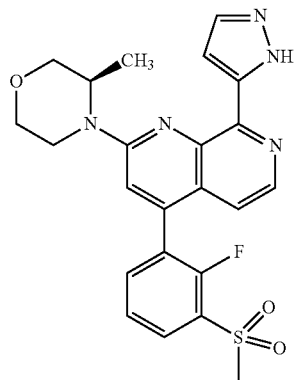 [SMILES: C[C@@H]1COCCN1c1cc(-c2cccc(S(C)(=O)=O)c2F)c2ccnc(-c3ccn[nH]3)c2n1]

A solution of 105 mg of crude 4-[2-fluoro-3-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.19 ml of 2N hydrochloric acid was stirred for 3 hours at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 14 mg (0.03 mmol) of the desired product.

$^1$H-NMR (400 MHz, DMSO-d6): δ [ppm]=1.32 (3H), 3.36-3.44 (4H), 3.58 (1H), 3.72 (1H), 3.83 (1H), 4.05 (1H), 4.23 (1H), 4.65 (1H), 7.18 (1H), 7.44 (1H), 7.52-7.82 (3H), 7.90-8.02 (1H), 8.02-8.16 (1H), 8.34 (1H), 13.43 (1H).

Example 133

2-[(3R)-3-methylmorpholin-4-yl]-4-[1-(oxetan-3-yl)-1H-pyrazol-5-yl]-8-(1H-pyrazol-5-yl)-1,7-naphthyridine Step a 2-[(3R)-3-methylmorpholin-4-yl]-4-[1-(oxetan-3-yl)-1H-pyrazol-5-yl]-8-[1-(tetrahydro-2H-pyran-2-yl)-1H-pyrazol-5-yl]-1,7-naphthyridine

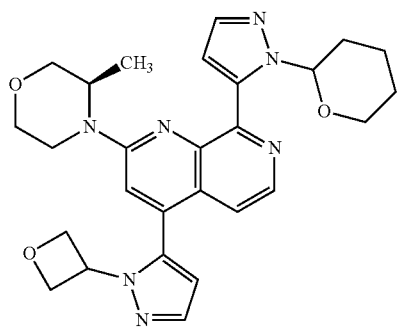 [SMILES: C[C@@H]1COCCN1c1cc(-c2ccnn2C2COC2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 94 mg (0.38 mmol) 1-(oxetan-3-yl)-5-(4,4,5,5-tetramethyl-1,3,2-dioxaborolan-2-yl)-1H-pyrazole, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-[1-(oxetan-3-yl)-1H-pyrazol-5-yl]-8-(1H-pyrazol-5-yl)-1,7-naphthyridine

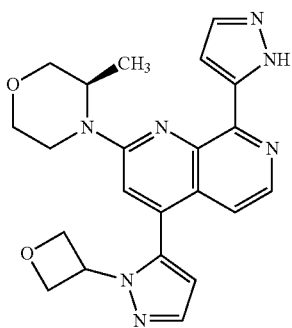 [SMILES: C[C@@H]1COCCN1c1cc(-c2ccnn2C2COC2)c2ccnc(-c3ccn[nH]3)c2n1]

A solution of 119 mg of crude 2-[(3R)-3-methylmorpholin-4-yl]-4-[1-(oxetan-3-yl)-1H-pyrazol-5-yl]-8-[1-(tetrahydro-2H-pyran-2-yl)-1H-pyrazol-5-yl]-1,7-naphthyridine from step a in 3.0 ml of methanol and 0.24 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 11 mg (0.03 mmol) of the desired product.

$^1$H-NMR (400 MHz, DMSO-d6): δ [ppm]=1.19-1.39 (3H), 3.57 (1H), 3.72 (1H), 3.83 (1H), 4.06 (1H), 4.21 (1H), 4.62 (1H), 4.73 (2H), 5.00 (2H), 5.25-5.44 (1H), 6.65 (1H), 7.09 (1H), 7.43 (1H), 7.48 (1H), 7.58-7.71 (1H), 7.88 (1H), 8.26-8.40 (1H), 13.45 (1H).

Example 134

4-[2-fluoro-4-(pyrrolidin-1-yl)phenyl]-2-[(3R)-3-methylmorpholin-4-yl]-8-(1H-pyrazol-5-yl)-1,7-naphthyridine Step a 4-[2-fluoro-4-(pyrrolidin-1-yl)phenyl]-2-[(3R)-3-methylmorpholin-4-yl]-8-[1-(tetrahydro-2H-pyran-2-yl)-1H-pyrazol-5-yl]-1,7-naphthyridine

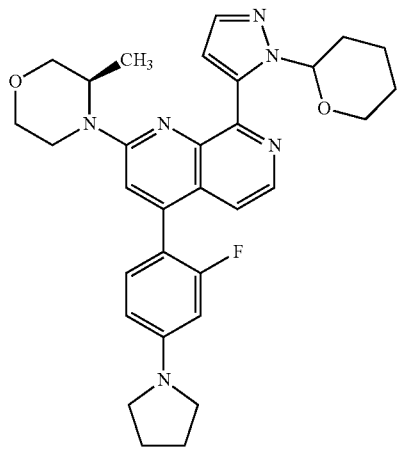 [SMILES: C[C@@H]1COCCN1c1cc(-c2ccc(N3CCCC3)cc2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 79 mg (0.38 mmol) [2-fluoro-4-(pyrrolidin-1-yl)phenyl]boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-fluoro-4-(pyrrolidin-1-yl)phenyl]-2-[(3R)-3-methylmorpholin-4-yl]-8-(1H-pyrazol-5-yl)-1,7-naphthyridine

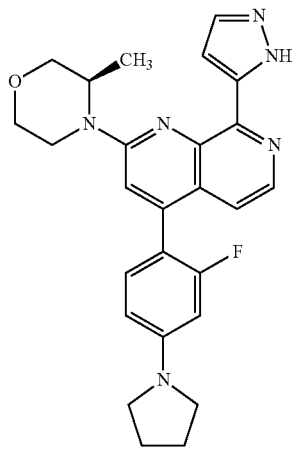 [SMILES: C[C@@H]1COCCN1c1cc(-c2ccc(N3CCCC3)cc2F)c2ccnc(-c3ccn[nH]3)c2n1]

A solution of 180 mg of crude 4-[2-fluoro-4-(pyrrolidin-1-yl)phenyl]-2-[(3R)-3-methylmorpholin-4-yl]-8-[1-(tetrahydro-2H-pyran-2-yl)-1H-pyrazol-5-yl]-1,7-naphthyridine from step a in 1.5 ml of methanol and 0.38 ml of 2N hydrochloric acid was stirred for 1 hours at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 44 mg (0.10 mmol) of the desired product.

¹H-NMR (400 MHz, DMSO-d6): δ [ppm]=1.30 (3H), 1.96-2.07 (4H), 3.27-3.33 (4H), 3.58 (1H), 3.72 (1H), 3.82 (1H), 4.05 (1H), 4.14-4.25 (1H), 4.56-4.70 (1H), 6.47-6.58 (2H), 7.24-7.48 (4H), 7.64 (1H), 8.31 (1H), 13.41 (1H).

Example 135

4-[3-(methoxymethyl)-5-methyl-1,2-oxazol-4-yl]-2-[(3R)-3-methylmorpholin-4-yl]-8-(1H-pyrazol-5-yl)-1,7-naphthyridine Step a 4-[3-(methoxymethyl)-5-methyl-1,2-oxazol-4-yl]-2-[(3R)-3-methylmorpholin-4-yl]-8-[1-(tetrahydro-2H-pyran-2-yl)-1H-pyrazol-5-yl]-1,7-naphthyridine

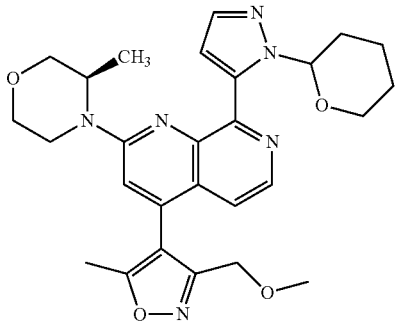 [SMILES: COCc1noc(C)c1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 24 mg (0.14 mmol) [3-(methoxymethyl)-5-methyl-1,2-oxazol-4-yl]boronic acid, 11 mg (0.014 mmol) of [1,1'-bis(diphenylphosphino)ferrocene]dichloropalladium(II) complex with dichloromethane (1:1, Pd(dppf)Cl₂) and 49 mg (0.36 mmol) of potassium carbonate in 3.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[3-(methoxymethyl)-5-methyl-1,2-oxazol-4-yl]-2-[(3R)-3-methylmorpholin-4-yl]-8-(1H-pyrazol-5-yl)-1,7-naphthyridine

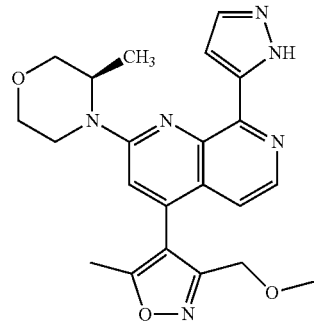 [SMILES: COCc1noc(C)c1-c1cc(N2CCOC[C@H]2C)nc2c(-c3ccn[nH]3)nccc12]

A solution of 111 mg of crude 4-[3-(methoxymethyl)-5-methyl-1,2-oxazol-4-yl]-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.22 ml of 2N hydrochloric acid was stirred for 60 minutes at room temperature. The reaction mixture was diluted with saturated aqueous sodium bicarbonate solution and extracted with ethyl acetate (2×). The combined organic phases were dried (MgSO₄), filtered and concentrated to dryness. The residue was purified by preparative HPLC (Autopurifier: basic conditions) to give 11 mg (0.02 mmol) of the desired product.

¹H-NMR (400 MHz, DMSO-d6): δ [ppm]=1.25-1.36 (3H), 2.34 (3H), 3.09 (3H), 3.37 (1H), 3.59 (1H), 3.73 (1H), 3.83 (1H), 4.07 (1H), 4.20 (1H), 4.37 (1H), 4.50 (1H), 4.54-4.64 (1H), 7.29 (1H), 7.41 (1H), 7.55 (1H), 7.65 (1H), 8.34 (1H), 13.14 (1H).

Example 136

2-[(3R)-3-methylmorpholin-4-yl]-4-(5-methyl-1,3,4-oxadiazol-2-yl)-8-(1H-pyrazol-5-yl)-1,7-naphthyridine

Step a

2-[(3R)-3-methylmorpholin-4-yl]-8-[1-(tetrahydro-2H-pyran-2-yl)-1H-pyrazol-5-yl]-1,7-naphthyridine-4-carbohydrazide

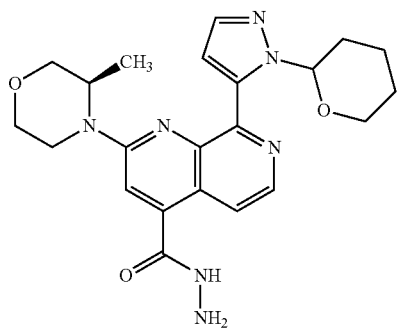 [SMILES: C[C@@H]1COCCN1c1cc(C(=O)NN)c2ccnc(-c3ccnn3C3CCCCO3)c2n1]

0.06 ml (1.14 mmol) hydrazine hydrate was added to a solution of 50 mg (0.11 mmol) of methyl 2-[(3R)-3-methylmorpholin-4-yl]-8-[1-(tetrahydro-2H-pyran-2-yl)-1H-pyrazol-5-yl]-1,7-naphthyridine-4-carboxylate in 2 ml of ethanol and the mixture was stirred at 100° C. for 5 hours. The mixture was concentrated to give the crude product that was used without further purification in the next step.

Step b

2-[(3R)-3-methylmorpholin-4-yl]-4-(5-methyl-1,3,4-oxadiazol-2-yl)-8-[1-(tetrahydro-2H-pyran-2-yl)-1H-pyrazol-5-yl]-1,7-naphthyridine

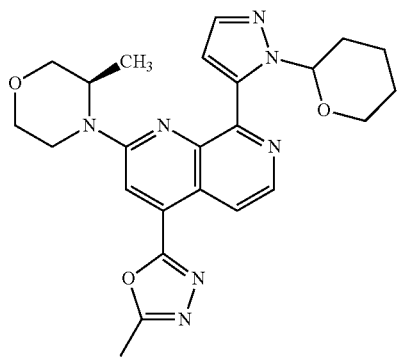 [SMILES: Cc1nnc(-c2cc(N3CCOC[C@H]3C)nc3c(-c4ccnn4C4CCCCO4)nccc23)o1]

0.03 ml (0.34 mmol) trifluoroacetic acid was added to a solution of crude 2-[(3R)-3-methylmorpholin-4-yl]-8-[1-(tetrahydro-2H-pyran-2-yl)-1H-pyrazol-5-yl]-1,7-naphthyridine-4-carbohydrazide from step a in 1.5 ml of trimethyl orthoacetate. The mixture was stirred at 95° C. for 60 minutes. After cooling the reaction mixture was concentrated to give the crude product that was used without further purification in the next step.

Step c

2-[(3R)-3-methylmorpholin-4-yl]-4-(5-methyl-1,3,4-oxadiazol-2-yl)-8-(1H-pyrazol-5-yl)-1,7-naphthyridine

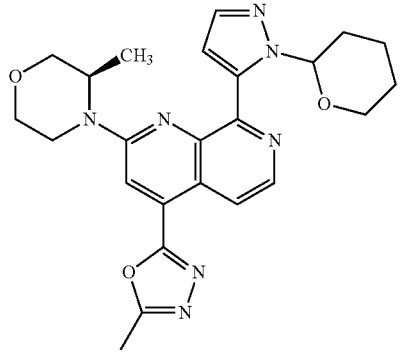 [SMILES: Cc1nnc(-c2cc(N3CCOC[C@H]3C)nc3c(-c4ccnn4C4CCCCO4)nccc23)o1]

A solution of 47 mg of crude 2-[(3R)-3-methylmorpholin-4-yl]-4-(5-methyl-1,3,4-oxadiazol-2-yl)-8-[1-(tetrahydro-2H-pyran-2-yl)-1H-pyrazol-5-yl]-1,7-naphthyridine from step b in 3.0 ml of methanol and 0.10 ml of 2N hydrochloric acid was stirred for 60 minutes at room temperature. The reaction mixture was diluted with saturated aqueous sodium bicarbonate solution and extracted with ethyl acetate (2×). The combined organic phases were dried (MgSO$_4$), filtered and concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=1.31 (3H), 2.63-2.82 (3H), 3.37-3.46 (1H), 3.59 (1H), 3.74 (1H), 3.85 (1H), 4.08 (1H), 4.21 (1H), 4.65 (1H), 7.40 (1H), 7.66 (1H), 7.96 (1H), 8.49 (1H), 8.62 (1H), 13.45 (1H).

Example 137

N-{2-[(3R)-3-methylmorpholin-4-yl]-8-(1H-pyrazol-5-yl)-1,7-naphthyridin-4-yl}tetrahydro-1H-1λ$^4$-thiophen-1-imine 1-oxide

Step a

N-{2-[(3R)-3-methylmorpholin-4-yl]-8-[1-(tetrahydro-2H-pyran-2-yl)-1H-pyrazol-5-yl]-1,7-naphthyridin-4-yl}tetrahydro-1H-1λ$^4$-thiophen-1-imine 1-oxide

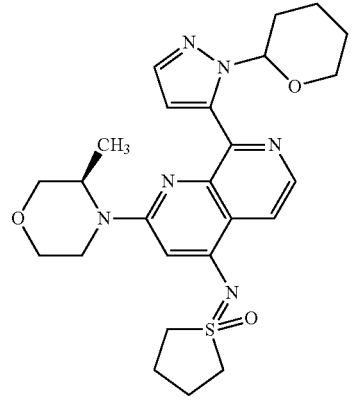 [SMILES: C[C@@H]1COCCN1c1cc(N=S2(=O)CCCC2)c2ccnc(-c3ccnn3C3CCCCO3)c2n1]

Under argon, 8 mg (0.014 mmol) 4,5-bis(diphenylphosphino)-9,9-dimethylxanthene and 7 mg (0.007 mmol) tris(dibenzylideneacetone)dipalladium(0) were added to a mixture of 75 mg (0.142 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 22 mg (0.19 mmol) tetrahydro-1H-1λ⁴-thiophen-1-imine 1-oxide and 69 mg (0.21 mmol) caesium carbonate in 0.67 ml toluene. The mixture was stirred at 110° C. for 3 hours. After cooling, the reaction mixture was diluted with ethyl acetate and washed with an aqueous solution of sodium chloride. The organic phase was filtered using a Whatman filter and concentrated to give the crude product that was used without further purification.

Step b

N-{2-[(3R)-3-methylmorpholin-4-yl]-8-(1H-pyrazol-5-yl)-1,7-naphthyridin-4-yl}tetrahydro-1H-1λ⁴-thiophen-1-imine 1-oxide

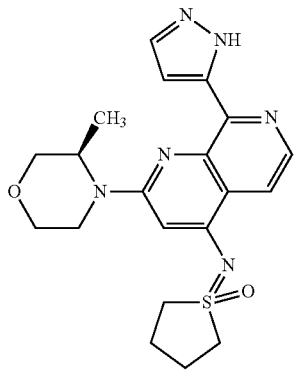 [SMILES: C[C@@H]1COCCN1c1cc(N=S2(=O)CCCC2)c2ccnc(-c3ccn[nH]3)c2n1]

0.15 ml (0.29 mmol) 2N aqueous solution of hydrogen chloride was added to a solution of 72 mg crude N-{2-[(3R)-3-methylmorpholin-4-yl]-8-[1-(tetrahydro-2H-pyran-2-yl)-1H-pyrazol-5-yl]-1,7-naphthyridin-4-yl}tetrahydro-1H-1λ⁴-thiophen-1-imine 1-oxide in 3.3 ml methanol and the reaction mixture was stirred at room temperature for 1 hour. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 26 mg (0.06 mmol) of the desired product.

¹H-NMR (400 MHz, DMSO-d6): δ [ppm]=1.26 (3H), 2.07-2.24 (2H), 2.24-2.37 (2H), 3.18-3.30 (1H), 3.44-3.69 (5H), 3.72 (1H), 3.83 (1H), 3.95-4.13 (2H), 4.44 (1H), 6.67 (1H), 7.35 (1H), 7.60 (1H), 7.89 (1H), 8.29 (1H), 13.36 (1H).

Example 138

4-{[(4-fluorophenyl)(methyl)oxido-λ⁶-sulfanylidene]amino}-2-[(3R)-3-methylmorpholin-4-yl]-8-(1H-pyrazol-5-yl)-1,7-naphthyridine, mixture of 2 diastereoisomers Step a 4-{[(4-fluorophenyl)(methyl)oxido-λ⁶-sulfanylidene]amino}-2-[(3R)-3-methylmorpholin-4-yl]-8-[1-(tetrahydro-2H-pyran-2-yl)-1H-pyrazol-5-yl]-1,7-naphthyridine

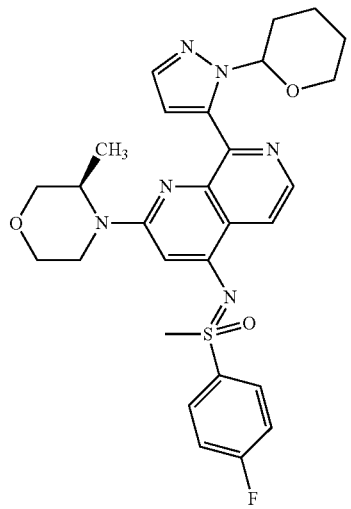 [SMILES: C[C@@H]1COCCN1c1cc(N=S(C)(=O)c2ccc(F)cc2)c2ccnc(-c3ccnn3C3CCCCO3)c2n1]

Under argon, 8 mg (0.014 mmol) 4,5-bis(diphenylphosphino)-9,9-dimethylxanthene and 7 mg (0.007 mmol) tris(dibenzylideneacetone)dipalladium(0) were added to a mixture of 75 mg (0.142 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 32 mg (0.19 mmol) 1-fluoro-4-(S-methylsulfonimidoyl)benzene and 69 mg (0.21 mmol) caesium carbonate in 0.67 ml toluene. The mixture was stirred at 110° C. for 3 hours. After cooling, the reaction mixture was diluted with ethyl acetate and washed with an aqueous solution of sodium chloride. The organic phase was filtered using a Whatman filter and concentrated to give the crude product that was used without further purification.

269

Step b

4-{[(4-fluorophenyl)(methyl)oxido-λ⁶-sulfanylidene]amino}-2-[(3R)-3-methylmorpholin-4-yl]-8-(1H-pyrazol-5-yl)-1,7-naphthyridine, mixture of 2 diastereoisomers

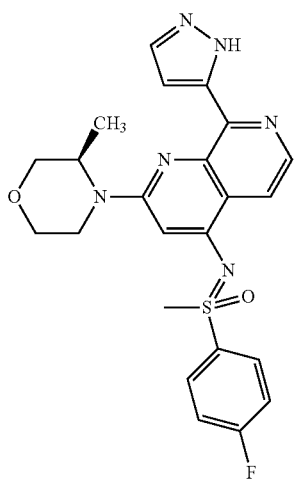 [SMILES: C[C@@H]1COCCN1c1cc(N=S(C)(=O)c2ccc(F)cc2)c2ccnc(-c3ccn[nH]3)c2n1]

0.23 ml (0.29 mmol) 2N aqueous solution of hydrogen chloride was added to a solution of 125 mg crude 4-{[(4-fluorophenyl)(methyl)oxido-λ⁶-sulfanylidene]amino}-2-[(3R)-3-methylmorpholin-4-yl]-8-[1-(tetrahydro-2H-pyran-2-yl)-1H-pyrazol-5-yl]-1,7-naphthyridine in 5.1 ml methanol and the reaction mixture was stirred at room temperature for 90 minutes. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 24 mg (0.05 mmol) of the desired product as a mixture of 2 stereoisomers.

$^1$H-NMR (400 MHz, DMSO-d6): δ [ppm]=0.82 (3H), 1.16 (3H), 3.00-3.17 (2H), 3.41-3.55 (2H), 3.55-3.67 (2H), 3.67-3.78 (8H), 3.78-3.92 (2H), 3.98 (3H), 4.14 (1H), 6.44 (1H), 6.56 (1H), 7.28 (2H), 7.49 (4H), 7.56 (2H), 7.92-8.17 (6H), 8.33 (2H), 13.29 (2H).

270

Example 139

4-{[(2-fluorophenyl)(methyl)oxido-λ⁶-sulfanylidene]amino}-2-[(3R)-3-methylmorpholin-4-yl]-8-(1H-pyrazol-5-yl)-1,7-naphthyridine, mixture of 2 diastereoisomers

Step a

4-{[(2-fluorophenyl)(methyl)oxido-λ⁶-sulfanylidene]amino}-2-[(3R)-3-methylmorpholin-4-yl]-8-[1-(tetrahydro-2H-pyran-2-yl)-1H-pyrazol-5-yl]-1,7-naphthyridine

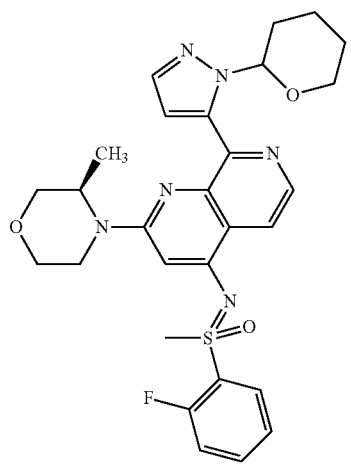 [SMILES: C[C@@H]1COCCN1c1cc(N=S(C)(=O)c2ccccc2F)c2ccnc(-c3ccnn3C3CCCCO3)c2n1]

Under argon, 8 mg (0.014 mmol) 4,5-bis(diphenylphosphino)-9,9-dimethylxanthene and 7 mg (0.007 mmol) tris(dibenzylideneacetone)dipalladium(0) were added to a mixture of 75 mg (0.142 mmol) 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 32 mg (0.19 mmol) 1-fluoro-2-(S-methylsulfonimidoyl)benzene and 69 mg (0.21 mmol) caesium carbonate in 0.67 ml toluene. The mixture was stirred at 110° C. for 3 hours. After cooling, the reaction mixture was diluted with ethyl acetate and washed with an aqueous solution of sodium chloride. The organic phase was filtered using a Whatman filter and concentrated to give the crude product that was used without further purification.

Step b

4-{[(2-fluorophenyl)(methyl)oxido-λ⁶-sulfanylidene]amino}-2-[(3R)-3-methylmorpholin-4-yl]-8-(1H-pyrazol-5-yl)-1,7-naphthyridine, mixture of 2 diastereoisomers

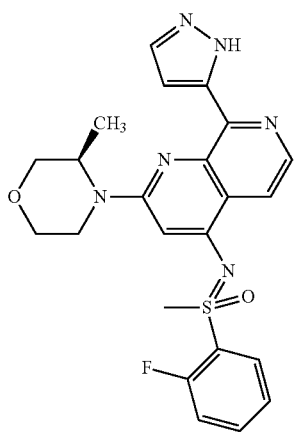 [SMILES: C[C@@H]1COCCN1c1cc(N=S(C)(=O)c2ccccc2F)c2ccnc(-c3ccn[nH]3)c2n1]

0.20 ml (0.29 mmol) 2N aqueous solution of hydrogen chloride was added to a solution of 110 mg crude 4-{[(2-fluorophenyl)(methyl)oxido-λ⁶-sulfanylidene]amino}-2-[(3R)-3-methylmorpholin-4-yl]-8-[1-(tetrahydro-2H-pyran-2-yl)-1H-pyrazol-5-yl]-1,7-naphthyridine in 4.5 ml methanol and the reaction mixture was stirred at room temperature for 90 minutes. The mixture was basified by addition of an aqueous sodium bicarbonate solution and extracted with ethyl acetate (2×). The combined organic phases were filtered using a Whatman filter and concentrated. The residue was purified by preparative HPLC (Autopurifier: basic conditions) to give 28 mg (0.06 mmol) of the desired product as a mixture of 2 stereoisomers.

¹H-NMR (400 MHz, DMSO-d6): δ [ppm]=0.82 (3H), 1.15 (3H), 2.99-3.17 (2H), 3.46 (2H), 3.57 (1H), 3.60-3.67 (1H), 3.71 (2H), 3.74-3.92 (8H), 3.92-4.06 (3H), 4.12 (1H), 6.47 (1H), 6.52 (1H), 7.27 (2H), 7.38-7.54 (4H), 7.56 (2H), 7.73-7.84 (2H), 7.91-7.96 (2H), 8.11 (1H), 8.11 (1H), 8.27-8.34 (2H), 13.28 (2H).

Examples 140 and 141

4-{[(2-fluorophenyl)(methyl)oxido-λ⁶-sulfanylidene]amino}-2-[(3R)-3-methylmorpholin-4-yl]-8-(1H-pyrazol-5-yl)-1,7-naphthyridine, diastereoisomer 1

4-{[(2-fluorophenyl)(methyl)oxido-λ⁶-sulfanylidene]amino}-2-[(3R)-3-methylmorpholin-4-yl]-8-(1H-pyrazol-5-yl)-1,7-naphthyridine, diastereoisomer 2

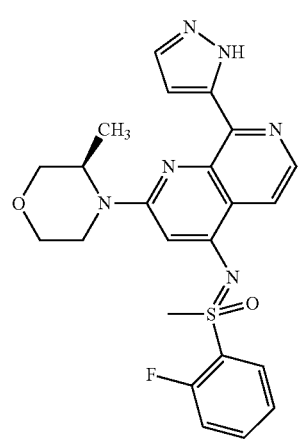 [SMILES: C[C@@H]1COCCN1c1cc(N=S(C)(=O)c2ccccc2F)c2ccnc(-c3ccn[nH]3)c2n1]

The mixture of 2 stereoisomers from example 139 was separated into the single stereoisomers using preparative chiral HPLC:

| | |
|---|---|
| System: | Labomatic Pump HD-5000, Labomatic SP-3000, Labocord 5000, Labomatic Labcol Vario 4000, Gilson GX-241 |
| Column: | Chiralpak IA 5 μm 250 × 30 mm |
| Solvent: | EtOH/Methanol/diethylamine 50:50:0.1 (v/v/v) |
| Flow: | 35 mL/min |
| Temperature: | RT |
| Solution: | 25 mg/3 mL DCM/MeOH |
| Injection: | 5 × 0.6 mL |
| Detection: | UV 254 nm |

| | Retention time in min | purity in % | yield |
|---|---|---|---|
| Example 140 Stereoisomer 1 | 7.4-7.9 | 93 | 6 mg (0.01 mmol) |
| Example 141 Stereoisomer 2 | 8.6-9.2 | 93 | 6 mg (0.01 mmol) |

Example 142

4-(dimethylphosphoryl)-2-[(3R)-3-methylmorpholin-4-yl]-8-(1H-pyrazol-5-yl)-1,7-naphthyridine

Step a 4-(dimethylphosphoryl)-2-[(3R)-3-methylmorpholin-4-yl]-8-[1-(tetrahydro-2H-pyran-2-yl)-1H-pyrazol-5-yl]-1,7-naphthyridine

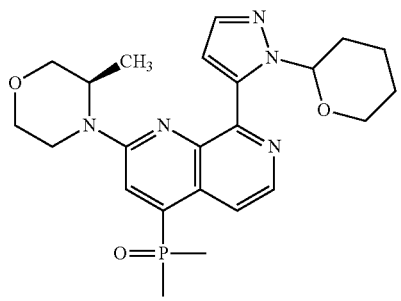 [SMILES: C[C@@H]1COCCN1c1cc(P(C)(C)=O)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 35 mg (0.32 mmol) dimethylphosphinoxide, 33 mg (0.028 mmol tetrakis(triphenylphosphine)palladium(0) and 0.06 ml (0.43 mmol) of triethylamine in 0.9 ml of acetonitrile was degased with argon. Under argon, the reaction mixture was stirred at 90° C. for 3 hours. After cooling the reaction mixture was diluted with ethyl acetate and washed with aqueous chloride solution. The organic phase was filtered using a Whatman filter and then concentrated to give the crude product that was used without further purification in the next step.

Step b 4-(dimethylphosphoryl)-2-[(3R)-3-methylmorpholin-4-yl]-8-(1H-pyrazol-5-yl)-1,7-naphthyridine

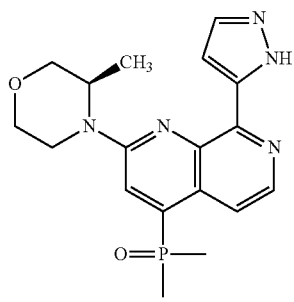 [SMILES: C[C@@H]1COCCN1c1cc(P(C)(C)=O)c2ccnc(-c3ccn[nH]3)c2n1]

A solution of 210 mg of crude 4-(dimethylphosphoryl)-2-[(3R)-3-methylmorpholin-4-yl]-8-[1-(tetrahydro-2H-pyran-2-yl)-1H-pyrazol-5-yl]-1,7-naphthyridine from step a in 2.1 ml of methanol and 0.53 ml of 2N hydrochloric acid was stirred for 10 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 13 mg (0.04 mmol) of the desired product.

$^1$H-NMR (400 MHz, DMSO-d6): δ [ppm]=1.30 (3H), 1.94 (3H), 1.90 (3H), 3.36-3.43 (1H), 3.57 (1H), 3.72 (1H), 3.85 (1H), 4.07 (1H), 4.18 (1H), 4.55-4.71 (1H), 7.37 (1H), 7.54-7.74 (2H), 8.32-8.51 (2H), 13.40 (1H).

Example 143

4-(diethylphosphoryl)-2-[(3R)-3-methylmorpholin-4-yl]-8-(1H-pyrazol-5-yl)-1,7-naphthyridine

Step a 4-(diethylphosphoryl)-2-[(3R)-3-methylmorpholin-4-yl]-8-[1-(tetrahydro-2H-pyran-2-yl)-1H-pyrazol-5-yl]-1,7-naphthyridine

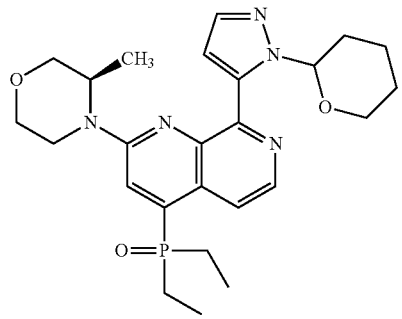 [SMILES: CCP(=O)(CC)c1cc(N2CCOC[C@H]2C)nc2c(-c3ccnn3C3CCCCO3)nccc12]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 32 mg (0.28 mmol) diethylphosphane oxide, 1.3 mg (0.006 mmol) palladium(II) acetate, 3.5 mg (0.006 mmol) of 1,1'-bis(diphenylphosphino)ferrocene and 0.06 ml (0.37 mmol) of ethyldiisopropylamine in 1.2 ml of DMF and 0.14 ml 1,2-dimethoxyethane was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The aqueous phase was saturated with solid sodium chloride and extracted with a mixture of THF and ethyl acetet (1:1). The combined organic phases were filtered using a Whatman filter and then concentrated to give the crude product that was used without further purification in the next step.

Step b 4-(diethylphosphoryl)-2-[(3R)-3-methylmorpholin-4-yl]-8-(1H-pyrazol-5-yl)-1,7-naphthyridine

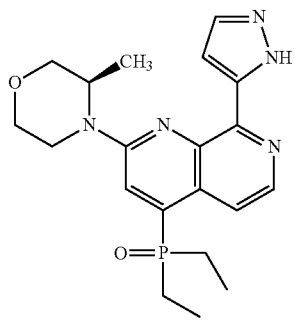 [SMILES: CCP(=O)(CC)c1cc(N2CCOC[C@H]2C)nc2c(-c3ccn[nH]3)nccc12]

A solution of 190 mg of crude 4-(diethylphosphoryl)-2-[(3R)-3-methylmorpholin-4-yl]-8-[1-(tetrahydro-2H-pyran-2-yl)-1H-pyrazol-5-yl]-1,7-naphthyridine from step a in 1.8 ml of methanol and 0.45 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 25 mg (0.06 mmol) of the desired product.

$^1$H-NMR (400 MHz, DMSO-d6): δ [ppm]=0.89-1.12 (6H), 1.18-1.35 (3H), 2.09-2.31 (4H), 3.59 (1H), 3.74 (1H), 3.84 (1H), 4.07 (1H), 4.18 (1H), 4.62 (1H), 7.37 (1H), 7.54-7.81 (2H), 8.39 (1H), 8.50 (1H), 13.40 (1H).

Example 144 ethyl isobutyl{2-[(3R)-3-methylmorpholin-4-yl]-8-(1H-pyrazol-5-yl)-1,7-naphthyridin-4-yl}phosphinate Step a ethyl isobutyl{2-[(3R)-3-methylmorpholin-4-yl]-8-[1-(tetrahydro-2H-pyran-2-yl)-1H-pyrazol-5-yl]-1,7-naphthyridin-4-yl}phosphinate

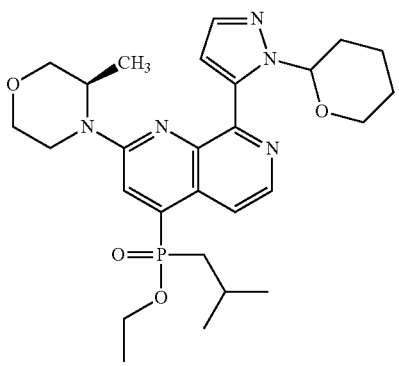 [SMILES: CCOP(=O)(CC(C)C)c1cc(N2CCOC[C@H]2C)nc2c(-c3ccnn3C3CCCCO3)nccc12]

A mixture of 250 mg (0.47 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 71 mg (0.47 mmol) ethyl (2-methylpropyl)phosphinate, 2.1 mg (0.009 mmol) palladium(II) acetate, 5.8 mg (0.01 mmol) of 1,1'-bis(diphenylphosphino)ferrocene and 0.11 ml (0.62 mmol) of ethyldiisopropylamine in 2.1 ml of DMF and 0.24 ml 1,2-dimethoxyethane was degased with argon. Under argon, the reaction mixture was stirred at room temperature for 10 minutes and then at 110° C. overnight. After cooling the reaction mixture was diluted with ethyl acetate and washed with saturated aqueous sodium bicarbonate solution and saturated aqueous sodium chloride solution. The aqueous phase was saturated with solid sodium chloride and extracted with a mixture of THF and ethyl acetet (1:1). The combined organic phases were filtered using a Whatman filter and then concentrated to give the crude product that was used without further purification in the next step.

Step b ethyl isobutyl{2-[(3R)-3-methylmorpholin-4-yl]-8-(1H-pyrazol-5-yl)-1,7-naphthyridin-4-yl}phosphinate

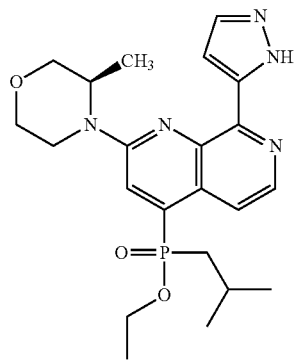 [SMILES: CCOP(=O)(CC(C)C)c1cc(N2CCOC[C@H]2C)nc2c(-c3ccn[nH]3)nccc12]

A solution of 456 mg of crude ethyl isobutyl{2-[(3R)-3-methylmorpholin-4-yl]-8-[1-(tetrahydro-2H-pyran-2-yl)-1H-pyrazol-5-yl]-1,7-naphthyridin-4-yl}phosphinate from step a in 3.9 ml of methanol and 1.0 ml of 2N hydrochloric acid was stirred for 60 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 29 mg (0.07 mmol) of the desired product.

$^1$H-NMR (400 MHz, DMSO-d6): δ [ppm]=0.79-0.96 (3H), 1.03 (3H), 1.13-1.42 (6H), 1.90-2.19 (4H), 3.59 (1H), 3.73 (1H), 3.79-3.93 (2H), 3.97-4.27 (3H), 4.42-4.72 (1H), 7.38 (1H), 7.64 (1H), 7.81 (1H), 8.10 (1H), 8.45 (1H), 13.42 (1H).

Example 145

2-[(3R)-3-methylmorpholin-4-yl]-4-(morpholin-4-yl)-8-(1H-pyrazol-5-yl)-1,7-naphthyridine

Step a

2-[(3R)-3-methylmorpholin-4-yl]-8-[1-(tetrahydro-2H-pyran-2-yl)-1H-pyrazol-5-yl]-1,7-naphthyridine

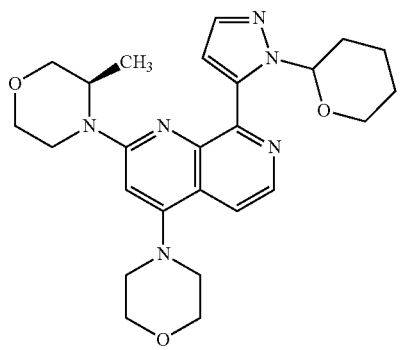 [SMILES: C[C@@H]1COCCN1c1cc(N2CCOCC2)c2ccnc(-c3ccnn3C3CCCCO3)c2n1]

A mixture of 50 mg (0.095 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 28 mg (0.32 mmol) morpholine in 0.14 ml of MeCN was stirred at 70° C. for 150 minutes under argon. After cooling the reaction mixture was diluted with ethyl acetate and THF and washed with saturated aqueous sodium chloride solution. The organic phase was filtered using a Whatman filter and then concentrated to give the crude product that was used without further purification in the next step.

Step b

2-[(3R)-3-methylmorpholin-4-yl]-4-(morpholin-4-yl)-8-(1H-pyrazol-5-yl)-1,7-naphthyridine

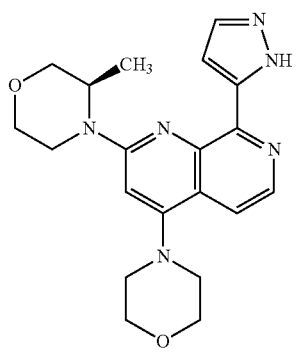 [SMILES: C[C@@H]1COCCN1c1cc(N2CCOCC2)c2ccnc(-c3ccn[nH]3)c2n1]

A solution of 45 mg of crude 2-[(3R)-3-methylmorpholin-4-yl]-4-(morpholin-4-yl)-8-[1-(tetrahydro-2H-pyran-2-yl)-1H-pyrazol-5-yl]-1,7-naphthyridine] from step a in 0.45 ml of methanol and 0.11 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 16 mg (0.04 mmol) of the desired product.

$^1$H-NMR (400 MHz, DMSO-d6): δ [ppm]=1.25 (3H), 3.07-3.23 (4H), 3.54 (1H), 3.69 (1H), 3.77-3.91 (5H), 3.98-4.07 (1H), 4.11 (1H), 4.57 (1H), 6.77 (1H), 7.33 (1H), 7.59 (1H), 7.63 (1H), 8.29 (1H), 13.33 (1H).

Example 146

4-(1-isobutyl-1H-pyrazol-5-yl)-2-[(3R)-3-methylmorpholin-4-yl]-8-(1H-pyrazol-5-yl)-1,7-naphthyridine

Step a 4-(1-isobutyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine

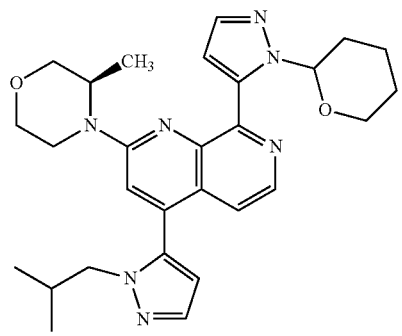 [SMILES: CC(C)Cn1nccc1-c1cc(N2CCOC[C@H]2C)nc2c(-c3ccnn3C3CCCCO3)nccc12]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 36 mg (0.14 mmol) 1-isobutyl-5-(4,4,5,5-tetramethyl-1,3,2-dioxaborolan-2-yl)-1H-pyrazole, 11 mg (0.019 mmol) of [1,1'-bis(diphenylphosphino)ferrocene]dichloropalladium(II) complex with dichloromethane (1:1, Pd(dppf)Cl$_2$) and 49 mg (0.36 mmol) of potassium carbonate in 3.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(1-isobutyl-1H-pyrazol-5-yl)-2-[(3R)-3-methyl-morpholin-4-yl]-8-(1H-pyrazol-5-yl)-1,7-naphthyridine

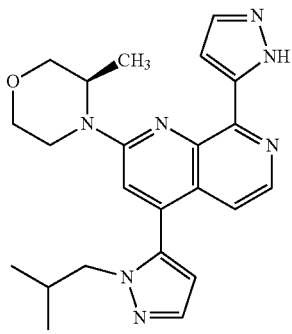 [SMILES: CC(C)Cn1nccc1-c1cc(N2CCOC[C@H]2C)nc2c(-c3ccn[nH]3)nccc12]

A solution of 105 mg of crude 4-(1-isobutyl-1H-pyrazol-5-yl)-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.21 ml of 2N hydrochloric acid was stirred for 60 minutes at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: acidic conditions) to give 8 mg (0.02 mmol) of the desired product.

$^1$H-NMR (400 MHz, DMSO-d6): δ [ppm]=0.64 (6H), 1.16-1.36 (3H), 1.82-2.04 (1H), 3.50-3.67 (1H), 3.69-3.96 (4H), 3.98-4.14 (1H), 4.23 (1H), 4.62 (1H), 6.56 (1H), 7.23 (1H), 7.44 (1H), 7.57 (1H), 7.65 (1H), 7.71 (1H), 8.36 (1H), 13.43 (1H).

Example 147

4-[5-fluoro-6-(methylsulfonyl)pyridin-3-yl]-2-[(3R)-3-methylmorpholin-4-yl]-8-(1H-pyrazol-5-yl)-1,7-naphthyridine Step a 4-[5-fluoro-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine

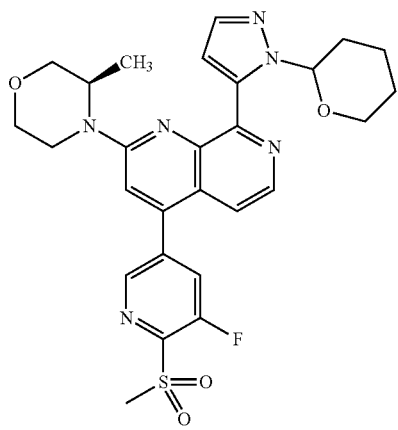 [SMILES: C[C@@H]1COCCN1c1cc(-c2cnc(S(C)(=O)=O)c(F)c2)c2ccnc(-c3ccnn3C3CCCCO3)c2n1]

A suspension of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 86 mg (0.28 mmol) 3-fluoro-2-(methylsulfonyl)-5-(4,4,5,5-tetra methyl-1,3,2-dioxaborolan-2-yl)pyridine, 12 mg (0.014 mmol) of [1,1'-bis(diphenylphosphino)ferrocene]dichloropalladium(II) complex with dichloromethane (1:1, Pd(dppf)Cl$_2$) and 185 mg (0.57 mmol) of caesium carbonate in 1.0 ml of dioxane was degased with argon. Under argon, the reaction mixture was stirred at 110° C. for 2 hours. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[5-fluoro-6-(methylsulfonyl)pyridin-3-yl]-2-[(3R)-3-methylmorpholin-4-yl]-8-(1H-pyrazol-5-yl)-1,7-naphthyridine

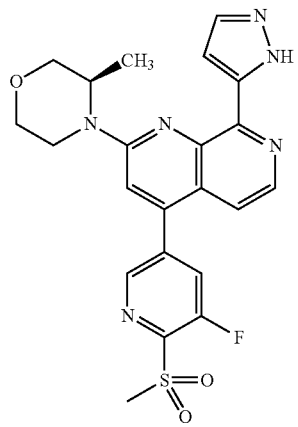 [SMILES: C[C@@H]1COCCN1c1cc(-c2cnc(S(C)(=O)=O)c(F)c2)c2ccnc(-c3ccn[nH]3)c2n1]

A solution of 118 mg of crude 4-[5-fluoro-6-(methylsulfonyl)pyridin-3-yl]-2-[(3R)-3-methylmorpholin-4-yl]-8-[1-(tetrahydro-2H-pyran-2-yl)-1H-pyrazol-5-yl]-1,7-naphthyridine from step a in 1.0 ml of methanol and 0.25 ml of 2N hydrochloric acid was stirred for 1 hours at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 1 mg (0.002 mmol) of the desired product.

$^1$H-NMR (400 MHz, DMSO-d6): δ [ppm]=1.27-1.33 (3H), 3.45-3.63 (5H), 3.71 (1H), 3.83 (1H), 4.05 (1H), 4.23 (1H), 4.65 (1H), 7.33-7.54 (2H), 7.64 (2H), 8.34 (1H), 8.43 (1H), 8.80 (1H), 13.42 (1H).

Example 148

4-[(3R)-3-methylmorpholin-4-yl]-2-(morpholin-4-yl)-8-(1H-pyrazol-5-yl)-1,7-naphthyridine Step a 4-[(3R)-3-methylmorpholin-4-yl]-2-(morpholin-4-yl)-8-[1-(tetrahydro-2H-pyran-2-yl)-1H-pyrazol-5-yl]-1,7-naphthyridine

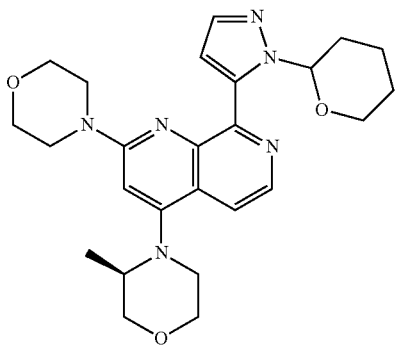 [SMILES: C[C@@H]1COCCN1c1cc(N2CCOCC2)nc2c(-c3ccnn3C3CCCCO3)nccc12]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 100 mg (0.99 mmol) (3R)-3-methylmorpholine in 0.43 ml of MeCN was stirred at 70° C. overnight under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[(3R)-3-methylmorpholin-4-yl]-2-(morpholin-4-yl)-8-(1H-pyrazol-5-yl)-1,7-naphthyridine

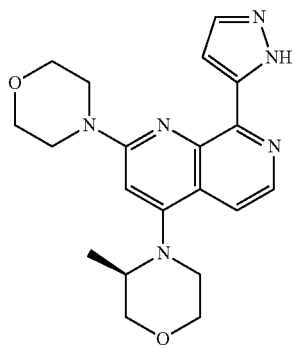 [SMILES: C[C@@H]1COCCN1c1cc(N2CCOCC2)nc2c(-c3ccn[nH]3)nccc12]

A solution of 190 mg of crude 4-[(3R)-3-methylmorpholin-4-yl]-2-(morpholin-4-yl)-8-[1-(tetrahydro-2H-pyran-2-yl)-1H-pyrazol-5-yl]-1,7-naphthyridine from step a in 1.9 ml of methanol and 0.47 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 18 mg (0.05 mmol) of the desired product.

$^1$H-NMR (400 MHz, DMSO-d6): δ [ppm]=0.93 (3H), 2.82 (1H), 3.38-3.47 (1H), 3.54 (1H), 3.65-3.86 (10H), 3.91 (1H), 3.98 (1H), 6.96 (1H), 7.36 (1H), 7.61 (1H), 7.71 (1H), 8.33 (1H), 13.35 (1H).

Example 149

2-[(3R)-3-methylmorpholin-4-yl]-4-(4-methyl-1H-pyrazol-5-yl)-8-(1H-pyrazol-5-yl)-1,7-naphthyridine Step a 2-[(3R)-3-methylmorpholin-4-yl]-4-(4-methyl-1H-pyrazol-5-yl)-8-[1-(tetrahydro-2H-pyran-2-yl)-1H-pyrazol-5-yl]-1,7-naphthyridine

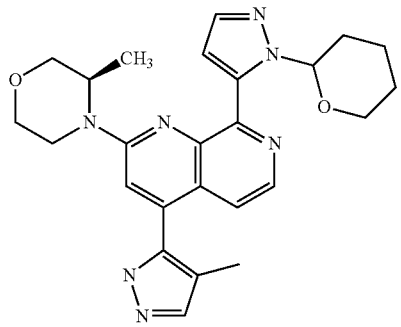 [SMILES: Cc1cn[nH]c1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 48 mg (0.38 mmol) 1-isobutyl-5-(4,4,5,5-tetramethyl-1,3,2-dioxaborolan-2-yl)-1H-pyrazole, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(4-methyl-1H-pyrazol-5-yl)-8-(1H-pyrazol-5-yl)-1,7-naphthyridine

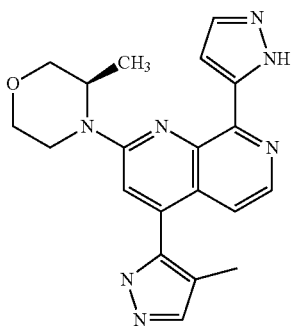 [SMILES: Cc1cn[nH]c1-c1cc(N2CCOC[C@H]2C)nc2c(-c3ccn[nH]3)nccc12]

A solution of 111 mg of crude 2-[(3R)-3-methylmorpholin-4-yl]-4-(4-methyl-1H-pyrazol-5-yl)-8-[1-(tetrahydro-2H-pyran-2-yl)-1H-pyrazol-5-yl]-1,7-naphthyridine from step a in 5.0 ml of methanol and 0.24 ml of 2N hydrochloric acid was stirred for 60 minutes at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: acidic conditions) to give 12 mg (0.03 mmol) of the desired product.

$^1$H-NMR (400 MHz, DMSO-d6): δ [ppm]=1.30 (3H), 2.07 (3H), 3.59 (1H), 3.73 (1H), 3.83 (1H), 4.06 (1H), 4.20 (1H), 4.62 (1H), 7.25-7.52 (2H), 7.64 (2H), 7.76 (1H), 8.34 (1H), 13.11 (1H), 13.41 (1H).

Example 150

4-[2-fluoro-5-(methylsulfonyl)phenyl]-2-[(3R)-3-methylmorpholin-4-yl]-8-(1H-pyrazol-5-yl)-1,7-naphthyridine Step a 4-[2-fluoro-5-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine

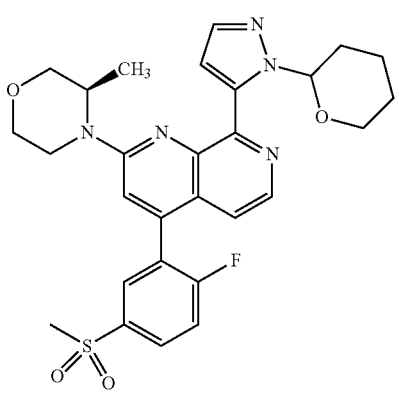 [SMILES: C[C@@H]1COCCN1c1cc(-c2cc(S(C)(=O)=O)ccc2F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 83 mg (0.38 mmol) [2-fluoro-5-(methylsulfonyl)phenyl]boronic acid, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[2-fluoro-5-(methylsulfonyl)phenyl]-2-[(3R)-3-methylmorpholin-4-yl]-8-(1H-pyrazol-5-yl)-1,7-naphthyridine

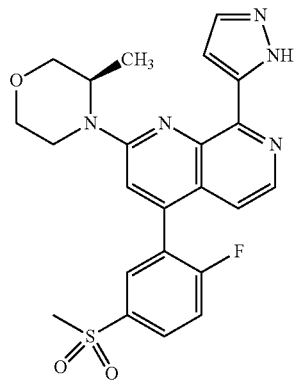 [SMILES: C[C@@H]1COCCN1c1cc(-c2cc(S(C)(=O)=O)ccc2F)c2ccnc(-c3ccn[nH]3)c2n1]

A solution of 83 mg of crude 4-[2-fluoro-5-(methylsulfonyl)phenyl]-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.15 ml of 2N hydrochloric acid was stirred for 3 hours at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: acidic conditions) to give 29 mg (0.06 mmol) of the desired product.

$^1$H-NMR (400 MHz, DMSO-d6): δ [ppm]=1.32 (3H), 3.37 (1H), 3.35 (3H), 3.58 (1H), 3.72 (1H), 4.05 (1H), 4.21 (1H), 4.65 (1H), 7.17 (1H), 7.45 (1H), 7.65 (2H), 7.77 (1H), 8.07-8.28 (2H), 8.33 (1H), 13.45 (1H).

Example 151

4-[4-(isopropylsulfonyl)phenyl]-2-[(3R)-3-methyl-morpholin-4-yl]-8-(1H-pyrazol-5-yl)-1,7-naphthyridine

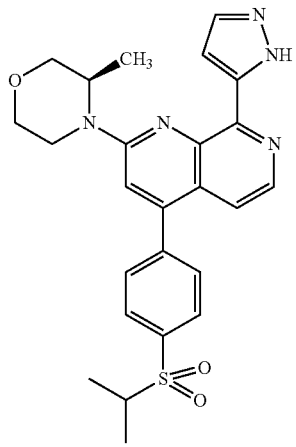 [SMILES: CC(C)S(=O)(=O)c1ccc(-c2cc(N3CCOC[C@H]3C)nc3c(-c4ccn[nH]4)nccc23)cc1]

4-[4-(isopropylsulfonyl)phenyl]-2-[(3R)-3-methylmorpholin-4-yl]-8-(1H-pyrazol-5-yl)-1,7-naphthyridine was isolated as a side product in minor amounts in the preparation of example 25.

$^1$H-NMR (400 MHz, DMSO-d6): δ [ppm]=1.25 (6H), 3.55 (1H), 3.81 (8H), 7.38 (1H), 7.44 (1H), 7.59 (1H), 7.65 (1H), 7.74-7.94 (2H), 7.95-8.15 (2H), 8.35 (1H), 13.43 (1H).

Example 152

4-(6-fluoropyridin-2-yl)-2-[(3R)-3-methylmorpholin-4-yl]-8-(1H-pyrazol-5-yl)-1,7-naphthyridine

Step a 4-(6-fluoropyridin-2-yl)-2-[(3R)-3-methylmorpholin-4-yl]-8-[1-(tetrahydro-2H-pyran-2-yl)-1H-pyrazol-5-yl]-1,7-naphthyridine

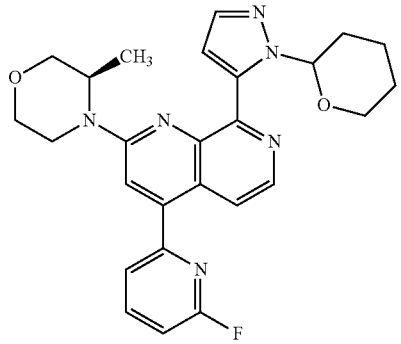 [SMILES: C[C@@H]1COCCN1c1cc(-c2cccc(F)n2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) (6-fluoropyridin-2-yl)boronic acid, 15 mg (0.019 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 4-(6-fluoropyridin-2-yl)-2-[(3R)-3-methylmorpholin-4-yl]-8-(1H-pyrazol-5-yl)-1,7-naphthyridine

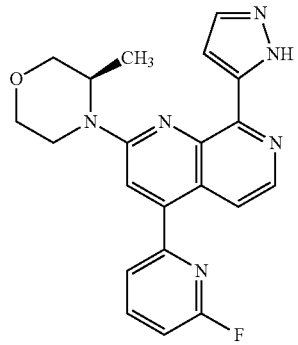 [SMILES: C[C@@H]1COCCN1c1cc(-c2cccc(F)n2)c2ccnc(-c3ccn[nH]3)c2n1]

A solution of 92 mg of crude 4-(6-fluoropyridin-2-yl)-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.19 ml of 2N hydrochloric acid was stirred for 1 hour at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: basic conditions) to give 12 mg (0.03 mmol) of the desired product.

$^1$H-NMR (400 MHz, DMSO-d6): δ [ppm]=1.31 (3H), 3.35-3.42 (1H), 3.58 (1H), 3.73 (1H), 3.84 (1H), 4.06 (1H), 4.16-4.29 (1H), 4.59-4.75 (1H), 7.37-7.46 (2H), 7.59-7.67 (2H), 7.72 (1H), 7.82 (1H), 8.26 (1H), 8.36 (1H), 13.43 (1H).

Example 153

4-(1-ethyl-1H-imidazol-4-yl)-2-[(3R)-3-methylmorpholin-4-yl]-8-(1H-pyrazol-5-yl)-1,7-naphthyridine

Step a 4-(1-ethyl-1H-imidazol-4-yl)-2-[(3R)-3-methylmorpholin-4-yl]-8-[1-(tetrahydro-2H-pyran-2-yl)-1H-pyrazol-5-yl]-1,7-naphthyridine

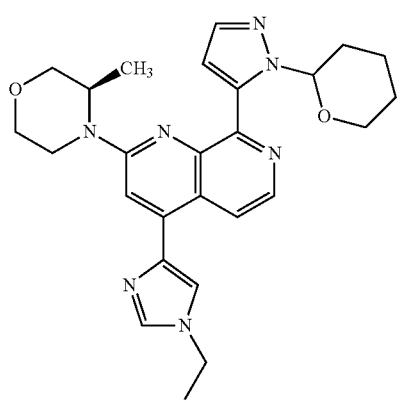 [SMILES: CCn1cnc(-c2cc(N3CCOC[C@H]3C)nc3c(-c4ccnn4C4CCCCO4)nccc23)c1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 83 mg (0.38 mmol) 1-ethyl-4-(4,4,5,5-tetramethyl-1,3,2-dioxaborolan-2-yl)-1H-imidazole, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combinded organic phases were filtered using a Whatman filter and then concentrated to give the crude product that was used without further purification in the next step.

Step b 4-(1-ethyl-1H-imidazol-4-yl)-2-[(3R)-3-methylmorpholin-4-yl]-8-(1H-pyrazol-5-yl)-1,7-naphthyridine

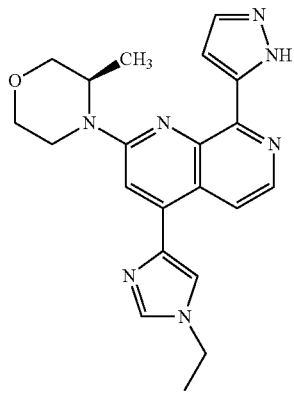 [SMILES: CCn1cnc(-c2cc(N3CCOC[C@H]3C)nc3c(-c4ccn[nH]4)nccc23)c1]

A solution of 130 mg of crude 4-(1-ethyl-1H-imidazol-4-yl)-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.28 ml of 2N hydrochloric acid was stirred for 1 hour at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: basic conditions) to give 12 mg (0.03 mmol) of the desired product.

$^1$H-NMR (400 MHz, DMSO-d6): δ [ppm]=1.29 (3H), 1.46 (3H), 3.51-3.64 (1H), 3.74 (1H), 3.85 (1H), 3.99-4.26 (4H), 4.62 (1H), 7.38 (1H), 7.51-7.73 (2H), 7.88-8.00 (1H), 8.09 (1H), 8.36 (1H), 8.61 (1H), 13.38 (1H).

Example 154

1-{2-[(3R)-3-methylmorpholin-4-yl]-8-(1H-pyrazol-5-yl)-1,7-naphthyridin-4-yl}prolinamide Step a 1-{2-[(3R)-3-methylmorpholin-4-yl]-8-[1-(tetrahydro-2H-pyran-2-yl)-1H-pyrazol-5-yl]-1,7-naphthyridin-4-yl}prolinamide

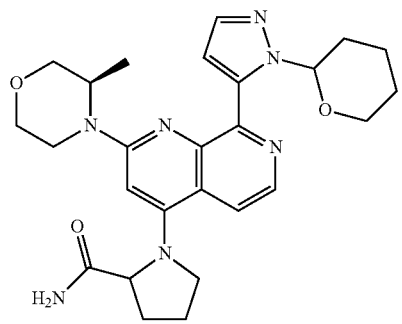 [SMILES: C[C@@H]1COCCN1c1cc(N2CCCC2C(N)=O)c2ccnc(-c3ccnn3C3CCCCO3)c2n1]

A mixture of 150 mg (0.28 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 110 mg (0.97 mmol) prolinamide in 0.42 ml of MeCN was stirred at 70° C. for 3 hours under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

1-{2-[(3R)-3-methylmorpholin-4-yl]-8-(1H-pyrazol-5-yl)-1,7-naphthyridin-4-yl}prolinamide

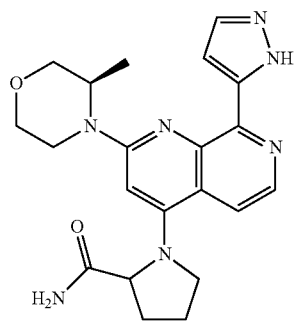 [SMILES: C[C@@H]1COCCN1c1cc(N2CCCC2C(N)=O)c2ccnc(-c3ccn[nH]3)c2n1]

A solution of 233 mg of crude 1-{2-[(3R)-3-methylmorpholin-4-yl]-8-[1-(tetrahydro-2H-pyran-2-yl)-1H-pyrazol-5-yl]-1,7-naphthyridin-4-yl}prolinamide from step a in 2.2 ml of methanol and 0.55 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 18 mg (0.05 mmol) of the desired product.

$^1$H-NMR (400 MHz, DMSO-d6): δ [ppm]=1.16-1.32 (3H), 1.82-2.10 (3H), 2.28-2.36 (1H), 3.24 (1H), 3.45-3.61 (1H), 3.68 (2H), 3.82 (1H), 4.01-4.21 (3H), 4.26-4.52 (2H), 6.20 (1H), 7.16 (1H), 7.31 (1H), 7.58 (1H), 7.66 (1H), 7.87 (1H), 8.21 (1H), 13.36 (1H).

Example 155

3-{2-[(3R)-3-methylmorpholin-4-yl]-8-(1H-pyrazol-5-yl)-1,7-naphthyridin-4-yl}pyridin-2-amine Step a 3-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-amine

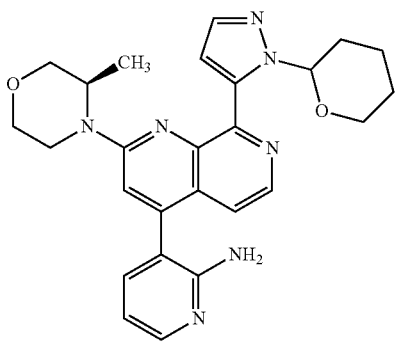 [SMILES: C[C@@H]1COCCN1c1cc(-c2cccnc2N)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 42 mg (0.19 mmol) 3-(4,4,5,5-tetramethyl-1,3,2-dioxaborolan-2-yl)pyridin-2-amine, 15 mg (0.019 mmol) of [1,1'-bis(diphenylphosphino)ferrocene]dichloropalladium (II) complex with dichloromethane (1:1, Pd(dppf)Cl$_2$) and 247 mg (0.76 mmol) of caesium carbonate in 1.5 ml of dioxane was degased with argon. Under argon, the reaction mixture was stirred at 110° C. for 90 minutes. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

3-{2-[(3R)-3-methylmorpholin-4-yl]-8-(1H-pyrazol-5-yl)-1,7-naphthyridin-4-yl}pyridin-2-amine

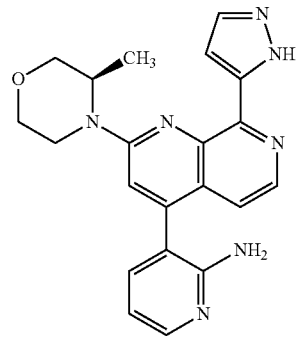 [SMILES: C[C@@H]1COCCN1c1cc(-c2cccnc2N)c2ccnc(-c3ccn[nH]3)c2n1]

A solution of 76 mg of crude 3-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-amine from step a in 3.0 ml of methanol and 0.16 ml of 2N hydrochloric acid was stirred for 1 hour at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: basic conditions) to give 7 mg (0.02 mmol) of the desired product.

$^1$H-NMR (400 MHz, DMSO-d6): δ [ppm]=1.31 (3H), 3.57 (1H), 3.71 (1H), 3.82 (1H), 4.06 (1H), 4.21 (1H), 4.57-4.67 (1H), 5.71 (2H), 6.72 (1H), 7.12 (1H), 7.29-7.54 (3H), 7.64 (1H), 8.11 (1H), 8.29 (1H), 13.42 (1H).

Example 156

2-[(3R)-3-methylmorpholin-4-yl]-8-(1H-pyrazol-5-yl)-4-[1-(2,2,2-trifluoroethyl)-1H-pyrazol-5-yl]-1,7-naphthyridine Step a 2-[(3R)-3-methylmorpholin-4-yl]-8-[1-(tetrahydro-2H-pyran-2-yl)-1H-pyrazol-5-yl]-4-[1-(2,2,2-trifluoroethyl)-1H-pyrazol-5-yl]-1,7-naphthyridine

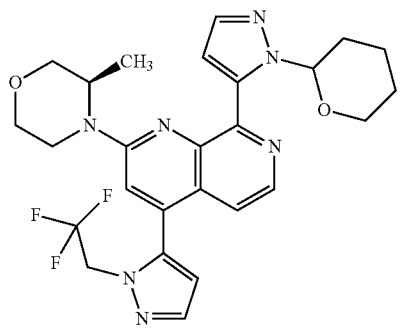 [SMILES: C[C@@H]1COCCN1c1cc(-c2ccnn2CC(F)(F)F)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 74 mg (0.38 mmol) [1-(2,2,2-trifluoroethyl)-1H-pyrazol-5-yl]boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 2.0 ml of dioxane was degased with argon. Under argon, the reaction mixture was stirred at 110° C. for 1 hour. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-8-(1H-pyrazol-5-yl)-4-[1-(2,2,2-trifluoroethyl)-1H-pyrazol-5-yl]-1,7-naphthyridine

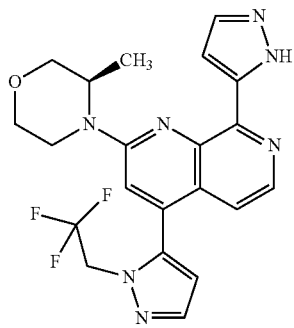 [SMILES: C[C@@H]1COCCN1c1cc(-c2ccnn2CC(F)(F)F)c2ccnc(-c3ccn[nH]3)c2n1]

A solution of 107 mg of crude 2-[(3R)-3-methylmorpholin-4-yl]-8-[1-(tetrahydro-2H-pyran-2-yl)-1H-pyrazol-5-yl]-4-[1-(2,2,2-trifluoroethyl)-1H-pyrazol-5-yl]-1,7-naphthyridine from step a in 3.0 ml of methanol and 0.20 ml of 2N hydrochloric acid was stirred for 1 hour at room temperature. The reaction mixture was diluted with ethyl acetate and washed with aqueous sodium chloride solution. The organic phase was dried (MgSO$_4$), filtered and concentrated to dryness. The residue was purified by preparative HPLC (Autopurifier: basic conditions) to give 7 mg (0.02 mmol) of the desired product.

$^1$H-NMR (400 MHz, CDCl$_3$): δ [ppm]=1.48 (3H), 3.61 (1H), 3.68-3.81 (1H), 3.81-4.00 (2H), 4.05 (1H), 4.20 (1H), 4.50 (1H), 4.89 (2H), 6.79 (1H), 7.33 (1H), 7.42 (1H), 7.67-7.79 (2H), 8.08 (1H), 8.47 (1H).

Example 157

1-methyl-4-{2-[(3R)-3-methylmorpholin-4-yl]-8-(1H-pyrazol-5-yl)-1,7-naphthyridin-4-yl}piperazin-2-one Step a 1-methyl-4-{2-[(3R)-3-methylmorpholin-4-yl]-8-[1-(tetrahydro-2H-pyran-2-yl)-1H-pyrazol-5-yl]-1,7-naphthyridin-4-yl}piperazin-2-one

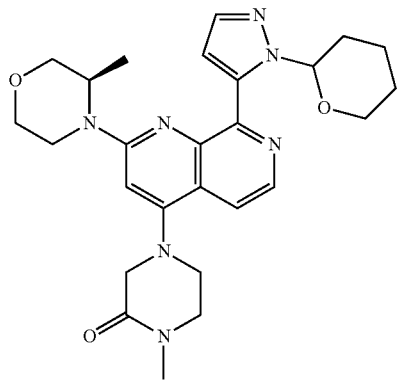 [SMILES: C[C@@H]1COCCN1c1cc(N2CCN(C)C(=O)C2)c2ccnc(-c3ccnn3C3CCCCO3)c2n1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 150 mg (0.99 mmol) 1-methylpiperazin-2-one hydrochloride and 0.28 ml (1.99 mmol) of triethylamine in 0.43 ml of MeCN was stirred at 70° C. overnight under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 1-methyl-4-{2-[(3R)-3-methylmorpholin-4-yl]-8-(1H-pyrazol-5-yl)-1,7-naphthyridin-4-yl}piperazin-2-one

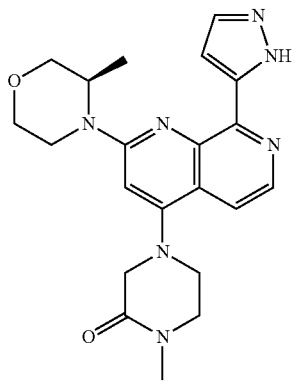 [SMILES: C[C@@H]1COCCN1c1cc(N2CCN(C)C(=O)C2)c2ccnc(-c3ccn[nH]3)c2n1]

A solution of 207 mg of crude 1-methyl-4-{2-[(3R)-3-methylmorpholin-4-yl]-8-[1-(tetrahydro-2H-pyran-2-yl)-

1H-pyrazol-5-yl]-1,7-naphthyridin-4-yl}piperazin-2-one from step a in 2.0 ml of methanol and 0.50 ml of 2N hydrochloric acid was stirred for 1 h at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 11 mg (0.03 mmol) of the desired product.

$^1$H-NMR (400 MHz, DMSO-d6): δ [ppm]=2.96 (3H), 3.49 (2H), 3.61 (2H), 3.76 (8H), 3.86 (2H), 6.84 (1H), 7.35 (1H), 7.47-7.75 (2H), 8.33 (1H), 13.36 (1H).

Example 158 and 159

4-[1-(2-fluoroethyl)-1H-pyrazol-3-yl]-2-[(3R)-3-methylmorpholin-4-yl]-8-(1H-pyrazol-5-yl)-1,7-naphthyridine 4-[1-(2-fluoroethyl)-1H-pyrazol-5-yl]-2-[(3R)-3-methylmorpholin-4-yl]-8-(1H-pyrazol-5-yl)-1,7-naphthyridine Step a 2-[(3R)-3-methylmorpholin-4-yl]-4-(1H-pyrazol-5-yl)-8-[1-(tetrahydro-2H-pyran-2-yl)-1H-pyrazol-5-yl]-1,7-naphthyridine

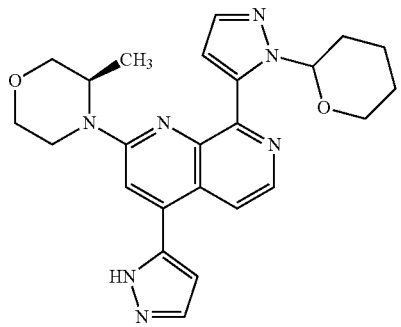 [SMILES: C[C@@H]1COCCN1c1cc(-c2ccn[nH]2)c2ccnc(-c3ccnn3C3CCCCO3)c2n1]

A suspension of 200 mg (0.38 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 136 mg (0.76 mmol) 5-(5,5-dimethyl-1,3,2-dioxaborinan-2-yl)-1H-pyrazole, 31 mg (0.038 mmol) of [1,1'-bis(diphenylphosphino)ferrocene]dichloropalladium (II) complex with dichloromethane (1:1, Pd(dppf)Cl$_2$) and 131 mg (0.95 mmol) of potassium carbonate in 3.9 ml of acetonitrile and 2.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was purified by column chromatography on silica gel (hexane/ethylacetate 40% to ethyl acetate) to give 134 mg of the desired product containing slight impurities.

Step b

4-[1-(2-fluoroethyl)-1H-pyrazol-3-yl]-2-[(3R)-3-methylmorpholin-4-yl]-8-[1-(tetrahydro-2H-pyran-2-yl)-1H-pyrazol-5-yl]-1,7-naphthyridine 4-[1-(2-fluoroethyl)-1H-pyrazol-5-yl]-2-[(3R)-3-methylmorpholin-4-yl]-8-[1-(tetrahydro-2H-pyran-2-yl)-1H-pyrazol-5-yl]-1,7-naphthyridine

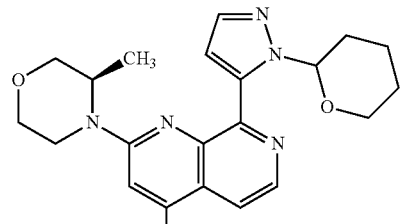

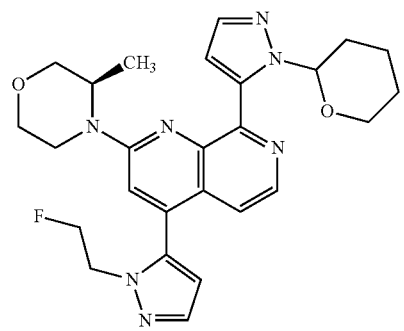

A mixture of 45 mg (0.10 mmol) 2-[(3R)-3-methylmorpholin-4-yl]-4-(1H-pyrazol-5-yl)-8-[1-(tetrahydro-2H-pyran-2-yl)-1H-pyrazol-5-yl]-1,7-naphthyridine from step a, 35 mg (0.20 mmol) of 1-fluoro-2-iodoethane and 66 mg (0.20 mmol) of caesium carbonate in 1.0 ml DMF was stirred at 50° C. for 3 hours. After cooling, the mixture was diluted with ethyl acetate and washed with aqueous sodium chloride solution and aqueous sodium bicarbonate solution. The organic phase was filtered using a Whatman filter and concentrated to dryness to give a mixture of the crude products 4-[1-(2-fluoroethyl)-1H-pyrazol-3-yl]-2-[(3R)-3-methylmorpholin-4-yl]-8-[1-(tetrahydro-2H-pyran-2-yl)-1H-pyrazol-5-yl]-1,7-naphthyridine and 4-[1-(2-fluoroethyl)-1H-pyrazol-5-yl]-2-[(3R)-3-methylmorpholin-4-yl]-8-[1-(tetrahydro-2H-pyran-2-yl)-1H-pyrazol-5-yl]-1,7-naphthyridine that was used without further purification.

Step c

4-[1-(2-fluoroethyl)-1H-pyrazol-3-yl]-2-[(3R)-3-methylmorpholin-4-yl]-8-(1H-pyrazol-5-yl)-1,7-naphthyridine 4-[1-(2-fluoroethyl)-1H-pyrazol-5-yl]-2-[(3R)-3-methylmorpholin-4-yl]-8-(1H-pyrazol-5-yl)-1,7-naphthyridine

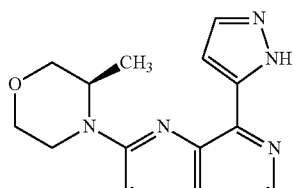

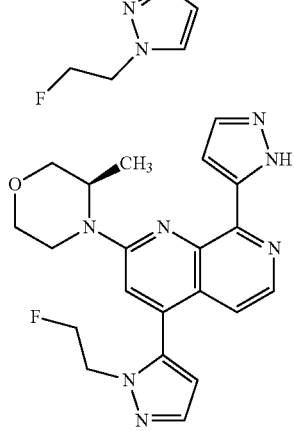

A solution of 55 mg of a crude misture of 4-[1-(2-fluoroethyl)-1H-pyrazol-3-yl]-2-[(3R)-3-methylmorpholin-4-yl]-8-[1-(tetrahydro-2H-pyran-2-yl)-1H-pyrazol-5-yl]-1,7-naphthyridine and 4-[1-(2-fluoroethyl)-1H-pyrazol-5-yl]-2-[(3R)-3-methylmorpholin-4-yl]-8-[1-(tetrahydro-2H-pyran-2-yl)-1H-pyrazol-5-yl]-1,7-naphthyridine from step b in 0.5 ml of methanol and 0.13 ml of 2N hydrochloric acid was stirred for 1 hour at room temperature. The reaction mixture was diluted with an aqueous solution of sodium bicarbonate and extracted with ethyl acetate (2×). The combined organic phases were filtered using a Whatman filter and concentrated to dryness. The residue was purified by preparative HPLC (Autopurifier: basic conditions) to give 12 mg (0.03 mmol) of 4-[1-(2-fluoroethyl)-1H-pyrazol-3-yl]-2-[(3R)-3-methylmorpholin-4-yl]-8-(1H-pyrazol-5-yl)-1,7-naphthyridine (example 158) and 2 mg (0.005 mmol) of 4-[1-(2-fluoroethyl)-1H-pyrazol-5-yl]-2-[(3R)-3-methylmorpholin-4-yl]-8-(1H-pyrazol-5-yl)-1,7-naphthyridine (example 159).

Example 158

$^1$H-NMR (400 MHz, DMSO-d6): δ [ppm]=1.21-1.37 3H), 3.59 (1H), 3.74 (1H), 3.85 (1H), 4.07 (1H), 4.22 (1H), 4.59 (1H), 4.62-4.72 (2H), 4.83 (1H), 4.95 (1H), 7.03 (1H), 7.40 (1H), 7.64 (2H), 7.84-8.13 (1H), 8.39 (1H), 8.47-8.58 (1H), 13.40 (1H).

Example 159

$^1$H-NMR (400 MHz, DMSO-d6): δ [ppm]=1.29 (3H), 3.58 (1H), 3.72 (1H), 3.82 (1H), 4.06 (1H), 4.21 (1H), 4.25-4.39 (2H), 4.53-4.68 (2H), 4.72 (1H), 6.60 (1H), 7.23 (1H), 7.42 (1H), 7.53 (1H), 7.65 (1H), 7.77 (1H), 8.29-8.36 (1H), 13.32 (1H).

Example 160

2-(3-{2-[(3R)-3-methylmorpholin-4-yl]-8-(1H-pyrazol-5-yl)-1,7-naphthyridin-4-yl}-1H-pyrazol-1-yl)ethanol

Step a

2-[(3R)-3-methylmorpholin-4-yl]-4-{1-[2-(tetrahydro-2H-pyran-2-yloxy)ethyl]-1H-pyrazol-3-yl}-8-[1-(tetrahydro-2H-pyran-2-yl)-1H-pyrazol-5-yl]-1,7-naphthyridine

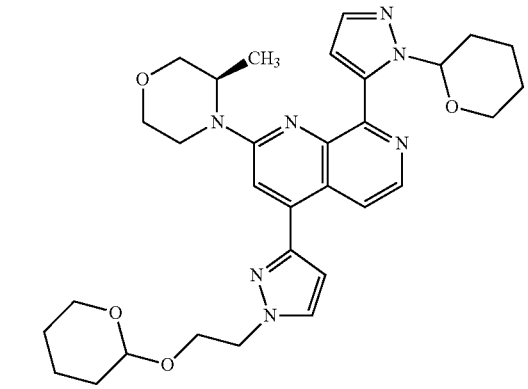 [SMILES: C[C@@H]1COCCN1c1cc(-c2ccn(CCOC3CCCCO3)n2)c2ccnc(-c3ccnn3C3CCCCO3)c2n1]

A mixture of 45 mg (0.10 mmol) 2-[(3R)-3-methylmorpholin-4-yl]-4-(1H-pyrazol-5-yl)-8-[1-(tetrahydro-2H-pyran-2-yl)-1H-pyrazol-5-yl]-1,7-naphthyridine, 25 mg (0.12 mmol) of 2-(2-bromoethoxy)tetrahydro-2H-pyran and 39 mg (0.12 mmol) of caesium carbonate in 0.2 ml DMF was stirred at 70° C. for 7 hours. After cooling, the mixture was diluted with ethyl acetate and washed with aqueous sodium chloride solution. The organic phase was filtered using a Whatman filter and concentrated to dryness to give a mixture of the crude products that was used without further purification.

Step b 2-(3-{2-[(3R)-3-methylmorpholin-4-yl]-8-(1H-pyrazol-5-yl)-1,7-naphthyridin-4-yl}-1H-pyrazol-1-yl)ethanol

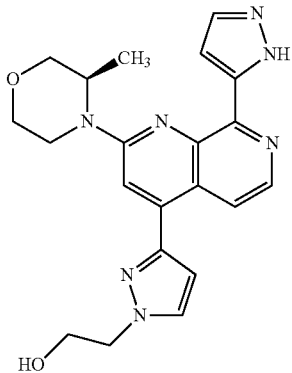 [SMILES: C[C@@H]1COCCN1c1cc(-c2ccn(CCO)n2)c2ccnc(-c3ccn[nH]3)c2n1]

A solution of 52 mg crude 2-[(3R)-3-methylmorpholin-4-yl]-4-{1-[2-(tetrahydro-2H-pyran-2-yloxy)ethyl]-1H-pyrazol-3-yl}-8-[1-(tetrahydro-2H-pyran-2-yl)-1H-pyrazol-5-yl]-1,7-naphthyridine from step a in 0.8 ml of methanol and 0.21 ml of 2N hydrochloric acid was stirred for 90 minutes at room temperature. The reaction mixture was diluted with an aqueous solution of sodium bicarbonate and extracted with ethyl acetate and THF (2×). The combined organic phases were filtered using a Whatman filter and concentrated to dryness. The residue was purified by preparative HPLC (Autopurifier: basic conditions) to give 11 mg (0.03 mmol) of the desired product.

$^1$H-NMR (400 MHz, DMSO-d6): δ [ppm]=1.29 (3H), 3.35-3.41 (1H), 3.53-3.63 (1H), 3.70-3.79 (1H), 3.85 (3H), 4.00-4.10 (1H), 4.17-4.24 (1H), 4.31 (2H), 4.63-4.73 (1H), 5.00 (1H), 6.98 (1H), 7.40 (1H), 7.62 (2H), 7.94 (1H), 8.38 (1H), 8.56 (1H), 13.41 (1H).

Example 161

2-methyl-1-(3-{2-[(3R)-3-methylmorpholin-4-yl]-8-(1H-pyrazol-5-yl)-1,7-naphthyridin-4-yl}-1H-pyrazol-1-yl)propan-2-ol Step a 2-methyl-1-(3-{2-[(3R)-3-methylmorpholin-4-yl]-8-[1-(tetrahydro-2H-pyran-2-yl)-1H-pyrazol-5-yl]-1,7-naphthyridin-4-yl}-1H-pyrazol-1-yl)propan-2-ol

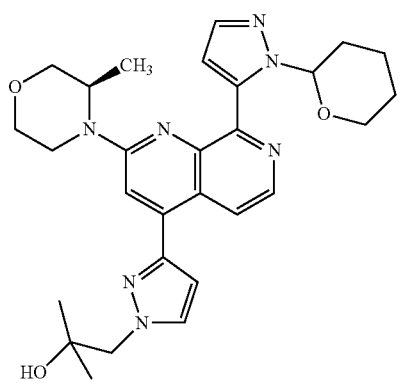 [SMILES: C[C@@H]1COCCN1c1cc(-c2ccn(CC(C)(C)O)n2)c2ccnc(-c3ccnn3C3CCCCO3)c2n1]

In a closed vessel under argon, a mixture of 50 mg (0.11 mmol) 2-[(3R)-3-methylmorpholin-4-yl]-4-(1H-pyrazol-5-yl)-8-[1-(tetrahydro-2H-pyran-2-yl)-1H-pyrazol-5-yl]-1,7-naphthyridine, 16 mg (0.22 mmol) of 2,2-dimethyloxirane and 23 mg (0.17 mmol) of potassium carbonate in 0.5 ml DMF was stirred at 130° C. in a microwave oven for 10 minutes. After cooling, 31 mg (0.29 mmol) of 2,2-dimethyloxirane was added and the mixture was stirred at 130° C. in a microwave oven for 10 minutes. After cooling, the mixture was diluted with ethyl acetate and washed with water. The organic phase was filtered using a Whatman filter and concentrated to dryness to give a mixture of the crude products that was used without further purification.

Step b 2-methyl-1-(3-{2-[(3R)-3-methylmorpholin-4-yl]-8-(1H-pyrazol-5-yl)-1,7-naphthyridin-4-yl}-1H-pyrazol-1-yl)propan-2-ol

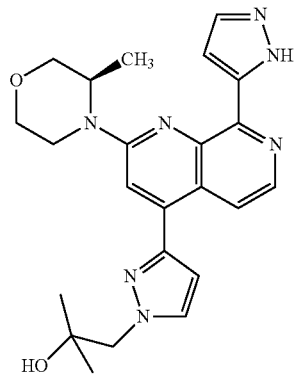 [SMILES: C[C@@H]1COCCN1c1cc(-c2ccn(CC(C)(C)O)n2)c2ccnc(-c3ccn[nH]3)c2n1]

A solution of 30 mg crude 2-methyl-1-(3-{2-[(3R)-3-methylmorpholin-4-yl]-8-[1-(tetrahydro-2H-pyran-2-yl)-1H-pyrazol-5-yl]-1,7-naphthyridin-4-yl}-1H-pyrazol-1-yl)propan-2-ol from step a in 1.5 ml of methanol and 0.06 ml of 2N hydrochloric acid was stirred for 90 minutes at room temperature. The reaction mixture was diluted with an aqueous solution of sodium bicarbonate and extracted with ethyl acetate and THF (2×). The combined organic phases were filtered using a Whatman filter and concentrated to dryness. The residue was purified by preparative HPLC (Autopurifier: basic conditions) to give 8 mg (0.02 mmol) of the desired product.

$^1$H-NMR (400 MHz, DMSO-d6): δ [ppm]=1.17 (6H), 1.30 (3H), 3.50-3.67 (1H), 3.74 (1H), 3.85 (1H), 3.99-4.15 (1H), 4.15-4.40 (3H), 4.68 (1H), 4.81 (1H), 7.00 (1H), 7.40 (1H), 7.54-7.70 (2H), 7.89 (1H), 8.37 (1H), 8.56 (1H), 13.40 (1H).

Example 162

4-[(2R)-2-methylmorpholin-4-yl]-2-(morpholin-4-yl)-8-(1H-pyrazol-5-yl)-1,7-naphthyridine

Step a

4-[(2R)-2-methylmorpholin-4-yl]-2-(morpholin-4-yl)-8-[1-(tetrahydro-2H-pyran-2-yl)-1H-pyrazol-5-yl]-1,7-naphthyridine

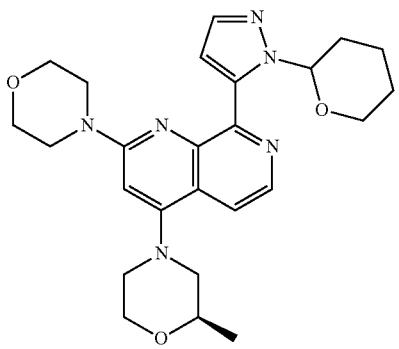 [SMILES: C[C@@H]1CN(c2cc(N3CCOCC3)nc3c(-c4ccnn4C4CCCCO4)nccc23)CCO1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 103 mg (1.02 mmol) (2R)-2-methylmorpholine hydrochloride and 0.14 ml (1.02 mmol) trimethylamine in 0.5 ml of MeCN was stirred at 70° C. overnight under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[(2R)-2-methylmorpholin-4-yl]-2-(morpholin-4-yl)-8-(1H-pyrazol-5-yl)-1,7-naphthyridine

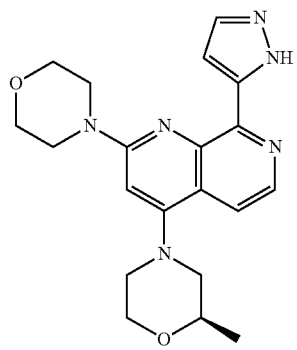 [SMILES: C[C@@H]1CN(c2cc(N3CCOCC3)nc3c(-c4ccn[nH]4)nccc23)CCO1]

A solution of 178 mg of crude 4-[(2R)-2-methylmorpholin-4-yl]-2-(morpholin-4-yl)-8-[1-(tetrahydro-2H-pyran-2-yl)-1H-pyrazol-5-yl]-1,7-naphthyridine from step a in 8.6 ml of methanol and 0.38 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 64 mg (0.17 mmol) of the desired product.

$^1$H-NMR (400 MHz, DMSO-d6): δ [ppm]=1.16 (3H), 2.57-2.69 (1H), 2.87 (1H), 3.32-3.41 (2H), 3.71 (4H), 3.77 (4H), 3.81-3.97 (3H), 6.81 (1H), 7.33 (1H), 7.59 (1H), 7.63 (1H), 8.31 (1H), 13.32 (1H).

Example 163

4-(5-fluoropyridin-2-yl)-2-[(3R)-3-methylmorpholin-4-yl]-8-(1H-pyrazol-5-yl)-1,7-naphthyridine

Step a 4-(5-fluoropyridin-2-yl)-2-[(3R)-3-methylmorpholin-4-yl]-8-[1-(tetrahydro-2H-pyran-2-yl)-1H-pyrazol-5-yl]-1,7-naphthyridine

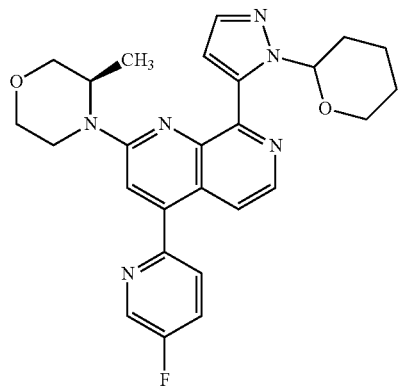 [SMILES: C[C@@H]1COCCN1c1cc(-c2ccc(F)cn2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) (5-fluoropyridin-2-yl)boronic acid, 15 mg (0.019 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 150 minutes. After cooling the reaction mixture was diluted with saturated aqueous ammonium chloride solution and extracted with ethyl acetate (2×). The combined organic phases were filtered using a Whatman filter and then concentrated to give the crude product that was used without further purification in the next step.

Step b 4-(5-fluoropyridin-2-yl)-2-[(3R)-3-methylmorpholin-4-yl]-8-(1H-pyrazol-5-yl)-1,7-naphthyridine

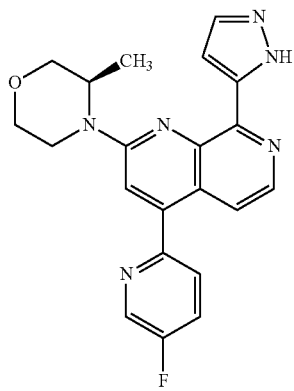 [SMILES: C[C@@H]1COCCN1c1cc(-c2ccc(F)cn2)c2ccnc(-c3ccn[nH]3)c2n1]

A solution of 106 mg of crude 4-(5-fluoropyridin-2-yl)-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.22 ml of 2N hydrochloric acid was stirred for 2 hour at room temperature. The reaction mixture was diluted with ethyl acetate and washed with aqueous sodium chloride solution. The organic phase was filtered using a Whatman filter and concentrated to dryness. The residue was purified by preparative HPLC (Autopurifier: basic conditions) to give 3 mg (0.01 mmol) of the desired product.

$^1$H-NMR (400 MHz, CDCl$_3$): δ [ppm]=1.26-1.39 (3H), 3.53-3.65 (2H), 3.73 (1H), 3.84 (1H), 4.06 (1H), 4.24 (1H), 4.67 (1H), 7.42 (1H), 7.44-7.53 (1H), 7.60 (1H), 7.62-7.67 (1H), 7.68-7.74 (1H), 7.87-8.13 (2H), 8.28-8.44 (1H), 8.84 (1H), 13.20 (1H).

Example 164

2-[(3R)-3-methylmorpholin-4-yl]-4-(6-methylpyridin-2-yl)-8-(1H-pyrazol-5-yl)-1,7-naphthyridine Step a 2-[(3R)-3-methylmorpholin-4-yl]-4-(6-methylpyridin-2-yl)-8-[1-(tetrahydro-2H-pyran-2-yl)-1H-pyrazol-5-yl]-1,7-naphthyridine

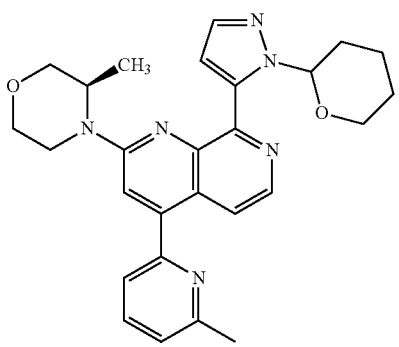 [SMILES: Cc1cccc(-c2cc(N3CCOC[C@H]3C)nc3c(-c4ccnn4C4CCCCO4)nccc23)n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 52 mg (0.38 mmol) (6-methylpyridin-2-yl) boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted with saturated aqueous ammonium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(6-methylpyridin-2-yl)-8-(1H-pyrazol-5-yl)-1,7-naphthyridine

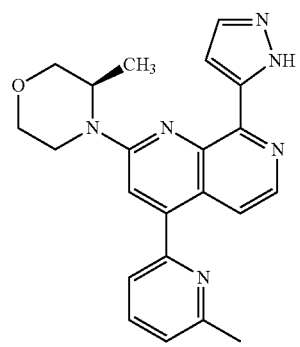 [SMILES: Cc1cccc(-c2cc(N3CCOC[C@H]3C)nc3c(-c4ccn[nH]4)nccc23)n1]

A solution of 113 mg of crude 2-[(3R)-3-methylmorpholin-4-yl]-4-(6-methylpyridin-2-yl)-8-[1-(tetrahydro-2H-pyran-2-yl)-1H-pyrazol-5-yl]-1,7-naphthyridine from step a in 5.4 ml of methanol and 0.24 ml of 2N hydrochloric acid was stirred for 2 hour at room temperature. The reaction mixture was diluted with ethyl acetate and washed with aqueous sodium chloride solution. The organic phase was filtered using a Whatman filter and concentrated to dryness. The residue was purified by preparative HPLC (Autopurifier: basic conditions) to give 4 mg (0.01 mmol) of the desired product.

$^1$H-NMR (400 MHz, CDCl$_3$): δ [ppm]=1.30 (3H), 2.57-2.63 (3H), 3.53-3.64 (1H), 3.73 (1H), 3.80-3.89 (1H), 4.06 (1H), 4.22 (1H), 4.66 (1H), 7.44 (2H), 7.55 (1H), 7.58-7.68 (2H), 7.72 (1H), 7.93 (1H), 8.33 (1H), 13.42 (1H).

Example 165

2-[(3R)-3-methylmorpholin-4-yl]-4-(3-methylpyridin-2-yl)-8-(1H-pyrazol-5-yl)-1,7-naphthyridine

Step a

2-[(3R)-3-methylmorpholin-4-yl]-4-(3-methylpyridin-2-yl)-8-[1-(tetrahydro-2H-pyran-2-yl)-1H-pyrazol-5-yl]-1,7-naphthyridine

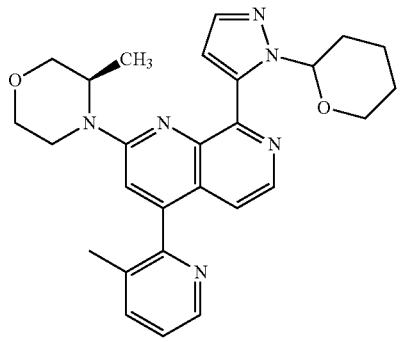 [SMILES: Cc1cccnc1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 52 mg (0.38 mmol) (3-methylpyridin-2-yl)boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted with saturated aqueous ammonium chloride solution and extracted with ethyl acetate (2×). The combined organic phases were filtered using a Whatman filter and then concentrated to give the crude product that was used without further purification in the next step.

Step b

2-[(3R)-3-methylmorpholin-4-yl]-4-(3-methylpyridin-2-yl)-8-(1H-pyrazol-5-yl)-1,7-naphthyridine

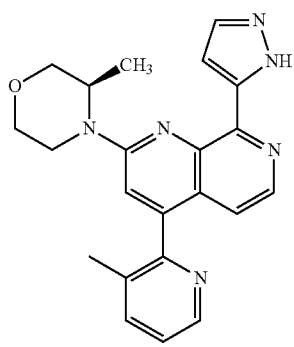 [SMILES: Cc1cccnc1-c1cc(N2CCOC[C@H]2C)nc2c(-c3ccn[nH]3)nccc12]

A solution of 113 mg of crude 2-[(3R)-3-methylmorpholin-4-yl]-4-(3-methylpyridin-2-yl)-8-[1-(tetrahydro-2H-pyran-2-yl)-1H-pyrazol-5-yl]-1,7-naphthyridine from step a in 4.3 ml of methanol and 0.19 ml of 2N hydrochloric acid was stirred for 2 hour at room temperature. The reaction mixture was diluted with ethyl acetate and washed with aqueous sodium chloride solution. The organic phase was filtered using a Whatman filter and concentrated to dryness. The residue was purified by preparative HPLC (Autopurifier: basic conditions) to give 4 mg (0.01 mmol) of the desired product.

$^1$H-NMR (400 MHz, CDCl$_3$): δ [ppm]=1.29 (d, 3H), 2.13 (s, 3H), 3.57 (d, 1H), 3.67-3.79 (m, 1H), 3.79-3.90 (m, 1H), 4.05 (d, 1H), 4.15-4.30 (m, 2H), 4.61 (1H), 6.96 (1H), 7.38-7.57 (3H), 7.65 (1H), 7.89 (1H), 8.27 (1H), 8.59 (1H), 13.43 (1H).

Example 166

N-(2-{2-[(3R)-3-methylmorpholin-4-yl]-8-(1H-pyrazol-5-yl)-1,7-naphthyridin-4-yl}phenyl)acetamide

Step a

N-(2-{2-[(3R)-3-methylmorpholin-4-yl]-8-[1-(tetrahydro-2H-pyran-2-yl)-1H-pyrazol-5-yl]-1,7-naphthyridin-4-yl}phenyl)acetamide

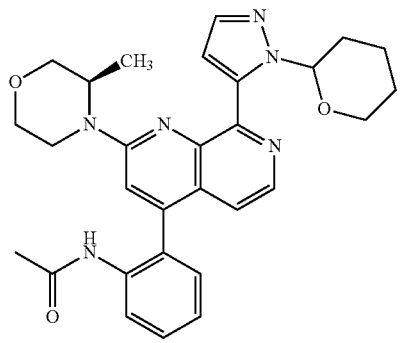 [SMILES: CC(=O)Nc1ccccc1-c1cc(N2CCOC[C@H]2C)nc2c(-c3ccnn3C3CCCCO3)nccc12]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 68 mg (0.38 mmol) (2-acetamidophenyl)boronic acid, 15 mg (0.019 mmol) of [1,1'-bis(diphenylphosphino)ferrocene]-dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 7 hours. After cooling the reaction mixture was diluted with ethyl acetate and washed with aqueous sodium chloride solution. The organic phase was filtered using a Whatman filter and then concentrated to give the crude product that was used without further purification in the next step.

Step b

N-(2-{2-[(3R)-3-methylmorpholin-4-yl]-8-(1H-pyrazol-5-yl)-1,7-naphthyridin-4-yl}phenyl)acetamide

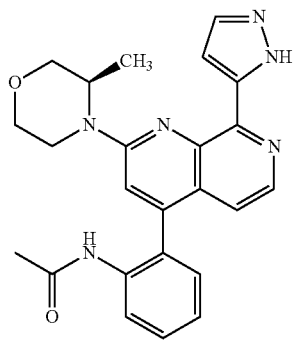 [SMILES: CC(=O)Nc1ccccc1-c1cc(N2CCOC[C@H]2C)nc2c(-c3ccn[nH]3)nccc12]

A solution of 164 mg of crude N-(2-{2-[(3R)-3-methylmorpholin-4-yl]-8-[1-(tetrahydro-2H-pyran-2-yl)-1H-pyrazol-5-yl]-1,7-naphthyridin-4-yl}phenyl)acetamide from step a in 1.5 ml of methanol and 0.37 ml of 2N hydrochloric acid was stirred for 1 hour at room temperature. The reaction mixture was diluted with ethyl acetate and washed with aqueous sodium chloride solution. The organic phase was filtered using a Whatman filter and concentrated to dryness. The residue was purified by preparative HPLC (Autopurifier: basic conditions) to give 11 mg (0.03 mmol) of the desired product.

$^1$H-NMR (400 MHz, CDCl$_3$): δ [ppm]=1.32 (3H), 1.71 (3H), 3.50-3.64 (1H), 3.64-3.78 (1H), 3.78-3.92 (1H), 4.07 (1H), 4.23 (1H), 4.59 (1H), 7.02 (1H), 7.20-7.47 (4H), 7.47-7.60 (1H), 7.65 (1H), 7.74 (1H), 8.24 (1H), 9.16 (1H), 12.82 (1H).

Example 167

3-{2-[(3R)-3-methylmorpholin-4-yl]-8-(1H-pyrazol-5-yl)-1,7-naphthyridin-4-yl}pyridin-2-ol Step a 3-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-ol

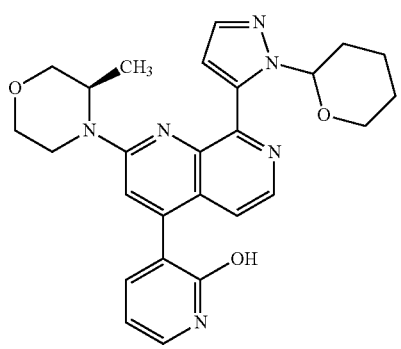

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) (2-hydroxypyridin-3-yl) boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted aqueous sodium chloride solution and extracted with ethyl acetate (2×). The combined organic phases were filtered using a Whatman filter and then concentrated to give the crude product that was used without further purification in the next step.

Step b

3-{2-[(3R)-3-methylmorpholin-4-yl]-8-(1H-pyrazol-5-yl)-1,7-naphthyridin-4-yl}pyridin-2-ol

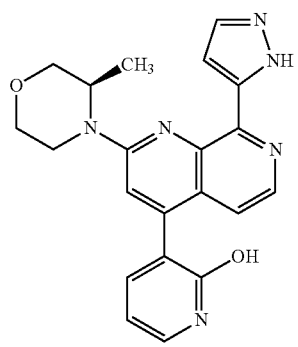

A solution of 96 mg of crude 3-{2-[(3R)-3-methylmorpholin-4-yl]-8-[1-(tetrahydro-2H-pyran-2-yl)-1H-pyrazol-5-yl]-1,7-naphthyridin-4-yl}pyridin-2-ol from step a in 5.1 ml of methanol and 0.20 ml of 2N hydrochloric acid was stirred for 3 hours at room temperature. The reaction mixture was diluted with aqueous sodium chloride solution and extracted with ethyl acetate (2×). The combined organic phases were filtered using a Whatman filter and concentrated to dryness. The residue was purified by preparative HPLC (Autopurifier: basic conditions) to give 2 mg (0.005 mmol) of the desired product.

$^1$H-NMR (400 MHz, CDCl$_3$): δ [ppm]=1.30 (3H), 3.57 (1H), 3.71 (1H), 3.82 (1H), 4.04 (1H), 4.18 (1H), 4.62 (1H), 6.39 (1H), 7.27 (1H), 7.40 (2H), 7.50-7.75 (3H), 8.28 (1H), 12.05 (1H), 13.39 (1H).

Example 168

2-(3-{2-[(3R)-3-methylmorpholin-4-yl]-8-(1H-pyrazol-5-yl)-1,7-naphthyridin-4-yl}phenyl)propan-2-ol

Step a 2-(3-{2-[(3R)-3-methylmorpholin-4-yl]-8-[1-(tetrahydro-2H-pyran-2-yl)-1H-pyrazol-5-yl]-1,7-naphthyridin-4-yl}phenyl)propan-2-ol

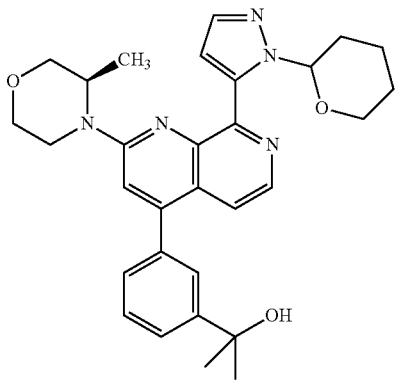 [SMILES: C[C@@H]1COCCN1c1cc(-c2cccc(C(C)(C)O)c2)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 53 mg (0.38 mmol) (2-hydroxypyridin-3-yl) boronic acid, 15 mg (0.019 mmol) of [1,1'-bis(diphenylphosphino)ferrocene]dichloropalladium(II) complex with dichloromethane (1:1, Pd(dppf)Cl$_2$) and 247 mg (0.76 mmol) of caesium carbonate in 1.4 ml of dioxane was degased with argon. Under argon, the reaction mixture was stirred at 110° C. for 2 hours. After cooling the reaction mixture was diluted aqueous sodium chloride solution and extracted with ethyl acetate (2×). The combined organic phases were filtered using a Whatman filter and then concentrated to give the crude product that was used without further purification in the next step.

Step b 2-(3-{2-[(3R)-3-methylmorpholin-4-yl]-8-(1H-pyrazol-5-yl)-1,7-naphthyridin-4-yl}phenyl)propan-2-ol

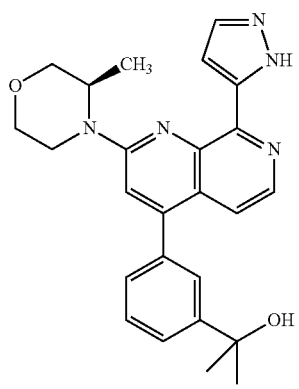 [SMILES: C[C@@H]1COCCN1c1cc(-c2cccc(C(C)(C)O)c2)c2ccnc(-c3ccn[nH]3)c2n1]

A solution of 96 mg of crude 2-(3-{2-[(3R)-3-methylmorpholin-4-yl]-8-[1-(tetrahydro-2H-pyran-2-yl)-1H-pyrazol-5-yl]-1,7-naphthyridin-4-yl}phenyl)propan-2-ol from step a in 5.1 ml of methanol and 0.20 ml of 2N hydrochloric acid was stirred for 3 hours at room temperature. The reaction mixture was diluted with aqueous sodium chloride solution and extracted with ethyl acetate (2×). The combined organic phases were filtered using a Whatman filter and concentrated to dryness. The residue was purified by preparative HPLC (Autopurifier: basic conditions) to give 2 mg (0.005 mmol) of the desired product.

$^1$H-NMR (400 MHz, CDCl$_3$): δ [ppm]=1.30 (3H), 3.57 (1H), 3.71 (1H), 3.82 (1H), 4.04 (1H), 4.18 (1H), 4.62 (1H), 6.39 (1H), 7.27 (1H), 7.40 (2H), 7.50-7.75 (3H), 8.28 (1H), 12.05 (1H), 13.39 (1H).

Example 169

4-(5,6-dihydroimidazo[1,2-a]pyrazin-7(8H)-yl)-2-(morpholin-4-yl)-8-(1H-pyrazol-5-yl)-1,7-naphthyridine

Step a 4-(5,6-dihydroimidazo[1,2-a]pyrazin-7(8H)-yl)-2-(morpholin-4-yl)-8-[1-(tetrahydro-2H-pyran-2-yl)-1H-pyrazol-5-yl]-1,7-naphthyridine

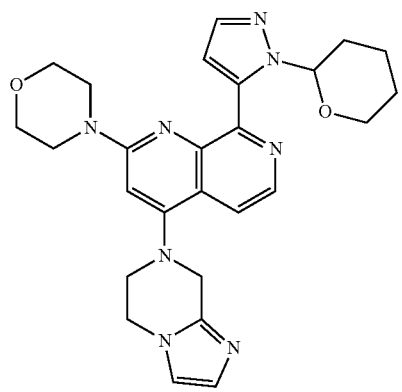 [SMILES: c1cc2c(N3CCn4ccnc4C3)cc(N3CCOCC3)nc2c(-c2ccnn2C2CCCCO2)n1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 122 mg (0.99 mmol) 5,6,7,8-tetrahydroimidazo[1,2-a]pyrazine in 0.4 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 4-(5,6-dihydroimidazo[1,2-a]pyrazin-7(8H)-yl)-2-(morpholin-4-yl)-8-(1H-pyrazol-5-yl)-1,7-naphthyridine

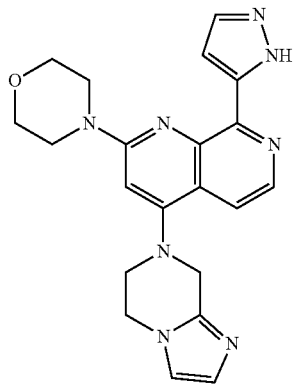 [SMILES: c1cc(-c2nccc3c(N4CCn5ccnc5C4)cc(N4CCOCC4)nc23)[nH]n1]

A solution of 200 mg of crude 4-(5,6-dihydroimidazo[1,2-a]pyrazin-7(8H)-yl)-2-(morpholin-4-yl)-8-[1-(tetrahydro-2H-pyran-2-yl)-1H-pyrazol-5-yl]-1,7-naphthyridine from step a in 1.9 ml of methanol and 0.47 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 5 mg (0.01 mmol) of the desired product.

$^1$H-NMR (400 MHz, DMSO-d6): δ [ppm]=3.66 (2H), 3.72-3.87 (8H), 4.27-4.40 (2H), 4.47 (2H), 6.85-7.05 (2H), 7.23 (1H), 7.36 (1H), 7.62 (1H), 7.68 (1H), 8.34 (1H), 13.37 (1H).

Example 170

4-[(2S)-2-methylmorpholin-4-yl]-2-(morpholin-4-yl)-8-(1H-pyrazol-5-yl)-1,7-naphthyridine

Step a

4-[(2S)-2-methylmorpholin-4-yl]-2-(morpholin-4-yl)-8-[1-(tetrahydro-2H-pyran-2-yl)-1H-pyrazol-5-yl]-1,7-naphthyridine

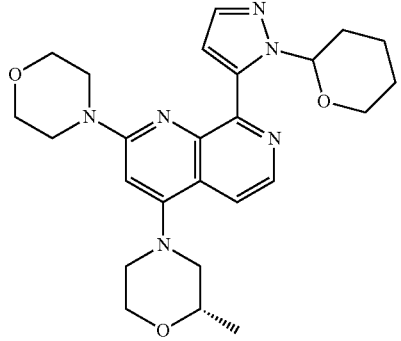 [SMILES: C[C@H]1CN(c2cc(N3CCOCC3)nc3c(-c4ccnn4C4CCCCO4)nccc23)CCO1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 103 mg (1.02 mmol) (2S)-2-methylmorpholine in 0.5 ml of MeCN was stirred at 70° C. overnight under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[(2S)-2-methylmorpholin-4-yl]-2-(morpholin-4-yl)-8-(1H-pyrazol-5-yl)-1,7-naphthyridine

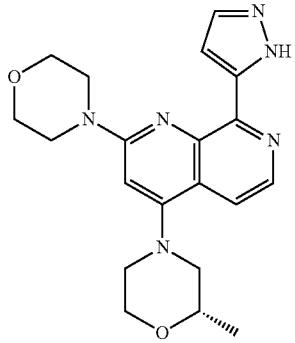 [SMILES: C[C@H]1CN(c2cc(N3CCOCC3)nc3c(-c4ccn[nH]4)nccc23)CCO1]

A solution of 146 mg of crude 4-[(2S)-2-methylmorpholin-4-yl]-2-(morpholin-4-yl)-8-[1-(tetrahydro-2H-pyran-2-yl)-1H-pyrazol-5-yl]-1,7-naphthyridine from step a in 7.0 ml of methanol and 0.31 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 62 mg (0.16 mmol) of the desired product.

$^1$H-NMR (400 MHz, DMSO-d6): δ [ppm]=1.16 (3H), 2.57-2.69 (1H), 2.87 (1H), 3.32-3.41 (2H), 3.71 (4H), 3.77 (4H), 3.81-3.97 (3H), 6.81 (1H), 7.33 (1H), 7.59 (1H), 7.63 (1H), 8.31 (1H), 13.32 (1H).

Example 171

4-[(trans)-2-methylcyclopropyl]-2-[(3R)-3-methylmorpholin-4-yl]-8-(1H-pyrazol-5-yl)-1,7-naphthyridine

Step a

4-[(trans)-2-methylcyclopropyl]-2-[(3R)-3-methylmorpholin-4-yl]-8-[1-(tetrahydro-2H-pyran-2-yl)-1H-pyrazol-5-yl]-1,7-naphthyridine

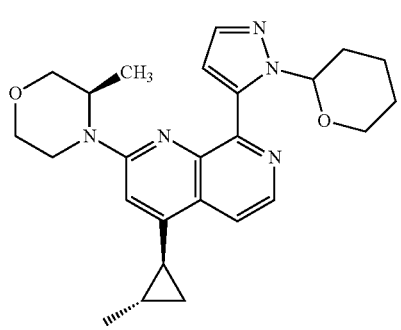 [SMILES: C[C@@H]1COCCN1c1cc([C@H]2C[C@@H]2C)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 69 mg (0.38 mmol) trans-1-methyl-cyclopropyl-2-boronic ester, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b

4-[(trans)-2-methylcyclopropyl]-2-[(3R)-3-methyl-morpholin-4-yl]-8-(1H-pyrazol-5-yl)-1,7-naphthyridine

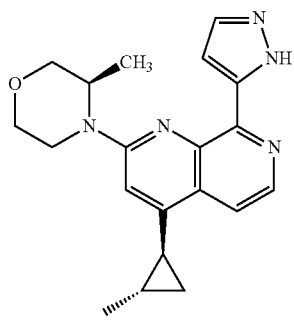 [SMILES: C[C@@H]1COCCN1c1cc([C@H]2C[C@@H]2C)c2ccnc(-c3ccn[nH]3)c2n1]

A solution of 113 mg of crude 4-[(trans)-2-methylcyclopropyl]-2-[(3R)-3-methylmorpholin-4-yl]-8-[1-(tetrahydro-2H-pyran-2-yl)-1H-pyrazol-5-yl]-1,7-naphthyridine from step a in 3.0 ml of methanol and 0.26 ml of 2N hydrochloric acid was stirred for 3 hours at room temperature. The reaction mixture was diluted with saturated aqueous sodium chloride solution and extracted with ethyl acetate (2×). The combined organic phases were dried (MgSO$_4$), filtered and concentrated to dryness. The residue was purified by preparative HPLC (Autopurifier: basic conditions) to give 8 mg (0.02 mmol) of the desired product.

$^1$H-NMR (400 MHz, DMSO-d6): δ [ppm]=0.86-0.94 (1H), 1.19-1.28 (5H), 1.28-1.34 (3H), 2.14-2.24 (1H), 3.22-3.32 (1H), 3.54 (1H), 3.69 (1H), 3.81 (1H), 4.03 (1H), 4.09-4.24 (1H), 4.49-4.77 (1H), 7.00 (1H), 7.37 (1H), 7.61 (1H), 7.93 (1H), 8.41 (1H), 13.38 (1H).

Example 172

4-(difluoromethoxy)-2-[(3R)-3-methylmorpholin-4-yl]-8-(1H-pyrazol-5-yl)-1,7-naphthyridine Step a 4-(difluoromethoxy)-2-[(3R)-3-methylmorpholin-4-yl]-8-[1-(tetrahydro-2H-pyran-2-yl)-1H-pyrazol-5-yl]-1,7-naphthyridine

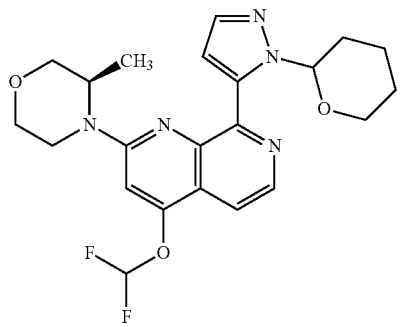 [SMILES: C[C@@H]1COCCN1c1cc(OC(F)F)c2ccnc(-c3ccnn3C3CCCCO3)c2n1]

A mixture of 100 mg (0.25 mmol) of 2-[(3R)-3-methylmorpholin-4-yl]-8-[1-(tetrahydro-2H-pyran-2-yl)-1H-pyrazol-5-yl]-1,7-naphthyridin-4-ol, 66 mg (0.51 mmol) chlorodifluoroacetic acid and 42 mg (0.30 mmol) of potassium carbonate in 0.9 ml of DMF and 0.9 ml water was degased with argon. Under argon, the reaction mixture was stirred at 120° C. for 90 minutes. After cooling the reaction mixture was diluted with ethyl acetate and washed with aqueous sodium chloride solution. The organic phase was filtered using a Whatman filter and then concentrated to give the crude product that was used without further purification in the next step.

Step b 4-(difluoromethoxy)-2-[(3R)-3-methylmorpholin-4-yl]-8-(1H-pyrazol-5-yl)-1,7-naphthyridine

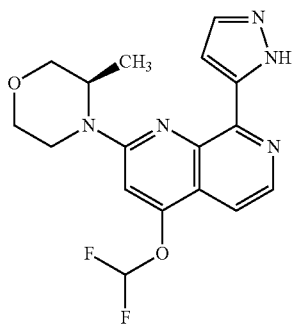 [SMILES: C[C@@H]1COCCN1c1cc(OC(F)F)c2ccnc(-c3ccn[nH]3)c2n1]

A solution of 71 mg of crude 4-(difluoromethoxy)-2-[(3R)-3-methylmorpholin-4-yl]-8-[1-(tetrahydro-2H-pyran-2-yl)-1H-pyrazol-5-yl]-1,7-naphthyridine from step a in 0.7 ml of methanol and 0.18 ml of 2N hydrochloric acid was stirred for 1 hour at room temperature. The reaction mixture was diluted with aqueous bicarbonate solution and extracted with ethyl acetate (2×). The combined organic phases were filtered using a Whatman filter and concentrated to dryness. The residue was purified by preparative HPLC (Autopurifier: basic conditions) to give 7 mg (0.02 mmol) of the desired product.

¹H-NMR (400 MHz, DMSO-d6): δ [ppm]=1.29 (3H), 3.56 (1H), 3.66-3.79 (1H), 3.84 (1H), 4.05 (1H), 4.15 (d, 1H), 4.58 (1H), 7.16 (1H), 7.39 (1H), 7.62 (1H), 7.66-7.74 (2H), 8.40 (1H), 13.40 (1H).

Example 173

2-[2-(morpholin-4-yl)-8-(1H-pyrazol-5-yl)-1,7-naphthyridin-4-yl]propan-2-ol

Step a

2-{2-(morpholin-4-yl)-8-[1-(tetrahydro-2H-pyran-2-yl)-1H-pyrazol-5-yl]-1,7-naphthyridin-4-yl}propan-2-ol

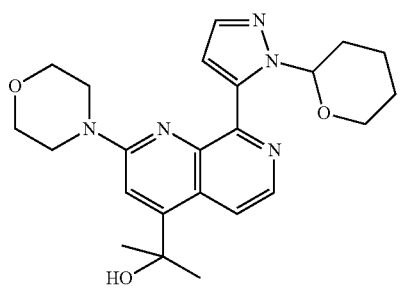 [SMILES: CC(C)(O)c1cc(N2CCOCC2)nc2c(-c3ccnn3C3CCCCO3)nccc12]

0.24 ml (0.71 mmol) of a 3.0 M solution of methylmagnesium bromide in diethylether was added dropwise to a stirred solution of 100 mg (0.24 mmol) methyl 2-(morpholin-4-yl)-8-[1-(tetrahydro-2H-pyran-2-yl)-1H-pyrazol-5-yl]-1,7-naphthyridine-4-carboxylate in 4.0 ml of THF at 0° C. The mixture was stirred at 0° C. for 30 minutes and then the icebath was removed and the mixture was stirred at room temperature overnight. The mixture was diluted with a saturated aqueous solution of ammonium chloride and extracted with ethyl acetate (2×). The combined organic phases were filtered using a Whatman filter and then concentrated to give the crude product that was used without further purification in the next step.

Step b

2-[2-(morpholin-4-yl)-8-(1H-pyrazol-5-yl)-1,7-naphthyridin-4-yl]propan-2-ol

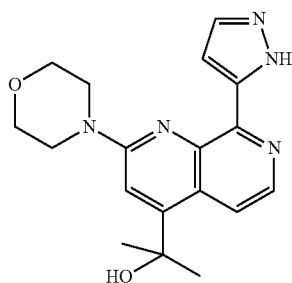 [SMILES: CC(C)(O)c1cc(N2CCOCC2)nc2c(-c3ccn[nH]3)nccc12]

A solution of 80 mg of crude 2-{2-(morpholin-4-yl)-8-[1-(tetrahydro-2H-pyran-2-yl)-1H-pyrazol-5-yl]-1,7-naphthyridin-4-yl}propan-2-ol from step a in 2.0 ml of methanol and 0.19 ml of 2N hydrochloric acid was stirred for 1 hour at room temperature. The reaction mixture was diluted with saturated aqueous sodium bicarbonate solution and extracted with ethyl acetate (2×). The combined organic phases were dried (MgSO₄), filtered and concentrated to dryness to give 34 mg (0.09 mmol) of the desired product.

¹H-NMR (400 MHz, DMSO-d6): δ [ppm]=1.69 (6H), 3.73 (4H), 3.77-3.93 (4H), 5.60 (1H), 7.35 (1H), 7.46 (1H), 7.61 (1H), 8.28-8.45 (2H), 13.35 (1H).

Example 174

2-(morpholin-4-yl)-4-(3-oxa-8-azabicyclo[3.2.1]oct-8-yl)-8-(1H-pyrazol-5-yl)-1,7-naphthyridine Step a 2-(morpholin-4-yl)-4-(3-oxa-8-azabicyclo[3.2.1]oct-8-yl)-8-[1-(tetrahydro-2H-pyran-2-yl)-1H-pyrazol-5-yl]-1,7-naphthyridine

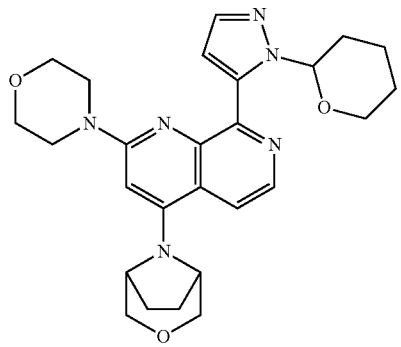 [SMILES: c1cc2c(N3C4CCC3COC4)cc(N3CCOCC3)nc2c(-c2ccnn2C2CCCCO2)n1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 153 mg (1.02 mmol) 3-oxa-8-azabicyclo[3.2.1]octane hydrochloride (1:1) and 0.14 ml (1.02 mmol) triethylamine in 0.5 ml of MeCN was stirred at 70° C. for 72 hours under argon. After cooling the reaction mixture was diluted with DCM and washed with saturated aqueous sodium chloride solution. The organic phase was filtered using a Whatman filter and then concentrated to give the crude product that was used without further purification in the next step.

Step b 2-(morpholin-4-yl)-4-(3-oxa-8-azabicyclo[3.2.1]oct-8-yl)-8-(1H-pyrazol-5-yl)-1,7-naphthyridine

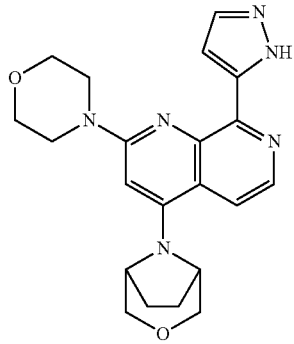 [SMILES: c1cc(-c2nccc3c(N4C5CCC4COC5)cc(N4CCOCC4)nc23)[nH]n1]

A solution of 152 mg of crude 2-(morpholin-4-yl)-4-(3-oxa-8-azabicyclo[3.2.1]oct-8-yl)-8-[1-(tetrahydro-2H-pyran-2-yl)-1H-pyrazol-5-yl]-1,7-naphthyridine from step a in 7.2 ml of methanol and 0.32 ml of 2N hydrochloric acid was stirred overnight at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 12 mg (0.03 mmol) of the desired product.

$^1$H-NMR (400 MHz, DMSO-d6): δ [ppm]=1.92 (3H), 3.58-3.72 (6H), 3.72-3.86 (4H), 3.94 (2H), 4.15 (2H), 6.70 (1H), 7.34 (1H), 7.60 (1H), 7.71 (1H), 8.31 (1H), 13.34 (1H).

Example 175

2-[(3R)-3-methylmorpholin-4-yl]-8-(1H-pyrazol-5-yl)-4-(pyrrolidin-1-yl)-1,7-naphthyridine Step a 2-[(3R)-3-methylmorpholin-4-yl]-4-(pyrrolidin-1-yl)-8-[1-(tetrahydro-2H-pyran-2-yl)-1H-pyrazol-5-yl]-1,7-naphthyridine

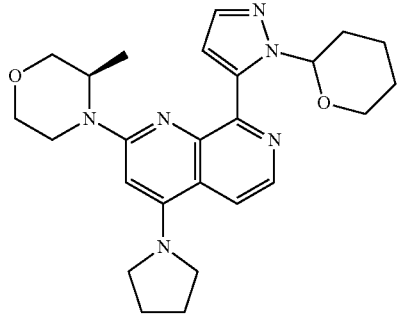 [SMILES: C[C@@H]1COCCN1c1cc(N2CCCC2)c2ccnc(-c3ccnn3C3CCCCO3)c2n1]

A mixture of 75 mg (0.14 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate and 35 mg (0.50 mmol) pyrrolidine in 0.21 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

2-[(3R)-3-methylmorpholin-4-yl]-8-(1H-pyrazol-5-yl)-4-(pyrrolidin-1-yl)-1,7-naphthyridine

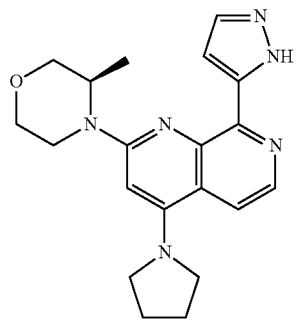 [SMILES: C[C@@H]1COCCN1c1cc(N2CCCC2)c2ccnc(-c3ccn[nH]3)c2n1]

A solution of 10 mg of crude 2-[(3R)-3-methylmorpholin-4-yl]-4-(pyrrolidin-1-yl)-8-[1-(tetrahydro-2H-pyran-2-yl)-1H-pyrazol-5-yl]-1,7-naphthyridine from step a in 0.5 ml of methanol and 0.02 ml of 2N hydrochloric acid was stirred overnight at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 2 mg (0.005 mmol) of the desired product.

$^1$H-NMR (400 MHz, CDCl3): δ [ppm]=1.47 (3H), 2.20 (4H), 3.55 (1H), 3.66-3.94 (7H), 4.04 (1H), 4.16-4.37 (2H), 5.75 (1H), 7.12 (1H), 7.77 (1H), 7.90 (1H), 8.53 (1H).

Example 176

4-[2-(morpholin-4-yl)-8-(1H-pyrazol-5-yl)-1,7-naphthyridin-4-yl]piperazin-2-one

Step a

4-{2-(morpholin-4-yl)-8-[1-(tetrahydro-2H-pyran-2-yl)-1H-pyrazol-5-yl]-1,7-naphthyridin-4-yl}piperazin-2-one

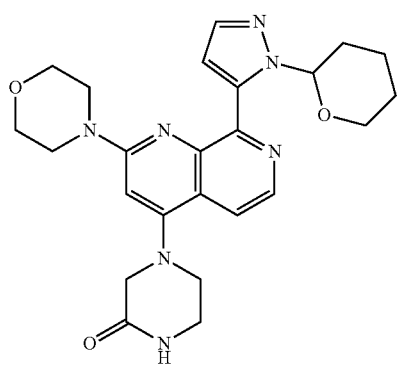 [SMILES: O=C1CN(c2cc(N3CCOCC3)nc3c(-c4ccnn4C4CCCCO4)nccc23)CCN1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 99 mg (0.99 mmol) piperazin-2-one in 0.4 ml of MeCN was stirred at 70° C. for 3 hours under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[2-(morpholin-4-yl)-8-(1H-pyrazol-5-yl)-1,7-naphthyridin-4-yl]piperazin-2-one

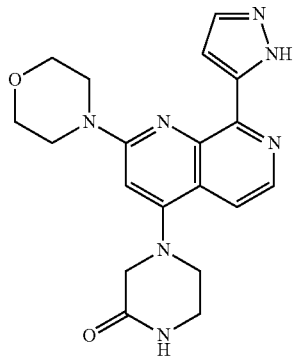 [SMILES: O=C1CN(c2cc(N3CCOCC3)nc3c(-c4ccn[nH]4)nccc23)CCN1]

A solution of 182 mg of crude 4-{2-(morpholin-4-yl)-8-[1-(tetrahydro-2H-pyran-2-yl)-1H-pyrazol-5-yl]-1,7-naphthyridin-4-yl}piperazin-2-one from step a in 1.8 ml of methanol and 0.45 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 32 mg (0.08 mmol) of the desired product.

$^1$H-NMR (400 MHz, DMSO-d6): δ [ppm]=3.39-3.45 (2H), 3.45-3.55 (2H), 3.64-3.88 (10H), 6.84 (1H), 7.35 (1H), 7.63 (2H), 8.11 (1H), 8.32 (1H), 13.36 (1H).

Example 177

4-(dimethylphosphoryl)-2-(morpholin-4-yl)-8-(1H-pyrazol-5-yl)-1,7-naphthyridine

Step a 4-(dimethylphosphoryl)-2-(morpholin-4-yl)-8-[1-(tetrahydro-2H-pyran-2-yl)-1H-pyrazol-5-yl]-1,7-naphthyridine

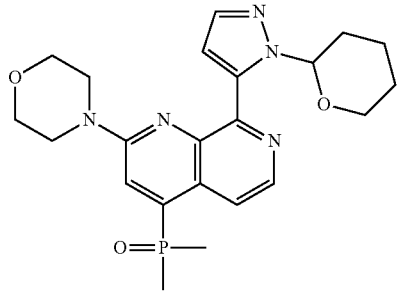 [SMILES: CP(C)(=O)c1cc(N2CCOCC2)nc2c(-c3ccnn3C3CCCCO3)nccc12]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 36 mg (0.33 mmol) dimethylphosphinoxide, 34 mg (0.029 mmol tetrakis (triphenylphosphine)palladium(0) and 0.06 ml (0.44 mmol) of triethylamine in 0.9 ml of acetonitrile was degased with argon. Under argon, the reaction mixture was stirred at 90° C. for 3 hours. After cooling the reaction mixture was diluted with ethyl acetate and washed with aqueous chloride solution. The organic phase was filtered using a Whatman filter and then concentrated to give the crude product that was used without further purification in the next step.

Step b 4-(dimethylphosphoryl)-2-(morpholin-4-yl)-8-(1H-pyrazol-5-yl)-1,7-naphthyridine

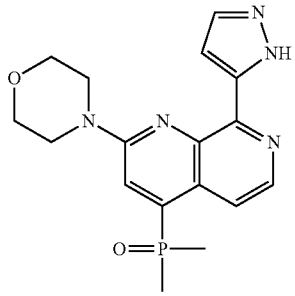 [SMILES: CP(C)(=O)c1cc(N2CCOCC2)nc2c(-c3ccn[nH]3)nccc12]

A solution of 210 mg of crude 4-(dimethylphosphoryl)-2-(morpholin-4-yl)-8-[1-(tetrahydro-2H-pyran-2-yl)-1H-pyrazol-5-yl]-1,7-naphthyridine from step a in 2.2 ml of methanol and 0.55 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: basic conditions) to give 21 mg (0.06 mmol) of the desired product.

$^1$H-NMR (400 MHz, DMSO-d6): δ [ppm]=1.88 (3H), 1.92 (3H), 3.78 (8H), 7.35 (1H), 7.55-7.79 (2H), 8.33-8.51 (2H), 13.37 (1H).

Example 178

4-[(trans)-2,5-dimethylpiperazin-1-yl]-2-(morpholin-4-yl)-8-(1H-pyrazol-5-yl)-1,7-naphthyridine Step a 4-[(trans)-2,5-dimethylpiperazin-1-yl]-2-(morpholin-4-yl)-8-[1-(tetrahydro-2H-pyran-2-yl)-1H-pyrazol-5-yl]-1,7-naphthyridine

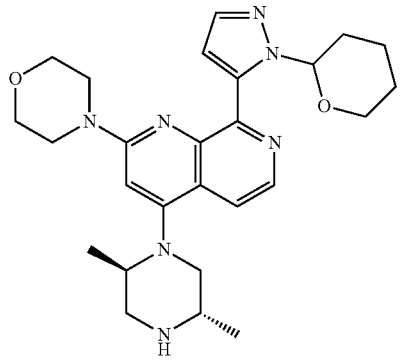 [SMILES: C[C@@H]1CN[C@@H](C)CN1c1cc(N2CCOCC2)nc2c(-c3ccnn3C3CCCCO3)nccc12]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 113 mg (0.99 mmol) (trans)-2,5-dimethylpiperazine in 0.4 ml of MeCN was stirred at 70° C. for 3 hours under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[(trans)-2,5-dimethylpiperazin-1-yl]-2-(morpholin-4-yl)-8-(1H-pyrazol-5-yl)-1,7-naphthyridine

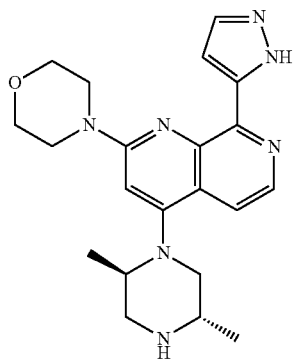 [SMILES: C[C@@H]1CN[C@@H](C)CN1c1cc(N2CCOCC2)nc2c(-c3ccn[nH]3)nccc12]

A solution of 117 mg of crude 4-[(trans)-2,5-dimethylpiperazin-1-yl]-2-(morpholin-4-yl)-8-[1-(tetrahydro-2H-pyran-2-yl)-1H-pyrazol-5-yl]-1,7-naphthyridine from step a in 1.1 ml of methanol and 0.28 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 3 mg (0.008 mmol) of the desired product.

$^1$H-NMR (400 MHz, DMSO-d6): δ [ppm]=0.81-0.95 (3H), 0.95-1.06 (3H), 2.24-2.40 (1H), 2.63-2.75 (1H), 3.02-3.21 (4H), 3.67-3.77 (4H), 3.77-3.85 (4H), 7.12 (1H), 7.36 (1H), 7.62 (1H), 7.79 (1H), 8.24 (1H), 8.36 (1H).

Example 179

4-[(cis)-3,5-dimethylpiperazin-1-yl]-2-(morpholin-4-yl)-8-(1H-pyrazol-5-yl)-1,7-naphthyridine Step a 4-[(cis)-3,5-dimethylpiperazin-1-yl]-2-(morpholin-4-yl)-8-[1-(tetrahydro-2H-pyran-2-yl)-1H-pyrazol-5-yl]-1,7-naphthyridine

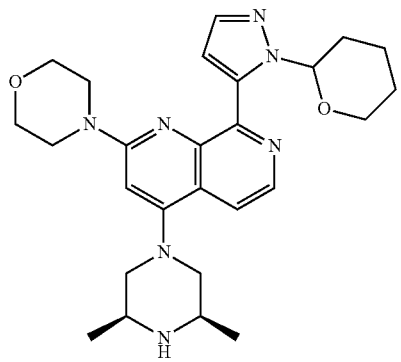 [SMILES: C[C@@H]1CN(c2cc(N3CCOCC3)nc3c(-c4ccnn4C4CCCCO4)nccc23)C[C@H](C)N1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 113 mg (0.99 mmol) (cis)-2,6-dimethylpiperazine in 0.4 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

4-[(cis)-3,5-dimethylpiperazin-1-yl]-2-(morpholin-4-yl)-8-(1H-pyrazol-5-yl)-1,7-naphthyridine

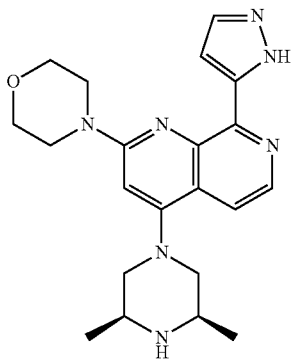 [SMILES: C[C@@H]1CN(c2cc(N3CCOCC3)nc3c(-c4ccn[nH]4)nccc23)C[C@H](C)N1]

A solution of 189 mg of crude 4-[(cis)-3,5-dimethylpiperazin-1-yl]-2-(morpholin-4-yl)-8-[1-(tetrahydro-2H-pyran-2-yl)-1H-pyrazol-5-yl]-1,7-naphthyridine from step a in 1.8 ml of methanol and 0.46 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 51 mg (0.13 mmol) of the desired product.

$^1$H-NMR (400 MHz, DMSO-d6): δ [ppm]=1.03 (6H), 2.30-2.42 (2H), 2.94-3.16 (2H), 3.35 (2H), 3.63-3.74 (4H), 3.74-3.87 (4H), 6.75 (1H), 7.34 (1H), 7.59 (2H), 8.28-8.35 (1H), 13.33 (1H).

Example 180

1-[2-(morpholin-4-yl)-8-(1H-pyrazol-5-yl)-1,7-naphthyridin-4-yl]-3-(trifluoromethyl)azetidin-3-ol Step a 1-{2-(morpholin-4-yl)-8-[1-(tetrahydro-2H-pyran-2-yl)-1H-pyrazol-5-yl]-1,7-naphthyridin-4-yl}-3-(trifluoromethyl)azetidin-3-ol

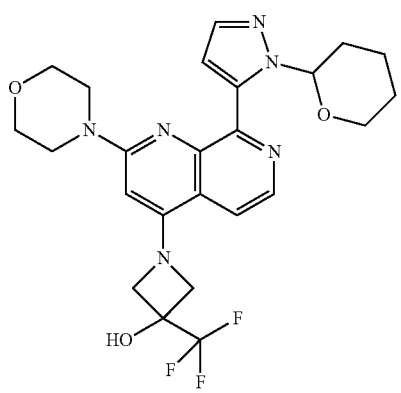 [SMILES: OC1(C(F)(F)F)CN(c2cc(N3CCOCC3)nc3c(-c4ccnn4C4CCCCO4)nccc23)C1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 182 mg (1.02 mmol) 3-(trifluoromethyl)azetidin-3-ol hydrochloride (1:1) and 0.14 ml (1.02 mmol) trimethylamine in 0.5 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b

1-[2-(morpholin-4-yl)-8-(1H-pyrazol-5-yl)-1,7-naphthyridin-4-yl]-3-(trifluoromethyl)azetidin-3-ol

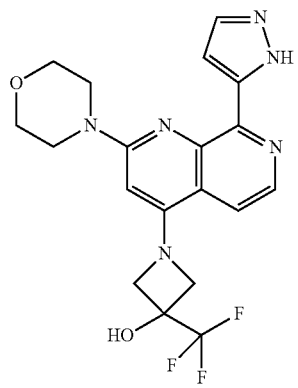 [SMILES: OC1(C(F)(F)F)CN(c2cc(N3CCOCC3)nc3c(-c4ccn[nH]4)nccc23)C1]

A solution of 156 mg of crude 1-{2-(morpholin-4-yl)-8-[1-(tetrahydro-2H-pyran-2-yl)-1H-pyrazol-5-yl]-1,7-naphthyridin-4-yl}-3-(trifluoromethyl)azetidin-3-ol from step a in 7.0 ml of methanol and 0.31 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 6 mg (0.02 mmol) of the desired product.

$^1$H-NMR (400 MHz, DMSO-d6): δ [ppm]=3.53-3.71 (4H), 3.71-3.84 (4H), 4.30 (2H), 4.64 (2H), 6.23 (1H), 7.30 (1H), 7.47 (1H), 7.54-7.68 (2H), 8.22 (1H), 13.33 (1H).

Example 181 methyl hydrogen {4-[2-(morpholin-4-yl)-8-(1H-pyrazol-5-yl)-1,7-naphthyridin-4-yl]phenyl}phosphonate

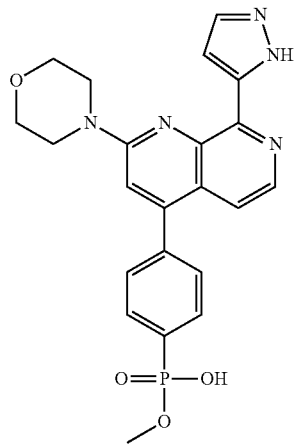 [SMILES: COP(=O)(O)c1ccc(-c2cc(N3CCOCC3)nc3c(-c4ccn[nH]4)nccc23)cc1]

A mixture of 33 mg (0.07 mmol) of dimethyl {4-[2-(morpholin-4-yl)-8-(1H-pyrazol-5-yl)-1,7-naphthyridin-4-yl]phenyl}phosphonate and 0.14 ml (0.28 mmol) aqueous 2N sodium hydroxide solution in 0.14 ml of MeOH was stirred at 70° C. for 4 hours. The pH was adjusted to 6 by the addition of aqueous sodium bicarbonate solution and the mixture was extracted with THF (3×). The combined organic phases were filtered using a Whatman filter and concentrated. The residue was purified by preparative HPLC (Autopurifier: acidic conditions) to give 1 mg (0.002 mmol) of the desired product.

$^1$H-NMR (400 MHz, DMSO-d6): δ [ppm]=3.56-3.63 (8H), 3.80 (3H), 7.40 (1H), 7.41 (1H), 7.52 (1H), 7.65 (1H), 7.69 (2H), 7.89 (3H), 8.33 (1H)

Example 182

4-(4-methylpiperazin-1-yl)-2-(morpholin-4-yl)-8-(1H-pyrazol-5-yl)-1,7-naphthyridine Step a 4-(4-methylpiperazin-1-yl)-2-(morpholin-4-yl)-8-[1-(tetrahydro-2H-pyran-2-yl)-1H-pyrazol-5-yl]-1,7-naphthyridine

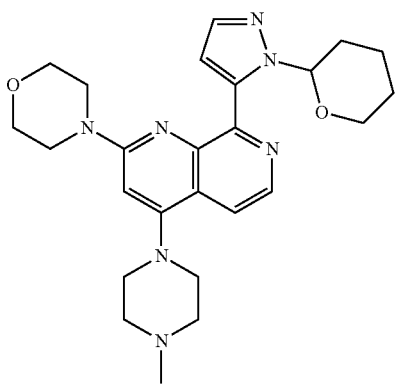 [SMILES: CN1CCN(c2cc(N3CCOCC3)nc3c(-c4ccnn4C4CCCCO4)nccc23)CC1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate and 100 mg (0.99 mmol) 1-methylpiperazine in 0.4 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 2-(morpholin-4-yl)-8-(1H-pyrazol-5-yl)-4-[(3aR,6aS)-tetrahydro-1H-furo[3,4-c]pyrrol-5(3H)-yl]-1,7-naphthyridine

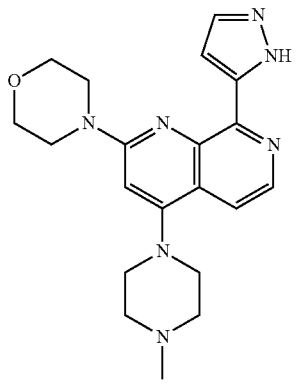 [SMILES: CN1CCN(c2cc(N3CCOCC3)nc3c(-c4ccn[nH]4)nccc23)CC1]

A solution of 204 mg of crude 2-(morpholin-4-yl)-4-[(3aR,6aS)-tetrahydro-1H-furo[3,4-c]pyrrol-5(3H)-yl]-8-[1-(tetrahydro-2H-pyran-2-yl)-1H-pyrazol-5-yl]-1,7-naphthyridine from step a in 2.0 ml of methanol and 0.51 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 7 mg (0.02 mmol) of the desired product.

$^1$H-NMR (400 MHz, DMSO-d6): δ [ppm]=2.30 (3H), 2.61 (4H), 3.18 (4H), 3.62-3.75 (4H), 3.78 (4H), 6.81 (1H), 7.35 (1H), 7.53-7.69 (2H), 8.32 (1H), 13.35 (1H).

Example 183

2-(morpholin-4-yl)-8-(1H-pyrazol-5-yl)-4-[(3aR,6aS)-tetrahydro-1H-furo[3,4-c]pyrrol-5(3H)-yl]-1,7-naphthyridine Step a 2-(morpholin-4-yl)-4-[(3aR,6aS)-tetrahydro-1H-furo[3,4-c]pyrrol-5(3H)-yl]-8-[1-(tetrahydro-2H-pyran-2-yl)-1H-pyrazol-5-yl]-1,7-naphthyridine

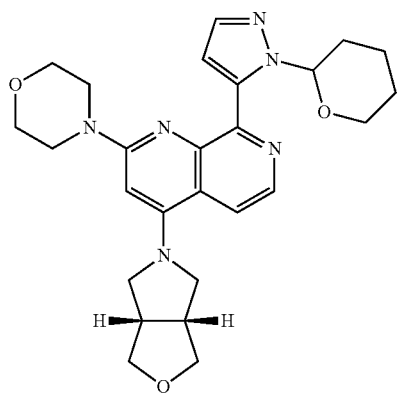 [SMILES: c1cc2c(N3C[C@H]4COC[C@H]4C3)cc(N3CCOCC3)nc2c(-c2ccnn2C2CCCCO2)n1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 153 mg (1.00 mmol) (3aR,6aS)-hexahydro-1H-furo[3,4-c]pyrrole hydrochloride and 0.14 ml (1.00 mol) of triethylamine in 0.4 ml of MeCN was stirred at 70° C. for 3 hours under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 4-(4-methylpiperazin-1-yl)-2-(morpholin-4-yl)-8-(1H-pyrazol-5-yl)-1,7-naphthyridine

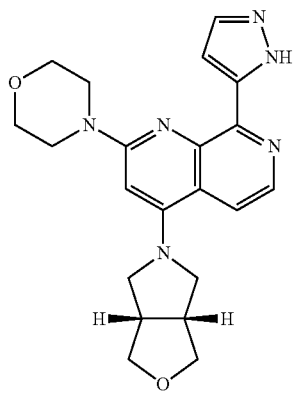 [SMILES: c1cc(-c2nccc3c(N4C[C@H]5COC[C@H]5C4)cc(N4CCOCC4)nc23)[nH]n1]

A solution of 176 mg of crude 2-(morpholin-4-yl)-4-[(3aR,6aS)-tetrahydro-1H-furo[3,4-c]pyrrol-5(3H)-yl]-8-[1-(tetrahydro-2H-pyran-2-yl)-1H-pyrazol-5-yl]-1,7-naphthyridine from step a in 8.2 ml of methanol and 0.37 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 13 mg (0.03 mmol) of the desired product.

$^1$H-NMR (400 MHz, DMSO-d6): δ [ppm]=2.30 (3H), 2.61 (4H), 3.18 (4H), 3.62-3.75 (4H), 3.78 (4H), 6.81 (1H), 7.35 (1H), 7.53-7.69 (2H), 8.32 (1H), 13.35 (1H).

Example 184

4-(3-methoxy-3-methylazetidin-1-yl)-2-(morpholin-4-yl)-8-(1H-pyrazol-5-yl)-1,7-naphthyridine Step a 4-(3-methoxy-3-methylazetidin-1-yl)-2-(morpholin-4-yl)-8-[1-(tetrahydro-2H-pyran-2-yl)-1H-pyrazol-5-yl]-1,7-naphthyridine

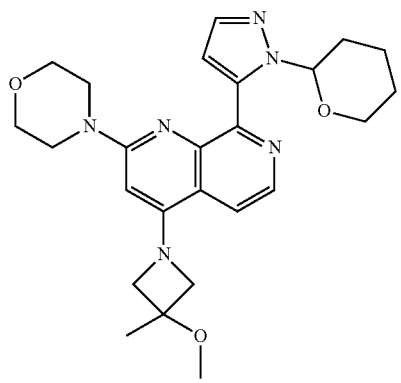 [SMILES: COC1(C)CN(c2cc(N3CCOCC3)nc3c(-c4ccnn4C4CCCCO4)nccc23)C1]

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 137 mg (0.99 mmol) 3-methoxy-3-methylazetidine hydrochloride and 0.28 ml (1.99 mmol) trimethylamine in 0.4 ml of MeCN was stirred at 70° C. for 90 minutes under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 4-(3-methoxy-3-methylazetidin-1-yl)-2-(morpholin-4-yl)-8-(1H-pyrazol-5-yl)-1,7-naphthyridine

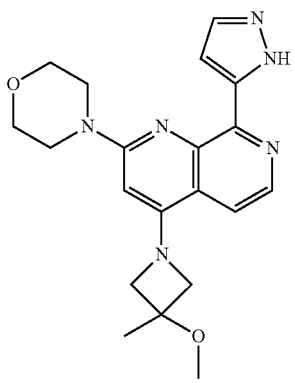 [SMILES: COC1(C)CN(c2cc(N3CCOCC3)nc3c(-c4ccn[nH]4)nccc23)C1]

A solution of 225 mg of crude 4-(3-methoxy-3-methyl-azetidin-1-yl)-2-(morpholin-4-yl)-8-[1-(tetrahydro-2H-pyran-2-yl)-1H-pyrazol-5-yl]-1,7-naphthyridine from step a in 2.3 ml of methanol and 0.56 ml of 2N hydrochloric acid was stirred for 1 hour at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 3 mg (0.01 mmol) of the desired product.

$^1$H-NMR (400 MHz, DMSO-d6): δ [ppm]=1.52 (3H), 3.25 (3H), 3.59-3.71 (4H), 3.71-3.85 (4H), 4.17 (2H), 4.27 (2H), 6.11 (1H), 7.31 (1H), 7.59 (1H), 7.65 (1H), 8.22 (1H), 13.36 (1H).

Example 185

2-(morpholin-4-yl)-4-[(1S,4S)-2-oxa-5-azabicyclo[2.2.1]hept-5-yl]-8-(1H-pyrazol-5-yl)-1,7-naphthyridine Step a 2-(morpholin-4-yl)-4-[(1S,4S)-2-oxa-5-azabicyclo[2.2.1]hept-5-yl]-8-[1-(tetrahydro-2H-pyran-2-yl)-1H-pyrazol-5-yl]-1,7-naphthyridine

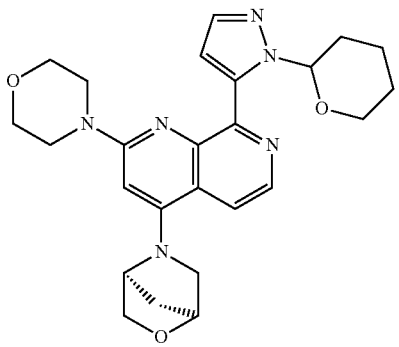

A mixture of 150 mg (0.29 mmol) of 2-(morpholin-4-yl)-8-[1-(tetrahydro-2H-pyran-2-yl)-1H-pyrazol-5-yl]-1,7-naphthyridin-4-yl trifluoromethanesulfonate, 139 mg (1.00 mmol) (1S,4S)-2-oxa-5-azabicyclo[2.2.1]heptane hydrochloride and 0.14 ml (1.02 mmol) trimethylamine in 0.4 ml of MeCN was stirred at 70° C. overnight under argon. After cooling the reaction mixture was diluted with ethyl acetate and washed with saturated aqueous sodium chloride solution. The organic phase was filtered using a Whatman filter and then concentrated to give the crude product that was used without further purification in the next step.

Step b 2-(morpholin-4-yl)-4-[(1S,4S)-2-oxa-5-azabicyclo[2.2.1]hept-5-yl]-8-(1H-pyrazol-5-yl)-1,7-naphthyridine

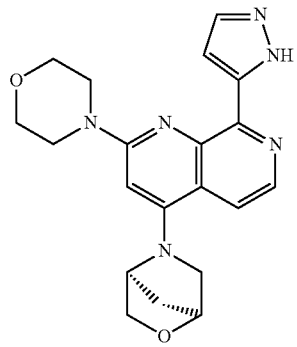

A solution of 172 mg of crude 2-(morpholin-4-yl)-4-[(1S,4S)-2-oxa-5-azabicyclo[2.2.1]hept-5-yl]-8-[1-(tetrahydro-2H-pyran-2-yl)-1H-pyrazol-5-yl]-1,7-naphthyridine from step a in 8.3 ml of methanol and 0.37 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and then concentrated to dryness. The residue was purified by preparative HPLC (Autopurifier: basic conditions) to give 39 mg (0.10 mmol) of the desired product.

$^1$H-NMR (400 MHz, DMSO-d6): δ [ppm]=1.91 (1H), 2.03 (1H), 3.38 (1H), 3.56-3.72 (4H), 3.72-3.86 (5H), 3.89-4.14 (2H), 4.64 (1H), 4.78 (1H), 6.44 (1H), 7.29 (1H), 7.58 (1H), 7.70 (1H), 8.20 (1H), 13.32 (1H).

Example 186

2-[(3R)-3-methylmorpholin-4-yl]-4-[(methylsulfanyl)methyl]-8-(1H-pyrazol-5-yl)-1,7-naphthyridine Step a 2-[(3R)-3-methylmorpholin-4-yl]-8-(1-{[2-(trimethylsilyl)ethoxy]methyl}-1H-pyrazol-5-yl)-1,7-naphthyridin-4-ol

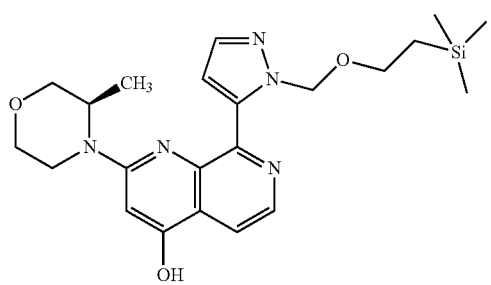 [SMILES: C[C@@H]1COCCN1c1cc(O)c2ccnc(-c3ccnn3COCC[Si](C)(C)C)c2n1]

A suspension of 2310 mg (8.3 mmol) of 8-chloro-2-(3-methylmorpholin-4-yl)-1,7-naphthyridin-4-ol, 3000 mg (12.4 mmol) (1-{[2-(trimethylsilyl)ethoxy]methyl}-1H-pyrazol-5-yl)boronic acid, 1348 mg (1.7 mmol) of [1,1'-bis (diphenylphosphino)ferrocene]dichloropalladium(II) complex with dichloromethane (1:1, Pd(dppf)Cl$_2$) and 4251 mg (13.0 mmol) of caesium carbonate in 69 ml of dioxane was degased with argon. Under argon, the reaction mixture was stirred at 110° C. for 1 hour. After cooling the reaction mixture was diluted with aqueous sodium chloride solution and extracted with ethyl acetate (3×). The combined organic phases were filtered using a Whatman filter and then concentrated. The residue was purified by column chromatography (gradient from 100% Hex to 100% EtOAc) to give 1710 mg (3.9 mmol) of the desired product.

$^1$H-NMR (400 MHz, DMSO-d6): δ [ppm]=−0.35-0.27 (9H), 0.47-0.61 (2H), 1.18 (3H), 3.06-3.29 (3H), 3.46 (1H), 3.63 (1H), 3.74 (1H), 3.95 (2H), 4.32 (1H), 5.81 (1H), 5.88 (1H), 6.59 (1H), 6.98 (1H), 7.63 (1H), 7.78 (1H), 8.32 (1H), 11.49 (1H).

Step b

2-[(3R)-3-methylmorpholin-4-yl]-8-(1-{[2-(trimethylsilyl)ethoxy]methyl}-1H-pyrazol-5-yl)-1,7-naphthyridin-4-yl trifluoromethanesulfonate

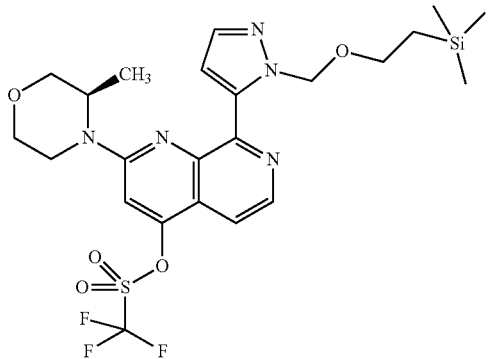 [SMILES: C[C@@H]1COCCN1c1cc(OS(=O)(=O)C(F)(F)F)c2ccnc(-c3ccnn3COCC[Si](C)(C)C)c2n1]

A mixture of 1710 mg (3.9 mmol) 2-[(3R)-3-methylmorpholin-4-yl]-8-(1-{[2-(trimethylsilyl)ethoxy]methyl}-1H-pyrazol-5-yl)-1,7-naphthyridin-4-ol, 1549 mg (4.3 mmol) 1,1,1-trifluoro-N-phenyl-N-[(trifluoromethyl)sulfonyl]methanesulfonamide and 1.35 ml (7.7 mmol) of N,N-diisopropyethylamin in 22 ml of DCM was stirred at room temperature for 2 hours. The mixture was concentrated and the residue was purified by column chromatography (gradient from 100% Hex to hexane/EtOAc 50%) to give 1870 mg (3.3 mmol) of the desired product.

$^1$H-NMR (400 MHz, DMSO-d6): δ [ppm]=−0.37 (9H), 0.43-0.64 (2H), 1.23 (3H), 3.13-3.30 (3H), 3.49 (1H), 3.64 (1H), 3.79 (1H), 3.96-4.03 (1H), 4.14 (1H), 4.48 (1H), 5.82 (1H), 5.89 (1H), 7.05 (1H), 7.64 (1H), 7.68 (1H), 7.76 (1H), 8.54 (1H).

Step c methyl 2-[(3R)-3-methylmorpholin-4-yl]-8-(1-{[2-(trimethylsilyl)ethoxy]methyl}-1H-pyrazol-5-yl)-1,7-naphthyridine-4-carboxylate

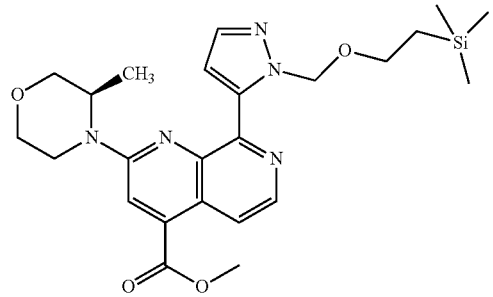 [SMILES: COC(=O)c1cc(N2CCOC[C@H]2C)nc2c(-c3ccnn3COCC[Si](C)(C)C)nccc12]

In an autoclave, a mixture of 1800 mg (3.14 mmol) of 2-[(3R)-3-methylmorpholin-4-yl]-8-(1-{[2-(trimethylsilyl)ethoxy]methyl}-1H-pyrazol-5-yl)-1,7-naphthyridin-4-yl trifluoromethanesulfonate, 133 mg (0.31 mmol) 1,3-bis(diphenylphosphino)propane, 70 mg (0.31 mmol) palladium(II) acetate and 0.9 ml triethylamine (6.3 mmol) in 22 ml of DMF and 12 ml of methanol was purged with carbon monoxide at room temperature. The autoclave was pressured with carbonmonoxide to 13.7 bar and the mixture was stirred at room temperature for 30 minutes. The autoclave was depressurized and then pressured with carbon monoxide to 16.1 bar. The mixture was stirred at 80° C. for 24 hours. The autoclave was depressurized and after cooling, the mixture was diluted with ethyl acetate and washed with aqueous sodium chloride solution. The organic phase was dried (Na$_2$SO$_4$), filtered and concentrated. The residue was purified by column chromatography (gradient from 100% Hex to 100% EtOAc) to give 720 mg (1.49 mmol) of the desired product.

$^1$H-NMR (400 MHz, DMSO-d6): δ [ppm]=−0.48-0.30 (9H), 0.42-0.61 (2H), 1.22 (3H), 3.20 (3H), 3.48 (1H), 3.54-3.68 (1H), 3.75 (1H), 3.88-4.05 (4H), 4.10 (1H), 4.50 (1H), 5.78 (1H), 5.85 (1H), 6.96 (1H), 7.66 (1H), 7.87 (1H), 8.19 (1H), 8.46 (1H).

Step d

{2-[(3R)-3-methylmorpholin-4-yl]-8-(1-{[2-(trimethylsilyl)ethoxy]methyl}-1H-pyrazol-5-yl)-1,7-naphthyridin-4-yl}methanol

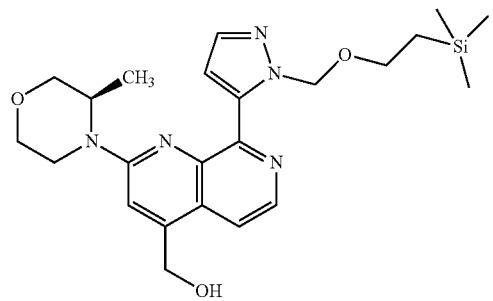 [SMILES: C[C@@H]1COCCN1c1cc(CO)c2ccnc(-c3ccnn3COCC[Si](C)(C)C)c2n1]

3.0 ml (3.00 mmol) of a 1M solution of DIBAL in toluene was added to a solution of 720 mg (1.49 mmol) of methyl 2-[(3R)-3-methylmorpholin-4-yl]-8-(1-{[2-(trimethylsilyl)ethoxy]methyl}-1H-pyrazol-5-yl)-1,7-naphthyridine-4-carboxylate in 17 ml of dry THF at room temperature and the mixture was stirred at 70° C. for 4 hours. After cooling, the mixture was diluted with 25 ml of a saturated solution of ammonium chloride and stirred at room temperature overnight. The mixture was diluted with ethyl acetate and filtered using a Whatman filter. The organic phase was concentrated and the residue was purified by column chromatography (gradient from 100% Hex to 100% EtOAc) to give 405 mg (0.89 mmol) of the desired product.

$^1$H-NMR (400 MHz, DMSO-d6): δ [ppm]=−0.37-0.25 (9H), 0.39-0.62 (2H), 1.13-1.31 (3H), 3.12-3.28 (3H), 3.48 (1H), 3.63 (1H), 3.77 (1H), 3.98 (1H), 4.11 (1H), 4.47 (1H), 4.93 (2H), 5.65 (1H), 5.80 (1H), 5.86 (1H), 6.96 (1H), 7.45 (1H), 7.64 (1H), 7.72 (1H), 8.38 (1H).

Step e 4-(chloromethyl)-2-[(3R)-3-methylmorpholin-4-yl]-8-(1-{[2-(trimethylsilyl)ethoxy]methyl}-1H-pyrazol-5-yl)-1,7-naphthyridine and 4-(chloromethyl)-2-[(3R)-3-methylmorpholin-4-yl]-8-(1H-pyrazol-5-yl)-1,7-naphthyridine

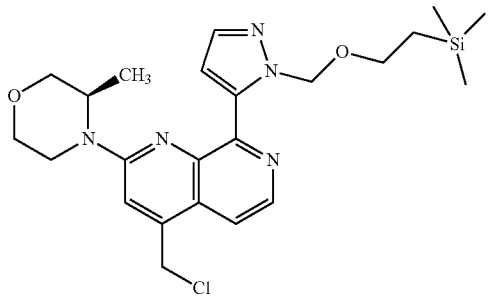

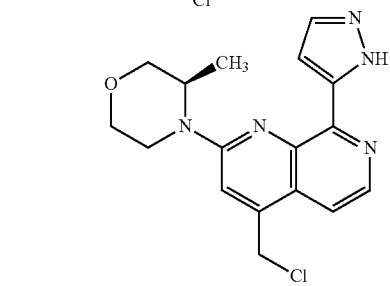

0.05 ml (0.66 mmol) thiony chloride was added to a stirred solution of {2-[(3R)-3-methylmorpholin-4-yl]-8-(1-{[2-(trimethylsilyl)ethoxy]methyl}-1H-pyrazol-5-yl)-1,7-naphthyridin-4-yl}methanol in 33 ml of dry DMF at 0° C. The mixture was stirred at 5° C. for 1 hour. Toluene was added and the mixture was concentrated to give a crude mixture of 4-(chloromethyl)-2-[(3R)-3-methylmorpholin-4-yl]-8-(1-{[2-(trimethylsilyl)ethoxy]methyl}-1H-pyrazol-5-yl)-1,7-naphthyridine and 4-(chloromethyl)-2-[(3R)-3-methylmorpholin-4-yl]-8-(1H-pyrazol-5-yl)-1,7-naphthyridine.

Step f

2-[(3R)-3-methylmorpholin-4-yl]-4-[(methylsulfanyl)methyl]-8-(1-{[2-(trimethylsilyl)ethoxy]methyl}-1H-pyrazol-5-yl)-1,7-naphthyridine and 2-[(3R)-3-methylmorpholin-4-yl]-4-[(methylsulfanyl)methyl]-8-(1H-pyrazol-5-yl)-1,7-naphthyridine

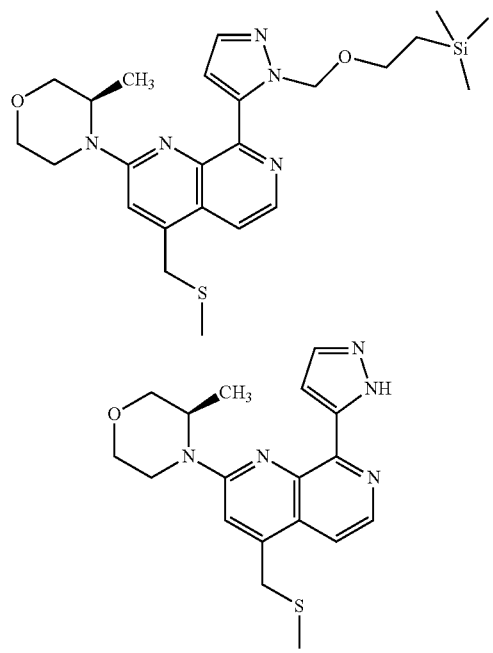

0.56 ml (1.71 mmol) of an aqueous solution of sodium methanethiolate (21%) was added to 184 mg of a crude mixture of 4-(chloromethyl)-2-[(3R)-3-methylmorpholin-4-yl]-8-(1-{[2-(trimethylsilyl)ethoxy]methyl}-1H-pyrazol-5-yl)-1,7-naphthyridine and 4-(chloromethyl)-2-[(3R)-3-methylmorpholin-4-yl]-8-(1H-pyrazol-5-yl)-1,7-naphthyridine from step e in 4.3 ml of acetone at room temperature. The mixture was stirred at room temperature for 150 minutes before it was diluted with ethyl acetate and washed with an aqueous solution of sodium chloride. The organic phase was filtered using a Whatman filter and concentrated. The residue was purified by preparative HPLC (Autopurifier: basic conditions) to give 33 mg (0.07 mmol) 2-[(3R)-3-methylmorpholin-4-yl]-4-[(methylsulfanyl)methyl]-8-(1-{[2-(trimethylsilyl)ethoxy]methyl}-1H-pyrazol-5-yl)-1,7-naphthyridine and 32 mg (0.09 mmol) of 2-[(3R)-3-methylmorpholin-4-yl]-4-[(methylsulfanyl)methyl]-8-(1H-pyrazol-5-yl)-1,7-naphthyridine.

2-[(3R)-3-methylmorpholin-4-yl]-4-[(methylsulfanyl)methyl]-8-(1-{[2-(trimethylsilyl)ethoxy]methyl}-1H-pyrazol-5-yl)-1,7-naphthyridine $^1$H-NMR (400 MHz, DMSO-d6): δ [ppm]=−0.14-0.02 (9H), 0.86 (2H), 1.24 (3H), 2.02 (3H), 3.26 (1H), 3.53 (1H), 3.60 (2H), 3.64-3.73 (1H), 3.77 (1H), 3.91-4.05 (1H), 4.10 (2H), 4.18 (1H), 4.53 (1H), 5.50 (2H), 7.17 (1H), 7.39 (1H), 7.81 (1H), 7.95 (1H), 8.35 (1H).

2-[(3R)-3-methylmorpholin-4-yl]-4-[(methylsulfa-nyl)methyl]-8-(1H-pyrazol-5-yl)-1,7-naphthyridine ¹H-NMR (400 MHz, DMSO-d6): δ [ppm]=1.20-1.36 (3H), 2.02 (3H), 3.32 (1H), 3.52-3.67 (1H), 3.73 (1H), 3.84 (1H), 3.96-4.23 (4H), 4.55 (1H), 7.38 (1H), 7.47 (1H), 7.62 (1H), 7.83 (1H), 8.37 (1H), 13.38 (1H).

Example 187

N,N-dimethyl-5-[2-(morpholin-4-yl)-8-(1H-pyrazol-5-yl)-1,7-naphthyridin-4-yl]pyridin-2-amine

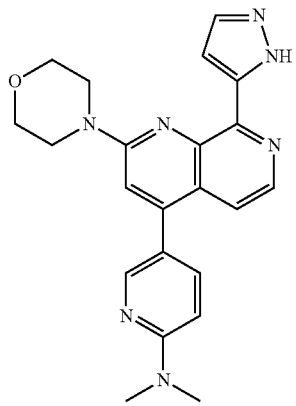 [SMILES: CN(C)c1ccc(-c2cc(N3CCOCC3)nc3c(-c4ccn[nH]4)nccc23)cn1]

Example 187 was prepared using Automated Medicinal Chemistry (see examples 346-437). However, initial purity was not sufficient for testing and therefore the sample had to be purified by a second preparative HPLC (Autopurifier: basic conditions) to give 1 mg (0.002 mmol) of the desired product.
¹H-NMR (400 MHz, DMSO-d6): δ [ppm]=3.13 (6H), 3.80 (8H), 6.83 (1H), 7.31-7.49 (2H), 7.53 (1H), 7.64 (1H), 7.77 (1H), 8.18-8.39 (2H), 13.42 (1H).

Example 188

4-(2-methylpyridin-4-yl)-2-(morpholin-4-yl)-8-(1H-pyrazol-5-yl)-1,7-naphthyridine

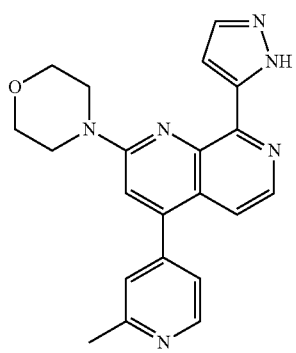 [SMILES: Cc1cc(-c2cc(N3CCOCC3)nc3c(-c4ccn[nH]4)nccc23)ccn1]

Example 187 was prepared using Automated Medicinal Chemistry (see examples 346-437). However, initial purity was not sufficient for testing and therefore the sample had to be purified by a second preparative HPLC (Autopurifier: basic conditions) to give 0.7 mg (0.002 mmol) of the desired product.

¹H-NMR (400 MHz, DMSO-d6): δ [ppm]=2.60 (3H), 3.80 (8H), 7.40 (2H), 7.43 (1H), 7.48 (1H), 7.54 (1H), 7.65 (1H), 8.34 (1H), 8.64 (1H), 13.44 (1H).

Example 189

1-{2-[(3R)-3-methylmorpholin-4-yl]-8-(1H-pyrazol-5-yl)-1,7-naphthyridin-4-yl}cyclohexanol Step a 1-{2-[(3R)-3-methylmorpholin-4-yl]-8-(1-{[2-(trim-ethylsilyl)ethoxy]methyl}-1H-pyrazol-5-yl)-1,7-naphthyridin-4-yl}cyclohexanol

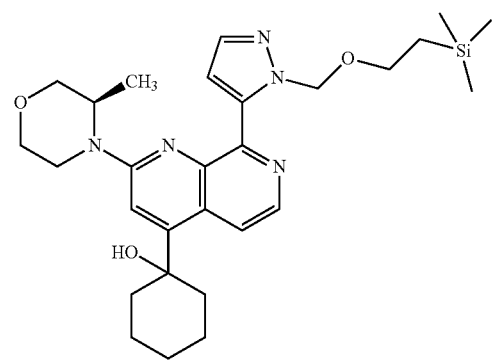 [SMILES: C[C@@H]1COCCN1c1cc(C2(O)CCCCC2)c2ccnc(-c3ccnn3COCC[Si](C)(C)C)c2n1]

0.23 ml (0.12 mmol) of a solution of 0.5M pentamethyl-enebis(magnesium bromide) in THF was added to a solution of 56 mg (0.12 mmol) methyl 2-[(3R)-3-methylmorpholin-4-yl]-8-(1-{[2-(trimethylsilyl)ethoxy]methyl}-1H-pyrazol-5-yl)-1,7-naphthyridine-4-carboxylate in 3.0 ml of THF at 0° C. under argon. The mixture was stirred at 0° C. for 30 minutes and then 1 hour at room temperature. Additional 0.12 ml (0.06 mmol) of the solution of 0.5M pentamethyl-enebis(magnesium bromide) in THF was added and the mixture was stirred for 150 minutes at room temperature. The mixture was diluted with aqueous ammonium chloride solution and extracted with ethyl acetate (2×). The combined organic phases were filtered using a Whatman filter and concentrated. The residue was purified by column chroma-tography (gradient from 100% Hex hexane/EtOAc 50%) to give 26 mg (0.05 mmol) the desired product.

Step b

1-{2-[(3R)-3-methylmorpholin-4-yl]-8-(1H-pyrazol-5-yl)-1,7-naphthyridin-4-yl}cyclohexanol

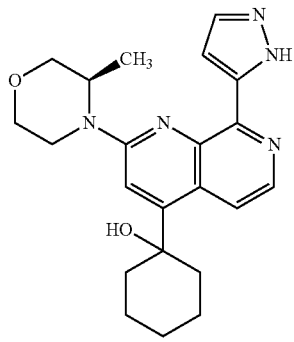 [SMILES: C[C@@H]1COCCN1c1cc(C2(O)CCCCC2)c2ccnc(-c3ccn[nH]3)c2n1]

0.04 ml (0.08 mmol) of a 2N aqueous hydrogen chloride solution was added to a solution of 20 mg (0.038 mmol) of 1-{2-[(3R)-3-methylmorpholin-4-yl]-8-(1-{[2-(trimethylsilyl)ethoxy]methyl}-1H-pyrazol-5-yl)-1,7-naphthyridin-4-yl}cyclohexanol from step a in 0.4 ml of dioxane. The mixture was stirred at room temperature for 7 hours. The mixture was diluted with aqueous sodium chloride solution and extracted with ethyl acetat (2×) and DCM (1×). The combined organic phases were filtered using a Whatman filter and concentrated. The residue was purified by preparative HPLC (Autopurifier: basic conditions) to give 4 mg (0.01 mmol) of the desired product.

$^1$H-NMR (400 MHz, DMSO-d6): δ [ppm]=1.25 (3H), 1.41-1.57 (2H), 1.57-1.68 (1H), 1.70-1.84 (1H), 1.96-2.11 (2H), 3.31 (1H), 3.56 (1H), 3.71 (1H), 3.82 (1H), 4.05 (1H), 4.12 (1H), 4.53 (1H), 4.89-5.01 (2H), 5.09-5.29 (1H), 5.61 (1H), 5.77 (1H), 7.36 (1H), 7.49 (1H), 7.60 (1H), 7.77 (1H), 8.34 (1H), 13.36 (1H).

Example 190

5-fluoro-2-{2-[(3R)-3-methylmorpholin-4-yl]-8-(1H-pyrazol-5-yl)-1,7-naphthyridin-4-yl}aniline

Step a 2-fluoro-6-{2-[(3R)-3-methylmorpholin-4-yl]-8-[1-(tetrahydro-2H-pyran-2-yl)-1H-pyrazol-5-yl]-1,7-naphthyridin-4-yl}aniline

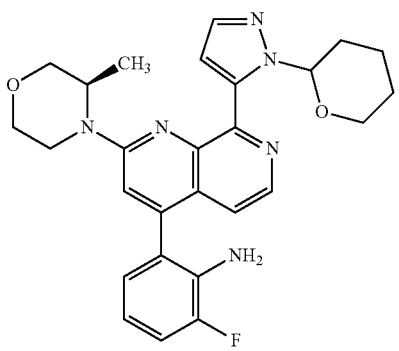 [SMILES: C[C@@H]1COCCN1c1cc(-c2cccc(F)c2N)c2ccnc(-c3ccnn3C3CCCCO3)c2n1]

A suspension of 100 mg (0.19 mmol) of 2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate, 90 mg (0.38 mmol) 2-fluoro-6-(4,4,5,5-tetramethyl-1,3,2-dioxaborolan-2-yl)aniline, 15 mg (0.019 mmol) of [1,1'-bis(diphenylphosphino)ferrocene]dichloropalladium(II) complex with dichloromethane (1:1, Pd(dppf)Cl$_2$) and 65 mg (0.47 mmol) of potassium carbonate in 2.0 ml of acetonitrile and 1.0 ml water was degased with argon. Under argon, the reaction mixture was stirred at 130° C. for 10 minutes in a microwave oven. After cooling the reaction mixture was diluted with saturated aqueous sodium chloride solution and extracted with ethyl acetate (2×). The combined organic phases were filtered using a Whatman filter and then concentrated to give the crude product that was used without further purification in the next step.

Step b 2-fluoro-6-{2-[(3R)-3-methylmorpholin-4-yl]-8-(1H-pyrazol-5-yl)-1,7-naphthyridin-4-yl}aniline

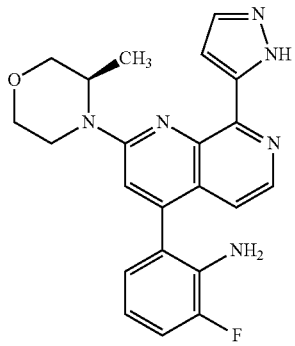 [SMILES: C[C@@H]1COCCN1c1cc(-c2cccc(F)c2N)c2ccnc(-c3ccn[nH]3)c2n1]

A solution of 156 mg of crude 2-fluoro-6-{2-[(3R)-3-methylmorpholin-4-yl]-8-[1-(tetrahydro-2H-pyran-2-yl)-1H-pyrazol-5-yl]-1,7-naphthyridin-4-yl}aniline from step a in 5.8 ml of methanol and 0.30 ml of 2N hydrochloric acid was stirred for 90 minutes at room temperature. The reaction mixture was diluted with saturated aqueous sodium bicarbonate solution and extracted with ethyl acetate (2×). The combined organic phases were filtered using a Whatman filter and concentrated to dryness. The residue was purified by preparative HPLC (Autopurifier: acidic conditions) to give 2 mg (0.005 mmol) of the desired product.

$^1$H-NMR (400 MHz, DMSO-d6): δ [ppm]=1.22-1.40 (3H), 3.51-3.64 (1H), 3.71 (1H), 3.82 (1H), 4.05 (1H), 4.21 (1H), 4.54-4.70 (1H), 4.89 (2H), 6.62-6.76 (1H), 6.90 (1H), 6.97-7.26 (2H), 7.39 (1H), 7.44 (1H), 7.55-7.74 (1H), 8.28 (1H), 13.42 (1H).

Example 191

(methyl{4-[2-(morpholin-4-yl)-8-(1H-pyrazol-5-yl)-1,7-naphthyridin-4-yl]phenyl}oxido-λ⁶-sulfanylidene)cyanamide

Step a

4-[4-(methylsulfonimidoyl)phenyl]-2-(morpholin-4-yl)-8-{1-[(2)-tetrahydro-2H-pyran-2-yl]-1H-pyrazol-5-yl}-1,7-naphthyridine

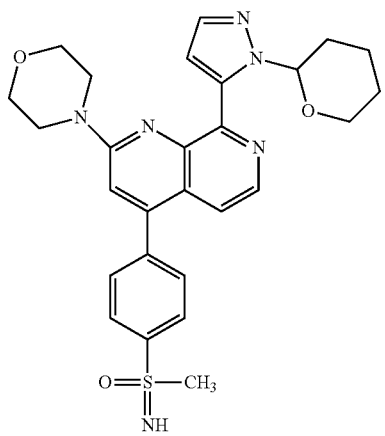 [SMILES: CS(=N)(=O)c1ccc(-c2cc(N3CCOCC3)nc3c(-c4ccnn4C4CCCCO4)nccc23)cc1]

4-[(2-(Morpholin-4-yl)-8-[2-(tetrahydropyran-2-yl)-2H-pyrazol-3-yl]-[1,7]naphthyridine-4-yl]phenyl-N-ethoxycarbonyl-S-methylsulphoximide (1.00 g, 1.52 mmol) was solubilised in a solution of NaOMe (30% solution in MeOH, 25 mL). the reaction was stirred at 60° C. for 3 h. The reaction mixture was concentrated under reduced pressure and diluted with DCM and H₂O. The aqueous phase was extracted two times with DCM. The combined organic phases were washed with brine, dried (silicon filter) and concentrated under reduced pressure. The titled compound was obtain in quantitative yield without further purification.

¹H-NMR (400 MHz, DMSO-d₆): δ [ppm]=1.40-1.66 (m, 3H), 1.99 (br. s., 2H), 2.30-2.47 (m, 1H), 3.17 (s, 3H), 3.22-3.30 (m, 1H), 3.72 (s, 8H), 4.35 (s, 1H), 5.75 (s, 1H), 6.06-6.12 (m, 1H), 6.93 (d, 1H), 7.41 (d, 1H), 7.50 (s, 1H), 7.64 (d, 1H), 7.82 (d, 2H), 8.13 (d, 2H), 8.38 (d, 1H).

Step b (methyl{4-[2-(morpholin-4-yl)-8-(1H-pyrazol-5-yl)-1,7-naphthyridin-4-yl]phenyl}oxido-λ⁶-sulfanylidene)cyanamide

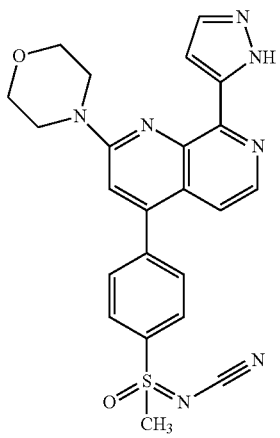 [SMILES: CS(=O)(=NC#N)c1ccc(-c2cc(N3CCOCC3)nc3c(-c4ccn[nH]4)nccc23)cc1]

4-[4-(Methylsulfonimidoyl)phenyl]-2-(morpholin-4-yl)-8-{1-[(2)-tetrahydro-2H-pyran-2-yl]-1H-pyrazol-5-yl}-1,7-naphthyridine (200 mg, 0.39 mmol) was solubilised in DCM (6 mL). DMAP (51 mg, 0.42 mmol) and BrCN (82 mg, 0.77 mmol, 3M solution) were added sequentially. The reaction was stirred at rt for 16 h. The reaction mixture was concentrated under reduced pressure and diluted with MeOH. The suspension was filtered, washed with MeOH and dried under reduced pressure. The crude solid (74 mg) was then solubilized in DCM (2 mL) and 3M HCl (1.5 mL) was added. The reaction was stirred for 1 h at rt. The reaction was quenched by addition of sat. bicarbonate and the solid was filtered and dried. The title compound was obtained without further purification in (60 mg).

¹H-NMR (400 MHz, DMSO-d₆): δ [ppm]=3.76-3.85 (m, 11H), 7.33 (d, 1H), 7.43 (br. s, 1H), 7.60-7.68 (m, 2H), 8.00 (d, 2H), 8.26 (d, 2H), 8.36 (d, 1H), 13.42 (br. s, 1H).

Example 192

1-ethyl-3-(methyl{4-[2-(morpholin-4-yl)-8-(1H-pyrazol-5-yl)-1,7-naphthyridin-4-yl]phenyl}oxido-λ⁶-sulfanylidene)urea

Step a (methyl{4-[2-(morpholin-4-yl)-8-(1H-pyrazol-5-yl)-1,7-naphthyridin-4-yl]phenyl}oxido-λ⁶-sulfanylidene)cyanamide

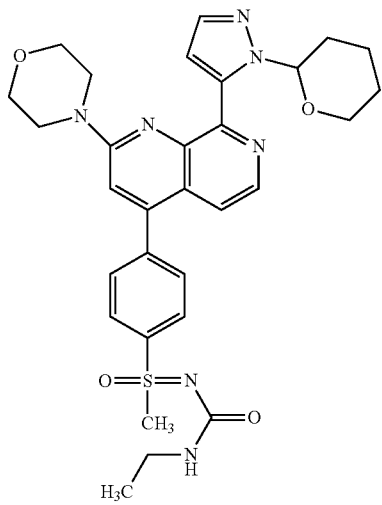 [SMILES: CCNC(=O)N=S(C)(=O)c1ccc(-c2cc(N3CCOCC3)nc3c(-c4ccnn4C4CCCCO4)nccc23)cc1]

4-[4-(Methylsulfonimidoyl)phenyl]-2-(morpholin-4-yl)-8-{1-[(2)-tetrahydro-2H-pyran-2-yl]-1H-pyrazol-5-yl}-1,7-naphthyridine (100 mg, 0.19 mmol) was solubilised in DCM (6 mL). Triethylamine (39 mg, 0.39 mmol) and ethyl isocyanate (27 mg, 0.39 mmol) were added. The reaction was stirred for 16 h at rt and triethylamine (195 mg, 3.89 mmol) and ethyl isocyanate (135 mg, 1.95 mmol) were added. The reaction was stirred for 16 h at rt and concentrated under reduced pressure. The crude material was solubilized in DMF (6 mL) and triethylamine (195 mg, 3.89 mmol) and ethyl isocyanate (135 mg, 1.95 mmol) were added. The reaction was stirred for 48 h at 60° C. The reaction was diluted with water and extracted with DCM. The organic phase was dried (silicon filter) and concentrated under reduced pressure. The crude material was purified by flash chromatography (100% Hexane to 100% AcOEt to 20% MeOH). The titled compound was obtained in 78% yield (93 mg). ¹H-NMR (400 MHz, DMSO-d₆): δ [ppm]=0.99 (t, 3H), 1.40-1.66 (m, 3H), 1.99 (s, 2H), 2.34-2.45 (m, 1H), 2.90-3.04 (m, 2H), 3.23-3.29 (m, 1H), 3.45 (s, 3H), 3.72 (s, 9H), 6.09 (dd, 1H), 6.94 (d, 1H), 7.00 (t, 1H), 7.41 (d, 1H), 7.53 (s, 1H), 7.64 (d, 1H), 7.87 (d, 2H), 8.11 (d, 2H), 8.39 (d, 1H).

Step b 1-ethyl-3-(methyl{4-[2-(morpholin-4-yl)-8-(1H-pyrazol-5-yl)-1,7-naphthyridin-4-yl]phenyl}oxido-λ⁶-sulfanylidene)urea

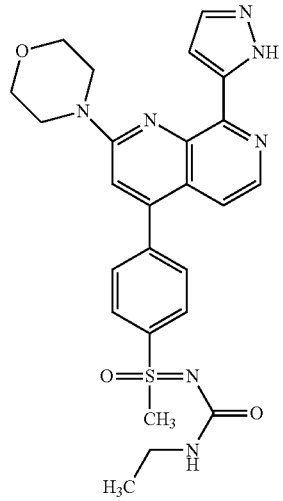 [SMILES: CCNC(=O)N=S(C)(=O)c1ccc(-c2cc(N3CCOCC3)nc3c(-c4ccn[nH]4)nccc23)cc1]

(Methyl{4-[2-(morpholin-4-yl)-8-(1H-pyrazol-5-yl)-1,7-naphthyridin-4-yl]phenyl}oxido-λ⁶-sulfanylidene)cyanamide (93 mg, 46 mmol) was solubilized in DCM (3 mL) and 3M HCl (2 mL) was added. The reaction was stirred 16 h at rt and then quenched with sat NaHCO3. The aqueous phase was extracted with DCM and the organic phase was dried (silicon filter) and concentrated under reduced pressure. The crude material was purified by flash column chromatography (100% Hexane to 100% AcOEt to 20% MeOH) and the titled compound was obtained in 85% yield (68 mg). ¹H-NMR (400 MHz, DMSO-d₆): δ [ppm]=0.99 (t, 3H), 2.90-3.03 (m, 2H), 3.45 (s, 3H), 3.80 (s, 8H), 7.00 (t, 1H), 7.35 (d, 1H), 7.43 (br. s, 1H), 7.57 (s, 1H), 7.65 (br. s, 1H), 7.86 (d, 2H), 8.11 (d, 2H), 8.35 (d, 1H), 13.37-13.47 (m, 1H).

Example 193

3-({2-[(3R)-3-methylmorpholin-4-yl]-8-(1H-pyrazol-5-yl)-1,7-naphthyridin-4-yl}oxy)propan-1-amine

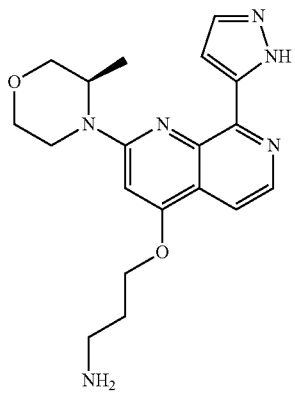 [SMILES: C[C@@H]1COCCN1c1cc(OCCCN)c2ccnc(-c3ccn[nH]3)c2n1]

Tert-butyl [3-({2-[(3R)-3-methylmorpholin-4-yl]-8-[1-(tetrahydro-2H-pyran-2-yl)-1H-pyrazol-5-yl]-1,7-naphthyridin-4-yl}oxy)propyl]carbamate (80 mg, 0.15 mmol) was solubilised in DCM (2 mL) and TFA (0.22 mL, 2.9 mmol) was added. The reaction was stirred 2 h at rt and quenched with sat. NaHCO$_3$. The aqueous phase was extracted with DCM and the organic phase was dried (silicon filter) and concentrated under reduced pressure.

The crude material was purified by preparative HPLC (ACN/H$_2$O/formic acid system). The titled compound was obtained in 18% yield (10 mg). $^1$H-NMR (400 MHz, DMSO-d$_6$): δ [ppm]=1.27 (d, 3H), 2.11 (quin, 2H), 2.99 (t, 2H), 3.30 (dt, 1H), 3.56 (dt, 1H), 3.72 (dd, 1H), 3.83 (d, 1H), 4.05 (dd, 1H), 4.15 (d, 1H), 4.36 (t, 2H), 4.56-4.64 (m, 1H), 6.82 (s, 1H), 7.36 (d, 1H), 7.61 (d, 1H), 7.75 (d, 1H), 8.30-8.41 (m, 2H).

Example 194

4-(4-cyclopropyl-1H-1,2,3-triazol-5-yl)-2-[(3R)-3-methylmorpholin-4-yl]-8-(1H-pyrazol-5-yl)-1,7-naphthyridine Step a 4-(cyclopropylethynyl)-2-[(3R)-3-methylmorpholin-4-yl]-8-{1-[tetrahydro-2H-pyran-2-yl]-1H-pyrazol-5-yl}-1,7-naphthyridine

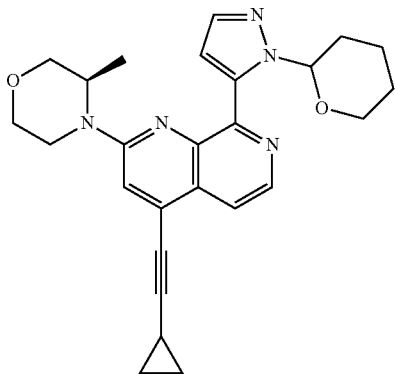 [SMILES: C[C@@H]1COCCN1c1cc(C#CC2CC2)c2ccnc(-c3ccnn3C3CCCCO3)c2n1]

2-[(3R)-3-methylmorpholin-4-yl]-8-{1-[tetrahydro-2H-pyran-2-yl]-1H-pyrazol-5-yl}-1,7-naphthyridin-4-yltrifluoromethanesulfonate (150 mg, 284 µmol), copper(I) iodide (5.53 mg, 98% purity, 28.4 µmol) and triethylamine (790 µl, 5.7 mmol) were dissolved in acetonitrile (4.0 mL). The reaction mixture was degassed with Argon. Ethynylcyclopropane (74 µl, 98% purity, 850 µmol) and: Bis(triphenylphosphin)palladium(II)chlorid (8.15 mg, 98% purity, 11.4 µmol) were added sequentially and the reaction was stirred for 16 h at 45° C. The reaction was then filtered and concentrated under reduced pressure. The residue was dissolved in DCM and water and the aqueous phase was extracted 3× with DCM. The combined organic layers were dried (silicone filter) and concentrated under reduced pressure. The crude material was purified by flash column chromatography (Hex/EtOAc mixture) and the title compound was obtained in 87% yield (110 mg). 1H-NMR (400 MHz, DMSO-d6): δ [ppm]=0.90-0.98 (m, 2H), 1.01-1.08 (m, 2H), 1.15-1.22 (m, 3H), 1.39-1.50 (m, 2H), 1.52-1.65 (m, 1H), 1.72-1.81 (m, 1H), 1.94-2.01 (m, 2H), 2.31-2.39 (m, 1H), 3.11-3.30 (m, 2H), 3.40-3.51 (m, 1H), 3.56-3.64 (m, 1H), 3.65-3.77 (m, 2H), 3.90-3.98 (m, 1H), 4.07-4.16 (m, 1H), 4.42-4.53 (m, 1H), 6.07 (ddd, 1H), 6.92 (dd, 1H), 7.53 (d, 1H), 7.62 (d, 1H), 7.80 (d, 1H), 8.44 (d, 1H).

Step b 4-(4-cyclopropyl-1H-1,2,3-triazol-5-yl)-2-[(3R)-3-methylmorpholin-4-yl]-8-(1H-pyrazol-5-yl)-1,7-naphthyridine

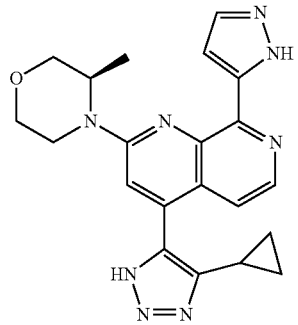 [SMILES: C[C@@H]1COCCN1c1cc(-c2[nH]nnc2C2CC2)c2ccnc(-c3ccn[nH]3)c2n1]

4-(cyclopropylethynyl)-2-[(3R)-3-methylmorpholin-4-yl]-8-{1-[(2R)-tetrahydro-2H-pyran-2-yl]-1H-pyrazol-5-yl}-1,7-naphthyridine (70.0 mg, 158 µmol) was solubilised in tert. Butanol (1.8 mL) and water (1.8 mL). Sodium azide (10.3 mg, 158 µmol) was added and the mixture was stirred for 5 min. at rt. Copper(II) sulphate hydrate (19.7 mg, 78.9 µmol) and (+)-sodium L-ascorbate (15.6 mg, 78.9 µmol) were added and the mixture was stirred for 16 h at 100° C.

The reaction was then cooled to rt, diluted with DCM and washed with H2O. The organic phase was dried and concentrated under reduced pressure. The crude material was purified by preparative HPLC (H$_2$O/CAN/formic acid mixture). The title compound was obtained in 1% yield (1 mg).

1H-NMR (400 MHz, DMSO-d6): δ [ppm]=0.82-0.89 (m, 2H), 0.94-1.00 (m, 2H), 1.22-1.29 (m, 1H), 1.31 (d, 3H), 1.89-1.99 (m, 1H), 3.52-3.65 (m, 2H), 3.71-3.77 (m, 1H), 3.81-3.86 (m, 1H), 4.07 (dd, 1H), 4.17-4.24 (m, 1H), 4.56-4.64 (m, 1H), 7.42 (s, 1H), 7.61 (s, 1H), 7.65 (s, 1H), 7.77 (d, 1H), 8.37 (d, 1H), 13.44 (br. s., 1H).

The following compounds of Table 1 were prepared according to Scheme 3 and in analogy to example 54.

TABLE 1

| Example | Structure | NMR Name |
|---|---|---|
| 195 | 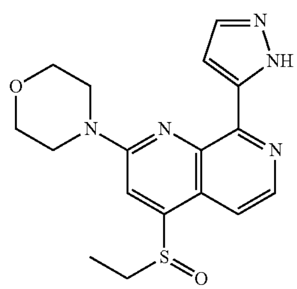 [SMILES: CCS(=O)c1cc(N2CCOCC2)nc2c(-c3ccn[nH]3)nccc12] | 1H-NMR (400 MHz, DMSO-d6): d [ppm] = 1.12 (t, 3H), 2.86-2.97 (m, 1H), 3.23-3.29 (m, 1H), 3.81 (s, 8H), 7.41 (s, 1H), 7.61-7.68 (m, 2H), 7.74 (s, 1H), 8.41 (d, 1H), 13.43 (s, 1H).<br>4-ethylsulfinyl-2-(morpholin-4-yl)-8-(1H-pyrazol-5-yl)-1,7-naphthyridine |
| 196 | 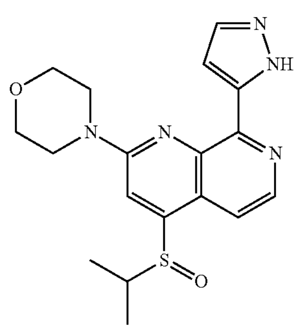 [SMILES: CC(C)S(=O)c1cc(N2CCOCC2)nc2c(-c3ccn[nH]3)nccc12] | 1H-NMR (400 MHz, DMSO-d6): d [ppm] = 0.94 (d, 3H), 1.40 (d, 3H), 3.18-3.27 (m, 1H), 3.81 (d, 8H), 7.41 (s, 1H), 7.63-7.71 (m, 3H), 8.41 (d, 1H), 13.45 (s, 1H).<br>2-(morpholin-4-yl)-4-[propan-2-ylsulfinyl]-8-(1H-pyrazol-5-yl)-1,7-naphthyridine |
| 197 | 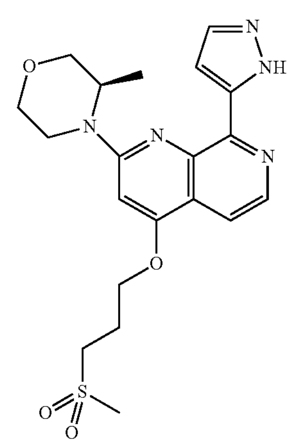 [SMILES: C[C@@H]1COCCN1c1cc(OCCCS(C)(=O)=O)c2ccnc(-c3ccn[nH]3)c2n1] | 1H-NMR (400 MHz, DMSO-d6): d [ppm] = 1.27 (d, 3H), 2.25-2.35 (m, 2H), 3.07 (s, 3H), 3.28-3.34 (m, 1H), 3.37-3.45 (m, 2H), 3.56 (td, 1H), 3.71 (dd, 1H), 3.83 (d, 1H), 4.05 (dd, 1H), 4.16 (d, 1H), 4.40 (t, 2H), 4.56-4.65 (m, 1H), 6.83 (s, 1H), 7.37 (s, 1H), 7.61 (s, 1H), 7.82 (d, 1H), 8.34 (d, 1H), 13.36 (br. s., 1H).<br>2-[(3R)-3-methylmorpholin-4-yl]-4-[3-(methylsulfonyl)propoxy]-8-(1H-pyrazol-5-yl)-1,7-naphthyridine |
| 198 | 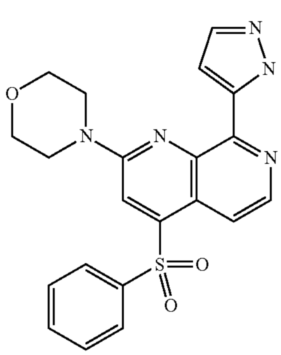 [SMILES: O=S(=O)(c1ccccc1)c1cc(N2CCOCC2)nc2c(-c3ccn[nH]3)nccc12] | 1H-NMR (400 MHz, DMSO-d6): d [ppm] = 3.83 (s, 8H), 7.35 (br. s., 1H), 7.54 (t, 3H), 7.62 (br. s., 1H), 7.71 (d, 1H), 7.89-7.95 (m, 2H), 8.07 (s, 1H), 8.30 (d, 1H), 13.38 (br. s, 1H).<br>2-(morpholin-4-yl)-4-(phenylsulfonyl)-8-(1H-pyrazol-5-yl)-1,7-naphthyridine |

TABLE 1-continued

| Example | Structure | NMR Name |
|---|---|---|
| 199 | 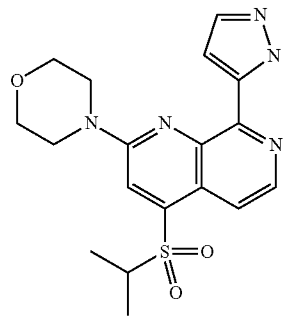 [SMILES: CC(C)S(=O)(=O)c1cc(N2CCOCC2)nc2c(-c3ccn[nH]3)nccc12] | 1H-NMR (400 MHz, DMSO-d6): d [ppm] = 1.25 (d, 6H), 3.69 (spt, 1H), 3.80 (br. s., 8H), 7.37 (br. s, 1H), 7.64 (br. s, 1H), 7.90 (s, 1H), 8.15 (d, 1H), 8.48 (d, 1H), 13.46 (br. s, 1H).<br>2-(morpholin-4-yl)-4-(propan-2-ylsulfonyl)-8-(1H-pyrazol-5-yl)-1,7-naphthyridine |
| 200 | 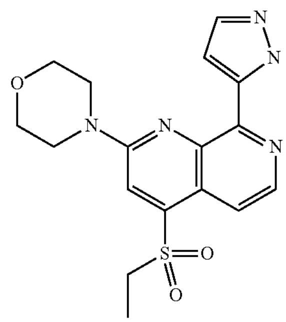 [SMILES: CCS(=O)(=O)c1cc(N2CCOCC2)nc2c(-c3ccn[nH]3)nccc12] | 1H-NMR (400 MHz, DMSO-d6): d [ppm] = 1.19 (t, 3H), 3.56 (q, 2H), 3.80 (s, 8H), 7.37 (br. s, 1H), 7.64 (br. s, 1H), 7.91 (br. s, 1H), 8.14 (d, 1H), 8.49 (d, 1H), 13.44 (br. s, 1H).<br>4-(ethylsulfonyl)-2-(morpholin-4-yl)-8-(1H-pyrazol-5-yl)-1,7-naphthyridine |
| 201 | 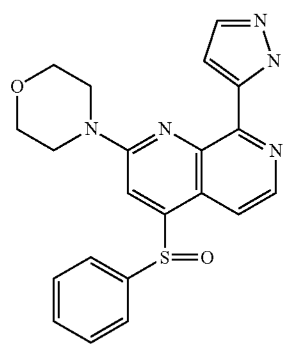 [SMILES: O=S(c1ccccc1)c1cc(N2CCOCC2)nc2c(-c3ccn[nH]3)nccc12] | 1H-NMR (400 MHz, DMSO-d6): d [ppm] = 3.83 (s, 8H), 7.30 (br. s, 1H), 7.60-7.69 (m, 3H), 7.72-7.77 (m, 1H), 7.99 (d, 1H), 8.12-8.17 (m, 2H), 8.21 (s, 1H), 8.37 (d, 1H), 13.40 (br. s, 1H).<br>2-(morpholin-4-yl)-4-(phenylsulfinyl)-8-(1H-pyrazol-5-yl)-1,7-naphthyridine |
| 202 | 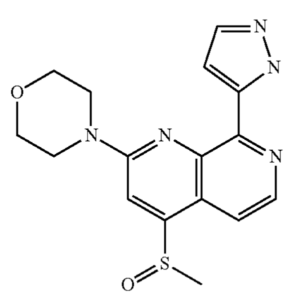 [SMILES: CS(=O)c1cc(N2CCOCC2)nc2c(-c3ccn[nH]3)nccc12] | 1H-NMR (400 MHz, DMSO-d6): d [ppm] = 2.93 (s, 3H), 3.80 (s, 8H), 7.39 (d, 1H), 7.61 (d, 1H), 7.65 (d, 1H), 7.82 (s, 1H), 8.41 (d, 1H), 13.42 (br. s, 1H).<br>4-(methylsulfinyl)-2-(morpholin-4-yl)-8-(1H-pyrazol-5-yl)-1,7-naphthyridine |

TABLE 1-continued

| Example | Structure | NMR Name |
|---|---|---|
| 203 | 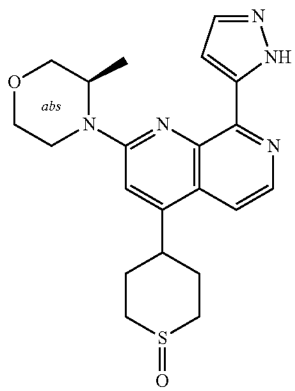 [SMILES: C[C@@H]1COCCN1c1cc(C2CCS(=O)CC2)c2ccnc(-c3ccn[nH]3)c2n1] | 1H-NMR (400 MHz, DMSO-d6): d [ppm] = 1.20-1.32 (m, 3H), 1.79-1.88 (m, 1H), 2.55-2.65 (m, 1H), 2.83-2.97 (m, 1H), 2.97-3.10 (m, 2H), 3.17-3.30 (m, 1H), 3.29-3.38 (m, 2H), 3.44-3.62 (m, 2H), 3.64-3.75 (m, 2H), 3.77-3.85 (m, 1H), 3.99-4.08 (m, 1H), 4.14-4.24 (m, 1H), 4.56-4.70 (m, 1H), 7.29-7.41 (m, 2H), 7.58-7.88 (m, 2H), 8.31-8.41 (m, 1H), 13.37 (br. s, 1H). 2-[(3R)-3-methylmorpholin-4-yl]-4-[1-oxidotetrahydro-2H-thiopyran-4-yl]-8-(1H-pyrazol-5-yl)-1,7-naphthyridine |
| 204 | 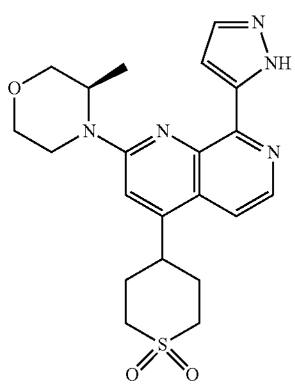 [SMILES: C[C@@H]1COCCN1c1cc(C2CCS(=O)(=O)CC2)c2ccnc(-c3ccn[nH]3)c2n1] | 1H-NMR (400 MHz, DMSO-d6): d [ppm] = 1.20-1.31 (m, 3H), 2.11-2.21 (m, 1H), 2.25-2.40 (m, 1H), 2.96-3.04 (m, 1H), 3.14-3.24 (m, 1H), 3.26-3.37 (m, 2H), 3.43-3.60 (m, 3H), 3.65-3.74 (m, 1H), 3.77-3.85 (m, 1H), 3.96-4.08 (m, 2H), 4.14-4.26 (m, 1H), 4.56-4.71 (m, 1H), 5.79 (t, 1H), 7.31-7.42 (m, 2H), 7.58-7.91 (m, 2H), 8.38 (dd, 1H), 13.32-13.43 (m, 1H). 4-(1,1-dioxidotetrahydro-2H-thiopyran-4-yl)-2-[(3R)-3-methylmorpholin-4-yl]-8-(1H-pyrazol-5-yl)-1,7-naphthyridine |

The following compounds of Table 2 were prepared according to Scheme 4 and in analogy to examples 63, 70, 85 and 107.

TABLE 2

| Example | Structure | NMR Name |
|---|---|---|
| 205 | 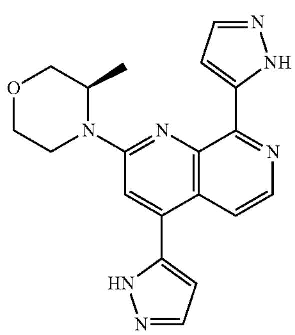 [SMILES: C[C@@H]1COCCN1c1cc(-c2ccn[nH]2)c2ccnc(-c3ccn[nH]3)c2n1] | 1H-NMR (400 MHz, DMSO-d6): d [ppm] = 1.29 (d, 3H), 3.38 (dd, 1H), 3.59 (dt, 1H), 3.73 (dd, 1H), 3.84 (d, 1H), 4.06 (dd, 1H), 4.21 (d, 1H), 4.62-4.71 (m, 1H), 7.00 (br. s, 1H), 7.39 (d, 1H), 7.63 (s, 2H), 7.99 (br. s, 1H), 8.38 (d, 1H), 8.49-8.57 (m, 1H), 12.95-13.63 (m, 2H). 2-[(3R)-3-methylmorpholin-4-yl]-4,8-di(1H-pyrazol-5-yl)-1,7-naphthyridine |

TABLE 2-continued

| Example | Structure | NMR Name |
|---|---|---|
| 206 | 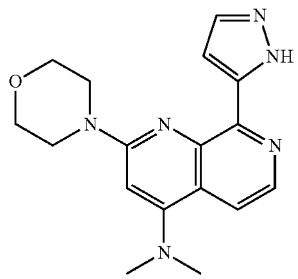 [SMILES: CN(C)c1cc(N2CCOCC2)nc2c(-c3ccn[nH]3)nccc12] | 1H-NMR (400 MHz, DMSO-d6): d [ppm] = 2.97 (s, 6H), 3.70 (t, 4H), 3.78 (t, 4H), 6.68 (s, 1H), 7.33 (d, 1H), 7.68 (d, 1H), 8.18 (s, 1H), 8.29 (d, 1H), 13.07-13.60 (m, 1H). N,N-dimethyl-2-(morpholin-4-yl)-8-(1H-pyrazol-5-yl)-1,7-naphthyridin-4-amine |
| 207 | 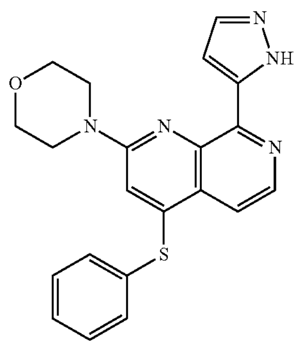 [SMILES: c1ccc(Sc2cc(N3CCOCC3)nc3c(-c4ccn[nH]4)nccc23)cc1] | 1H-NMR (400 MHz, DMSO-d6): d [ppm] = 3.50-3.59 (m, 4H), 3.69-3.77 (m, 4H), 7.00 (s, 1H), 7.36 (d, 1H), 7.46-7.59 (m, 5H), 7.63 (d, 1H), 7.76 (d, 1H), 8.38 (d, 1H). 2-(morpholin-4-yl)-4-(phenylsulfanyl)-8-(1H-pyrazol-5-yl)-1,7-naphthyridine |
| 208 | 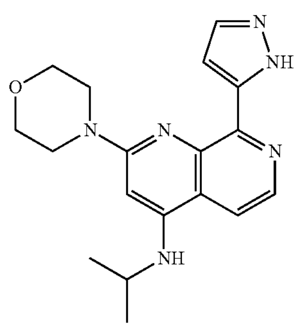 [SMILES: CC(C)Nc1cc(N2CCOCC2)nc2c(-c3ccn[nH]3)nccc12] | 1H-NMR (400 MHz, DMSO-d6): d [ppm] = 1.27 (d, 6H), 3.59-3.67 (m, 4H), 3.73-3.82 (m, 4H), 3.90-4.01 (m, 1H), 6.24 (s, 1H), 6.69 (d, 1H), 7.30 (s, 1H), 7.58 (s, 1H), 7.98 (d, 1H), 8.25 (d, 1H), 13.38 (br. s., 1H). 2-(morpholin-4-yl)-N-(propan-2-yl)-8-(1H-pyrazol-5-yl)-1,7-naphthyridin-4-amine |
| 209 | 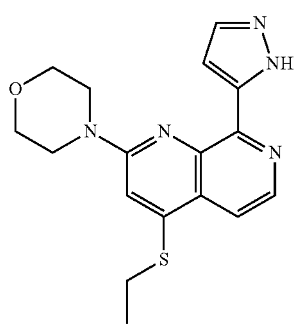 [SMILES: CCSc1cc(N2CCOCC2)nc2c(-c3ccn[nH]3)nccc12] | 1H-NMR (400 MHz, DMSO-d6): d [ppm] = 1.38 (t, 3H), 3.27 (q, 2H), 3.74-3.8 (m, 8H), 7.21 (s, 1H), 7.37 (br. s., 1H), 7.61 (s, 1H), 7.67 (d, 1H), 8.36 (d, 1H), 13.37 (br. s., 1H). 4-(ethylsulfanyl)-2-(morpholin-4-yl)-8-(1H-pyrazol-5-yl)-1,7-naphthyridine |
| 210 | 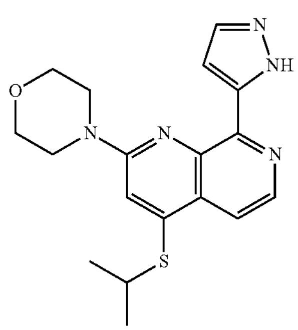 [SMILES: CC(C)Sc1cc(N2CCOCC2)nc2c(-c3ccn[nH]3)nccc12] | 1H-NMR (400 MHz, DMSO-d6): d [ppm] = 1.40 (d, 6H), 3.74-3.80 (m, 8H), 4.02 (spt, 1H), 7.32 (s, 1H), 7.36 (br. s., 1H), 7.62 (br. s, 1H), 7.70 (d, 1H), 8.36 (d, 1H), 13.36 (br. s., 1H). 2-(morpholin-4-yl)-4-(propan-2-ylsulfanyl)-8-(1H-pyrazol-5-yl)-1,7-naphthyridine |

TABLE 2-continued

| Example | Structure | NMR Name |
|---|---|---|
| 211 | 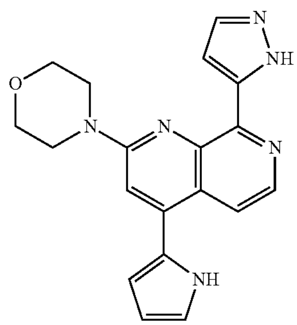 [SMILES: c1c[nH]c(-c2cc(N3CCOCC3)nc3c(-c4ccn[nH]4)nccc23)c1] | 1H-NMR (400 MHz, DMSO-d6): d [ppm] = 3.73-3.86 (m, 8H), 6.29-6.36 (m, 1H), 6.68-6.74 (m, 1H), 7.11-7.17 (m, 1H), 7.37 (d, 1H), 7.45 (s, 1H), 7.63 (d, 1H), 8.01 (d, 1H), 8.38 (d, 1H), 11.66 (br. s, 1H), 13.36 (br. s, 1H). 2-(morpholin-4-yl)-8-(1H-pyrazol-5-yl)-4-(1H-pyrrol-2-yl)-1,7-naphthyridine |
| 212 | 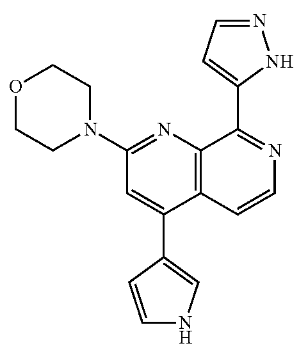 [SMILES: c1cc(-c2nccc3c(-c4cc[nH]c4)cc(N4CCOCC4)nc23)[nH]n1] | 1H-NMR (400 MHz, DMSO-d6): d [ppm] = 3.71-3.87 (m, 8H), 6.53-6.58 (m, 1H), 6.97-7.01 (m, 1H), 7.33-7.43 (m, 3H), 7.62 (br. s, 1H), 7.97 (d, 1H), 8.35 (d, 1H), 11.37 (br. s, 1H), 13.37 (br. s, 1H). 2-(morpholin-4-yl)-8-(1H-pyrazol-5-yl)-4-(1H-pyrrol-3-yl)-1,7-naphthyridine |
| 213 | 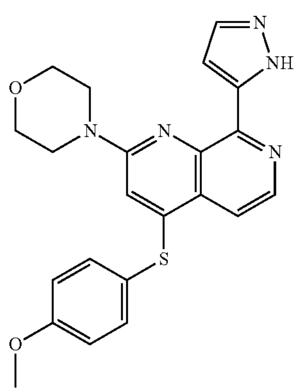 [SMILES: COc1ccc(Sc2cc(N3CCOCC3)nc3c(-c4ccn[nH]4)nccc23)cc1] | 1H-NMR (400 MHz, DMSO-d6): d [ppm] = 3.49 (t, 4H), 3.71 (t, 4H), 3.83 (s, 3H), 6.71 (s, 1H), 7.10-7.16 (m, 2H), 7.36 (br. s, 1H), 7.56-7.65 (m, 3H), 7.79 (d, 1H), 8.40 (d, 1H), 13.39 (br. s, 1H). 4-[(4-methoxyphenyl)sulfanyl]-2-(morpholin-4-yl)-8-(1H-pyrazol-5-yl)-1,7-naphthyridine |
| 214 | 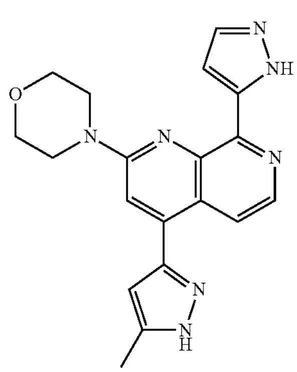 [SMILES: Cc1cc(-c2cc(N3CCOCC3)nc3c(-c4ccn[nH]4)nccc23)n[nH]1] | 1H-NMR (400 MHz, DMSO-d6): d [ppm] = 2.35 (s, 3H), 3.79 (d, 8H), 6.74 (s, 1H), 7.38 (br. s., 1H), 7.63 (d, 2H), 8.38 (d, 1H), 8.57 (d, 1H), 13.06 (br. s., 1H), 13.37 (br. s, 1H). 4-(5-methyl-1H-pyrazol-3-yl)-2-(morpholin-4-yl)-8-(1H-pyrazol-5-yl)-1,7-naphthyridine |

TABLE 2-continued

| Example | Structure | NMR Name |
|---|---|---|
| 215 | 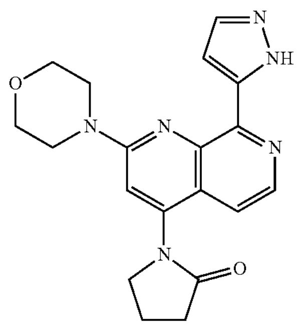 [SMILES: O=C1CCCN1c1cc(N2CCOCC2)nc2c(-c3ccn[nH]3)nccc12] | 1H-NMR (400 MHz, DMSO-d6): d [ppm] = 2.25 (q, 2H), 2.55 (d, 2H), 3.77 (dd, 8H), 3.92 (t, 2H), 7.38 (s, 1H), 7.48 (d, 1H), 7.55 (s, 1H), 7.62 (s, 1H), 8.33 (d, 1H), 13.39 (s, 1H). 1-[2-(morpholin-4-yl)-8-(1H-pyrazol-5-yl)-1,7-naphthyridin-4-yl]pyrrolidin-2-one |
| 216 | 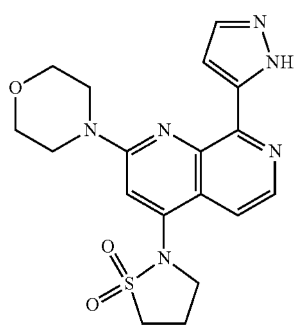 [SMILES: O=S1(=O)CCCN1c1cc(N2CCOCC2)nc2c(-c3ccn[nH]3)nccc12] | 1H-NMR (400 MHz, DMSO-d6): d [ppm] = 2.54-2.58 (m, 2H), 3.57 (t, 2H), 3.71-3.86 (m, 8H), 4.00 (t, 2H), 7.37 (d, 1H), 7.54 (s, 1H), 7.63 (d, 1H), 7.94 (d, 1H), 8.38 (d, 1H), 13.34 (br. s, 1H). 4-(1,1-dioxido-1,2-thiazolidin-2-yl)-2-(morpholin-4-yl)-8-(1H-pyrazol-5-yl)-1,7-naphthyridine |
| 217 | 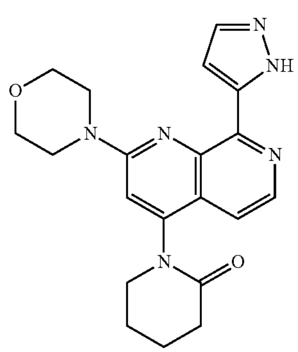 [SMILES: O=C1CCCCN1c1cc(N2CCOCC2)nc2c(-c3ccn[nH]3)nccc12] | 1H-NMR (400 MHz, DMSO-d6): d [ppm] = 1.86-2.05 (m, 4H), 2.36-2.65 (m, 2H), 3.45-3.54 (m, 1H), 3.71-3.84 (m, 9H), 7.36-7.43 (m, 2H), 7.59-7.64 (m, 2H), 8.34 (d, 1H), 13.34-13.42 (m, 1H). 1-[2-(morpholin-4-yl)-8-(1H-pyrazol-5-yl)-1,7-naphthyridin-4-yl]piperidin-2-one |
| 218 | 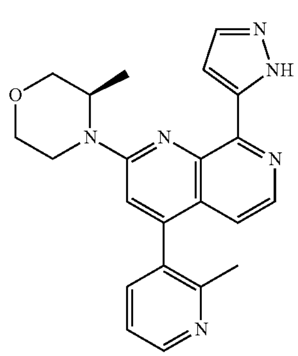 [SMILES: Cc1ncccc1-c1cc(N2CCOC[C@H]2C)nc2c(-c3ccn[nH]3)nccc12] | 1H-NMR (400 MHz, DMSO-d6): d [ppm] = 1.30 (t, 3H), 2.25 (d, 3H), 3.34-3.40 (m, 1H), 3.52-3.63 (m, 1H), 3.67-3.76 (m, 1H), 3.78-3.85 (m, 1H), 4.00-4.09 (m, 1H), 4.17-4.27 (m, 1H), 4.57-4.67 (m, 1H), 6.93-6.99 (m, 1H), 7.38-7.46 (m, 2H), 7.49 (d, 1H), 7.64 (br. s, 1H), 7.72 (dd, 1H), 8.29 (d, 1H), 8.64 (dd, 1H), 13.42 (br. s, 1H). 2-[(3R)-3-methylmorpholin-4-yl]-4-(2-methylpyridin-3-yl)-8-(1H-pyrazol-5-yl)-1,7-naphthyridine |

TABLE 2-continued

| Example | Structure | NMR Name |
|---|---|---|
| 219 | 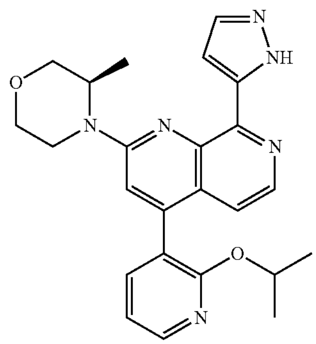 [SMILES: CC(C)Oc1ncccc1-c1cc(N2CCOC[C@H]2C)nc2c(-c3ccn[nH]3)nccc12] | 1H-NMR (400 MHz, DMSO-d6): d [ppm] = 1.13 (dd, 6H), 1.26-1.34 (m, 3H), 3.33-3.39 (m, 1H), 3.57 (dt, 1H), 3.71 (dd, 1H), 3.82 (br. d, 1H), 4.04 (dd, 1H), 4.22 (d, 1H), 4.57-4.65 (m, 1H), 5.34 (spt, 1H), 7.12 (d, 1H), 7.17 (dd, 1H), 7.41 (br. s, 1H), 7.45 (br. s, 1H), 7.64 (br. s, 1H), 7.81 (dd, 1H), 8.28 (s, 1H), 8.34 (dd, 1H), 13.38 (br. s, 1H). 2-[(3R)-3-methylmorpholin-4-yl]-4-[2-(propan-2-yloxy)pyridin-3-yl]-8-(1H-pyrazol-5-yl)-1,7-naphthyridine |
| 220 | 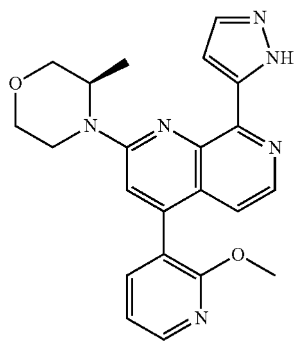 [SMILES: COc1ncccc1-c1cc(N2CCOC[C@H]2C)nc2c(-c3ccn[nH]3)nccc12] | 1H-NMR (400 MHz, DMSO-d6): d [ppm] = 1.30 (d, 3H), 3.34 (dt, 1H), 3.56 (dt, 1H), 3.67-3.74 (m, 1H), 3.80 (s, 4H), 4.03 (d, 1H), 4.16-4.23 (m, 1H), 4.58-4.66 (m, 1H), 7.06 (d, 1H), 7.22 (dd, 1H), 7.44 (d, 2H), 7.63 (br. s, 1H), 7.82 (dd, 1H), 8.28 (d, 1H), 8.37 (dd, 1H), 13.39 (s, 1H). 4-(2-methoxypyridin-3-yl)-2-[(3R)-3-methylmorpholin-4-yl]-8-(1H-pyrazol-5-yl)-1,7-naphthyridine |
| 221 | 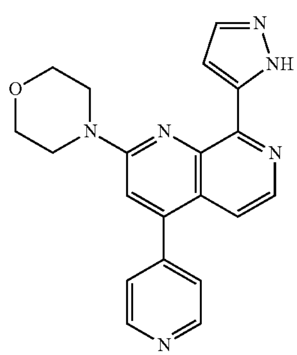 [SMILES: c1cc(-c2cc(N3CCOCC3)nc3c(-c4ccn[nH]4)nccc23)ccn1] | 1H-NMR (400 MHz, DMSO-d6): d [ppm] = 3.79 (s, 8H), 7.34-7.45 (m, 2H), 7.52-7.68 (m, 4H), 8.34 (d, 1H), 8.79 (dd, 2H), 13.42 (s, 1H). 2-(morpholin-4-yl)-8-(1H-pyrazol-5-yl)-4-(pyridin-4-yl)-1,7-naphthyridine |
| 222 | 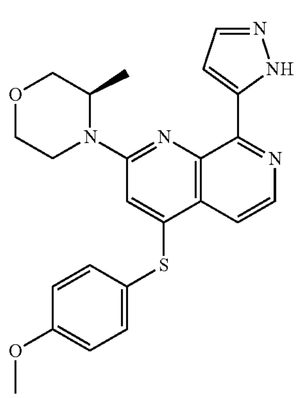 [SMILES: COc1ccc(Sc2cc(N3CCOC[C@H]3C)nc3c(-c4ccn[nH]4)nccc23)cc1] | 1H-NMR (400 MHz, DMSO-d6): d [ppm] = 1.13 (d, 3H), 3.13-3.25 (m, 1H), 3.43-3.53 (m, 1H), 3.57-3.65 (m, 1H), 3.71-3.78 (m, 1H), 3.78-3.86 (m, 4H), 3.95-4.01 (m, 1H), 4.08-4.17 (m, 1H), 6.63 (s, 1H), 7.09-7.16 (m, 2H), 7.36 (s, 1H), 7.56-7.63 (m, 3H), 7.78 (d, 1H), 8.39 (d, 1H), 13.38 (br. s, 1H). 4-[(4-methoxyphenyl)sulfanyl]-2-[(3R)-3-methylmorpholin-4-yl]-8-(1H-pyrazol-5-yl)-1,7-naphthyridine |

TABLE 2-continued

| Example | Structure | NMR Name |
|---|---|---|
| 223 | 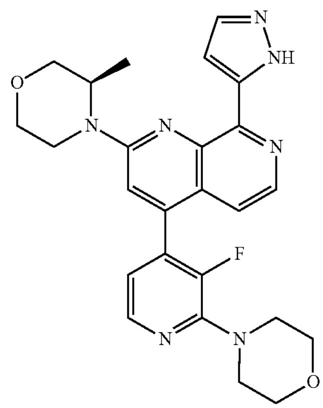 [SMILES: C[C@@H]1COCCN1c1cc(-c2ccnc(N3CCOCC3)c2F)c2ccnc(-c3ccn[nH]3)c2n1] | 1H-NMR (400 MHz, DMSO-d6): d [ppm] = 1.30 (d, 3H), 3.33-3.40 (m, 1H), 3.41-3.49 (m, 4H), 3.52-3.61 (m, 1H), 3.67-3.78 (m, 5H), 3.79-3.85 (m, 1H), 3.99-4.08 (m, 1H), 4.16-4.25 (m, 1H), 4.57-4.68 (m, 1H), 7.04 (t, 1H), 7.21 (dd, 1H), 7.42 (br. s, 1H), 7.52-7.68 (m, 2H), 8.20 (d, 1H), 8.33 (d, 1H), 13.40 (br. s, 1H). 4-[3-fluoro-2-(morpholin-4-yl)pyridin-4-yl]-2-[(3R)-3-methylmorpholin-4-yl]-8-(1H-pyrazol-5-yl)-1,7-naphthyridine |
| 224 | 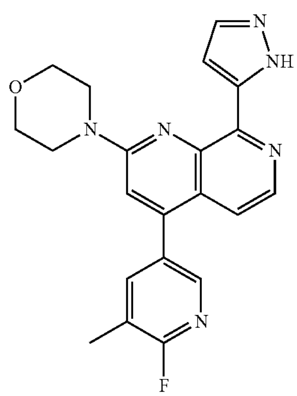 [SMILES: Cc1cc(-c2cc(N3CCOCC3)nc3c(-c4ccn[nH]4)nccc23)cnc1F] | 1H-NMR (400 MHz, DMSO-d6): d [ppm] = 2.12 (s, 3H), 3.79 (s, 8H), 7.01 (d, 1H), 7.33 (s, 1H), 7.42 (d, 1H), 7.55 (s, 1H), 7.65 (d, 1H), 8.16 (s, 1H), 8.30 (d, 1H), 13.39 (br. s, 1H). 4-(6-fluoro-5-methylpyridin-3-yl)-2-(morpholin-4-yl)-8-(1H-pyrazol-5-yl)-1,7-naphthyridine |
| 225 | 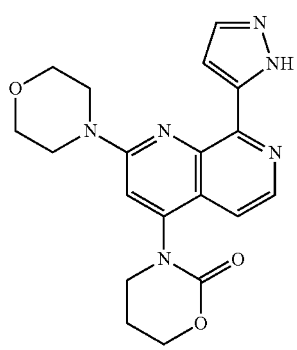 | 1H-NMR (400 MHz, DMSO-d6): d [ppm] = 3.77 (d, 8H), 4.20 (br. s., 2H), 4.61 (br. s., 2H), 7.31-7.42 (m, 1H), 7.64 (br. s, 3H), 8.36 (br. s., 1H), 13.30-13.48 (m, 1H) 3-[2-(morpholin-4-yl)-8-(1H-pyrazol-5-yl)-1,7-naphthyridin-4-yl]-1,3-oxazinan-2-one |
| 226 | 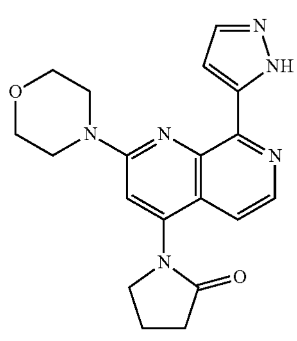 [SMILES: O=C1CCCN1c1cc(N2CCOCC2)nc2c(-c3ccn[nH]3)nccc12] | 1H-NMR (400 MHz, DMSO-d6): d [ppm] = 2.14-2.32 (m, 2H), 3.72-3.83 (m, 9H), 4.41-4.60 (m, 2H), 7.37 (s, 1H), 7.54 (d, 1H), 7.62-7.66 (m, 1H), 7.73 (s, 1H), 8.37 (d, 1H), 13.27-13.54 (m, 1H). 3-[2-(morpholin-4-yl)-8-(1H-pyrazol-5-yl)-1,7-naphthyridin-4-yl]-1,3-oxazolidin-2-one |

TABLE 2-continued

| Example | Structure | NMR Name |
|---|---|---|
| 227 | 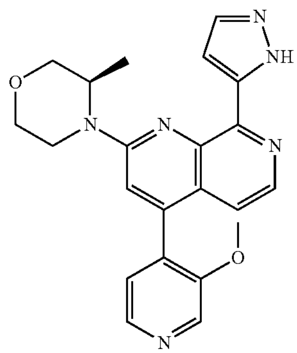 [SMILES: COc1cnccc1-c1cc(N2CCOC[C@H]2C)nc2c(-c3ccn[nH]3)nccc12] | 1H-NMR (400 MHz, DMSO-d6): d [ppm] = 1.30 (d, 3H), 3.34-3.39 (m, 1H), 3.51-3.61 (m, 1H), 3.67-3.74 (m, 1H), 3.78-3.86 (m, 4H), 3.99-4.07 (m, 1H), 4.16-4.24 (m, 1H), 4.57-4.66 (m, 1H), 7.04 (d, 1H), 7.38-7.48 (m, 3H), 7.64 (br. s, 1H), 8.27 (d, 1H), 8.41 (d, 1H), 8.60 (s, 1H), 13.40 (br. s, 1H). 4-(3-methoxypyridin-4-yl)-2-[(3R)-3-methylmorpholin-4-yl]-8-(1H-pyrazol-5-yl)-1,7-naphthyridine |
| 228 | 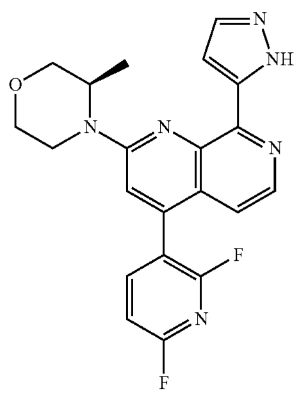 [SMILES: C[C@@H]1COCCN1c1cc(-c2ccc(F)nc2F)c2ccnc(-c3ccn[nH]3)c2n1] | 1H-NMR (400 MHz, DMSO-d6): d [ppm] = 1.30 (d, 3H), 3.30-3.41 (m, 1H), 3.52-3.61 (m, 1H), 3.68-3.74 (m, 1H), 3.80-3.85 (m, 1H), 4.01-4.08 (m, 1H), 4.16-4.24 (m, 1H), 4.57-4.66 (m, 1H), 7.25 (dd, 1H), 7.39-7.48 (m, 2H), 7.62-7.67 (m, 2H), 8.32 (d, 1H), 8.38 (q, 1H). 4-(2,6-difluoropyridin-3-yl)-2-[(3R)-3-methylmorpholin-4-yl]-8-(1H-pyrazol-5-yl)-1,7-naphthyridine |
| 229 | 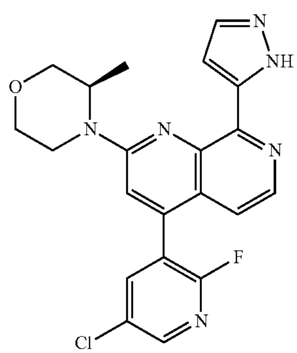 [SMILES: C[C@@H]1COCCN1c1cc(-c2cc(Cl)cnc2F)c2ccnc(-c3ccn[nH]3)c2n1] | 1H-NMR (400 MHz, DMSO-d6): d [ppm] = 1.31 (d, 3H), 3.37-3.41 (m, 1H), 3.52-3.62 (m, 1H), 3.67-3.75 (m, 1H), 3.79-3.87 (m, 1H), 4.01-4.09 (m, 1H), 4.17-4.26 (m, 1H), 4.56-4.67 (m, 1H), 7.25 (dd, 1H), 7.41 (br. s, 1H), 7.62-7.70 (m, 2H), 8.33 (d, 1H), 8.40 (dd, 1H), 8.55 (br. s, 1H). 4-(5-chloro-2-fluoropyridin-3-yl)-2-[(3R)-3-methylmorpholin-4-yl]-8-(1H-pyrazol-5-yl)-1,7-naphthyridine |
| 230 | 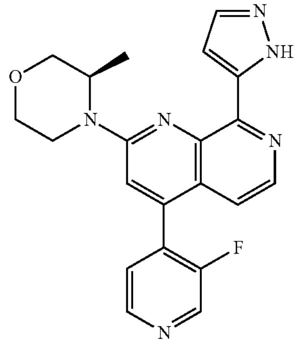 [SMILES: C[C@@H]1COCCN1c1cc(-c2ccncc2F)c2ccnc(-c3ccn[nH]3)c2n1] | 1H-NMR (400 MHz, DMSO-d6): d [ppm] = 1.30 (d, 3H), 3.34-3.42 (m, 1H), 3.51-3.62 (m, 1H), 3.67-3.76 (m, 1H), 3.81 (s, 1H), 4.00-4.09 (m, 1H), 4.17-4.26 (m, 1H), 4.58-4.67 (m, 1H), 7.17 (dd, 1H), 7.43 (s, 1H), 7.60-7.72 (m, 3H), 8.33 (d, 1H), 8.66 (dd, 1H), 8.83 (d, 1H), 13.44 (br. s., 1H). 4-(3-fluoropyridin-4-yl)-2-[(3R)-3-methylmorpholin-4-yl]-8-(1H-pyrazol-5-yl)-1,7-naphthyridine |

TABLE 2-continued

| Example | Structure | NMR / Name |
|---|---|---|
| 231 | 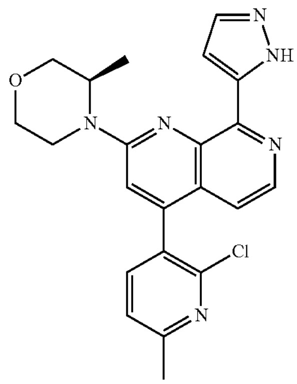 [SMILES: Cc1ccc(-c2cc(N3CCOC[C@H]3C)nc3c(-c4ccn[nH]4)nccc23)c(Cl)n1] | 1H-NMR (400 MHz, DMSO-d6): d [ppm] = 1.29 (t, 3H), 2.59 (s, 3H), 3.28-3.39 (m, 1H), 3.51-3.62 (m, 1H), 3.67-3.75 (m, 1H), 3.77-3.86 (m, 1H), 4.00-4.08 (m, 1H), 4.16-4.25 (m, 1H), 4.55-4.64 (m, 1H), 7.03 (dd, 1H), 7.42 (br. s., 1H), 7.48-7.56 (m, 2H), 7.65 (s, 1H), 7.90 (d, 1H), 8.30 (d, 1H), 13.42 (br. s, 1H).<br>4-(2-chloro-6-methylpyridin-3-yl)-2-[(3R)-3-methylmorpholin-4-yl]-8-(1H-pyrazol-5-yl)-1,7-naphthyridine |
| 232 | 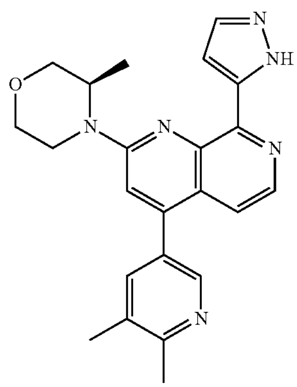 [SMILES: Cc1cc(-c2cc(N3CCOC[C@H]3C)nc3c(-c4ccn[nH]4)nccc23)cnc1C] | 1H-NMR (400 MHz, DMSO-d6): d [ppm] = 1.30 (d, 3H), 2.37 (s, 3H), 2.54 (s, 3H), 3.28-3.40 (m, 1H), 3.50-3.62 (m, 1H), 3.66-3.76 (m, 1H), 3.78-3.87 (m, 1H), 4.00-4.09 (m, 1H), 4.18-4.27 (m, 1H), 4.60-4.71 (m, 1H), 7.36-7.49 (m, 3H), 7.63 (s, 1H), 7.77 (d, 1H), 8.33 (d, 1H), 8.45 (d, 1H), 13.43 (s, 1H).<br>4-(5,6-dimethylpyridin-3-yl)-2-[(3R)-3-methylmorpholin-4-yl]-8-(1H-pyrazol-5-yl)-1,7-naphthyridine |
| 233 | 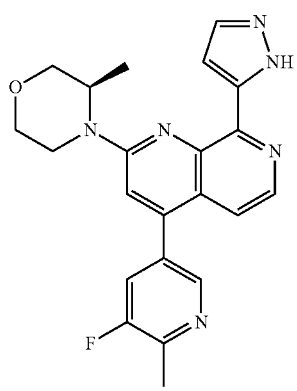 [SMILES: Cc1ncc(-c2cc(N3CCOC[C@H]3C)nc3c(-c4ccn[nH]4)nccc23)cc1F] | 1H-NMR (400 MHz, DMSO-d6): d [ppm] = 1.30 (d, 3H), 2.57 (d, 3H), 3.29-3.40 (m, 1H), 3.50-3.62 (m, 1H), 3.66-3.76 (m, 1H), 3.78-3.87 (m, 1H), 4.01-4.09 (m, 1H), 4.19-4.28 (m, 1H), 4.61-4.71 (m, 1H), 7.42 (d, 2H), 7.54 (s, 1H), 7.64 (br. s, 1H), 7.97 (dd, 1H), 8.34 (d, 1H), 8.52 (s, 1H), 13.43 (br. s, 1H).<br>4-(5-fluoro-6-methylpyridin-3-yl)-2-[(3R)-3-methylmorpholin-4-yl]-8-(1H-pyrazol-5-yl)-1,7-naphthyridine |
| 234 | 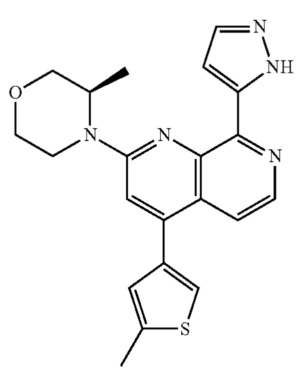 [SMILES: Cc1cc(-c2cc(N3CCOC[C@H]3C)nc3c(-c4ccn[nH]4)nccc23)cs1] | 1H-NMR (400 MHz, DMSO-d6): d [ppm] = 1.29 (d, 3H), 2.56 (d, 3H), 3.28-3.39 (m, 1H), 3.51-3.61 (m, 1H), 3.67-3.75 (m, 1H), 3.78-3.86 (m, 1H), 4.00-4.08 (m, 1H), 4.16-4.24 (m, 1H), 4.59-4.69 (m, 1H), 7.18 (t, 1H), 7.36-7.45 (m, 2H), 7.60-7.70 (m, 3H), 8.35 (d, 1H), 13.41 (br. s., 1H).<br>2-[(3R)-3-methylmorpholin-4-yl]-4-(5-methylthiophen-3-yl)-8-(1H-pyrazol-5-yl)-1,7-naphthyridine |

TABLE 2-continued

| Example | Structure | NMR Name |
|---|---|---|
| 235 | 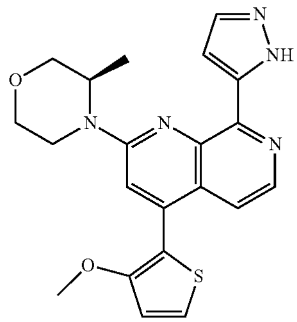 [SMILES: COc1ccsc1-c1cc(N2CCOC[C@H]2C)nc2c(-c3ccn[nH]3)nccc12] | 1H-NMR (400 MHz, DMSO-d6): d [ppm] = 1.28 (d, 3H), 3.27-3.38 (m, 1H), 3.52-3.61 (m, 1H), 3.68-3.75 (m, 1H), 3.78-3.85 (m, 4H), 4.00-4.07 (m, 1H), 4.10-4.19 (m, 1H), 4.55-4.63 (m, 1H), 7.27 (d, 1H), 7.36-7.44 (m, 2H), 7.50 (d, 1H), 7.63 (d, 1H), 7.79 (d, 1H), 8.34 (d, 1H), 13.32 (br. s, 1H). 4-(3-methoxythiophen-2-yl)-2-[(3R)-3-methylmorpholin-4-yl]-8-(1H-pyrazol-5-yl)-1,7-naphthyridine |
| 236 | 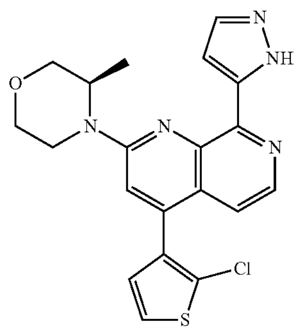 [SMILES: C[C@@H]1COCCN1c1cc(-c2ccsc2Cl)c2ccnc(-c3ccn[nH]3)c2n1] | 1H-NMR (400 MHz, DMSO-d6): d [ppm] = 1.29 (d, 3H), 3.29-3.39 (m, 1H), 3.52-3.62 (m, 1H), 3.68-3.74 (m, 1H), 3.78-3.85 (m, 1H), 4.01-4.07 (m, 1H), 4.17-4.25 (m, 1H), 4.57-4.66 (m, 1H), 7.22 (d, 1H), 7.27 (d, 1H), 7.42 (br. s, 1H), 7.50 (br. s, 1H), 7.61-7.66 (m, 1H), 7.74 (d, 1H), 8.34 (d, 1H), 13.42 (br. s, 1H). 4-(2-chlorothiophen-3-yl)-2-[(3R)-3-methylmorpholin-4-yl]-8-(1H-pyrazol-5-yl)-1,7-naphthyridine |
| 237 | 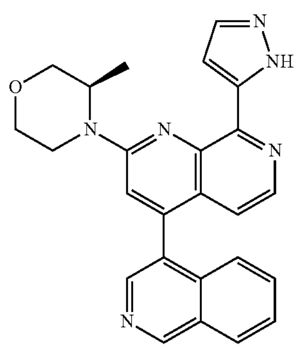 [SMILES: C[C@@H]1COCCN1c1cc(-c2cncc3ccccc23)c2ccnc(-c3ccn[nH]3)c2n1] | 1H-NMR (400 MHz, DMSO-d6): d [ppm] = 1.32 (dd, 3H), 3.34-3.42 (m, 1H), 3.53-3.63 (m, 1H), 3.68-3.76 (m, 1H), 3.77-3.84 (m, 1H), 4.04 (d, 1H), 4.24 (d, 1H), 4.60-4.70 (m, 1H), 6.81-6.87 (m, 1H), 7.37-7.42 (m, 1H), 7.46-7.51 (m, 1H), 7.63-7.68 (m, 2H), 7.69-7.80 (m, 2H), 8.19 (d, 1H), 8.26-8.33 (m, 1H), 8.57 (d, 1H), 9.52 (s, 1H), 13.44 (br. s, 1H). 4-(isoquinolin-4-yl)-2-[(3R)-3-methylmorpholin-4-yl]-8-(1H-pyrazol-5-yl)-1,7-naphthyridine |
| 238 | 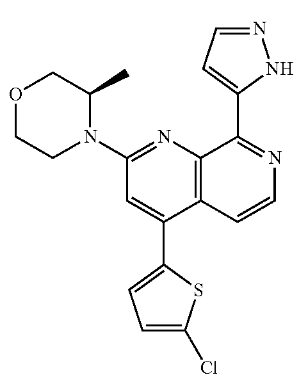 [SMILES: C[C@@H]1COCCN1c1cc(-c2ccc(Cl)s2)c2ccnc(-c3ccn[nH]3)c2n1] | 1H-NMR (400 MHz, DMSO-d6): d [ppm] = 1.28 (d, 3H), 3.35-3.39 (m, 1H), 3.50-3.61 (m, 1H), 3.67-3.75 (m, 1H), 3.77-3.86 (m, 1H), 4.00-4.08 (m, 1H), 4.16-4.24 (m, 1H), 4.60-4.68 (m, 1H), 7.36 (d, 1H), 7.40 (s, 1H), 7.46 (d, 1H), 7.49 (s, 1H), 7.61-7.65 (m, 1H), 7.79 (d, 1H), 8.38 (d, 1H), 13.42 (br. s, 1H). 4-(5-chlorothiophen-2-yl)-2-[(3R)-3-methylmorpholin-4-yl]-8-(1H-pyrazol-5-yl)-1,7-naphthyridine |

TABLE 2-continued

| Example | Structure | NMR Name |
|---|---|---|
| 239 | 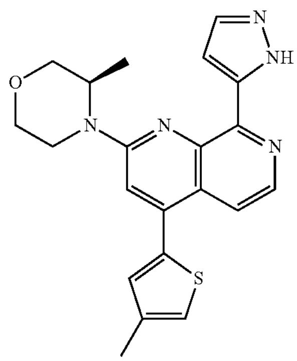 [SMILES: Cc1csc(-c2cc(N3CCOC[C@H]3C)nc3c(-c4ccn[nH]4)nccc23)c1] | 1H-NMR (400 MHz, DMSO-d6): d [ppm] = 1.29 (d, 3H), 2.34 (d, 3H), 3.35-3.41 (m, 1H), 3.52-3.62 (m, 1H), 3.69-3.75 (m, 1H), 3.80-3.87 (m, 1H), 4.01-4.09 (m, 1H), 4.16-4.24 (m, 1H), 4.60-4.68 (m, 1H), 7.39-7.43 (m, 2H), 7.46 (s, 2H), 7.64 (s, 1H), 7.87 (d, 1H), 8.39 (d, 1H), 13.42 (br. s, 1H). 2-[(3R)-3-methylmorpholin-4-yl]-4-(4-methylthiophen-2-yl)-8-(1H-pyrazol-5-yl)-1,7-naphthyridine |
| 240 | 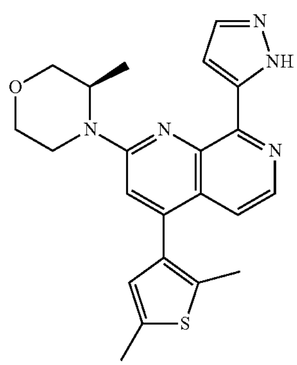 [SMILES: Cc1cc(-c2cc(N3CCOC[C@H]3C)nc3c(-c4ccn[nH]4)nccc23)c(C)s1] | 1H-NMR (400 MHz, DMSO-d6): d [ppm] = 1.28 (d, 3H), 2.25 (s, 3H), 2.54 (s, 3H), 3.24-3.31 (m, 1H), 3.52-3.63 (m, 1H), 3.68-3.74 (m, 1H), 3.77-3.84 (m, 1H), 3.99-4.09 (m, 1H), 4.16-4.25 (m, 1H), 4.55-4.67 (m, 1H), 6.79-6.84 (m, 1H), 7.28 (d, 1H), 7.36 (s, 1H), 7.42 (s, 1H), 7.63 (s, 1H), 8.32 (d, 1H), 13.41 (br. s, 1H). 4-(2,5-dimethylthiophen-3-yl)-2-[(3R)-3-methylmorpholin-4-yl]-8-(1H-pyrazol-5-yl)-1,7-naphthyridine |
| 241 | 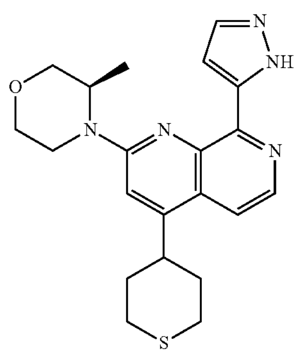 [SMILES: C[C@@H]1COCCN1c1cc(C2CCSCC2)c2ccnc(-c3ccn[nH]3)c2n1] | 1H-NMR (400 MHz, DMSO-d6): d [ppm] = 1.22-1.36 (m, 3H), 1.86-2.03 (m, 2H), 2.11 (t, 2H), 2.63-2.78 (m, 2H), 2.95-3.08 (m, 2H), 3.22-3.32 (m, 1H), 3.36-3.44 (m, 1H), 3.57 (td, 1H), 3.71 (dd, 1H), 3.82 (d, 1H), 3.99-4.12 (m, 1H), 4.20 (d, 1H), 4.59-4.71 (m, 1H), 7.30 (s, 1H), 7.36 (d, 1H), 7.62 (d, 1H), 7.85 (d, 1H), 8.37 (d, 1H), 13.34 (br. s., 1H). 2-[(3R)-3-methylmorpholin-4-yl]-8-(1H-pyrazol-5-yl)-4-(tetrahydro-2H-thiopyran-4-yl)-1,7-naphthyridine |
| 242 | 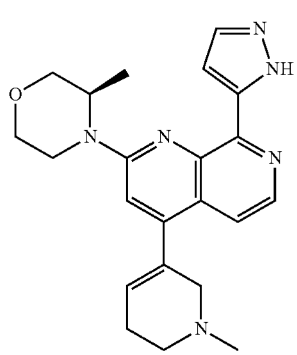 [SMILES: C[C@@H]1COCCN1c1cc(C2=CCCN(C)C2)c2ccnc(-c3ccn[nH]3)c2n1] | 1H-NMR (400 MHz, DMSO-d6): d [ppm] = 1.27 (d, 3H), 2.33 (s, 3H), 2.36 (m, 2H), 2.60 (t, 2H), 3.16 (br. s., 2H), 3.25-3.32 (m, 1H), 3.55 (td, 1H), 3.66-3.73 (m, 1H), 3.77-3.86 (m, 1H), 4.03 (dd, 1H), 4.14-4.21 (m, 1H), 4.57-4.68 (m, 1H), 5.90 (dt, 1H), 7.30 (s, 1H), 7.38 (br. s., 1H), 7.62 (d, 2H), 8.34 (d, 1H), 13.38 (br. s., 1H). 2-[(3R)-3-methylmorpholin-4-yl]-4-(1-methyl-1,2,5,6-tetrahydropyridin-3-yl)-8-(1H-pyrazol-5-yl)-1,7-naphthyridine |

TABLE 2-continued

| Example | Structure | NMR Name |
|---|---|---|
| 243 | 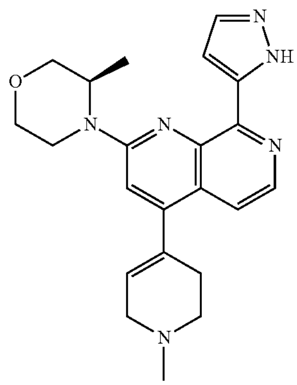 [SMILES: C[C@@H]1COCCN1c1cc(C2=CCN(C)CC2)c2ccnc(-c3ccn[nH]3)c2n1] | 1H-NMR (400 MHz, METHANOL-d4): d [ppm] = 1.38 (d, 3H), 2.49 (s, 3H), 2.57-2.63 (m, 2H), 2.83 (t, 2H), 3.20-3.26 (m, 2H), 3.40-3.51 (m, 1H), 3.64-3.73 (m, 1H), 3.79-3.92 (m, 2H), 4.06-4.17 (m, 2H), 4.53-4.63 (m, 1H), 5.86-5.91 (m, 1H), 7.26 (s, 1H), 7.32 (s, 1H), 7.64-7.68 (m, 1H), 7.71 (d, 1H), 8.32 (d, 1H). 2-[(3R)-3-methylmorpholin-4-yl]-4-(1-methyl-1,2,3,6-tetrahydropyridin-4-yl)-8-(1H-pyrazol-5-yl)-1,7-naphthyridine |
| 244 | 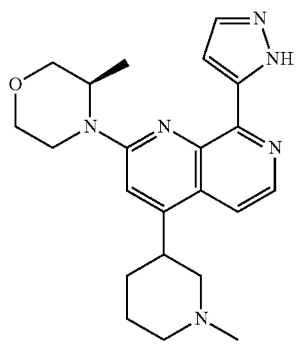 [SMILES: C[C@@H]1COCCN1c1cc(C2CCCN(C)C2)c2ccnc(-c3ccn[nH]3)c2n1] | 1H-NMR (400 MHz, DMSO-d6): d [ppm] = 1.27 (dd, 3H), 1.62 (td, 1H), 1.71-1.81 (m, 2H), 1.88 (d, 1H), 1.99-2.09 (m, 1H), 2.18 (td, 1H), 2.24 (d, 3H), 2.79-2.92 (m, 2H), 3.24-3.31 (m, 1H), 3.41-3.51 (m, 1H), 3.57 (td, 1H), 3.72 (dd, 1H), 3.83 (d, 1H), 4.05 (dd, 1H), 4.16 (d, 1H), 4.57-4.65 (m, 1H), 7.32-7.38 (m, 2H), 7.62 (d, 1H), 7.79 (d, 1H), 8.38 (d, 1H), 13.33 (br. s., 1H). 2-[(3R)-3-methylmorpholin-4-yl]-4-[1-methylpiperidin-3-yl]-8-(1H-pyrazol-5-yl)-1,7-naphthyridine |
| 245 | 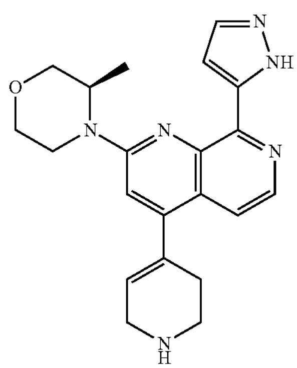 [SMILES: C[C@@H]1COCCN1c1cc(C2=CCNCC2)c2ccnc(-c3ccn[nH]3)c2n1] | 1H-NMR (400 MHz, DMSO-d6): d [ppm] = 1.21-1.30 (m, 4H), 2.34-2.40 (m, 1H), 2.41-2.48 (m, 1H), 2.97-3.02 (m, 1H), 3.25-3.31 (m, 1H), 3.40-3.46 (m, 2H), 3.50-3.60 (m, 1H), 3.66-3.74 (m, 1H), 3.78-3.85 (m, 1H), 3.99-4.07 (m, 1H), 4.12-4.21 (m, 1H), 4.56-4.64 (m, 1H), 5.86-5.93 (m, 1H), 7.27 (d, 1H), 7.38 (s, 1H), 7.58-7.68 (m, 2H), 8.33 (d, 1H), 13.38 (br. s, 1H). 2-[(3R)-3-methylmorpholin-4-yl]-8-(1H-pyrazol-5-yl)-4-(1,2,3,6-tetrahydropyridin-4-yl)-1,7-naphthyridine |
| 246 | 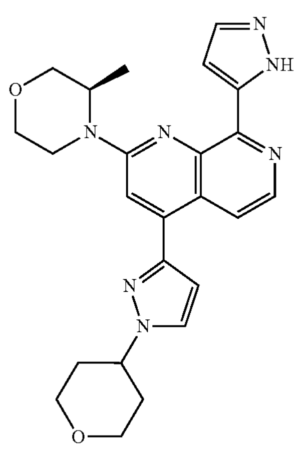 [SMILES: C[C@@H]1COCCN1c1cc(-c2ccn(C3CCOCC3)n2)c2ccnc(-c3ccn[nH]3)c2n1] | 1H-NMR (400 MHz, DMSO-d6): d [ppm] = 1.29 (d, 3H), 1.64-1.93 (m, 2H), 2.04-2.19 (m, 2H), 3.19-3.27 (m, 2H), 3.36-3.43 (m, 1H), 3.53-3.64 (m, 1H), 3.68-3.77 (m, 1H), 3.78-3.90 (m, 3H), 4.02-4.10 (m, 1H), 4.10-4.18 (m, 1H), 4.19-4.29 (m, 1H), 4.56-4.68 (m, 1H), 6.54 (d, 1H), 7.16 (d, 1H), 7.45 (br. s., 1H), 7.56 (s, 1H), 7.64-7.68 (m, 1H), 7.74 (d, 1H), 8.35 (d, 1H), 13.45 (br. s., 1H). 2-[(3R)-3-methylmorpholin-4-yl]-8-(1H-pyrazol-5-yl)-4-[1-(tetrahydro-2H-pyran-4-yl)-1H-pyrazol-3-yl]-1,7-naphthyridine |

TABLE 2-continued

| Example | Structure | NMR Name |
|---|---|---|
| 247 | 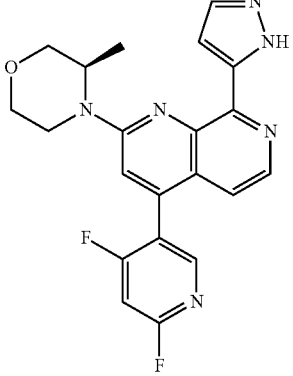 | 1H-NMR (400 MHz, DMSO-d6): d [ppm] = 1.30 (s, 3H), 3.34-3.41 (m, 1H), 3.51-3.63 (m, 1H), 3.68-3.75 (m, 1H), 3.80-3.87 (m, 1H), 4.01-4.09 (m, 1H), 4.17-4.26 (m, 1H), 4.59-4.67 (m, 1H), 7.21-7.27 (m, 1H), 7.43 (s, 1H), 7.60 (dd, 1H), 7.65 (d, 2H), 8.32 (d, 1H), 8.51 (d, 1H), 13.44 (br. s, 1H). 4-(4,6-difluoropyridin-3-yl)-2-[(3R)-3-methylmorpholin-4-yl]-8-(1H-pyrazol-5-yl)-1,7-naphthyridine |
| 248 | 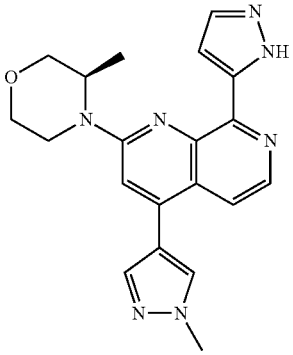 [SMILES: C[C@@H]1COCCN1c1cc(-c2cnn(C)c2)c2ccnc(-c3ccn[nH]3)c2n1] | 1H-NMR (400 MHz, DMSO-d6): d [ppm] = 1.29 (d, 3H), 3.30-3.38 (m, 1H) 3.52-3.62 (m, 1H), 3.72 (dd, 1H), 3.80-3.87 (m, 1H), 3.97 (s, 3H), 4.06 (dd, 1H), 4.21 (d, 1H), 4.65 (d, 1H), 7.40 (s, 1H), 7.45 (s, 1H), 7.63 (s, 1H), 7.84 (d, 1H), 7.98 (s, 1H), 8.31-8.40 (m, 2H), 13.41 (br. s., 1H). 2-[(3R)-3-methylmorpholin-4-yl]-4-(1-methyl-1H-pyrazol-4-yl)-8-(1H-pyrazol-5-yl)-1,7-naphthyridine |
| 249 | 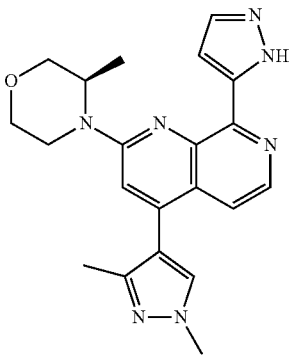 [SMILES: Cc1nn(C)cc1-c1cc(N2CCOC[C@H]2C)nc2c(-c3ccn[nH]3)nccc12] | 1H-NMR (400 MHz, DMSO-d6): d [ppm] = 1.28 (d, 3H), 2.17 (s, 3H), 3.27-3.40 (m, 1H), 3.53-3.63 (m, 1H), 3.72 (dd, 1H), 3.83 (d, 1H), 3.89 (s, 3H), 4.01-4.09 (m, 1H), 4.19 (d, 1H), 4.60 (d, 1H), 7.34 (s, 1H), 7.41 (s, 1H), 7.52 (d, 1H), 7.63 (s, 1H), 8.01 (s, 1H), 8.34 (d, 1H), 13.41 (br. s., 1H). 4-(1,3-dimethyl-1H-pyrazol-4-yl)-2-[(3R)-3-methylmorpholin-4-yl]-8-(1H-pyrazol-5-yl)-1,7-naphthyridine |
| 250 | 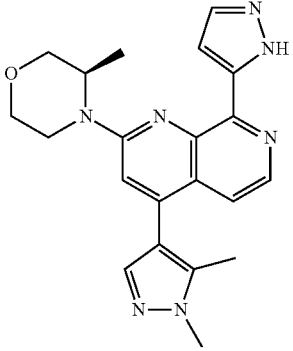 [SMILES: Cc1c(-c2cc(N3CCOC[C@H]3C)nc3c(-c4ccn[nH]4)nccc23)cnn1C] | 1H-NMR (400 MHz, DMSO-d6): d [ppm] = 1.29 (d, 3H), 2.27 (s, 3H), 3.29-3.33 (m, 1H), 3.58 (td, 1H), 3.72 (dd, 1H), 3.83 (d, 1H), 3.87 (s, 3H), 4.05 (dd, 1H), 4.19 (d, 1H), 4.60 (d, 1H), 7.30 (s, 1H), 7.42 (br. s., 1H), 7.49 (d, 1H), 7.64 (br. s., 1H), 7.65 (s, 1H), 8.33 (d, 1H), 13.41 (br. s., 1H). 4-(1,5-dimethyl-1H-pyrazol-4-yl)-2-[(3R)-3-methylmorpholin-4-yl]-8-(1H-pyrazol-5-yl)-1,7-naphthyridine |

TABLE 2-continued

| Example | Structure | NMR Name |
|---|---|---|
| 251 | 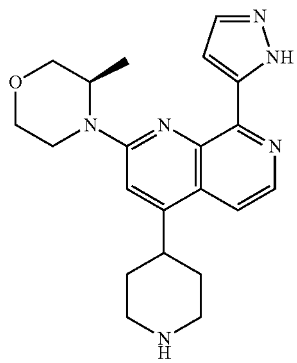 [SMILES: C[C@@H]1COCCN1c1cc(C2CCNCC2)c2ccnc(-c3ccn[nH]3)c2n1] | 1H-NMR (400 MHz, CHLOROFORM-d): d [ppm] = 1.38-1.46 (m, 4H), 1.77-1.87 (m, 2H), 1.96-2.06 (m, 2H), 2.94 (t, 2H), 3.27-3.39 (m, 2H), 3.53 (td, 1H), 3.72 (td, 1H), 3.82-4.05 (m, 3H), 4.18 (dd, 1H), 4.36-4.47 (m, 1H), 7.12 (s, 1H), 7.28 (d, 1H), 7.61 (d, 1H), 7.71 (d, 1H), 8.43-8.49 (m, 1H). 2-[(3R)-3-methylmorpholin-4-yl]-4-(piperidin-4-yl)-8-(1H-pyrazol-5-yl)-1,7-naphthyridine |
| 252 | 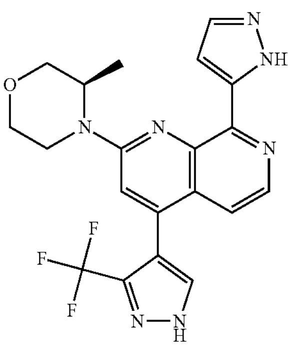 [SMILES: C[C@@H]1COCCN1c1cc(-c2c[nH]nc2C(F)(F)F)c2ccnc(-c3ccn[nH]3)c2n1] | 1H-NMR (400 MHz, DMSO-d6): d [ppm] = 1.28 (d, 3H), 3.36-3.44 (m, 1H), 3.58 (td, 1H), 3.72 (dd, 1H), 3.82 (d, 1H), 4.05 (dd, 1H), 4.18 (d, 1H), 4.56 (d, 1H), 7.27 (d, 1H), 7.41 (s, 1H), 7.44 (s, 1H), 7.64-7.66 (m, 1H), 8.33 (s, 2H), 13.41 (br. s., 1H), 14.11 (br. s., 1H). 2-[(3R)-3-methylmorpholin-4-yl]-8-(1H-pyrazol-5-yl)-4-[3-(trifluoromethyl)-1H-pyrazol-4-yl]-1,7-naphthyridine |
| 253 | 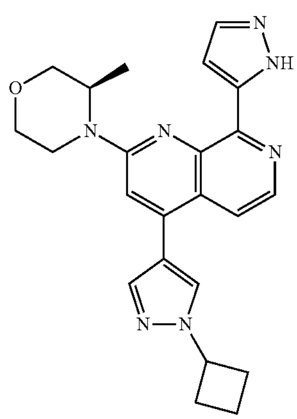 [SMILES: C[C@@H]1COCCN1c1cc(-c2cnn(C3CCC3)c2)c2ccnc(-c3ccn[nH]3)c2n1] | 1H-NMR (400 MHz, CHLOROFORM-d): d [ppm] = 1.46 (d, 3H), 1.90-2.03 (m, 2H), 2.56-2.72 (m, 4H), 3.57 (td, 1H), 3.74 (td, 1H), 3.86-3.98 (m, 2H), 4.04 (dd, 1H), 4.20 (dd, 1H), 4.46 (dd, 1H), 4.91 (dd, 1H), 7.16 (s, 1H), 7.32 (d, 1H), 7.73 (d, 1H), 7.74 (d, 1H), 7.80 (s, 1H), 7.85 (s, 1H), 8.46 (d, 1H). 4-(1-cyclobutyl-1H-pyrazol-4-yl)-2-[(3R)-3-methylmorpholin-4-yl]-8-(1H-pyrazol-5-yl)-1,7-naphthyridine |
| 254 | 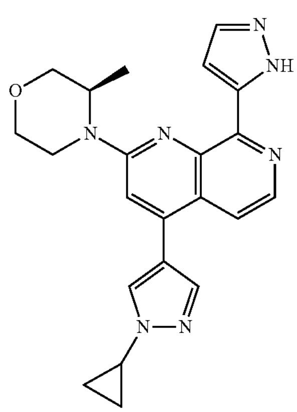 [SMILES: C[C@@H]1COCCN1c1cc(-c2cnn(C3CC3)c2)c2ccnc(-c3ccn[nH]3)c2n1] | 1H-NMR (400 MHz, DMSO-d6): d [ppm] = 1.00-1.08 (m, 2H), 1.14-1.20 (m, 2H), 1.28 (d, 3H), 3.34 (s, 1H), 3.51-3.61 (m, 1H), 3.68-3.75 (m, 1H), 3.80-3.89 (m, 2H), 4.02-4.08 (m, 1H), 4.16-4.23 (m, 1H), 4.60-4.69 (m, 1H), 7.39 (s, 1H), 7.45 (s, 1H), 7.63 (d, 1H), 7.83 (d, 1H), 7.97 (d, 1H), 8.36 (d, 1H), 8.41 (s, 1H), 13.38 (br. s, 1H). 4-(1-cyclopropyl-1H-pyrazol-4-yl)-2-[(3R)-3-methylmorpholin-4-yl]-8-(1H-pyrazol-5-yl)-1,7-naphthyridine |

TABLE 2-continued

| Example | Structure | NMR Name |
|---|---|---|
| 255 | 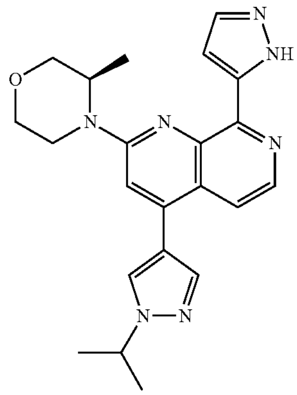 [SMILES: CC(C)n1cc(-c2cc(N3CCOC[C@H]3C)nc3c(-c4ccn[nH]4)nccc23)cn1] | 1H-NMR (400 MHz, DMSO-d6): d [ppm] = 1.29 (d, 3H), 1.52 (d, 6H), 3.29-3.39 (m, 1H), 3.52-3.62 (m, 1H), 3.68-3.76 (m, 1H), 3.80-3.87 (m, 1H), 4.01-4.09 (m, 1H), 4.16-4.24 (m, 1H), 4.57-4.69 (m, 2H), 7.39 (s, 1H), 7.45 (s, 1H), 7.62 (s, 1H), 7.85 (d, 1H), 7.98 (s, 1H), 8.34-8.41 (m, 2H), 13.38 (br. s, 1H). 2-[(3R)-3-methylmorpholin-4-yl]-4-[1-(propan-2-yl)-1H-pyrazol-4-yl]-8-(1H-pyrazol-5-yl)-1,7-naphthyridine |
| 256 | 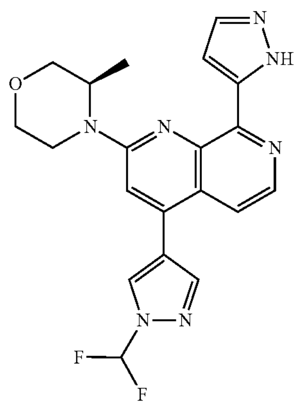 [SMILES: C[C@@H]1COCCN1c1cc(-c2cnn(C(F)F)c2)c2ccnc(-c3ccn[nH]3)c2n1] | 1H-NMR (400 MHz, DMSO-d6): d [ppm] = 1.29 (d, 3H), 3.29-3.40 (m, 1H), 3.51-3.61 (m, 1H), 3.68-3.75 (m, 1H), 3.81-3.87 (m, 1H), 4.02-4.08 (m, 1H), 4.19-4.26 (m, 1H), 4.62-4.70 (m, 1H), 7.40 (s, 1H), 7.57 (s, 1H), 7.64 (s, 1H), 7.74 (d, 1H), 7.88 (t, 1H), 8.33 (s, 1H), 8.38 (d, 1H), 8.85 (s, 1H), 13.41 (br. s, 1H). 4-[1-(difluoromethyl)-1H-pyrazol-4-yl]-2-[(3R)-3-methylmorpholin-4-yl]-8-(1H-pyrazol-5-yl)-1,7-naphthyridine |
| 257 | 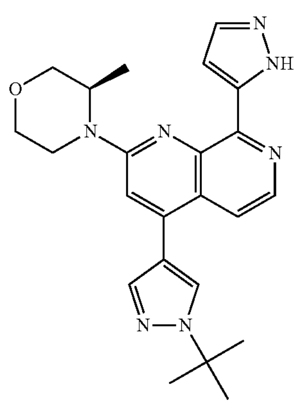 [SMILES: C[C@@H]1COCCN1c1cc(-c2cnn(C(C)(C)C)c2)c2ccnc(-c3ccn[nH]3)c2n1] | 1H-NMR (400 MHz, DMSO-d6): d [ppm] = 1.30 (d, 3H), 1.63 (s, 9H), 3.34-3.39 (m, 1H), 3.58 (td, 1H), 3.73 (dd, 1H), 3.85 (d, 1H), 4.07 (dd, 1H), 4.21 (d, 1H), 4.67 (d, 1H), 7.40 (br. s., 1H), 7.46 (s, 1H), 7.63 (s, 1H), 7.86 (d, 1H), 7.99 (s, 1H), 8.38 (d, 1H), 8.41 (s, 1H), 13.39 (br. s., 1H). 4-(1-tert-butyl-1H-pyrazol-4-yl)-2-[(3R)-3-methylmorpholin-4-yl]-8-(1H-pyrazol-5-yl)-1,7-naphthyridine |
| 258 | 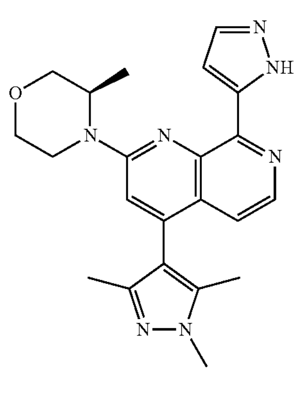 [SMILES: Cc1nn(C)c(C)c1-c1cc(N2CCOC[C@H]2C)nc2c(-c3ccn[nH]3)nccc12] | 1H-NMR (400 MHz, DMSO-d6): d [ppm] = 1.28 (d, 3H), 2.02 (d, 3H), 2.12 (d, 3H), 3.27-3.33 (m, 1H), 3.51-3.65 (m, 1H), 3.69-3.76 (m, 1H), 3.78 (s, 3H), 3.79-3.85 (m, 1H), 4.00-4.11 (m, 1H), 4.20 (d, 1H), 4.53-4.67 (m, 1H), 7.25 (d, 1H), 7.31 (d, 1H), 7.42 (s, 1H), 7.63 (s, 1H), 8.31 (d, 1H), 13.41 (br. s., 1H). 2-[(3R)-3-methylmorpholin-4-yl]-8-(1H-pyrazol-5-yl)-4-(1,3,5-trimethyl-1H-pyrazol-4-yl)-1,7-naphthyridine |

TABLE 2-continued

| Example | Structure | NMR Name |
|---|---|---|
| 259 | 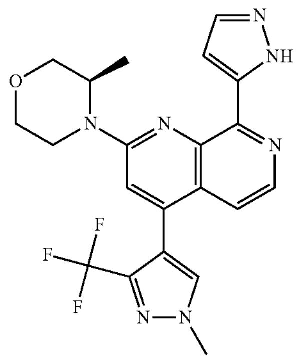 [SMILES: C[C@@H]1COCCN1c1cc(-c2cn(C)nc2C(F)(F)F)c2ccnc(-c3ccn[nH]3)c2n1] | 1H-NMR (400 MHz, DMSO-d6): d [ppm] = 1.27 (d, 3H), 3.28-3.38 (m, 1H), 3.58 (td, 1H), 3.72 (dd, 1H), 3.82 (d, 1H), 4.02-4.11 (m, 4H), 4.17 (d, 1H), 4.50-4.59 (m, 1H), 7.32 (d, 1H), 7.41 (br. s., 1H), 7.44 (s, 1H), 7.63 (br. s., 1H), 8.28 (s, 1H), 8.34 (d, 1H), 13.41 (br. s., 1H).<br>2-[(3R)-3-methylmorpholin-4-yl]-4-[1-methyl-3-(trifluoromethyl)-1H-pyrazol-4-yl]-8-(1H-pyrazol-5-yl)-1,7-naphthyridine |
| 260 | 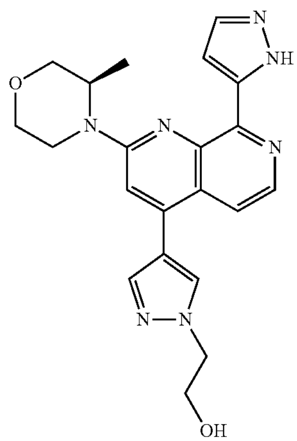 [SMILES: C[C@@H]1COCCN1c1cc(-c2cnn(CCO)c2)c2ccnc(-c3ccn[nH]3)c2n1] | 1H-NMR (400 MHz, DMSO-d6): d [ppm] = 1.29 (d, 3H), 3.34-3.40 (m, 1H), 3.58 (td, 1H), 3.69-3.75 (m, 1H), 3.80-3.87 (m, 3H), 4.06 (dd, 1H), 4.21 (d, 1H), 4.27 (t, 2H), 4.65 (d, 1H), 5.00 (br. s., 1H), 7.39 (s, 1H), 7.45 (s, 1H), 7.64 (d, 1H), 7.86 (d, 1H), 8.01 (s, 1H), 8.34 (s, 1H), 8.37 (d, 1H), 13.37 (br. s., 1H).<br>2-(4-{2-[(3R)-3-methylmorpholin-4-yl]-8-(1H-pyrazol-5-yl)-1,7-naphthyridin-4-yl}-1H-pyrazol-1-yl)ethanol |
| 261 | 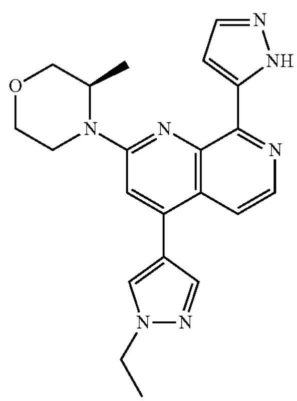 [SMILES: CCn1cc(-c2cc(N3CCOC[C@H]3C)nc3c(-c4ccn[nH]4)nccc23)cn1] | 1H-NMR (400 MHz, DMSO-d6): d [ppm] = 1.29 (d, 3H), 1.48 (t, 3H), 3.33-3.40 (m, 1H), 3.53-3.62 (m, 1H), 3.69-3.76 (m, 1H), 3.80-3.88 (m, 1H), 4.02-4.10 (m, 1H), 4.17-4.23 (m, 1H), 4.26 (q, 2H), 4.61-4.70 (m, 1H), 7.40 (s, 1H), 7.46 (s, 1H), 7.63 (s, 1H), 7.85 (d, 1H), 7.99 (s, 1H), 8.35-8.40 (m, 2H), 13.39 (br. s, 1H).<br>4-(1-ethyl-1H-pyrazol-4-yl)-2-[(3R)-3-methylmorpholin-4-yl]-8-(1H-pyrazol-5-yl)-1,7-naphthyridine |
| 262 | 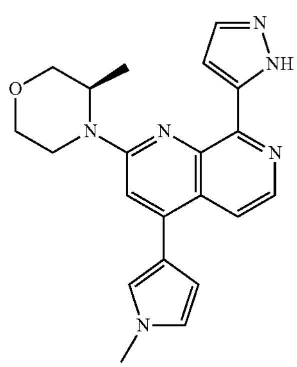 [SMILES: C[C@@H]1COCCN1c1cc(-c2ccn(C)c2)c2ccnc(-c3ccn[nH]3)c2n1] | 1H-NMR (400 MHz, DMSO-d6): d [ppm] = 1.27 (d, 3H), 3.25-3.32 (m, 1H), 3.52-3.61 (m, 1H), 3.68-3.77 (m, 4H), 3.81 (s, 1H), 4.01-4.08 (m, 1H), 4.14-4.21 (m, 1H), 4.57-4.66 (m, 1H), 6.51 (dd, 1H), 6.94 (t, 1H), 7.31 (s, 1H), 7.34 (t, 1H), 7.38 (d, 1H), 7.62 (d, 1H), 7.97 (d, 1H), 8.34 (d, 1H), 13.12 (br. s, 1H).<br>2-[(3R)-3-methylmorpholin-4-yl]-4-(1-methyl-1H-pyrrol-3-yl)-8-(1H-pyrazol-5-yl)-1,7-naphthyridine |

TABLE 2-continued

| Example | Structure | NMR Name |
|---|---|---|
| 263 | 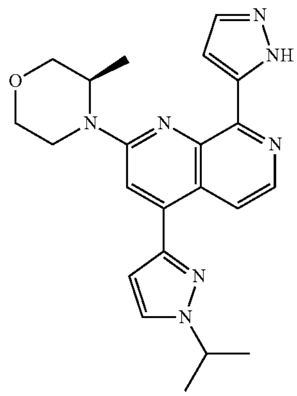 [SMILES: CC(C)n1ccc(-c2cc(N3CCOC[C@H]3C)nc3c(-c4ccn[nH]4)nccc23)n1] | 1H-NMR (400 MHz, DMSO-d6): d [ppm] = 1.29 (d, 3H), 1.52 (d, 6H), 3.27-3.42 (m, 1H), 3.57 (td, 1H), 3.73 (dd, 1H), 3.84 (d, 1H), 4.06 (dd, 1H), 4.21 (d, 1H), 4.56-4.72 (m, 2H), 7.40 (s, 1H), 7.46 (s, 1H), 7.64 (d, 1H), 7.86 (d, 1H), 7.99 (s, 1H), 8.35-8.42 (m, 2H), 13.40 (br. s., 1H). 2-[(3R)-3-methylmorpholin-4-yl]-4-[1-(propan-2-yl)-1H-pyrazol-3-yl]-8-(1H-pyrazol-5-yl)-1,7-naphthyridine |
| 264 | 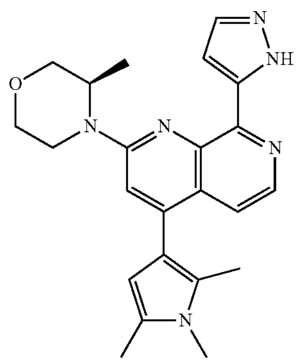 [SMILES: Cc1cc(-c2cc(N3CCOC[C@H]3C)nc3c(-c4ccn[nH]4)nccc23)c(C)n1C] | 1H-NMR (400 MHz, DMSO-d6): d [ppm] = 1.27 (d, 3H), 2.18 (s, 3H), 2.26 (s, 3H), 3.26-3.32 (m, 1H), 3.49 (s, 3H), 3.51-3.62 (m, 1H), 3.72 (dd, 1H), 3.82 (d, 1H), 4.05 (dd, 1H), 4.16 (d, 1H), 4.51-4.60 (m, 1H), 6.00 (d, 1H), 7.16 (s, 1H), 7.39 (s, 1H), 7.60-7.66 (m, 2H), 8.30 (d, 1H), 13.38 (br. s., 1H). 2-[(3R)-3-methylmorpholin-4-yl]-8-(1H-pyrazol-5-yl)-4-(1,2,5-trimethyl-1H-pyrrol-3-yl)-1,7-naphthyridine |
| 265 | 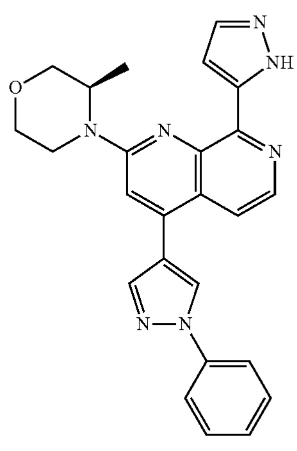 [SMILES: C[C@@H]1COCCN1c1cc(-c2cnn(-c3ccccc3)c2)c2ccnc(-c3ccn[nH]3)c2n1] | 1H-NMR (400 MHz, DMSO-d6): d [ppm] = 1.32 (d, 3H), 3.36-3.43 (m, 1H), 3.59 (td, 1H), 3.74 (dd, 1H), 3.86 (d, 1H), 4.08 (dd, 1H), 4.24 (d, 1H), 4.69 (d, 1H), 7.35-7.45 (m, 2H), 7.54-7.62 (m, 3H), 7.65 (s, 1H), 7.94 (d, 1H), 7.99 (dd, 2H), 8.32 (s, 1H), 8.40 (d, 1H), 9.10 (s, 1H), 13.43 (br. s., 1H). 2-[(3R)-3-methylmorpholin-4-yl]-4-(1-phenyl-1H-pyrazol-4-yl)-8-(1H-pyrazol-5-yl)-1,7-naphthyridine |
| 266 | 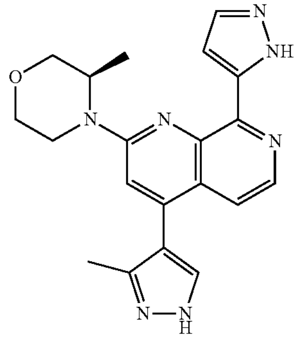 [SMILES: Cc1n[nH]cc1-c1cc(N2CCOC[C@H]2C)nc2c(-c3ccn[nH]3)nccc12] | 1H-NMR (400 MHz, DMSO-d6): d [ppm] = 1.29 (d, 3H), 2.26 (br. s., 3H), 3.58 (td, 1H), 3.28-3.39 (m, 1H), 3.72 (dd, 1H), 3.83 (d, 1H), 4.06 (dd, 1H), 4.19 (d, 1H), 4.61 (d, 1H), 7.34 (s, 1H), 7.42 (br. s., 1H), 7.51 (d, 1H), 7.63 (s, 1H), 7.69-7.87 (m, 1H), 8.34 (d, 1H), 13.02 (br. s., 1H), 13.41 (br. s., 1H). 2-[(3R)-3-methylmorpholin-4-yl]-4-(3-methyl-1H-pyrazol-4-yl)-8-(1H-pyrazol-5-yl)-1,7-naphthyridine |

TABLE 2-continued

| Example | Structure | NMR Name |
|---|---|---|
| 267 | 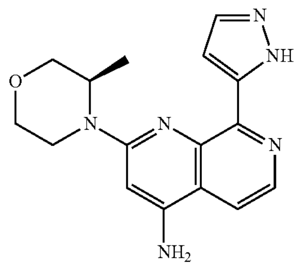 [SMILES: C[C@@H]1COCCN1c1cc(N)c2ccnc(-c3ccn[nH]3)c2n1] | 1H-NMR (400 MHz, DMSO-d6): d [ppm] = 1.23 (d, 3H), 3.24 (td, 1H), 3.55 (td, 1H), 3.70 (dd, 1H), 3.81 (d, 1H), 3.92 (d, 1H), 4.03 (dd, 1H), 4.34 (dd, 1H), 6.36 (s, 1H), 6.73 (s, 2H), 7.30 (s, 1H), 7.58 (s, 1H), 7.83 (d, 1H), 8.24 (d, 1H), 13.40 (br. s., 1H).<br>2-[(3R)-3-methylmorpholin-4-yl]-8-(1H-pyrazol-5-yl)-1,7-naphthyridin-4-amine |
| 268 | 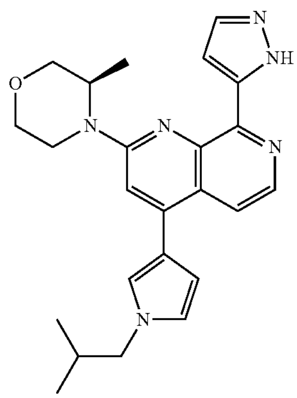 [SMILES: CC(C)Cn1ccc(-c2cc(N3CCOC[C@H]3C)nc3c(-c4ccn[nH]4)nccc23)c1] | 1H-NMR (400 MHz, CHLOROFORM-d): d [ppm] = 1.01 (d, 6H), 1.46 (d, 3H), 2.33 (dt, 1H), 3.51-3.61 (m, 1H), 3.72 (td, 1H), 3.84-3.90 (m, 1H), 3.90-3.97 (m, 1H), 3.99-4.08 (m, 3H), 4.18 (dd, 1H), 4.42-4.50 (m, 1H), 7.15 (s, 1H), 7.31 (d, 1H), 7.69 (d, 1H), 7.71-7.75 (m, 2H), 7.81 (s, 1H), 8.44 (d, 1H).<br>2-[(3R)-3-methylmorpholin-4-yl]-4-[1-(2-methylpropyl)-1H-pyrazol-4-yl]-8-(1H-pyrazol-5-yl)-1,7-naphthyridine |
| 269 | 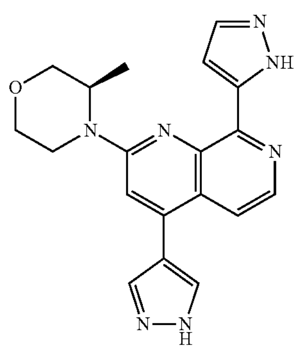 [SMILES: C[C@@H]1COCCN1c1cc(-c2cn[nH]c2)c2ccnc(-c3ccn[nH]3)c2n1] | 1H-NMR (400 MHz, DMSO-d6): d [ppm] = 1.29 (d, 3H), 3.30-3.38 (m, 1H), 3.53-3.62 (m, 1H), 3.73 (dd, 1H), 3.84 (d, 1H), 4.03-4.09 (m, 1H), 4.21 (d, 1H), 4.66 (d, 1H), 7.41 (s, 1H), 7.47 (s, 1H), 7.63 (s, 1H), 7.84 (d, 1H), 8.03 (s, 1H), 8.37 (d, 2H), 13.37 (br. s., 1H), 13.41 (br. s., 1H).<br>2-[(3R)-3-methylmorpholin-4-yl]-4-(1H-pyrazol-4-yl)-8-(1H-pyrazol-5-yl)-1,7-naphthyridine |
| 270 | 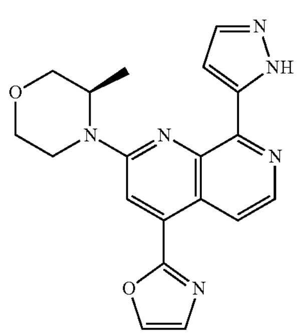 [SMILES: C[C@@H]1COCCN1c1cc(-c2ncco2)c2ccnc(-c3ccn[nH]3)c2n1] | 1H-NMR (400 MHz, DMSO-d6): d [ppm] = 1.31 (d, 3H), 3.40-3.44 (m, 1H), 3.55-3.64 (m, 1H), 3.71-3.77 (m, 1H), 3.82-3.87 (m, 1H), 4.03-4.11 (m, 1H), 4.19-4.25 (m, 1H), 4.62-4.69 (m, 1H), 7.40 (br. s., 1H), 7.64 (br. s., 1H), 7.68 (d, 1H), 8.00 (s, 1H), 8.47 (d, 1H), 8.49 (d, 1H), 8.82 (d, 1H), 13.44 (br. s., 1H).<br>2-[(3R)-3-methylmorpholin-4-yl]-4-(1,3-oxazol-2-yl)-8-(1H-pyrazol-5-yl)-1,7-naphthyridine |

TABLE 2-continued

| Example | Structure | NMR Name |
|---|---|---|
| 271 | 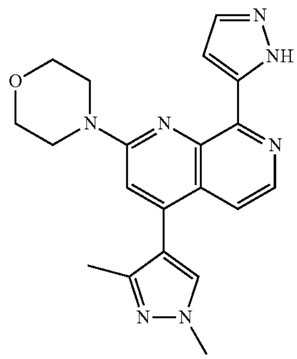 [SMILES: Cc1nn(C)cc1-c1cc(N2CCOCC2)nc2c(-c3ccn[nH]3)nccc12] | 1H-NMR (400 MHz, DMSO-d6): d [ppm] = 2.16 (s, 3H), 3.72-3.84 (m, 8H), 3.88 (s, 3H), 7.35-7.43 (m, 2H), 7.50 (d, 1H), 7.63 (br. s., 1H), 8.00 (s, 1H), 8.34 (d, 1H), 13.40 (br. s., 1H). 4-(1,3-dimethyl-1H-pyrazol-4-yl)-2-(morpholin-4-yl)-8-(1H-pyrazol-5-yl)-1,7-naphthyridine |
| 272 | 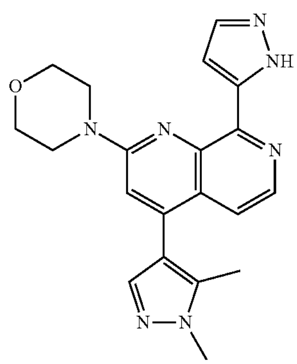 [SMILES: Cc1c(-c2cc(N3CCOCC3)nc3c(-c4ccn[nH]4)nccc23)cnn1C] | 1H-NMR (400 MHz, DMSO-d6): d [ppm] = 2.25 (s, 3H), 3.71-3.82 (m, 8H), 3.86 (s, 3H), 7.35 (s, 1H), 7.40 (br. s., 1H), 7.48 (d, 1H), 7.64 (s, 2H), 8.33 (d, 1H), 13.40 (br. s., 1H). 4-(1,5-dimethyl-1H-pyrazol-4-yl)-2-(morpholin-4-yl)-8-(1H-pyrazol-5-yl)-1,7-naphthyridine |
| 273 | 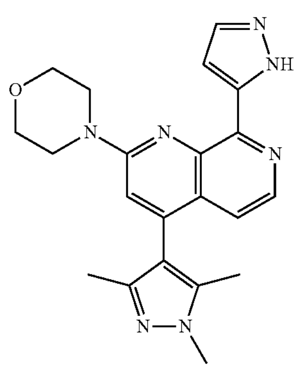 [SMILES: Cc1nn(C)c(C)c1-c1cc(N2CCOCC2)nc2c(-c3ccn[nH]3)nccc12] | 1H-NMR (400 MHz, DMSO-d6): d [ppm] = 2.00 (s, 3H), 2.10 (s, 3H), 3.71-3.86 (m, 11H), 7.24 (d, 1H), 7.36 (s, 1H), 7.41 (br. s., 1H), 7.64 (s, 1H), 8.32 (d, 1H). 2-(morpholin-4-yl)-8-(1H-pyrazol-5-yl)-4-(1,3,5-trimethyl-1H-pyrazol-4-yl)-1,7-naphthyridine |

The following compounds of Table 3 were prepared according to Scheme 6 and in analogy to example 126.

TABLE 3

| Example | Structure | NMR Name |
|---|---|---|
| 274 | 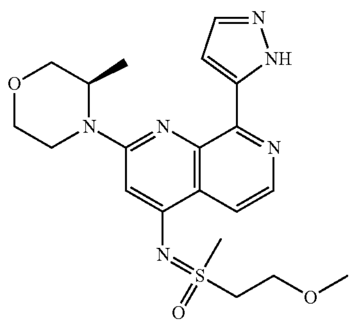 [SMILES: COCCS(C)(=O)=Nc1cc(N2CCOC[C@H]2C)nc2c(-c3ccn[nH]3)nccc12] | 1H-NMR (400 MHz, DMSO-d6): d [ppm] = 1.25 (d, 3H), 3.23-3.29 (m, 1H), 3.30 (s, 3H), 3.35-3.41 (m, 1H), 3.43 (d, 2H), 3.56 (td, 1H), 3.67-3.74 (m, 1H), 3.78-3.92 (m, 5H), 3.95-4.08 (m, 2H), 4.34-4.47 (m, 1H), 6.81 (d, 1H), 7.35 (s, 1H), 7.60 (s, 1H), 7.87 (d, 1H), 8.29 (d, 1H), 13.36 (br. s., 1H). 4-{[(2-methoxyethyl)(methyl)oxido-$\lambda^6$-sulfanylidene]amino}-2-[(3R)-3-methylmorpholin-4-yl]-8-(1H-pyrazol-5-yl)-1,7-naphthyridine |
| 275 | 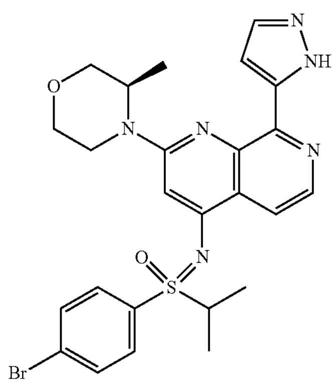 [SMILES: CC(C)S(=O)(=Nc1cc(N2CCOC[C@H]2C)nc2c(-c3ccn[nH]3)nccc12)c1ccc(Br)cc1] | 1H-NMR (400 MHz, DMSO-d6): d [ppm] = 0.94 (dd, 3H), 1.31 (dd, 3H), 1.48 (q, 3H), 3.03-3.15 (m, 1H), 3.41-3.52 (m, 1H), 3.53-3.92 (m, 4H), 3.93-4.10 (m, 2H), 6.45 (d, 1H), 7.26-7.32 (m, 1H), 7.58 (s, 1H), 7.79 (t, 2H), 7.84-7.91 (m, 2H), 8.06 (q, 1H), 8.36 (d, 1H), 13.29 (br. s, 1H). 4-{[(4-bromophenyl)(oxido)propan-2-yl-$\lambda^6$-sulfanylidenelamino}-2-[(3R)-3-methylmorpholin-4-yl]-8-(1H-pyrazol-5-yl)-1,7-naphthyridine |
| 276 | 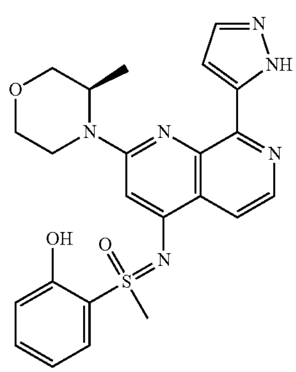 [SMILES: C[C@@H]1COCCN1c1cc(N=S(C)(=O)c2ccccc2O)c2ccnc(-c3ccn[nH]3)c2n1] | 1H-NMR (400 MHz, DMSO-d6): d [ppm] = 0.80-1.18 (m, 3H), 3.61-3.66 (m, 1H), 3.69 (s, 4H), 3.72-3.89 (m, 2H), 3.93-4.04 (m, 2H), 4.05-4.13 (m, 1H), 6.42 (d, 1H), 6.83-6.94 (m, 1H), 6.96-7.05 (m, 1H), 7.24-7.30 (m, 1H), 7.40-7.50 (m, 1H), 7.56 (s, 1H), 7.91-8.00 (m, 2H), 8.26-8.30 (m, 1H), 11.28 (br. s, 1H). 2-(methyl-N-{2-[(3R)-3-methylmorpholin-4-yl]-8-(1H-pyrazol-5-yl)-1,7-naphthyridin-4-yl}sulfonimidoyl)phenol |
| 277 | 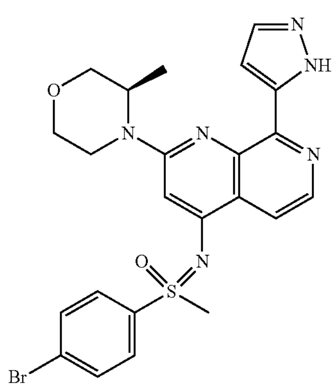 [SMILES: C[C@@H]1COCCN1c1cc(N=S(C)(=O)c2ccc(Br)cc2)c2ccnc(-c3ccn[nH]3)c2n1] | 1H-NMR (400 MHz, DMSO-d6): d [ppm] = 0.81 (d, 1H), 1.17 (d, 2H), 3.06-3.18 (m, 1H), 3.42-3.54 (m, 1H), 3.55-3.67 (m, 1H), 3.68-3.79 (m, 4H), 3.81-3.92 (m, 1H), 3.93-4.03 (m, 1H), 4.09-4.18 (m, 1H), 6.49 (d, 1H), 7.29 (d, 1H), 7.57 (s, 1H), 7.84-7.90 (m, 2H), 7.91-7.99 (m, 2H), 8.03 (dd, 1H), 8.34 (dd, 1H), 13.31 (br. s, 1H). 4-{[(4-bromophenyl)(methyl)oxido-$\lambda^6$-sulfanylidene]amino}-2-[(3R)-3-methylmorpholin-4-yl]-8-(1H-pyrazol-5-yl)-1,7-naphthyridine |

TABLE 3-continued

| Example | Structure | NMR Name |
|---|---|---|
| 278 | 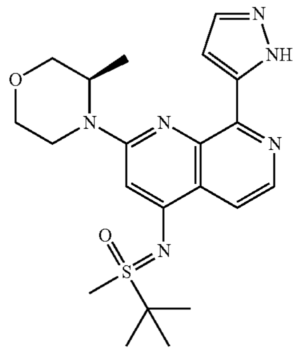 [SMILES: C[C@@H]1COCCN1c1cc(N=S(C)(=O)C(C)(C)C)c2ccnc(-c3ccn[nH]3)c2n1] | 1H-NMR (400 MHz, DMSO-d6): d [ppm] = 1.22-1.29 (m, 3H), 1.55 (d, 9H), 3.25-3.30 (m, 1H), 3.32 (s, 3H), 3.52-3.62 (m, 1H), 3.72 (dd, 1H), 3.80-3.86 (m, 1H), 3.94-4.09 (m, 2H), 4.33-4.48 (m, 1H), 6.83-6.93 (m, 1H), 7.29-7.37 (m, 1H), 7.60 (d, 1H), 7.84 (d, 1H), 8.29 (d, 1H), 13.15-13.44 (m, 1H). 4-{[tert-butyl(methyl)oxido-$\lambda^6$-sulfanylidene]amino}-2-[(3R)-3-methylmorpholin-4-yl]-8-(1H-pyrazol-5-yl)-1,7-naphthyridine |
| 279 | 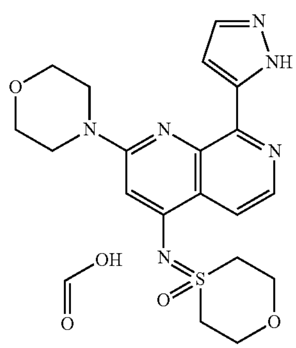 [SMILES: O=S1(=Nc2cc(N3CCOCC3)nc3c(-c4ccn[nH]4)nccc23)CCOCC1 ; O=CO] | 1H-NMR (400 MHz, DMSO-d6): d [ppm] = 3.59-3.67 (m, 6H), 3.77-3.86 (m, 6H), 3.96 (t, 2H), 4.13-4.20 (m, 2H), 6.84 (s, 1H), 7.35 (d, 1H), 7.61 (d, 1H), 7.98 (d, 1H), 8.17 (s, 1H), 8.33 (d, 1H). formic acid-N42-(morpholin-4-yl)-8-(1H-pyrazol-5-yl)-1,7-naphthyridin-4-yl]-1,4$\lambda^4$-oxathian-4-imine 4-oxide (1:1) |
| 280 | 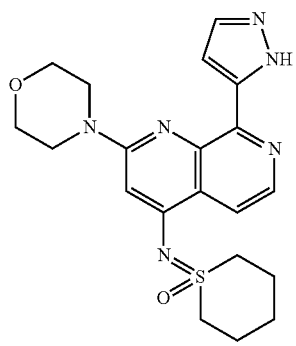 [SMILES: O=S1(=Nc2cc(N3CCOCC3)nc3c(-c4ccn[nH]4)nccc23)CCCCC1] | 1H-NMR (400 MHz, DMSO-d6): d [ppm] = 1.55-1.75 (m, 2H), 1.85-2.07 (m, 4H), 3.42-3.53 (m, 2H), 3.62 (t, 4H), 3.71 (d, 2H), 3.76-3.84 (m, 4H), 6.82 (s, 1H), 7.36 (s, 1H), 7.60 (s, 1H), 7.95 (d, 1H), 8.32 (d, 1H), 13.37 (s, 1H). N-[2-(morpholin-4-yl)-8-(1H-pyrazol-5-yl)-1,7-naphthyridin-4-yl]hexahydro-1$\lambda^4$-thiopyran-1-imine 1-oxide |

Example 281

3-methyl-2-{2-[(3R)-3-methylmorpholin-4-yl]-8-(1H-pyrazol-5-yl)-1,7-naphthyridin-4-yl}butan-2-ol

Step a

2-[(3R)-3-methylmorpholin-4-yl]-8-{1-[(2R)-tetrahydro-2H-pyran-2-yl]-1H-pyrazol-5-yl}-1,7-naphthyridine-4-carboxylic acid

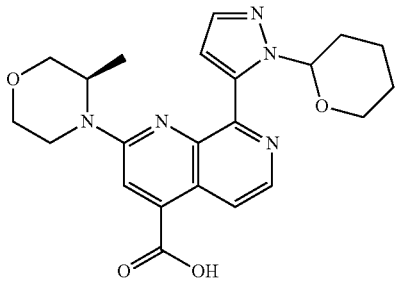 [SMILES: C[C@@H]1COCCN1c1cc(C(=O)O)c2ccnc(-c3ccnn3C3CCCCO3)c2n1]

Methyl 2-[(3R)-3-methylmorpholin-4-yl]-8-{1-[(2E)-tetrahydro-2H-pyran-2-yl]-1H-pyrazol-5-yl}-1,7-naphthyridine-4-carboxylate (1.10 g, 2.51 mmol) was solubilized in THF (11 mL) and methanol (5 mL9). NaOH solution (2.8 ml, 1.0 M, 2.8 mmol) was added and the mixture was stirred for 10 min at rt. The solvent was removed under reduced pressure and the aqueous phase was acidified to pH 5 using 1M HCl. The aqueous solution was lyophilised and the title compound was obtained without further purification in 99% yield (1.10 g).

1H-NMR (400 MHz, DMSO-d6): d [ppm]=1.18 (dd, 3H), 1.37-1.49 (m, 2H), 1.51-1.64 (m, 1H), 1.88-2.03 (m, 2H), 2.29-2.40 (m, 1H), 3.09-3.19 (m, 1H), 3.19-3.28 (m, 1H), 3.41-3.51 (m, 1H), 3.58-3.65 (m, 1H), 3.66-3.78 (m, 2H), 3.89-4.00 (m, 1H), 4.06 (t, 1H), 4.36-4.51 (m, 1H), 5.92-6.08 (m, 1H), 6.84 (dd, 1H), 7.48 (d, 1H), 7.60 (s, 1H), 8.32 (d, 1H), 8.46-8.53 (m, 1H).

Step b

N-methoxy-N-methyl-2-[(3R)-3-methylmorpholin-4-yl]-8-{1-[(2R)-tetrahydro-2H-pyran-2-yl]-1H-pyrazol-5-yl}-1,7-naphthyridine-4-carboxamide

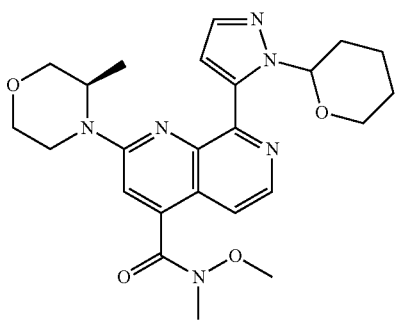 [SMILES: CON(C)C(=O)c1cc(N2CCOC[C@H]2C)nc2c(-c3ccnn3C3CCCCO3)nccc12]

N-methoxymethanamine hydrochloride (1:1) (861 mg, 8.83 mmol) was solubilized in DMF (20 mL). N,N-Diisopropylethylamin (3.1 ml, 18 mmol) and HATU (2.52 g, 6.62 mmol) were added and the mixture stirred for 10 min at rt. 2-[(3R)-3-Methylmorpholin-4-yl]-8-{1-[(2R)-tetrahydro-2H-pyran-2-yl]-1H-pyrazol-5-yl}-1,7-naphthyridine-4-carboxylic acid (1.10 g, 85% purity, 2.21 mmol) was then added and the mixture stirred 16 h at rt. N,N-Diisopropylethylamin (3.1 ml, 18 mmol) and HATU (2.52 g, 6.62 mmol) were added again and the reaction stirred for 16 h at rt. Water was added and the mixture was stirred for 10 min. The aqueous phase was extracted with EtOAc and the combined organic layers were washed with half sat. NaCl-solution. The organic layer was dried over a silicone filter and concentrated under reduced pressure. The crude material was purified by flash column chromatograpy (from Hx/EtOAc: 0-100% to 100% EtOAc to EtOAc/EtOH: 0-20%) and the title compound was obtained in quantitative yield.

1H-NMR (400 MHz, DMSO-d6): d [ppm]=1.19-1.25 (m, 3H), 1.41-1.54 (m, 2H), 1.54-1.66 (m, 1H), 1.92-1.99 (m, 2H), 2.69 (s, 2H), 3.15-3.32 (m, 2H), 3.42 (br. s., 3H), 3.50 (br. s., 3H), 3.60-3.72 (m, 2H), 3.72-3.80 (m, 1H), 3.93-4.01 (m, 1H), 4.12-4.22 (m, 1H), 4.46-4.57 (m, 1H), 6.04-6.17 (m, 1H), 6.97 (dd, 1H), 7.44 (d, 1H), 7.58-7.67 (m, 2H), 8.41 (d, 1H).

Step c 1-(2-[(3R)-3-methylmorpholin-4-yl]-8-{1-[(2R)-tetrahydro-2H-pyran-2-yl]-1H-pyrazol-5-yl}-1,7-naphthyridin-4-yl)ethanone

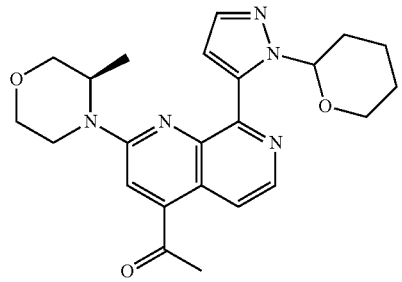 [SMILES: CC(=O)c1cc(N2CCOC[C@H]2C)nc2c(-c3ccnn3C3CCCCO3)nccc12]

N-methoxy-N-methyl-2-[(3R)-3-methylmorpholin-4-yl]-8-{1-[(2R)-tetra hydro-2H-pyran-2-yl]-1H-pyrazol-5-yl}-1,7-naphthyridine-4-carboxamide (710 mg, 1.52 mmol) was solubilized in THF and cooled to 0° C. Methylmagnesium bromide (1.5 ml, 3.0 M, 4.6 mmol) was added dropwise and the reaction was stirred at 0° C. for 30 min. and 1.5 h at rt. Methylmagnesium bromide (1.5 ml, 3.0 M, 4.6 mmol) was added again and the reaction was stirred for 16 h. The reaction was quenched with sat. NH4Cl and extracted with DCM. The organic phase was filtered and concentrated under reduced pressure. The title compound was used without further purification.

1H-NMR (400 MHz, DMSO-d6): d [ppm]=1.23 (dd, 3H), 1.40-1.48 (m, 2H), 1.53-1.64 (m, 1H), 1.95-2.00 (m, 1H), 2.32-2.40 (m, 1H), 2.69 (s, 3H), 2.78 (s, 2H), 3.19-3.30 (m, 2H), 3.64-3.73 (m, 2H), 3.75-3.81 (m, 1H), 3.95-4.02 (m, 1H), 4.14-4.21 (m, 1H), 4.55-4.63 (m, 1H), 5.97-6.07 (m, 1H), 6.88 (dd, 1H), 7.63 (t, 1H), 7.85 (d, 1H), 7.95 (d, 1H), 8.42 (d, 1H).

Step d 3-methyl-2-{2-[(3R)-3-methylmorpholin-4-yl]-8-(1H-pyrazol-5-yl)-1,7-naphthyridin-4-yl}butan-2-ol

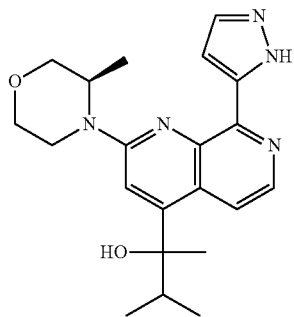 [SMILES: CC(C)C(C)(O)c1cc(N2CCOC[C@H]2C)nc2c(-c3ccn[nH]3)nccc12]

1-(2-[(3R)-3-methylmorpholin-4-yl]-8-{1-[(2R)-tetrahydro-2H-pyran-2-yl]-1H-pyrazol-5-yl}-1,7-naphthyridin-4-yl)ethanone (33.0 mg, 78.3 μmol) was solubilized in THF (2.0 mL) and the mixture was cooled to 0° C. Chloro(propan-2-yl)magnesium (120 μl, 2.0 M, 230 μmol) was added dropwise. The mixture was stirred at 0° C. 0.5 h and 1.5 h at rt. The reaction mixture was quenched with water and of 3M aq. HCl (0.5 mL) was added. The mixture was stirred for 16 h at rt. The reaction was quenched with NaHCO$_3$ and extracted with DCM. The organic phase was dried over a silicone filter and concentrated under reduced pressure. The crude material was purified by preparative HPLC (ACN/H$_2$O/NH$_4$OH mixture) and the title compound was obtained in 27% yield (9 mg).

1H-NMR (400 MHz, DMSO-d6): δ [ppm]=0.75-0.89 (m, 6H), 1.26 (d, 3H), 1.63 (d, 3H), 3.59 (t, 1H), 3.71-3.78 (m, 1H), 3.80-3.88 (m, 1H), 4.03-4.16 (m, 2H), 4.50-4.60 (m, 1H), 5.39 (d, 1H), 7.35 (s, 1H), 7.43 (s, 1H), 7.60 (s, 1H), 8.27-8.32 (m, 2H), 13.34 (br. s., 1H).

Example 282

1-{2-[(3R)-3-methylmorpholin-4-yl]-8-(1H-pyrazol-5-yl)-1,7-naphthyridin-4-yl}-1-(tetrahydro-2H-pyran-4-yl)ethanol

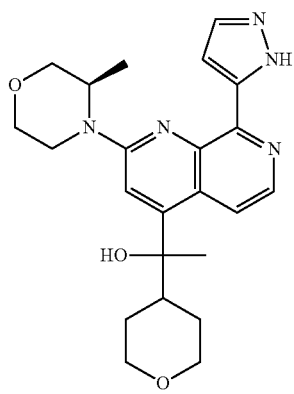 [SMILES: C[C@@H]1COCCN1c1cc(C(C)(O)C2CCOCC2)c2ccnc(-c3ccn[nH]3)c2n1]

1-(2-[(3R)-3-methylmorpholin-4-yl]-8-{1-[(2R)-tetrahydro-2H-pyran-2-yl]-1H-pyrazol-5-yl}-1,7-naphthyridin-4-yl)ethanone (33.0 mg, 78.3 μmol) was solubilized in THF (2.0 mL) and the mixture was cooled to 0° C. Chloro(tetrahydro-2H-pyran-4-yl)magnesium (1.4 ml, 0.50 M, 710 μmol) was added dropwise. The mixture was stirred at 0° C. 0.5 h and 1.5 h at rt. The mixture was cooled to 0° C. and chloro(tetrahydro-2H-pyran-4-yl)magnesium (1.4 ml, 0.50 M, 710 μmol) was again added. The reaction was stirred at 0° C. for 30 min and 45 at rt. The reaction mixture was quenched with water and of 3M aq. HCl (0.5 mL) was added. The mixture was stirred for 72 h at rt. The reaction was quenched with NaHCO$_3$ and extracted with DCM. The organic phase was dried over a silicone filter and concentrated under reduced pressure. The crude material was purified by preparative HPLC (ACN/H$_2$O/NH$_4$OH mixture) and the title compound was obtained in 23% yield (25 mg).

1H-NMR (400 MHz, DMSO-d6): d [ppm]=1.25 (d, 4H), 1.34-1.45 (m, 2H), 1.45-1.56 (m, 1H), 1.64-1.68 (m, 3H), 2.24-2.35 (m, 1H), 3.06-3.24 (m, 2H), 3.26-3.32 (m, 1H), 3.57 (t, 1H), 3.69-3.90 (m, 5H), 4.02-4.14 (m, 2H), 4.48-4.58 (m, 1H), 5.48 (d, 1H), 7.33 (br. s., 1H), 7.45 (d, 1H), 7.60 (s, 1H), 8.24-8.34 (m, 2H), 13.33 (br. s., 1H).

Example 283

3,3-dimethyl-2-{2-[(3R)-3-methylmorpholin-4-yl]-8-(1H-pyrazol-5-yl)-1,7-naphthyridin-4-yl}butan-2-ol

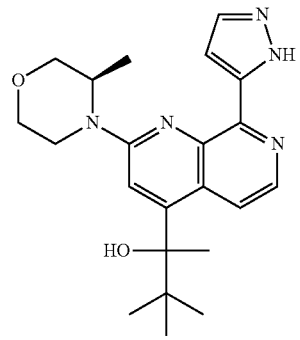 [SMILES: C[C@@H]1COCCN1c1cc(C(C)(O)C(C)(C)C)c2ccnc(-c3ccn[nH]3)c2n1]

1-(2-[(3R)-3-methylmorpholin-4-yl]-8-{1-[(2R)-tetrahydro-2H-pyran-2-yl]-1H-pyrazol-5-yl}-1,7-naphthyridin-4-yl)ethanone (33.0 mg, 78.3 μmol) was solubilized in THF (2.0 mL) and the mixture was cooled to 0° C. tert-butyl(chloro)magnesium (710 μl, 1.0 M, 710 μmol) was added dropwise. The mixture was stirred at 0° C. 0.5 h and 1.5 h at rt. The reaction mixture was quenched with water and of 3M aq. HCl (0.5 mL) was added. The mixture was stirred for 72 h at rt. The reaction was quenched with NaHCO$_3$ and extracted with DCM. The organic phase was dried over a silicone filter and concentrated under reduced pressure. The crude material was purified by preparative HPLC (ACN/H$_2$O/NH$_4$OH mixture) and the title compound was obtained in 24% yield (25 mg).

1H-NMR (400 MHz, DMSO-d6): d [ppm]=0.94 (s, 9H), 1.14-1.30 (m, 3H), 1.70 (s, 3H), 3.19-3.31 (m, 1H), 3.58 (t, 1H), 3.67-3.75 (m, 1H), 3.75-3.86 (m, 1H), 3.98-4.17 (m, 2H), 4.53 (br. s., 1H), 5.59 (s, 1H), 7.10 (br. s., 1H), 7.31 (br. s., 1H), 7.58 (s, 1H), 8.26 (d, 1H), 8.92 (br. s., 1H), 13.30 (br. s., 1H).

Example 284

2-{2-[(3R)-3-methylmorpholin-4-yl]-8-(1H-pyrazol-5-yl)-1,7-naphthyridin-4-yl}hexan-2-ol

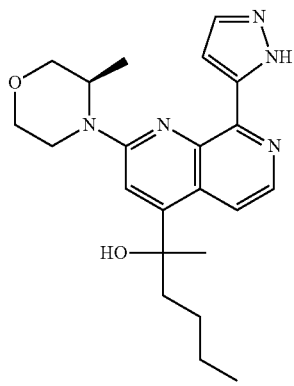 [SMILES: CCCCC(C)(O)c1cc(N2CCOC[C@H]2C)nc2c(-c3ccn[nH]3)nccc12]

1-(2-[(3R)-3-methylmorpholin-4-yl]-8-{1-[(2R)-tetrahydro-2H-pyran-2-yl]-1H-pyrazol-5-yl}-1,7-naphthyridin-4-yl)ethanone (33.0 mg, 78.3 μmol) was solubilized in THF (2.0 mL) and the mixture was cooled to 0° C. Butyl(chloro)magnesium (360 μl, 2.0 M, 710 μmol) was added dropwise. The mixture was stirred at 0° C. 0.5 h and 1.5 h at rt. The reaction mixture was quenched with water and of 3M aq. HCl (0.5 mL) was added. The mixture was stirred for 72 h at rt. The reaction was quenched with NaHCO₃ and extracted with DCM. The organic phase was dried over a silicone filter and concentrated under reduced pressure. The crude material was purified by preparative HPLC (ACN/H₂O/NH₄OH mixture) and the title compound was obtained in 7% yield (7 mg).

1H-NMR (400 MHz, DMSO-d6): d [ppm]=0.77 (td, 3H), 0.97-1.08 (m, 1H), 1.12-1.22 (m, 3H), 1.27 (d, 4H), 1.68 (d, 3H), 1.87-2.00 (m, 1H), 2.02-2.14 (m, 1H), 3.58 (t, 1H), 3.73 (d, 1H), 3.84 (d, 1H), 4.01-4.16 (m, 2H), 4.55 (d, 1H), 5.47 (d, 1H), 7.35 (s, 1H), 7.47 (d, 1H), 7.61 (s, 1H), 8.22 (dd, 1H), 8.32 (d, 1H), 13.35 (br. s., 1H).

Example 285

2-[(3R)-3-methylmorpholin-4-yl]-8-(1H-pyrazol-3-yl)-1,7-naphthyridine-4-carboxamide

Step a 2-((R)-3-methylmorpholin-4-yl)-8-[2-(tetrahydropyran-2-yl)-2H-pyrazol-3-yl]-[1,7]naphthyridine-4-carboxamide

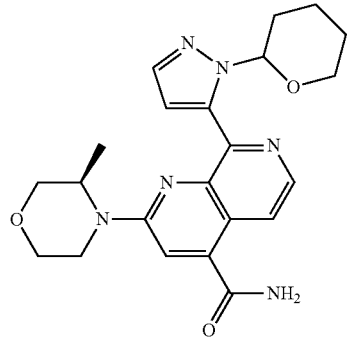 [SMILES: C[C@@H]1COCCN1c1cc(C(N)=O)c2ccnc(-c3ccnn3C3CCCCO3)c2n1]

2-((R)-3-methylmorpholin-4-yl)-8-(1H-pyrazol-5-yl)-1,7-naphthyridine-4-carbonitrile (1.5 g, 3.882 mmol) were suspended in 2-methoxyethanol (15 ml). Then KOH (0.653 g, 11.645 mmol) in water (367 μl) were added and the reaction was stirred at 150° C. for 7 hours and at 130° C. for 14 hours. The solvent was removed by distillation under reduced pressure and the residue was crystallized from a mixture of isopropanol (5 ml) and diethylether (25 ml). The title compound was obtained by filtration as a yellow solid in 6% yield (95 mg). LC-MS (method 1): m/z: [M+H]+= 423.2, R_f=3.01 min.

Step b

2-[(3R)-3-methylmorpholin-4-yl]-8-(1H-pyrazol-3-yl)-1,7-naphthyridine-4-carboxamide

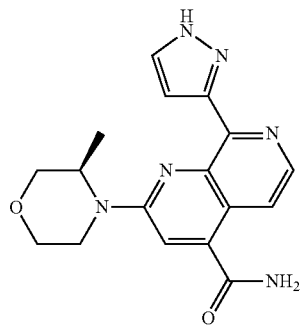 [SMILES: C[C@@H]1COCCN1c1cc(C(N)=O)c2ccnc(-c3cc[nH]n3)c2n1]

To 2-((R)-3-methylmorpholin-4-yl)-8-[2-(tetra hydropyran-2-yl)-2H-pyrazol-3-yl]-[1,7]naphthyridine-4-carboxamide (95 mg, 0.22 mmol) was added a drop of water and trifluoroacetic acid (1 ml, 13 mmol). After 2 hours LCMS indicated the complete removal of the protective group. The trifluoroacetic acid was removed under reduced pressure and the residue was adjusted to pH 7 by addition of aq. NaHCO₃ solution. The aqueous layer was extracted with a mixture of dichloromethane/isopropanol (10:1, 5×). The combined organic layers were dried over sodium sulfate and the solvent was evaporated. The residue was purified in a flashmaster chromatography (25 g of silica gel 60, 30 μM) with chloroform/methanol 90:10 as eluent. The title compound was obtained in 19% yield (14 mg) as a yellow solid. Melting point: 145-147° C. ¹H-NMR (400 MHz, CD₃OD): δ [ppm]=1.40-1.41 (m, 3H), 3.49-3.52 (m, 1H), 3.65-3.71 (m, 1H), 3.82-3.91 (m, 2H), 4.10-4.18 (m, 2H), 4.60-4.61 (m, 1H), 7.34 (s, 1H), 7.56 (s, 1H), 7.67 (s, 1H), 7.86-7.87 (m, 1H), 8.37-8.38 (m, 1H). LC-MS (method 1): m/z: [M+H]+=339.2, R_t=2.23 min.

Example 286

2-[(3R)-3-methylmorpholin-4-yl]-4-[1-(methylsulfonyl)cyclopropyl]-8-(1H-pyrazol-5-yl)-1,7-naphthyridine

Step a

{2-((R)-3-methylmorpholin-4-yl)-8-[2-(tetrahydropyran-2-yl)-2H-pyrazol-3-yl]-[1,7]naphthyridine-4-yl}methanol

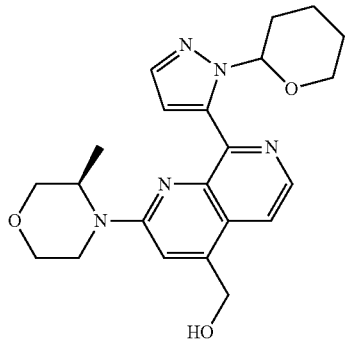 [SMILES: C[C@@H]1COCCN1c1cc(CO)c2ccnc(-c3ccnn3C3CCCCO3)c2n1]

To a solution of methyl-2-((R)-3-Methylmorpholin-4-yl)-8-[2-(tetrahydropyran-2-yl)-2H-pyrazol-3-yl]-[1,7]naphthyridine-4-carboxylate (190.5 mg, 0.435 mmol) in absolute THF (19 ml) was added diisobutylaluminium hydride solution (1M in toluene, 871 µl, 0.871 mmol) under argon at ambient temperature and the reaction was stirred for 1.5 hours at 80° C. The reaction mixture was cooled with ice, a saturated aqueous ammonium chloride solution (20 ml) was added and the aqueous layer was extracted with ethyl acetate (3×30 ml). The combined organic layers were dried over sodium sulfate and the solvent was removed under reduced pressure. The residue was purified in a Flashmaster chromatography (silica gel 60, 30 µM) using chloroform/methanol 98:2 as eluent. The title compound was obtained in 66% yield (118 mg). LC-MS (method 1): m/z: [M+H]+=410.3, $R_t$=3.07 min.

Step b

{2-[(3R)-3-methylmorpholin-4-yl]-8-[1-(tetrahydro-2H-pyran-2-yl)-1H-pyrazol-5-yl]-1,7-naphthyridin-4-yl}methyl methanesulfonate

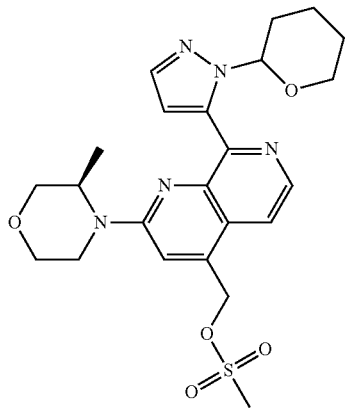 [SMILES: C[C@@H]1COCCN1c1cc(COS(C)(=O)=O)c2ccnc(-c3ccnn3C3CCCCO3)c2n1]

To a solution of {2-((R)-3-Methylmorpholin-4-yl)-8-[2-(tetrahydropyran-2-yl)-2H-pyrazol-3-yl]-[1,7]naphthyridine-4-yl}methanol (118 mg, 0.288 mmol) and trimethylamine (52 µl, 0.375 mmol) in absolute THF (5 ml) was added dropwise under argon at 0° C. methansulfonyl chloride (25 µl, 0.317 mmol) and the reaction was allowed to stir for one hour at 0° C. With intervals of two hours additional methansulfonyl chloride (3×25 µl, 0.317 mmol) were added and the reaction was allowed to stir for another 16 hours at ambient temperature. After addition of another portion of methansulfonyl chloride (25 µl, 0.317 mmol) the reaction was stirred at 40° C. for two hours. The reaction mixture was filtered and the filtrate was evaporated. The title compound was obtained in quantitative yield (219 mg) and used without further purification in the next step. LC-MS (method 1): m/z: [M+H]+=488.2, Rt=3.32 min.

Step c

2-[(3R)-3-methylmorpholin-4-yl]-4-[(methylsulfonyl)methyl]-8-[1-(tetrahydro-2H-pyran-2-yl)-1H-pyrazol-5-yl]-1,7-naphthyridine

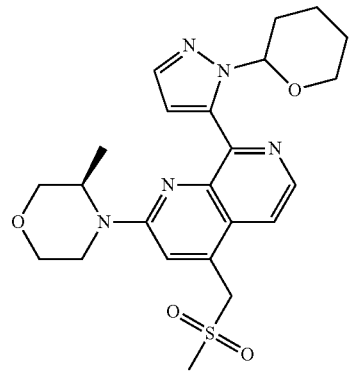 [SMILES: C[C@@H]1COCCN1c1cc(CS(C)(=O)=O)c2ccnc(-c3ccnn3C3CCCCO3)c2n1]

To a solution of {2-[(3R)-3-methylmorpholin-4-yl]-8-[1-(tetrahydro-2H-pyran-2-yl)-1H-pyrazol-5-yl]-1,7-naphthyridin-4-yl}methyl methanesulfonate (219 mg, 0.45 mmol) in absolute DMSO (2 ml) was added portionwise sodium methylsulfinate (161 mg, 1.572 mmol) and the reaction was allowed to stir at 120° C. for 20 minutes. The reaction was diluted with water (10 ml) and extracted with dichloromethane (3×10 ml). The combined organic layers were dried over sodium sulfate and the solvent was removed under reduced pressure. The residue was purified by Puri-Flash chromatography (25 g of silica gel 60, 30 µm) using dichloromethane/methanol 95:5 as eluent. The title compound was obtained in 40% yield (84 mg) as a yellow solid. LC-MS (method 1): m/z: [M+H]+=472.3, $R_t$=3.06 min.

Step d

2-[(3R)-3-methylmorpholin-4-yl]-4-[1-(methylsulfonyl)cyclopropyl]-8-[1-(tetrahydro-2H-pyran-2-yl)-1H-pyrazol-5-yl]-1,7-naphthyridine

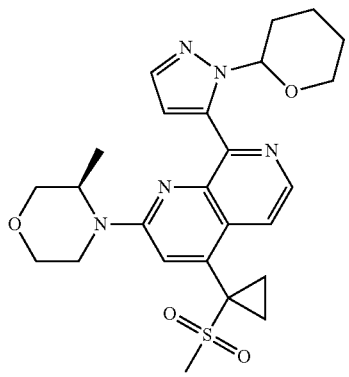 [SMILES: C[C@@H]1COCCN1c1cc(C2(S(C)(=O)=O)CC2)c2ccnc(-c3ccnn3C3CCCCO3)c2n1]

To a solution of 2-[(3R)-3-methylmorpholin-4-yl]-4-[(methylsulfonyl)methyl]-8-[1-(tetrahydro-2H-pyran-2-yl)-1H-pyrazol-5-yl]-1,7-naphthyridine (84 mg, 0.178 mmol), 1,2-dibromoethane (15 µl, 0.178 mmol) and tetrabutylammoniumbromide (6 mg, 0.018 mmol) in absolute THF (1.68 ml) was added a NaOH solution (50% in water, 185 µl) and the reaction was stirred at ambient temperature for one hour. The suspension changed its color to dark green/dark brown. Additional 1,2-dibromoethane (15 µl, 0.178 mmol), tetrabutylammoniumbromide (6 mg, 0.018 mmol) and NaOH solution (50% in water, 185 µl) were added and the reaction was stirred at 60° C. for 5 hours. The reaction was diluted with water (10 ml) and extracted with dichloromethane (3×10 ml). The combined organic layers were dried over sodium sulfate and the solvent was removed under reduced pressure. The residue was purified in a Flashmaster chromatography (25 g of silica gel 60, 30 µm) using dichloromethane/methanol 95:5 as eluent. The title compound was obtained in 28% yield (25 mg) as yellow solid. The product was used in the next step without further purification. LC-MS (method 1): m/z: [M+H]⁺=498.3, $R_t$=3.27 min.

Step e

2-[(3R)-3-methylmorpholin-4-yl]-4-[1-(methylsulfonyl)cyclopropyl]-8-(1H-pyrazol-5-yl)-1,7-naphthyridine

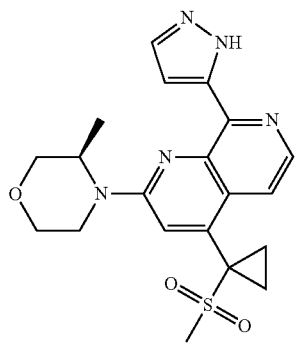 [SMILES: C[C@@H]1COCCN1c1cc(C2(S(C)(=O)=O)CC2)c2ccnc(-c3ccn[nH]3)c2n1]

To a solution of 2-[(3R)-3-methylmorpholin-4-yl]-4-[1-(methylsulfonyl)cyclopropyl]-8-[1-(tetrahydro-2H-pyran-2-yl)-1H-pyrazol-5-yl]-1,7-naphthyridine (25 mg, 0.05 mmol) in methanol (2 ml) was added HCl (2N in water). The reaction was stirred for 18 hours at 50° C. The LCMS indicated complete removal of the protective group. Methanol was removed under reduced pressure and the pH value of the residue was adjusted to seven by addition of aqueous NaHCO₃ solution. The aqueous layer was extracted with dichloromethane (3×10 ml). The combined organic layers were dried over sodium sulfate and the solvent was removed under reduced pressure. The title compound was obtained in 73% yield (16 mg) as a yellow solid. Melting point: 240-248° C. ¹H-NMR (400 MHz, CDCl₃): δ [ppm]=0.06-0.09 (m, 3H), 0.83-089 (m, 1H), 1.22-1.53 (m, 1H), 1.97-2.36 (m, 2H), 2.86 (s, 3H), 3.51-3.58 (m, 1H), 3.67-3.75 (m, 1H), 3.83-3.88 (m, 1H), 3.91-3.95 (m, 1H), 3.98-4.03 (m, 1H), 4.16-4.20 (m, 1H), 4.39-4.46 (m, 1H), 7.32 (s, 1H), 7.45 (s, 1H), 7.71 (s, 1H), 7.82-7.83 (m, 1H), 8.48-8.49 (m, 1H). LC-MS (method 1): m/z: [M+H]+=414.2, $R_t$=2.65 min.

Example 287

2-(morpholin-4-yl)-8-(1H-pyrazol-5-yl)-4-(tetrahydro-2H-pyran-4-ylmethoxy)-1,7-naphthyridine

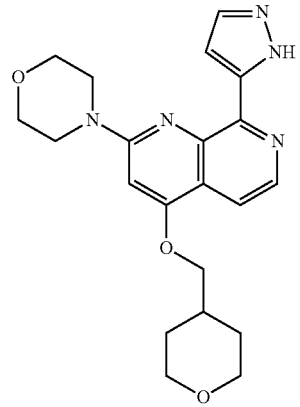 [SMILES: c1cc(-c2nccc3c(OCC4CCOCC4)cc(N4CCOCC4)nc23)[nH]n1]

A mixture of 2-(morpholin-4-yl)-8-[1-(tetrahydro-2H-pyran-2-yl)-1H-pyrazol-5-yl]-1,7-naphthyridin-4-ol (75 mg, 0.1 mmol), 4-(bromomethyl)tetrahydro-2H-pyran (26.4 mg, 147.5 µmol) and cesiumcarbonate (41.6 mg, 127.8 µM) in DMF (0.6 ml) was heated in a microwave reactor at 100° C. for one hour. The reaction mixture was cooled to ambient temperature and conc. HCl (0.13 ml) was added slowly (gas evolution). The reaction was stirred at ambient temperature for 14 hours. The solvent was evaporated and the residue was extracted with dichloromethane (10 ml) and water (10 ml). The layers were separated and the aqueous layer was extracted with dichloromethane (2×10 ml). The combined organic layers were dried over sodium sulfate and the solvent was removed under reduced pressure. The title compound was obtained after HPLC separation in 3% yield (1 mg). ¹H-NMR (400 MHz, CD₂Cl₂, selected peaks): δ [ppm]=1.86 (m, 2H), 3.52 (m, 2H), 3.64 (m, 1H), 3.77 (m, 4H), 3.95 (m, 4H), 4.07 (m, 4H), 6.51 (s, 1H), 7.26 (d, 1H), 7.67 (d, 1H), 7.79 (d, 1H), 8.42 (d, 1H).

Example 288

N,N-dimethyl-3-[2-(morpholin-4-yl)-8-(1H-pyrazol-5-yl)-1,7-naphthyridin-4-yl]benzamide

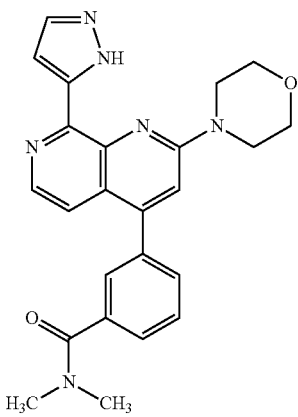 [SMILES: CN(C)C(=O)c1cccc(-c2cc(N3CCOCC3)nc3c(-c4ccn[nH]4)nccc23)c1]

To a solution of [3-(dimethylcarbamoyl)phenyl]boronic acid (530 µl, 0.57 M, 300 µmol) in 0.52 mL DMF was added 2-(morpholin-4-yl)-8-[2-(tetrahydropyran-2-yl)-2H-pyrazol-3-yl]-[1,7]naphthyridin-4-yl-trifluoromethanesulphonate (1.0 ml, 0.15 M, 150 µmol; Intermediate-3) in 1 mL DMF, aqueous sodium carbonate solution (200 µl, 2.3 M, 450 µmol) and 1,1'-bis(diphenylphosphino)ferrocenedichloropalladium(II) (400 µl, 0.038 M in DMF, 15 µmol). The reaction mixture was shaked at 90° C. for 12 h.

To the crude reaction mixture aqueous hydrochloric acid (240 µl, 1.9 M, 470 µmol) was added and the corresponding mixture was shaked over night at room temperature.

The reaction mixture was purified by preparative HPLC to give 22 mg of the product as solid material.

LC-MS Method 4: $R_t$=0.75 min; MS (ESIpos) m/z=429 [M+H]$^+$.

The following examples (Table 4) were prepared in analogy to example 288:

TABLE 4

| Example | Structure | Name | Retention time [min] | LC-MS m/z [M + H]$^+$ |
|---|---|---|---|---|
| 289 | 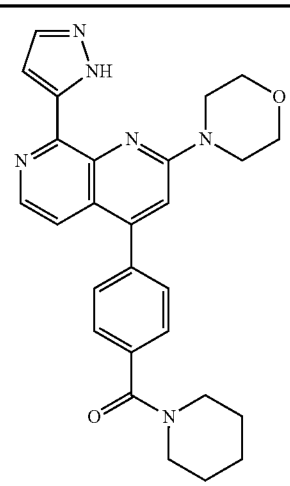 | {4-[2-(morpholin-4-yl)-8-(1H-pyrazol-5-yl)-1,7-naphthyridin-4-yl]phenyl}(piperidin-1-yl)methanone | 0.88 | 469 |
| 290 | 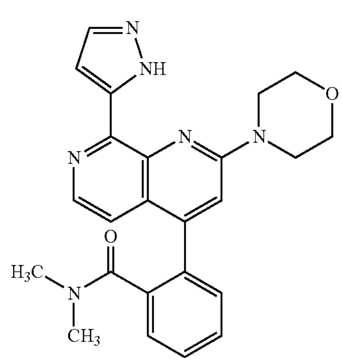 [SMILES: CN(C)C(=O)c1ccccc1-c1cc(N2CCOCC2)nc2c(-c3ccn[nH]3)nccc12] | N,N-dimethyl-2-[2-(morpholin-4-yl)-8-(1H-pyrazol-5-yl)-1,7-naphthyridin-4-yl]benzamide | 0.74 | 429 |

TABLE 4-continued

| Example | Structure | Name | Retention time [min] | LC-MS m/z [M + H]$^+$ |
|---|---|---|---|---|
| 291 | 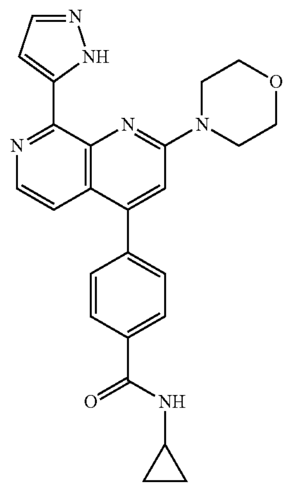 [SMILES: O=C(NC1CC1)c1ccc(-c2cc(N3CCOCC3)nc3c(-c4ccn[nH]4)nccc23)cc1] | N-cyclopropyl-4-[2-(morpholin-4-yl)-8-(1H-pyrazol-5-yl)-1,7-naphthyridin-4-yl]benzamide | 0.76 | 441 |
| 292 | 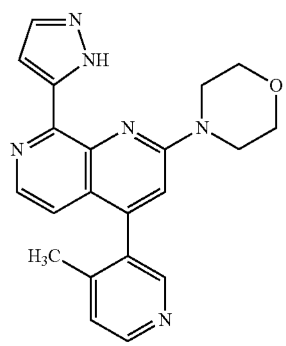 [SMILES: Cc1ccncc1-c1cc(N2CCOCC2)nc2c(-c3ccn[nH]3)nccc12] | 4-(4-methylpyridin-3-yl)-2-(morpholin-4-yl)-8-(1H-pyrazol-5-yl)-1,7-naphthyridine | 0.65 | 373 |
| 293 | 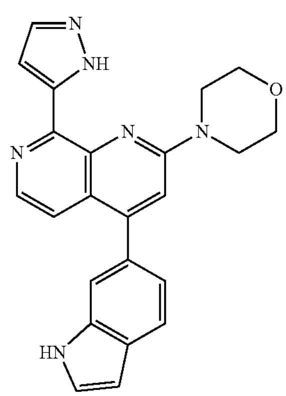 [SMILES: c1cc(-c2nccc3c(-c4ccc5cc[nH]c5c4)cc(N4CCOCC4)nc23)[nH]n1] | 4-(1H-indol-6-yl)-2-(morpholin-4-yl)-8-(1H-pyrazol-5-yl)-1,7-naphthyridine | 0.86 | 397 |
| 294 | 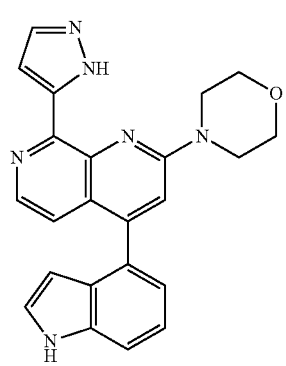 [SMILES: c1cc(-c2cc(N3CCOCC3)nc3c(-c4ccn[nH]4)nccc23)c2cc[nH]c2c1] | 4-(1H-indol-4-yl)-2-(morpholin-4-yl)-8-(1H-pyrazol-5-yl)-1,7-naphthyridine | 0.82 | 397 |

TABLE 4-continued

| Example | Structure | Name | Retention time [min] | LC-MS m/z [M + H]+ |
|---|---|---|---|---|
| 295 | 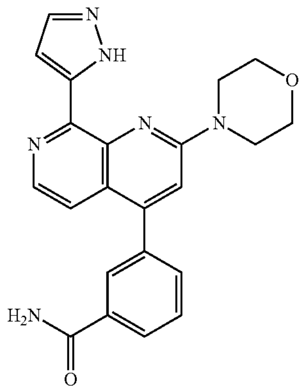 [SMILES: NC(=O)c1cccc(-c2cc(N3CCOCC3)nc3c(-c4ccn[nH]4)nccc23)c1] | 3-[2-(morpholin-4-yl)-8-(1H-pyrazol-5-yl)-1,7-naphthyridin-4-yl]benzamide | 0.68 | 401 |
| 296 | 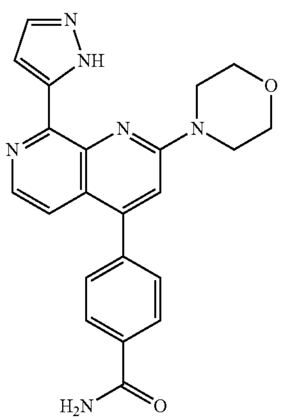 [SMILES: NC(=O)c1ccc(-c2cc(N3CCOCC3)nc3c(-c4ccn[nH]4)nccc23)cc1] | 4-[2-(morpholin-4-yl)-8-(1H-pyrazol-5-yl)-1,7-naphthyridin-4-yl]benzamide | 0.66 | 401 |
| 297 | 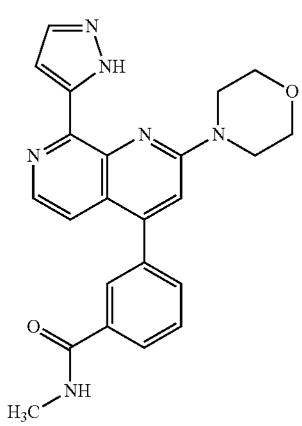 [SMILES: CNC(=O)c1cccc(-c2cc(N3CCOCC3)nc3c(-c4ccn[nH]4)nccc23)c1] | N-methyl-3-[2-(morpholin-4-yl)-8-(1H-pyrazol-5-yl)-1,7-naphthyridin-4-yl]benzamide | 0.71 | 415 |

TABLE 4-continued

| Example | Structure | Name | Retention time [min] | LC-MS m/z [M + H]+ |
| --- | --- | --- | --- | --- |
| 298 | 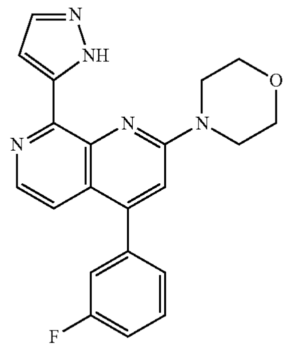 [SMILES: Fc1cccc(-c2cc(N3CCOCC3)nc3c(-c4ccn[nH]4)nccc23)c1] | 4-(3-fluorophenyl)-2-(morpholin-4-yl)-8-(1H-pyrazol-5-yl)-1,7-naphthyridine | 0.92 | 376 |
| 299 | 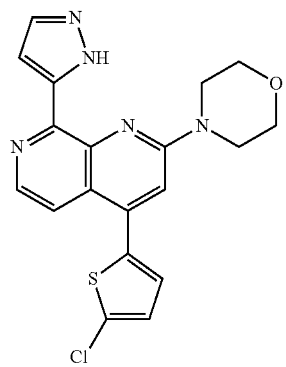 [SMILES: Clc1ccc(-c2cc(N3CCOCC3)nc3c(-c4ccn[nH]4)nccc23)s1] | 4-(5-chlorothiophen-2-yl)-2-(morpholin-4-yl)-8-(1H-pyrazol-5-yl)-1,7-naphthyridine | 1.06 | 398 |
| 300 | 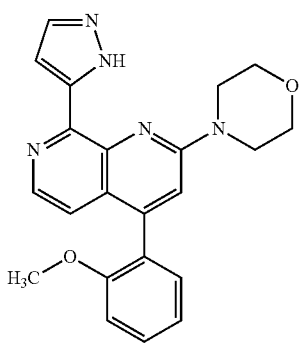 [SMILES: COc1ccccc1-c1cc(N2CCOCC2)nc2c(-c3ccn[nH]3)nccc12] | 4-(2-methoxyphenyl)-2-(morpholin-4-yl)-8-(1H-pyrazol-5-yl)-1,7-naphthyridine | 0.86 | 388 |
| 301 | 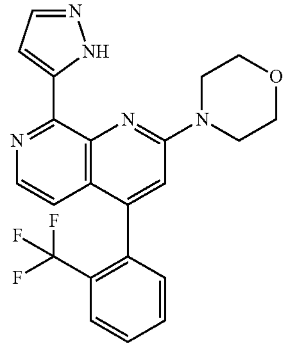 [SMILES: FC(F)(F)c1ccccc1-c1cc(N2CCOCC2)nc2c(-c3ccn[nH]3)nccc12] | 2-(morpholin-4-yl)-8-(1H-pyrazol-5-yl)-4-[2-(trifluoromethyl)phenyl]-1,7-naphthyridine | 1.00 | 426 |

TABLE 4-continued

| Example | Structure | Name | Retention time [min] | LC-MS m/z [M + H]+ |
| --- | --- | --- | --- | --- |
| 302 | 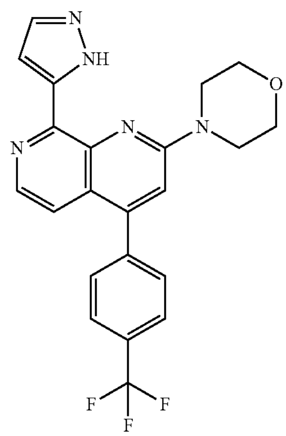 [SMILES: FC(F)(F)c1ccc(-c2cc(N3CCOCC3)nc3c(-c4ccn[nH]4)nccc23)cc1] | 2-(morpholin-4-yl)-8-(1H-pyrazol-5-yl)-4-[4-(trifluoromethyl)phenyl]-1,7-naphthyridine | 1.08 | 426 |
| 303 | 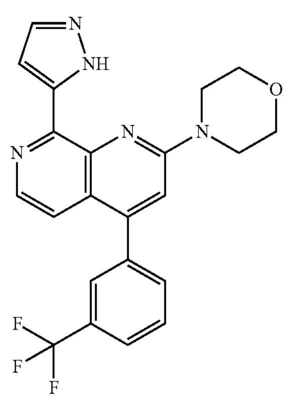 [SMILES: FC(F)(F)c1cccc(-c2cc(N3CCOCC3)nc3c(-c4ccn[nH]4)nccc23)c1] | 2-(morpholin-4-yl)-8-(1H-pyrazol-5-yl)-4-[3-(trifluoromethyl)phenyl]-1,7-naphthyridine | 1.06 | 426 |
| 304 | 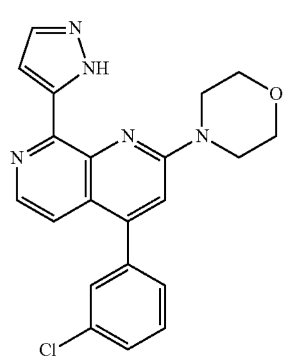 [SMILES: Clc1cccc(-c2cc(N3CCOCC3)nc3c(-c4ccn[nH]4)nccc23)c1] | 4-(3-chlorophenyl)-2-(morpholin-4-yl)-8-(1H-pyrazol-5-yl)-1,7-naphthyridine | 1.01 | 392 |

TABLE 4-continued

| Example | Structure | Name | Retention time [min] | LC-MS m/z [M + H]+ |
|---|---|---|---|---|
| 305 | 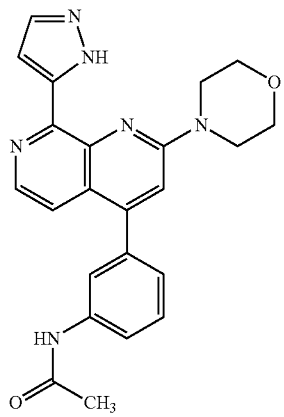 [SMILES: CC(=O)Nc1cccc(-c2cc(N3CCOCC3)nc3c(-c4ccn[nH]4)nccc23)c1] | N-{3-[2-(morpholin-4-yl)-8-(1H-pyrazol-5-yl)-1,7-naphthyridin-4-yl]phenyl}acetamide | 0.73 | 415 |
| 306 | 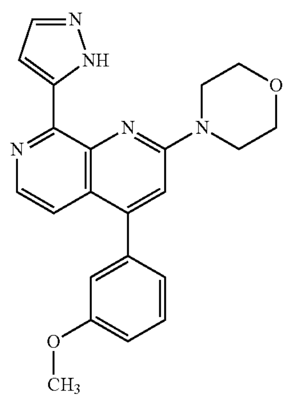 [SMILES: COc1cccc(-c2cc(N3CCOCC3)nc3c(-c4ccn[nH]4)nccc23)c1] | 4-(3-methoxyphenyl)-2-(morpholin-4-yl)-8-(1H-pyrazol-5-yl)-1,7-naphthyridine | 0.90 | 388 |
| 307 | 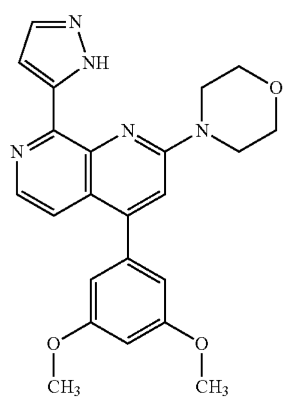 [SMILES: COc1cc(OC)cc(-c2cc(N3CCOCC3)nc3c(-c4ccn[nH]4)nccc23)c1] | 4-(3,5-dimethoxyphenyl)-2-(morpholin-4-yl)-8-(1H-pyrazol-5-yl)-1,7-naphthyridine | 0.93 | 418 |
| 308 | 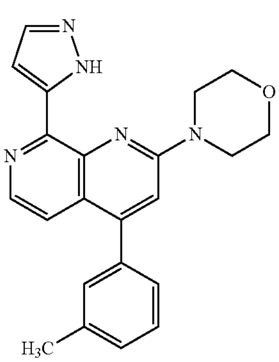 [SMILES: Cc1cccc(-c2cc(N3CCOCC3)nc3c(-c4ccn[nH]4)nccc23)c1] | 4-(3-methylphenyl)-2-(morpholin-4-yl)-8-(1H-pyrazol-5-yl)-1,7-naphthyridine | 0.96 | 372 |

TABLE 4-continued

| Example | Structure | Name | Retention time [min] | LC-MS m/z [M + H]+ |
|---|---|---|---|---|
| 309 | 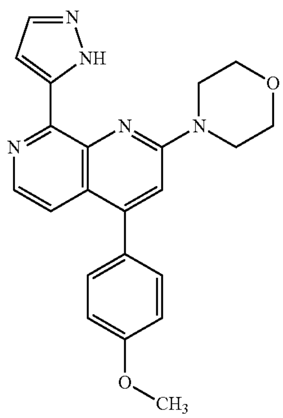 [SMILES: COc1ccc(-c2cc(N3CCOCC3)nc3c(-c4ccn[nH]4)nccc23)cc1] | 4-(4-methoxyphenyl)-2-(morpholin-4-yl)-8-(1H-pyrazol-5-yl)-1,7-naphthyridine | 0.88 | 388 |
| 310 | 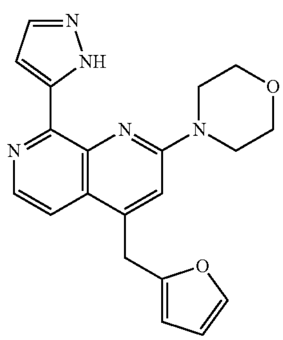 [SMILES: c1coc(Cc2cc(N3CCOCC3)nc3c(-c4ccn[nH]4)nccc23)c1] | 4-(furan-2-ylmethyl)-2-(morpholin-4-yl)-8-(1H-pyrazol-5-yl)-1,7-naphthyridine | 0.78 | 362 |
| 311 | 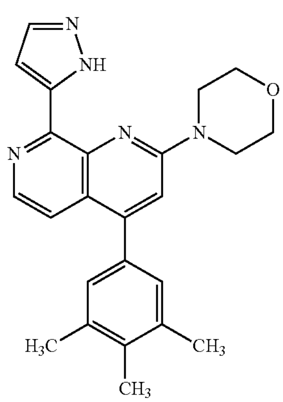 [SMILES: Cc1cc(-c2cc(N3CCOCC3)nc3c(-c4ccn[nH]4)nccc23)cc(C)c1C] | 2,6-dimethyl-4-[2-(morpholin-4-yl)-8-(1H-pyrazol-5-yl)-1,7-naphthyridin-4-yl]phenol | 0.83 | 402 |
| 312 | 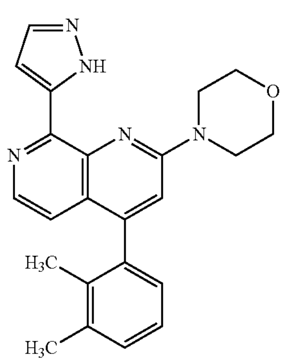 [SMILES: Cc1cccc(-c2cc(N3CCOCC3)nc3c(-c4ccn[nH]4)nccc23)c1C] | 4-(2,3-dimethylphenyl)-2-(morpholin-4-yl)-8-(1H-pyrazol-5-yl)-1,7-naphthyridine | 1.00 | 386 |

TABLE 4-continued

| Example | Structure | Name | Retention time [min] | LC-MS m/z [M + H]+ |
|---|---|---|---|---|
| 313 | 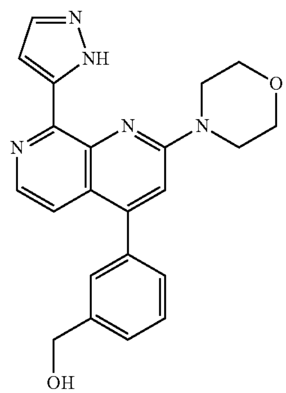 [SMILES: OCc1cccc(-c2cc(N3CCOCC3)nc3c(-c4ccn[nH]4)nccc23)c1] | {3-[2-(morpholin-4-yl)-8-(1H-pyrazol-5-yl)-1,7-naphthyridin-4-yl]phenyl}methanol | 0.73 | 388 |
| 314 | 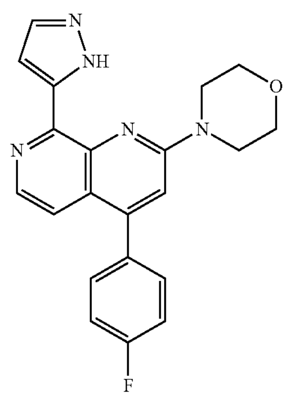 [SMILES: Fc1ccc(-c2cc(N3CCOCC3)nc3c(-c4ccn[nH]4)nccc23)cc1] | 4-(4-fluorophenyl)-2-(morpholin-4-yl)-8-(1H-pyrazol-5-yl)-1,7-naphthyridine | 0.90 | 376 |
| 315 | 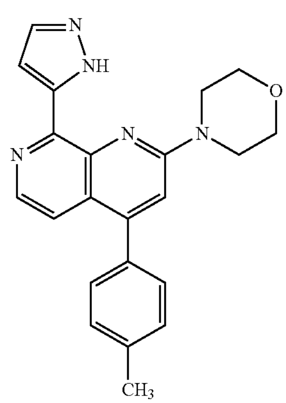 [SMILES: Cc1ccc(-c2cc(N3CCOCC3)nc3c(-c4ccn[nH]4)nccc23)cc1] | 4-(4-methylphenyl)-2-(morpholin-4-yl)-8-(1H-pyrazol-5-yl)-1,7-naphthyridine | 0.96 | 372 |
| 316 | 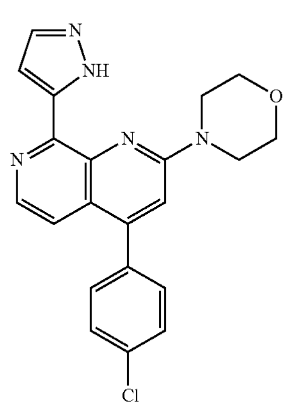 [SMILES: Clc1ccc(-c2cc(N3CCOCC3)nc3c(-c4ccn[nH]4)nccc23)cc1] | 4-(4-chlorophenyl)-2-(morpholin-4-yl)-8-(1H-pyrazol-5-yl)-1,7-naphthyridine | 1.01 | 392 |

TABLE 4-continued

| Example | Structure | Name | Retention time [min] | LC-MS m/z [M + H]+ |
|---|---|---|---|---|
| 317 | 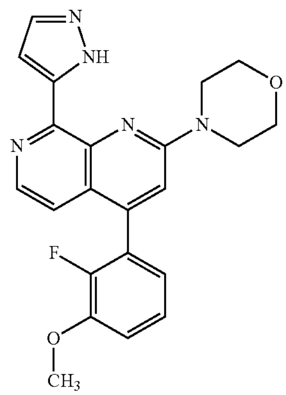 [SMILES: COc1cccc(-c2cc(N3CCOCC3)nc3c(-c4ccn[nH]4)nccc23)c1F] | 4-(2-fluoro-3-methoxyphenyl)-2-(morpholin-4-yl)-8-(1H-pyrazol-5-yl)-1,7-naphthyridine | 0.90 | 406 |
| 318 | 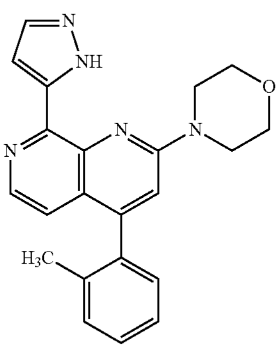 [SMILES: Cc1ccccc1-c1cc(N2CCOCC2)nc2c(-c3ccn[nH]3)nccc12] | 4-(2-methylphenyl)-2-(morpholin-4-yl)-8-(1H-pyrazol-5-yl)-1,7-naphthyridine | 0.94 | 372 |
| 319 | 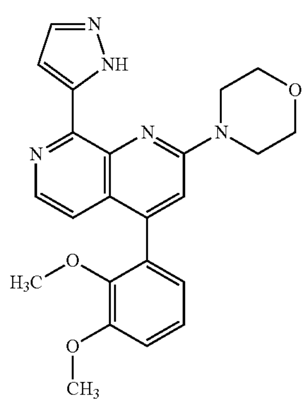 [SMILES: COc1cccc(-c2cc(N3CCOCC3)nc3c(-c4ccn[nH]4)nccc23)c1OC] | 4-(2,3-dimethoxyphenyl)-2-(morpholin-4-yl)-8-(1H-pyrazol-5-yl)-1,7-naphthyridine | 0.87 | 418 |
| 320 | 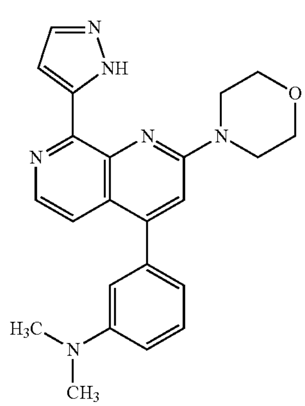 [SMILES: CN(C)c1cccc(-c2cc(N3CCOCC3)nc3c(-c4ccn[nH]4)nccc23)c1] | N,N-dimethyl-3-[2-(morpholin-4-yl)-8-(1H-pyrazol-5-yl)-1,7-naphthyridin-4-yl]aniline | 0.93 | 401 |

TABLE 4-continued

| Example | Structure | Name | Retention time [min] | LC-MS m/z [M + H]+ |
|---|---|---|---|---|
| 321 | 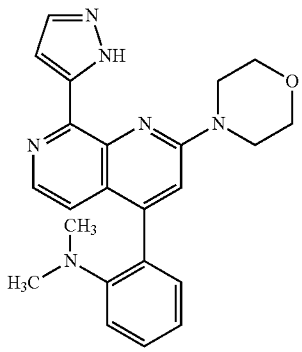 [SMILES: CN(C)c1ccccc1-c1cc(N2CCOCC2)nc2c(-c3ccn[nH]3)nccc12] | N,N-dimethyl-2-[2-(morpholin-4-yl)-8-(1H-pyrazol-5-yl)-1,7-naphthyridin-4-yl]aniline | 0.92 | 401 |
| 322 | 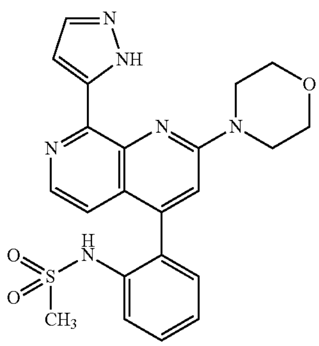 [SMILES: CS(=O)(=O)Nc1ccccc1-c1cc(N2CCOCC2)nc2c(-c3ccn[nH]3)nccc12] | N-{2-[2-(morpholin-4-yl)-8-(1H-pyrazol-5-yl)-1,7-naphthyridin-4-yl]phenyl}methanesulfonamide | 0.75 | 451 |
| 323 | 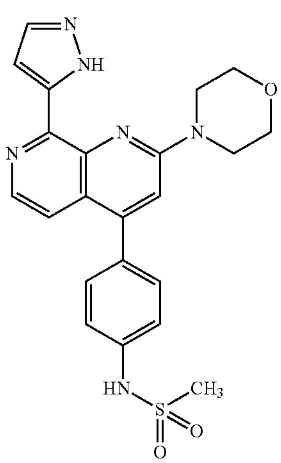 [SMILES: CS(=O)(=O)Nc1ccc(-c2cc(N3CCOCC3)nc3c(-c4ccn[nH]4)nccc23)cc1] | N-{4-[2-(morpholin-4-yl)-8-(1H-pyrazol-5-yl)-1,7-naphthyridin-4-yl]phenyl}methanesulfonamide | 0.74 | 451 |

TABLE 4-continued

| Example | Name | Retention time [min] | LC-MS m/z [M + H]+ |
|---|---|---|---|
| 324 | N,N-dimethyl-4-[2-(morpholin-4-yl)-8-(1H-pyrazol-5-yl)-1,7-naphthyridin-4-yl]benzamide | 0.74 | 429 |
| 325 | 2-(morpholin-4-yl)-4-[(1E)-prop-1-en-1-yl]-8-(1H-pyrazol-5-yl)-1,7-naphthyridine | 0.76 | 322 |
| 326 | 4-[2-(morpholin-4-yl)-8-(1H-pyrazol-5-yl)-1,7-naphthyridin-4-yl]phenol | 0.72 | 374 |
| 327 | 4-(2-fluorophenyl)-2-(morpholin-4-yl)-8-(1H-pyrazol-5-yl)-1,7-naphthyridine | 0.90 | 376 |

TABLE 4-continued

| Example | Structure | Name | Retention time [min] | LC-MS m/z [M + H]+ |
|---|---|---|---|---|
| 328 | 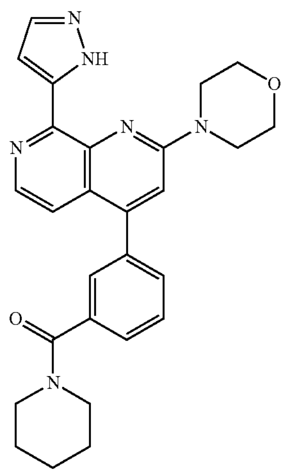 [SMILES: O=C(c1cccc(-c2cc(N3CCOCC3)nc3c(-c4ccn[nH]4)nccc23)c1)N1CCCCC1] | {3-[2-(morpholin-4-yl)-8-(1H-pyrazol-5-yl)-1,7-naphthyridin-4-yl]phenyl}(piperidin-1-yl)methanone | 0.88 | 469 |
| 329 | 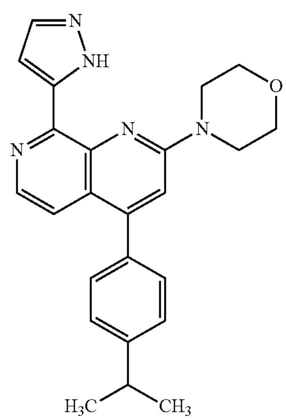 [SMILES: CC(C)c1ccc(-c2cc(N3CCOCC3)nc3c(-c4ccn[nH]4)nccc23)cc1] | 2-(morpholin-4-yl)-4-[4-(propan-2-yl)phenyl]-8-(1H-pyrazol-5-yl)-1,7-naphthyridine | 1.12 | 400 |
| 330 | 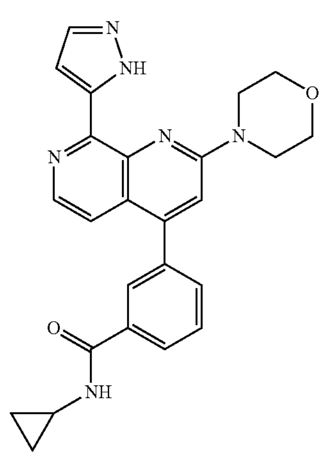 [SMILES: O=C(NC1CC1)c1cccc(-c2cc(N3CCOCC3)nc3c(-c4ccn[nH]4)nccc23)c1] | N-cyclopropyl-3-[2-(morpholin-4-yl)-8-(1H-pyrazol-5-yl)-1,7-naphthyridin-4-yl]benzamide | 0.77 | 441 |

TABLE 4-continued

| Example | Structure | Name | Retention time [min] | LC-MS m/z [M + H]⁺ |
|---|---|---|---|---|
| 331 | 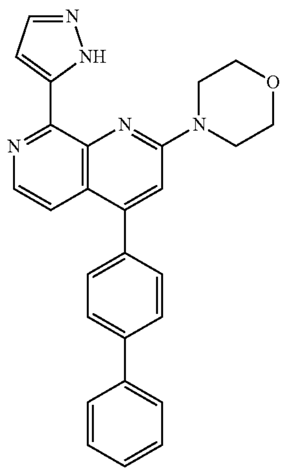 [SMILES: c1ccc(-c2ccc(-c3cc(N4CCOCC4)nc4c(-c5ccn[nH]5)nccc34)cc2)cc1] | 4-(biphenyl-4-yl)-2-(morpholin-4-yl)-8-(1H-pyrazol-5-yl)-1,7-naphthyridine | 1.14 | 434 |
| 332 | 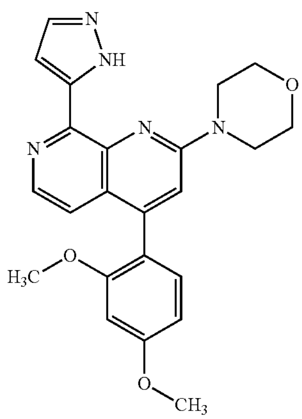 [SMILES: COc1ccc(-c2cc(N3CCOCC3)nc3c(-c4ccn[nH]4)nccc23)c(OC)c1] | 4-(2,4-dimethoxyphenyl)-2-(morpholin-4-yl)-8-(1H-pyrazol-5-yl)-1,7-naphthyridine | 0.87 | 418 |
| 333 | 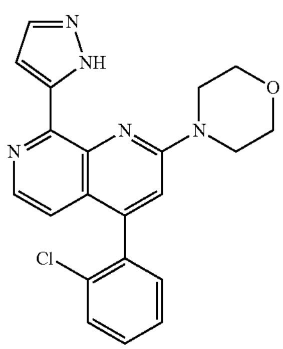 [SMILES: Clc1ccccc1-c1cc(N2CCOCC2)nc2c(-c3ccn[nH]3)nccc12] | 4-(2-chlorophenyl)-2-(morpholin-4-yl)-8-(1H-pyrazol-5-yl)-1,7-naphthyridine | 0.96 | 392 |
| 334 | 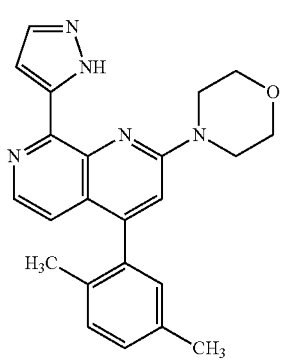 [SMILES: Cc1ccc(C)c(-c2cc(N3CCOCC3)nc3c(-c4ccn[nH]4)nccc23)c1] | 4-(2,5-dimethylphenyl)-2-(morpholin-4-yl)-8-(1H-pyrazol-5-yl)-1,7-naphthyridine | 1.02 | 386 |

TABLE 4-continued

| Example | Structure | Name | Retention time [min] | LC-MS m/z [M + H]+ |
|---|---|---|---|---|
| 335 | 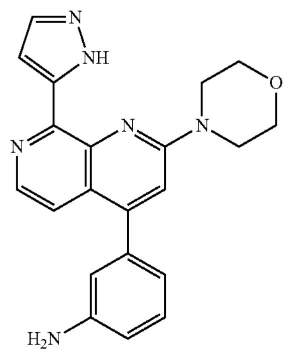 [SMILES: Nc1cccc(-c2cc(N3CCOCC3)nc3c(-c4ccn[nH]4)nccc23)c1] | 3-[2-(morpholin-4-yl)-8-(1H-pyrazol-5-yl)-1,7-naphthyridin-4-yl]aniline | 0.72 | 373 |
| 336 | 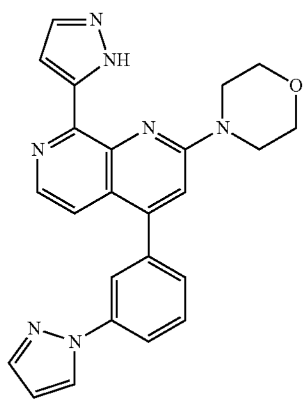 [SMILES: c1cc(-c2cc(N3CCOCC3)nc3c(-c4ccn[nH]4)nccc23)cc(-n2cccn2)c1] | 2-(morpholin-4-yl)-8-(1H-pyrazol-5-yl)-4-[3-(1H-pyrazol-1-yl)phenyl]-1,7-naphthyridine | 0.89 | 424 |
| 337 | 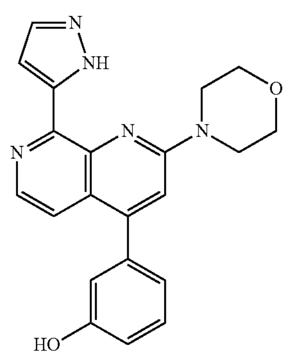 [SMILES: Oc1cccc(-c2cc(N3CCOCC3)nc3c(-c4ccn[nH]4)nccc23)c1] | 3-[2-(morpholin-4-yl)-8-(1H-pyrazol-5-yl)-1,7-naphthyridin-4-yl]phenol | 0.75 | 374 |
| 338 | 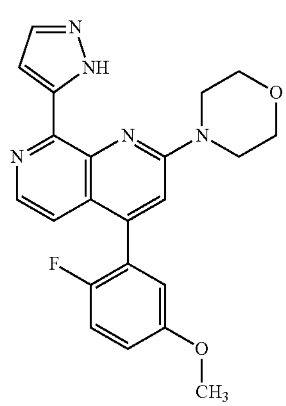 [SMILES: COc1ccc(F)c(-c2cc(N3CCOCC3)nc3c(-c4ccn[nH]4)nccc23)c1] | 4-(2-fluoro-5-methoxyphenyl)-2-(morpholin-4-yl)-8-(1H-pyrazol-5-yl)-1,7-naphthyridine | 0.93 | 406 |

TABLE 4-continued

| Example | Structure | Name | Retention time [min] | LC-MS m/z [M + H]+ |
|---|---|---|---|---|
| 339 | 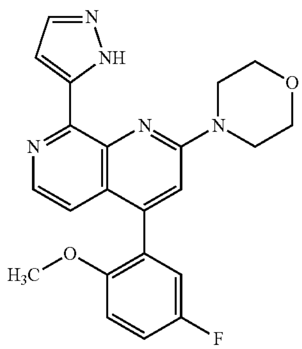 [SMILES: COc1ccc(F)cc1-c1cc(N2CCOCC2)nc2c(-c3ccn[nH]3)nccc12] | 4-(5-fluoro-2-methoxyphenyl)-2-(morpholin-4-yl)-8-(1H-pyrazol-5-yl)-1,7-naphthyridine | 0.90 | 406 |
| 340 | 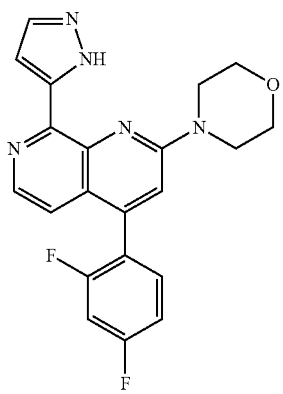 [SMILES: Fc1ccc(-c2cc(N3CCOCC3)nc3c(-c4ccn[nH]4)nccc23)c(F)c1] | 4-(2,4-difluorophenyl)-2-(morpholin-4-yl)-8-(1H-pyrazol-5-yl)-1,7-naphthyridine | 0.94 | 394 |
| 341 | 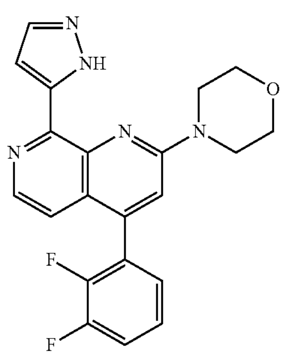 [SMILES: Fc1cccc(-c2cc(N3CCOCC3)nc3c(-c4ccn[nH]4)nccc23)c1F] | 4-(2,3-difluorophenyl)-2-(morpholin-4-yl)-8-(1H-pyrazol-5-yl)-1,7-naphthyridine | 0.95 | 394 |
| 342 | 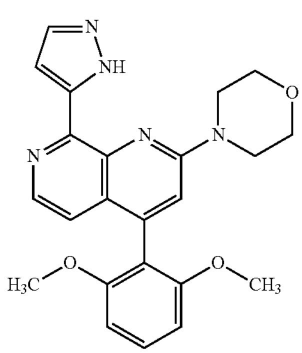 [SMILES: COc1cccc(OC)c1-c1cc(N2CCOCC2)nc2c(-c3ccn[nH]3)nccc12] | 4-(2,6-dimethoxyphenyl)-2-(morpholin-4-yl)-8-(1H-pyrazol-5-yl)-1,7-naphthyridine | 0.85 | 418 |

TABLE 4-continued

| Example | Structure | Name | Retention time [min] | LC-MS m/z [M + H]+ |
|---|---|---|---|---|
| 343 | 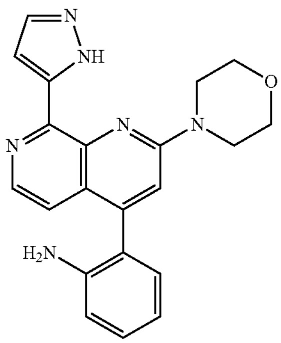 [SMILES: Nc1ccccc1-c1cc(N2CCOCC2)nc2c(-c3ccn[nH]3)nccc12] | 2-[2-(morpholin-4-yl)-8-(1H-pyrazol-5-yl)-1,7-naphthyridin-4-yl]aniline | 0.79 | 373 |
| 344 | 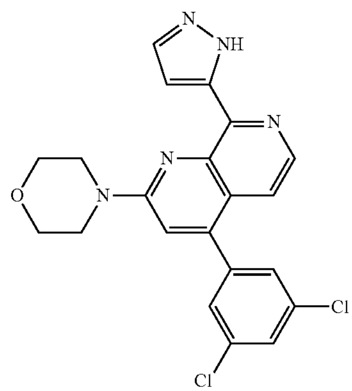 [SMILES: Clc1cc(Cl)cc(-c2cc(N3CCOCC3)nc3c(-c4ccn[nH]4)nccc23)c1] | 4-(3,5-dichlorophenyl)-2-(morpholin-4-yl)-8-(1H-pyrazol-5-yl)-1,7-naphthyridine | 1.19 | 426 |
| 345 | 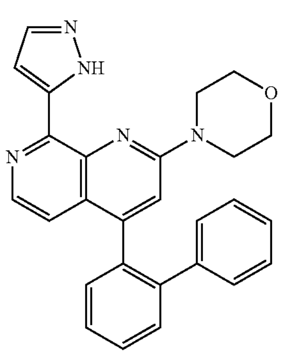 [SMILES: c1ccc(-c2ccccc2-c2cc(N3CCOCC3)nc3c(-c4ccn[nH]4)nccc23)cc1] | 4-(biphenyl-2-yl)-2-(morpholin-4-yl)-8-(1H-pyrazol-5-yl)-1,7-naphthyridine | 1.05 | 434 |

The examples in the following table (Table 5) were prepared in analogy to this procedure:

To 2-5 eq of boronic acid derivative were added 0.15 mmol 2-(morpholin-4-yl)-8-[1-(tetrahydro-2H-pyran-2-yl)-1H-pyrazol-5-yl]-1,7-naphthyridin-4-yl trifluoromethanesulfonate (0.25 M in NMP, 600 μL), 30 μmol 1,1'-BIS(DIPHENYLPHOSPHINO)FERROCENE] DICHLOROPALLADIUM(II) (0.04 M in NMP, 750 μL) and 0.45 mmol potassium carbonate (1 M in water, 450 μL) and the mixture was heated in a microwave oven at 110° C. for 5 hours. After cooling, 0.9 mmol HCl (2M in water, 450 μL) were added and the mixture was heated in a microwave oven for 10 hours at 50° C. After cooling, the mixture was filtered, washed with NMP and subjected to preparative HPLC to yield the target product.

LC-MS Method 4

TABLE 5

| Example | Structure | Name | Retention time [min] | LC-MS m/z [M + H]+ |
|---------|-----------|------|----------------------|---------------------|
| 346 | 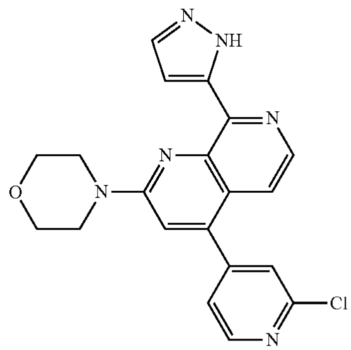 [SMILES: Clc1cc(-c2cc(N3CCOCC3)nc3c(-c4ccn[nH]4)nccc23)ccn1] | 4-(2-chloropyridin-4-yl)-2-(morpholin-4-yl)-8-(1H-pyrazol-5-yl)-1,7-naphthyridine | 0.84 | 393.8 |
| 347 | 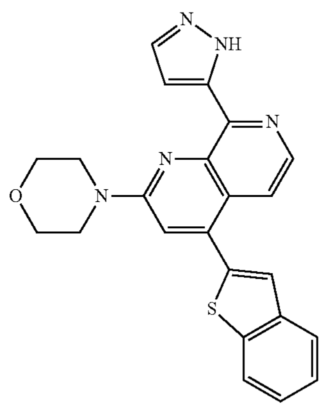 [SMILES: c1ccc2sc(-c3cc(N4CCOCC4)nc4c(-c5ccn[nH]5)nccc34)cc2c1] | 4-(1-benzothiophen-2-yl)-2-(morpholin-4-yl)-8-(1H-pyrazol-5-yl)-1,7-naphthyridine | 1.1 | 414.5 |
| 348 | 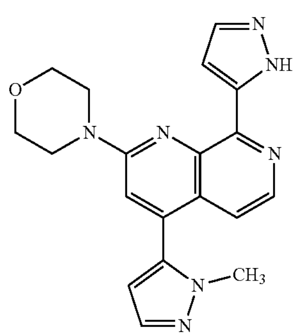 [SMILES: Cn1nccc1-c1cc(N2CCOCC2)nc2c(-c3ccn[nH]3)nccc12] | 4-(1-methyl-1H-pyrazol-5-yl)-2-(morpholin-4-yl)-8-(1H-pyrazol-5-yl)-1,7-naphthyridine | 0.71 | 362.4 |
| 349 | 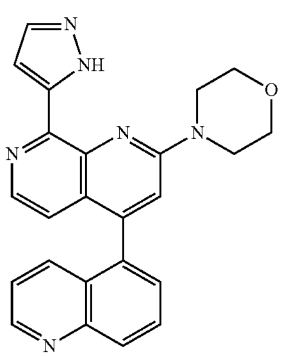 [SMILES: c1cc(-c2cc(N3CCOCC3)nc3c(-c4ccn[nH]4)nccc23)c2cccnc2c1] | 2-(morpholin-4-yl)-8-(1H-pyrazol-5-yl)-4-(quinolin-5-yl)-1,7-naphthyridine | 0.74 | 409.5 |

TABLE 5-continued

| Example | Structure | Name | Retention time [min] | LC-MS m/z [M + H]+ |
|---|---|---|---|---|
| 350 | 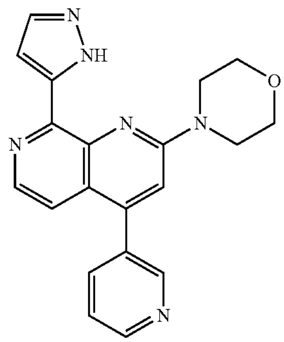 [SMILES: c1cncc(-c2cc(N3CCOCC3)nc3c(-c4ccn[nH]4)nccc23)c1] | 2-(morpholin-4-yl)-8-(1H-pyrazol-5-yl)-4-(pyridin-3-yl)-1,7-naphthyridine | 0.66 | 359.4 |
| 351 | 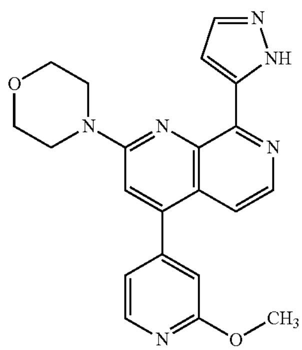 [SMILES: COc1cc(-c2cc(N3CCOCC3)nc3c(-c4ccn[nH]4)nccc23)ccn1] | 4-(2-methoxypyridin-4-yl)-2-(morpholin-4-yl)-8-(1H-pyrazol-5-yl)-1,7-naphthyridine | 0.83 | 389.4 |
| 352 | 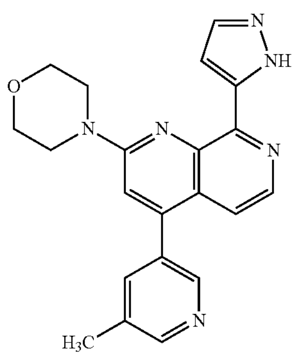 [SMILES: Cc1cncc(-c2cc(N3CCOCC3)nc3c(-c4ccn[nH]4)nccc23)c1] | 4-(5-methylpyridin-3-yl)-2-(morpholin-4-yl)-8-(1H-pyrazol-5-yl)-1,7-naphthyridine | 0.7 | 373.4 |
| 353 | 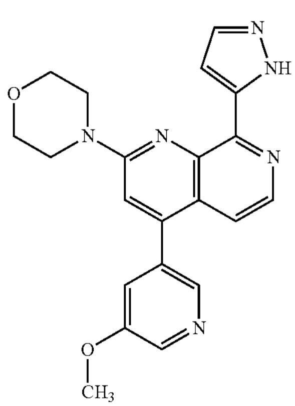 [SMILES: COc1cncc(-c2cc(N3CCOCC3)nc3c(-c4ccn[nH]4)nccc23)c1] | 4-(5-methoxypyridin-3-yl)-2-(morpholin-4-yl)-8-(1H-pyrazol-5-yl)-1,7-naphthyridine | 0.73 | 389.4 |

TABLE 5-continued

| Example | Structure | Name | Retention time [min] | LC-MS m/z [M + H]+ |
|---|---|---|---|---|
| 354 | 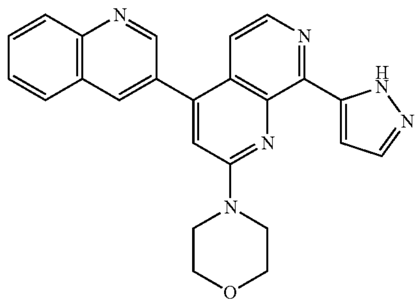 [SMILES: c1ccc2ncc(-c3cc(N4CCOCC4)nc4c(-c5ccn[nH]5)nccc34)cc2c1] | 2-(morpholin-4-yl)-8-(1H-pyrazol-5-yl)-4-(quinolin-3-yl)-1,7-naphthyridine | 0.84 | 409.5 |
| 355 | 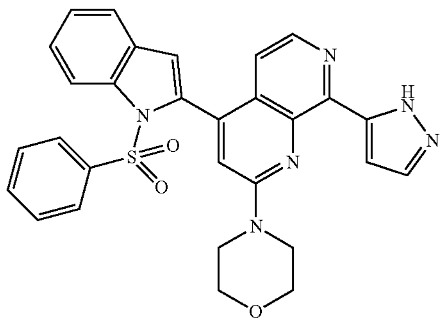 [SMILES: O=S(=O)(c1ccccc1)n1c(-c2cc(N3CCOCC3)nc3c(-c4ccn[nH]4)nccc23)cc2ccccc21] | 2-(morpholin-4-yl)-4-[1-(phenylsulfonyl)-1H-indol-2-yl]-8-(1H-pyrazol-5-yl)-1,7-naphthyridine | 1.12 | 537.6 |
| 356 | 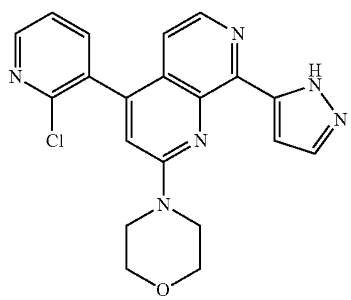 [SMILES: Clc1ncccc1-c1cc(N2CCOCC2)nc2c(-c3ccn[nH]3)nccc12] | 4-(2-chloropyridin-3-yl)-2-(morpholin-4-yl)-8-(1H-pyrazol-5-yl)-1,7-naphthyridine | 0.77 | 393.8 |
| 357 | 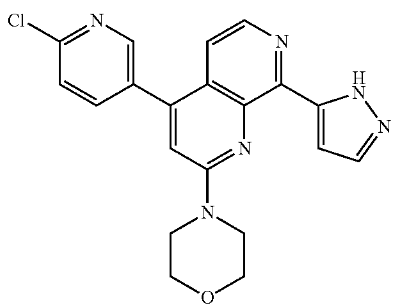 [SMILES: Clc1ccc(-c2cc(N3CCOCC3)nc3c(-c4ccn[nH]4)nccc23)cn1] | 4-(6-chloropyridin-3-yl)-2-(morpholin-4-yl)-8-(1H-pyrazol-5-yl)-1,7-naphthyridine | 0.82 | 393.8 |
| 358 | 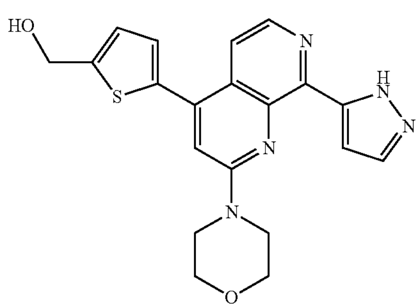 [SMILES: OCc1ccc(-c2cc(N3CCOCC3)nc3c(-c4ccn[nH]4)nccc23)s1] | {5-[2-(morpholin-4-yl)-8-(1H-pyrazol-5-yl)-1,7-naphthyridin-4-yl]thiophen-2-yl}methanol | 0.73 | 394.5 |

TABLE 5-continued

| Example | Structure | Name | Retention time [min] | LC-MS m/z [M + H]+ |
|---|---|---|---|---|
| 359 | 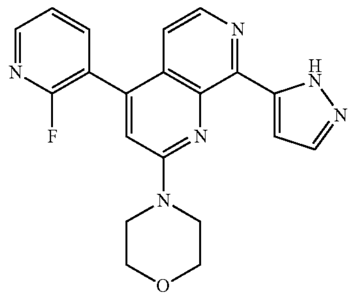 [SMILES: Fc1ncccc1-c1cc(N2CCOCC2)nc2c(-c3ccn[nH]3)nccc12] | 4-(2-fluoropyridin-3-yl)-2-(morpholin-4-yl)-8-(1H-pyrazol-5-yl)-1,7-naphthyridine | 0.75 | 377.4 |
| 360 | 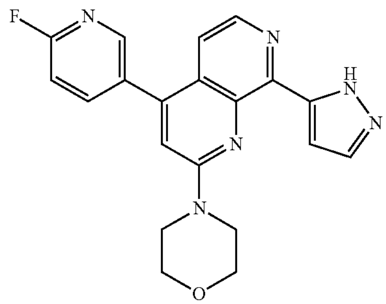 [SMILES: Fc1ccc(-c2cc(N3CCOCC3)nc3c(-c4ccn[nH]4)nccc23)cn1] | 4-(6-fluoropyridin-3-yl)-2-(morpholin-4-yl)-8-(1H-pyrazol-5-yl)-1,7-naphthyridine | 0.77 | 377.4 |
| 361 | 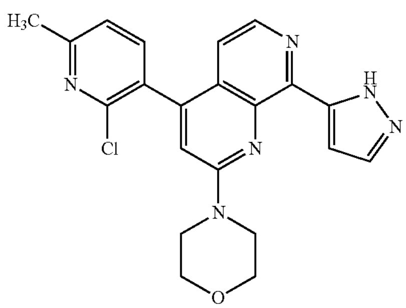 [SMILES: Cc1ccc(-c2cc(N3CCOCC3)nc3c(-c4ccn[nH]4)nccc23)c(Cl)n1] | 4-(2-chloro-6-methylpyridin-3-yl)-2-(morpholin-4-yl)-8-(1H-pyrazol-5-yl)-1,7-naphthyridine | 0.83 | 407.9 |
| 362 | 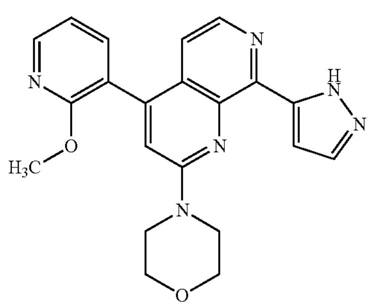 [SMILES: COc1ncccc1-c1cc(N2CCOCC2)nc2c(-c3ccn[nH]3)nccc12] | 4-(2-methoxypyridin-3-yl)-2-(morpholin-4-yl)-8-(1H-pyrazol-5-yl)-1,7-naphthyridine | 0.79 | 389.4 |
| 363 | 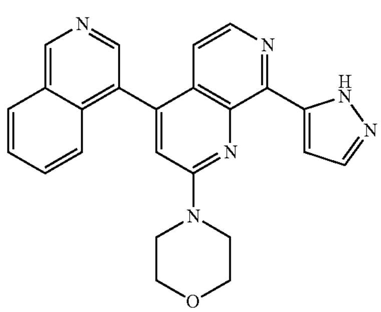 [SMILES: c1ccc2c(-c3cc(N4CCOCC4)nc4c(-c5ccn[nH]5)nccc34)cncc2c1] | 4-(isoquinolin-4-yl)-2-(morpholin-4-yl)-8-(1H-pyrazol-5-yl)-1,7-naphthyridine | 0.77 | 409.5 |

TABLE 5-continued

| Example | Structure | Name | Retention time [min] | LC-MS m/z [M + H]+ |
|---|---|---|---|---|
| 364 | 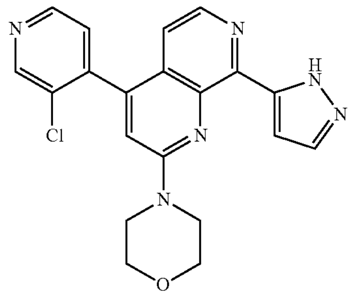 [SMILES: Clc1cnccc1-c1cc(N2CCOCC2)nc2c(-c3ccn[nH]3)nccc12] | 4-(3-chloropyridin-4-yl)-2-(morpholin-4-yl)-8-(1H-pyrazol-5-yl)-1,7-naphthyridine | 0.79 | 393.8 |
| 365 | 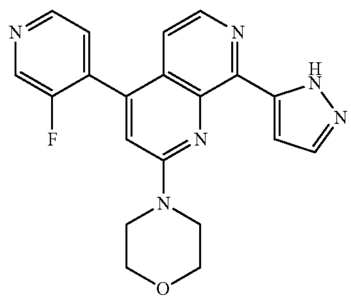 [SMILES: Fc1cnccc1-c1cc(N2CCOCC2)nc2c(-c3ccn[nH]3)nccc12] | 4-(3-fluoropyridin-4-yl)-2-(morpholin-4-yl)-8-(1H-pyrazol-5-yl)-1,7-naphthyridine | 0.74 | 377.4 |
| 366 | 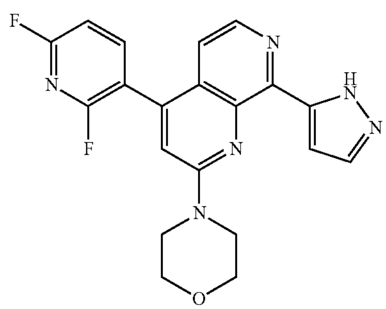 [SMILES: Fc1ccc(-c2cc(N3CCOCC3)nc3c(-c4ccn[nH]4)nccc23)c(F)n1] | 4-(2,6-difluoropyridin-3-yl)-2-(morpholin-4-yl)-8-(1H-pyrazol-5-yl)-1,7-naphthyridine | 0.85 | 395.4 |
| 367 | 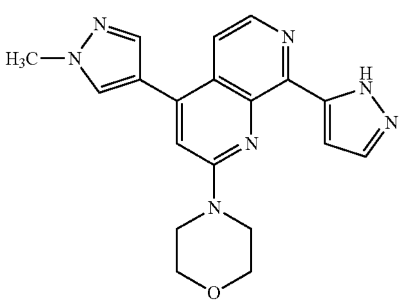 [SMILES: Cn1cc(-c2cc(N3CCOCC3)nc3c(-c4ccn[nH]4)nccc23)cn1] | 4-(1-methyl-1H-pyrazol-4-yl)-2-(morpholin-4-yl)-8-(1H-pyrazol-5-yl)-1,7-naphthyridine | 0.67 | 362.4 |
| 368 | 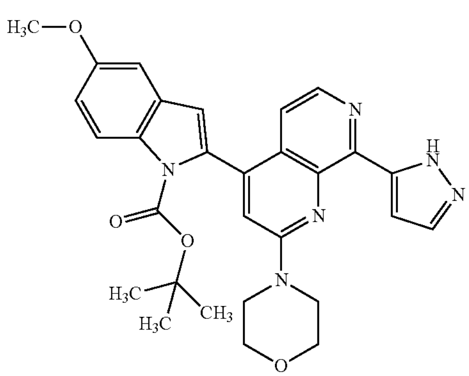 [SMILES: COc1ccc2c(c1)cc(-c1cc(N3CCOCC3)nc3c(-c4ccn[nH]4)nccc13)n2C(=O)OC(C)(C)C] | tert-butyl 5-methoxy-2[2-(morpholin-4-yl)-8-(1H-pyrazol-5-yl)-1,7-naphthyridin-4-yl]-1H-indole-1-carboxylate | 1.19 | 527.6 |

TABLE 5-continued

| Example | Structure | Name | Retention time [min] | LC-MS m/z [M + H]+ |
|---|---|---|---|---|
| 369 | 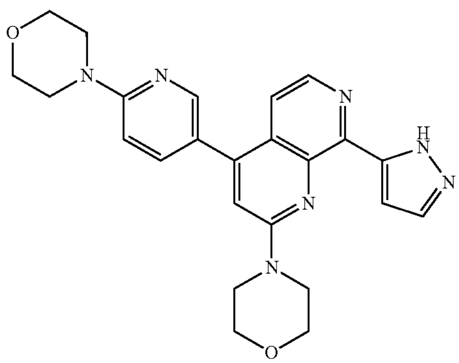 [SMILES: c1cc(-c2nccc3c(-c4ccc(N5CCOCC5)nc4)cc(N4CCOCC4)nc23)[nH]n1] | 2-(morpholin-4-yl)-4-[6-(morpholin-4-yl)pyridin-3-yl]-8-(1H-pyrazol-5-yl)-1,7-naphthyridine | 0.76 | 444.5 |
| 370 | 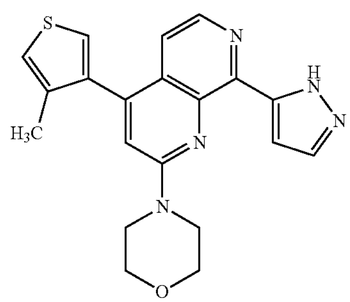 [SMILES: Cc1cscc1-c1cc(N2CCOCC2)nc2c(-c3ccn[nH]3)nccc12] | 4-(4-methylthiophen-3-yl)-2-(morpholin-4-yl)-8-(1H-pyrazol-5-yl)-1,7-naphthyridine | 0.9 | 378.5 |
| 371 | 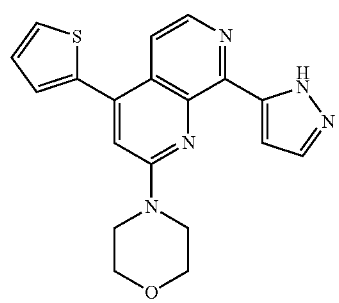 [SMILES: c1csc(-c2cc(N3CCOCC3)nc3c(-c4ccn[nH]4)nccc23)c1] | 2-(morpholin-4-yl)-8-(1H-pyrazol-5-yl)-4-(thiophen-2-yl)-1,7-naphthyridine | 0.87 | 364.4 |
| 372 | 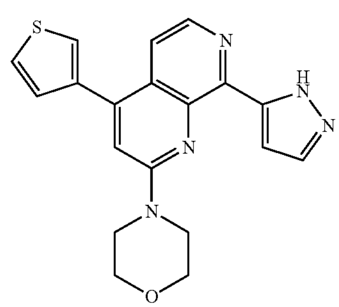 [SMILES: c1cc(-c2nccc3c(-c4ccsc4)cc(N4CCOCC4)nc23)[nH]n1] | 2-(morpholin-4-yl)-8-(1H-pyrazol-5-yl)-4-(thiophen-3-yl)-1,7-naphthyridine | 0.83 | 364.4 |

TABLE 5-continued

| Example | Structure | Name | Retention time [min] | LC-MS m/z [M + H]+ |
|---|---|---|---|---|
| 373 | 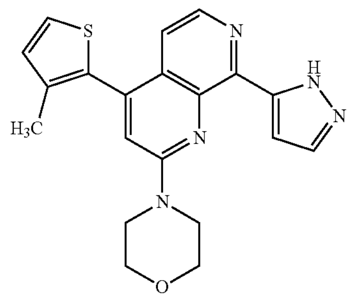 [SMILES: Cc1ccsc1-c1cc(N2CCOCC2)nc2c(-c3ccn[nH]3)nccc12] | 4-(3-methylthiophen-2-yl)-2-(morpholin-4-yl)-8-(1H-pyrazol-5-yl)-1,7-naphthyridine | 0.93 | 378.5 |
| 374 | 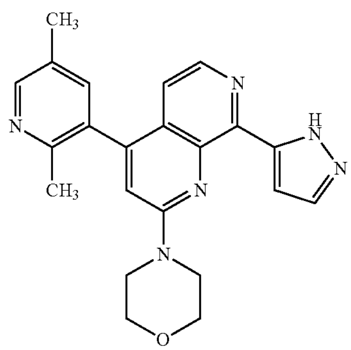 [SMILES: Cc1cnc(C)c(-c2cc(N3CCOCC3)nc3c(-c4ccn[nH]4)nccc23)c1] | 4-(2-chloro-5-methylpyridin-3-yl)-2-(morpholin-4-yl)-8-(1H-pyrazol-5-yl)-1,7-naphthyridine | 0.84 | 407.9 |
| 375 | 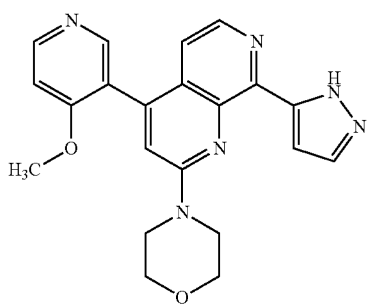 [SMILES: COc1ccncc1-c1cc(N2CCOCC2)nc2c(-c3ccn[nH]3)nccc12] | 4-(4-methoxypyridin-3-yl)-2-(morpholin-4-yl)-8-(1H-pyrazol-5-yl)-1,7-naphthyridine | 0.56 | 389.4 |
| 376 | 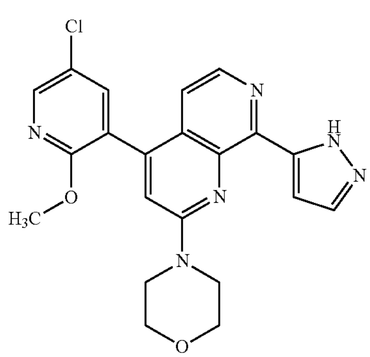 [SMILES: COc1ncc(Cl)cc1-c1cc(N2CCOCC2)nc2c(-c3ccn[nH]3)nccc12] | 4-(5-chloro-2-methoxypyridin-3-yl)-2-(morpholin-4-yl)-8-(1H-pyrazol-5-yl)-1,7-naphthyridine | 0.96 | 423.9 |

TABLE 5-continued

| Example | Structure | Name | Retention time [min] | LC-MS m/z [M + H]+ |
|---|---|---|---|---|
| 377 | 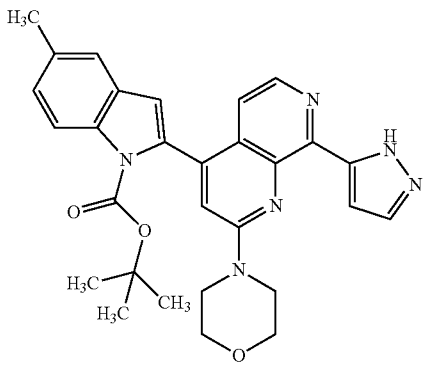 [SMILES: Cc1ccc2c(c1)cc(-c1cc(N3CCOCC3)nc3c(-c4ccn[nH]4)nccc13)n2C(=O)OC(C)(C)C] | tert-butyl 5-methyl-2-[2-(morpholin-4-yl)-8-(1H-pyrazol-5-yl)-1,7-naphthyridin-4-yl]-1H-indole-1-carboxylate | 1.29 | 511.6 |
| 378 | 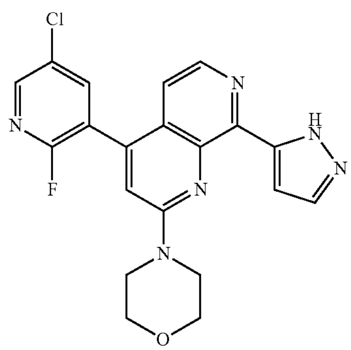 [SMILES: Fc1ncc(Cl)cc1-c1cc(N2CCOCC2)nc2c(-c3ccn[nH]3)nccc12] | 4-(5-chloro-2-fluoropyridin-3-yl)-2-(morpholin-4-yl)-8-(1H-pyrazol-5-yl)-1,7-naphthyridine | 0.91 | 411.8 |
| 379 | 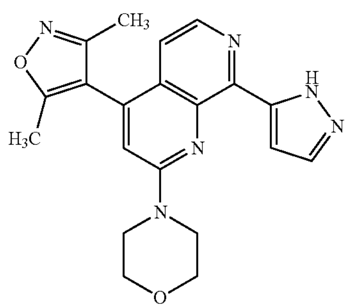 [SMILES: Cc1noc(C)c1-c1cc(N2CCOCC2)nc2c(-c3ccn[nH]3)nccc12] | 4-(3,5-dimethyl-1,2-oxazol-4-yl)-2-(morpholin-4-yl)-8-(1H-pyrazol-5-yl)-1,7-naphthyridine | 0.77 | 377.4 |
| 380 | 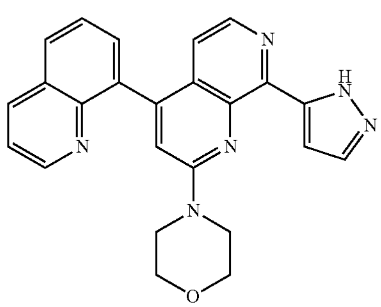 [SMILES: c1cnc2c(-c3cc(N4CCOCC4)nc4c(-c5ccn[nH]5)nccc34)cccc2c1] | 2-(morpholin-4-yl)-8-(1H-pyrazol-5-yl)-4-(quinolin-8-yl)-1,7-naphthyridine | 0.81 | 409.5 |

TABLE 5-continued

| Example | Structure | Name | Retention time [min] | LC-MS m/z [M + H]+ |
|---|---|---|---|---|
| 381 | 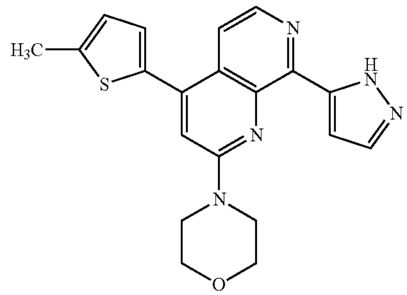 [SMILES: Cc1ccc(-c2cc(N3CCOCC3)nc3c(-c4ccn[nH]4)nccc23)s1] | 4-(5-methylthiophen-2-yl)-2-(morpholin-4-yl)-8-(1H-pyrazol-5-yl)-1,7-naphthyridine | 0.95 | 378.5 |
| 382 | 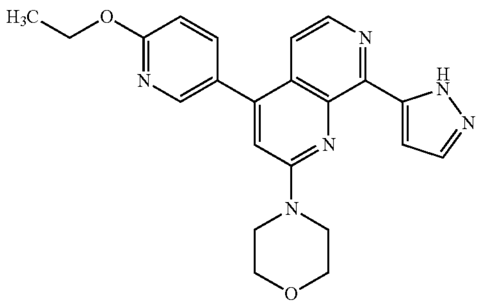 [SMILES: CCOc1ccc(-c2cc(N3CCOCC3)nc3c(-c4ccn[nH]4)nccc23)cn1] | 4-(6-ethoxypyridin-3-yl)-2-(morpholin-4-yl)-8-(1H-pyrazol-5-yl)-1,7-naphthyridine | 0.9 | 403.4 |
| 383 | 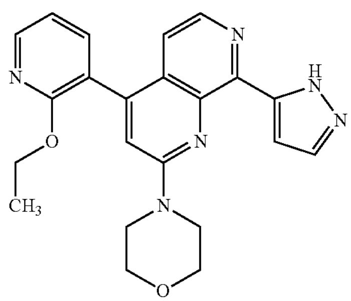 [SMILES: CCOc1ncccc1-c1cc(N2CCOCC2)nc2c(-c3ccn[nH]3)nccc12] | 4-(2-ethoxypyridin-3-yl)-2-(morpholin-4-yl)-8-(1H-pyrazol-5-yl)-1,7-naphthyridine | 0.85 | 403.4 |
| 384 | 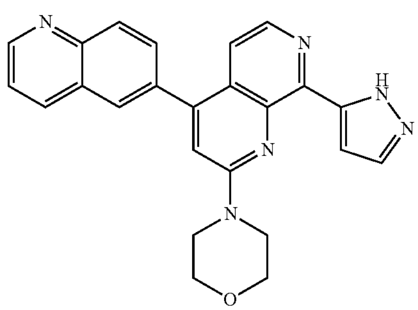 [SMILES: c1cnc2ccc(-c3cc(N4CCOCC4)nc4c(-c5ccn[nH]5)nccc34)cc2c1] | 2-(morpholin-4-yl)-8-(1H-pyrazol-5-yl)-4-(quinolin-6-yl)-1,7-naphthyridine | 0.74 | 409.5 |
| 385 | 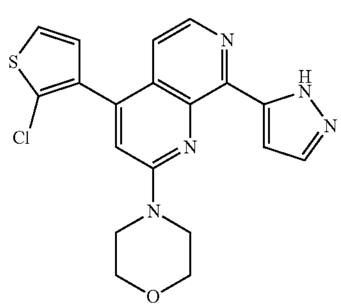 [SMILES: Clc1sccc1-c1cc(N2CCOCC2)nc2c(-c3ccn[nH]3)nccc12] | 4-(2-chlorothiophen-3-yl)-2-(morpholin-4-yl)-8-(1H-pyrazol-5-yl)-1,7-naphthyridine | 0.95 | 398.9 |

TABLE 5-continued

| Example | Structure | Name | Retention time [min] | LC-MS m/z [M + H]+ |
|---|---|---|---|---|
| 386 | 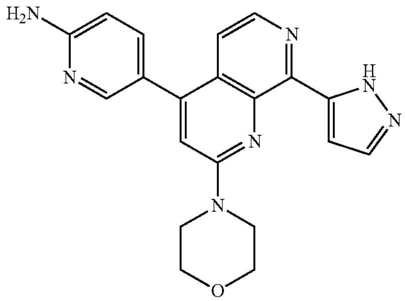 | 5-[2-(morpholin-4-yl)-8-(1H-pyrazol-5-yl)-1,7-naphthyridin-4-yl]pyridin-2-amine | 0.53 | 374.4 |
| 387 | 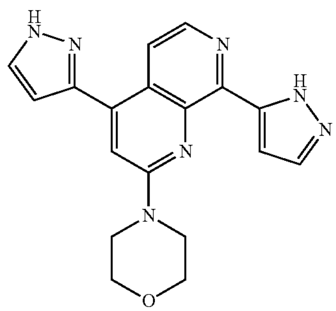 [SMILES: c1cc(-c2nccc3c(-c4cc[nH]n4)cc(N4CCOCC4)nc23)[nH]n1] | 2-(morpholin-4-yl)-4-(1H-pyrazol-3-yl)-8-(1H-pyrazol-5-yl)-1,7-naphthyridine | 0.66 | 348.4 |
| 388 | 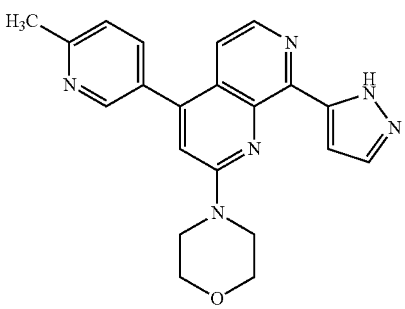 [SMILES: Cc1ccc(-c2cc(N3CCOCC3)nc3c(-c4ccn[nH]4)nccc23)cn1] | 4-(6-methylpyridin-3-yl)-2-(morpholin-4-yl)-8-(1H-pyrazol-5-yl)-1,7-naphthyridine | 0.66 | 373.4 |
| 389 | 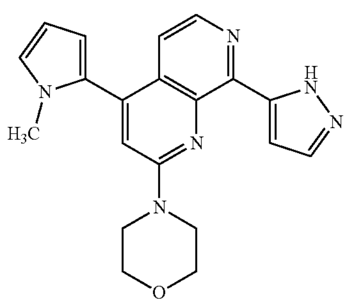 [SMILES: Cn1cccc1-c1cc(N2CCOCC2)nc2c(-c3ccn[nH]3)nccc12] | 4-(1-methyl-1H-pyrrol-2-yl)-2-(morpholin-4-yl)-8-(1H-pyrazol-5-yl)-1,7-naphthyridine | 0.82 | 361.4 |
| 390 | 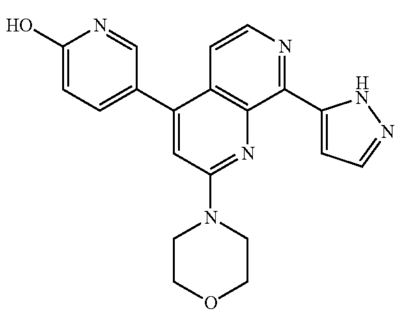 [SMILES: Oc1ccc(-c2cc(N3CCOCC3)nc3c(-c4ccn[nH]4)nccc23)cn1] | 5-[2-(morpholin-4-yl)-8-(1H-pyrazol-5-yl)-1,7-naphthyridin-4-yl]pyridin-2-ol | 0.6 | 375.4 |

TABLE 5-continued

| Example | Structure | Name | Retention time [min] | LC-MS m/z [M + H]+ |
|---|---|---|---|---|
| 391 | 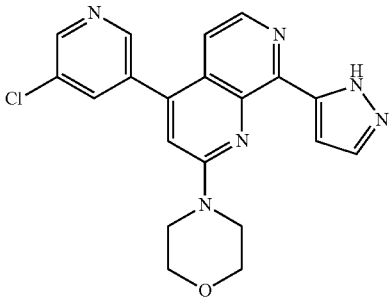 [SMILES: Clc1cncc(-c2cc(N3CCOCC3)nc3c(-c4ccn[nH]4)nccc23)c1] | 4-(5-chloropyridin-3-yl)-2-(morpholin-4-yl)-8-(1H-pyrazol-5-yl)-1,7-naphthyridine | 0.83 | 393.8 |
| 392 | 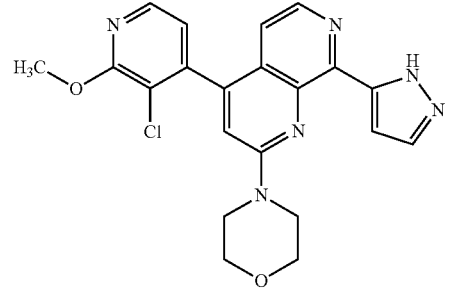 [SMILES: COc1nccc(-c2cc(N3CCOCC3)nc3c(-c4ccn[nH]4)nccc23)c1Cl] | 4-(3-chloro-2-methoxypyridin-4-yl)-2-(morpholin-4-yl)-8-(1H-pyrazol-5-yl)-1,7-naphthyridine | 0.93 | 423.9 |
| 393 | 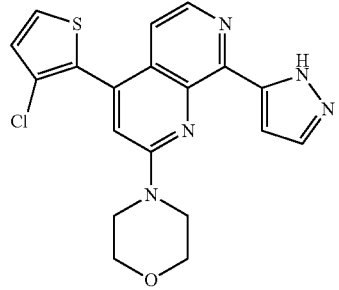 [SMILES: Clc1ccsc1-c1cc(N2CCOCC2)nc2c(-c3ccn[nH]3)nccc12] | 4-(3-chlorothiophen-2-yl)-2-(morpholin-4-yl)-8-(1H-pyrazol-5-yl)-1,7-naphthyridine | 0.96 | 398.9 |
| 394 | 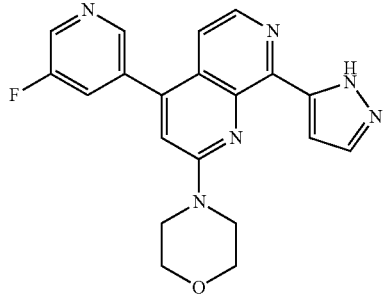 [SMILES: Fc1cncc(-c2cc(N3CCOCC3)nc3c(-c4ccn[nH]4)nccc23)c1] | 4-(5-fluoropyridin-3-yl)-2-(morpholin-4-yl)-8-(1H-pyrazol-5-yl)-1,7-naphthyridine | 0.76 | 377.4 |
| 395 | 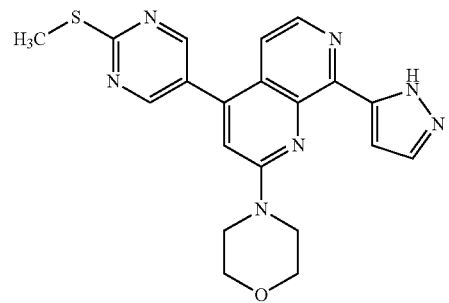 [SMILES: CSc1ncc(-c2cc(N3CCOCC3)nc3c(-c4ccn[nH]4)nccc23)cn1] | 4-[2-(methylsulfanyl)pyrimidin-5-yl]-2-(morpholin-4-yl)-8-(1H-pyrazol-5-yl)-1,7-naphthyridine | 0.84 | 406.5 |

TABLE 5-continued

| Example | Name | Retention time [min] | LC-MS m/z [M + H]+ |
|---|---|---|---|
| 396 | N-cyclopropyl-5-[2-(morpholin-4-yl)-8-(1H-pyrazol-5-yl)-1,7-naphthyridin-4-yl]pyrimidin-2-amine | 0.74 | 415.5 |
| 397 | 4-(isoquinolin-5-yl)-2-(morpholin-4-yl)-8-(1H-pyrazol-5-yl)-1,7-naphthyridine | 0.68 | 409.5 |
| 398 | N-methyl-5-[2-(morpholin-4-yl)-8-(1H-pyrazol-5-yl)-1,7-naphthyridin-4-yl]pyridine-2-carboxamide | 0.71 | 416.4 |
| 399 | N-tert-butyl-5-[2-(morpholin-4-yl)-8-(1H-pyrazol-5-yl)-1,7-naphthyridin-4-yl]pyridine-3-carboxamide | 0.82 | 458.5 |

TABLE 5-continued

| Example | Structure | Name | Retention time [min] | LC-MS m/z [M + H]+ |
|---|---|---|---|---|
| 400 | 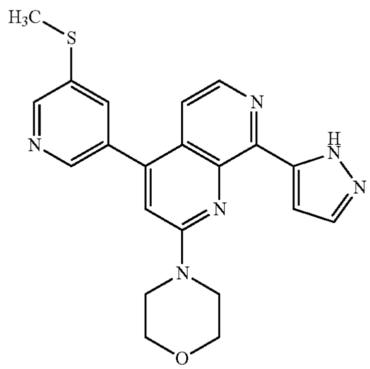 [SMILES: CSc1cncc(-c2cc(N3CCOCC3)nc3c(-c4ccn[nH]4)nccc23)c1] | 4-[5-(methylsulfanyl)pyridin-3-yl]-2-(morpholin-4-yl)-8-(1H-pyrazol-5-yl)-1,7-naphthyridine | 0.82 | 405.5 |
| 401 | 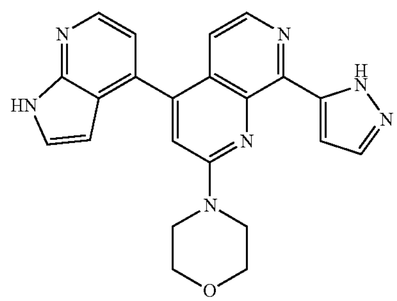 [SMILES: c1cc(-c2nccc3c(-c4ccnc5[nH]ccc45)cc(N4CCOCC4)nc23)[nH]n1] | 2-(morpholin-4-yl)-8-(1H-pyrazol-5-yl)-4-(1H-pyrrolo[2,3-b]pyridin-4-yl)-1,7-naphthyridine | 0.72 | 398.4 |
| 402 | 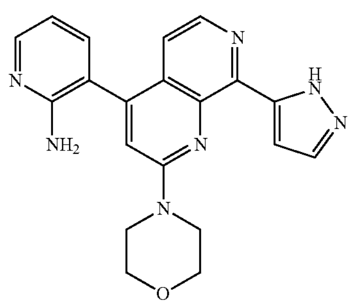 [SMILES: Nc1ncccc1-c1cc(N2CCOCC2)nc2c(-c3ccn[nH]3)nccc12] | 3-[2-(morpholin-4-yl)-8-(1H-pyrazol-5-yl)-1,7-naphthyridin-4-yl]pyridin-2-amine | 0.55 | 374.4 |
| 403 | 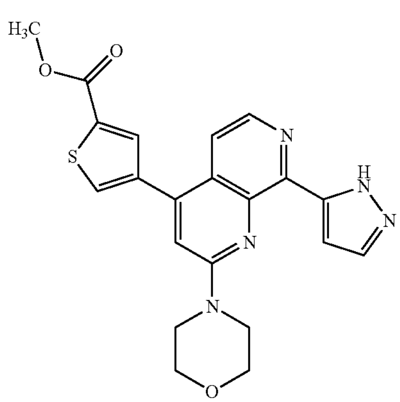 [SMILES: COC(=O)c1cc(-c2cc(N3CCOCC3)nc3c(-c4ccn[nH]4)nccc23)cs1] | methyl 4-[2-(morpholin-4-yl)-8-(1H-pyrazol-5-yl)-1,7-naphthyridin-4-yl]thiophene-2-carboxylate | 0.88 | 422.5 |

TABLE 5-continued

| Example | Structure | Name | Retention time [min] | LC-MS m/z [M + H]+ |
|---|---|---|---|---|
| 404 | 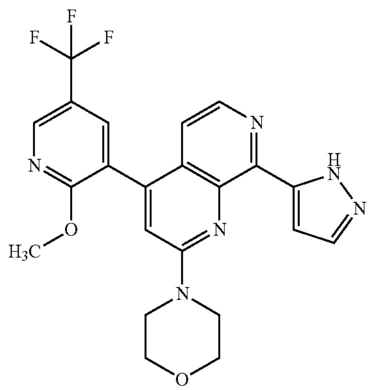 [SMILES: COc1ncc(C(F)(F)F)cc1-c1cc(N2CCOCC2)nc2c(-c3ccn[nH]3)nccc12] | 4-[2-methoxy-5-(trifluoromethyl)pyridin-3-yl]-2-(morpholin-4-yl)-8-(1H-pyrazol-5-yl)-1,7-naphthyridine | 1.02 | 457.4 |
| 405 | 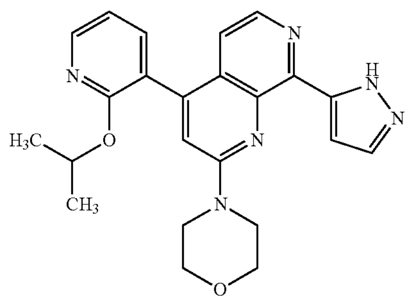 [SMILES: CC(C)Oc1ncccc1-c1cc(N2CCOCC2)nc2c(-c3ccn[nH]3)nccc12] | 2-(morpholin-4-yl)-4-[2-(propan-2-yloxy)pyridin-3-yl]-8-(1H-pyrazol-5-yl)-1,7-naphthyridine | 0.93 | 417.5 |
| 406 | 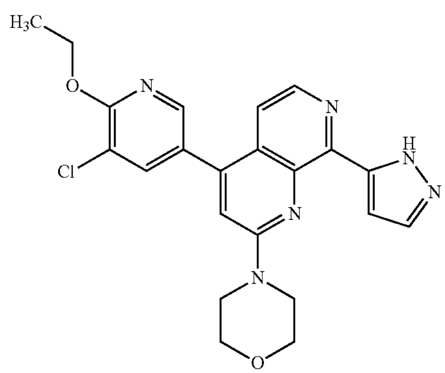 [SMILES: CCOc1ncc(-c2cc(N3CCOCC3)nc3c(-c4ccn[nH]4)nccc23)cc1Cl] | 4-(5-chloro-6-ethoxypyridin-3-yl)-2-(morpholin-4-yl)-8-(1H-pyrazol-5-yl)-1,7-naphthyridine | 1.06 | 437.9 |
| 407 | 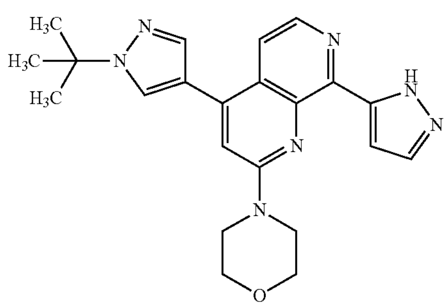 [SMILES: CC(C)(C)n1cc(-c2cc(N3CCOCC3)nc3c(-c4ccn[nH]4)nccc23)cn1] | 4-(1-tert-butyl-1H-pyrazol-4-yl)-2-(morpholin-4-yl)-8-(1H-pyrazol-5-yl)-1,7-naphthyridine | 0.85 | 404.5 |

The examples in the following table (Table 6) were prepared in analogy to this procedure:

To 2-5 eq of amine derivative were added 0.15 mmol 2-(morpholin-4-yl)-8-[1-(tetrahydro-2H-pyran-2-yl)-1H-pyrazol-5-yl]-1,7-naphthyridin-4-yl trifluoromethanesulfonate (0.25 M in NMP, 600 μL) and the mixture was heated at 70° C. overnight. After cooling, 1.5 mmol HCl (2M in water, 750 μL) were added and the mixture was heated overnight at 50° C. After cooling, the mixture was subjected to preparative HPLC to yield the target product.

LC-MS Method 4

TABLE 6

| Example | Structure | Name | Retention time [min] | LC-MS m/z [M + H]+ |
|---|---|---|---|---|
| 408 | 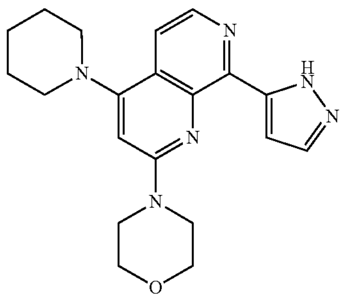 [SMILES: c1cc(-c2nccc3c(N4CCCCC4)cc(N4CCOCC4)nc23)[nH]n1] | 2-(morpholin-4-yl)-4-(piperidin-1-yl)-8-(1H-pyrazol-5-yl)-1,7-naphthyridine | 0.83 | 365.4 |
| 409 | 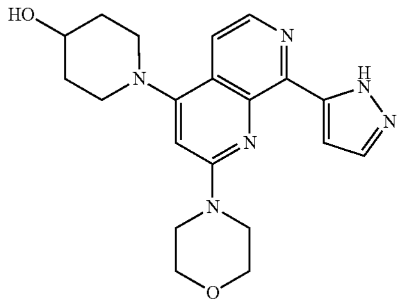 [SMILES: OC1CCN(c2cc(N3CCOCC3)nc3c(-c4ccn[nH]4)nccc23)CC1] | 1-[2-(morpholin-4-yl)-8-(1H-pyrazol-5-yl)-1,7-naphthyridin-4-yl]piperidin-4-ol | 0.66 | 381.4 |
| 410 | 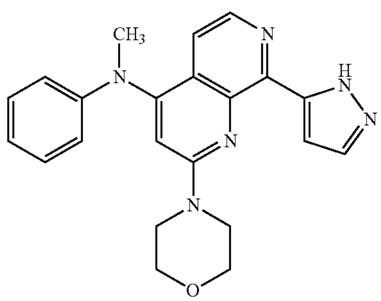 [SMILES: CN(c1ccccc1)c1cc(N2CCOCC2)nc2c(-c3ccn[nH]3)nccc12] | N-methyl-2-(morpholin-4-yl)-N-phenyl-8-(1H-pyrazol-5-yl)-1,7-naphthyridin-4-amine | 0.85 | 387.4 |
| 411 | 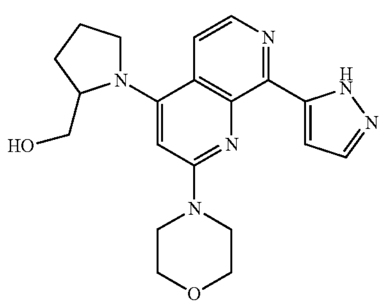 [SMILES: OCC1CCCN1c1cc(N2CCOCC2)nc2c(-c3ccn[nH]3)nccc12] | {1-[2-(morpholin-4-yl)-8-(1H-pyrazol-5-yl)-1,7-naphthyridin-4-yl]pyrrolidin-2-yl}methanol | 0.68 | 381.4 |
| 412 | 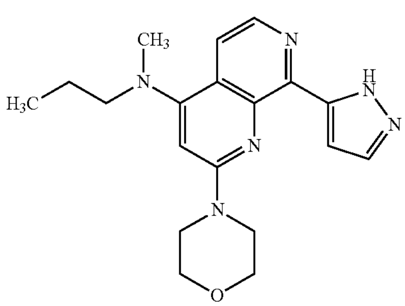 [SMILES: CCCN(C)c1cc(N2CCOCC2)nc2c(-c3ccn[nH]3)nccc12] | N-methyl-2-(morpholin-4-yl)-N-propyl-8-(1H-pyrazol-5-yl)-1,7-naphthyridin-4-amine | 0.8 | 353.4 |

TABLE 6-continued

| Example | Structure | Name | Retention time [min] | LC-MS m/z [M + H]+ |
|---|---|---|---|---|
| 413 | 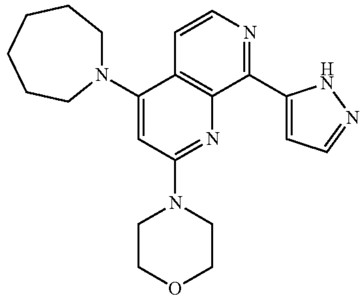 [SMILES: c1cc(-c2nccc3c(N4CCCCCC4)cc(N4CCOCC4)nc23)[nH]n1] | 4-(azepan-1-yl)-2-(morpholin-4-yl)-8-(1H-pyrazol-5-yl)-1,7-naphthyridine | 0.86 | 379.5 |
| 414 | 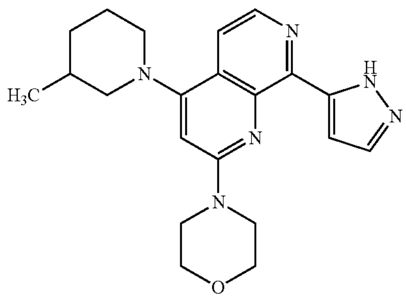 [SMILES: CC1CCCN(c2cc(N3CCOCC3)nc3c(-c4ccn[nH]4)nccc23)C1] | 4-(3-methylpiperidin-1-yl)-2-(morpholin-4-yl)-8-(1H-pyrazol-5-yl)-1,7-naphthyridine | 0.89 | 379.5 |
| 415 | 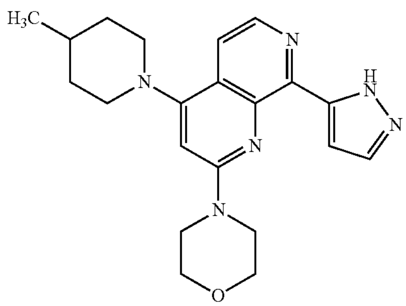 [SMILES: CC1CCN(c2cc(N3CCOCC3)nc3c(-c4ccn[nH]4)nccc23)CC1] | 4-(4-methylpiperidin-1-yl)-2-(morpholin-4-yl)-8-(1H-pyrazol-5-yl)-1,7-naphthyridine | 0.89 | 379.5 |
| 416 | 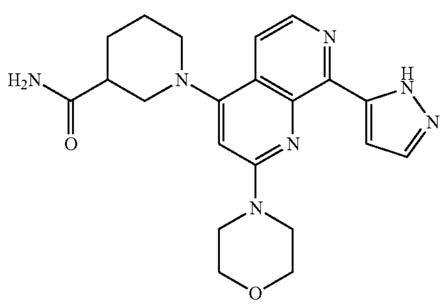 [SMILES: NC(=O)C1CCCN(c2cc(N3CCOCC3)nc3c(-c4ccn[nH]4)nccc23)C1] | 1-[2-(morpholin-4-yl)-8-(1H-pyrazol-5-yl)-1,7-naphthyridin-4-yl]piperidine-3-carboxamide | 0.66 | 408.5 |
| 417 | 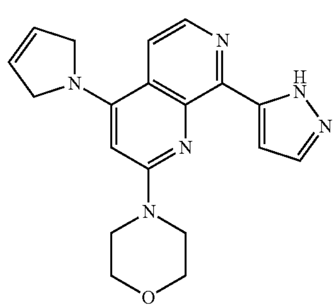 [SMILES: C1=CCN(c2cc(N3CCOCC3)nc3c(-c4ccn[nH]4)nccc23)C1] | 4-(2,5-dihydro-1H-pyrrol-1-yl)-2-(morpholin-4-yl)-8-(1H-pyrazol-5-yl)-1,7-naphthyridine | 0.74 | 349.4 |

TABLE 6-continued

| Example | Structure | Name | Retention time [min] | LC-MS m/z [M + H]+ |
|---|---|---|---|---|
| 418 | 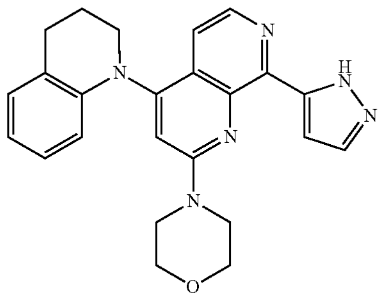 [SMILES: c1ccc2c(c1)CCCN2c1cc(N2CCOCC2)nc2c(-c3ccn[nH]3)nccc12] | 4-(3,4-dihydroquinolin-1(2H)-yl)-2-(morpholin-4-yl)-8-(1H-pyrazol-5-yl)-1,7-naphthyridine | 0.93 | 413.5 |
| 419 | 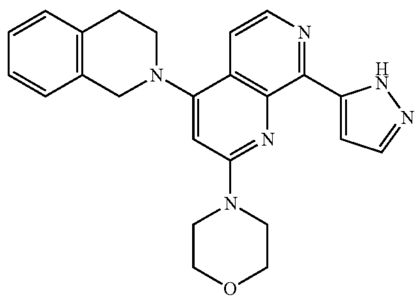 [SMILES: c1ccc2c(c1)CCN(c1cc(N3CCOCC3)nc3c(-c4ccn[nH]4)nccc13)C2] | 4-(3,4-dihydroisoquinolin-2(1H)-yl)-2-(morpholin-4-yl)-8-(1H-pyrazol-5-yl)-1,7-naphthyridine | 0.91 | 413.5 |
| 420 | 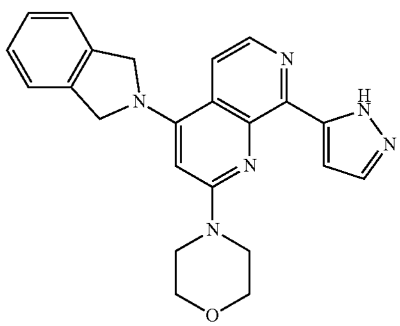 [SMILES: c1ccc2c(c1)CN(c1cc(N3CCOCC3)nc3c(-c4ccn[nH]4)nccc13)C2] | 4-(1,3-dihydro-2H-isoindol-2-yl)-2-(morpholin-4-yl)-8-(1H-pyrazol-5-yl)-1,7-naphthyridine | 0.87 | 399.5 |
| 421 | 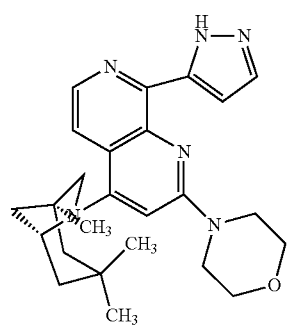 [SMILES: CC1(C)C[C@@H]2C[C@@](C)(CN2c2cc(N3CCOCC3)nc3c(-c4ccn[nH]4)nccc23)C1] | 2-(morpholin-4-yl)-8-(1H-pyrazol-5-yl)-4-[1,3,3-trimethyl-6-azabicyclo[3.2.1]oct-6-yl]-1,7-naphthyridine | 1 | 433.6 |
| 422 | 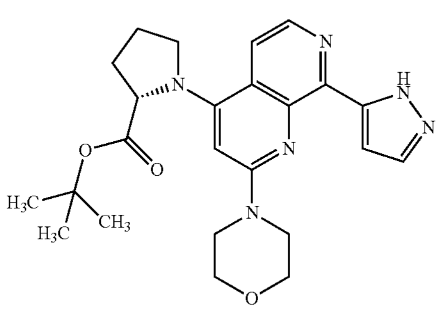 [SMILES: CC(C)(C)OC(=O)[C@@H]1CCCN1c1cc(N2CCOCC2)nc2c(-c3ccn[nH]3)nccc12] | tert-butyl 1-[2-(morpholin-4-yl)-8-(1H-pyrazol-5-yl)-1,7-naphthyridin-4-yl]-prolinate | 0.88 | 451.5 |

TABLE 6-continued

| Example | Structure | Name | Retention time [min] | LC-MS m/z [M + H]+ |
|---|---|---|---|---|
| 423 | 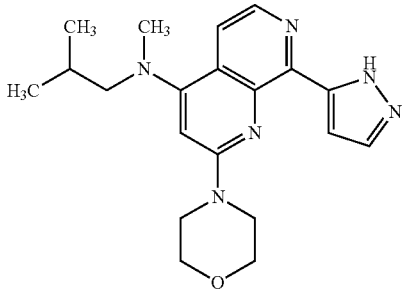 [SMILES: CC(C)CN(C)c1cc(N2CCOCC2)nc2c(-c3ccn[nH]3)nccc12] | N-methyl-N-(2-methylpropyl)-2-(morpholin-4-yl)-8-(1H-pyrazol-5-yl)-1,7-naphthyridin-4-amine | 0.85 | 367.5 |
| 424 | 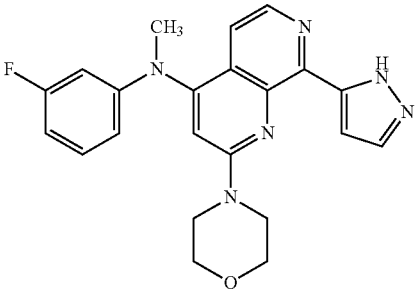 [SMILES: CN(c1cccc(F)c1)c1cc(N2CCOCC2)nc2c(-c3ccn[nH]3)nccc12] | N-(3-fluorophenyl)-N-methyl-2-(morpholin-4-yl)-8-(1H-pyrazol-5-yl)-1,7-naphthyridin-4-amine | 0.87 | 405.4 |
| 425 | 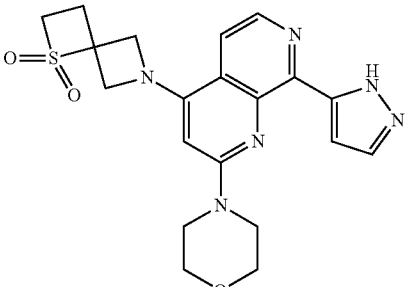 | 4-(1,1-dioxido-1-thia-6-azaspiro[3.3]hept-6-yl)-2-(morpholin-4-yl)-8-(1H-pyrazol-5-yl)-1,7-naphthyridine | 0.68 | 427.5 |
| 426 | 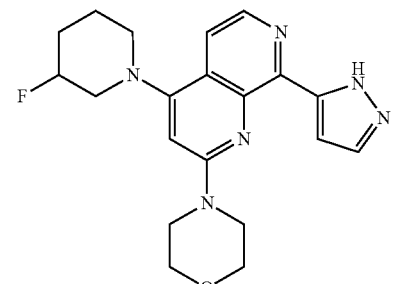 | 4-(3-fluoropiperidin-1-yl)-2-(morpholin-4-yl)-8-(1H-pyrazol-5-yl)-1,7-naphthyridine | 0.88 | 383.4 |
| 427 | 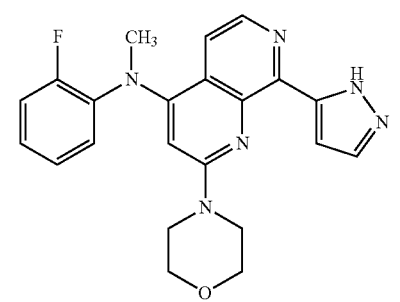 [SMILES: CN(c1ccccc1F)c1cc(N2CCOCC2)nc2c(-c3ccn[nH]3)nccc12] | N-(2-fluorophenyl)-N-methyl-2-(morpholin-4-yl)-8-(1H-pyrazol-5-yl)-1,7-naphthyridin-4-amine | 0.96 | 405.4 |

TABLE 6-continued

| Example | Structure | Name | Retention time [min] | LC-MS m/z [M + H]+ |
|---|---|---|---|---|
| 428 | 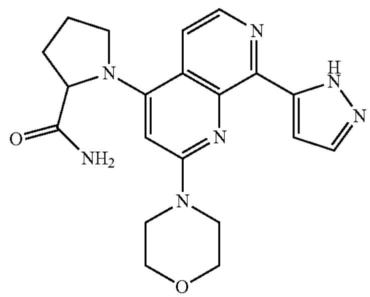 [SMILES: NC(=O)C1CCCN1c1cc(N2CCOCC2)nc2c(-c3ccn[nH]3)nccc12] | 1-[2-(morpholin-4-yl)-8-(1H-pyrazol-5-yl)-1,7-naphthyridin-4-yl]-prolinamide | 0.66 | 394.4 |
| 429 | 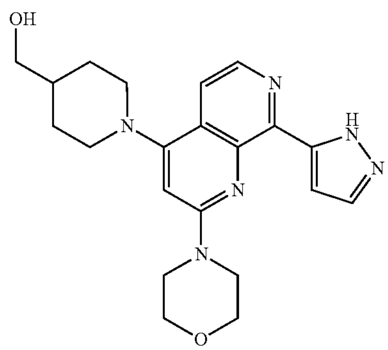 [SMILES: OCC1CCN(c2cc(N3CCOCC3)nc3c(-c4ccn[nH]4)nccc23)CC1] | {1-[2-(morpholin-4-yl)-8-(1H-pyrazol-5-yl)-1,7-naphthyridin-4-yl]piperidin-4-yl}methanol | 0.75 | 395.5 |
| 430 | 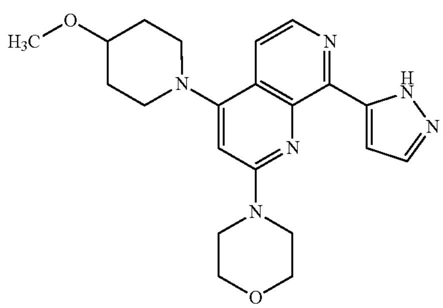 [SMILES: COC1CCN(c2cc(N3CCOCC3)nc3c(-c4ccn[nH]4)nccc23)CC1] | 4-(4-methoxypiperidin-1-yl)-2-(morpholin-4-yl)-8-(1H-pyrazol-5-yl)-1,7-naphthyridine | 0.85 | 395.5 |
| 431 | 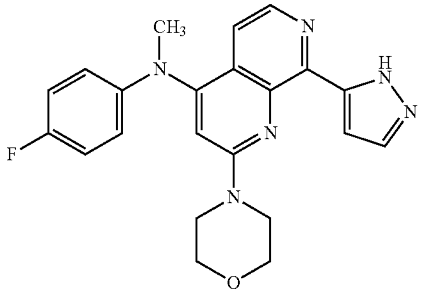 [SMILES: CN(c1ccc(F)cc1)c1cc(N2CCOCC2)nc2c(-c3ccn[nH]3)nccc12] | N-(4-fluorophenyl)-N-methyl-2-(morpholin-4-yl)-8-(1H-pyrazol-5-yl)-1,7-naphthyridin-4-amine | 0.97 | 405.4 |
| 432 | 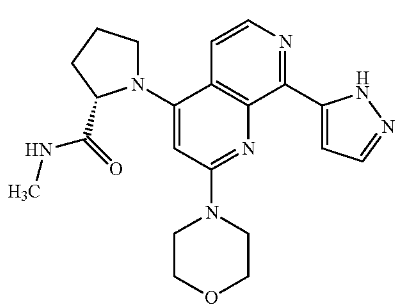 [SMILES: CNC(=O)[C@@H]1CCCN1c1cc(N2CCOCC2)nc2c(-c3ccn[nH]3)nccc12] | N-methyl-1-[2-(morpholin-4-yl)-8-(1H-pyrazol-5-yl)-1,7-naphthyridin-4-yl]-prolinamide | 0.69 | 408.5 |

TABLE 6-continued

| Example | Structure | Name | Retention time [min] | LC-MS m/z [M + H]+ |
|---------|-----------|------|----------------------|---------------------|
| 433 | 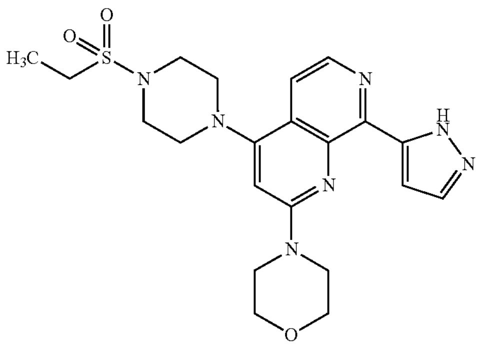 [SMILES: CCS(=O)(=O)N1CCN(c2cc(N3CCOCC3)nc3c(-c4ccn[nH]4)nccc23)CC1] | 4-[4-(ethylsulfonyl)piperazin-1-yl]-2-(morpholin-4-yl)-8-(1H-pyrazol-5-yl)-1,7-naphthyridine | 0.8 | 458.6 |
| 434 | 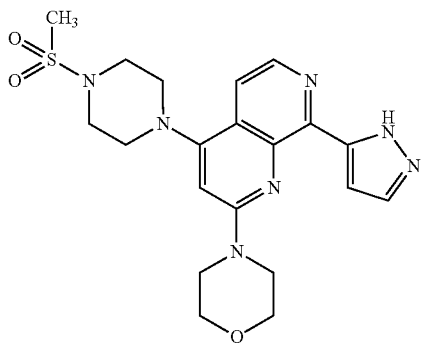 [SMILES: CS(=O)(=O)N1CCN(c2cc(N3CCOCC3)nc3c(-c4ccn[nH]4)nccc23)CC1] | 4-[4-(methylsulfonyl)piperazin-1-yl]-2-(morpholin-4-yl)-8-(1H-pyrazol-5-yl)-1,7-naphthyridine | 0.74 | 444.5 |
| 435 | 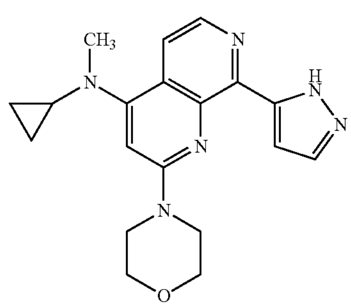 [SMILES: CN(c1cc(N2CCOCC2)nc2c(-c3ccn[nH]3)nccc12)C1CC1] | N-cyclopropyl-N-methyl-2-(morpholin-4-yl)-8-(1H-pyrazol-5-yl)-1,7-naphthyridin-4-amine | 0.85 | 351.4 |
| 436 | 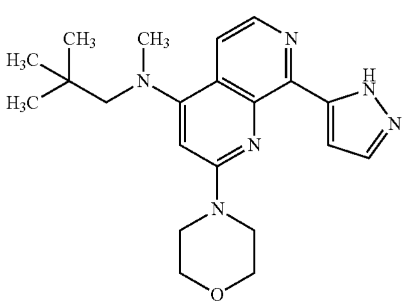 [SMILES: CN(CC(C)(C)C)c1cc(N2CCOCC2)nc2c(-c3ccn[nH]3)nccc12] | N-(2,2-dimethylpropyl)-N-methyl-2-(morpholin-4-yl)-8-(1H-pyrazol-5-yl)-1,7-naphthyridin-4-amine | 1.02 | 381.5 |

TABLE 6-continued

| Example | Structure | Name | Retention time [min] | LC-MS m/z [M + H]+ |
|---|---|---|---|---|
| 437 | 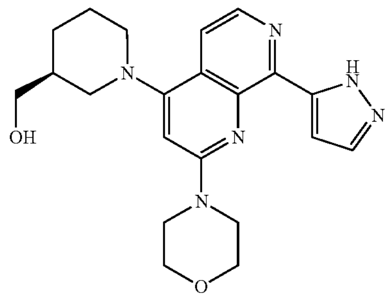 [SMILES: OC[C@H]1CCCN(c2cc(N3CCOCC3)nc3c(-c4ccn[nH]4)nccc23)C1] | {1-[2-(morpholin-4-yl)-8-(1H-pyrazol-5-yl)-1,7-naphthyridin-4-yl]piperidin-3-yl}methanol | 0.79 | 395.5 |

The title compounds described in the example section were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Expression of ATR/ATRIP in HEK 293-6E Cells:

The cDNAs encoding the protein sequences of full-length human ATR sequence (Q13535) with an N-terminally fused Flag tag as well as the full-length human ATRIP (Q8WXE1) were optimized for expression in eukaryotic cells and synthesized by the GeneArt Technology at Life Technologies. Both cDNAs also encoded att-site sequences at the 5' and 3' ends for subcloning into the following destination vectors using the Gateway Technology: pD-MamA (an in-house derivate of the vector pEAK from EdgeBioSystems but with a human CMV promotor) which provides a N-terminal fusion of a GST-tag to the integrated gene of interest; pD-MamB (an in-house derivative of pTT5 from NRCC, Y. Durocher) which provides a N-terminal fusion of a STREP II-tag to the integrated gene. The cDNAs of ATR and ATR-DN were cloned into pD-MamA and the ATRIP-FL into pD-MamB. The cDNA sequence of codon-optimized ATR including a GST tag is described in SEQ ID No. 1 of the attached sequence listing, its corresponding protein sequence in SEQ ID No. 3. The cDNA sequence of codon-optimized ATRIP including a STREP II tag is described in SEQ ID No. 2, its corresponding protein sequence in SEQ ID No. 4.

Coexpression of ATR and ATRIP by Transient Transfection in HEK293-6E Cells:

For transient transfection of HEK293-6E suspension cells a Biostat Cultibag Bioreactor with 5 L culture volume (starting volume) in a 20 L culture bag was used. The cells were cultured in F17 Medium (Gibco, Invitrogen, Cat #05-0092DK) with the following supplements Pluronic F68 (10 mL/L of 10% solution, Gibco #24040), Gluta-Max (20 ml of 100× solution/L, L-Alanyl-Glutamine (200 mM, Invitrogen #25030), G418 (final concentration 25 µg/ml, PAA # P02-012). The applied culture conditions were 37° C., rocking rate 18 rpm, pH 7.0, pO2 55%. At the day of transfection the cell culture had reached a cell density of $1.6 \times 10^6$ cells/mL and a viability of 99%. For preparation of the transfection solution to 500 mL F17 medium (without the supplements) 4 mg of the ATR encoding plasmid, 1 mg of the ATRIP encoding plasmid and 10 mg PEI (Polyethylenimin, linear, Polysciences #23966, as 1 mg/mL stock solution) were subsequently added, carefully mixed and incubated at room temperature for 15 min. This transfection solution was then added to the 5 L cell culture in the culture bag. This cell culture was incubated for 5 h and afterwards 5 L of F17 medium with the mentioned supplements were added and the rocking rate increased to 19 rpm. 48 h after transfection the cells were harvested by centrifugation (30 min., 1000 g, 15° C.) and the cell pellets stored at −80° C.

Purification:

Purification of the ATR (Flag-Tag)/ATRIP(Strep-Tag) complex was achieved by affinity chromatography using anti-FLAG-resin (Sigma, # A220).

Cells were harvested by centrifugation (4000×g) and lysed in buffer A (50 mM Tris-HCl pH 7.5; 150 mM NaCl, 5% Glycerol, 1 mM Na3VO4, 1 mM NaF, 10 mM β-glycerophosphate, 1% Tween 20; 0.1% NP40; Complete with EDTA) for 1 h at 4° C. The supernatant (20.000×g) was than bound to Flag-Agarose and eluted after several washing steps using Buffer B (50 mM Tris-HCl pH7.4; 150 mM NaCl; 10% Glycerin, 200 µg/ml Flag Peptides from Sigma, # F3290). Elution fractions were aliquoted and shock frozen using liquid nitrogen. The final concentration of ATR in the final preparation was 250 µg/ml calculated densitrometrically using BSA as a standard in a Coomassie stained gel. The yield of copurified ATRIP was far below a 1:1 ratio compared to ATR but was essential for ATR activity.

471

Tracer A

3',6'-bis(dimethylamino)-N-(4-{[2-(1H-indol-4-yl)-
6-(morpholin-4-yl)pyrimidin-4-yl]amino}butyl)-3-
oxo-3H-spiro[2-benzofuran-1,9'-xanthene]-5-carbox-
amide Step a tert-butyl (4-{[2-(1H-indol-4-yl)-6-(morpholin-4-yl)
pyrimidin-4-yl]amino}butyl)carbamate

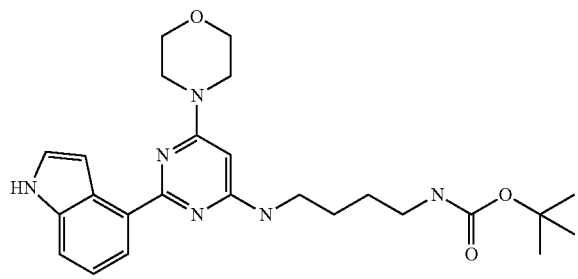 [SMILES: CC(C)(C)OC(=O)NCCCCNc1cc(N2CCOCC2)nc(-c2cccc3[nH]ccc23)n1]

The starting material 4-[4-chloro-6-(morpholin-4-yl)pyrimidin-2-yl]-1H-indole was synthesized according to the literature (WO2008/125833). A solution of 4-[4-chloro-6-(morpholin-4-yl)pyrimidin-2-yl]-1H-indole (980 mg, 3.11 mmol), diisopropylethylamine (805 mg, 1.09 ml, 6.23 mmol) and N—BOC-1,4-diaminobutane (879 mg, 4.67 mmol) in 1-methyl-2-pyrrolidinone (24.5 ml) was stirred overnight at 150° C. The mixture was allowed to cool to ambient temperature. Ethyl acetate (50 ml) and brine (50 ml) were added, the layers were separated and the organic layer was washed with brine (3×50 ml). The organic layer was dried over sodium sulphate and the solvent was removed under reduced pressure. The title compound was obtained as crude mixture (purity 40%, 2.37 g) and used without further purification in the next step.

472

Step b

N-[2-(1H-indol-4-yl)-6-(morpholin-4-yl)pyrimidin-
4-yl]butane-1,4-diamine

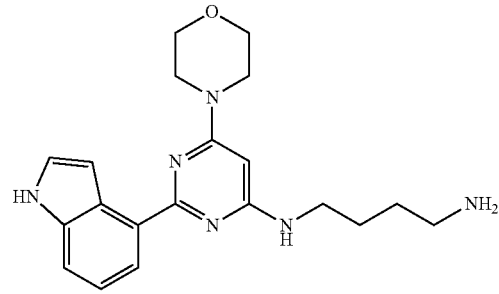 [SMILES: NCCCCNc1cc(N2CCOCC2)nc(-c2cccc3[nH]ccc23)n1]

Tert-butyl (4-{[2-(1H-indol-4-yl)-6-(morpholin-4-yl)pyrimidin-4-yl]amino}butyl)carbamate (2.37 g, 2.03 mmol) was dissolved in HCl/dioxane (4M, 20 ml) and stirred at ambient temperature for 10 minutes. Ethyl acetate (50 ml) and water (50 ml) were added and the phases separated. By addition of aqueous NaOH (2N, 50 ml) the pH of the aqueous layer was basified and extracted with ethyl acetate (2×50 ml). The combined organic layers were dried over sodium sulphate and the solvent was removed under reduced pressure. The title compound was obtained in 77% yield (770 mg) and used without further purification in the next step.

Step c

3',6'-bis(dimethylamino)-N-(4-{[2-(1H-indol-4-yl)-
6-(morpholin-4-yl)pyrimidin-4-yl]amino}butyl)-3-
oxo-3H-spiro[2-benzofuran-1,9'-xanthene]-6-carbox-
amide and 3',6'-bis(dimethylamino)-N-(4-{[2-(1H-indol-4-yl)-
6-(morpholin-4-yl)pyrimidin-4-yl]amino}butyl)-3-
oxo-3H-spiro[2-benzofuran-1,9'-xanthene]-5-carbox-
amide

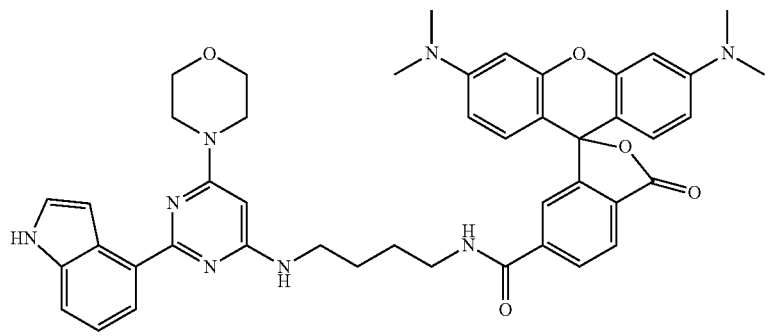

Isomer 1

+

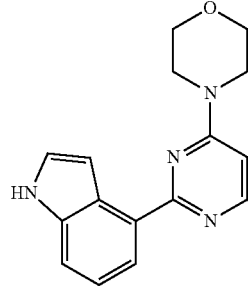

Isomer 2

N-[2-(1H-indol-4-yl)-6-(morpholin-4-yl)pyrimidin-4-yl]butane-1,4-diamine (70 mg, 0.14 mmol) was dissolved in DMF (3 mL). DIPEA (74 µl, 0.43 mmol, 3 eq.) and a mixture of commercially available 5-carboxytetramethylrhodamine N-succinimidyl ester and 6-carboxytetramethylrhodamine N-succinimidyl ester (75 mg, 0.14 mmol, 1 eq.) were added sequentially. The mixture was stirred for 15 minutes at ambient temperature and concentrated under reduced pressure. The two title compounds were separated by preparative HPLC (H$_2$O(NH$_4$OH)/CH$_3$CN: 85:15 to 45:55).

Isomer 1 was obtained in 22% yield (25 mg). $^1$H-NMR (300 MHz, DMSO-d$_6$): δ [ppm]: 1.56 (4H), 2.92 (12H), 3.49 (4H), 3.69 (4H), 5.53 (1H), 6.48 (6H), 6.74 (1H), 7.06 (1H), 7.33 (2H), 7.43 (1H), 7.63 (1H), 8.03 (2H), 8.15 (1H), 8.71 (1H), 11.11 (1H).

Isomer 2 was obtained in 34% yield (31 mg). $^1$H-NMR (400 MHz, DMSO-d$_6$): δ [ppm]: 1.67 (4H), 2.93 (12H), 3.38 (4H), 3.52 (4H), 3.71 (4H), 5.58 (1H), 6.47 (6H), 6.80 (1H), 7.09 (1H), 7.28 (1H), 7.36 (2H), 7.44 (1H), 8.02 (1H), 8.22 (1H), 8.44 (1H), 8.83 (1H).

Isomer 2 was used as ligand for the ATR binding assay which is described infra.

Tracer B

3',6'-bis(dimethylamino)-N-[4-({2-[(3R)-3-methyl-morpholin-4-yl]-8-(1H-pyrazol-5-yl)-1,7-naphthyridin-4-yl}oxy)butyl]-3-oxo-3H-spiro[2-benzofuran-1,9'-xanthene]-5-carboxamide Step a tert-butyl [4-({2-[(3R)-3-methylmorpholin-4-yl]-8-[1-(tetrahydro-2H-pyran-2-yl)-1H-pyrazol-5-yl]-1,7-naphthyridin-4-yl}oxy)butyl]carbamate

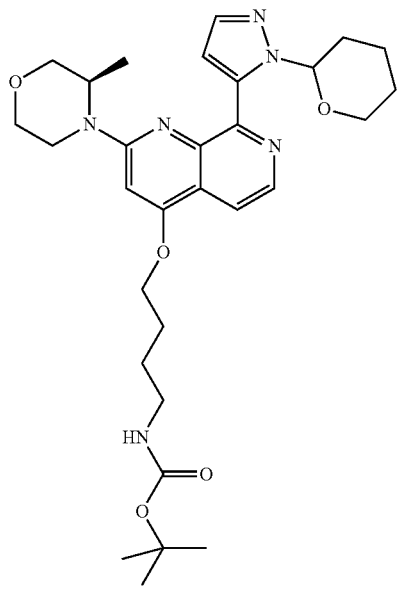 [SMILES: C[C@@H]1COCCN1c1cc(OCCCCNC(=O)OC(C)(C)C)c2ccnc(-c3ccnn3C3CCCCO3)c2n1]

2-[(3R)-3-Methylmorpholin-4-yl]-8-[1-(tetrahydro-2H-pyran-2-yl)-1H-pyrazol-5-yl]-1,7-naphthyridin-4-ol (0.41 g, 1.0 mmol, 1 eq.) was solubilized in DMF (12 mL). 4-(Boc-amino)butyl bromide (0.53 g, 2.1 mmol, 2 eq.) and $K_2CO_3$ (0.72 g, 5.2 mmol, 5 eq.) were added to the mixture. The reaction was stirred at ambient temperature for 16 hours. The suspension was diluted with EtOAc and filtered. The organic phase was concentrated under reduced pressure and the crude material purified by flash chromatography (gradient Hex/EtOAc 9/1 to 100% EtOAc). The desired product was obtained in 87% yield (0.52 g). $^1$H-NMR (400 MHz, DMSO-$d_6$): δ [ppm]: 1.14-1.24 (m, 3H), 1.38 (s, 9H), 1.41-1.69 (m, 5H), 1.80-1.90 (m, 2H), 1.99 (s, 2H), 2.30-2.42 (m, 1H), 3.03 (q, 2H), 3.10-3.29 (m, 2H), 3.40-3.52 (m, 1H), 3.73 (d, 3H), 3.91-3.99 (m, 1H), 4.12 (t, 1H), 4.27 (t, 2H), 4.45-4.58 (m, 1H), 6.01-6.13 (m, 1H), 6.75 (d, 1H), 6.84-6.95 (m, 2H), 7.60 (s, 1H), 7.75 (d, 1H), 8.35 (d, 1H). LC-MS (Method A): m/z: [M+H]$^+$=567, $R_t$=1.31 min.

Step b 4-({2-[(3R)-3-methylmorpholin-4-yl]-8-(1H-pyrazol-5-yl)-1,7-naphthyridin-4-yl}oxy)butan-1-amine

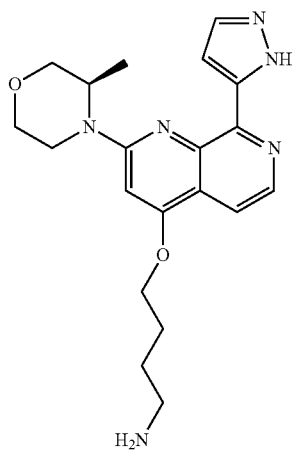 [SMILES: C[C@@H]1COCCN1c1cc(OCCCCN)c2ccnc(-c3ccn[nH]3)c2n1]

4-({2-[(3R)-3-methylmorpholin-4-yl]-8-(1H-pyrazol-5-yl)-1,7-naphthyridin-4-yl}oxy)butan-1-amine (0.10 g, 0.18 mmol, 1 eq.) was solubilized in $CH_2Cl_2$ (1.1 mL) and TFA was added (0.27 mL, 3.5 mmol, 20 eq.). The reaction was stirred at ambient temperature for 30 minutes. The mixture was then quenched with saturated $NaHCO_3$ solution and the suspension was filtered. The solid was dried under reduced pressure and the desired compound was obtained without further purification in quantitative yield. $^1$H-NMR (400 MHz, DMSO-$d_6$): δ [ppm]: 1.27 (d, 3H), 1.73-1.84 (m, 2H), 1.88-1.97 (m, 2H), 2.92 (s, 2H), 3.49-3.61 (m, 1H), 3.65-3.74 (m, 1H), 3.80-3.87 (m, 1H), 4.02-4.09 (m, 1H), 4.11-4.19 (m, 1H), 4.30 (s, 2H), 4.56-4.65 (m, 1H), 6.82 (s, 1H), 7.34-7.40 (m, 1H), 7.50-7.65 (m, 4H), 7.71 (d, 1H), 8.33 (d, 1H), 13.31-13.41 (m, 1H).

Step c

3',6'-bis(dimethylamino)-N-[4-({2-[(3R)-3-methyl-morpholin-4-yl]-8-(1H-pyrazol-5-yl)-1,7-naphthyridin-4-yl}oxy)butyl]-3-oxo-3H-spiro[2-benzofuran-1,9'-xanthene]-5-carboxamide

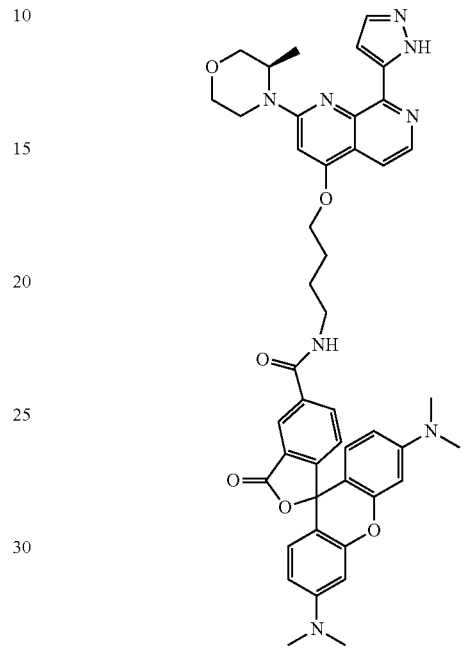

4-({2-[(3R)-3-Methylmorpholin-4-yl]-8-(1H-pyrazol-5-yl)-1,7-naphthyridin-4-yl}oxy)butan-1-amine (18 mg, 0.047 mmol, 1 eq.) was solubilized in DMF (1 mL). DIPEA (25 μL, 0.14 mmol, 3 eq.) and a mixture of commercially available 5-carboxytetramethylrhodamine N-succinimidyl ester and 6-carboxytetramethylrhodamine N-succinimidyl ester (25 mg, 0.047 mmol, 1 eq.) were added sequentially. The reaction was stirred for 15 minutes at ambient temperature and concentrated under reduced pressure. The crude product was purified by preparative HPLC ($H_2O(NH_4OH)$/$CH_3CN$: 85:15 to 45:55) and the desired compound was obtained in 49% yield (18 mg). $^1$H-NMR (400 MHz, DMSO-$d_6$): δ [ppm]: 1.26 (d, 3H), 1.79-1.88 (m, 2H), 1.92-2.02 (m, 2H), 2.94 (s, 12H), 3.46 (q, 2H), 3.52-3.60 (m, 1H), 3.67-3.73 (m, 1H), 3.82 (d, 1H), 4.01-4.07 (m, 1H), 4.12-4.19 (m, 1H), 4.34 (t, 2H), 4.56-4.64 (m, 1H), 6.44-6.53 (m, 6H), 6.83 (s, 1H), 7.32 (d, 1H), 7.37 (br. s., 1H), 7.61 (s, 1H), 7.73 (d, 1H), 8.24 (dd, 1H), 8.32 (d, 1H), 8.46 (s, 1H), 8.88 (t, 1H), 13.36 (br. s., 1H).

1. Binding Assay ATR

To determine of binding activity of the test compounds, full-length human ATR protein was expressed and purified together with ATRIP as described above. Furthermore, a fluorescently labelled compound (either tracer A or B as described above) was used as a tracer molecule. Detection of the binding event of the tracer was achieved by time-resolved fluorescence energy transfer (TR-FRET). We used an anti-GST-Terbium antibody (CisBio) that binds to the GST-tag at the N-terminus of ATR-kinase. Excitation of Terbium with 337 nm light results in emission of fluorescent light with 545 nm. In case a tetrameric complex has formed (antiGST-Tb+GST-ATR+Strp2-ATRIP+tracer), part of the energy will be transferred from the Terbium to the fluorophore that itself emits light of 570 nm. Displacement of the fluorescent tracer by a test compound leads to a reduction of the TR-FRET-signal.

For the assay 50 nl of a 100-fold concentrated solution of the test compound in DMSO was pipetted into a black low volume 384 well microtiter plate (MTP, Greiner Bio-One, Frickenhausen, Germany). To prepare the ATR-working solution, ATR/ATRIP stock solution was diluted in assay buffer [50 mM HEPES (pH 7.0), 10 mM MgCl2, 1 mM DTT, 0.01% (w/v) Igepal, 0.01% (w/v) BSA] to 4.2 nM protein concentration (concentration may vary from lot to lot of protein preparation). AntiGST-Tb antibody was diluted to 4.2 nM. The ATR-working solution was incubated for 30 min at 22° C. prior to dispensing to pre-form the complex of antiGST-Tb+GST-ATR+ATRIP. Then, 3 µl of the ATR-working solution were added to the test compound and the mixture was incubated for 10 min at 22° C. to allow pre-binding of the test compounds to ATR/ATRIP. Then, 2 µl of a 100 nM solution of either tracer A or B in assay buffer were added to the ATR-working solution. The resulting mixture was incubated for 30 min at 22° C. The measurement of the TR-FRET signal was performed in a standard HTRF-compatible MTP reader instrument (e.g. BMG Pherastar) by recording the fluorescence emissions at 545 nm and 570 nm after excitation at 337-350 nm. The ratio between emission at 570 nm divided by emission at 545 nm was calculated to give the well ratio. The experimental data (well ratios) were normalised by the following way: positive control contained ATR-working solution plus either tracer A or B solution (=0% inhibition), the negative control contained all components except GST-ATR/ATRIP (=100% inhibition). Usually the compounds were tested on the same MTP in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM). The dilution series were prepared separately before the assay on the level of the 100 fold concentrated solutions in DMSO by serial 1:3.4 dilutions in duplicate values for each concentration. $IC_{50}$ values were calculated by a 4 parameter fit using standard software (GraphPad prism or equivalent).

TABLE 7

| | ATR binding | |
|---|---|---|
| Example No | ATR binding (tracer A) $IC_{50}$ [M] | ATR binding (tracer B) $IC_{50}$ [M] |
| 1 | 3.68E−8 | 2.39E−8 |
| 2 | 9.52E−8 | 3.83E−8 |
| 3 | 5.69E−8 | 3.87E−8 |
| 4 | 6.17E−8 | 4.35E−8 |
| 5 | 6.43E−8 | 3.41E−8 |
| 6 | 6.86E−8 | |
| 7 | 5.87E−8 | 2.65E−8 |
| 8 | 1.18E−7 | 6.92E−8 |
| 9 | 1.20E−7 | 1.27E−7 |
| 10 | 1.26E−7 | 4.39E−8 |
| 11 | 1.35E−7 | 8.68E−8 |
| 12 | 1.35E−7 | 4.72E−8 |
| 13 | 1.41E−7 | 1.04E−7 |
| 14 | 1.62E−7 | 7.99E−8 |
| 15 | 1.63E−7 | 1.74E−7 |
| 16 | 1.73E−7 | |
| 17 | 1.85E−7 | 1.17E−7 |
| 18 | 2.28E−7 | 7.51E−8 |
| 19 | 2.93E−7 | 1.81E−7 |
| 20 | 8.16E−7 | 3.20E−7 |
| 21 | 1.90E−7 | |
| 22 | 4.65E−7 | |
| 23 | 4.43E−7 | |
| 24 | 3.82E−8 | 2.07E−8 |
| 25 | 1.10E−7 | 7.51E−8 |
| 26 | 1.56E−8 | 6.36E−9 |
| 27 | 1.72E−8 | 1.09E−8 |
| 28 | 1.76E−8 | 8.40E−9 |
| 29 | 2.15E−8 | 9.23E−9 |
| 30 | 2.28E−8 | 9.48E−9 |
| 31 | 8.66E−8 | 4.51E−8 |
| 32 | 8.47E−8 | 3.67E−8 |
| 33 | 1.98E−8 | 1.03E−8 |
| 34 | 3.57E−7 | 5.36E−7 |
| 35 | 1.22E−7 | 7.55E−8 |
| 36 | 1.50E−6 | |
| 37 | 1.70E−7 | 1.27E−7 |
| 38 | 5.02E−7 | 4.05E−7 |
| 39 | 6.01E−8 | 3.53E−8 |
| 40 | 1.25E−7 | 9.90E−8 |
| 41 | 3.39E−7 | 2.30E−7 |
| 42 | 4.84E−7 | 5.33E−7 |
| 43 | 4.93E−7 | 2.58E−7 |
| 44 | 5.43E−7 | 3.27E−7 |
| 45 | 2.93E−7 | |
| 46 | 2.62E−7 | |
| 47 | 1.39E−6 | |
| 48 | 1.61E−7 | |
| 49 | 2.00E−7 | |
| 50 | 4.10E−7 | 5.14E−7 |
| 51 | 3.80E−8 | 2.33E−8 |
| 52 | 1.01E−7 | 7.89E−8 |
| 53 | 1.92E−7 | 6.35E−8 |
| 54 | 2.88E−7 | 1.29E−7 |
| 55 | 1.62E−7 | |
| 56 | 7.51E−7 | 3.24E−7 |
| 57 | 2.30E−7 | |
| 58 | 4.13E−7 | 6.15E−7 |
| 59 | 7.30E−7 | 1.25E−6 |
| 60 | 2.41E−8 | 1.57E−8 |
| 61 | 7.09E−7 | 5.03E−7 |
| 62 | 9.97E−7 | 7.07E−7 |
| 63 | 8.07E−8 | 3.07E−8 |
| 64 | 2.74E−8 | |
| 65 | 3.35E−7 | 2.76E−7 |
| 66 | 8.72E−8 | |
| 67 | 1.00E−6 | 1.27E−6 |
| 68 | 5.89E−7 | 4.72E−7 |
| 69 | 5.34E−9 | |
| 70 | 5.17E−9 | |
| 71 | 5.65E−9 | |
| 72 | 6.33E−9 | |
| 73 | 6.71E−9 | |
| 74 | 7.10E−9 | |
| 75 | 6.97E−9 | |
| 76 | 8.91E−9 | |
| 77 | 8.92E−9 | |
| 78 | 1.10E−8 | |
| 79 | 1.20E−8 | |
| 80 | 1.21E−8 | |
| 81 | 1.43E−8 | |
| 82 | 4.90E−9 | |
| 83 | 5.38E−9 | |
| 84 | 6.60E−9 | |
| 85 | 1.19E−8 | |
| 86 | 1.09E−8 | |
| 87 | 8.71E−9 | |
| 88 | 1.53E−8 | |
| 89 | 8.11E−9 | |
| 90 | 1.06E−8 | |
| 91 | 1.00E−8 | |
| 92 | 1.37E−8 | |
| 93 | 1.09E−8 | |
| 94 | 1.37E−8 | |
| 95 | 1.13E−8 | |
| 96 | 1.27E−8 | |
| 97 | 1.39E−8 | |

TABLE 7-continued

| Example No | ATR binding (tracer A) IC$_{50}$ [M] | ATR binding (tracer B) IC$_{50}$ [M] |
|---|---|---|
| 98 | 1.31E−8 | |
| 99 | 6.38E−9 | |
| 100 | 1.65E−8 | |
| 101 | 1.13E−8 | |
| 102 | 1.23E−8 | |
| 103 | 1.01E−8 | |
| 104 | 1.41E−8 | |
| 105 | 8.67E−9 | |
| 106 | 1.31E−8 | |
| 107 | 1.37E−8 | |
| 108 | 1.15E−8 | |
| 109 | 9.14E−9 | |
| 110 | 1.35E−8 | |
| 111 | 7.24E−9 | |
| 112 | 4.74E−9 | |
| 113 | 5.71E−9 | |
| 114 | 7.35E−9 | |
| 115 | 7.44E−9 | |
| 116 | 9.51E−9 | |
| 117 | 8.16E−9 | |
| 118 | 1.01E−8 | |
| 119 | 1.17E−8 | |
| 120 | 1.31E−8 | |
| 121 | 1.74E−8 | |
| 122 | 1.94E−8 | |
| 123 | 2.13E−8 | |
| 124 | 1.36E−8 | |
| 125 | 1.72E−8 | |
| 126 | 2.15E−8 | |
| 127 | 2.55E−8 | |
| 128 | 3.26E−8 | |
| 129 | 3.53E−8 | |
| 130 | 2.16E−8 | |
| 131 | 2.31E−8 | |
| 132 | 2.37E−8 | |
| 133 | 2.70E−8 | |
| 134 | 3.43E−8 | |
| 135 | 3.29E−8 | |
| 136 | 3.58E−8 | |
| 137 | 2.60E−8 | |
| 138 | 2.90E−8 | |
| 139 | 4.17E−8 | |
| 140 | 7.65E−8 | |
| 141 | 3.86E−7 | |
| 142 | 4.41E−8 | |
| 143 | 2.77E−8 | |
| 144 | 7.51E−8 | |
| 145 | 1.82E−8 | |
| 146 | 3.57E−8 | |
| 147 | 4.54E−8 | |
| 148 | 4.79E−8 | |
| 149 | 4.84E−8 | |
| 150 | 5.03E−8 | |
| 151 | 5.12E−8 | 2.32E−8 |
| 152 | 5.18E−8 | |
| 153 | 5.47E−8 | |
| 154 | 5.50E−8 | |
| 155 | 6.33E−8 | |
| 156 | 8.01E−8 | |
| 157 | 9.18E−8 | |
| 158 | 1.35E−8 | |
| 159 | 1.65E−8 | |
| 160 | 3.72E−8 | |
| 161 | 6.26E−8 | |
| 162 | 1.00E−7 | |
| 163 | 1.07E−7 | |
| 164 | 1.61E−7 | |
| 165 | 2.24E−7 | |
| 166 | 3.65E−7 | |
| 167 | 4.08E−7 | |
| 168 | 5.30E−7 | |
| 169 | 1.15E−7 | |
| 170 | 1.68E−7 | |
| 171 | 9.47E−8 | |
| 172 | 8.28E−8 | |
| 173 | 2.05E−7 | |
| 174 | 2.13E−7 | |
| 175 | 2.21E−7 | |
| 176 | 2.23E−7 | |
| 177 | 2.50E−7 | |
| 178 | 3.77E−7 | |
| 179 | 4.54E−7 | |
| 180 | 4.87E−7 | |
| 181 | 5.39E−7 | |
| 182 | 6.32E−7 | |
| 183 | 6.49E−7 | |
| 184 | 7.63E−7 | |
| 185 | 8.52E−7 | |
| 186 | 6.74E−8 | |
| 187 | 9.68E−8 | |
| 188 | 2.51E−7 | |
| 189 | 2.14E−8 | |
| 190 | 9.50E−9 | |
| 191 | 4.41E−8 | |
| 192 | 1.15E−7 | |
| 193 | 2.45E−7 | |
| 194 | 3.76E−8 | |
| 195 | 7.14E−8 | |
| 196 | 7.26E−8 | |
| 197 | 7.24E−8 | |
| 198 | 2.93E−7 | |
| 199 | 1.38E−7 | |
| 200 | 8.69E−8 | |
| 201 | 4.00E−8 | |
| 202 | 7.83E−8 | |
| 203 | 1.13E−8 | |
| 204 | 6.76E−9 | |
| 205 | 4.93E−8 | |
| 206 | 4.04E−7 | |
| 207 | 5.42E−7 | |
| 208 | 1.16E−6 | |
| 209 | 3.85E−7 | |
| 210 | 2.31E−7 | |
| 211 | 5.47E−7 | |
| 212 | >2.00E−5 | |
| 213 | 5.35E−8 | |
| 214 | 1.76E−7 | |
| 215 | 3.17E−7 | |
| 216 | 8.44E−8 | |
| 217 | 8.02E−7 | |
| 218 | 1.18E−8 | |
| 219 | 1.32E−7 | |
| 220 | 3.24E−8 | |
| 221 | 1.96E−7 | |
| 222 | 5.02E−8 | |
| 223 | 1.24E−7 | |
| 224 | 5.21E−8 | |
| 225 | 4.47E−7 | |
| 226 | 1.14E−6 | |
| 227 | 7.55E−8 | |
| 228 | 3.01E−8 | |
| 229 | 2.84E−8 | |
| 230 | 3.17E−8 | |
| 232 | 3.91E−8 | |
| 233 | 4.20E−8 | |
| 234 | 2.92E−8 | |
| 235 | 2.13E−8 | |
| 236 | 2.82E−8 | |
| 237 | 1.82E−8 | |
| 238 | 3.45E−8 | |
| 239 | 2.03E−8 | |
| 240 | 3.00E−8 | |
| 241 | 4.06E−9 | |
| 242 | 9.59E−8 | |
| 243 | 3.65E−8 | |
| 244 | 1.59E−7 | |
| 245 | 3.20E−8 | |
| 246 | 6.80E−8 | |
| 247 | 2.16E−8 | |
| 248 | 2.41E−8 | |

TABLE 7-continued

ATR binding

| Example No | ATR binding (tracer A) IC$_{50}$ [M] | ATR binding (tracer B) IC$_{50}$ [M] |
|---|---|---|
| 249 | 1.37E−8 | |
| 250 | 6.62E−9 | |
| 251 | 2.75E−8 | |
| 252 | 6.45E−9 | |
| 253 | 3.37E−8 | |
| 254 | 4.48E−8 | |
| 255 | 4.27E−8 | |
| 256 | 5.62E−8 | |
| 257 | 5.88E−8 | |
| 258 | 7.66E−9 | |
| 259 | 1.71E−8 | |
| 260 | 2.81E−8 | |
| 261 | 2.92E−8 | |
| 262 | 4.22E−8 | |
| 263 | 1.93E−8 | |
| 264 | 2.55E−8 | |
| 265 | 7.46E−8 | |
| 266 | 8.31E−9 | |
| 267 | 1.01E−6 | |
| 268 | 1.93E−8 | |
| 269 | 1.27E−8 | |
| 270 | 3.37E−8 | |
| 271 | 4.16E−8 | |
| 272 | 2.13E−8 | |
| 273 | 1.40E−8 | |
| 274 | 6.27E−8 | |
| 275 | 3.04E−7 | |
| 276 | 2.37E−7 | |
| 277 | 7.82E−8 | |
| 278 | 2.69E−8 | |
| 279 | 2.93E−7 | |
| 280 | 4.68E−8 | |
| 281 | 1.36E−8 | |
| 282 | 1.27E−8 | |
| 283 | 3.37E−8 | |
| 284 | 4.16E−8 | |
| 285 | 5.09E−7 | |
| 286 | 1.45E−8 | |
| 287 | 6.75E−7 | 4.61E−7 |
| 288 | 3.45E−7 | |
| 289 | 2.99E−6 | |
| 290 | 1.19E−6 | |
| 291 | 8.37E−8 | |
| 292 | 1.08E−7 | |
| 293 | 3.28E−7 | |
| 294 | 3.72E−8 | |
| 295 | 1.13E−7 | |
| 296 | 7.68E−8 | |
| 297 | 1.19E−7 | |
| 298 | 5.92E−8 | |
| 299 | 5.52E−8 | |
| 300 | 1.81E−7 | |
| 301 | 2.16E−8 | |
| 302 | 1.88E−7 | |
| 303 | 8.61E−8 | |
| 304 | 5.72E−8 | |
| 305 | 1.33E−7 | |
| 306 | 8.23E−8 | |
| 307 | 1.89E−7 | |
| 308 | 1.31E−7 | |
| 309 | 1.46E−7 | |
| 310 | 9.77E−8 | |
| 311 | 3.76E−7 | |
| 312 | 2.37E−8 | |
| 313 | 2.90E−8 | |
| 314 | 6.79E−8 | |
| 316 | 5.32E−8 | |
| 317 | 6.65E−8 | |
| 318 | 3.06E−8 | |
| 319 | 3.25E−7 | |
| 320 | 4.68E−8 | |
| 321 | 4.44E−8 | |
| 322 | 8.09E−8 | |
| 324 | 7.77E−8 | |
| 325 | 3.44E−8 | |
| 326 | 7.32E−8 | |
| 327 | 1.77E−8 | |
| 328 | 2.96E−7 | |
| 329 | 1.69E−7 | |
| 330 | 9.13E−8 | |
| 331 | 3.76E−7 | |
| 332 | 6.81E−8 | |
| 333 | 2.53E−8 | |
| 334 | 5.81E−8 | |
| 335 | 6.62E−8 | |
| 336 | 1.20E−7 | |
| 337 | 2.84E−8 | |
| 338 | 1.03E−7 | |
| 339 | 8.96E−8 | |
| 340 | 3.35E−8 | |
| 341 | 2.64E−8 | |
| 342 | 2.77E−6 | |
| 343 | 1.98E−8 | |
| 344 | 1.74E−7 | |
| 345 | 5.56E−8 | |
| 346 | 1.40E−7 | |
| 347 | 2.41E−7 | |
| 348 | 5.53E−8 | |
| 349 | 1.19E−7 | |
| 350 | 1.62E−7 | |
| 351 | 1.54E−7 | |
| 352 | 1.75E−7 | |
| 353 | 2.42E−7 | |
| 354 | 8.47E−8 | |
| 355 | 4.84E−7 | |
| 356 | 7.95E−8 | |
| 357 | 5.35E−8 | |
| 358 | 4.64E−8 | |
| 359 | 8.55E−8 | |
| 360 | 9.38E−8 | |
| 361 | 5.22E−8 | |
| 362 | 2.95E−7 | |
| 363 | 1.91E−7 | |
| 364 | 5.64E−8 | |
| 365 | 1.03E−7 | |
| 366 | 5.21E−8 | |
| 367 | 2.15E−7 | |
| 368 | 3.95E−6 | |
| 369 | 1.15E−7 | |
| 370 | 3.50E−8 | |
| 371 | 1.22E−7 | |
| 372 | 1.34E−7 | |
| 373 | 3.81E−8 | |
| 374 | 1.36E−7 | |
| 375 | 8.94E−7 | |
| 376 | 3.57E−7 | |
| 377 | 2.99E−6 | |
| 378 | 9.27E−8 | |
| 379 | 6.98E−8 | |
| 380 | 1.46E−6 | |
| 381 | 1.21E−7 | |
| 382 | 1.99E−7 | |
| 383 | 2.39E−7 | |
| 384 | 8.92E−8 | |
| 385 | 8.51E−8 | |
| 386 | 1.73E−7 | |
| 387 | 2.18E−7 | |
| 388 | 7.91E−8 | |
| 389 | 2.66E−8 | |
| 390 | 6.63E−7 | |
| 391 | 1.76E−7 | |
| 392 | 4.43E−8 | |
| 393 | 4.15E−8 | |
| 394 | 1.19E−7 | |
| 395 | 1.49E−7 | |
| 396 | 1.74E−7 | |
| 397 | 9.55E−8 | |
| 398 | 1.20E−7 | |
| 399 | 6.18E−7 | |
| 400 | 3.00E−7 | |

TABLE 7-continued

ATR binding

| Example No | ATR binding (tracer A) IC$_{50}$ [M] | ATR binding (tracer B) IC$_{50}$ [M] |
|---|---|---|
| 401 | 8.75E−8 | |
| 402 | 2.99E−7 | |
| 403 | 1.94E−7 | |
| 404 | 4.24E−7 | |
| 405 | 4.19E−7 | |
| 406 | 3.64E−7 | |
| 407 | 3.09E−7 | |
| 408 | 6.51E−8 | |
| 409 | 1.39E−7 | |
| 410 | 1.53E−7 | |
| 412 | 1.62E−7 | |
| 413 | 2.79E−7 | |
| 414 | 9.08E−8 | |
| 415 | 3.27E−8 | |
| 416 | 2.51E−7 | |
| 417 | 1.07E−6 | |
| 418 | 9.41E−8 | |
| 419 | 1.18E−7 | |
| 420 | 6.02E−7 | |
| 421 | 1.79E−6 | |
| 422 | 2.24E−6 | |
| 423 | 8.39E−8 | |
| 424 | 2.41E−7 | |
| 425 | 1.00E−6 | |
| 426 | 1.59E−7 | |
| 427 | 1.12E−7 | |
| 428 | 6.98E−8 | |
| 429 | 4.48E−8 | |
| 430 | 6.13E−8 | |
| 431 | 3.47E−8 | |
| 432 | 2.04E−6 | |
| 433 | 4.16E−8 | |
| 434 | 3.18E−8 | |
| 435 | 6.51E−8 | |
| 436 | 2.40E−8 | |
| 437 | 1.18E−7 | |

2. ATR Activity Assay

ATR kinase phosphorylates a biotinylated peptide derived from Rad17 (sequence: biotin-PEG2-ASELPASQPQPFS-amide, produced by Biosyntan GmbH, Berlin). The assay measures the amount of phosphorylated peptide by time-resolved fluorescence (TR-FRET). Streptavidin-XL665 (Cisbio, reference #610SAXLB), an anti-Rad17-phospho-serine 645 specific antibody (available from either Imgenex/Biomol, reference # IMG-6386A, or from Lifespan, reference # LS-C43028) and antiRabbit-IgG-Europium (Perkin Elmer, reference # AD0083) are employed to specifically detect phosphorylated biotin-peptide, but not non-phosphorylated peptide. Excitation of Europium with 337 nm light results in emission of fluorescent light with 620 nm. In case a tetrameric detection complex has formed, part of the energy will be transferred to the Streptavidin-XL665 fluorophor that itself emits light of 665 nm. Unphosphorylated peptide does not give rise to light emission at 665 nm, because no FRET-competent detection complex can be formed.

For the assay 50 nl of a 100-fold concentrated solution of the test compound in DMSO was pipetted into a black low volume 384 well microtiter plate (MTP, Greiner Bio-One, Frickenhausen, Germany). To prepare the ATR-working solution, ATR/ATRIP stock solution (expression and purification: see above) was diluted in assay buffer [50 mM HEPES (pH 7.0), 10 mM MgCl2, 1 mM dithiothreitol (DTT), 0.01% (w/v) Igepal, 0.2% (w/v) bovine gamma globulin (BGG)] to 10 nM protein concentration (concentration may vary from lot to lot of protein preparation). A substrate working solution was prepared by diluting the biotinylated Rad17 peptide to 0.5 µM together with ATP to 20 µM in assay buffer. A stop/detection working solution was prepared containing 50 mM Hepes pH 7.0, 0.15% (w/v) bovine serum albumin (BSA), 150 mM EDTA, 200 nM Streptavidin-XL665, 2.5 nM anti phospho Rad17-pS645 (IMG-6386A) and 1.5 nM anti-Rabbit-IgG-Eu. The amount of the antibodies is dependent on the batch used and was optimized by variation the activity of the batch. All solutions were kept at 20° C. First, 2.5 µl of ATR-working solution were dispensed into the wells of the MTP containing the test compounds. After 10 minutes pre-incubation to allow binding of the compounds to ATR, 2.5 µl of substrate working solution was dispensed to the wells. After 180 minutes, 5 µl of stop/detection solution were dispensed into the wells. The resulting mixture was incubated for 60 min at 20° C. The measurement of the TR-FRET signal was performed in a standard HTRF-compatible MTP reader instruments (e.g. BMG Pherastar or Perkin Elmer ViewLux) by recording the fluorescence emissions at 620 nm and 665 nm after excitation at 337-350 nm. The ratio between emission at 665 nm divided by emission at 620 nm was calculated to give the well ratio. The experimental data (well ratios) were normalised by the following way: positive control was composed of ATR-working solution+substrate solution (=0% inhibition), the negative control contains the same reagents, but ATR-working solution is replaced by assay buffer (=100% inhibition). Usually the compounds were tested on the same MTP in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM) The dilution series were prepared separately before the assay on the level of the 100 fold concentrated solutions in DMSO by serial 1:3.4 dilutions in duplicate values for each concentration. IC$_{50}$ values were calculated by a 4 parameter fit using with standard software (GraphPad prism or equivalent).

3. Proliferation Assay

Human tumour cells (Table 8) were originally obtained from the American Type Culture Collection (ATCC), the Deutsche Sammlung von Mikroorganismen und Zellkulturen (DSMZ, German Collection of Microorganisms and Cell Cultures), or Epo GmbH Berlin. Adherently growing cells (HeLa, HeLa-MaTu-ADR, HT-144, Lovo, HT-29, NCI-H460, DU145, Caco2, B16F10) were plated out in a density of 1500-4000 cells/measurement point, depending on the rate of growth of the cell line, in a 96-well multititre plate in 200 µl of growth medium (DMEM/HAMS F12, 2 mM L-glutamine, 10% foetal calf serum). After 24 hours, the cells of one plate (zero plate) were dyed with crystal violet (see below), whereas the medium of the other plates was replaced with fresh culture medium (200 µl) to which the test substances were added in various concentrations (0 µM, and also in the range of 0.001-10 µM; the final concentration of the solvent dimethyl sulphoxide was 0.1 or 0.5%). The cells were incubated for 4 days in the presence of the test substances. Cell proliferation was determined by staining the cells with crystal violet: the cells were fixed at room temperature for 15 min by adding 20 µl/measurement point of an 11% strength glutaraldehyde solution. After washing the fixed cells three times with water, the plates were dried at room temperature. The cells were stained by adding 100 µl/measurement point of a 0.1% strength crystal violet solution (pH adjusted to pH 3 by adding acetic acid). After washing the cells three times with water, the plates were dried at room temperature. The dye was dissolved by adding 100 µl/measurement point of a 10% strength acetic acid solution. Absorbance was determined photometrically at a wavelength of 595 nm. The percentage change in cell growth was calculated by normalizing the measured values to the absorbance values of the zero plate (=0%) and the absorbance of the untreated (0 W) cells (=100%). The $IC_{50}$ values were determined by means of a four parameter fit.

Cells growing in suspension (GRANTA-519, Jeko-1) were plated out in a cell density of 2000-4000 cells/measurement point, depending on the rate of growth of the cell line, in a black-walled, clear-bottom 96-well multititre plate in 100 μl of growth medium (DMEM/HAMS F12, 2 mM L-glutamine, 10% foetal calf serum). After 24 hours, cell density was determined in one plate (zero plate) by adding 60 μl/measurement point of CTG solution (Promega Cell Titer-Glo solution (catalogue numbers G755B and G756B)), subsequent incubation for 2 min followed by 10 min shaking (in the dark) and measurement of luminescence (VICTOR V, Perkin Elmer).

For the test plates, the test substances were prepared in various concentrations (0 μM, and also in the range of 0.001-10 μM; the final concentration of the solvent dimethyl sulphoxide was 0.1 or 0.5%) as 3× concentrated solutions in fresh growth medium. Aliquots of 50 μl each were added to the cell suspensions and the cells were incubated for 4 days in the presence of the test substances. Subsequently, cell density was determined using CTG solution as described above and $IC_{50}$ values were calculated by means of a four parameter fit.

The substances were investigated in the following cell lines, which, by way of example, represent the specified indications (Table 8).

TABLE 8

List of the cell lines investigated in the proliferation assays.

| Tumour indication | Cell line | Source |
|---|---|---|
| Cervical cancer | HeLa | DSMZ ACC-57 |
|  | HeLa-MaTu-ADR (multi-drug resistant) | Epo GmbH |
| Colon & colorectal cancer | Lovo | DSMZ ACC-500 |
|  | HT29 | DSMZ ACC-299 |
|  | Caco-2 | DSMZ ACC-169 |
| Lymphoma, mantle cell | GRANTA-519 | DSMZ ACC-342 |
|  | Jeko-1 | DSMZ ACC-553 |
| Melanoma, malignant | HT-144 | ATCC HTB-63 |
|  | B16F10 | ATCC CRL-6475 |
| Non-small cell lung cancer | NCI-H460 | ATCC HTB-177 |
| Prostate cancer (hormone independent) | DU145 | DSMZ ACC-261 |

The results of the proliferation assays demonstrate the efficacy of test compounds in the human tumour cells investigated. These data suggest a possible use of the test compounds in the tumour types investigated.

TABLE 9

Inhibition of proliferation of HeLa, HeLa-MaTu-ADR, NCI-H460, DU145, Caco-2 and B16F10 cells by compounds according to the present invention, determined as described above. All $IC_{50}$ (inhibitory concentration at 50% of maximal effect) values are indicated in M, "n.t." means that the compounds have not been tested in the respective assay.
Table 9: Inhibition of proliferation

| ① | ② | ③ | ④ | ⑤ | ⑥ | ⑦ |
|---|---|---|---|---|---|---|
| 3 | 2.77E−6 |  |  |  |  |  |
| 5 |  | >3.00E−6 | 6.41E−7 | 3.68E−7 | 2.19E−6 | 2.98E−6 |
| 6 | 1.49E−6 |  |  |  |  |  |
| 7 | 1.33E−6 | 2.31E−6 >1.00E−5 8.97E−6 | 1.02E−6 | 1.59E−6 | 5.95E−6 | 2.98E−6 |
| 8 | 2.26E−6 | >3.00E−6 | 9.09E−7 | 2.05E−6 | >3.00E−6 | >3.00E−6 |
| 9 | 1.01E−6 |  |  |  |  |  |
| 10 | 4.96E−7 | 1.30E−6 | 4.47E−7 | 8.27E−7 | 1.46E−6 | 2.98E−6 |
| 11 | >1.00E−5 3.05E−6 2.28E−6 |  |  |  |  |  |
| 14 | 1.99E−6 |  |  |  |  |  |
| 15 | 1.41E−6 | >3.00E−6 | 5.28E−7 | 8.17E−7 | 1.72E−6 | >3.00E−6 |
| 24 |  | 3.41E−6 | 3.78E−7 | 1.35E−6 | 8.33E−7 | 3.65E−6 |
| 26 | 2.96E−7 | >1.00E−6 | 5.86E−7 | 7.25E−7 | >1.00E−6 | >1.00E−6 |
| 27 | 3.55E−7 |  |  |  |  |  |
| 28 | 3.16E−7 |  |  |  |  |  |
| 29 | 3.94E−7 | 4.98E−7 | 2.43E−7 | 2.91E−7 | 5.77E−7 | 1.58E−6 |
| 30 | 5.12E−7 | >3.00E−6 | 2.93E−7 | 3.25E−7 | 2.89E−6 | 1.37E−6 |
| 31 | 1.25E−6 | >3.00E−6 | 6.85E−7 | 1.11E−6 | >3.00E−6 | >3.00E−6 |
| 32 | 1.56E−6 | >3.00E−6 | >3.00E−6 1.95E−6 | 1.84E−6 | >3.00E−6 | >3.00E−6 |
| 33 |  | >3.00E−6 | 2.69E−7 | 1.01E−6 | 6.53E−7 | 1.08E−6 |
| 34 | 1.02E−6 | >3.00E−6 | 1.63E−6 | 2.39E−6 | 4.99E−6 | >3.00E−6 |
| 37 | 5.08E−6 |  |  |  |  |  |
| 39 | 1.05E−6 |  | 4.00E−7 | 8.37E−7 |  |  |
| 40 | 2.72E−6 | 2.26E−6 | 6.72E−7 | 1.15E−6 | 1.97E−6 | 2.82E−6 >3.00E−6 |
| 43 | 3.88E−6 |  |  |  |  |  |
| 44 | 1.01E−6 | >1.00E−5 | 2.01E−6 | 4.45E−6 | 7.69E−6 | >1.00E−5 |
| 50 | >1.00E−5 >1.00E−5 |  |  |  |  |  |
| 51 | 1.23E−6 | 1.80E−6 | 3.91E−7 | 8.95E−7 | 2.93E−6 | >3.00E−6 |
| 53 | 1.41E−6 |  |  |  |  |  |

TABLE 9-continued

Inhibition of proliferation of HeLa, HeLa-MaTu-ADR, NCI-H460, DU145, Caco-2 and B16F10 cells by compounds according to the present invention, determined as described above. All $IC_{50}$ (inhibitory concentration at 50% of maximal effect) values are indicated in M, "n.t." means that the compounds have not been tested in the respective assay.

Table 9: Inhibition of proliferation

| ① | ② | ③ | ④ | ⑤ | ⑥ | ⑦ |
|---|---|---|---|---|---|---|
| 57 |  | 6.98E−6 | 3.74E−7 | 1.56E−6 | 5.51E−7 | 6.32E−6 |
|  |  | >3.00E−6 |  |  | >3.00E−6 | >3.00E−6 |
| 60 | 9.98E−7 | 2.17E−6 | 6.91E−7 | 7.30E−7 | 1.98E−6 | >3.00E−6 |
| 62 | 1.64E−7 | >3.00E−6 | >3.00E−6 | >3.00E−6 | <3.00E−8 | 1.31E−7 |
|  |  | 1.13E−6 | >3.00E−6 | 2.29E−7 | >3.00E−6 | 2.18E−5 |
|  |  |  |  |  |  | >3.00E−6 |
| 63 |  | 1.53E−6 | 3.08E−7 | 9.15E−7 | 1.54E−6 | 2.19E−6 |
| 64 |  | 1.17E−6 | 9.23E−8 | 5.06E−7 | 8.44E−7 | 8.76E−7 |
| 66 |  | 8.90E−6 | 1.27E−7 | 7.26E−7 | 3.35E−6 | 2.98E−6 |
|  |  | >3.00E−6 |  | >3.00E−6 |  |  |
| 69 | 1.91E−7 |  |  |  |  |  |
| 70 | 2.01E−7 |  |  |  |  |  |
| 71 | 1.67E−7 |  |  |  |  |  |
| 72 | 2.00E−7 |  |  |  |  |  |
| 73 | 1.81E−7 | 1.79E−6 | 5.90E−8 | 7.48E−7 | 6.31E−7 | 6.04E−7 |
| 74 | 2.03E−7 | >1.00E−6 | >1.00E−6 | >1.00E−6 | >1.00E−6 | >1.00E−6 |
| 75 | 2.71E−7 |  |  |  |  |  |
| 76 | 9.68E−7 |  |  |  |  |  |
| 77 | 2.54E−7 |  |  |  |  |  |
| 78 | 6.55E−7 |  |  |  |  |  |
| 79 | 3.03E−7 | 2.30E−6 | 9.37E−8 | 6.56E−7 | 8.68E−7 | 1.06E−6 |
| 80 | 1.87E−7 |  |  |  |  |  |
| 81 | 2.45E−7 |  |  |  |  |  |
| 82 | 5.29E−7 |  |  |  |  |  |
| 83 | 3.31E−7 |  |  |  |  |  |
| 84 | 1.30E−7 |  |  |  |  |  |
| 85 | 4.38E−7 |  |  |  |  |  |
| 87 | 5.43E−7 |  |  |  |  |  |
| 88 | 1.57E−7 | 2.91E−7 | 8.17E−8 | 1.04E−7 | 2.86E−7 | 4.98E−7 |
| 89 | 1.42E−7 |  |  |  |  |  |
| 90 | 9.20E−8 |  |  |  |  |  |
| 91 | 1.08E−7 |  |  |  |  |  |
| 92 | 1.17E−7 |  |  |  |  |  |
| 93 | 1.79E−7 |  |  |  |  |  |
| 94 | 2.68E−7 |  |  |  |  |  |
| 95 | 2.11E−7 |  |  |  |  |  |
| 96 | 1.69E−7 |  |  |  |  |  |
| 97 | 2.52E−7 |  |  |  |  |  |
| 98 | 4.40E−7 |  |  |  |  |  |
| 99 | 4.00E−7 |  |  |  |  |  |
| 100 | 9.50E−7 |  |  |  |  |  |
| 101 | 3.41E−7 |  |  |  |  |  |
| 102 | 6.04E−7 |  |  |  |  |  |
| 103 | 3.74E−7 |  |  |  |  |  |
| 104 | 4.99E−7 |  |  |  |  |  |
| 105 | 1.00E−6 |  |  |  |  |  |
| 106 | 4.34E−7 |  |  |  |  |  |
| 107 | 3.06E−7 |  |  |  |  |  |
| 108 | 4.56E−7 |  |  |  |  |  |
| 109 | 2.98E−7 |  |  |  |  |  |
| 110 | 2.06E−7 |  |  |  |  |  |
| 111 | 1.56E−7 | 2.26E−7 | 6.50E−8 | 1.10E−7 | 2.37E−7 | 7.11E−7 |
| 112 | 9.95E−8 |  |  |  |  |  |
| 113 | 1.22E−7 |  |  |  |  |  |
| 114 | 1.77E−7 |  |  |  |  |  |
| 115 | 1.99E−7 |  |  |  |  |  |
| 116 | 2.84E−7 |  |  |  |  |  |
| 117 | 2.25E−7 |  |  |  |  |  |
| 118 | 1.71E−7 |  |  |  |  |  |
| 119 | 4.25E−7 |  |  |  |  |  |
| 120 | 3.54E−7 |  |  |  |  |  |
| 121 | 3.52E−7 |  |  |  |  |  |
| 122 | 7.06E−7 |  |  |  |  |  |
| 123 | 4.31E−7 |  |  |  |  |  |
| 124 | 1.56E−7 |  |  |  |  |  |
| 125 | 7.05E−7 | >3.00E−6 | 5.61E−7 | 7.12E−7 | >3.00E−6 | >3.00E−6 |
|  |  | >3.00E−6 | 5.41E−7 | 7.64E−7 | 2.63E−6 | >3.00E−6 |
| 126 | 1.70E−7 | 5.95E−7 | 8.84E−8 | 9.40E−8 | 3.40E−7 | 9.06E−7 |
| 127 | 5.78E−7 |  |  |  |  |  |
| 128 | 7.70E−7 |  |  |  |  |  |
| 129 | 6.86E−7 |  |  |  |  |  |

TABLE 9-continued

Inhibition of proliferation of HeLa, HeLa-MaTu-ADR, NCI-H460, DU145, Caco-2 and B16F10 cells by compounds according to the present invention, determined as described above. All IC$_{50}$ (inhibitory concentration at 50% of maximal effect) values are indicated in M, "n.t." means that the compounds have not been tested in the respective assay.
Table 9: Inhibition of proliferation

| ① | ② | ③ | ④ | ⑤ | ⑥ | ⑦ |
|---|---|---|---|---|---|---|
| 130 | 3.74E−7 | | | | | |
| 131 | 3.49E−7 | | | | | |
| 132 | 5.07E−7 | | | | | |
| 133 | 1.07E−6 | | | | | |
| 134 | 1.53E−6 | | | | | |
| 135 | 1.82E−6 | | | | | |
| 136 | 5.75E−7 | | | | | |
| 137 | 3.83E−7 | 7.91E−7 | 1.53E−7 | 1.46E−7 | 5.49E−7 | 7.79E−7 |
| 138 | 6.19E−7 | | | | | |
| 139 | 1.37E−6 | | | | | |
| 142 | 1.59E−6 | | | | | |
| 143 | 5.43E−7 | | | | | |
| 144 | >3.00E−6 | | | | | |
| 145 | 2.48E−7 | 5.22E−7 | 9.06E−8 | 3.05E−8 | 4.92E−7 | 1.09E−6 |
| 146 | 1.11E−6 | | | | | |
| 147 | 9.53E−7 | | | | | |
| 148 | 8.05E−7 | | | | | |
| 151 | 9.21E−7 | 2.15E−6 | 6.73E−7 | 1.90E−6 | 2.05E−6 | 2.13E−6 |
| 152 | 6.71E−7 | | | | | |
| 153 | 7.59E−7 | | | | | |
| 155 | 9.59E−7 | | | | | |
| 156 | | | | | | |
| 157 | 8.72E−7 | >3.00E−6 | >3.00E−6 | >3.00E−6 | >3.00E−6 | >3.00E−6 |
|  |  | >3.00E−6 | >3.00E−6 | >3.00E−6 | >3.00E−6 | >3.00E−6 |
| 158 | 3.28E−7 | | | | | |
| 159 | 6.16E−8 | | | | | |
| 160 | 4.51E−7 | | | | | |
| 161 | 5.88E−7 | | | | | |
| 162 | 1.22E−6 | | | | | |
| 169 | 7.31E−7 | >3.00E−6 | 2.62E−6 | 2.82E−6 | >3.00E−6 | >3.00E−6 |
|  |  | >3.00E−6 | 5.62E−7 | 5.91E−7 | >3.00E−6 | >3.00E−6 |
| 170 | 2.41E−6 | | | | | |
| 172 | 2.10E−6 | | | | | |
| 173 | >3.00E−6 | | | | | |
| 176 | 2.52E−6 | | | | | |
| 177 | >3.00E−6 | | | | | |
| 178 | >3.00E−6 | | | | | |
| 179 | >3.00E−6 | | | | | |
| 185 | >3.00E−6 | | | | | |
| 186 | 7.89E−7 | | | | | |
| 189 | 1.01E−6 | | | | | |
| 190 | 3.34E−7 | | | | | |
| 191 | 2.12E−6 | | | | | |
| 194 | 8.92E−7 | | | | | |
| 195 | 3.01E−6 | | | | | |
| 196 | 1.02E−6 | >3.00E−6 | 2.91E−7 | 1.44E−7 | 8.69E−7 | 1.47E−6 |
| 197 | 1.01E−6 | >3.00E−6 | 5.16E−7 | 1.29E−7 | >3.00E−6 | 2.96E−6 |
| 198 | >3.00E−6 | | | | | |
| 199 | 8.57E−7 | 9.65E−7 | 3.20E−7 | 2.44E−7 | 7.08E−7 | >1.00E−6 |
| 200 | 1.96E−6 | | | | | |
| 201 | >3.00E−6 | | | | | |
| 202 | 1.53E−6 | | | | | |
| 203 | 9.98E−7 | | | | | |
| 204 | 5.68E−7 | | | | | |
| 205 | 6.72E−7 | 1.49E−6 | 2.19E−7 | 6.52E−7 | 1.24E−6 | 1.70E−6 |
| 213 | >3.00E−6 | | | | | |
| 214 | >3.00E−6 | | | | | |
| 215 | >3.00E−6 | | | | | |
| 216 | 1.01E−6 | >3.00E−6 | 1.11E−6 | 1.66E−6 | >3.00E−6 | >3.00E−6 |
|  |  | >3.00E−6 | 1.02E−6 | 1.33E−6 | >3.00E−6 | >3.00E−6 |
| 218 | 3.00E−7 | | | | | |
| 219 | 2.98E−6 | | | | | |
| 220 | 6.04E−7 | 9.93E−7 | 3.03E−7 | 3.34E−7 | >1.00E−6 | >1.00E−6 |
| 221 | >3.00E−6 | | | | | |
| 222 | 9.75E−7 | | | | | |
| 227 | 1.94E−6 | | | | | |
| 228 | 2.25E−7 | 5.94E−7 | 2.33E−7 | 3.13E−7 | 6.37E−7 | 2.60E−6 |
| 229 | 4.47E−7 | | | | | |
| 230 | 3.80E−7 | | | | | |
| 232 | 3.41E−7 | | | | | |
| 233 | 1.80E−7 | | | | | |

TABLE 9-continued

Inhibition of proliferation of HeLa, HeLa-MaTu-ADR, NCI-H460, DU145, Caco-2 and B16F10 cells by compounds according to the present invention, determined as described above. All $IC_{50}$ (inhibitory concentration at 50% of maximal effect) values are indicated in M, "n.t." means that the compounds have not been tested in the respective assay.

Table 9: Inhibition of proliferation

| ① | ② | ③ | ④ | ⑤ | ⑥ | ⑦ |
|---|---|---|---|---|---|---|
| 234 | 1.21E−6 | | | | | |
| 235 | 9.50E−7 | | | | | |
| 236 | 7.92E−7 | | | | | |
| 237 | 5.28E−7 | | | | | |
| 238 | 1.18E−6 | | | | | |
| 239 | 1.13E−6 | | | | | |
| 241 | 1.71E−7 | | | | | |
| 242 | 8.11E−7 | | | | | |
| 243 | 3.60E−7 | | | | | |
| 245 | 3.43E−7 | | | | | |
| 246 | 2.84E−6 | | | | | |
| 247 | 2.28E−7 | | | | | |
| 248 | 4.51E−7 | | | | | |
| 249 | 4.09E−7 | | | | | |
| 250 | 1.16E−7 | | | | | |
| 251 | 8.00E−7 | | | | | |
| 252 | 2.22E−7 | | | | | |
| 253 | 5.58E−7 | | | | | |
| 254 | 3.12E−7 | | | | | |
| 255 | 4.58E−7 | | | | | |
| 258 | 2.63E−7 | | | | | |
| 259 | 4.97E−7 | | | | | |
| 260 | 4.85E−7 | | | | | |
| 261 | 4.20E−7 | | | | | |
| 262 | 4.71E−7 | | | | | |
| 263 | 3.32E−7 | | | | | |
| 264 | 1.98E−7 | | | | | |
| 266 | 1.54E−7 | | | | | |
| 267 | 2.97E−6 | | | | | |
| 268 | 4.15E−7 | | | | | |
| 269 | 4.05E−7 | | | | | |
| 270 | 5.65E−7 | | | | | |
| 271 | 1.33E−6 | | | | | |
| 272 | 6.48E−7 | | | | | |
| 273 | 9.99E−7 | | | | | |
| 274 | 6.10E−7 | | | | | |
| 277 | 4.01E−7 | | | | | |
| 278 | 1.68E−7 | | | | | |
| 280 | 4.17E−7 | | | | | |
| 281 | 2.59E−7 | | | | | |
| 282 | 1.18E−6 | | | | | |
| 283 | 1.46E−7 | | | | | |
| 284 | 8.52E−7 | | | | | |
| 286 | 2.93E−7 | 8.82E−7 | 7.56E−8 | 4.86E−8 | 5.29E−7 | 5.86E−7 |
| 291 | 1.52E−6 | | | | | |
| 292 | 2.64E−6 | | | | | |
| 294 | 2.45E−6 | | | | | |
| 296 | 2.74E−6 | | | | | |
| 298 | 2.44E−6 | | | | | |
| 299 | >3.00E−6 | | | | | |
| 301 | 2.82E−6 | | | | | |
| 303 | >3.00E−6 | | | | | |
| 304 | >3.00E−6 | | | | | |
| 306 | >3.00E−6 | | | | | |
| 310 | >3.00E−6 | | | | | |
| 312 | >3.00E−6 | | | | | |
| 313 | 2.54E−6 | | | | | |
| 314 | >3.00E−6 | | | | | |
| 316 | >3.00E−6 | | | | | |
| 317 | 2.98E−6 | | | | | |
| 318 | 2.00E−6 | | | | | |
| 320 | >3.00E−6 | | | | | |
| 321 | >3.00E−6 | | | | | |
| 322 | >3.00E−6 | | | | | |
| 323 | 2.22E−6 | | | | | |
| 324 | 2.42E−6 | | | | | |
| 325 | 9.99E−7 | | | | | |
| 326 | 2.92E−6 | | | | | |
| 327 | 1.89E−6 | | | | | |
| 330 | >3.00E−6 | | | | | |
| 332 | >3.00E−6 | | | | | |

TABLE 9-continued

Inhibition of proliferation of HeLa, HeLa-MaTu-ADR, NCI-H460, DU145, Caco-2 and B16F10 cells by compounds according to the present invention, determined as described above. All IC$_{50}$ (inhibitory concentration at 50% of maximal effect) values are indicated in M, "n.t." means that the compounds have not been tested in the respective assay.
Table 9: Inhibition of proliferation

| ① | ② | ③ | ④ | ⑤ | ⑥ | ⑦ |
|---|---|---|---|---|---|---|
| 333 | >3.00E−6 | | | | | |
| 334 | >3.00E−6 | | | | | |
| 335 | 2.96E−6 | | | | | |
| 337 | 1.71E−6 | | | | | |
| 339 | >3.00E−6 | | | | | |
| 340 | 2.95E−6 | | | | | |
| 341 | 1.59E−6 | | | | | |
| 343 | 1.71E−6 | | | | | |
| 345 | >3.00E−6 | | | | | |
| 348 | 6.13E−7 | 9.40E−7 | 3.99E−7 | 5.18E−7 | 8.22E−7 | 2.22E−6 |
| 349 | >3.00E−6 | | | | | |
| 350 | >3.00E−6 | | | | | |
| 351 | 3.00E−6 | | | | | |

①Example Number
②Inhibition of HeLa cell proliferation
③Inhibition of HeLa-MaTu-ADR cell proliferation
④Inhibition of NCI-H460 cell proliferation
⑤Inhibition of DU145 cell proliferation
⑥Inhibition of Caco-2 cell proliferation
⑦Inhibition of B16F10 cell proliferation

4. Phospho-H2AX Assay

Phospho-Ser139 Histone H2AX (also known as ɣH2AX, UniProtKB/Swiss-Prot P16104) represents an cellular early marker for DNA damage response. In particular, H2AX gets phosphorylated by ATR upon DNA replication stress. HT-29 human colorectal adenoadenocarcinoma cells, originally obtained from the DSMZ, were plated out in a density of 12000 cells/measurement point a black-walled, clear-bottom 96-well multititre plate in 100 µl of growth medium (DMEM/HAMS F12, 2 mM L-glutamine, 10% foetal calf serum). After 24 hours, the test substances were added in various concentrations (0 µM, and also in the range of 0.001-10 µM in quadruplicates; the final concentration of the solvent dimethyl sulphoxide was 0.1%) followed by addition of a hydroxyurea solution to achieve a finale concentration of 2.5 mM and a final assay volume of 200 µL. One control plate was left untreated and further processed in parallel. The cells were incubated for 30 min at 37° C. Subsequently, the growth medium was carefully evaporated and the cells were fixed with 50 µL/well of ice-cold methanol for 15 min. The cells were washed once with 100 µL/well of PBS, followed by incubation with 50 µL/well of blocking buffer (Liqor, 927-40000) for 1 h at room temperature. Subsequently, the cells were incubated with 50 µL/well of anti-phospho-H2AX (Ser 139) antibody (Merck Millipore, clone JBW301, 05-636) diluted 1:500 in blocking buffer for 1 h at room temperature (or over night at 4° C.). The cells were washed three time with 100 µL/well of PBS, followed by incubation with 50 µL/well of a 1:500 diluted solution of Alexa Fluor 488 conjugated donkey anti-mouse IgG antibody (Life Technologies, A-21202) in TBST for 1 h at room temperature and protected from light. After the cells were washed three time with 100 µL/well of PBS, the wells were filled with 100 µL of PBS and fluorescence was determined using an Acumen laser scanning cytometer (TTP Labtech). The percentage change in hydroxy urea induced phospho-H2AX content was calculated by normalizing the measured values to the fluorescence values of untreated control wells (=0%) and the fluorescence of the hydroxy urea control wells without test compounds (0 µM, =100%). The IC$_{50}$ values were determined by means of a four parameter fit.

5. Caco-2 Permeation Assay

Caco-2 cells (purchased from DSMZ Braunschweig, Germany) were seeded at a density of 4.5×104 cell per well on 24 well insert plates, 0.4 µm pore size, and grown for 15 days in DMEM medium supplemented with 10% fetal bovine serum, 1% GlutaMAX (100×, GIBCO), 100 U/ml penicillin, 100 µg/ml streptomycin (GIBCO) and 1% non essential amino acids (100×). Cells were maintained at 37° C. in a humified 5% CO2 atmosphere. Medium was changed every 2-3 day.

Before running the permeation assay, the culture medium was replaced by a FCS-free hepes-carbonate transport puffer (pH 7.2) For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp=(Vr/Po)(1/S)(P2/t)$$

Where Vr is the volume of medium in the receiver chamber, Po is the measured peak area of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated. As assay control reference compounds were analyzed in parallel.

The invention claimed is:

1. A compound of formula 5

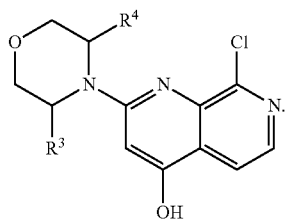

5 wherein R³ is hydrogen; and R⁴ is hydrogen or methyl.

2. A process for preparing a compound of formula 5 according to claim 1,

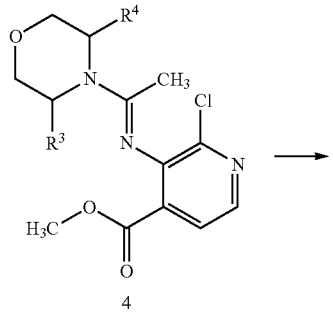

4

→

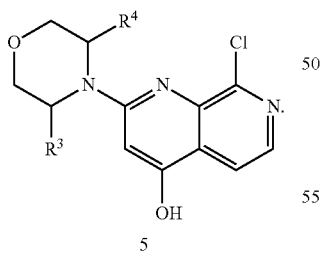

5 wherein R³ is hydrogen; and R⁴ is hydrogen or methyl, comprising:

reacting a compound of formula 4 in an organic solvent with a strong base at a temperature between −20° C. and the organic solvent's boiling point to obtain the compound of formula 5.

3. The process according to claim 2, in which wherein the strong base is lithium bis(trimethylsilyl)amide (LiHMDS), potassium bis(trimethylsilyl)amide (KHMDS), sodium bis(trimethylsilyl)amide (NaHMDS), or lithium diisopropylamide (LDA).

4. The process according to claim 2, wherein the organic solvent is an aprotic organic solvent.

5. The process according to claim 4, wherein the organic solvent is tetrahydrofuran or N,N-dimethylformamide.

6. The process according to claim 2, wherein the compound of formula 4 is reacted in an organic solvent with a strong base at a temperature between −5° C. and 30° C. to obtain the compound of formula 5.

7. A compound of formula 11

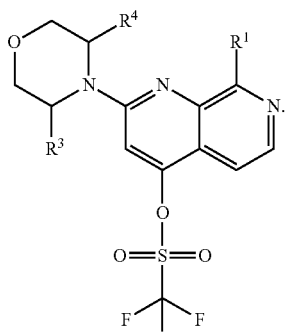

11 wherein

R¹ is

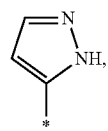

wherein * indicates the point of attachment of said group with the rest of the molecule;

R³ is hydrogen; and

R⁴ is hydrogen or methyl.

8. A compound of formula 12

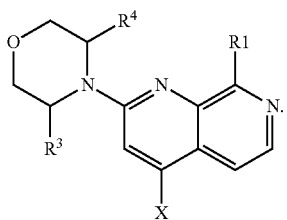

R¹ is

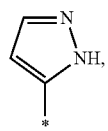

wherein * indicates the point of attachment of said group with the rest of the molecule;
R³ is hydrogen;
R⁴ is hydrogen or methyl; and
X is chloro, bromo or iodo.

9. A compound of formula 39

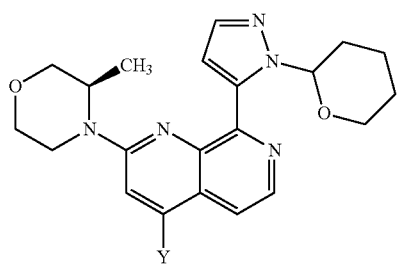

wherein Y is OH, —O—SO$_2$—CF$_3$, Cl, Br, I, SH, or SO$_2$Cl.

10. A compound of formula 9

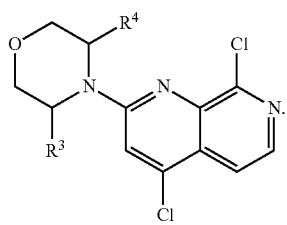

wherein R³ is hydrogen; and R⁴ is hydrogen or methyl.

11. A compound of formula 15

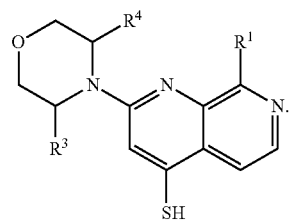

wherein
R¹ is

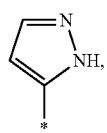

wherein * indicates the point of attachment of said group with the rest of the molecule;
R³ is hydrogen; and
R⁴ is hydrogen or methyl.

12. A compound of formula 16

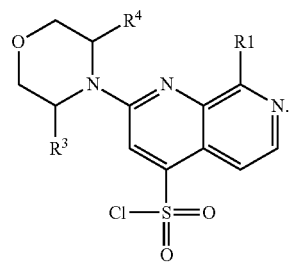

wherein
R¹ is

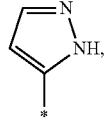

wherein * indicates the point of attachment of said group with the rest of the molecule;
R³ is hydrogen; and
R⁴ is hydrogen or methyl.

* * * * *

UNITED STATES PATENT AND TRADEMARK OFFICE
CERTIFICATE OF CORRECTION

PATENT NO.        : 10,772,893 B2
APPLICATION NO.   : 15/974536
DATED             : September 15, 2020
INVENTOR(S)       : Lars Wortmann et al.

Page 1 of 3

It is certified that error appears in the above-identified patent and that said Letters Patent is hereby corrected as shown below:

In the Claims

Column 523, Claim 1, Line 21, delete "5";

Column 523, Claim 1, Line 21-29, replace

" 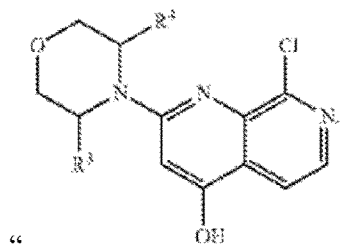 " with -- 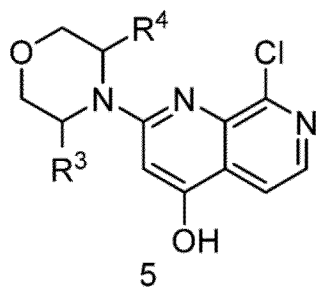 ,--;

Column 523, Claim 2, Line 47-57, replace

" 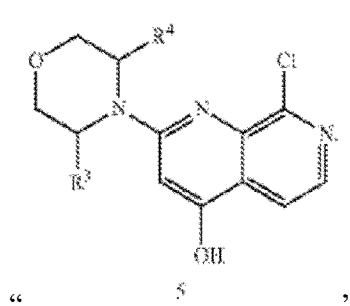 " with -- 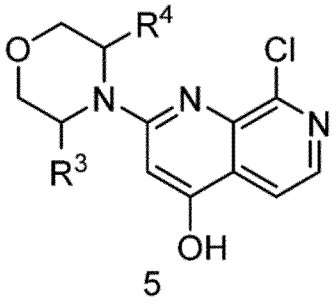 ,--;

Column 524, Claim 7, Line 33, delete "11";

Column 524, Claim 7, Line 33-46, replace

Signed and Sealed this
Second Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,772,893 B2

Page 2 of 3

" 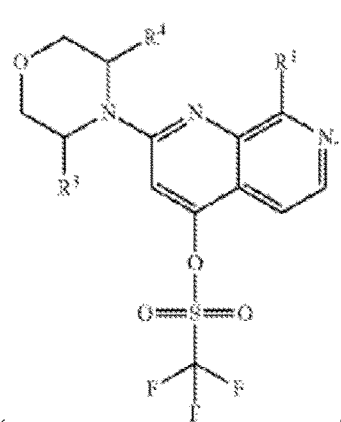 " with -- 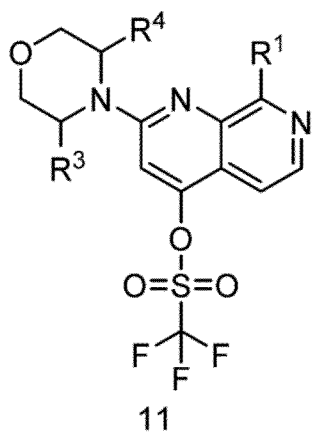 ,--;

Column 525, Claim 8, Line 4, delete "12";

Column 525, Claim 8, Line 5-12, replace

" 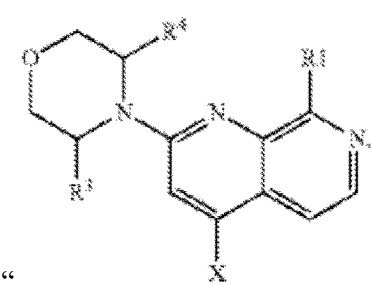 " with -- 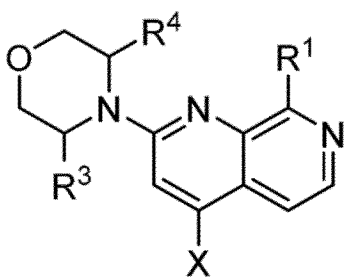 ,--;

Column 525, Claim 8, Line 14, replace "$R^1$ is" with --wherein $R^1$ is--;

Column 525, Claim 9, Line 31, delete "39";

Column 525, Claim 9, Line 32-41, replace

" 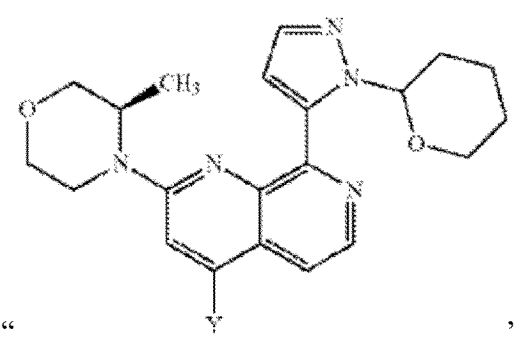 " with -- 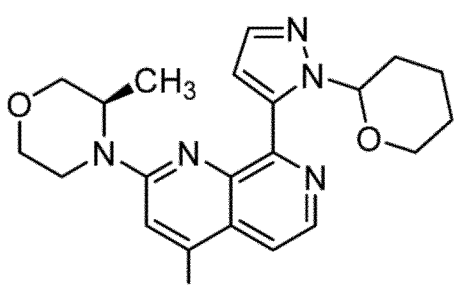 --;

Column 525, Claim 10, Line 48, delete "9";

Column 525, Claim 10, Line 48-56, replace

CERTIFICATE OF CORRECTION (continued)
U.S. Pat. No. 10,772,893 B2

Page 3 of 3

" 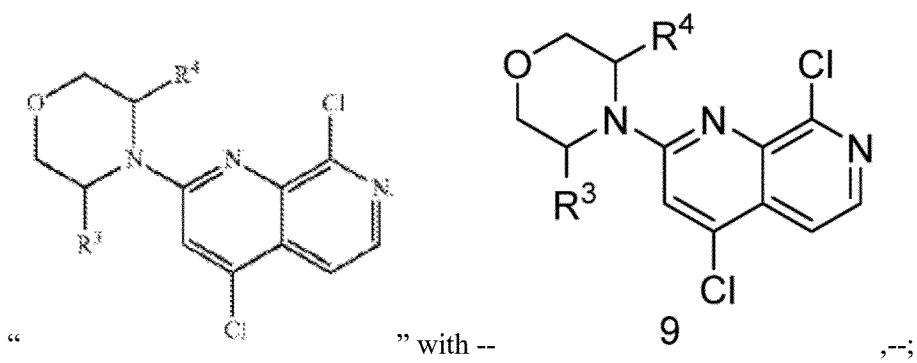 " with -- ,--;

Column 526, Claim 11, Line 4, delete "15";

Column 526, Claim 11, Line 5-13, replace

" 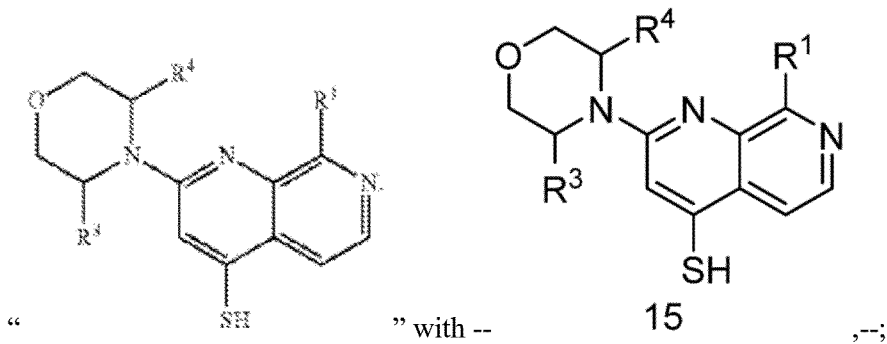 " with -- ,--;

Column 526, Claim 12, Line 32, delete "16";

Column 526, Claim 12, Line 33-43, replace

" 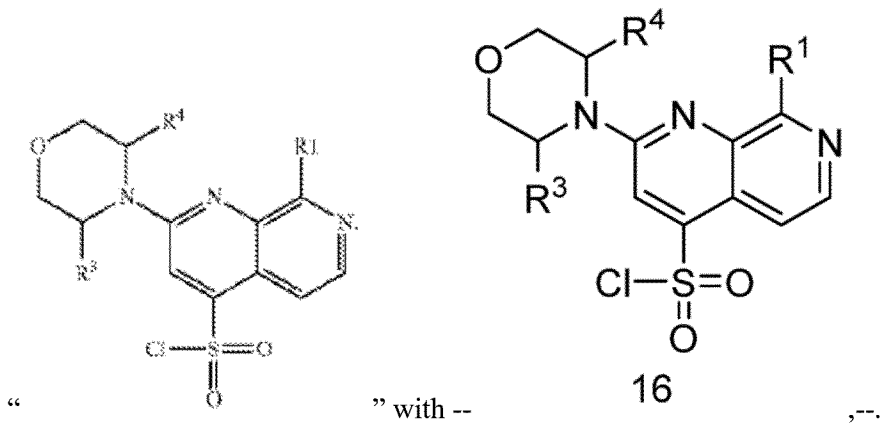 " with -- ,--.